（12) United States Patent
Pohlmann et al.

(10) Patent No.: US 10,487,075 B2
(45) Date of Patent: Nov. 26, 2019

(54) SUBSTITUTED MONO- AND POLYAZANAPHTHALENE DERIVATIVES AND THEIR USE

(71) Applicant: Basilea Pharmaceutica International AG, Basel (CH)

(72) Inventors: Jens Pohlmann, Basel (CH); Martin Stieger, Basel (CH); Stefan Reinelt, Basel (CH); Heidi Lane, Basel (CH)

(73) Assignee: Basilea Pharmaceutica International AG, Basel (CH)

( * ) Notice: Subject to any disclaimer, the term of this patent is extended or adjusted under 35 U.S.C. 154(b) by 0 days.

(21) Appl. No.: 15/545,149

(22) PCT Filed: Feb. 10, 2016

(86) PCT No.: PCT/EP2016/052828
§ 371 (c)(1),
(2) Date: Jul. 20, 2017

(87) PCT Pub. No.: WO2016/128465
PCT Pub. Date: Aug. 18, 2016

(65) Prior Publication Data
US 2018/0002321 A1 Jan. 4, 2018

(30) Foreign Application Priority Data

Feb. 11, 2015 (EP) .................................... 15154685
Dec. 4, 2015 (EP) .................................... 15197976

(51) Int. Cl.
*A61K 31/4375* (2006.01)
*C07D 471/04* (2006.01)
(Continued)

(52) U.S. Cl.
CPC ......... *C07D 405/14* (2013.01); *C07D 217/04* (2013.01); *C07D 217/12* (2013.01);
(Continued)

(58) Field of Classification Search
CPC .......................... A61K 31/4375; C07D 471/04
See application file for complete search history.

(56) References Cited

U.S. PATENT DOCUMENTS

2006/0030584 A1 2/2006 Hanson et al.
2014/0296233 A1 10/2014 D'Agostino et al.
(Continued)

FOREIGN PATENT DOCUMENTS

EP 1217000 A1 6/2002
EP 2418203 A1 2/2012
(Continued)

OTHER PUBLICATIONS

The International Search Report and Written Opinion, dated Mar. 21, 2016, in the corresponding PCT Appl. No. PCT/EP2016/052828.
(Continued)

*Primary Examiner* — Brenda L Coleman

(57) ABSTRACT

Disclosed are compounds of formula (I) wherein A is CH or N, B is CR or N; and D is CR; R represents hydrogen, OH or $NH_2$; R1 and R2, independently of each other, represent hydrogen, $N(R3)_2$, halogen, cyano, nitro, R4-C1-C4alkyl, R4-C1-C4halogenoalkyl, OH, R4-C1-C4alkoxy, R4-C1-C4halogenoalkoxy, SH, R4-C1-C4alkythio, R4-C1-C4halogenoalkylthio; R3 represents, independently at each occurrence, hydrogen, R4-C1-C4alkyl or R4-C1-C4halogenoalkyl; R3a represents, independently at each occurrence, hydrogen or C1-C4 alkyl; R4 represents, independently at each occurrence, hydrogen, halogen, cyano, OH, SH, $NH_2$, $NH(CH_3)$ or $N(CH_3)_2$; X represents a group of formula -E- or -E-F—, wherein E and F are different from each other and represent a group selected from —C(R3a)2-, —(C═O)—, —NR3a- and —O— and F is linked to Y, with the proviso that if X represents -E-F— one of E or F represents —$C(R3a)_2$- or —(C═O)—; Y represents a group selected from C1-C6alkyl, mono- or bicyclic C3-C11cycloalkyl, which may be partially unsaturated, mono- or bicyclic 3 to 11-membered heterocycloalkyl, which may be partially unsaturated, a mono- or bicyclic group comprising at least one aryl or heteroaryl cycle, wherein said heterocycloalkyl group and said group comprising at least one heteroaryl cycle comprise one or more heteroatoms selected from nitrogen, oxygen and sulfur and said group Y is either unsubstituted or substituted by one or more substituents and comprises including its substituents one or more than one nitrogen atom having a lone electron pair; and Z represents a mono- or bicyclic group comprising at least one aryl or heteroaryl cycle, said heteroaryl cycle comprising one or more heteroatoms selected from nitrogen, oxygen and sulfur, which aryl or heteroaryl group is unsubstituted or substituted by one or more substituents; including tautomers of said compounds, mixtures of two tautomeric forms of said compounds, and pharmaceutically acceptable salts of said compounds, tautomers thereof or mixtures of two tautomeric forms thereof, preferably with the proviso that Y comprises one or more primary amino group —$NH_2$, when X represents —(C═O)— or —(C═O)—NR3a-, wherein R3a represents hydrogen or C1-C4alkyl; which are useful for the treatment of proliferation disorders or diseases, such as cancer.

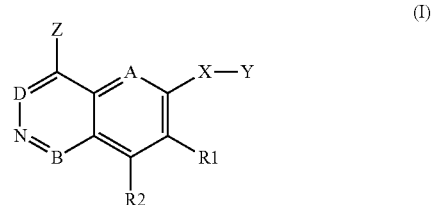

41 Claims, No Drawings

(51) Int. Cl.

| | | |
|---|---|---|
| *C07D 405/14* | (2006.01) | |
| *C07D 401/14* | (2006.01) | |
| *C07D 413/14* | (2006.01) | |
| *C07D 217/04* | (2006.01) | |
| *C07D 217/12* | (2006.01) | |
| *C07D 217/22* | (2006.01) | |
| *C07D 401/06* | (2006.01) | |
| *C07D 401/12* | (2006.01) | |
| *C07D 237/28* | (2006.01) | |
| *C07D 405/04* | (2006.01) | |
| *C07D 405/12* | (2006.01) | |
| *C07D 409/14* | (2006.01) | |
| *C07D 401/04* | (2006.01) | |
| *C07D 417/14* | (2006.01) | |
| *C07D 491/048* | (2006.01) | |

(52) U.S. Cl.
CPC ......... *C07D 217/22* (2013.01); *C07D 237/28* (2013.01); *C07D 401/04* (2013.01); *C07D 401/06* (2013.01); *C07D 401/12* (2013.01); *C07D 401/14* (2013.01); *C07D 405/04* (2013.01); *C07D 405/12* (2013.01); *C07D 409/14* (2013.01); *C07D 413/14* (2013.01); *C07D 417/14* (2013.01); *C07D 471/04* (2013.01); *C07D 491/048* (2013.01)

(56) References Cited

U.S. PATENT DOCUMENTS

| 2016/0016951 A1 | 1/2016 | Schiemann et al. |
| 2018/0177784 A1 | 6/2018 | Wu et al. |

FOREIGN PATENT DOCUMENTS

| EP | 2463276 A1 | 6/2012 |
| WO | 9220642 A1 | 11/1992 |
| WO | 9414435 A1 | 7/1994 |
| WO | 0119788 A2 | 3/2001 |
| WO | 2004087153 A2 | 10/2004 |
| WO | 2005/028444 A1 | 3/2005 |
| WO | 2007/100880 A1 | 9/2007 |
| WO | 2007/103554 A1 | 9/2007 |
| WO | 2007103260 A1 | 9/2007 |
| WO | 2009025823 A1 | 2/2009 |
| WO | 2010/101949 A1 | 9/2010 |
| WO | 2010/112826 A2 | 10/2010 |
| WO | 2012/176856 A2 | 12/2012 |
| WO | 2013/142390 A1 | 9/2013 |
| WO | 2014/079787 A1 | 5/2014 |
| WO | 2014/177596 A1 | 11/2014 |
| WO | 2015086523 A1 | 6/2015 |

OTHER PUBLICATIONS

The European Search Report, dated Sep. 16, 2017, in the related European Patent Appl. No. 15154685.0.

Florentino et al., "Synthesis of Polysubstituted Isoquinolines through Cross-Coupling Reactions with a-Alkoxytosylhydrazones," Organic Letters, May 4, 2012, pp. 2323-2325, vol. 14, No. 9.

Awuah et al., "Strategies and Synthetic Methods Directed Toward the Preparation of Libraries of Substituted Isoquinolines,"J. Org. Chem. Aug. 20, 2010, pp. 5627-5634, vol. 75, No. 16.

Hu et al., "Discovery of potent, selective, and metabolically stable 4-(pyridin-3-yl)cinnolines as novel phosphodiesterase 10A (PDE10A) inhibitors," Bioorganic & Medicinal Chemistry Letters, Jan. 23, 2012, pp. 2262-2265, vol. 22, No. 6.

Hu et al., "Rapid Identification of a Novel Small Molecule Phosphodiesterase 10A (PDE10A) Tracer," Journal of Medicinal Chemistry, May 24, 2012, pp. 4776-4787, vol. 55, No. 10.

The European Communication, dated Nov. 14, 2018, in the related European Appl. No. 16703791.0.

Hu et al., "Use of structure based design to increase selectivity of pyridyl-cinnoline phosphodiesterase 10A (PDE10A) inhibitors against phosphodiesterase 3 (PDE3)," Bioorg Med Chem Lett. Nov. 15, 2012;22(22): 6938-42.

Malinger et al. "2,8-Disubstituted-1,6-Naphthyridines and 4,6-Disubstituted-Isoquinolines with Potent, Selective Affinity for CDK8/19", ACS Med. Chem. Lett, 7, 573-578, 2016.

SUBSTITUTED MONO- AND POLYAZANAPHTHALENE DERIVATIVES AND THEIR USE

This application is a National Stage Application of PCT/EP2016/052828 filed Feb. 10, 2016, which claims priority from European Patent Application No. 15154685.0, filed on Feb. 11, 2015 and European Patent Application No. 15197976.2, filed on Dec. 4, 2015. Each of the prior mentioned applications is hereby incorporated by reference herein in its entirety.

The present invention relates to novel mono- and polyazanaphthalene derivatives of formula I:

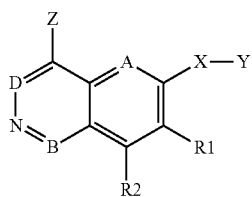

wherein A is CH or N, B is CR or N and D is CR or N, with the proviso that only one of B and D is N, preferably that only one of A, B and D is N and R, R1, R2, X, Y and Z have the meanings described herein below and their use for the treatment of proliferation disorders or diseases like cancer.

WO2005/028444A1 discloses 1,4-substituted isoquinoline derivatives of formula:

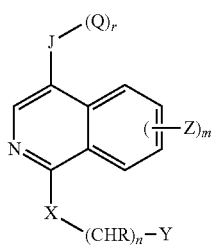

wherein J is e.g. an aryl or heteroaryl residue which is unsubstituted or substituted once or twice by a list of substituents Q, X represents a number of linkers including e.g. a bond, —N(R)— like in particular —NH—, —O— and —NH—(C=O)—, Y represents hydrogen, lower alkyl or unsubstituted or substituted cycloalkyl, aryl or heteroaryl, n is 0 or 1, Z represents a conventional substituent and m is 0 to 2, preferably 0; and their use as RAF kinase inhibitors useful as therapeutic agents for the treatment of proliferative diseases characterized by an aberrant MAP kinase signaling pathway.

Subject of the present invention are compounds of formula I:

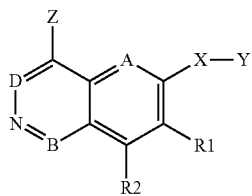

wherein
A is CH or N,
B is CR or N and
D is CR;
R represents hydrogen, OH or $NH_2$;
R1 and R2, independently of each other, represent hydrogen, $N(R3)_2$, halogen, cyano, nitro, R4-C1-C4alkyl, R4-C1-C4halogenoalkyl, OH, R4-C1-C4alkoxy, R4-C1-C4halogenoalkoxy, SH, R4-C1-C4alkythio, R4-C1-C4halogenoalkylthio;
R3 is, independently at each occurrence, hydrogen, R4-C1-C4alkyl or R4-C1-C4halogenoalkyl;
R3a represents, independently at each occurrence, hydrogen or C1-C4 alkyl;
R4 represents, independently at each occurrence, hydrogen, halogen, cyano, OH, SH, $NH_2$, $NH(CH_3)$ or $N(CH_3)_2$;
X represents a group of formula -E- or -E-F—, wherein E and F are different from each other and represent a group selected from —$C(R3a)_2$-, —(C=O)—, —NR3a- and —O— and F is linked to Y, with the proviso that if X represents -E-F—, one of E or F represents —$C(R3a)_2$- or —(C=O)—;
Y represents a group selected from C1-C6alkyl, mono- or bicyclic C3-C11cycloalkyl, which may be partially unsaturated, mono- or bicyclic 3 to 11-membered heterocycloalkyl, which may be partially unsaturated, a mono- or bicyclic group comprising at least one aryl or heteroaryl cycle, wherein said heterocycloalkyl group and said group comprising at least one heteroaryl cycle comprise one or more heteroatoms selected from nitrogen, oxygen and sulfur and said group Y is either unsubstituted or substituted by one or more substituents and comprises including its substituents one or more than one nitrogen atom having a lone electron pair; and
Z represents a mono- or bicyclic group comprising at least one aryl or heteroaryl cycle, said heteroaryl cycle comprising one or more heteroatoms selected from nitrogen, oxygen and sulfur, which aryl or heteroaryl group is unsubstituted or substituted by one or more substituents;
including tautomers of said compounds, mixtures of two tautomeric forms of said compounds, and pharmaceutically acceptable salts of said compounds, tautomers thereof or mixtures of two tautomeric forms thereof.

Preferably A is CH in formula (I).

Certain compounds of formula I may contain one, two or more centres of chirality. The term compound of formula I as used herein is therefore understood to include both, all pure enantiomers and all pure diastereoisomers, and also mixtures thereof in any mixing ratio. The present invention moreover also includes all cis/trans-isomers of the compounds of the general formula I and mixtures thereof.

The compounds of formula I are useful in particular for the treatment of proliferation disorders or diseases like e.g. cancer.

In particular, the compounds of the invention are active against malignancies, e.g. epithelial neoplasms, squamous cell neoplasms, basal cell neoplasms, transitional cell papillomas and carcinomas, adenomas und adenocarcinomas, adnexal and skin appendage neoplasms, mucoepidermoid neoplasms, cystic neoplasms, mucinous and serous neoplasms, ductal-, lobular and medullary neoplasms, acinar cell neoplasms, complex epithelial neoplasms, specialized gonadal neoplasms, paragangliomas and glomus tumors, naevi and melanomas, soft tissue tumors and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumors, lymphatic vessel tumors, osseous and chondromatous neoplasms, giant cell tumors, miscellaneous bone tumors, odontogenic tumors, gliomas, neuroepitheliomatous neoplasms, meningiomas, nerve sheath tumors, granular cell tumors and alveolar soft part sarcomas, Hodgkin's and non Hodgkin's lymphomas, other lymphoreticular neoplasms, plasma cell tumors, mast cell tumors, immunoproliferative diseases, leukemias, miscellaneous myeloproliferative disorders, lymphoproliferative disorders and myelodysplastic syndromes.

In particular, a compound of formula (I) according to the invention shows therapeutic efficacy especially against solid neoplastic diseases, e.g. epithelial neoplasms, squamous cell neoplasms, basal cell neoplasms, transitional cell papillomas and carcinomas, adenomas und adenocarcinomas, adnexal and skin appendage neoplasms, mucoepidermoid neoplasms, cystic neoplasms, mucinous and serous neoplasms, ductal-, lobular and medullary neoplasms, acinar cell neoplasms, complex epithelial neoplasms, specialized gonadal neoplasms, paragangliomas and glomus tumors, naevi and melanomas, soft tissue tumors and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumors, lymphatic vessel tumors, osseous and chondromatous neoplasms, giant cell tumors, miscellaneous bone tumors, odontogenic tumors, gliomas, neuroepitheliomatous neoplasms, meningiomas, nerve sheath tumors, granular cell tumors and alveolar soft part sarcomas.

Many of the compounds of formula I have furthermore been found to significantly inhibit human MAP kinase-interacting kinases (MNKs or MKNKs). The MNKs are a group of four proteins encoded by two genes (Gene Symbols: MKNK1 and MKNK2) (Buxade M. et al., Frontiers in Bioscience 5359-5373, 2008). The MNKs are ubiquitously expressed protein-serine/threonine kinases. The MNK1b and MNK2b variants lack a MAP-kinase binding domain which can be located at the C-terminus of MNK1a and MNK2a. The catalytic domain of MNK1a/b and MNK2a/b is a highly conserved typical kinase domain which displays three unusual properties. The MNK kinases feature a DFD-tripeptide in the ATP-binding region instead of the typical DFG-tripeptide found in all other kinases (Jauch R. et al., Structure 13, 1559-1568, 2005 and Jauch R. et al., EMBO J., 25, 4020-4032, 2006). In addition the MNKs share two short inserts in comparison to other protein kinases. The upstream kinase ERK can bind to and activate both MNK1a and MNK2a. In contrast the p38 MAP kinases only activate MNK1a. MNK1b has minor activity under all conditions while MNK2b has a basal activity independent of p38 MAP or ERK kinase (Cargnello M. and Roux P. P., Microbiol. Mol. Biol. Rev., 75, 50-83, 2011).

The MNKs have been demonstrated to phosphorylate several protein substrates. Amongst the targets of MNK phosphorylation, the most extensively characterized is the eukaryotic initiation factor eIF4E. In addition it has been reported that the MNKs phosphorylate the proteins heterogeneous nuclear ribonucleoprotein A1 (hnRNPA1), Sprouty 2, polypyrimidine-tract binding protein-associated splicing factor (PSF) and cytoplasmic phospholipase A2 (cPLA2) (Joshi S. and Platanias L. C., World J. Biol. Chem., 5. 321-333, 2014).

The eukaryotic translation initiation factor eIF4E is an oncogene that is overexpressed in many cancers (Mamane Y. et al., Oncogene, 23, 3172-3179, 2004; De Benedetti A. and Graff J. R., Oncogene, 23, 3189-3199, 2004 and Bjornsti M. A and Houghton P. J., Cancer Cell, 5, 519-523, 2004). It is exclusively phosphorylated by MNKs on serine 209 as demonstrated by the complete absence of phosphorylation in MNK1/2 Knock-out mice (Ueda T et al. Mol. Cell Biol., 24, 6539-6549, 2004). eIF4E together with eIF4G and eIF4A forms the eIF4F complex which is instrumental for the translation of cellular mRNAs (Sonenberg N. and Hinnebusch, A. G., Mol. Cell, 28, 721-729, 2007). The eIF4E subunit of the eIF4F complex is binding to the 7-methyl-guanosine cap which is found at the 5' end of mRNAs leading to the delivery of mRNAs to the ribosomes (Pestova T. V. et al., Proc. Natl, Acad. Sci. USA, 98, 7029-7036, 2001). A subset of mRNAs is especially dependent on increased eIF4E activity for translation. These mRNAs have long and complex 5' untranslated regions; many of them encode proteins that play important roles in tumorigenesis and tumor proliferation e.g. c-myc, cyclin D1, VEGF, Bcl-2, survivin and others (Koromilas A. E. et al., EMBO J., 11, 4153-4158, 1992 and Hay N. and Sonenberg N., Genes Dev., 18, 1926-1945, 2004). Overexpression of eIF4E is detected in many solid tumors including breast, prostate, bladder, head and neck and cervical tumors as well as leukemias (Zimmer S. G. et al., Anticancer Res., 20, 1343-1351, 2000 and Bitterman p. B and Polunovsky V. A., Biochim. Biophys. Acta, 2014). The activity and expression of eIF4E are tightly regulated at multiple levels by oncogenes and growth factors, indicating that eIF4E is positioned at a point where many transforming signaling pathways converge (Raught B. and Gingras A. C., The Int. J. Biochem.&Cell Biol., 31, 43-57, 1999). This is illustrated by the fact that overexpression of eIF4E leads to the neoplastic transformation of cell lines (Sonenberg N. and Hinnebusch A. G., Cell, 136, 731-745, 2009). By reducing the activity of eIF4E, either by lowering its levels with antisense RNA (Hong D. D. et al., Clin. Cancer Res., 17, 6582-6591, 2011) or by overexpressing the inhibitory 4E binding protein, the growth of many tumor cell lines can be suppressed (Alain T. et al. Cancer Res., 72, 6468-6476, 2012).

The increased phosphorylation of eIF4E is a poor prognostic factor for survival in non-small lung cancer patients (Yoshizawa A. et al., Clin. Cancer Res., 16, 240-248, 2010). Moreover, overexpression of constitutively active MNK but not of a kinase dead mutant in mouse embryonic fibroblast leads to cellular transformation (Topisirovic I. et al., Cancer Res., 64, 8639-8642, 2004). Furthermore constitutively active but not kinase inactive MNK1 speeds up tumor growth in a model of hematopoietic stem cells driven by an Eµ-Myc transgene (Wendel H. G., Genes Dev., 21, 3232-3237, 2007).

The inhibition of MNK enzymes has therefore been discussed already in the art as a promising strategy for cancer therapy (J. Hou, F. Lam, C. Proud, S. Wang, Oncotarget 2012, 3: 118-131). The effect of MNK inhibition on the proliferation of cancer cells has also already been demonstrated with the natural product-derived MNK inhibitor cercosporamide inhibiting the growth of a HCT116 colon carcinoma xenograft model in nude mice and reduceing the outgrowth of B16 melanoma pulmonary metastatic lesions (B. W. Konicek, J. R. Stephens, A. M. McNulty, Cancer Res. 2011, 71(5): 1849-1857).

The term "alkyl" as used herein refers preferably and if nothing else is stated to straight chain or branched hydrocarbon residues of the indicated chain length, in particular of 1 to 6 carbon atoms, preferably 1 to 4, and includes for example methyl, ethyl, n-propyl, isopropyl, n-butyl, isobutyl, sec.-butyl, tert.-butyl, n-pentyl, isopentyl, tert.-pentyl, neopentyl, n-hexyl or isohexyl and the like, which can be unsubstituted or substituted by one or more substituents, preferably up to three, especially one or two substituents. In combined designations of residues like e.g. alkoxy, alkylthio, halogenoalkyl, halogenoalkoxy, halogenoalkylthio, aralkyl, alkyl-aryl or alkyl-heteroaryl and the like, the same definition applies for the alkyl part of said residues. Preferred substituents of alkyl include halogen as defined below, cyano, OH, SH, C1-C4alkoxy, C1-C4alkylthio, carboxyl, (C=O)OC1-C4alkyl, $NH_2$, NH(C1-C4alkyl), N(C1-C4alkyl)$_2$, nitro, carbamoyl, oxo (=O), thioxo (=S) and the like.

The term "cycloalkyl" like e.g. "C3-C11cycloalkyl" as used herein refers preferably and if nothing else is stated to saturated or partially unsaturated, preferably mono- or bicyclic hydrocarbon groups with the indicated number of ring carbon atoms, which can be unsubstituted or substituted by one or more substituents, preferably up to three, especially one or two substituents. Examples of cycloalkyl groups preferably include monocyclic groups like e.g. cyclopropyl, cyclobutyl, cyclobutenyl, cyclobutadienyl, cyclopentyl, cyclopentenyl like e.g. 2-cyclopentenyl and other isomers thereof, cyclopentadienyl, cyclohexyl, cyclohexenyl isomers, cycloheptyl, cyclooctyl, cyclononyl and their partially unsaturated derivatives, or bicyclic groups like e.g. bicyclo[4.2.0]octanyl, octahydroindenyl, octahydronaphthyl or decahydronaphthyl and the like and their partially unsaturated derivatives. Preferred substituents of cycloalkyl groups include e.g. halogen as defined below, cyano, OH, SH, C1-C4alkoxy, C1-C4alkylthio, carboxyl, (C1-C4alkyl)carboxyl, $NH_2$, NH(C1-C4alkyl), N(C1-C4alkyl)$_2$, nitro, carbamoyl, oxo (=O), thioxo (=S) and the like.

The term "aryl" as used herein refers preferably and if nothing else is stated to a mono- or bicyclic hydrocarbon radical preferably having from 6 to 11 ring carbon atoms and comprising at least one aromatic ring, such as phenyl, naphthyl, indanyl or 1,2,3,4-tetrahydronaphthyl or 6,7,8,9-tetrahydro-5H-benzoheptyl, which are unsubstituted or substituted by one or more substituents, preferably up to three, especially one or two substituents, especially selected from halogen, cyano, nitro, R4-C1-C4alkyl, R4-C1-C4halogenoalkyl, OH, SH, R4-C1-C4alkoxy, R4-C1-C4halogenoalkoxy, R4-C1-C4alkylthio, R4-C1-C4halogenoalkylthio, —(C=O)—R3, —(C=O)—OR3, —N(R3)$_2$, —(C=O)—N(R3)$_2$, —N(R3)-(C=O)—R3, —N(R3)-(C=O)—N(R3)$_2$ such as in particular —NH—(C=O)—NH$_2$ or a group selected from X—Z1 and —N(R3)-(C=O)—NR3-Z1; wherein Z1 represents C3-C6cycloalkyl, C3-C6heterocycloalkyl, phenyl or 5- to 6-membered heteroaryl comprising one or more heteroatoms selected from nitrogen, oxygen and sulfur, preferably 1 or 2 and is unsubstituted or substituted by one, two or more substituents selected from halogen, cyano, nitro, R4-C1-C4alkyl, R4-C1-C4halogenoalkyl, OH, SH, R4-C1-C4alkoxy, R4-C1-C4halogenoalkoxy, R4-C1-C4alkylthio, R4-C1-C4halogenoalkylthio, (C=O)—R3; N(R3)$_2$, (C=O)—N(R3)$_2$, N(R3)-(C=O)—R3, and wherein R3 and R4 have one of the meanings mentioned above. If a non-aromatic cycle is present in an aryl group, it may also comprise one or two oxo (=O) or thioxo (=S) substituents. The bonding valence of a bicyclic aryl group can be located at either ring of the group.

Preferred aryl groups comprise 6 to 10 ring carbon atoms and are more preferably fully aromatic, i.e. consist only of aromatic cycles like phenyl or naphthyl. Phenyl is particularly preferred.

The term "heterocycloalkyl" like e.g. "C3-C11heterocycloalkyl" as used herein refers preferably and if nothing else is stated to saturated or partially unsaturated, preferably mono- or bicyclic groups with the indicated number of ring carbon atoms, which comprise altogether p heteroatoms with p being 1 to 4, independently selected from nitrogen, oxygen and sulfur, and (k−p) ring carbon atoms wherein k represents the number of ring atoms of said heterocycloalkyl group and with the proviso that (k−p) is 2 or more than 2, which groups can furthermore be unsubstituted or substituted by one or more substituents, preferably up to three, especially one or two substituents. Examples of heterocycloalkyl groups preferably include monocyclic groups like e.g. pyrrolidinyl, pyrrolinyl, like e.g. 2-pyrrolinyl or 3-pyrrolinyl, imidazolidinyl, triazolidinyl, piperidinyl, piperazinyl, octahydroindolyl, octahydroquinolinyl, octahydro-[1]pyrindinyl, tetrahydrofuranyl, tetrahydropyranyl, dioxanyl, octahydrobenzofuranyl, octahydrochromene, tetrahydrothienyl, octahydrothiopyranyl, octahydrothiochromenyl, oxazolidinyl, [1,3,4]oxadiazolidinyl, morpholinyl, thiomorpholinyl groups and the like.

Preferred are monocyclic 5 to 6-membered heterocycloalkyl groups comprising 1 or 2 ring heteroatoms selected from nitrogen and oxygen, preferably monocyclic 5 to 6-membered heterocycloalkyl groups comprising 1 or 2 nitrogen atoms as heteroatoms, in particular 6-membered heterocycloalkyl groups comprising 1 or 2 nitrogen atoms as heteroatoms.

Preferred substituents of heterocycloalkyl groups include e.g. halogen as defined below, cyano, OH, SH, C1-C4alkoxy, C1-C4alkylthio, carboxyl, (C1-C4alkyl)carboxyl, $NH_2$, NH(C1-C4alkyl), N(C1-C4alkyl)$_2$, nitro, carbamoyl, oxo (=O), thioxo (=S) and the like.

The term "heteroaryl" as used herein refers preferably and if nothing else is stated to a mono- or bicyclic group preferably having 5 to 11, more preferably 5 to 10 ring atoms and comprising at least one heteroaromatic ring, said heteroaryl group preferably comprising p heteroatoms with p being 1 to 4, independently selected from nitrogen, oxygen and sulfur, and (k−p) ring carbon atoms wherein k represents the number of ring atoms of said heteroaryl group and with the proviso that (k−p) is 2 or more than 2, which groups can be unsubstituted or substituted by one or more substituents, preferably up to three, especially one or two substituents. Said at least one heteroaromatic ring can be fused with one further heteroaromatic ring, carbocyclic aromatic ring, cycloalkyl or heterocycloalkyl ring such as described above, wherein the bonding valence can be located at either of said rings. Preferably bicyclic heteroaryl groups are groups consisting of a heteroaromatic cycle to which a further heteroaromatic cycle or a further carbocyclic aromatic ring is fused. Such groups are also referred to herein as fully aromatic bicyclic heteroaromatic groups.

Preferred examples of heteroaryl groups according to the invention include e.g. imidazolyl, thienyl, furyl, pyranyl, thianthrenyl, isobenzofuranyl, benzofuranyl, chromenyl, pyrrolyl, benzimidazolyl, 4,5,6,7-tetrahydro-1H-benzoimidazolyl, pyrazolyl, thiazolyl, isothiazolyl, oxazolyl, isoxazolyl, pyridyl, pyrazinyl, pyrimidinyl, pyridazinyl, indolizinyl, isoindolyl, indolyl, indazolyl, triazolyl, tetrazolyl, purinyl, quinolizinyl, isoquinolyl, quinolyl, naphthyridinyl, 1,2,3,4-Tetrahydro-[1,5]naphthyridinyl, 1,2,3,4-Tetrahydro-[1,8]naphthyridinyl, quinoxalyl, quinazolinyl, cinnolinyl, pteridinyl, and furazanyl, the free valence bond being located on either ring in case of a bicyclic heteroaryl group. Preferred heteroaryl groups are monocyclic or fully aromatic bicyclic heteroaromatic groups, preferably containing only nitrogen atoms as heteroatoms and being more preferably monocyclic.

Preferred substituents of heteroaryl groups according to the present invention are selected from halogen, cyano, nitro, R4-C1-C4alkyl, R4-C1-C4halogenoalkyl, OH, SH, R4-C1-C4alkoxy, R4-C1-C4halogenoalkoxy, R4-C1-C4 alkylthio, R4-C1-C4halogenoalkylthio, —(C═O)—R3; —(C═O)—OR3, —N(R3)₂, —(C═O)—N(R3)₂, —N(R3)-(C═O)—R3 or a group selected from X—Z1 and —N(R3)-(C═O)—NR3-Z1; wherein Z1 represents C3-C6cycloalkyl, C3-C6heterocycloalkyl, phenyl or 5- to 6-membered heteroaryl comprising one or more heteroatoms selected from nitrogen, oxygen and sulfur, preferably 1 or 2 and is unsubstituted or substituted by one, two or more substituents selected from halogen, cyano, nitro, R4-C1-C4alkyl, R4-C1-C4halogenoalkyl, OH, SH, R4-C1-C4alkoxy, R4-C1-C4halogenoalkoxy, R4-C1-C4 alkylthio, R4-C1-C4halogenoalkylthio, (C═O)—R3, N(R3)₂, (C═O)—N(R3)₂, N(R3)-(C═O)—R3, wherein R3 and R4 have one of the meanings mentioned above. If a non-aromatic cycle is present in a heteroaryl group, it may also comprise one or two oxo (═O) or thioxo (═S) substituents.

The term "halogen" as used herein refers to fluoro (fluorine), chloro (chlorine), bromo (bromine) and iodo (iodine).

According to the IUPAC a lone (electron) pair represents two paired electrons localized in the valence shell on a single atom. Instead of the term 'lone electron pair' the term 'nonbonding electron pair' is frequently used in the literature (PAC, 1994, 66, 1077 (*Glossary of terms used in physical organic chemistry* (*IUPAC Recommendations* 1994)) on page 1137). By way of example, the electron pair of the nitrogen atom in position 2 of the 1-Methyl-1H-pyrazol-5yl group Y of the compound of Example 96 of the present application:

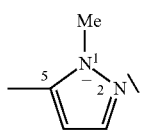

is localized in a sp2 orbital of this nitrogen atom and thus represents a lone electron pair, whereas the electron pair of the nitrogen atom in position 1 of said residue is delocalized and contributes to the aromatic pi electron system and thus does not represent a lone electron pair according to the common understanding. Other examples of lone electron pairs on nitrogen atoms of a residue Y are e.g. the electron pair on the nitrogen atom of a piperidinyl group like that of Example 153 of the present application, the electron pairs of the nitrogen atoms of the pyrimidinyl group Y of the compound of Example 128 or the pyridinyl group Y of the compound of Example 151, the electron pair on the nitrogen atom of the 1H-Pyridin-2-one group Y of the compound of Example 74, when this group is in its 2-pyridinol tautomeric form and the electron pairs on the nitrogen atoms of the various primary and secondary amino-substituents linked to groups Y.

Preferred residues Y comprising a nitrogen atom having a lone electron pair are groups comprising a primary, secondary or tertiary amino group including groups, wherein a secondary or tertiary amino group is part of a heterocycloalkyl residue and the residues of basic heteroaromats comprising a basic nitrogen atom in their ring structure. It is of course also possible that a group Y contains more than one, e.g. 2 or 3, nitrogen atoms with a lone electron pair, like e.g. the compounds of Example 180 (4-amino-piperidin-1-yl) and Example 190 (2-amino-pyridin-4-yl) of the present application.

Pharmaceutically acceptable salts include in particular corresponding acid addition salts like e.g. salts of pharmaceutically acceptable inorganic acids such as hydrochloric acid, hydrobromic acid, sulfuric acid or phosphoric acid or salts of organic acids, e.g. aliphatic, aromatic or arylaliphatic carboxylic or sulfonic acids such as acetic acid or trifluoroacetic acid. Preferred acid addition salts include hydrochlorides, hydrobromides, sulfates, phosphates, hydrogensulfates, hydrogenphosphates, trifluoroacetates and mesylates.

A preferred embodiment of the compounds according to the present invention are the compounds of formula (I), wherein group Y of the compounds comprises one or more structural element of formula:

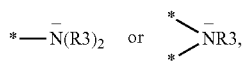

wherein R3 represents hydrogen or C1-C4alkyl and «—» indicates a lone electron pair at the nitrogen atom and «*» indicates a chemical bond to a further atom when X represents —(C═O)— or —(C═O)—NR3a- and R3a represents hydrogen or C1-C4alkyl.

A further preferred embodiment of the compounds according to the present invention are the compounds of formula (I), wherein group Y of the compounds comprises one or more substituents selected from NH₂, NH(CH₃) and N(CH₃)₂ when X represents —(C═O)— or —(C═O)—NR3a- and R3a represents hydrogen or C1-C4 alkyl.

A further preferred embodiment of the compounds according to the present invention are the compounds of formula (I), wherein group Y of the compounds comprises one or more primary amino group —NH₂ when X represents —(C═O)— or —(C═O)—NR3a- and R3a represents hydrogen or C1-C4alkyl.

A further preferred embodiment according to the present invention are compounds of formula (I), wherein X represents a group of formula -E- or -E-F—, wherein E and F are different from each other and represent a group selected from —C(R3a)₂-, —NR3a- and —O— and F is linked to Y, with the proviso that if X represents -E-F— one of E or F represents —C(R3a)₂.

A further preferred embodiment according to the present invention are compounds of formula (I), wherein X represents a spacer group of formula -E-, E represents —C(R3a)₂-, —NR3a- or —O—, R3a represents hydrogen or methyl, group Y comprises one or more substituents selected from NH₂, NH(CH₃) and N(CH₃)₂, and preferably wherein there are at least three concatenated atoms between at least one of said substituents and the X—Y bond.

A further preferred embodiment according to the present invention are compounds of formula (I), wherein X represents a spacer group of formula -E-, E represents —C(R3a)₂-, —NR3a- or —O—, R3a represents hydrogen or methyl, group Y comprises one or more primary amino group —NH₂, and preferably wherein there are at least three concatenated atoms between at least one of said primary amino groups and the X—Y bond.

A further preferred embodiment according to the present invention are compounds of formula (I), wherein X represents —CH₂—, —NH— or —O—, and group Y comprises one or more substituents selected from NH₂, NH(CH₃) and N(CH₃)₂, and preferably wherein there are at least three concatenated atoms between said at least one said substituents and the X—Y bond.

A further preferred embodiment according to the present invention are compounds of formula (I), wherein X represents —CH₂—, —NH— or —O—, Y comprises one or more primary amino group —NH₂, and preferably wherein there are at least three concatenated atoms between at least one of said primary amino groups and the X—Y bond.

A further preferred embodiment according to the present invention are compounds of formula (I), wherein group Y comprises one or more substituents selected from NH₂, NH(CH₃) and N(CH₃)₂.

Generally preferred are the compounds of formula (I) which comprise one or more than one primary amino group —NH₂. More generally preferred are compounds of formula (I) wherein group Y comprises one or more than one primary amino group —NH₂. Even more generally preferred are compounds of formula (I) wherein group Y comprises one or more than one primary amino group —NH₂ and wherein there are at least three concatenated atoms between at least one of said primary amino groups and the X—Y bond.

Also preferred are compounds of formula I according to the invention, wherein Y is unsubstituted or which are substituted by one, two or more substituents, preferably one, selected from halogen, cyano, nitro, —(C═O)—R3, —(C═O)—OR3, —N(R3)₂, in particular —NH₂, —(C═O)—N(R3)₂, —NR3-(C═O)—R3, —NR3-(C═O)—OR3, R4-C1-C4alkyl, R4-C1-C4halogenoalkyl, OH, SH, R4-C1-C4alkoxy, R4-C1-C4halogenoalkoxy, R4-C1-C4alkylthio and R4-C1-C4halogenoalkylthio, as well as oxo (═O) or thioxo (═S) in case that the substituent is not located at an aryl or heteroaryl cycle as well as compounds of formula I according to the invention, wherein Z is unsubstituted or substituted by one, two or more substituents, preferably one, selected from halogen, cyano, nitro, R4-C1-C4alkyl, R4-C1-C4halogenoalkyl, OH, SH, R4-C1-C4alkoxy, R4-C1-C4halogenoalkoxy, R4-C1-C4alkylthio, R4-C1-C4halogenoalkylthio, —(C═O)—R3, —(C═O)—OR3, —N(R3)₂, —(C═O)—N(R3)₂, —N(R3)-(C═O)—R3, —N(R3)-(C═O)—N(R3)₂ as well as oxo (═O) or thioxo (═S) in case that the substituent is not located at an aryl or heteroaryl cycle, or a group selected from X—Z1 and —N(R3)-(C═O)—NR3-Z1; wherein Z1 represents C3-C6cycloalkyl, C3-C6heterocycloalkyl, phenyl or 5- to 6-membered heteroaryl comprising one or more heteroatoms selected from nitrogen, oxygen and sulfur, preferably 1 or 2 and is unsubstituted or substituted by one, two or more substituents selected from halogen, cyano, nitro, R4-C1-C4alkyl, R4-C1-C4halogenoalkyl, OH, SH, R4-C1-C4alkoxy, R4-C1-C4halogenoalkoxy, R4-C1-C4alkylthio, R4-C1-C4halogenoalkylthio, (C═O)—R3, N(R3)₂, (C═O)—N(R3)₂ and N(R3)-(C═O)—R3.

The compounds of formula I include respective compounds, wherein A and B represent nitrogen, i.e. 4-(Z)-6-(X—Y)-substituted pyrido[3,2-c]pyridazines of formula:

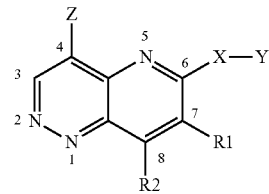

Preferred as compounds of formula I are however those, wherein either none or only one of group A and B represent a nitrogen atom.

Particularly preferred are:

(1) the respective compounds, wherein A and D are CH and B is CR, i.e. the respective 4-(Z)-6-(X—Y)-substituted isoquinoline derivatives of formula I-1:

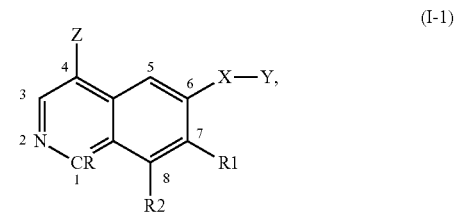

with compounds wherein B is CH or C—NH₂ being preferred, as well as the corresponding 4-(Z)-6-(X—Y)-substituted isoquinoline derivatives, wherein A and B are CH and D is CR:

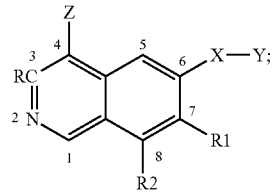

(2) the respective compounds, wherein B is N and A and D are CH, i.e. the respective 4-(Z)-6-(X—Y)-substituted cinnoline derivatives of formula I-2:

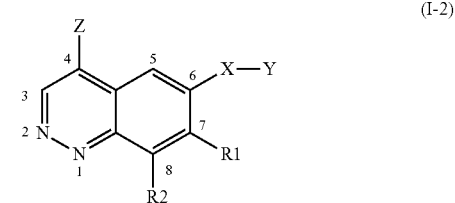

as well as the corresponding derivatives, wherein D is CR;

(3) the respective compounds, wherein A is N, B is CR and D is CH, i.e. the respective 8-(Z)-2-(X—Y)-substituted [1,6]naphthyridine derivatives of formula I-3:

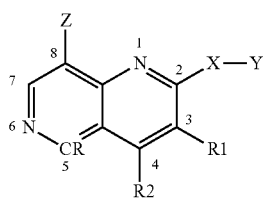

(I-3)

as well as the corresponding derivatives wherein D is CR.

R represents in the above formulae, in particular in formula I-1 and I-3, preferably hydrogen or $NH_2$, most preferably hydrogen.

A specific embodiment of the compounds of formula I-1 are the respective compounds of formula I-1a, wherein R is OH, or their tautomers, the 4-(Z)-6-(X—Y)-substituted 2H-isoquinoline-1-one compounds of formula I-1b:

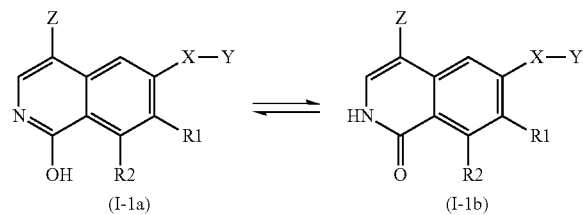

wherein R1, R2, X, Y and Z are as defined above, mixtures of these two tautomeric forms of said compounds of formula I-1a and I-1b or pharmaceutically acceptable salts thereof.

Compounds of formula I-1, wherein R is $NH_2$ show a corresponding tautomerism.

In an especially preferred group of the compounds of formula I according to the present invention X represents a spacer group of formula -E-, wherein E represents —C(R3a)$_2$-, —(C=O)—, —NR3a- or —O—, wherein R3a has one of the meanings mentioned above, in particular represents hydrogen or methyl. More preferably, X represents a spacer group of formula -E-, wherein E represents —C(R3a)$_2$-, —NR3a- or —O—, wherein R3a represents methyl or more preferably hydrogen. Even more preferably X is then —CH$_2$—, —NH— and —O—, most preferably —CH$_2$—.

In another group of the compounds of formula I according to the present invention X represents a spacer group of formula -E-F— selected from —C(R3a)$_2$-NR3a-, —NR3a-C(R3a)$_2$-, —(C=O)—NR3a-, —NR3a-(C=O)—, —C(R3a)$_2$-O—, —O—(CR3)$_2$-, wherein R3a has one of the meanings mentioned above and in particular represents at each occurrence in group X independently hydrogen or methyl. More preferably X is then —CH$_2$—NH— or CH$_2$—O— linked to the group Y via the NH group or the oxygen atom or —(C=O)—NH— or —NH—(C=O)—, most preferably —CH$_2$—NH— linked to the group Y via the NH group.

Further preferred compounds of formula I are the compounds, wherein Y comprises one or more structural element of formula:

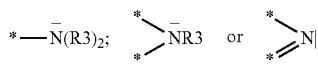

wherein R3 has a meaning as defined above and «—» indicates the lone electron pair at the nitrogen atom and «*» indicates a chemical bond to a further atom.

Particularly preferred especially in view of their activity against proliferation diseases like cancer are the compounds of formula I, wherein Y comprises one or more primary amino group —NH$_2$ as substituent as already indicated above.

In the compounds of formula I group Y is preferably a group selected from:
(A) C1-C4alkyl, which is unsubstituted or substituted as defined above for Y and saturated or partially unsaturated;
(B) a group which is unsubstituted or substituted as defined above for Y and saturated or partially unsaturated and selected from the groups of formula:

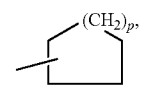

(Ba)

wherein p is 0, 1, 2 or 3;

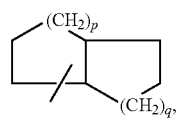

(Bb)

wherein p and q are independently selected from 0, 1, 2 or 3 so that (p+q) is 2 to 4 and the linking bond may be located at both cycles of the group;

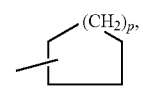

(Bc)

wherein p is 0, 1, 2 or 3 and wherein 1, 2 or 3 ring carbon atoms are replaced by nitrogen atoms and one ring carbon ring atom may furthermore be replaced by a sulfur or an oxygen atom and the number of remaining ring carbon atoms is at least 2;

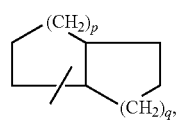

(Bd)

wherein p and q are independently selected from 0, 1, 2 and 3 so that (p+q) is 2 to 4, the linking bond may be located at both cycles of the group and wherein 1 to 4 ring carbon atoms of the group are replaced by nitrogen atoms and one ring carbon ring atom per cycle of the group may furthermore be replaced by a sulfur or an oxygen atom so that the number of remaining ring carbon atoms per cycle of the group is at least 2;
(C) an aryl group which is unsubstituted or substituted as defined above for Y and selected from (Ca): phenyl and
(Cb): naphthyl; and
(D): an unsubstituted or substituted heteroaryl group selected from the groups of formula:

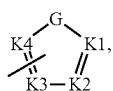
(Da)

wherein G is selected from NR3, preferably NH, O and S and one or two of K1, K2, K3 and K4 may be nitrogen and all others are selected from CH and C substituted as defined above for Y;

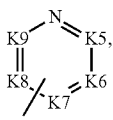
(Db)

wherein one or two of K5, K6, K7, K8 and K9 may be nitrogen and all others are selected from CH and C substituted as defined above for Y;

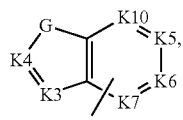
(Dc)

wherein G is selected from NR3, preferably NH, O and S and one of K3 and K4 may be nitrogen and the other is CH or C substituted as defined above for Y and one or two of K5, K6, K7, and K10 may be nitrogen and all others are selected from CH and C substituted as defined above for Y and the linking bond may be located at both cycles of the group; and

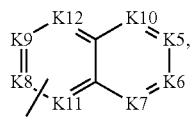
(Dd)

wherein one of K5, K6, K7, K8, K9, K10, K11 and K12 is nitrogen and one of the others in the same cycle and two of the others in the other cycle may also be nitrogen and all others in both cycles are selected from CH and C substituted as defined above for Y and the linking bond may be located at both cycles of the group.

More preferably, group Y is selected from substituted C1-C4alkyl or substituted monocyclic saturated 5-, 6- or 7-membered cycloalkyl, which comprise at least one substituent selected from $NH_2$, $NH(CH_3)$ and $N(CH_3)_2$, preferably $NH_2$, unsubstituted or substituted, monocyclic saturated 5-, 6- or 7-membered heterocycloalkyl, which comprises 1 or 2 nitrogen heteroatoms and optionally at least one substituent selected from $NH_2$, $NH(CH_3)$ and $N(CH_3)_2$, preferably $NH_2$, and a substituted fully aromatic mono- or bicyclic aryl group which comprises at least one substituent selected from $NH_2$, $NH(CH_3)$ and $N(CH_3)_2$, preferably $NH_2$, and an unsubstituted or substituted fully aromatic mono- or bicyclic heteroaryl group, which comprises 1 or 2 nitrogen heteroatoms per cycle present in said heteroaryl group and optionally at least one substituent selected from $NH_2$, $NH(CH_3)$ and $N(CH_3)_2$, preferably $NH_2$, and wherein when additionally substituted, preferably group Y is additionally substituted by one or two groups selected from C1-C4alkyl, hydroxy, nitro, C1-C4alkoxy, C1-C4fluoroalkyl, cyano, halogen, and C1-C4alkoxycarbonyl.

Even more preferably group Y is selected from substituted C1-C4alkyl or substituted monocyclic saturated 5-, 6- or 7-membered cycloalkyl, which comprise one substituent selected from $NH_2$, $NH(CH_3)$ and $N(CH_3)_2$, preferably $NH_2$, unsubstituted or substituted, monocyclic saturated 5-, 6- or 7-membered heterocycloalkyl, which comprises 1 or 2 nitrogen heteroatoms and, when substituted, one substituent selected from $NH_2$, $NH(CH_3)$ and $N(CH_3)_2$, preferably $NH_2$, and a substituted phenyl group which comprise one substituent selected from $NH_2$, $NH(CH_3)$ and $N(CH_3)_2$, preferably $NH_2$, and an unsubstituted or substituted 5- or 6-membered monocyclic heteroaryl group, which comprises 1 or 2 nitrogen heteroatoms and, when substituted, one substituent selected from $NH_2$, $NH(CH_3)$ and $N(CH_3)_2$, preferably $NH_2$.

In one group of preferred compounds group Y is selected from straight-chain C1-C4alkyl, preferably C2-C4alkyl, cyclopentyl, cyclohexyl, pyrrolidinyl, in particular pyrrolidin-1-yl or pyrrolidin-3-yl, piperidinyl, in particular piperidin-1-yl, piperidin-3-yl or piperidin 4-yl, piperazinyl, in particular piperazin-1-yl, morpholinyl, in particular morpholin-4-yl, phenyl, pyrazolyl, in particular pyrazol-5-yl, pyridinyl, in particular pyridinium-1-yl, pyridin-3-yl or pyridin-4-yl, pyrimidinyl, in particular pyrimidin-4-yl; pyridazinyl, in particular pyridazinium-1-yl, 1-H-pyrrolo[3,2-c]pyridine, 3H-pyrrolo[2,3-c]-pyridin-1-yl, which are unsubstituted or substituted by one or two groups selected fluoro, chloro, cyano, nitro, C1-C2alkyl, C1-C2fluoroalkyl, C1-C2alkoxy, C1-C2fluoroalkoxy, —$NH_2$, —$NH(CH_3)$, —$N(CH_3)_2$, $H_2N$—C1-C2alkyl, $H_2N$—C1-C2fluoro-alkyl, —OH and oxo, wherein Y is not substituted by oxo when Y is aromatic or heteroaromatic.

In another group of preferred compounds groups Y are: C2-C4alkyl, particularly when substituted with one or more substituent selected from $NHCH_3$, $N(CH_3)_2$ and especially —$NH_2$, e.g. 2-dimethylaminoethyl, 3-dimethylaminopropyl, in particular 2-aminoethyl, 3-aminopropyl and 4-aminobutyl;

cyclopentyl and cyclohexyl, particularly when substituted with one or more substituent selected from $NHCH_3$, $N(CH_3)_2$ and especially $NH_2$, e.g. 3-aminocyclopentyl and 3- or 4-aminocyclohexyl; pyrrolidinyl, e.g. pyrrolidin-3-yl or pyrrolidin-1-yl; imidazolidinyl, e.g. imidazolidin-4-yl or imidazolidin1-yl, pyrazolidinyl, e.g. pyrazolidin-3-yl or pyrazolidin-1-yl; piperidyl, e.g. piperidin-1-yl, piperidin-3-yl or piperidin-4-yl; piperazinyl, e.g. piperazin-1-yl, piperazin-2-yl or 2-oxo-piperazin-4-yl; 2-oxo-1H-pyridin-4yl; morpholinyl or thiomorpholinyl, e.g. morpholin-4-yl or morpholin-2-yl or -3-yl; 3-oxo-1,2-dihydro-pyrazol-1-yl, particularly when substituted with one or more substituent selected from $NHCH_3$, $N(CH_3)_2$ and especially $NH_2$ like e.g. 4-amino-piperidin-1-yl; phenyl, particularly when substituted with one or more substituent selected from $(CH_2)_{0-2}NHCH3$, $(CH_2)_{0-2}N(CH_3)_2$ and especially $(CH_2)_{0-2}NH_2$ like e.g. 3- or 4-aminophenyl, 4-aminomethylphenyl or 4-(2-aminoethyl)phenyl; 1H-pyrazolyl, e.g. 1H-pyrazol-5-yl or 1H-pyrazol-1-yl; pyridinyl, e.g. pyridin-4-yl; pyridin-3-yl; 2-hydroxypyridin-4-yl; pyrimidinyl, e.g. pyrimidin-4- or 5-yl; pyridazinyl, e.g. pyridazin-4- or 5-yl; quinolinyl, e.g.

quinolin-4-yl; pyridinium-1-yl; pyridazinium-1-yl; quinolinium-1-yl; 3H-pyrrolo[2,3-c]pyridin-1-yl; pyrrolo[3,2-c]pyridin-1-yl; 3H-indol-1-yl, particularly when substituted with one or more substituent selected from $NHCH_3$, $N(CH_3)_2$ and especially $NH_2$ like e.g. 2-aminopyridin-4-yl, 2-dimethylaminopyridin-4-yl, 2-aminopyridin-5-yl, 4-aminopyridinium-1-yl, 4-aminopyridazinium-1-yl, 5- or 6-amino-3H-indol-1-yl, 6-amino-pyrrolo[3,2-c]pyridin-1-yl or 4-aminoquinolinium-1-yl. The afore-mentioned groups can be further substituted, preferably by one or more, more preferably by one or two substituents selected from the substituents listed above for group Y, in particular selected from C1-C4alkyl, particularly methyl; hydroxy; nitro; C1-C4alkoxy, particularly methoxy; C1-C4fluoroalkyl, particularly $CF_3$; cyano; halogen, particularly fluoro, chloro or bromo; C1-C4alkoxycarbonyl, particularly methoxycarbonyl or carboxyl.

Most preferably Y is selected from 3-aminocyclopentyl, 3- or 4-aminocyclohexyl and 4-aminopiperidin-1-yl, in particular 4-aminocyclohexyl and 4-aminopiperidin-1-yl.

Preferred X—Y groupings are selected from

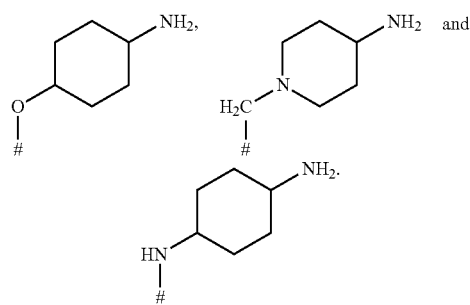

The configuration of the cyclohexyl groups above may be cis or trans, as depicted below.

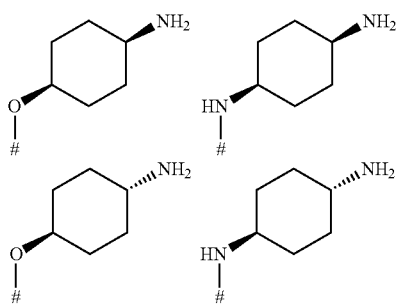

The invention includes substantially pure cis or trans isomers, and mixtures of cis-trans pairs thereof in any ratio.

In general group Y is unsubstituted or substituted preferably by one, two or more substituents, preferably one substituent, selected from halogen, cyano, nitro, —(C═O)—R3, —(C═O)—OR3, —N(R3)$_2$, —(C═O)—N(R3)$_2$; —NR3-(C═O)—R3, —NR3-(C═O)—OR3, R4-C1-C4alkyl, R4-C1-C4halogenoalkyl, OH, SH, R4-C1-C4alkoxy, R4-C1-C4halogenoalkoxy, R4-C1-C4alkylthio and R4-C1-C4halogenoalkylthio, as well as oxo in case that the substituent is not located at an aryl or heteroaryl cycle. Preferably when substituted, group Y is substituted by $NH_2$, $NH(CH_3)$ and $N(CH_3)_2$, preferably $NH_2$, and optionally by one further group selected from C1-C4alkyl, hydroxy, nitro, C1-C4alkoxy, C1-C4fluoroalkyl, cyano, halogen and C1-C4alkoxycarbonyl. Most preferably, when substituted, group Y is substituted by one group selected from $NH_2$, $NH(CH_3)$ and $N(CH_3)_2$, preferably $NH_2$.

In a further preferred group of the compounds of formula I group Z is selected from a monocyclic aryl group or a bicyclic group comprising at least one aryl cycle, more preferably two aryl cycles and having 6 to 10 ring atoms as well as a monocyclic heteroaryl group and a bicyclic group comprising at least one heteroaryl group, preferably fused with a further aryl or heteroaryl cycle, and having 5 to 10 ring atoms, wherein a heteroaryl cycle comprises 1 to 3 heteroatoms, preferably 1 or 2, and said groups Z are unsubstituted or substituted by one or more substituents as defined above.

More preferably group Z is in the compounds of formula I selected from:

(E) an unsubstituted aryl group or an aryl group substituted as defined above for Z, said aryl group being selected from (Ea): phenyl and (Eb): naphthyl; and (F): an unsubstituted heteroaryl group or a heteroaryl group substituted as defined above for Z, said heteroaryl group being selected from groups of formula:

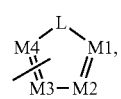 (Fa)

wherein L is selected from NR3, preferably NH, O and S and one or two of M1, M2, M3 and M4 may be nitrogen and all others are selected from CH and C substituted as defined above for Z;

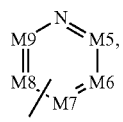 (Fb)

wherein one or two of M5, M6, M7, M8 and M9 may be nitrogen and all others are selected from CH and C substituted as defined above for Z;

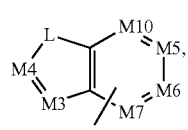 (Fc)

wherein L is selected from NR3, preferably NH, O and S and one of M3 and M4 may be nitrogen, CH or C substituted as defined above for Z and the other is CH or C substituted as defined above for Z and one or two of M5, M6, M7, and M10 may be nitrogen and all others are selected from CH and C substituted as defined above for Z and the linking bond may be located at both cycles of the group; and

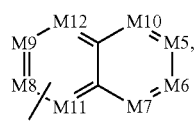

(Fd)

wherein one of M5, M6, M7, M8, M9, M10, M11 and M12 may be nitrogen and one of the others in the same cycle and two of the others in the other cycle may also be nitrogen and all others in both cycles are selected from CH or C substituted as defined above for Z and the linking bond may be located at both cycles of the group.

In a preferred group of compounds group Z is selected from (Ea), (Fa), wherein L is selected from NH, O and S, and (Fc), wherein L is selected from NH, O and S.

In another group of preferred compounds group Z is selected from phenyl, naphthyl and a group of one of the formulae:

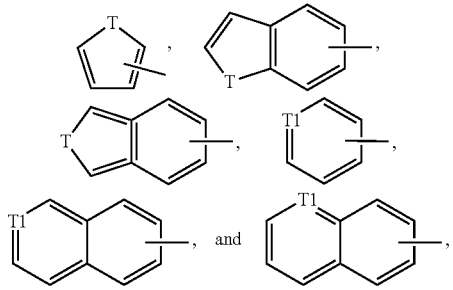

wherein T represents a group selected from NH and N(CH$_3$), or an O- or S-atom; T1 represents a N-atom; the free valence can be located at any of the ring carbon atoms of the entire group Z; and wherein one to three of the ring carbon atoms can furthermore be replaced by a N-atom; and wherein group Z is unsubstituted or substituted by one to three groups selected from halogen, C1-C4alkyl and C1-C4alkoxy.

Even more preferably group Z is selected from phenyl and a group of one of the formulae:

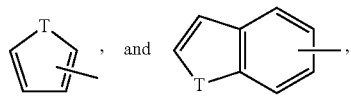

wherein T represents a group selected from NH and N(CH$_3$), or an O- or S-atom; the free valence can be located at any of the ring atoms of the entire group Z including the group T if T is not an O- or S-atom; and wherein one to three of the ring carbon atoms can furthermore be replaced by a N-atom, and wherein Z is unsubstituted or substituted by one to three groups selected from halogen, C1-C4alkyl and C1-C4alkoxy.

Yet more preferably group Z is selected from phenyl, which is unsubstituted of substituted by one or two substituents selected from fluoro and chloro a group of a group of one of the formulae

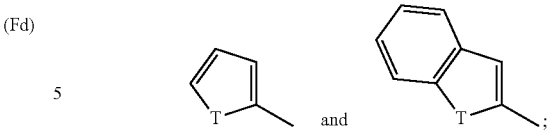

wherein T is selected from an O- or S-atom, e.g. phenyl, furan-2-yl, thiophen-2yl, or benzofuran-2-yl.

Most preferably Z is selected from phenyl, which is unsubstituted or substituted by Cl or F, and unsubstituted benzofuran-2-yl.

Examples of preferred groups Z are the following: phenyl, naphthyl; furanyl, e.g. furan-2- or 3-yl; thienyl, e.g. thien-2- or 3-yl; oxyzolyl, isooxyzolyl, furazanyl, thiazolyl, isothiazolyl, [1,2,5]thiadiazolyl, in particular furanyl, e.g. furan-2- or 3-yl; thienyl; benzofuranyl, e.g. benzofuran-2-yl or benzofuran-5-yl; benzothienyl, e.g. benzothien-2-yl or benzothien-5-yl; 1H-indolyl, e.g. 1H-indol-2-yl or 1H-indol-5-yl; benzooxazolyl; benzoisooxazolyl; benzothiazolyl; and benzoisothiazolyl as well as derivatives thereof, wherein 1 to 3 carbon atoms of the benzene ring are replaced by nitrogen, like e.g. furo-[2,3-b]pyridinyl, thieno-[2,3-b]pyrazinyl or furo- or thieno-[3,2-d]pyrimidinyl, 1H-pyrrolo [2,3-b]pyridinyl, 5-H-pyrrolo[2,3-b]pyrazinyl, 5H-pyrrolo-[3,2-d]pyrimidinyl, oxazolo- or thiazolo-[4,5-b]pyridinyl, isoxazolo- or isothiazolo-[4,5-b]pyridinyl, oxazolo- or thiazolo-[4,5-b]pyrazinyl, isoxazolo- or isothiazolo-[4,5-b] pyrazinyl and the like, in particular benzofuranyl, benzothienyl or 1H-indolyl; pyridinyl, in particular pyridin-4- or 3-yl; pyrazinyl, pyrimidinyl, pyridazinyl, quinolinyl, e.g. 2-quinolinyl, isoquinolinyl, naphthyridinyl, quinoxalinyl, quinazolinyl, cinnolinyl and the like, in particular pyridinyl and quinolinyl.

Z is preferably unsubstituted or substituted by one, two or more substituents, preferably one, which are selected from halogen, cyano, nitro, R4-C1-C4alkyl, R4-C1-C4halogenoalkyl, OH, SH, R4-C1-C4alkoxy, R4-C1-C4halogenoalkoxy, R4-C1-C4alkylthio, R4-C1-C4halogenoalkylthio, —(C═O)—R3; —(C═O)—OR3, —N(R3)$_2$, —(C═O)—N(R3)$_2$, —N(R3)-(C═O)—R3, —N(R3)-(C═O)—N(R3) or a group selected from X—Z1 and —N(R3)-(C═O)—NR3-Z1; wherein Z1 represents C3-C6cycloalkyl, C3-C6heterocycloalkyl, phenyl or 5- to 6-membered heteroaryl comprising one or more heteroatoms selected from nitrogen, oxygen and sulfur, preferably 1 or 2 and is unsubstituted or substituted by one, two or more substituents selected from halogen, cyano, nitro, R4-C1-C4alkyl, R4-C1-C4halogenoalkyl, OH, SH, R4-C1-C4alkoxy, R4-C1-C4halogenoalkoxy, R4-C1-C4alkylthio, R4-C1-C4halogenoalkylthio, (C═O)—R3; N(R3)$_2$, (C═O)—N(R3)$_2$ and N(R3)-(C═O)—R3.

More preferably Z is unsubstituted or substituted by one, two or more substituents, preferably one substituent, selected from halogen, cyano, nitro, R4-C1-C4alkyl, R4-C1-C4halogenoalkyl, OH, SH, R4-C1-C4alkoxy, R4-C1-C4halogenoalkoxy, R4-C1-C4alkylthio, R4-C1-C4halogenoalkylthio, —(C═O)—R3; —(C═O)—OR3, —N(R3)$_2$, —(C═O)—N(R3)$_2$, —N(R3)-(C═O)—R3, —N(R3)-(C═O)—N(R3)$_2$ and —N(R3)-(C═O)—NR3-Z1; wherein Z1 represents C3-C6cycloalkyl, phenyl or 5- to 6-membered heteroaryl comprising one or more heteroatoms selected from nitrogen, oxygen and sulfur, preferably 1 or 2, and is unsubstituted or substituted by one, two or more substituents selected from halogen, cyano, R4-C1-

C4alkyl, R4-C1-C4halogenoalkyl, OH, R4-C1-C4alkoxy and R4-C1-C4halogenoalkoxy.

Even more preferably group Z is unsubstituted or substituted by one to three groups selected from halogen, C1-C4alkyl and C1-C4alkoxy selected from halogen, C1-C4alkyl and C1-C4alkoxy.

When Z is phenyl it may be substituted at the ortho, meta and/or para positions. Para and/or meta substituted phenyl is preferred.

Each of the afore-mentioned preferred example groups Z can be substituted, preferably by one or more, more preferably by one or two substituents selected from the substituents listed above for group Z, in particular selected from $(CH_2)_{0-2}NHCH_3$, $(CH_2)_{0-2}N(CH_3)_2$ and especially $(CH_2)_{0-2}NH_2$; C1-C4alkyl, particularly methyl; hydroxy; hydroxymethyl; nitro; C1-C4alkoxy, particularly methoxy; C1-C4fluoroalkyl, particularly $CF_3$; cyano; halogen, particularly fluoro, chloro or bromo; C1-C4alkoxycarbonyl, particularly methoxycarbonyl, carboxyl or —NH—(C=O)—CH$_3$, —NH—(C=O)—NH$_2$, —NH—(C=O)—NH-phenyl, —NH—(C=O)—NH-halogenophenyl, wherein halogen represents preferably fluoro or chloro, —NH—(C=O)—NH-(5- or 6-membered heteroaryl) like in particular —NH—(C=O)—NH-pyridyl, e.g. —NH—(C=O)—NH-(2-pyridyl), —NH—(C=O)—NH-(3-pyridyl) or —NH—(C=O)—NH-(4-pyridyl).

A specifically preferred group of compounds according to the invention are the compounds, wherein R represents hydrogen or NH$_2$.

An important group of compounds in particular in view of their activity against proliferation disorders or diseases and/or their MNK1 and MNK2-inhibiting activity, in particular their MNK1 inhibiting activity include the isoquinoline derivatives of formula I-1 mentioned above, the cinnoline derivatives of formula I-2 mentioned above, the [1,6] naphthyridine derivatives of formula I-3 mentioned above and the compounds of formula I-1a and I-1b mentioned above as well as pharmaceutically acceptable salts thereof, in particular pharmaceutically acceptable acid addition salts thereof;

R1 and R2, independently of each other, represent hydrogen, halogen, NH$_2$, C1-C4alkyl, C1-C4halogenalkyl, C1-C4alkoxy, or C1-C4halogenalkoxy;

R3 represents, independently at each occurrence, hydrogen or methyl;

R3a represents, independently at each occurrence, hydrogen or methyl;

X represents, independently at each occurrence, a group of formula -E- or -E-F—, wherein E and F are different from each other and represent a group selected from —C(R3a)$_2$-, —(C=O)—, —NR3a- and —O— and F is linked to Y, with the proviso that if X represents -E-F—, one of E or F represents —C(R3a)$_2$- or —(C=O)—;

Y represents H$_2$N—C1-C4alkyl, CH$_3$NH—C1-C4alkyl, (CH$_3$)$_2$N—C1-C4alkyl or preferably a group selected from monocyclic, saturated C5 or C6cycloalkyl, monocyclic saturated 5 or 6-membered heterocycloalkyl, phenyl or 5- or, preferably, 6-membered heteroaryl or a bicyclic group comprising one 5- or 6-membered heteroaryl cycle, the other cycle being a benzene or a 6-membered heteroaryl cycle, wherein heterocycloalkyl and heteroaryl groups comprise one or more nitrogen heteroatoms, preferably one or two, and said group Y is either unsubstituted or substituted by one, two or more substituents as described above and comprises including its substituents one or more than one nitrogen atom having a lone electron pair, and Z represents a mono- or bicyclic group C6-C10 aryl group or a mono- or bicyclic heteroaryl group comprising at least one 5- or 6-membered heteroaryl cycle, the further cycle in case of a corresponding bicyclic group being selected from a benzene cycle or a 6-membered heteroaryl cycle, said mono- or bicyclic heteroaryl group comprising one or more heteroatoms selected from nitrogen, oxygen and sulfur, which aryl or heteroaryl group is unsubstituted or substituted by one or more substituents as described above;

including tautomers of said compounds, mixtures of two tautomeric forms of said compounds, and pharmaceutically acceptable salts of said compounds, tautomers thereof or mixtures of two tautomeric forms thereof.

In a preferred group of the afore-mentioned compounds the possible substituents of Y are selected from fluoro, chloro, cyano, nitro, C1-C2alkyl, C1-C2fluoroalkyl, C1-C2alkoxy, C1-C2fluoroalkoxy, —NH$_2$, —NH(CH$_3$), —N(CH$_3$)$_2$, H$_2$N—C1-C2alkyl, H$_2$N—C1-C2fluoro-alkyl and —OH and the possible substituents of Z are selected from fluoro, chloro, cyano, nitro, C1-C2alkyl, C1-C2fluoroalkyl, OH, HO—C1-C2alkyl, HO—C1-C2fluoroalkyl, H$_2$N—C1-C2alkyl, H$_2$N—C1-C2fluoroalkyl, C1-C2alkylcarbonyl, C1-C2alkoxy, C1-C2fluoroalkoxy, —(C=O)—C1-C2alkyl, —(C=O)—C1-C2fluoroalkyl, COOH, —(C=O)—O(C1-C2alkyl), —(C=O)—O(C1-C2fluoroalkyl)-NH$_2$, —NH$_2$, —NH(CH$_3$), —N(CH$_3$)$_2$, —(C=O)—NH$_2$, —NH—(C=O)—C1-C2alkyl and —NH—(C=O)—C1-C2fluoroalkyl.

In a preferred embodiment of the compounds of formula I according to the invention A and B are CH and D is CR; or
A and D are CH and B is CR; or
B is N and A and D are CH; or
A is N, B is CR and D is CH;
R represents hydrogen, OH or NH$_2$;
R1 and R2, independently of each other, represent hydrogen, N(R3)$_2$, halogen, cyano, nitro, R4-C1-C4alkyl, R4-C1-C4halogenoalkyl, OH, R4-C1-C4alkoxy, R4-C1-C4halogenoalkoxy;
R3 represents, independently at each occurrence, hydrogen, R4-C1-C4alkyl or R4-C1-C4halogenoalkyl;
R3a represents, independently at each occurrence, hydrogen or methyl;
R4 represents, independently at each occurrence, hydrogen, halogen, cyano, OH, NH$_2$, NH(CH$_3$) or N(CH$_3$)$_2$;
X represents C(R3a)$_2$-, —NR3a- or —O—;
Y is selected from substituted C1-C4alkyl or substituted monocyclic saturated 5-, 6- or 7-membered cycloalkyl, which comprise at least one substituent selected from NH$_2$, NH(CH$_3$) and N(CH$_3$)$_2$, preferably NH$_2$, unsubstituted or substituted, monocyclic saturated 5-, 6- or 7-membered heterocycloalkyl, which comprises 1 or 2 nitrogen heteroatoms and optionally at least one substituent selected from NH$_2$, NH(CH$_3$) and N(CH$_3$)$_2$, preferably NH$_2$, and a substituted mono- or bicyclic aryl group which comprise at least one substituent selected from NH$_2$, NH(CH$_3$) and N(CH$_3$)$_2$, preferably NH$_2$, and an unsubstituted or substituted mono- or bicyclic heteroaryl group, which comprises 1 or 2 nitrogen heteroatoms per cycle present in said heteroaryl group and optionally at least one substituent selected from NH$_2$, NH(CH$_3$) and N(CH$_3$)$_2$, preferably NH$_2$;
Z is selected from:
(E) an unsubstituted aryl group or an aryl group substituted as defined below, said aryl group being selected from
(Ea): phenyl and
(Eb): naphthyl; and (F) an unsubstituted heteroaryl group or a heteroaryl group substituted as defined below, said heteroaryl group being selected from the groups of formula:

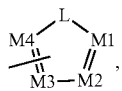

(Fa)

wherein L is selected from NR3, preferably NH, O and S and one or two of M1, M2, M3 and M4 may be nitrogen and all others are selected from CH and C substituted as defined below;

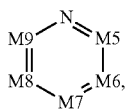

(Fb)

wherein one or two of M5, M6, M7, M8 and M9 may be nitrogen and all others are selected from CH and C substituted as defined below;

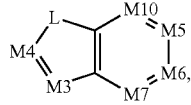

(Fc)

wherein L is selected from NR3, preferably NH, O and S, one of M3 and M4 may be nitrogen, CH or C substituted as defined below, the other is CH or C substituted as defined below and one or two of M5, M6, M7, and M10 may be nitrogen and all others are selected from CH and C substituted as defined below and the linking bond may be located at both cycles of the group; and

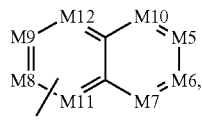

(Fd)

wherein one of M5, M6, M7, M8, M9, M10, M11 and M12 may be nitrogen and one of the others in the same cycle and two of the others in the other cycle may also be nitrogen and all others in both cycles are selected from CH and C substituted as defined below and the linking bond may be located at both cycles of the group;
when substituted group Z is substituted by one, two or more, preferably one, substituents selected from halogen, cyano, nitro, R4-C1-C4alkyl, R4-C1-C4halogenoalkyl, OH, R4-C1-C4alkoxy, R4-C1-C4halogenoalkoxy, R4-C1-C4alkylthio, R4-C1-C4halogenoalkylthio, —(C═O)—R3; —(C═O)—OR3, —N(R3)$_2$, —(C═O)—N(R3)$_2$, —N(R3)-(C═O)—R3, —N(R3)-(C═O)—N(R3)$_2$ or a group —N(R3)-(C═O)—NR3-Z1;
wherein Z1 represents C3-C6cycloalkyl, phenyl or 5- to 6-membered heteroaryl comprising one or more heteroatoms selected from nitrogen, oxygen and sulfur, preferably 1 or 2 and is unsubstituted or substituted by one, two or more substituents selected from halogen, cyano, nitro, R4-C1-C4alkyl, R4-C1-C4halogenoalkyl, OH, R4-C1-C4alkoxy and R4-C1-C4halogenoalkoxy.

In a further preferred embodiment of the compounds of formula I according to the invention the compound of formula I is a compound having the formula I-1, I-2 or I-3 wherein
R represents hydrogen, OH or NH$_2$;
R1 and R2, independently of each other, represent hydrogen, halogen, NH$_2$, C1-C4alkyl, C1-C4halogenalkyl, C1-C4alkoxy, or C1-C4halogenalkoxy;
R3 represents, independently at each occurrence, hydrogen or methyl;
R3a represents, independently at each occurrence, hydrogen or methyl;
R4 represents independently at each occurrence hydrogen, halogen, cyano, OH, NH$_2$, NH(CH$_3$) or N(CH$_3$)$_2$;
X represents C(R3a)$_2$-, —NR3a- or —O—;
Y is selected from substituted C1-C4alkyl or substituted monocyclic saturated 5-, 6- or 7-membered cycloalkyl, which comprise at least one substituent selected from NH$_2$, NH(CH$_3$) and N(CH$_3$)$_2$, preferably NH$_2$, unsubstituted or substituted, monocyclic saturated 5-, 6- or 7-membered heterocycloalkyl, which comprises 1 or 2 nitrogen heteroatoms and optionally at least one substituent selected from NH$_2$, NH(CH$_3$) and N(CH$_3$)$_2$, preferably NH$_2$, and a substituted mono- or bicyclic aryl group which comprise at least one substituent selected from NH$_2$, NH(CH$_3$) and N(CH$_3$)$_2$, preferably NH$_2$, and an unsubstituted or substituted mono- or bicyclic heteroaryl group, which comprises 1 or 2 nitrogen heteroatoms per cycle present in said heteroaryl group and optionally at least one substituent selected from NH$_2$, NH(CH$_3$) and N(CH$_3$)$_2$, preferably NH$_2$;
and wherein group Y may be additionally substituted by one group selected from C1-C4alkyl, hydroxy, nitro, C1-C4alkoxy, C1-C4fluoroalkyl, cyano, halogen, and C1-C4alkoxycarbonyl;
Z is selected from:
(E) an unsubstituted aryl group or an aryl group substituted as defined below, said aryl group being selected from
(Ea): phenyl and
(F) an unsubstituted heteroaryl group or a heteroaryl group substituted as defined below, said heteroaryl group being selected from the groups of formula:

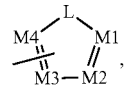

(Fa)

wherein L is selected from NH, O and S and one or two of M1, M2, M3 and M4 may be nitrogen and all others are selected from CH and C substituted as defined below;

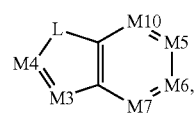

(Fc)

wherein L is selected from NH, O and S, one of M3 and M4 may be nitrogen, CH or C substituted as defined below, the other is CH or C substituted as defined below and one or two of M5, M6, M7, and M10 may be nitrogen and all others are selected from CH and C substituted as defined below and the linking bond may be located at both cycles of the group; and when substituted group Z is substituted by one, two or more, preferably one, substituents selected from halogen, cyano, nitro, R4-C1-C4alkyl, R4-C1-C4halogenoalkyl, OH, N(R3)$_2$, and R4-C1-C4alkoxy.

In a further preferred embodiment of the compounds of formula I according to the invention the compound of formula I is a compound having the formula I-1 or I-3 wherein

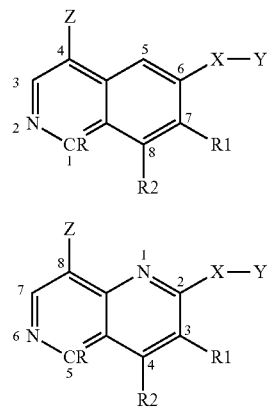

wherein
R represents hydrogen or NH$_2$;
R1 and R2, independently of each other, represent hydrogen, N(R3)$_2$, halogen, cyano, nitro, C1-C4alkyl, C1-C4halogenoalkyl, OH, C1-C4alkoxy or C1-C4halogenoalkoxy;
R3 is, independently at each occurrence, hydrogen or C1-C4alkyl;
X represents —CH$_2$—, —NH— or —O—;
Y is selected from substituted C1-C4alkyl or substituted monocyclic saturated 5-, 6- or 7-membered cycloalkyl, which comprise one substituent selected from NH$_2$, NH(CH$_3$) and N(CH$_3$)$_2$, preferably NH$_2$, unsubstituted or substituted, monocyclic saturated 5-, 6- or 7-membered heterocycloalkyl, which comprises 1 or 2 nitrogen heteroatoms and, when substituted, one substituent selected from NH$_2$, NH(CH$_3$) and N(CH$_3$)$_2$, preferably NH$_2$, and a substituted phenyl group which comprise one substituent selected from NH$_2$, NH(CH$_3$) and N(CH$_3$)$_2$, preferably NH$_2$, and an unsubstituted or substituted 5- or 6-membered monocyclic heteroaryl group, which comprises 1 or 2 nitrogen heteroatoms and, when substituted, one substituent selected from NH$_2$, NH(CH$_3$) and N(CH$_3$)$_2$, preferably NH$_2$;
Z is selected from phenyl and a group of one of the formulae:

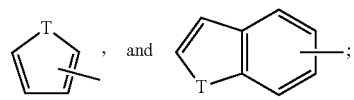

wherein T represents a group selected from NH and N(CH$_3$), or an O- or S-atom; the free valence can be located at any of the ring atoms of the entire group Z including the group T if T is not an O- or S-atom; and wherein one to three of the ring carbon atoms can furthermore be replaced by a N-atom, and wherein group Z is unsubstituted or substituted by one to three groups selected from halogen, C1-C4alkyl and C1-C4alkoxy.

In a further preferred embodiment of the compounds of formula I according to the invention the compound of formula I is a compound having the formula I-1 or I-3, preferably I-1
wherein
R represents hydrogen or —NH$_2$;
R1 and R2, independently of one another, represent hydrogen, fluoro, chloro, hydroxy, methoxy, ethoxy, propoxy, —NH$_2$ or nitro;
X—Y is selected from

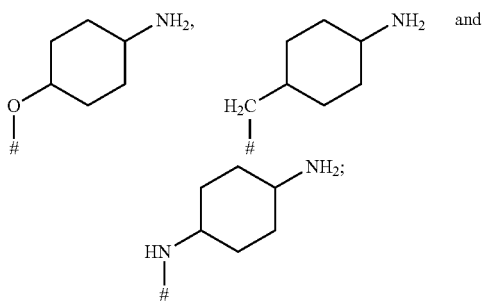

Z is selected from phenyl, which is unsubstituted of substituted by one or two substituents selected from fluoro and chloro; and a group of one of the formulae

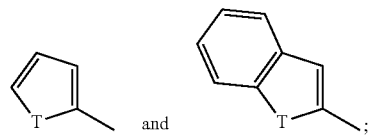

T is selected from an O- or S-atom; and, more preferably, Z is an unsubstituted group selected from phenyl, furan-2-yl, thiophen-2yl, and benzofuran-2-yl.

Further preferred embodiments of the compounds of formula I according to the invention include (1) compounds of formula I-1, wherein
R represents H or NH$_2$;
R1 and R2, independently of each other, are selected from hydrogen, NH$_2$, methyl, trifluoromethyl, methoxy, trifluoromethoxy, fluoro and chloro;
X represents a group selected from —CH$_2$— and —CH$_2$—NH— which is linked to Y via the NH group;
Y represents a group selected from saturated monocyclic 6 membered heterocycloalkyl and a mono- or bicyclic heteroaryl group, wherein said heterocycloalkyl group and heteroaryl group comprise one or two nitrogen heteroatoms and said group Y is either unsubstituted or substituted by one or two substituents independently selected from NH$_2$, methyl, trifluoromethyl, methoxy, fluoro and chloro; and
Z represents a mono- or bicyclic a mono- or bicyclic group comprising at least one heteroaryl cycle and having 5 to 10 ring atoms, said heteroaryl cycle comprising one or two heteroatoms selected from nitrogen, oxygen and sulfur, preferably one such heteroatom, which heteroaryl group is preferably unsubstituted or
pharmaceutically acceptable acid addition salts thereof;

(2) compounds of formula I-1, wherein
R represents H, —NH₂ or —OH;
R1 and R2, independently of each other, are selected from hydrogen, NH₂, methyl, trifluoromethyl, methoxy, trifluoromethoxy, fluoro and chloro;
X represents —NH— or —O—;
Y represents a group selected from amino-substituted C2-C4alkyl, amino-substituted, in particular 4-amino-substituted cyclohexyl, wherein amino preferably refers to NH₂, and saturated monocyclic 6 membered heterocycloalkyl, wherein said heterocycloalkyl group comprises one or two nitrogen heteroatoms and said group Y is further substituted by one or two substituents independently selected from NH₂, methyl, trifluoromethyl, methoxy, fluoro and chloro, or preferably further unsubstituted; and
Z represents a mono- or bicyclic a mono- or bicyclic group comprising at least one heteroaryl cycle and having 5 to 10 ring atoms, said heteroaryl cycle comprising one or two heteroatoms selected from nitrogen, oxygen and sulfur, preferably one such heteroatom, which aryl or heteroaryl group is preferably unsubstituted
including pharmaceutically acceptable acid addition salts thereof, tautomers of such compounds wherein R is C—OH having the formula I-1b, mixtures of two tautomeric forms of such compounds and pharmaceutically acceptable acid addition salts of such compounds, tautomers thereof and mixtures of two tautomeric forms;
(3) compounds of formula I-2, wherein
R1 and R2, independently of each other, are selected from hydrogen, NH₂, methyl, trifluoromethyl, methoxy, trifluoromethoxy, fluoro and chloro;
X represents —CH₂—;
Y represents a saturated monocyclic 6 membered heterocycloalkyl, wherein said heterocycloalkyl group comprises one or two nitrogen heteroatoms and said group Y is unsubstituted or substituted by one or two substituents independently selected from NH₂, methyl, trifluoromethyl, methoxy, fluoro and chloro, or preferably unsubstituted further substituted by NH₂; and
Z represents a mono- or bicyclic a mono- or bicyclic group comprising at least one heteroaryl cycle and having 5 to 10 ring atoms, said heteroaryl cycle comprising one or two heteroatoms selected from nitrogen, oxygen and sulfur, preferably one such heteroatom, which heteroaryl group is preferably unsubstituted;
including pharmaceutically acceptable acid addition salts thereof; or
(4) compounds of formula I-3, wherein R1 and R2, independently of each other, are selected from hydrogen, NH₂, methyl, trifluoromethyl, methoxy, trifluoromethoxy, fluoro and chloro;
X represents —(C=O)—NH₂—;
Y represents a saturated Y represents a group selected from amino-substituted C2-C4alkyl; and
Z represents a mono- or bicyclic a mono- or bicyclic group comprising at least one heteroaryl cycle and having 5 to 10 ring atoms, said heteroaryl cycle comprising one or two heteroatoms selected from nitrogen, oxygen and sulfur, preferably one such heteroatom, which heteroaryl group is preferably unsubstituted;
including pharmaceutically acceptable acid addition salts thereof.

A further preferred group of compounds based on their MNK1 inhibitory activity are Examples 1, 2, 25, 36, 44, 52, 54-61, 63, 65-74, 76, 86, 88, 93, 101, 103, 105, 121-123, 125, 127-131, 133, 140-142, 147, 148, 151-153, 157, 163, 165, 166, 171, 177, 178, 180, 189, 190, 206, 208-210, 213, 225, 232, 234, 239, 240, 242, 244, 245, 248-251, 253-255, 257-259, 261, 262, 264, 266, 268, 269, 272, 275-279, 282, 284-287, 290, 292, 300, 302-304, 306, 308-312, 315, 316, 319-322 below.

A further preferred group of compounds based on their potency to inhibit MiaPaCa2 cell growth are Examples 1, 31, 54, 55, 57, 66, 76, 78, 79-82, 87, 99, 100, 103, 114, 116, 119, 125, 130, 137, 140-144, 148, 151-153, 167, 170, 174, 177-179, 205, 210, 212-218, 220, 222, 223, 227, 229, 231, 232, 234-236, 239, 242, 245, 250, 251, 253, 256-259, 261, 267, 271, 274, 278, 281-284, 286-288, 291, 295, 297, 298, 304, 308-310, 312-315, 317-323 below.

The invention also includes use of compounds of the invention for the manufacture of a medicament for the treatment of proliferation diseases, in particular cancer. The invention also includes methods of treating proliferation diseases, in particular cancer, in a subject in need of such treatment comprising the administration of an antiproliferatively active amount of a compound of the invention. These aspects are described in more detail below.

Substituent definitions in the above embodiments and preferred groups of compounds may be combined with each other in any combination.

The compounds according to formula I can be manufactured e.g. by coupling a compound of formula II-A with a compound of formula M1-Z and a compound of formula M2-X—Y according to the following Reaction Scheme 1:

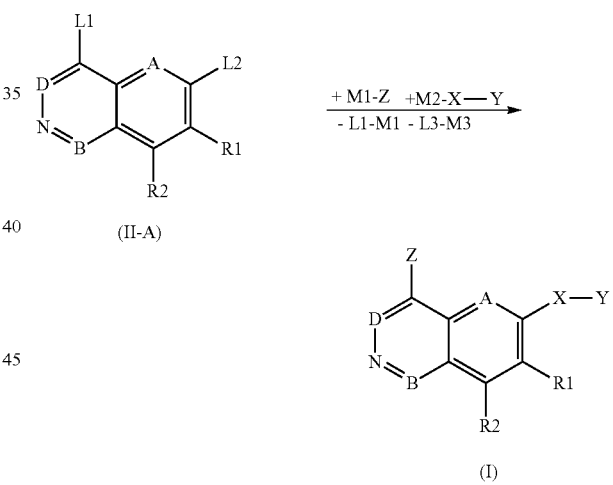

or by coupling a compound of formula II-B with a compound of formula M1-Z and a compound of formula M3-Y according to the following Reaction Scheme 2:

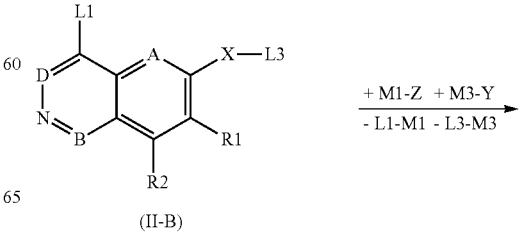

-continued

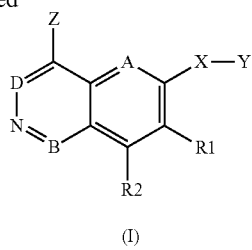

(I)

according to methods known in the art or analog to such methods including in particular methods and conditions as described in the Examples of the present application or analogs thereof.

A; B; D; R when present; R1; R2; X; Y and Z have in said Reaction Schemes 1 and 2 the same meaning as in formula I;

L1 is a leaving group reacting with the leaving group M1 of the compound M1-Z thereby forming a single bond between the group Z and the carbon atom to which L1 was linked in formula II-A;

L2 is a leaving group reacting with the leaving group M2 of the compound M2-X—Y thereby forming a single bond between the group X—Y and the carbon atom to which L2 was linked in formula II-A;

L3 is a leaving group reacting with the leaving group M3 of the compound M3-Y thereby forming a single bond between the group Y and the atom of the group X to which L3 was linked in formula II-A;

R when present, R1, R2 and any substituent of L and/orY requiring a protection under the reaction conditions applied for performing the reactions according to Scheme 1 or 2 are protected by suitable protecting groups as known in the art.

Suitable representatives of L1; L2; L3; M1; M2 and M3 and their method of use are known in the art and can be found e.g. in the Examples of the present application.

The present invention relates also to pharmaceutical compositions that comprise a compound of formula (I) as active ingredient and that can be used especially in the treatment of the diseases mentioned at the beginning. Compositions for enteral administration, such as nasal, buccal, rectal or, especially, oral administration, and for parenteral administration, such as intravenous, intramuscular or subcutaneous administration, to mammals, especially humans, are particularly preferred. The compositions comprise the active ingredient alone or, preferably, together with a pharmaceutically acceptable carrier. The dosage of the active ingredient depends upon the specific disease to be treated and upon the species, its age, weight, and individual condition, the individual pharmacokinetic data, and the mode of administration.

The present invention relates especially to pharmaceutical compositions that comprise a compound of formula (I), a tautomer, a prodrug or a pharmaceutically acceptable salt, or a hydrate or solvate or ester thereof, and at least one pharmaceutically acceptable carrier.

The invention relates also to pharmaceutical compositions for use in a method for the prophylactic or especially therapeutic management of the human or animal body, in particular in a method of treating proliferation disorders or diseases like e.g. cancer, in particular those mentioned hereinabove.

The invention relates also to processes and to the use of compounds of formula (I) thereof for the manufacture of pharmaceutical preparations, i.e. medicaments which comprise compounds of formula (I) as one active component (active ingredient).

A pharmaceutical composition for the prophylactic or especially therapeutic management of a neoplastic disease of a mammal, especially a human or a commercially useful mammal requiring such treatment, comprising a compound of formula (I) as an active ingredient in a quantity that is prophylactically or especially therapeutically active against the said diseases, is likewise preferred.

The pharmaceutical compositions comprise from approximately 1% to approximately 95% of active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories, or capsules. Further dosage forms are, for example, ointments, creams, pastes, foams, tinctures, lip-sticks, drops, sprays, dispersions, etc. Examples are capsules containing from about 0.05 g to about 1.0 g of active ingredient.

The pharmaceutical compositions of the present invention are prepared in a manner known per se, for example by means of conventional mixing, granulating, coating, dissolving or lyophilizing processes.

Suitable formulations may include solutions of the active ingredient, and also suspensions or dispersions, especially isotonic aqueous solutions, dispersions or suspensions suitable in particular for intravenous administration, which, for example in the case of lyophilized compositions comprising the active ingredient alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions, dispersions or suspensions may comprise viscosity-increasing agents, typically sodium carboxymethylcellulose, carboxymethylcellulose, dextran, polyvinylpyrrolidone, or gelatins, or also solubilizers, e.g. Tween 80® (polyoxyethylene(20)sorbitan mono-oleate).

Suspensions in oil comprise as the oil component usually a vegetable, synthetic, or semi-synthetic oils customary for injection purposes. In respect of such, special mention may be made of liquid fatty acid esters that contain as the acid component a long-chained fatty acid having from 8 to 22, especially from 12 to 22, carbon atoms. The alcohol component of these fatty acid esters has usually a maximum of 6 carbon atoms and is a monovalent or polyvalent, for example a mono-, di- or trivalent, alcohol, especially glycol and glycerol. As mixtures of fatty acid esters, vegetable oils such as cottonseed oil, almond oil, olive oil, castor oil, sesame oil, soybean oil and groundnut oil are especially useful.

The manufacture of injectable preparations is usually carried out under sterile conditions, as is the filling, for example, into ampoules or vials, and the sealing of the containers.

Suitable carriers are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration include e.g. hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration, aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers, are especially suitable. The active ingredient, optionally together with excipients, can also be in the form of a lyophilizate and can be made into a solution before parenteral administration by the addition of suitable solvents.

Solutions such as are used, for example, for parenteral administration can also be employed as infusion solutions.

Preferred preservatives for such solutions are, for example, antioxidants, such as ascorbic acid, or microbicides, such as sorbic acid or benzoic acid.

The present invention relates furthermore to a method for the treatment of a proliferation disease such as a neoplastic disease, which comprises administering a compound of formula (I) or a pharmaceutically acceptable salt thereof, wherein the radicals and symbols have the meanings as defined above for formula (I), in a quantity effective against said disease, to a mammal requiring such treatment. The compounds of formula (I) can be administered as such or especially in the form of pharmaceutical compositions, prophylactically or therapeutically, preferably in an amount effective against the said diseases, to the mammal, for example a human, requiring such treatment. In the case of an individual having a bodyweight of about 70 kg the daily dose administered is from approximately 0.05 g to approximately 5 g, preferably from approximately 0.25 g to approximately 1.5 g, of a compound of the present invention.

Suitable dosages can e.g. be determined in a usual Phase I Study of the respective compounds and correspond normally to the so-called maximum tolerated dose (MTD) which is defined as the dose which does not give rise to dose-limiting side effects or toxical effects in a maximum of 33 percent of the studied patients in the Phase I Study.

The present invention relates especially also to the use of a compound of formula (I), or a pharmaceutically acceptable salt thereof, especially a compound of formula (I) which is said to be preferred, or a pharmaceutically acceptable salt thereof, as such or in the form of a pharmaceutical formulation with at least one pharmaceutically acceptable carrier for the therapeutic and also prophylactic management of one or more of the proliferation diseases mentioned hereinabove. Preferred dose quantities, compositions, and the preparation of pharmaceutical formulations (medicines) which are to be used in each case are described above.

The compounds of formula (I) can also be used in combination with one or more other pharmaceutically active compounds, which are either effective against the same disease, preferably using a different mode of action, or which reduce or prevent possible undesired side effects of the compounds of formula (I). The combination partners can be administered in such a treatment either simultaneously, e.g. by incorporating them into a single pharmaceutical formulation, or consecutively by administration of two or more different dosage forms, each containing one or more than one of the combination partners.

EXAMPLES

Particular embodiments of the invention are described in the following Examples, which serve to illustrate the invention in more detail:

All reagents and anhydrous solvents are generally used as received from the commercial supplier;

reactions are routinely performed in well-dried glassware under an argon or nitrogen atmosphere;

evaporations are carried out by rotary evaporation in vacuo and work-up procedures are carried out after removal of residual solids by filtration;

all temperatures are given in ° C.; operations are carried at room temperature, if not otherwise stated, that is typically in the range 18-25° C.;

column chromatography (by the flash procedure) is used to purify compounds and is performed using Merck silica gel 60 (70-230 mesh ASTM) unless otherwise stated;

in general, the course of reactions is followed by TLC, HPLC, or LC/MS and reaction times are given for illustration only; yields are given for illustration only and are not necessarily the maximum attainable;

the structure of the final products of the invention is generally confirmed by NMR and mass spectral techniques. Proton NMR spectra are recorded on a Brucker 400 MHz spectrometer. Chemical shifts (δ) are reported in ppm relative to $Me_4Si$ or the solvent peak as internal standard, and J values are in Hertz (Hz). Each peak is denoted as a broad singlet (br), singlet (s), doublet (d), doublet of doublets (dd), triplet of doublets (td) or multiplet (m). Mass spectra are generated using a q-Tof Ultima (Waters AG) mass spectrometer in the positive ESI mode. The system is equipped with the standard Lockspray interface;

each intermediate is purified to the standard required for the subsequent stage and is characterized in sufficient detail to confirm that the assigned structure is correct;
all analytical and preparative HPLC investigations on non-chiral phases are performed using RP-C18 based columns;
the following abbreviations may be used:
Acetone-d6: Deuterated acetone
ACN: Acetonitrile
AcOH/HOAc: Acetic acid
BnOH: Benzyl alcohol
BINAP: 2, 2'-Bis(diphenylphosphino)-1, 1'-binapthyl
Boc tert-Butoxycarbonyl
Boc$_2$O: Di-tert butyl dicarbonate
BPO: Benzoyl Peroxide
BTC: Bis(trichloromethyl)carbonate
CDCl$_3$: Deuterated chloroform
DCM: Dichloromethane
DEAD: Diethyl azodicarboxylate
Diox.: 1, 4-Dioxane
DIPEA: N,N-Diisopropylethylamine
DMAP: 4-Dimethylaminopyridine
DMAC: N, N-dimethylacetamide
DMF: N,N-Dimethylformamide
DMSO-d6: Deuterated dimethyl sulphoxide
EA/EtOAc: Ethyl acetate
ELSD: Evaporative light scattering detection
EtOH: Ethanol
HATU: O-(7-Azabenzotriazol-1-yl)-N,N,N',N'-tetramethyl-uronium hexafluorophosphate
HPLC: High performance liquid chromatography
i-PrOH: Isopropanol
J: Coupling constant
Johnphos: 2-(Dicyclohexylphosphino)biphenyl
KOAc: Potassium acetate
KO$^t$Bu/$^t$BuOK: Potassium tert-butanolate
LC/MS: Liquid chromatography coupled to mass spectroscopy
mCPBA: 3-Chloroperoxybenzoic acid
MeOH-d4: Deuterated methanol
MeOH: Methanol
Me$_4$Si: Tetramethylsilane
MS: Mass spectroscopy
MsCl: Methanesulfonyl chloride
NMR: Nuclear magnetic resonance
NBS: N-Bromosuccinimide
Pcy$_3$: Tricyclohexyl phosphine
PE: Petroleum ether
Pd/C: Palladium on activated carbon
Pd(dppf)Cl$_2$: 1,1'-Bis(diphenylphosphino)ferrocene-palladium(II)dichloride dichloromethane complex
Pd(PPh$_3$)$_4$: Tetrakis(triphenylphosphine)palladium
Pd$_2$(dba)$_3$: Tris(dibenzylideneacetone)dipalladium
Pd(OAc)$_2$: Palladium diacetate
PPh$_3$: triphenylphosphine
Prep-HPLC: Preparative High Performance Liquid Chromatography
PTSA/TsOH: p-Toluenesulfonic acid
Rf: Retardation factor
rt: room temperature
SEMCl: 2-(Trimethylsilyl)ethoxymethyl chloride
S-PHOS: 2-Dicyclohexylphosphino-2',6'-dimethoxybiphenyl
tBuBrettPhos: 2-(Di-t-butylphosphino)-3,6-diMethoxy-2'-4'-6'-tri-i-propyl-1,1'-biphenyl
t-BuONa: Sodium tert-butoxide
TEA: Triethylamine
TEBAC: Benzyltriethylammonium chloride
TFA: Trifluoroacetic acid
THF: Tetrahydrofuran
TLC: Thin layer chromatography
TsCl: p-Toluenesulfonyl chloride
XantPhos: 9,9-Dimethyl-4,5-bis(diphenylphosphino)xanthene
X-phos: 2-Dicyclohexylphosphino-2',4',6'-tri-i-propyl-1,1'-biphenyl tert-Butyl N-[1-[(4-bromo-6-isoquinolyl)methyl]-4-piperidyl]carbamate

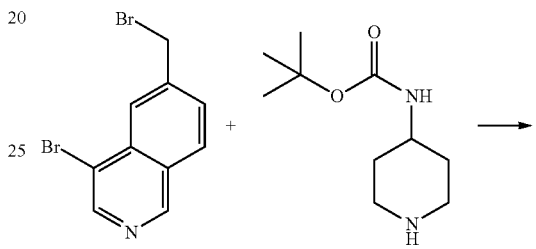

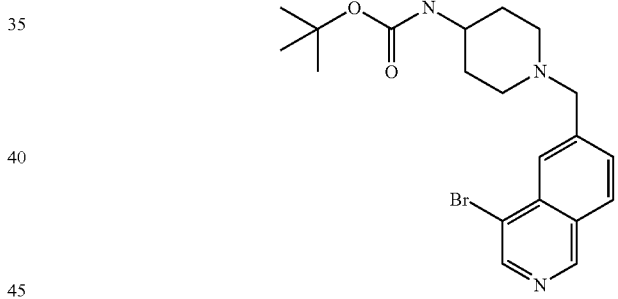

A solution of 455 mg (1.51 mmol) of 4-bromo-6-(bromomethyl)isoquinoline (CAS 98331-27-2), 303 mg (1.51 mmol) of tert-butyl N-(4-piperidyl)carbamate (CAS 73874-95-0) and 418 mg (3.0 mmol) of K$_2$CO$_3$ in 40 mL of DMF are stirred at 25° C. for 2 h. The mixture is diluted with EA, washed with water and brine, dried over Na$_2$SO$_4$, filtered and concentrated under reduced pressure. The residue is purified by silica gel column chromatography (PE/EA=1/3) to give 393 mg of the product as a white solid.

MS (ESI+): 420 [M+H].

$^1$H NMR (400 MHz, CDCl$_3$+D$_2$O) δ ppm: 9.14 (s, 1H), 8.71 (s, 1H), 8.05 (s, 1H), 7.95 (d, J=8.4 Hz, 1H), 7.77 (d, J=8.4 Hz, 1H), 3.78 (s, 2H), 3.53 (s, 1H), 2.89-2.23 (m, 4H), 1.98-1.53 (m, 4H), 1.45 (s, 9H).

tert-Butyl N-[1-[[4-(benzofuran-2-yl)-6-isoquinolyl]methyl]-4-piperidyl]carbamate

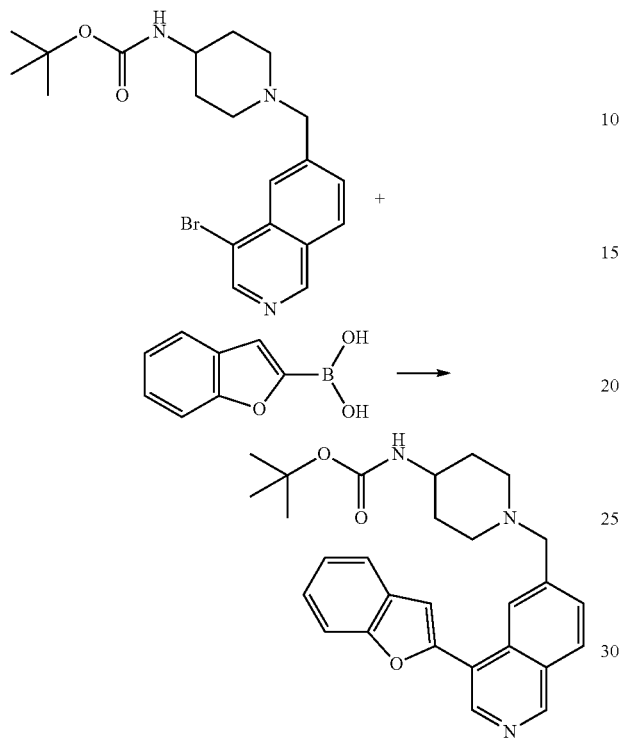

Under argon atmosphere, to a mixture of 300 mg (0.71 mmol) of tert-butyl N-[1-[(4-bromo-6-isoquinolyl)methyl]-4-piperidyl]carbamate, 139 mg (0.86 mmol) of benzofuran-2-ylboronic acid, 303 mg (1.43 mmol) of $K_3PO_4$ in a mixture 20 mL of DMF and 1.5 mL of water, 124 mg (0.075 mmol) of $Pd(PPh_3)_4$ are added. The mixture is stirred at 80° C. for 1 h. Then the reaction mixture is diluted with EA, washed with water and brine, dried over $Na_2SO_4$ and filtered. The filtrate is concentrated under reduced pressure and the residue is purified by silica gel column chromatography (DCM/MeOH=20/1) to afford 290 mg of the product as a light yellow solid.

MS (ESI+): 458.2 [M+H].

$^1$H NMR (400 MHz, DMSO-d6) δ ppm: 9.36 (s, 1H), 8.92 (s, 1H), 8.37 (s, 1H), 8.21 (d, J=8.8 Hz, 1H), 7.80-7.34 (m, 6H), 3.72 (s, 2H), 3.24 (s, 1H), 2.82-1.99 (m, 4H), 1.71-1.23 (m, 4H), 1.37 (s, 9H).

1-[[4-(Benzofuran-2-yl)-6-isoquinolyl]methyl]piperidin-4-amine (Example 1)

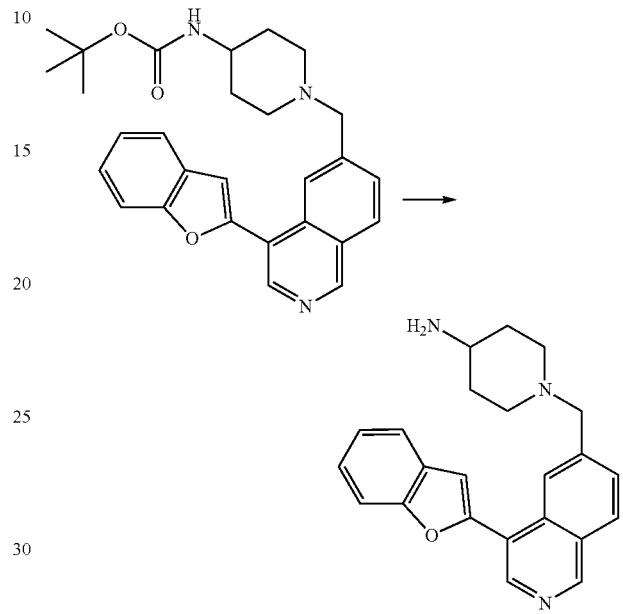

A mixture of 200 mg (0.44 mmol) of tert-butyl N-[1-[[4-(benzofuran-2-yl)-6-isoquinolyl]methyl]-4-piperidyl]carbamate in 20 mL of a 1.7 N solution of HCl in EA is stirred at rt for 1 h. Then the solvent is evaporated under reduced pressure. The residue is washed five times with EA to afford 190 mg of the HCl salt of the product as a light yellow solid.

MS (ESI+): 358.1 [M+H].

$^1$H NMR (400 MHz, DMSO-d6+$D_2O$) δ ppm: 9.49 (s, 1H), 9.00 (s, 1H), 8.68 (s, 1H), 8.41 (d, J=8.4 Hz, 1H), 7.95-7.34 (m, 6H), 4.59 (s, 2H), 3.47-3.12 (m, 5H), 2.11-1.79 (m, 4H).

The following examples were prepared accordingly to Example 1 by reaction of tert-butyl N-[1-[(4-bromo-6-isoquinolyl)methyl]-4-piperidyl]carbamate with the corresponding boronic acid or boronic acid ester in the presence of a Pd-catalyst and subsequent deprotection:

| Example | | $^1$H NMR (400 MHz) δ ppm | MS (+ESI) [M + H]$^+$ |
|---|---|---|---|
| 2 | (structure) | (DMSO-d$_6$) 9.49 (s, 1H), 8.48 (s, 1H), 8.43 (d, J = 8.8 Hz, 1H), 8.16 (s, 1H), 7.88 (dd, J = 8.4 Hz, 1.2 Hz, 1H), 7.44-7.41 (m, 2H), 7.01 (d, J = 8.4 Hz, 2H), 4.49 (s, 2H), 3.41-3.07 (m, 5H), 2.08-1.69 (m, 4H) | 333.2 |

-continued
| Example | | ¹H NMR (400 MHz) δ ppm | MS (+ESI) [M + H]⁺ |
|---|---|---|---|
| 3 | 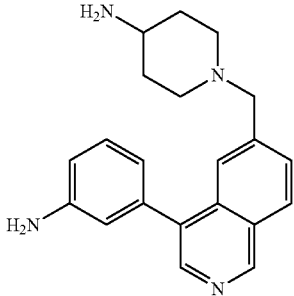 [SMILES: Nc1cccc(-c2cncc3ccc(CN4CCC(N)CC4)cc23)c1] | (DMSO-d₆ + D₂O) 9.62 (s, 1H), 8.59 (s, 1H), 8.48 (d, J = 8.4 Hz, 1H), 8.21 (s, 1H), 8.03 (d, J = 8.4 Hz, 1H), 7.64-7.35 (m, 4H), 4.54 (s, 2H), 3.42-3.12 (m, 5H), 2.11-1.85 (m, 4H) | 333.2 |
| 4 | 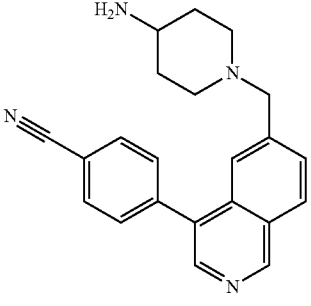 [SMILES: N#Cc1ccc(-c2cncc3ccc(CN4CCC(N)CC4)cc23)cc1] | (DMSO-d₆ + D₂O) 9.50 (s, 1H), 8.55 (s, 1H), 8.39 (d, J = 8.4 Hz, 1H), 8.05-7.80 (m, 6H), 4.46 (s, 2H), 3.39-3.05 (m, 5H), 2.08-1.70 (m, 4H) | 343.2 |
| 5 | 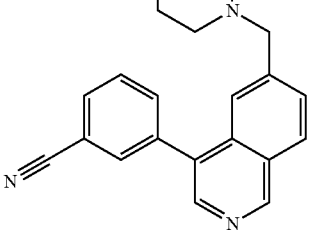 | (DMSO-d₆ + D₂O) 9.57 (s, 1H), 8.58 (s, 1H), 8.44 (d, J = 8.4 Hz, 1H), 8.08-7.57 (m, 6H), 4.49 (s, 2H), 3.42-3.06 (m, 5H), 2.09-1.79 (m, 4H) | 343.3 |
| 6 | 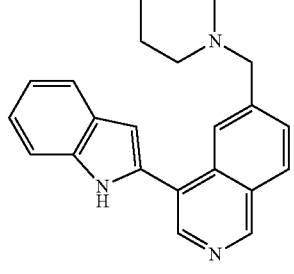 | (DMSO-d₆ + D₂O) 9.50 (s, 1H), 8.77 (s, 1H), 8.59 (s, 1H), 8.43 (d, J = 8.4 Hz, 1H), 7.97 (d, J = 8.4 Hz, 1H), 7.69-7.03 (m, 5H), 4.55 (s, 2H), 3.45-3.11 (m, 5H), 2.10-1.82 (m, 4H) | 357.2 |
| 7 | 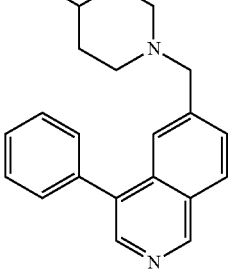 | (DMSO-d₆ + D₂O) 9.47 (s, 1H), 8.52 (s, 1H), 8.39 (d, J = 8.4 Hz, 1H), 8.05 (s, 1H), 7.85-7.55 (m, 6H), 4.47 (s, 2H), 3.39-3.05 (m, 5H), 2.08-1.69 (m, 4H) | 318.2 |

| Example | | ¹H NMR (400 MHz) δ ppm | MS (+ESI) [M + H]⁺ |
|---|---|---|---|
| 8 | 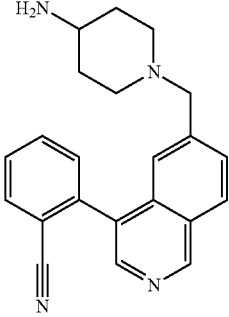 [SMILES: N#Cc1ccccc1-c1cncc2ccc(CN3CCC(N)CC3)cc12] | (DMSO-d₆) 9.42 (s, 1H), 8.49 (s, 1H), 8.25 (d, J = 8.4 Hz, 1H), 8.08 (t, J = 8.0 Hz, 1H), 7.90-7.94 (m, 1H), 7.69-7.80 (m, 3H), 7.42 (s, 1H), 3.62 (s, 2H), 2.95-2.83 (m, 1H), 2.78-2.85 + 1.94-2.05 (2m, 4H), 1.78-1.85 + 1.40-1.52 (2m, 4H) | 343.3 |
| 9 | 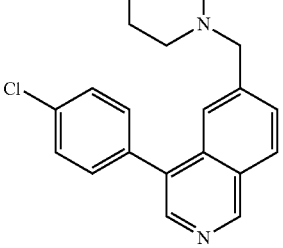 | (DMSO-d₆ + D₂O) 9.29 (s, 1H), 8.38 (s, 1H), 8.20 (d, J = 8.4 Hz, 1H), 7.64-7.71 (m, 2H), 7.55-7.64 (m, 4H), 3.62 (s, 2H), 2.90-3.00 (m, 1H), 2.76-2.82 + 1.96-2.05 (2m, 4H), 1.80-1.88 + 1.40-1.52 (2m, 4H) | 352.1 |
| 10 | 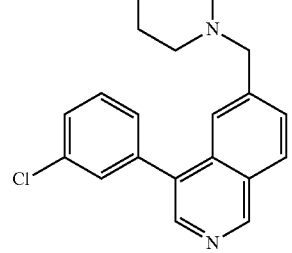 | (DMSO-d₆) 9.34 (s, 1H), 8.45 (s, 1H), 8.21 (d, J = 8.4 Hz, 1H), 7.58-7.70 (m, 5H), 7.53 (m, 1H), 3.63 (s, 2H), 2.88-2.96 (m, 1H), 2.79-2.87 + 1.98-2.08 (2m, 4H), 1.79-1.86 + 1.42-1.52 (2m, 4H) | 352.1 |
| 11 | 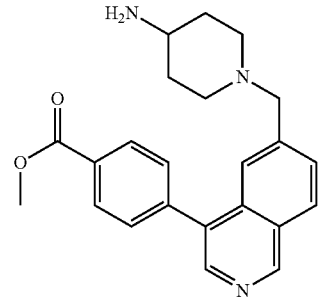 [SMILES: COC(=O)c1ccc(-c2cncc3ccc(CN4CCC(N)CC4)cc23)cc1] | (DMSO-d₆) 9.35 (s, 1H), 8.46 (s, 1H), 8.22 (d, J = 8.4 Hz, 1H), 8.16 (dd, J1 = 2.0 Hz, J2 = 6.8 Hz, 2H), 7.69-7.78 (m, 4H), 3.93 (s, 3H), 3.63 (s, 2H), 2.85-2.93 (m, 1H), 2.76-2.84 + 1.95-2.05 (2m, 4H), 1.78-1.85 + 1.40-1.50 (2m, 4H) | 376.1 |
| 12 | 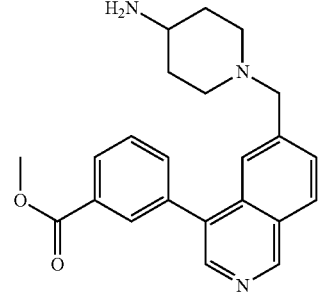 [SMILES: COC(=O)c1cccc(-c2cncc3ccc(CN4CCC(N)CC4)cc23)c1] | (DMSO-d₆) 9.35 (s, 1H), 8.46 (s, 1H), 8.22 (d, J = 8.8 Hz, 1H), 8.13 (m, 2H), 7.87 (d, J = 7.6 Hz, 1H), 7.77 (t, J = 7.6 Hz, 1H), 7.65-7.70 (m, 2H), 3.89 (s, 3H), 3.63 (s, 2H), 2.84-2.94 (m, 1H), 2.78-2.84 + 1.94-2.05 (2m, 4H), 1.75-1.85 + 1.38-1.50 (2m, 4H) | 376.2 |

-continued

| Example | | ¹H NMR (400 MHz) δ ppm | MS (+ESI) [M + H]⁺ |
|---|---|---|---|
| 13 | (structure) | (DMSO-d₆ + D₂O) 9.35 (s, 1H), 8.75 (dd, J1 = 1.2 Hz, J1 = 4.8 Hz, 2H), 8.45 (s, 1H), 8.22 (d, J = 8.4 Hz, 1H), 7.68-7.75 (m, 2H), 7.61 (dd, J1 = 1.2 Hz, J2 = 4.4 Hz, 2H), 3.64 (s, 2H), 2.90-3.00 (m, 1H), 2.76-2.82 + 1.97-2.08 (2m, 4H), 1.80-1.86 + 1.40-1.52 (2m, 4H) | 319.1 |
| 14 | (structure) | (DMSO-d₆ + D₂O) 9.33 (s, 1H), 8.72 (m, 2H), 8.44 (s, 1H), 8.22 (d, J = 8.4 Hz, 1H), 8.03 (m, 1H), 7.60-7.70 (m, 3H), 3.64 (s, 2H), 2.90-3.00 (m, 1H), 2.78-2.85 + 1.98-2.08 (2m, 4H), 1.78-1.85 + 1.40-1.52 (2m, 4H) | 319.2 |
| 15 | (structure) | (DMSO-d₆ + D₂O) 9.51 (s, 1H), 8.82 (d, J = 4.8 Hz, 1H), 8.70 (s, 1H), 8.32-8.39 (m, 2H), 8.09 (m, 1H), 7.86 (d, J = 8.0 Hz, 2H), 7.60 (m, 1H), 4.49 (s, 2H), 3.33-45 + 3.00-3.15 (2m, 4H), 3.17-3.30 (m, 1H), 2.00-2.14 + 1.60-1.80 (2m, 4H) | 319.4 |
| 16 | (structure) | (DMSO-d₆ + D₂O) 9.52 (s, 1H), 8.60 (s, 1H), 8.40 (d, J = 8.4 Hz, 1H), 8.00-8.05 (m, 2H), 7.87 (dd, J1 = 1.2 Hz, J2 = 8.4 Hz, 2H), 7.08-7.16 (m, 2H), 4.47 (s, 2H), 3.38-3.48 + 2.96-3.13 (2m, 4H), 3.20-3.30 (m, 1H), 2.03-2.12 + 1.60-1.80 (2m, 4H) | 334.4 |
| 17 | (structure) | (DMSO-d₆) 9.25 (s, 1H), 8.37 (s, 1H), 8.16 (d, J = 8.4 Hz, 1H), 8.07 (d, J = 2.4 Hz, 1H), 7.76 (s, 1H), 7.67, 7.59 (2m, 2H), 6.64 (d, J = 8.4 Hz, 1H), 6.21 (s, 2H), 3.65 (s, 2H), 2.93-3.00 (m, 1H), 2.80-2.85 + 1.98-2.08 (2m, 4H), 1.82-1.88 + 1.43-1.58 (2m, 4H) | 334.3 |

N-[4-[6-[(4-Amino-1-piperidyl)methyl]-4-isoquinolyl]phenyl]acetamide (Example 18)

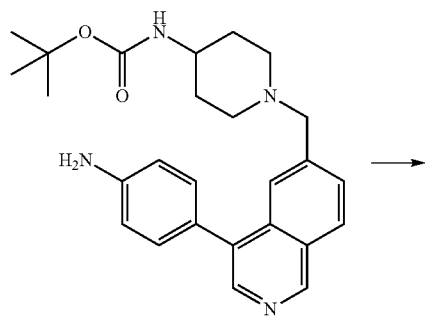

methyl]-4-piperidyl]carbamate), 68 μL (0.72 mmol) of acetic anhydride, 87 μL (1.08 mmol) of pyridine in 5 mL of DCM is stirred at 25° C. for 2 h. The solvent is removed under reduced pressure to give the crude product, which is purified via silica gel column chromatography (DCM/MeOH=10/1) to afford 143 mg of tert-butyl N-[1-[[4-(4-acetamidophenyl)-6-isoquinolyl]methyl]-4-piperidyl]carbamate as a light yellow solid. This intermediate is treated with HCl in EA as described above for Example 1 to provide 73 mg of the desired product as a light yellow solid.

MS (ESI+): 375.3 [M+H].

$^1$H NMR (400 MHz, DMSO-$d_6$+$D_2O$) δ ppm: 9.58 (s, 1H), 8.55 (s, 1H), 8.47 (d, J=8.8 Hz, 1H), 8.16 (s, 1H), 8.01 (d, J=8.8 Hz, 1H), 7.82-7.55 (m, 5H), 4.50 (s, 2H), 3.41-3.07 (m, 5H), 2.10-1.70 (m, 7H).

The following example was prepared as described for Example 18 from tert-butyl N-[1-[[4-(3-aminophenyl)-6-isoquinolyl]methyl]-4-piperidyl]carbamate:

| Example | | $^1$H NMR (400 MHz) δ ppm | MS (+ESI) [M + H]$^+$ |
|---|---|---|---|
| 19 | 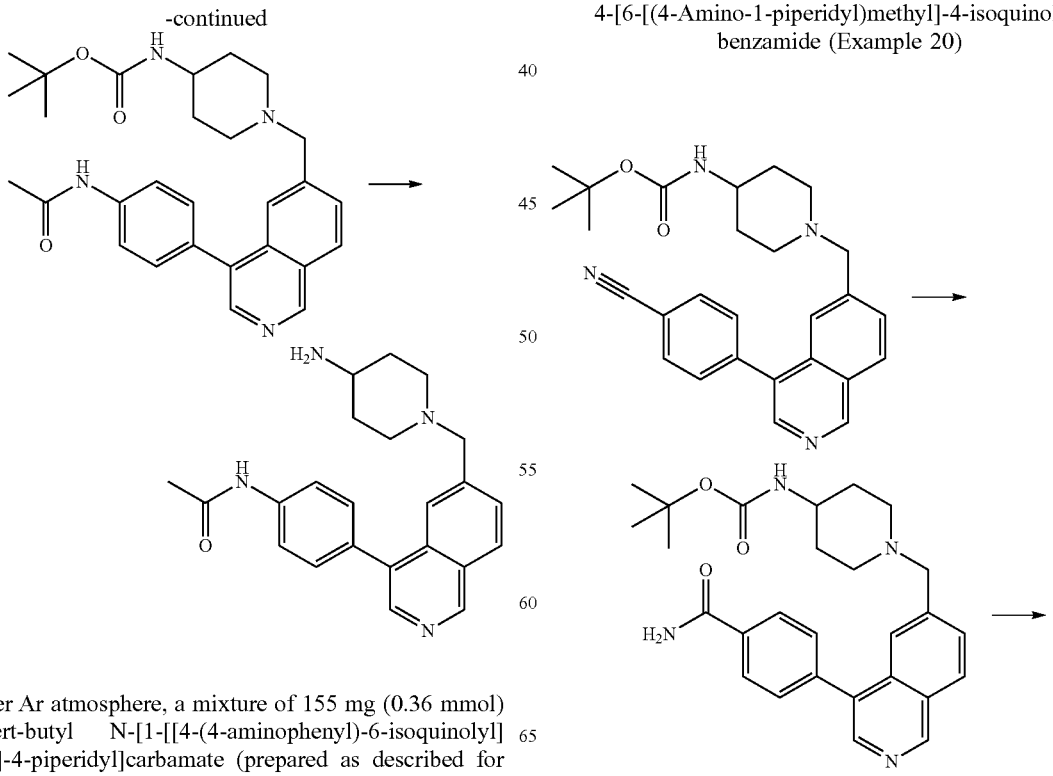 | (DMSO-$d_6$ + $D_2O$) 9.61 (s, 1H), 8.57 (s, 1H), 8.48 (d, J = 8.4 Hz, 1H), 8.16 (s, 1H), 8.02 (d, J = 8.4 Hz, 1H), 7.95-7.31 (m, 4H), 4.50 (s, 2H), 3.44-3.05 (m, 4H), 2.11-1.82 (m, 7H) | 375.2 |

4-[6-[(4-Amino-1-piperidyl)methyl]-4-isoquinolyl]benzamide (Example 20)

Under Ar atmosphere, a mixture of 155 mg (0.36 mmol) of tert-butyl N-[1-[[4-(4-aminophenyl)-6-isoquinolyl]methyl]-4-piperidyl]carbamate (prepared as described for tert-butyl N-[1-[[4-(benzofuran-2-yl)-6-isoquinolyl]

43
-continued

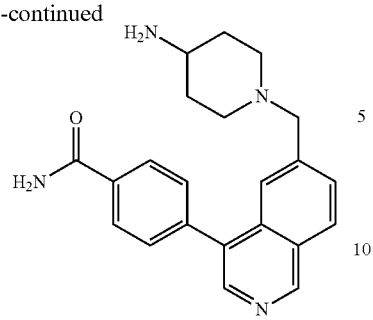

A solution of 160 mg (0.36 mmol) of tert-butyl N-[1-[[4-(4-cyanophenyl)-6-isoquinolyl]methyl]-4-piperidyl]carbamate (prepared as described for tert-butyl N-[1-[[4-(benzofuran-2-yl)-6-isoquinolyl]methyl]-4-piperidyl]carbamate), 200 mg (1.45 mmol) of K$_2$CO$_3$, 350 µL of H$_2$O$_2$ in 5 mL of DMSO is stirred at rt for 10 min. Then the reaction mixture is diluted with EA, washed with water and brine, dried over Na$_2$SO$_4$, filtered and concentrated, and the residue is purified by silica gel column chromatography (MeOH/DCM=1/10) to afford 158 mg of tert-butyl N-[1-[[4-(4-carbamoylphenyl)-6-isoquinolyl]methyl]-4-piperidyl]carbamate as a light yellow foam. This intermediate is treated with HCl in EA as described above for Example 1 to provide 98 mg of the desired product as a white solid after purification by preparative HPLC.

MS (ESI+): 361.3 [M+H].

$^1$H NMR (400 MHz, DMSO-d$_6$+D$_2$O) δ ppm: 9.48 (s, 1H), 8.55 (s, 1H), 8.39 (d, J=8.4 Hz, 1H), 8.09-7.68 (m, 6H), 4.47 (s, 2H), 3.39-3.05 (m, 5H), 2.33-1.69 (m, 4H).

The following example was prepared as described for Example 20 from tert-butyl N-[1-[[4-(3-cyanophenyl)-6-isoquinolyl]methyl]-4-piperidyl]carbamate:

44
4-[[4-(4-Hydroxyphenyl)-6-isoquinolyl]methyl]piperazin-2-one (Example 22)

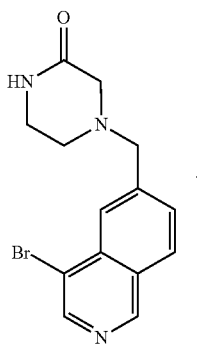

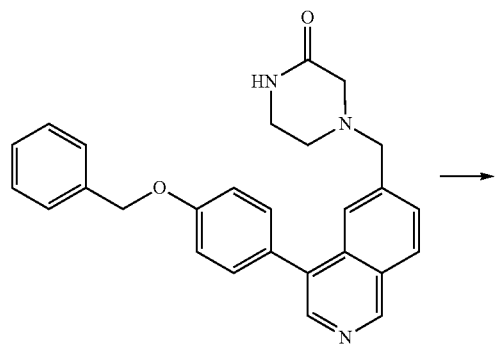

| | Example | $^1$H NMR (400 MHz) δ ppm | MS (+ESI) [M + H]$^+$ |
|---|---|---|---|
| 21 | 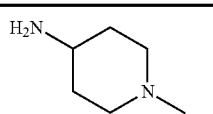 | (DMSO-d$_6$ + D$_2$O) 9.61 (s, 1H), 8.61 (s, 1H), 8.48 (d, J = 8.8 Hz, 1H), 8.09-7.70 (m, 6H), 4.50 (s, 2H), 3.42-3.04 (m, 5H), 2.09-1.79 (m, 4H) | 361.2 |

-continued

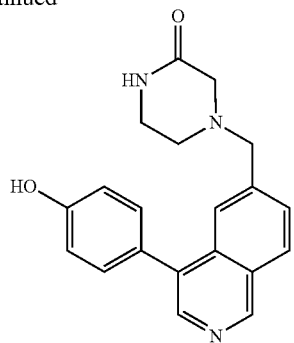

Under Ar atmosphere, 122 mg (0.11 mmol) of Pd(PPh$_3$)$_4$ are added to a mixture of 225 mg (0.7 mmol) of 4-[(4-bromo-6-isoquinolyl)methyl]piperazin-2-one (prepared as described for Example 1a), 327 mg (1.05 mmol) of 2-[4-(benzyloxy)phenyl]-4,4,5,5-tetramethyl-1,3,2-dioxaborolane (CAS 754226-40-9) and 374 mg (1.41 mmol) of K$_3$PO$_4$.3H$_2$O in 10 mL of DMF and 1 mL of water. The mixture is stirred at 80° C. for 1 h. The reaction mixture is diluted with EA, washed with water and brine, dried over Na$_2$SO$_4$ and concentrated. The residue is purified by silica gel chromatography (EA) to give 230 mg of 4-[[4-(4-benzyloxyphenyl)-6-isoquinolyl]methyl]piperazin-2-one as a yellow foam. 150 mg of this intermediate is stirred in 15 mL of TFA at 60° C. for 4 h. The reaction mixture is concentrated under reduced pressure and the residue is purified by preparative HPLC to give 112 mg of the desired product as a light yellow solid.

MS (ESI+): 334.3 [M+H].

$^1$H NMR (400 MHz, DMSO-d$_6$+D$_2$O) δ ppm: 9.53 (s, 1H), 8.51 (s, 1H), 8.44 (d, J=4.4 Hz, 1H), 8.14 (s, 1H), 7.92-7.89 (m, 1H), 7.45-7.43 (m, 2H), 7.01-6.99 (m, 2H), 4.45 (s, 2H), 3.57 (s, 2H), 3.34-3.27 (m, 4H).

The following compounds are prepared in analogy to Examples 1 and 22, starting from 4-bromo-6-(bromomethyl)isoquinoline and the corresponding amines, in which additional functional groups can be protected as required, and final deprotection.

| Example | | $^1$H NMR (400 MHz) δ ppm | MS (+ESI) [M + H]$^+$ |
|---|---|---|---|
| 23 | (structure) | (DMSO-d$_6$ + D$_2$O) 9.49 (s, 1H), 8.50 (s, 1H), 8.41 (d, J = 4.4 Hz, 1H), 8.18-8.13 (m, 1H), 7.92-7.86 (m, 1H), 7.45-7.41 (m, 2H), 7.02-6.98 (m, 2H), 4.54-4.48 (s, 2H), 3.91-3.68 (m, 1H, 3.33-2.97 (m, 4H), 1.97-1.49 (m, 4H) | 335.2 |
| 24 | (structure) | (DMSO-d$_6$ + D$_2$O) 9.43 (s, 1H), 8.47 (s, 1H), 8.38 (d, J = 4.2 Hz, 1H), 8.10 (s, 1H), 7.85-7.83 (m, 1H), 7.42-7.39 (m, 2H), 7.01-6.97 (m, 2H), 4.41 (s, 2H), 3.21 (t, J = 6.4 Hz, 2H), 3.10 (t, J = 6.8 Hz, 2H) | 294.3 |
| 25 | (structure) | (DMSO-d$_6$ + D$_2$O) 9.45 (s, 1H), 8.47 (s, 1H), 8.38 (d, J = 4.2 Hz, 1H), 8.10 (s, 1H), 7.86-7.84 (m, 1H), 7.43-7.40 (m, 2H), 7.00-6.98 (m, 2H), 4.34 (s, 2H), 3.02 (t, J = 7.6 Hz, 2H), 2.84 (t, J = 7.6 Hz, 2H), 1.92-1.84 (m, 2H) | 308.2 |

| Example | | ¹H NMR (400 MHz) δ ppm | MS (+ESI) [M + H]⁺ |
|---|---|---|---|
| 26 | 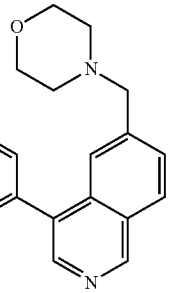 | (DMSO-d₆ + D₂O) 9.49 (s, 1H), 8.50 (s, 1H), 8.41 (d, J = 4.2 Hz, 1H), 8.16 (s, 1H), 7.90-7.87 (m, 1H), 7.45-7.42 (m, 2H), 7.02-6.98 (m, 2H), 4.56 (s, 2H), 3.88 (s, 4H), 3.20 (s, 4H) | 321.2 |

4-Bromoisoquinoline-6-carbaldehyde 4-(4-Benzyloxyphenyl)isoquinoline-6-carboxylic acid

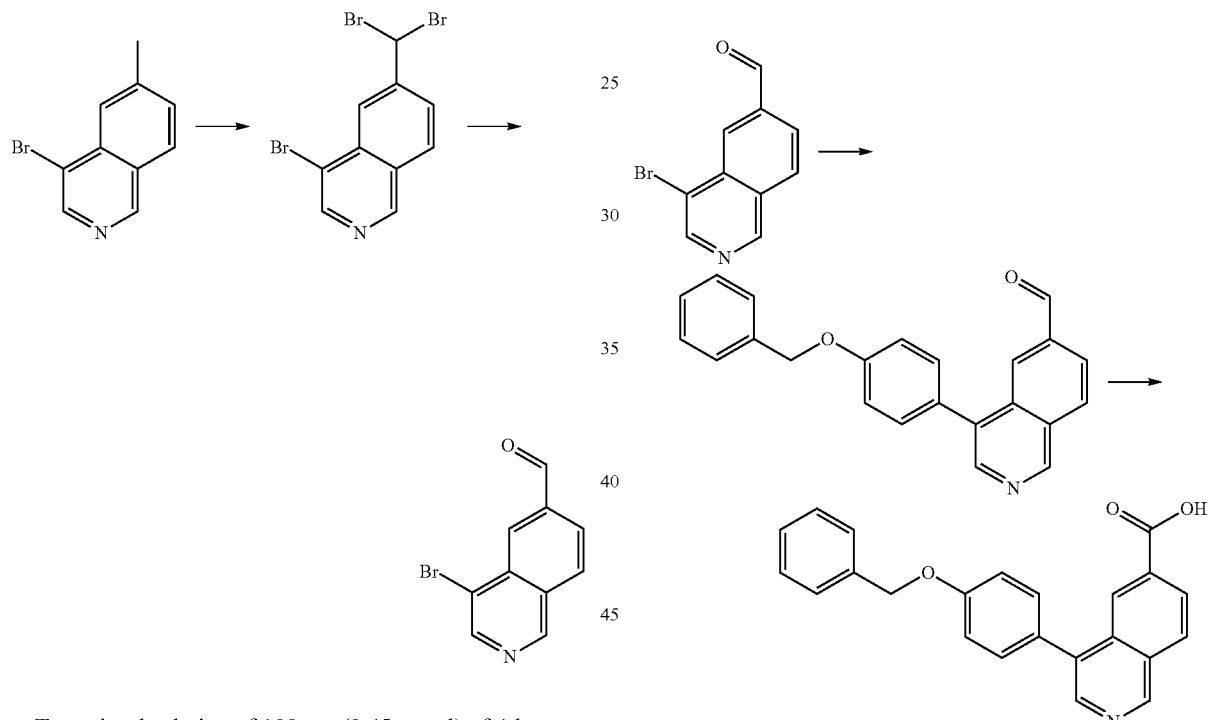

To a stirred solution of 100 mg (0.45 mmol) of 4-bromo-6-methyl-isoquinoline in 4 mL of CCl₄ are added 22 mg (0.09 mmol) of benzoyl peroxide and 176 mg (0.99 mmol) of NBS. The reaction mixture is heated to 80° C. for 20 h. Then the mixture is cooled down to rt, diluted with EA, washed with water and brine, dried over Na₂SO₄, concentrated to give 171 mg of the crude 4-bromo-6-(dibromomethyl)isoquinoline as a yellow solid.

This intermediate is dissolved in a mixture of 3 mL of ethanol and 3 mL of water and 153 mg (0.9 mmol) of AgNO₃ are added. The reaction mixture is stirred at 100° C. for 1 h. The solvent is evaporated under reduced pressure and the residue is purified by column chromatography (PE/EA=1/3) to give 56 mg of the desired product as a white semisolid.

MS (ESI+): 299.9 [M+H].

¹H NMR (400 MHz, CDCl₃) δ ppm: 10.31 (s, 1H), 9.29 (s, 1H), 8.87 (s, 1H), 8.67 (s, 1H), 8.26-8.12 (m, 2H).

4-(4-Benzyloxyphenyl)isoquinoline-6-carbaldehyde is prepared from 4-bromoisoquinoline-6-carbaldehyde and 2-[4-(benzyloxy)phenyl]-4,4,5,5-tetramethyl-1,3,2-dioxaborolane as described for Example 22.

A solution of 570 mg (1.68 mmol) of 4-(4-benzyloxyphenyl)isoquinoline-6-carbaldehyde in 8 mL of acetonitrile is cooled with an ice-water bath before a solution of 1519 mg (16.8 mmol) of NaClO₂ and 2015 mg (16.8 mmol) of NaH₂PO₄ in 10 mL of water is added dropwise. The solution is stirred at rt for 2 h. Then it is acidified to pH=4 with 0.1 N HCl solution and extracted with EA. The organic phase is washed with brine and dried over Na₂SO₄. The solvent is removed under reduced pressure to give 600 mg of the desired product as a light yellow solid.

MS (ESI+): 356.1 [M+H].

¹H NMR (400 MHz, DMSO-d₆) δ ppm: 9.41 (s, 1H), 8.50-8.49 (m, 2H), 8.31-8.13 (m, 2H), 7.51-7.22 (m, 9H), 5.21 (s, 2H).

(4-Amino-1-piperidyl)-[4-(4-hydroxyphenyl)-6-isoquinolyl]methanone (Example 28)

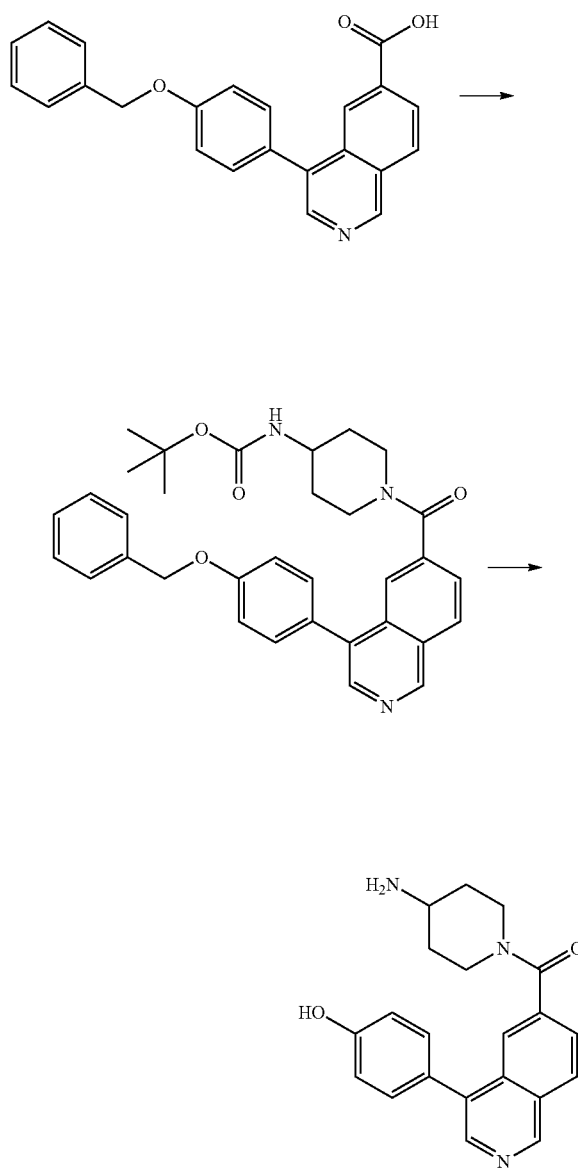

112 mg (0.56 mmol) of 4-N-Boc-aminopiperidine are added to a solution of 180 mg (0.51 mmol) of 4-(4-benzyloxyphenyl)isoquinoline-6-carboxylic acid, 289 mg (0.78 mmol) of HATU and 0.18 mL (1.01 mmol) of DIPEA in 12 mL of DMF and the mixture is stirred for 18 h at rt. Then it is diluted with EA, washed with water and brine, dried over Na₂SO₄ and concentrated to give 290 mg of the crude tert-butyl N-[1-[4-(4-benzyloxyphenyl)isoquinoline-6-carbonyl]-4-piperidyl]carbamate.

A mixture of 200 mg (0.37 mmol) of this intermediate in 15 mL of TFA is stirred at 60° C. for 4 h. The reaction mixture is concentrated under reduced pressure and the residue is purified by preparative HPLC to give 84 mg of the desired product.

MS (ESI+): 348.3 [M+H].

¹H NMR (400 MHz, DMSO-d₆+D₂O) δ ppm: 9.49 (s, 1H), 8.49 (s, 1H), 8.41 (d, J=4.2 Hz, 1H), 7.88 (s, 1H), 7.77-7.75 (m, 1H), 7.41-7.38 (m, 2H), 7.00-6.97 (m, 2H), 4.49-4.46 (m, 1H), 3.60-2.85 (m, 4H), 2.00-1.34 (m, 4H).

4-[6-[(4-Amino-1-piperidyl)methyl]-4-isoquinolyl]benzoic acid (Example 29)

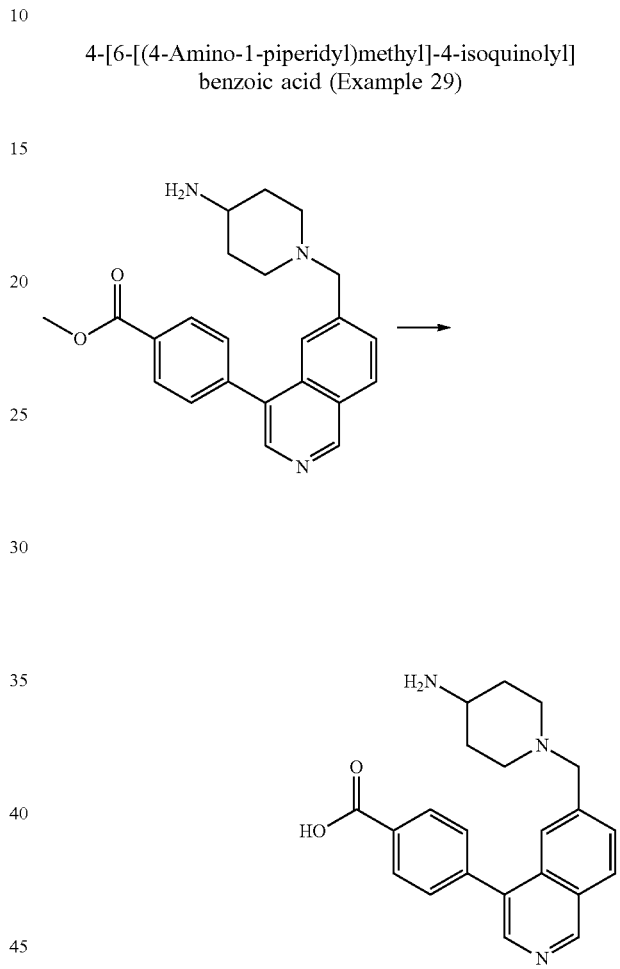

A mixture of 80 mg (0.21 mmol) of methyl 4-[6-[(4-amino-1-piperidyl)methyl]-4-isoquinolyl]benzoate and 511 mg (21.3 mmol) of LiOH in 6 mL of H₂O and 3 mL of EtOH was stirred at 25° C. for 10 h. After the reaction was complete, 37% hydrochloride acid was added until pH=8. The resulting solution was purified directly by preparative HPLC to give 66 mg of the product as a white solid.

MS (ESI+): 362.1 [M+H].

¹H NMR (400 MHz, DMSO-d₆+D₂O) δ ppm: 9.29 (s, 1H), 8.41 (s, 1H), 8.19 (d, J=8.8 Hz, 1H), 8.08 (d, J=8.0Hz, 2H), 7.76 (s, H, H-e), 7.67 (dd, J1=8.4 Hz, J1=1.2 Hz, 1H), 7.59 (d, J=8.0 Hz, 2H), 3.63 (s, 2H, H-f), 2.90-3.00 (m, 1H, H-i), 2.75-2.85+1.98-2.10 (2m, 4H), 1.78-1.88+1.40-1.52 (2m, 4H).

The following example was prepared accordingly to Example 29 by the hydrolization reaction of methyl 3-[6-[(4-amino-1-piperidyl)methyl]-4-isoquinolyl]benzoate with LiOH in H₂O/EtOH:

| Example | | ¹H NMR (400 MHz) δ ppm | MS (+ESI) [M + H]⁺ |
|---|---|---|---|
| 30 | 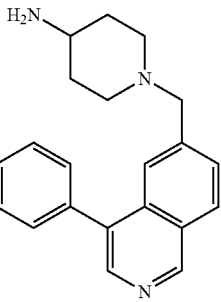 | (DMSO-d₆ + D₂O) δ ppm: 9.29 (s, 1H), 8.41 (s, 1H), 8.19 (d, J = 8.4 Hz, 1H), 8.04 (m, 2H), 7.81 (s, 1H), 7.62-7.72 (m, 3H), 3.63 (s, 2H), 2.90-2.98 (m, 1H), 2.75-2.82 + 2.00-2.10 (2m, 4H), 1.75-1.83 + 1.46-1.58 (2m, 4H) | 362.1 |

1-[4-[6-[(4-Amino-1-piperidyl)methyl]-4-isoquinolyl]phenyl]-3-phenyl-urea (Example 31)

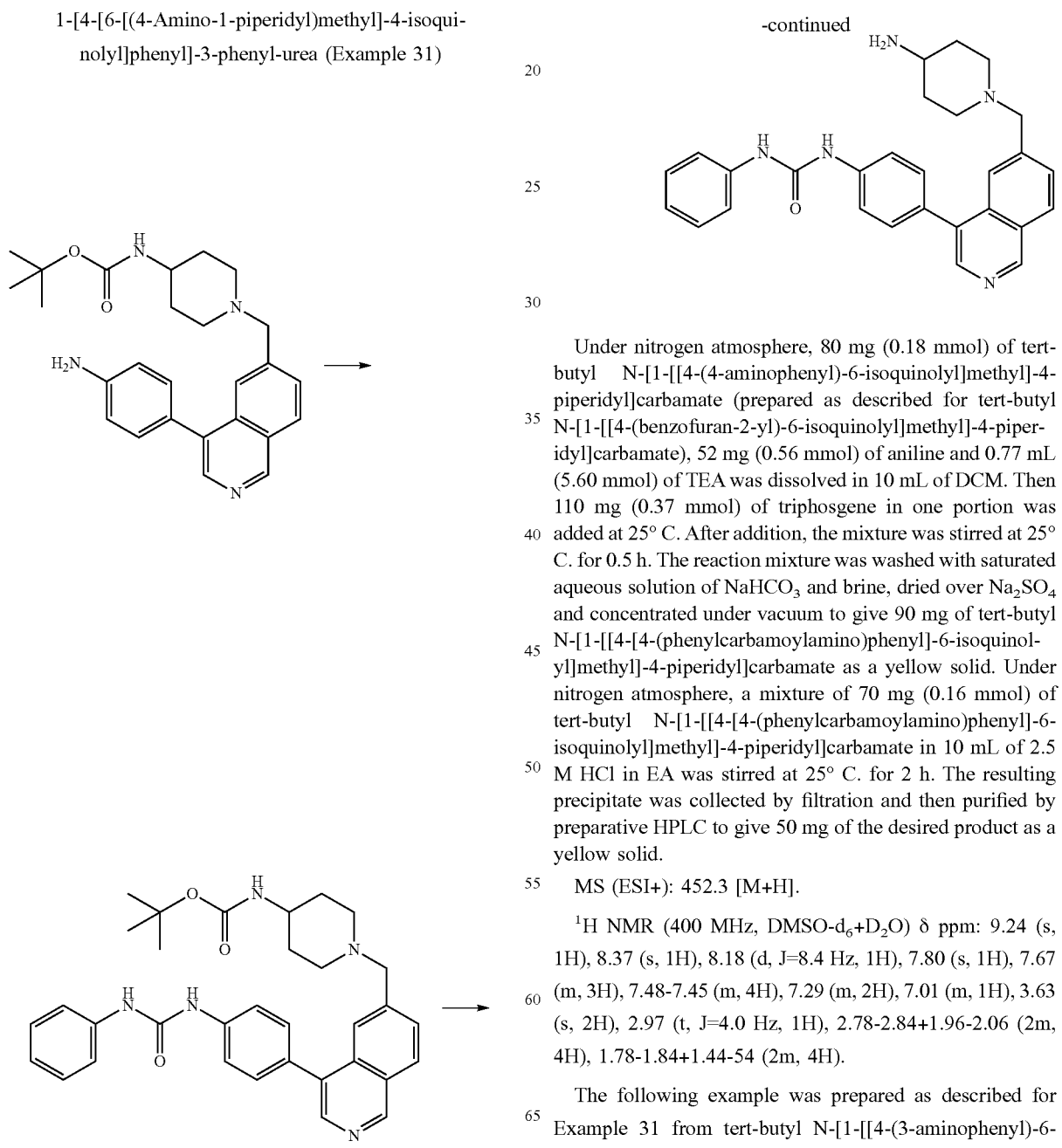

Under nitrogen atmosphere, 80 mg (0.18 mmol) of tert-butyl N-[1-[[4-(4-aminophenyl)-6-isoquinolyl]methyl]-4-piperidyl]carbamate (prepared as described for tert-butyl N-[1-[[4-(benzofuran-2-yl)-6-isoquinolyl]methyl]-4-piperidyl]carbamate), 52 mg (0.56 mmol) of aniline and 0.77 mL (5.60 mmol) of TEA was dissolved in 10 mL of DCM. Then 110 mg (0.37 mmol) of triphosgene in one portion was added at 25° C. After addition, the mixture was stirred at 25° C. for 0.5 h. The reaction mixture was washed with saturated aqueous solution of NaHCO₃ and brine, dried over Na₂SO₄ and concentrated under vacuum to give 90 mg of tert-butyl N-[1-[[4-[4-(phenylcarbamoylamino)phenyl]-6-isoquinolyl]methyl]-4-piperidyl]carbamate as a yellow solid. Under nitrogen atmosphere, a mixture of 70 mg (0.16 mmol) of tert-butyl N-[1-[[4-[4-(phenylcarbamoylamino)phenyl]-6-isoquinolyl]methyl]-4-piperidyl]carbamate in 10 mL of 2.5 M HCl in EA was stirred at 25° C. for 2 h. The resulting precipitate was collected by filtration and then purified by preparative HPLC to give 50 mg of the desired product as a yellow solid.

MS (ESI+): 452.3 [M+H].

¹H NMR (400 MHz, DMSO-d₆+D₂O) δ ppm: 9.24 (s, 1H), 8.37 (s, 1H), 8.18 (d, J=8.4 Hz, 1H), 7.80 (s, 1H), 7.67 (m, 3H), 7.48-7.45 (m, 4H), 7.29 (m, 2H), 7.01 (m, 1H), 3.63 (s, 2H), 2.97 (t, J=4.0 Hz, 1H), 2.78-2.84+1.96-2.06 (2m, 4H), 1.78-1.84+1.44-54 (2m, 4H).

The following example was prepared as described for Example 31 from tert-butyl N-[1-[[4-(3-aminophenyl)-6-isoquinolyl]methyl]-4-piperidyl]carbamate:

| Example | ¹H NMR (400 MHz) δ ppm | MS (+ESI) [M + H]⁺ |
|---|---|---|
| 32 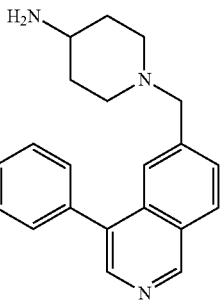 | (DMSO-d₆ + D₂O) δ ppm: 9.30 (s, 1H), 8.35 (s, 1H), 8.19 (d, J = 8.4 Hz, 1H), 7.80 (s, 1H), 7.71-7.67 (m, 2H), 7.54-7.43 (m, 4H), 7.28 (t, J = 8.0 Hz, 2H), 7.14 (m, 1H), 6.98 (t, J = 7.6 Hz, 1H), 3.63 (s, 2H), 2.90-3.00 (m, 1H), 2.78-2.85 + 1.98-2.08 (2m, 4H), 1.79-1.88 + 1.40-1.53 (2m, 4H) | 452.3 |

[4-[6-[(4-Amino-1-piperidyl)methyl]-4-isoquinolyl]phenyl]urea (Example 33)

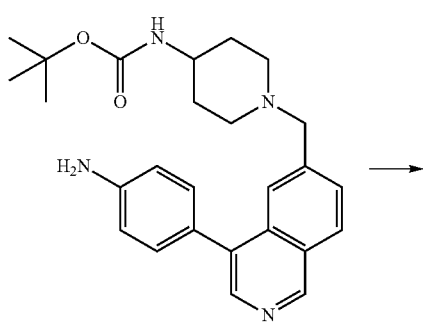

↓

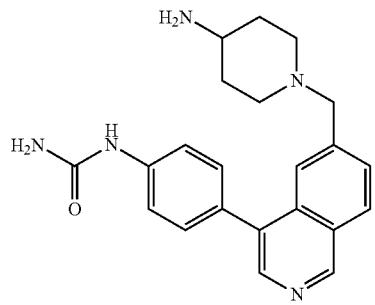

A mixture of 80 mg (0.18 mmol) of tert-butyl N-[1-[[4-(4-aminophenyl)-6-isoquinolyl]methyl]-4-piperidyl]carbamate (prepared as described for tert-butyl N-[1-[[4-(benzofuran-2-yl)-6-isoquinolyl]methyl]-4-piperidyl]carbamate) and 18 mg (0.22 mmol) of potassium cyanate in 1 mL of AcOH and 5 mL of water was stirred at 25° C. for 1 h. The resulting precipitate was collected by filtration to give 80 mg of tert-butyl N-[1-[[4-(4-ureidophenyl)-6-isoquinolyl]methyl]-4-piperidyl]carbamate as a yellow solid. Under nitrogen atmosphere, a mixture of 80 mg (0.17 mmol) of tert-butyl N-[1-[[4-(4-ureidophenyl)-6-isoquinolyl]methyl]-4-piperidyl]carbamate in 10 mL of 2.5M HCl in EA was stirred at 25° C. for 2 h. The resulting precipitate was collected by filtration and then purified by preparative HPLC to give 85 mg of the product as a yellow solid.

MS (ESI+): 376.3 [M+H].

¹H NMR (400 MHz, DMSO-d₆+D₂O) δ ppm: 9.44 (s, 1H), 8.50 (s, 1H), 8.39 (d, J=8.4 Hz, 1H), 8.37 (s, 1H), 7.85 (d, J=7.6 Hz, 1H), 7.63 (d, J=8.4Hz, 2H), 7.49 (d, J=8.4 Hz, 2H), 4.48 (s, 2H), 3.35-3.50+3.00-3.15 (2m, 4H), 3.20-3.30 (m, 1H), 2.00-2.10+1.60-1.80 (2m, 4H).

The following example was prepared as described for Example 33 from tert-butyl N-[1-[[4-(3-aminophenyl)-6-isoquinolyl]methyl]-4-piperidyl]carbamate:

| Example | | ¹H NMR (400 MHz) δ ppm | MS (+ESI) [M + H]⁺ |
|---|---|---|---|
| 34 | 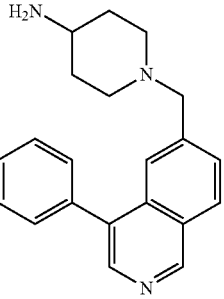 | (DMSO-d₆ + D₂O) δ ppm: 9.46 (s, 1H), 8.51 (s, 1H), 8.39 (d, J = 8.4 Hz, 1H), 8.09 (s, 1H), 7.84 (dd, J1 = 1.2 Hz, J2 = 8.4 Hz, 1H), 7.77 (s, 1H), 7.48-7.38 (m, 2H), 7.16 (dd, J1 = 1.2 Hz, J2 = 8.0 Hz, 1H), 4.47 (s, 2H), 3.36-3.46 + 3.00-3.15 (2m, 4H), 3.18-3.30 (m, 1H), 2.03-2.12 + 1.60-1.78 (2m, 4H) | 376.3 | tert-Butyl N-[4-[(4-bromo-6-isoquinolyl)methylamino]butyl]carbamate tert-Butyl N-[4-[[4-(4-hydroxyphenyl)-6-isoquinolyl]methylamino]butyl]carbamate

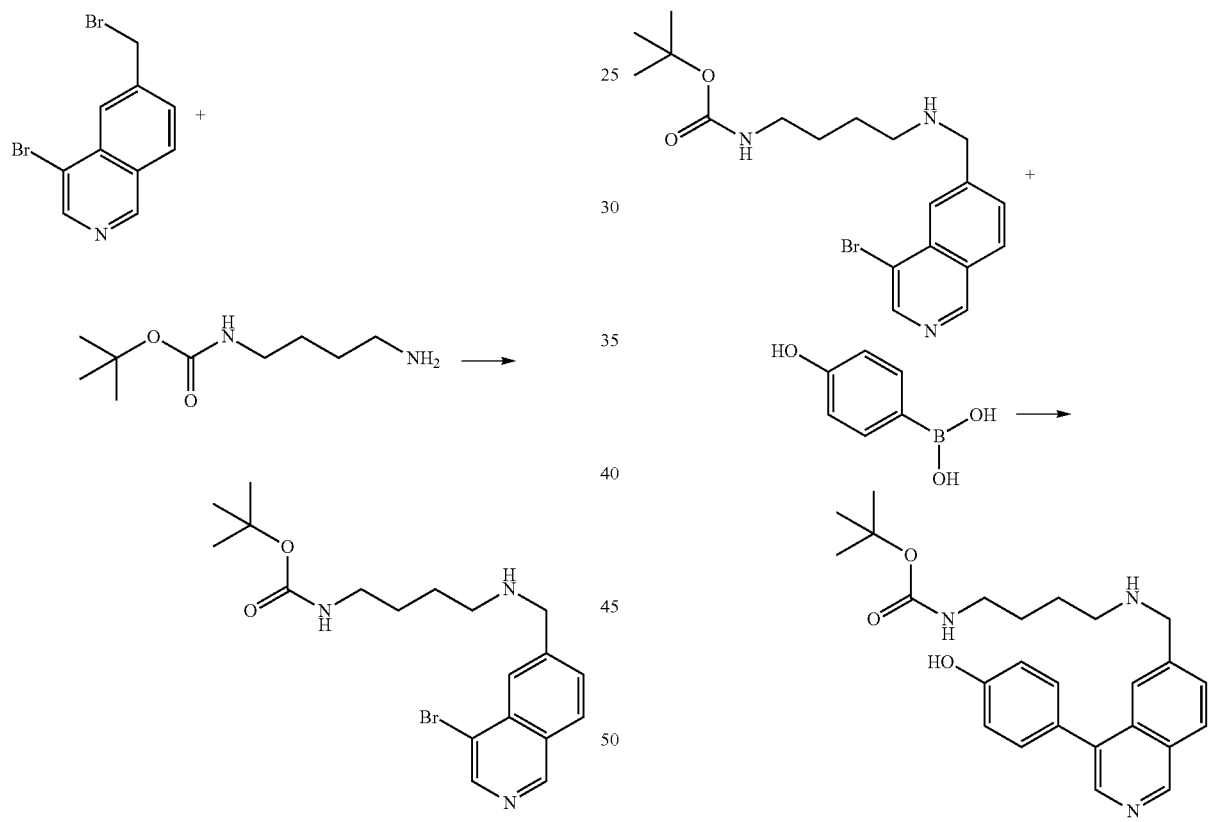

Under nitrogen atmosphere, a mixture of 200 mg (0.66 mmol) of 4-bromo-6-(bromomethyl)isoquinoline (CAS 98331-27-2), 150 mg (0.8 mmol) of N-boc-1,4-butanediamine (CAS 68076-36-8) and 138 mg (1.0 mmol) of K₂CO₃ in 10 mL of DMF was stirred at 25° C. for 1 h. The solvent was removed under vacuum. The residue was taken up in 20 mL of EA and then washed with water and brine, dried over Na₂SO₄ and concentrated under vacuum. The resulting residue was purified by silica gel column chromatography (DCM/MeOH=30/1) to give 165 mg of the product as a colorless oil.

MS (ESI+): 408.3, 410.3 [M+H].

To a solution of 165 mg (0.40 mmol) of tert-butyl N-[4-[(4-bromo-6-isoquinolyl)methylamino]butyl]carbamate, 67 mg (0.48 mmol) of 4-hydroxyphenylboronic acid (CAS 71597-85-8) and 112 mg (0.81 mmol) of K₂CO₃ in 10 mL of dioxane and 2 mL of H₂O was added 47 mg (0.04 mmol) of Pd(PPh₃)₄. Under nitrogen atmosphere, the mixture was stirred at 80° C. for 2 h. When TLC showed that the reaction was complete, the solvent was removed under reduced pressure. The residue was taken up in 30 mL of EA and then filtered through Celite. The filtrate was washed with water and brine, dried over Na₂SO₄ and concentrated under reduced pressure. The residue was purified by silica gel column chromatography (DCM/MeOH=15/1) to give 116 mg of the product as a yellow foam.

MS (ESI+): 422.5 [M+H].

4-[6-[(4-Aminobutylamino)methyl]-4-isoquinolyl]phenol (Example 35)

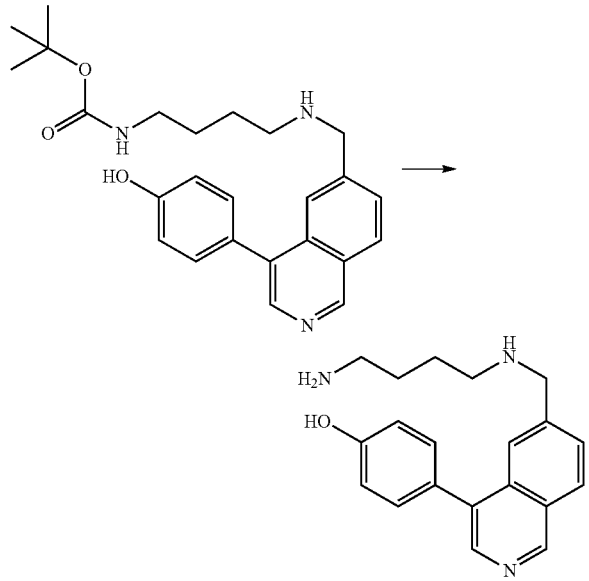

To a solution of 116 mg (0.28 mmol) of tert-butyl N-[4-[[4-(4-hydroxyphenyl)-6-isoquinolyl]methylamino]butyl]carbamate in 10 mL of EtOH at 20° C. was added 1 mL of 37% hydrochloric acid. Under nitrogen atmosphere, the mixture was stirred at 45° C. for 3 h. When TLC showed that the reaction was complete, the reaction mixture was cooled to 20° C. and the resulting precipitate was collected by filtration to give 54 mg of the product as a light yellow solid.

MS (ESI+): 322.2 [M+H].

$^1$H NMR (400 MHz, DMSO-d$_6$+D$_2$O) δ ppm: 9.66 (s, 1H), 8.54 (s, 1H), 8.53 (d, J=8.4 Hz, 1H), 8.21 (s, 1H), 8.05 (d, J=8.8 Hz, 1H), 7.48 (d, J=8.4 Hz, 2H), 7.03 (d, J=8.4 Hz, 2H), 4.39 (s, 2H), 2.99 (t, J=7.6 Hz, 2H), 2.79 (t, J=7.6 Hz, 2H), 1.46-1.73 (m, 4H).

The following examples were prepared accordingly to Example 35 by reaction of 4-bromo-6-(bromomethyl)isoquinoline (CAS 98331-27-2) with the corresponding amine, then Suzuki coupling with (4-hydroxyphenyl)boronic acid in the presence of a Pd-catalyst and subsequent deprotection:

| Example | | $^1$H NMR (400 MHz) δ ppm | MS (+ESI) [M + H]$^+$ |
|---|---|---|---|
| 36 | (structure) | (DMSO-d$_6$ + D$_2$O) δ ppm: 9.59 (s, 1H), 8.53 (s, 1H), 8.49 (d, J = 8.4 Hz, 1H), 8.22 (s, 1H), 8.05 (d, J = 8.4 Hz, 1H), 7.47 (d, J = 8.4 Hz, 2H), 7.01 (d, J = 8.4 Hz, 2H), 4.41-4.73 (m, 2H), 3.12-3.29 (m, 2H), 2.85 (t, J = 7.2 Hz, 2H), 2.68 (s, 3H), 2.00-2.12 (m, 2H) | 322.3 |
| 37 | (structure) | (DMSO-d$_6$ + D$_2$O) 9.62 (s, 0.3H), 9.61 (s, 0.7H), 8.53 (s, 1H), 8.51 (d, J = 8.4 Hz, 1H), 8.22 (s, 0.3H), 8.19 (s, 0.7H), 8.00-8.09 (m, 1H), 7.02-7.50 (m, 2H), 7.01 (d, J = 8.4 Hz, 2H), 4.44 (s, 0.6H), 4.41 (s, 1.4H), 2.89-3.32 (m, 2H), 1.25-2.20 (m, 8H) | 348.1 |

-continued
| Example | | ¹H NMR (400 MHz) δ ppm | MS (+ESI) [M + H]⁺ |
|---|---|---|---|
| 38 | 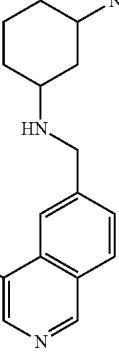 | (DMSO-d₆ + D₂O) 9.60 (s, 1 H), 8.52 (s, 1H), 8.48 (d, J = 8.4 Hz, 1H), 8.20 (s, 0.7H), 8.19 (s, 0.3H), 7.99-8.06 (m, 1H), 7.47 (d, J = 8.4 Hz, 2H), 7.01 (d, J = 8.4 Hz, 2H), 4.42-4.53 (m, 2H), 3.00-3.61 (m, 2H), 1.20-2.41 (m, 8H) | 348.3 |
| 39 | 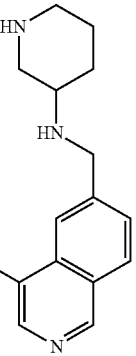 | (DMSO-d₆ + D₂O) 9.45 (s, 1 H), 8.48 (s, 1H), 8.39 (d, J = 8.4 Hz, 1H), 8.12 (s, 1H), 7.86 (d, J = 8.4 Hz, 1H), 7.41 (d, J = 8.4 Hz, 2H), 6.99 (d, J = 8.4 Hz, 2H), 4.44 (s, 2 H), 2.70-3.61 (m, 5H), 1.48-2.29 (m, 4H) | 334.1 |
| 40 | 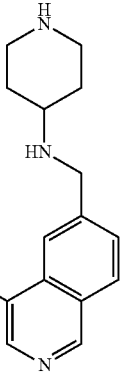 | (DMSO-d₆ + D₂O) 9.60 (s, 1 H), 8.52 (s, 1H), 8.50 (d, J = 8.4 Hz, 1H), 8.21 (s, 1H), 8.03 (d, J = 8.4 Hz, 1H), 7.47 (d, J = 8.4 Hz, 2H), 7.02 (d, J = 8.4 Hz, 2H), 4.43 (s, 2 H), 2.83-3.50 (m, 5H), 1.71-2.31 (m, 4H) | 334.1 |
| 41 | 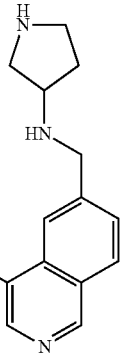 | (DMSO-d₆ + D₂O) 9.60 (s, 1 H), 8.53 (s, 1H), 8.51 (d, J = 8.4 Hz, 1H), 8.22 (s, 1H), 8.03 (d, J = 8.4 Hz, 1H), 7.47 (d, J = 8.4 Hz, 2H), 7.00 (d, J = 8.4 Hz, 2H), 4.46 (s, 2 H), 4.01 (m, 1H), 3.19-3.62 (m, 4H), 2.13-2.42 (m, 2H) | 320.2 |

2-(3-Hydroxycyclopentyl)isoindoline-1,3-dione

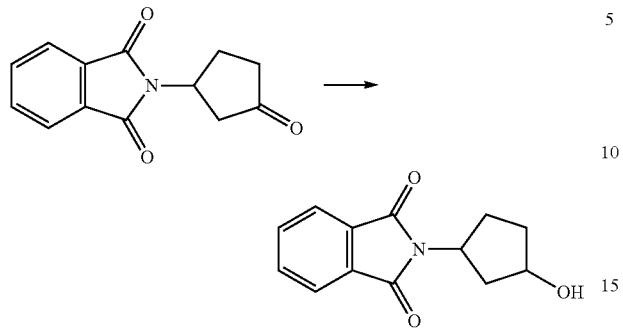

To a stirred solution of 200 mg (0.87 mmol) of 2-(3-oxocyclopentyl)isoindoline-1,3-dione (CAS 1029691-06-2) in 5 mL of DCM at 0° C. were added 10 mg (0.26 mmol) of NaBH$_4$ and then 1 mL of MeOH. The mixture was stirred at this temperature for 0.5 h. 20 mL of H$_2$O was added and the mixture was extracted with DCM. The combined organic layers were dried over Na$_2$SO$_4$ and then concentrated under vacuum. The residue was purified by silica gel column chromatography (PE/EA=2/1) to give 96 mg of the product as a white solid.

MS (ESI+): 232.0 [M+H].

$^1$H NMR (400 MHz, DMSO-d6) δ ppm: 7.76-7.83 (m, 5H), 4.80 (d, J=5.2 Hz, 1H), 4.43 (m, 1H), 4.06 (m, 1H), 1.64-2.15 (m, 6H).

[3-(1,3-Dioxoisoindolin-2-yl)cyclopentyl] methanesulfonate

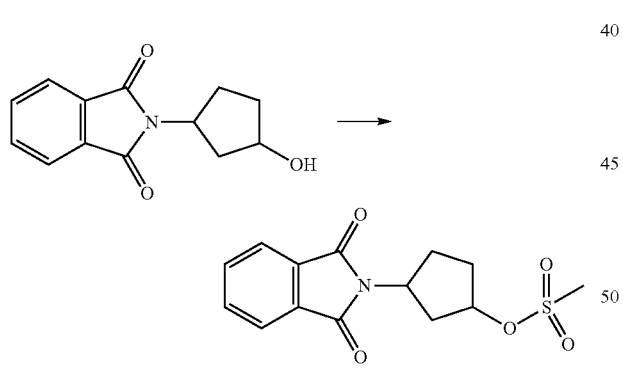

To a stirred solution of 90 mg (0.39 mmol) of 2-(3-hydroxycyclopentyl)isoindoline-1,3-dione and 163 μL (1.17 mmol) of TEA in 10 mL of DCM at 0° C. was added 45 μL (0.58 mmol) of MsCl. After stirred at this temperature for 1 h, the solution was diluted with DCM and then washed with saturated aqueous solution of NH$_4$Cl, dried over Na$_2$SO$_4$ and concentrated under vacuum to give 110 mg of the crude product as a white solid which was used directly in the next step without further purification.

MS (ESI+): 310.0 [M+H].

$^1$H NMR (400 MHz, CDCl$_3$) δ ppm: 7.70-7.88 (m, 4H), 5.16 (m, 1H), 4.61 (m, 1H), 3.07 (s, 3H), 1.90-2.61 (m, 6H).

2-(3-Azidocyclopentyl)isoindoline-1,3-dione

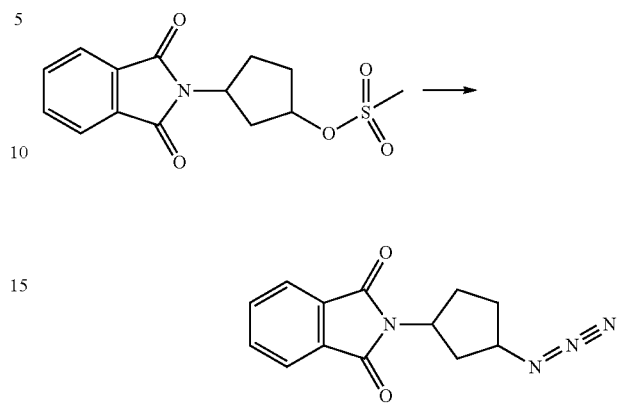

A mixture of 110 mg (0.36 mmol) of [3-(1,3-dioxoisoindolin-2-yl)cyclopentyl] methanesulfonate and 116 mg (1.78 mmol) of NaN$_3$ in 7 mL of DMF was heated to 80° C. and held for 2 h. The mixture was diluted with EA and then washed with saturated aqueous solution of NH$_4$Cl, and then dried over Na$_2$SO$_4$ and concentrated under vacuum to afford 90 mg of the crude product as a white solid which was used directly in the next step.

MS (ESI+): 257.1 [M+H].

$^1$H NMR (400 MHz, CDCl$_3$) δ ppm: 7.65-7.81 (m, 4H), 4.88 (m, 1H), 4.35 (m, 1H), 1.73-2.41 (m, 6H).

2-(3-Aminocyclopentyl)isoindoline-1,3-dione

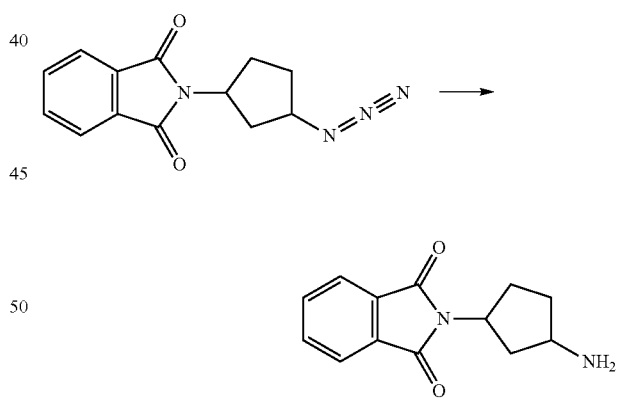

To a solution of 90 mg (0.35 mmol) of 2-(3-azidocyclopentyl)isoindoline-1,3-dione in 10 mL of MeOH at 20° C. was added 37 mg (0.04 mmol) of Pd/C (10%). The mixture was stirred at 20° C. for 16 h under hydrogen atmosphere (pressure: 1 Atm.). The mixture was filtered through Celite and the filtrate was concentrated under vacuum to give 72 mg of the crude product as a colorless oil which was used directly in the next step.

MS (ESI+): 231.0 [M+H].

$^1$H NMR (400 MHz, CDCl$_3$) δ ppm: 7.63-7.81 (m, 4H), 4.89 (m, 1H), 3.80 (m, 1H), 1.23-2.32 (m, 6H).

63

2-[3-[(4-Bromo-6-isoquinolyl)methylamino]cyclopentyl]isoindoline-1,3-dione

64

2-[3-[[4-(4-Hydroxyphenyl)-6-isoquinolyl]methylamino]cyclopentyl]isoindoline-1,3-dione

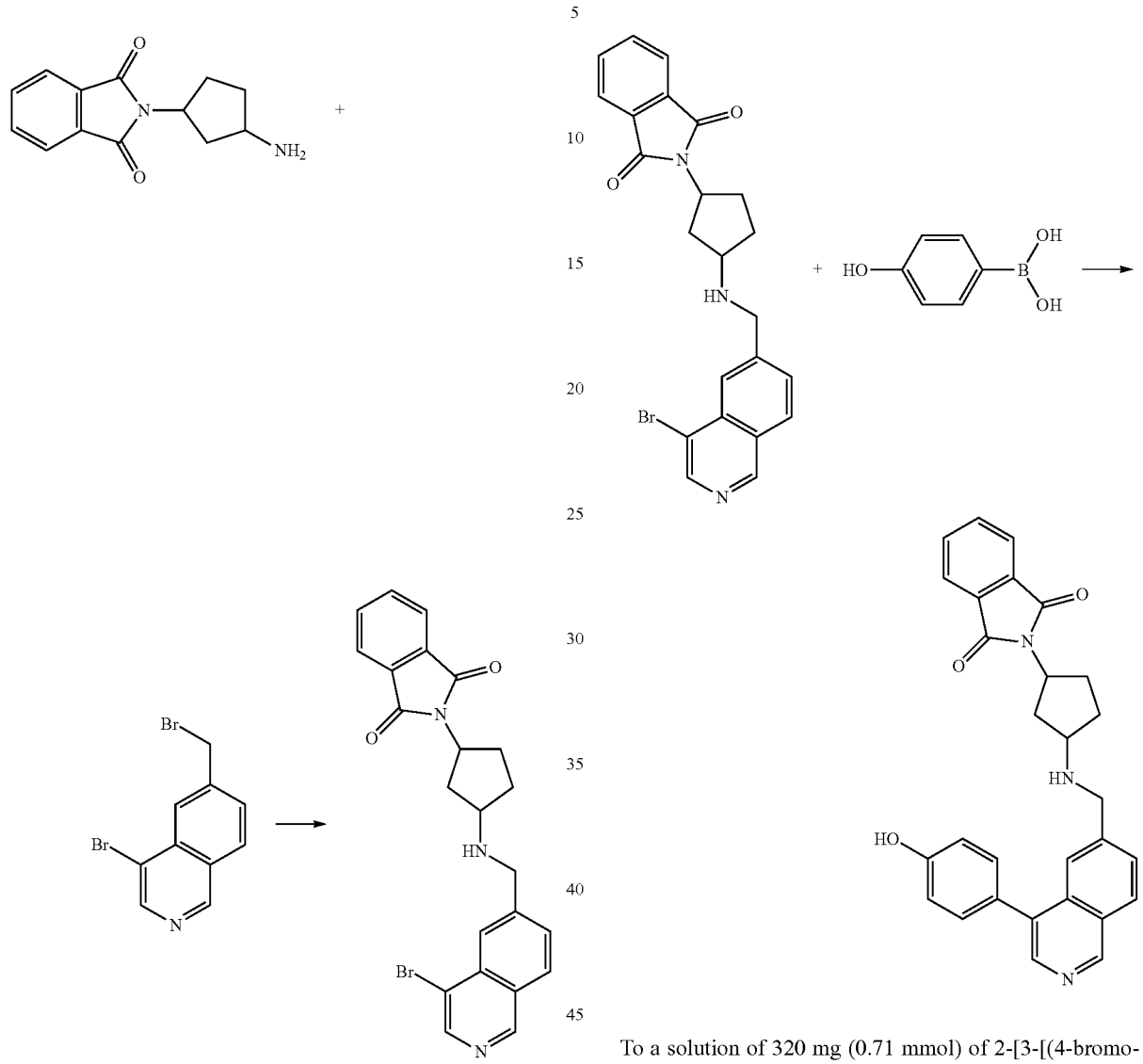

Under nitrogen atmosphere, a mixture of 270 mg (1.17 mmol) of 2-(3-aminocyclopentyl) isoindoline-1, 3-dione, 353 mg (1.17 mmol) of 4-bromo-6-(bromomethyl)isoquinoline (CAS 98331-27-2) and 243 mg (1.76 mmol) of $K_2CO_3$ in 20 mL of DMF was stirred at 20° C. for 1 h. The reaction mixture was concentrated under reduced pressure and the residue was taken up in 30 of EA. The resultant suspension was washed with saturated aqueous solution of $NH_4Cl$. The organic phase was dried over $Na_2SO_4$ and concentrated under vacuum. The residue was purified by silica gel column chromatography (DCM/MeOH=30/1) to give 320 mg of the product as a light yellow semisolid.

MS (ESI+): 450.0 [M+H].

To a solution of 320 mg (0.71 mmol) of 2-[3-[(4-bromo-6-isoquinolyl) methylamino] cyclopentyl]isoindoline-1,3-dione, 118 mg (0.85 mmol) of 4-hydroxyphenylboronic acid (CAS 71597-85-8) and 196 mg (1.42 mmol) of $K_2CO_3$ in 10 mL of ioxane and 2 mL of $H_2O$ was added 82 mg (0.07 mmol) of $Pd(PPh_3)_4$. Under nitrogen atmosphere, the mixture was stirred at 80° C. for 2 h. The solvent was removed under reduced pressure and the residue was taken up in 30 mL of EA. The mixture was filtered through Celite and the filtrate was washed with of $H_2O$ and brine successively. The organic phase was dried over $Na_2SO_4$ and concentrated under vacuum. The residue was purified by silica gel column chromatography (DCM/MeOH=15/1) to afford 243 mg of the product as a light yellow foam.

MS (ESI+): 464.1 [M+H].

65

4-[6-[[(3-Aminocyclopentyl)amino]methyl]-4-isoquinolyl]phenol (Example 42)

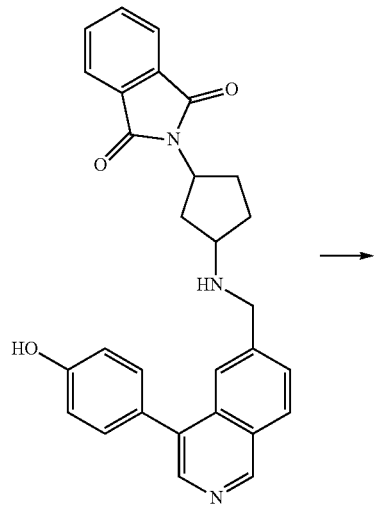

To a solution of 243 mg (0.52 mmol) of 2-[3-[[4-(4-hydroxyphenyl)-6-isoquinolyl] methylamino]cyclopentyl] isoindoline-1,3-dione in 15 mL of EtOH was added 1 mL of 80% hydrazine hydrate. The mixture was refluxed for 3.5 h. After cooling to 20° C., the resulting precipitate was filtered off and the filtrate was concentrated under vacuum. The residue was purified by preparative HPLC to give the product as a light yellow solid.

MS (ESI+): 334.2 [M+H].

$^1$H NMR (400 MHz, DMSO-d6+D$_2$O) δ ppm: 9.49 (s, 1 H), 8.49 (s, 1H), 8.42 (d, J=8.4 Hz, 1H), 8.14 (s, 1H), 7.89 (d, J=8.4 Hz, 1H), 7.42 (d, J=8.4 Hz, 2H), 7.00 (d, J=8.4 Hz, 2H), 4.29-4.41 (m, 2 H), 3.62-3.78 (m, 2H), 1.50-2.29 (m, 6H).

66 tert-Butyl N-[(4-bromo-6-isoquinolyl)methyl]-N-[3-(dimethylamino)propyl]carbamate

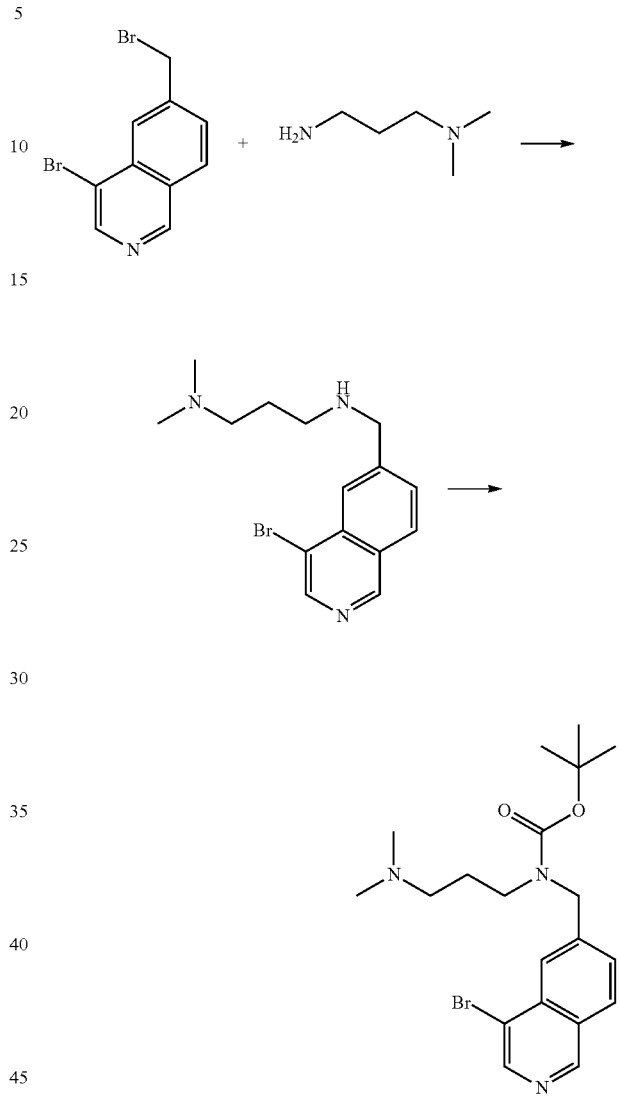

300 mg (1.0 mmol) of 4-bromo-6-(bromomethyl)isoquinoline (CAS 98331-27-2) was added in portions to 6 mL of N,N-dimethyl-propanediamine (CAS 109-55-7) at 0° C. After stirring for 0.5 h, the mixture was concentrated under vacuum. The residue was dissolved in 10 mL of DCM and 2 mL of CH$_3$CN. 0.42 mL (3.0 mmol) of TEA was added at 0° C., followed by addition of 653 mg (3.0 mmol) of Boc$_2$O. Then the mixture was stirred at 20° C. for 3 h. The reaction mixture was diluted with 20 mL of DCM and then washed with water and brine, dried over Na$_2$SO$_4$, and concentrated undervacuum. The residue was purified by silica gel column chromatography (DCM/MeOH=15/1) to give the product as a light yellow oil.

MS (ESI+) 422.4 [M+H].

tert-Butyl N-[3-(dimethylamino)propyl]-N-[[4-(4-hydroxyphenyl)-6-isoquinolyl]methyl] carbamate

4-[6-[[3-(Dimethylamino)propylamino]methyl]-4-isoquinolyl]phenol (Example 43)

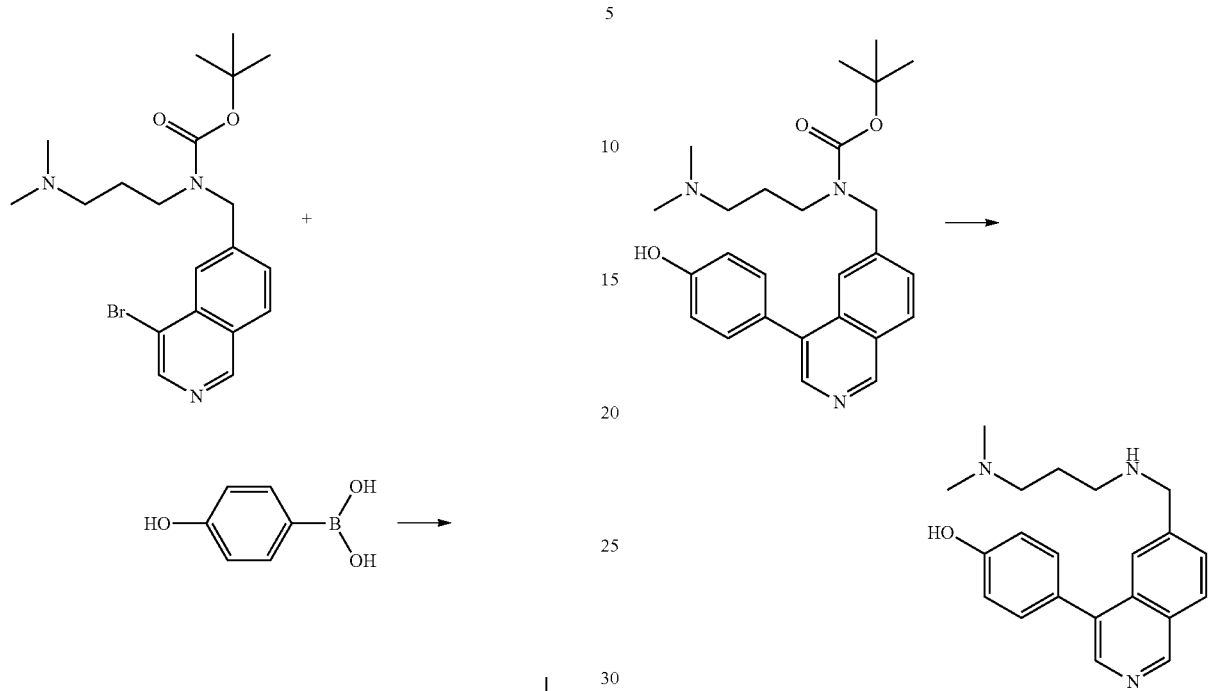

To a solution of 226 mg (0.52 mmol) of tert-butyl N-[3-(dimethylamino)propyl]-N-[[4-(4-hydroxyphenyl)-6-isoquinolyl]methyl] carbamate in 10 mL of EtOH at 20° C. was added 1 mL of 37% hydrochloric acid. The mixture was heated to 45° C. and held for 3 h. After cooling to 20° C., the resulting precipitate was collected by filtration to give the desired product as a light yellow solid.

MS (ESI+) 336.3 [M+H].

$^1$H NMR (400 MHz, DMSO-$d_6$+$D_2O$) δ ppm: 9.60 (s, 1H), 8.52 (s, 1H), 8.49 (d, J=8.4 Hz, 1H), 8.19 (s, 1H), 8.01 (d, J=8.4 Hz, 1H), 7.47 (d, J=8.4 Hz, 2H), 7.01 (d, J=8.4 Hz, 2H), 4.39 (s, 2H), 3.01-3.15 (m, 4H), 2.75 (s, 6H), 1.98-2.07 (m, 2H).

To a mixture of 0.133 g (0.32 mmol) of tert-butyl N-[(4-bromo-6-isoquinolyl)methyl]-N-[3-(dimethylamino)propyl] carbamate and 52 mg (0.38 mmol) of 4-hydroxyphenylboronic acid (CAS 71597-85-8) and 88 mg (0.63 mmol) of K$_2$CO$_3$ in 10 mL of dioxane and 2 mL of H$_2$O was added 37 mg (0.03 mmol) of Pd(PPh$_3$)$_4$. The mixture was heated to 80° C. and held for 2 hours under nitrogen atmosphere. The solvent was removed under reduced pressure and the residue was taken up in 30 mL of EA. The suspension was filtered through Celite and the filtrate was washed with H$_2$O and brine successively. The organic phase was dried over Na$_2$SO$_4$ and concentrated under reduced pressure to give 116 mg of the crude product as a light yellow foam which was used directly in the next step.

MS (ESI+) 436.6 [M+H].

tert-Butyl N-[3-[(4-bromo-6-isoquinolyl)methoxy]propyl]carbamate

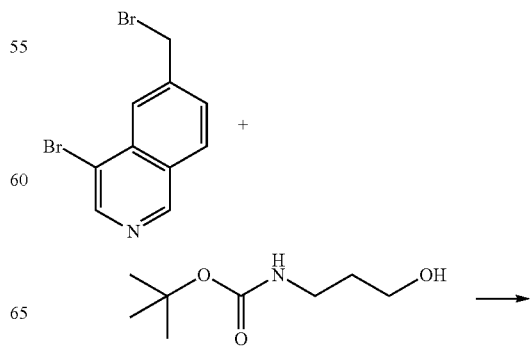

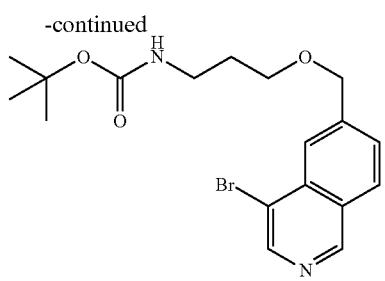

To a stirred solution of 0.14 mL (0.8 mmol) of 3-(Boc-amino)-1-propanol (CAS 58885-58-8) in 5 mL of DMF at 0° C. was added 40 mg (60% dispersion in mineral oil, 1.0 mmol) of NaH. After stirring for 0.5 h, a solution of 200 mg (0.66 mmol) of 4-bromo-6-(bromomethyl)isoquinoline (CAS 98331-27-2) in 2 mL of DMF was added dropwise. The resulting mixture was stirred at 20° C. for 16 h. The reaction was quenched with 30 mL of $H_2O$ and then extracted with EA. The combined organic layers were dried over $Na_2SO_4$ and concentrated under vacuum. The residue was purified by preparative TLC (PE/EA=2/1) to give 43 mg of the pure product as a colorless semisolid.

MS (ESI+) 395.4 [M+H].

tert-Butyl N-[3-[[4-(4-hydroxyphenyl)-6-isoquinolyl]methoxy]propyl]carbamate

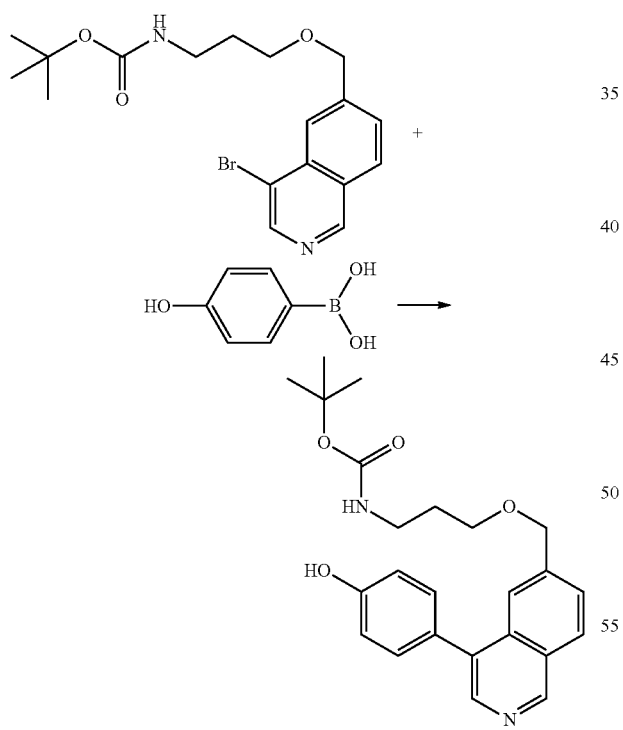

To a stirred mixture of 143 mg (0.36 mmol) of tert-butyl N-[3-[(4-bromo-6-isoquinolyl)methoxy]propyl]carbamate, 60 mg (0.43 mmol) of 4-hydroxyphenylboronic acid (CAS 71597-85-8) and 100 mg (0.72 mmol) of $K_2CO_3$ in 10 mL of dioxane and 2 mL of $H_2O$ was added 42 mg (0.04 mmol) of $Pd(PPh_3)_4$. Under nitrogen atmosphere, the mixture was heated to 80° C. and held for 2 h. The solvent was removed under reduced pressure and the residue was taken up in 30 mL of EA. The suspension was filtered through Celite and then washed with $H_2O$ and brine successively. The organic phase was dried over $Na_2SO_4$ and concentrated under vacuum. The residue was purified by silica gel column chromatography (PE/EA=1/1) to give 136 mg of the product as a light yellow foam.

MS (ESI+) 409.5 [M+H].

4-[6-(3-Aminopropoxymethyl)-4-isoquinolyl]phenol (Example 44)

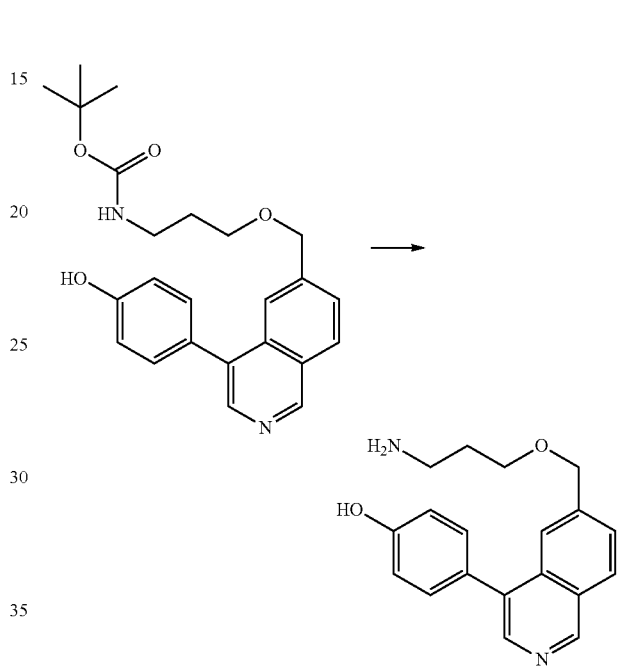

To a solution of 136 mg (0.33 mmol) of tert-butyl N-[3-[[4-(4-hydroxyphenyl)-6-isoquinolyl]methoxy]propyl]carbamate in 10 mL of EtOH at 20° C. was added 1 mL of 37% hydrochloric acid. Under nitrogen atmosphere, the mixture was stirred at 45° C. for 3 h. After cooling to 20° C., the resulting precipitate was collected by filtration to give 58 mg of the product as a light yellow solid.

MS (ESI+) 309.2 [M+H].

$^1$H NMR (400 MHz, DMSO-$d_6$+$D_2O$) δ ppm: 9.62 (s, 1H), 8.49 (s, 1H), 8.48 (d, J=8.4 Hz, 1H), 7.99 (s, 1H), 7.90 (d, J=8.4 Hz, 1H), 7.42 (d, J=8.4 Hz, 2H), 7.02 (d, J=8.4 Hz, 2H), 4.73 (s, 2H), 3.56 (t, J=6.0 Hz, 4H), 2.85 (t, J=7.6 Hz, 4H), 1.71-1.85 (m, 2H).

1-[(4-Bromo-6-isoquinolyl)methyl]-N,N-dimethyl-piperidin-4-amine

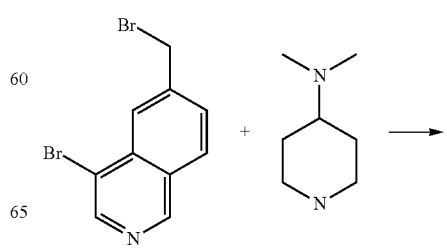

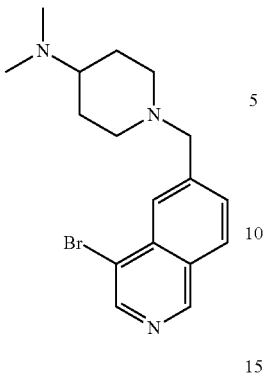

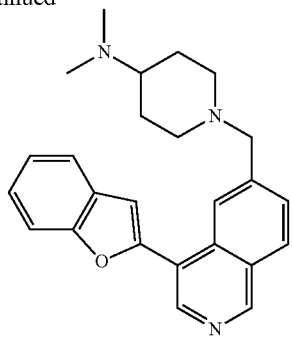

A mixture of 200 mg (0.66 mmol) of 4-bromo-6-(bromomethyl)isoquinoline (CAS 98331-27-2), 130 mg (0.66 mmol) of N,N-dimethylpiperidin-4-amine dihydrochloride (CAS 4876-59-9) and 320 mg (0.99 mmol) of K₂CO₃ in 8 mL of DMF was stirred at 25° C. for 2 h. The mixture was used directly in the next step.

MS (ESI+): 348.0/350.0 [M+H].

1-[[4-(Benzofuran-2-yl)-6-isoquinolyl]methyl]-N,N-dimethyl-piperidin-4-amine (Example 46)

Under argon atmosphere, the above mixture of 1-[(4-bromo-6-isoquinolyl)methyl]-N,N-dimethyl-piperidin-4-amine) was diluted with of 5 mL of dioxane and 5 mL of water. Then 130 mg (0.79 mmol) of benzofuran-2-ylboronic acid (CAS 98437-24-2), 180 mg (1.43 mmol) of K₂CO₃ and 76 mg (0.07 mmol) of Pd(PPh₃)₄ were added. The mixture was stirred at 80° C. for 2 h. Then the reaction mixture was filtered and the filtrate was concentrated under vacuum. The residue was purified by preparative HPLC to afford 150 mg of the product as a yellow solid.

MS (ESI+): 386.5 [M+H].

$^1$H NMR (400 MHz, DMSO-d$_6$+D$_2$O) δ ppm: 9.46 (s, 1H), 9.00 (s, 1H), 8.63 (s, 1H), 8.40 (d, 1H, J=7.6 Hz), 7.90-7.73 (m, 3H), 7.61 (d, 1H J=0.4 Hz), 7.46-7.34 (m, 2H), 4.61 (s, 2H), 3.55-3.05 (m, 5H), 2.74 (s, 6H), 2.20, 1.80 (m, 4H).

The following examples were prepared accordingly to Example 46 by reaction of 4-bromo-6-(bromomethyl)isoquinoline with the corresponding amines followed by coupling with benzofuran-2-ylboronic acid in the presence of Pd-catalyst:

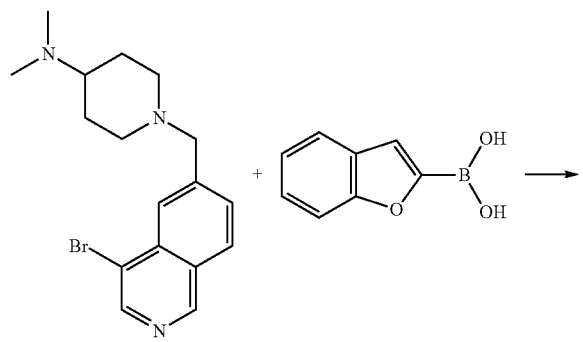

| Example | | $^1$H NMR (400 MHz) δ ppm | MS (+ESI) [M + H]$^+$ |
|---|---|---|---|
| 47 | | (DMSO-d$_6$ + D$_2$O) δ ppm: 9.8 (s, 1H), 8.85 (s, 1H), 8.48 (s, 1H), 8.36 (d, 1H, J = 7.6 Hz), 7.89-7.73 (m, 3H, H-d), 7.62 (d, 1H, J = 0.8 Hz), 7.46-7.34 (m, 2H), 4.08 (s, 2H), 3.50-2.60 (m, 8H), 2.79 (s, 3H) | 358.4 |

| Example | | ¹H NMR (400 MHz) δ ppm | MS (+ESI) [M + H]⁺ |
|---|---|---|---|
| 48 | 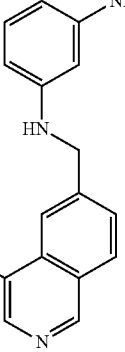 | (DMSO-d₆ + D₂O) 9.39 (s, 1H), 8.92 (s, 1H), 8.45 (s, 1H), 8.27 (d, 1H, J = 8.4 Hz), 7.82-7.60 (m, 3H), 7.44-7.33 (m, 3H), 7.19-7.14 (m, 1H), 6.64 (d, 1H, J = 8.0 Hz), 6.47-6.45 (m, 2H), 4.62 (s, 2H) | 366.4 |
| 50 | 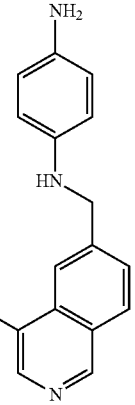 | (DMSO-d6 + D₂O) δ ppm: 9.29 (s, 1H), 8.85 (s, 1H), 8.36 (s, 1H), 8.19 (d, 1H, J = 8.4 Hz), 7.76-7.60 (m, 3H), 7.41-7.30 (m, 2H), 7.18 (s, 1H), 6.55-6.45 (m, 4H), 4.49 (s, 2H). | | tert-Butyl N-[[2-[[4-(benzofuran-2-yl)-6-isoquinolyl]methylamino]phenyl]methyl] carbamate

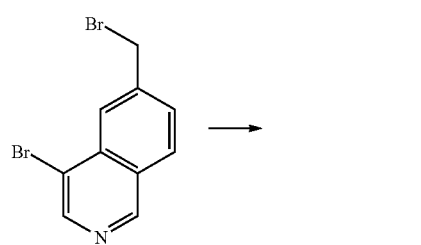

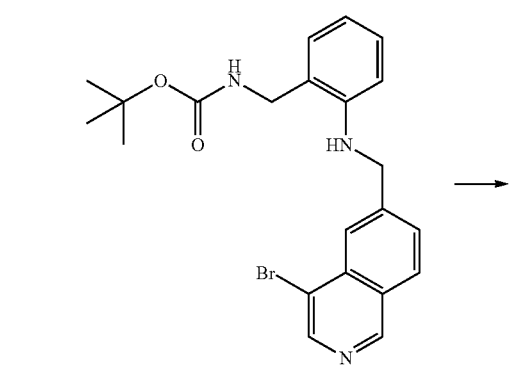

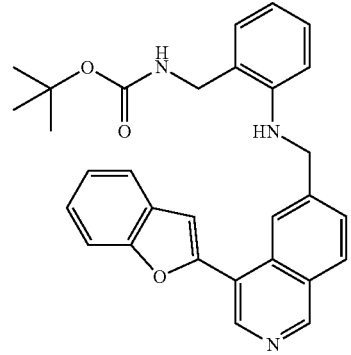

Under nitrogen atmosphere, a mixture of 200 mg (0.66 mmol) of 4-bromo-6-(bromomethyl)isoquinoline (CAS 98331-27-2), 150 mg (0.66 mmol) of tert-butyl-N-[(2-aminophenyl)methyl]carbamate (CAS 1620-50-6) and 140 mg (0.99 mmol) of K₂CO₃ in 8 mL of DMF was stirred at 100° C. for 3 h. When LCMS indicated that the reaction was complete, the mixture was cooled to 20° C. and then diluted with 5 mL of dioxane and 3 mL of H₂O followed by addition of 130 mg (0.79 mmol) of benzofuran-2-ylboronic acid (CAS 98437-24-2), 180 mg (1.32 mmol) of K₂CO₃ and 76 mg (0.07 mmol) of Pd(PPh₃)₄. The mixture was heated to 80° C. and held for 2 h. When LCMS indicated that the reaction was complete, the reaction mixture was diluted with 80 mL of EA and then washed with H₂O and brine successively. The organic phase was dried over anhydrous Na₂SO₄ and concentrated under vacuum. The residue was purified by silica gel column chromatography (PE/EA=2/1) to give 170 mg of the desired product as a yellow semisolid.

MS (ESI+): 480.3 [M+H].

2-(Aminomethyl)-N-[[4-(benzofuran-2-yl)-6-isoquinolyl]methyl]aniline (Example 51)

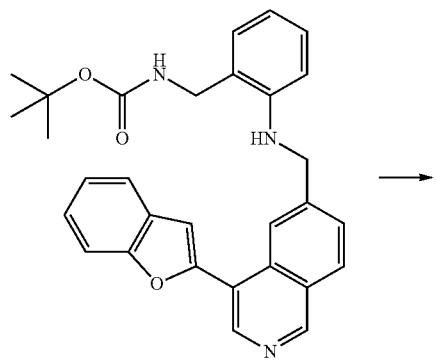

→

A mixture of 170 mg (0.35 mmol) of tert-butyl N-[[2-[[4-(benzofuran-2-yl)-6-isoquinolyl]methylamino]phenyl]methyl]carbamate in 10 mL of 2.0 M HCl in EA was stirred at 20° C. for 1 h. Then the solvent was evaporated under reduced pressure. The residue was purified by preparative HPLC to afford 95 mg of the product as a yellow solid.

MS (ESI+): 380.4 [M+H].

¹H NMR (400 MHz, DMSO-d₆+D₂O) δ ppm: 9.39 (s, 1H), 8.93 (s, 1H), 8.47 (s, 1H), 8.24 (d, 1H, J=8.4 Hz), 8.03 (br, 2H), 7.87-7.73 (m, 3H), 7.44-7.33 (m, 3H), 7.25-7.08 (m, 2H), 6.66 (m, 1H), 6.59 (d, 1H, J=7.6 Hz), 4.69 (s, 2H), 4.07 (t, 2H, J=5.6 Hz).

The following examples were prepared accordingly to Example 51 by reaction of 4-bromo-6-(bromomethyl)isoquinoline with the corresponding amines followed by coupling with benzofuran-2-ylboronic acid in the presence of a Pd-catalyst and subsequent deprotection:

| Example | | ¹H NMR (400 MHz) δ ppm | MS (+ESI) [M + H]⁺ |
|---|---|---|---|
| 52 | 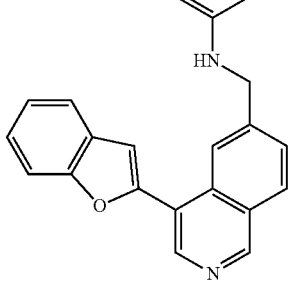 | (DMSO-d₆ + D₂O) 9.63 (s, 1H), 8.97 (s, 1H), 8.60 (s, 1H), 8.46 (d, 1H, J = 8.4 Hz), 7.98-7.62 (m, 3H), 7.51-7.35 (m, 3H), 7.14 (d, 2H, J = 8.8 Hz), 6.64 (d, 2H, J = 8.4 Hz), 4.69 (s, 2H), 3.79 (s, 1H) | 380.2 |

| Example | ¹H NMR (400 MHz) δ ppm | MS (+ESI) [M + H]⁺ |
|---|---|---|
| 53 | (DMSO-d₆ + D₂O) 9.61 (s, 1H), 8.96 (s, 1H), 8.56 (s, 1H), 8.45 (d, 1H, J = 8.8 Hz), 7.98-7.61 (m, 3H), 7.47-7.34 (m, 3H), 7.13 (t, 1H, J = 8.0 Hz), 6.71-6.63 (m, 3H), 4.68 (s, 2H), 3.81 (s, 1H) | 380.4 |

1-[(4-Bromo-6-isoquinolyl)methyl]quinolin-1-ium-4-amine

1-[[4-(Benzofuran-2-yl)-6-isoquinolyl]methyl]quinolin-1-ium-4-amine (Example 54)

Under nitrogen atmosphere, 30 mg (0.1 mmol) of 4-bromo-6-(bromomethyl)isoquinoline and 17 mg of Quinolin-4-amine (CAS 578-68-7) were dissolved in 2 mL of DMF. Then 0.033 mL of DIPEA (0.20 mmol) was added. After agitation at 100° C. for 16 hours, LCMS showed that the starting material was consumed. The reaction mixture was cooled to 30° C. and then concentrated under reduced pressure. The residue could be used directly in the next step without purification.

MS (ESI+): 364.1[M+H].

¹H NMR (400 MHz, DMSO-d6) δ ppm: 9.45 (s, 1H), 9.35 (s, 1H), 9.30 (s, 1H), 8.83 (d, J=7.2 Hz, 1H), 8.76 (s, 1H), 8.55 (d, J=8.4 Hz, 1H), 8.22 (d, J=8.4 Hz, 1H), 8.00 (d, J=8.4 Hz, 1H), 7.94 (m, 2H), 7.72 (m, 1H), 7.60 (dd, J1=1.6 Hz, J2=8.4 Hz, 1H), 7.00 (d, J=7.2 Hz, 1H), 6.18 (s, 2H).

Under argon atmosphere, 95 mg (0.21 mmol) of 1-[(4-bromo-6-isoquinolyl)methyl]quinolin-1-ium-4-amine was dissolved in 5 mL of DMF and 1 mL of H₂O. Then 41 mg (0.25 mmol) of Benzofuran-2-boronic acid (CAS 98437-24-2), 44 mg (0.42 mmol) of Na₂CO₃ and 15 mg (0.02 mmol) of Pd(dppf)₂Cl₂ (CAS 95464-05-4) were added. After agitation at 100° C. for 16 hours, the solvent was removed under vacuum and the residue was purified by preparative HPLC to give 42 mg of the product as a light yellow solid.

MS (ESI+): 402.2 [M+H].

¹H NMR (400 MHz, DMSO-d6+D₂O) δ ppm: 9.39 (s, 1H), 8.88 (s, 1H), 8.70 (d, J=7.2Hz, 1H), 8.50 (d, J=8.0Hz, 1H), 8.33 (d, J=8.8Hz, 1H), 7.88-7.99 (m, 3H), 7.67-7.79 (m, 3H), 7.30-7.44 (m, 3H), 7.25 (s, 1H), 6.93 (d, J=7.2Hz, 1H), 6.13 (s, 2H).

The following compounds were prepared accordingly to Example 54 by reaction of 4-bromo-6-(bromomethyl)isoquinoline with the corresponding aminopyridine derivatives and Suzuki-Miyaura reaction with benzofuran-2-boronic acid. If necessary, functional groups of some compounds are protected as required, and are finally deprotected.

| Example | | $^1$H NMR (400 MHz) δ ppm | MS (+ESI) [M + H]$^+$ |
|---|---|---|---|
| 55 | | (DMSO-d$_6$ + D$_2$O) 9.42 (s, 1H), 8.97 (s, 1H), 8.35 (d, J = 8.0 Hz, 1H), 8.30 (dd, J1 = 2.8 Hz, J2 = 10.4 Hz, 2H), 8.24 (s, 1H), 7.72-7.80 (m, 2H), 7.64 (d, J = 8.0 Hz, 1H), 7.55 (s, 1H), 7.43 (m, 1H), 7.35 (m, 1H), 6.87 (dd, J1 = 2.8 Hz, J2 = 10.4 Hz, 2H), 5.66 (s, 2H) | 352.3 |
| 56 | | (DMSO-d$_6$ + D$_2$O) δ ppm: 9.43 (s, 1H), 8.99 (s, 1H), 8.48 (s, 1H), 8.36 (d, J = 8.4 Hz, 1H), 8.31 (d, J = 5.6 Hz, 1H), 8.18 (d, J = 2.0 Hz, 1H), 7.80-7.60 (m, 6H), 7.43 (m, 1H), 7.36 (m, 1H), 5.96 (s, 2H) | 352.3 |
| 57 | | (DMSO-d$_6$ + D$_2$O) δ ppm: 9.42 (s, 1H), 8.96 (s, 1H), 8.25-8.35 (m, 4H), 7.75 (m, 2H), 7.61 (d, J = 8.0 Hz, 1H), 7.54 (s, 1H), 7.44 (m, 1H), 7.35 (m, 1H), 6.89 (d, J = 7.2 Hz, 1H), 5.64 (s, 2H), 2.07 (s, 3H) | 366.2 |
| 58 | | (DMSO-d$_6$ + D$_2$O) δ ppm: 9.44 (s, 1H), 9.11 (s, 1H), 8.98 (s, 1H), 8.32-8.45 (m, 3H), 7.80 (m, 2H), 7.65 (d, J = 8.4 Hz, 1H), 7.58 (s, 1H), 7.43 (m, 1H), 7.36 (m, 1H), 7.11 (d, J = 7.2 Hz, 1H), 5.74 (s, 2H) | 420.3 |

| Example | | ¹H NMR (400 MHz) δ ppm | MS (+ESI) [M + H]⁺ |
|---|---|---|---|
| 59 | 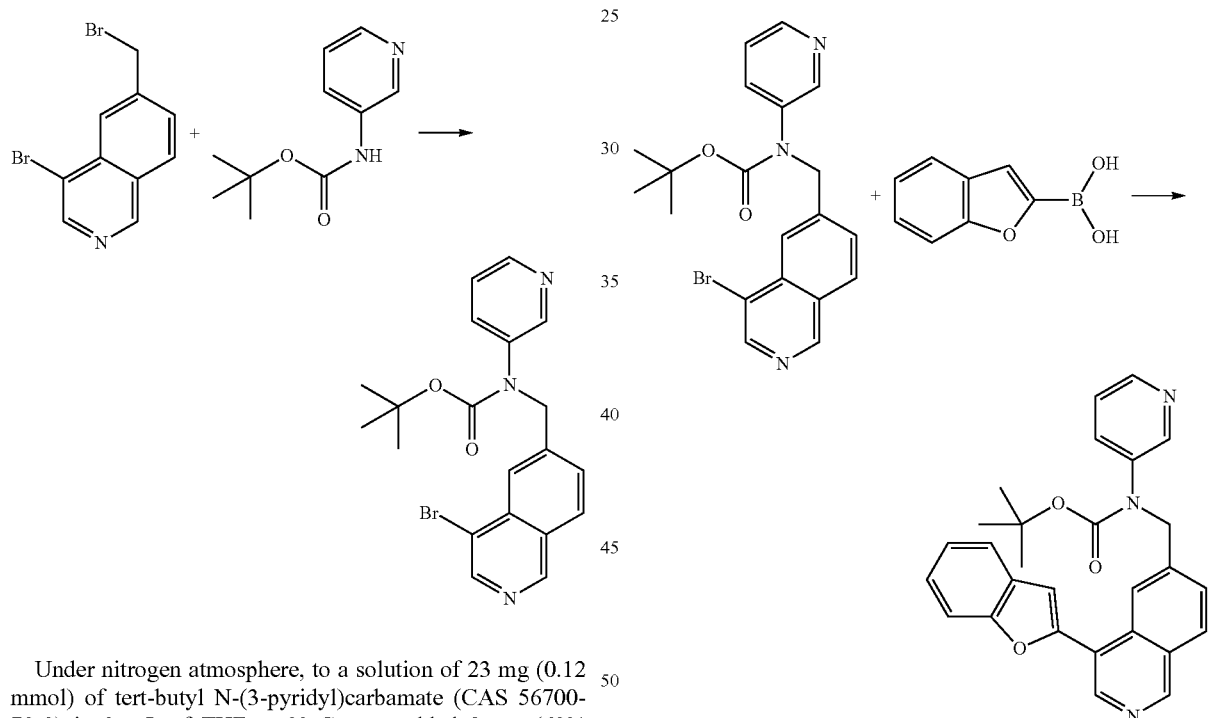 | (DMSO-d₆ + D₂O) δ ppm: 9.34 (s, 1H), 8.93 (s, 1H), 8.36 (s, 1H), 8.25 (m, 2H), 7.76 (d, J = 7.2 Hz, 1H), 7.66 (m, 2H), 7.49 (s, 1H), 7.42 (m, 1H), 7.34 (m, 1H), 7.10 (d, J = 1.6 Hz, 1H), 6.58 (d, J = 6.4 Hz, 1H), 5.46 (s, 2H) | 368.2 | tert-butyl N-[(4-Bromo-6-isoquinolyl)methyl]-N-(3-pyridyl)carbamate

Under nitrogen atmosphere, to a solution of 23 mg (0.12 mmol) of tert-butyl N-(3-pyridyl)carbamate (CAS 56700-70-0) in 3 mL of THF at 0° C. was added 8 mg (60% dispersion in mineral oil, 0.20 mmol) of NaH. The mixture was stirred at 0° C. for 1 h. Then 30 mg (0.10 mmol) of 4-bromo-6-(bromomethyl)isoquinoline (CAS 98331-27-2) was added at 0° C. Then the mixture was stirred at 25° C. for 16 h. The reaction was quenched by saturated aqueous solution of NH₄Cl and the mixture was concentrated under vacuum. The residue was purified by silica gel column chromatography (EA/PE=1/2) to give 16 mg of the product as a colorless oil.

MS (ESI+): 414.0 [M+H].

¹H NMR (400 MHz, CDCl₃) δ ppm: 9.15 (s, 1H), 8.72 (s, 1H), 8.52 (d, J=2.0 Hz, 1H), 8.42 (dd, J1=1.6 Hz, J2=4.8Hz, 1H), 7.95-8.00 (m, 2H), 7.50-7.61 (m, 2H), 7.25 (m, 1H), 5.11 (s, 2H), 1.47 (s, 9H)

tert-Butyl N-[[4-(benzofuran-2-yl)-6-isoquinolyl]methyl]-N-(3-pyridyl)carbamate

Under argon atmosphere, to a solution of 272 mg (0.66 mmol) of tert-butyl N-[(4-bromo-6-isoquinolyl)methyl]-N-(3-pyridyl)carbamate in 10 mL of dioxane and 2 mL of H₂O were added 161 mg (0.98 mmol) of benzofuran-2-boronic acid (CAS 98437-24-2), 141 mg (1.31 mmol) of Na₂CO₃ and 153 mg (0.13 mmol) of Pd(PPh₃)₄. After stirring at 80° C. for 3 h, the reaction mixture was filtered and the filtrate was concentrated under vacuum. The residue was purified by silica gel column chromatography (PE/EA=2/1) to give 172 mg of the product as a yellow semisolid.

MS (ESI+): 452.1 [M+H].

¹H NMR (400 MHz, CDCl3) δ ppm: 9.28 (s, 1H), 8.92 (s, 1H), 8.54 (d, J=2.0Hz, 1H), 7.20-8.50 (m, 11H), 5.10 (s, 2H), 1.40 (s, 9H).

N-[[4-(Benzofuran-2-yl)-6-isoquinolyl]methyl]pyridin-3-amine (Example 60)

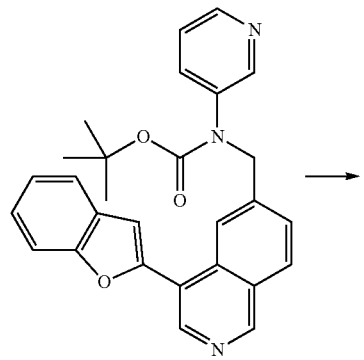

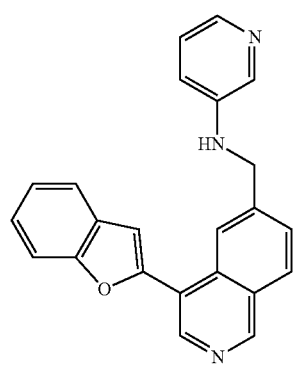

Under nitrogen atmosphere, to a solution of 169 mg (0.37 mmol) of tert-butyl N-[[4-(benzofuran-2-yl)-6-isoquinolyl]methyl]-N-(3-pyridyl)carbamate in 15 mL of DCM was added dropwise 5.0 mL of TFA. After stirring at 30° C. for 3.0 h, when LC-MS showed that the reaction was complete, the reaction mixture was concentrated under vacuum. The residue was purified by preparative HPLC to give 89 mg of the product as a yellow solid.

MS (ESI+): 352.2 [M+H].

$^1$H NMR (400 MHz, DMSO-$d_6$) δ ppm: 9.48 (s, 1H), 8.92 (s, 1H), 8.45 (d, J=1.6Hz, 1H), 8.34 (d, J=8.4Hz, 1H), 8.11 (s, 1H), 8.04 (dd, J1=0.8 Hz, J2=4.0 Hz, 1H), 7.85 (dd, J1=1.6 Hz, J2=8.4 Hz, 1H), 7.70-7.80 (m, 3H), 7.58 (dd, J1=0.8 Hz, J2=8.4 Hz, 1H), 7.50 (s, 1H), 7.30-7.45 (m, 2H), 4.78 (s, 2H).

The following examples were prepared accordingly to Example 60 by reaction of (4-bromo-6-(bromomethyl)isoquinoline with the corresponding Boc-protected amino-pyridine derivatives, Suzuki-Miyaura reaction with benzofuran-2-boronic acid and deprotection:

| Example | | $^1$H NMR (400 MHz) δ ppm | MS (+ESI) [M + H]$^+$ |
|---|---|---|---|
| 61 | | (DMSO-$d_6$ + $D_2O$) δ ppm: 9.44 (s, 1H), 8.91 (s, 1H), 8.41 (d, J = 1.6 Hz, 1H), 8.34 (d, J = 8.4 Hz, 1H), 8.15 (m, 2H), 7.81 (dd, J1 = 2.0 Hz, J2 = 8.4 Hz, 1H), 7.74 (dd, J1 = 0.8 Hz, J2 = 8.0 Hz, 1H), 7.57 (m, 1H), 7.50 (s, 1H), 7.42, 7.35 (m, 2H), 7.03 and 6.91 (m, 2H), 4.88 (s, 2H) | 352.2 |
| 62 | | (DMSO-$d_6$ + $D_2O$) δ ppm: 9.51 (s, 1H), 8.97 (s, 1H), 8.43 (d, J = 1.6 Hz, 1H), 8.39 (d, J = 8.4 Hz, 1H), 7.97 (d, J = 6.4 Hz, 1H), 7.84 (dd, J1 = 1.6 Hz, J2 = 8.4 Hz, 1H), 7.77 (d, J = 7.6 Hz, 1H), 7.58 (d, J = 8.0 Hz, 1H), 7.49 (s, 1H), 7.36 and 7.45 (m, 2H), 6.87 (d, J = 1.6 Hz, 1H), 6.76 (dd, J1 = 1.6 Hz, J2 = 6.4 Hz, 1H), 4.82 (s, 2H) | 386.2 |

| Example | | ¹H NMR (400 MHz) δ ppm | MS (+ESI) [M + H]⁺ |
|---|---|---|---|
| 63 | 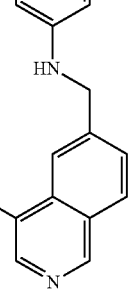 | (DMSO-d6 + D₂O) δ ppm: 9.69 (s, 1H), 8.99 (s, 1H), 8.50-8.55 (m, 2H), 7.98 (dd, J = 1.2, 8.4 Hz, 1H,), 7.70-7.80 (m, 2H), 7.50-7.60 (m, 2H), 7.37 and 7.45 (m, 2H), 6.61 (d, J = 5.6 Hz, 1H), 6.26 (s, 1H), 4.80 (s, 2H) | 370.2 |
| 64 | 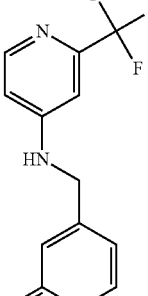 | (DMSO-d6 + D₂O) δ ppm: 9.52 (s, 1H), 8.95 (s, 1H), 8.45 (s, 1H), 8.40 (d, J = 8.8 Hz), 8.19 (d, J = 6.0 Hz, 1H), 7.88 (d, J = 1.2, 8.4 Hz, 1H), 7.73 (m, 1H), 7.45-7.50 (m, 2H), 7.31-7.41 (m, 2H), 7.12 (s, 1H), 6.80 (m, 1H), 4.82 (s, 2H) | 420.3 |
| 65 | 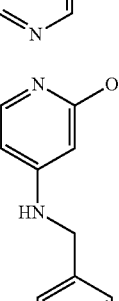 | (DMSO-d6 + D₂O) δ ppm: 9.57 (s, 1H), 8.97 (s, 1H), 8.53 (s, 1H), 8.44 (d, J = 8.4 Hz, 1H), 7.90 (m, 1H), 7.70-7.85 (m, 2H), 7.50-7.70 (m, 2H), 7.36 and 7.44 (m, 2H), 6.66 (m, 1H), 6.40 (m, 1H), 4.94 (s, 2H), 3.90 (s, 3H) | 382.2 |
| 66 | 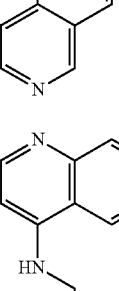 | (DMSO-d6 + D₂O) δ ppm: 9.42 (s, 1H), 8.90 (s, 1H), 8.56 (d, J = 8.0 Hz, 1H), 8.45 (m, 2H), 8.35 (d, J = 8.4 Hz), 8.02 (m, 1H), 7.95 (d, J = 8.0 Hz, 1H), 7.89 (m, 1H), 7.79 (m, 1H), 7.62 (m, 1H), 7.41 (s, 1H), 7.26 (m, 2H), 7.02 (m, 1H), 6.86 (d, J = 7.2 Hz, 1H), 5.15 (s, 2H) | 420.3 |

-continued

| Example | ¹H NMR (400 MHz) δ ppm | MS (+ESI) [M + H]⁺ |
|---|---|---|
| 67 | (DMSO-d6 + D₂O) δ ppm: 9.43 (s, 1H), 8.94 (s, 1H), 8.10-8.36 (m, 4H), 8.72 (m, 2H), 7.55 (d, J = 8.4 Hz, 1H), 7.30-7.45 (m, 3H), 7.10-7.20 (m, 2H), 5.20 (s, 2H), 3.32 (s, 3H) | 366.2 |
| 68 | (DMSO-d6 + D₂O) δ ppm: 9.40 (s, 1H), 8.91 (s, 1H), 8.45 (brs, 1H), 8.31 (d, J = 8.8 Hz, 1H), 7.70-7.83 (m, 2H), 7.30-7.65 (m, 5H), 6.35 (d, J = 7.2 Hz, 1H), 5.75 (brs, 1H), 4.79 (s, 2H), 2.94 (s, 6H) | 395.2 |
| 69 | (DMSO-d6 + D₂O) δ ppm: 9.44 (s, 1H), 8.92 (s, H), 8.38 (s, 1H), 8.33 (d, J = 8.4 Hz, 1H), 8.14 (s, 1H), 8.09 (d, J = 7.2 Hz, 1H), 7.82 (d, J = 5.6 Hz, 1H), 7.76 (d, J = 7.2 Hz, 1H), 7.56 (d, J = 8.4 Hz, 1H), 7.47 (s, 1H), 7.44 (m, 1H), 7.35 (m, 1H), 6.85 (d, J = 7.2 Hz, 1H), 4.95 (s, 2H), 2.23 (s, 3H) | 366.2 |
| 70 | (DMSO-d6 + D₂O) δ ppm: 9.42 (s, 1H), 8.93 (s, 1H), 8.62 (d, J = 6.4 Hz, 1H), 8.43 (s, 1H), 8.32 (d, J = 8.4 Hz, 1H), 8.16 (d, J = 6.4 Hz, 1H), 7.82 (d, J = 8.4 Hz, 1H), 7.77 (d, J = 8.4 Hz, 1H), 7.59 (d, J = 8.4 Hz, 1H), 7.51 (s, 1H), 7.42 (m, 1H), 7.35 (m, 1H), 7.15 (m, 1H), 4.95 (s, 2H) | 370.2 |

| Example | | ¹H NMR (400 MHz) δ ppm | MS (+ESI) [M + H]⁺ |
|---|---|---|---|
| 71 | 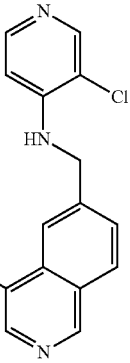 | (DMSO-d6 + D₂O) δ ppm: 9.42 (s, 1H), 8.93 (s, 1H), 8.62 (s, 1H), 8.38 (s, 1H), 8.34 (d, J = 8.4 Hz, 1H), 8.17 (d, J = 7.2 Hz, 1H), 7.82 (d, J = 8.4 Hz, 1H), 7.76 (d, J = 8.4 Hz, 1H), 7.57 (d, J = 8.4 Hz, 1H), 7.48 (s, 1H), 7.42 (m, 1H), 7.35 (m, 1H), 7.05 (d, J = 7.2 Hz, 1H), 4.99 (s, 2H) | 386.2 |
| 72 | 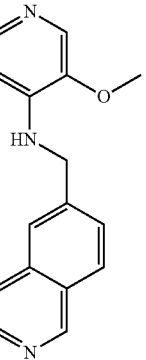 | (DMSO-d6 + D₂O) δ ppm: 9.40 (s, 1H), 8.89 (s, 1H), 8.30 (m, 2H), 8.01 (s, 1H), 7.99 (d, J = 7.2 Hz, 1H), 7.76 (m, 2H), 7.51 (d, J = 8.4 Hz, 1H), 7.43 (m, 2H), 7.35 (m, 1H), 6.89 (d, J = 7.2 Hz, 1H), 4.90 (s, 2H), 3.92 (s, 3H) | 382.2 |
| 73 | 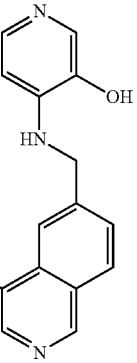 | (DMSO-d6 + D₂O) δ ppm: 9.41 (s, 1H), 8.91 (s, 1H), 8.38 (s, 1H), 8.32 (d, J = 8.4 Hz, 1H), 7.90 (d, J = 6.4 Hz, 1H), 7.81 (d, J = 8.4 Hz, 1H), 7.74 (m, 2H), 7.53 (d, J = 8.4 Hz, 1H), 7.44 (m, 2H), 7.35 (m, 1H), 6.85 (d, J = 6.4 Hz, 1H) | 368.2 |
| 74 | 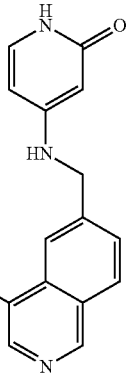 | (DMSO-d₆ + D₂O) δ ppm: 9.32 (s, 1H), 8.87 (s, 1H), 8.35 (s, 1H), 8.23 (d, J = 8.4 Hz, 1H), 7.72 (m, 2H), 7.63 (d, J = 8.0 Hz), 7.30-7.42 (m, 3H), 7.09 (d, J = 7.2 Hz, 1H), 5.86 (dd, J1 = 2.4 Hz, J2 = 7.2 Hz, 1H), 5.18 (s, 1H), 4.55 (s, 2H) | 368.2 |

N-[(4-Bromo-6-isoquinolyl)methyl]-N-(3-nitro-4-pyridyl)acetamide

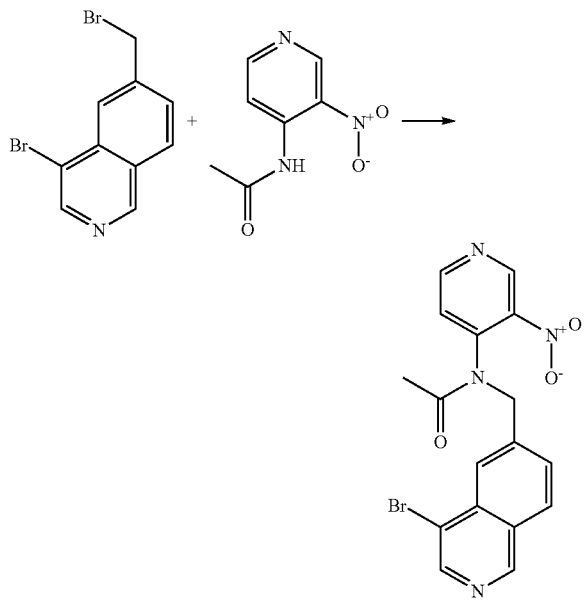

Under nitrogen atmosphere, to the suspension of 49 mg (60%, 1.21 mmol) of NaH in 4 mL of anhydrous THF at 0° C. was added 200 mg (1.10 mmol) of 4-acetamido-3-nitropyridine (CAS 79371-42-9) at 0° C. After stirring at 0° C. for 1 h, a solution of 302 mg (0.99 mmol) of 4-bromo-6-(bromomethyl)isoquinoline (CAS 98331-27-2) in 3 mL of anhydrous THF was added at 0° C. and then the reaction mixture was stirred at 25° C. for 36 h. The solvent was removed under vacuum. The residue was taken up in of EA, washed with water and brine, dried over Na₂SO₄, filtered and concentrated under reduced pressure. The residue was purified by silica gel column chromatography (DCM/MeOH=100/1) to give 163 mg of the product as a yellow semisolid.

MS (ESI+): 401.1 [M+H].

¹H NMR (400 MHz, CDCl₃) δ ppm: 9.05 (s, 1H), 8.91 (s, 1H), 8.79 (s, 1H), 8.05-8.30 (m, 3H), 7.75-7.90 (m, 2H), 5.57 (s, 2H), 2.32 (s, 3H).

N-[(4-Bromo-6-isoquinolyl)methyl]-3-nitro-pyridin-4-amine

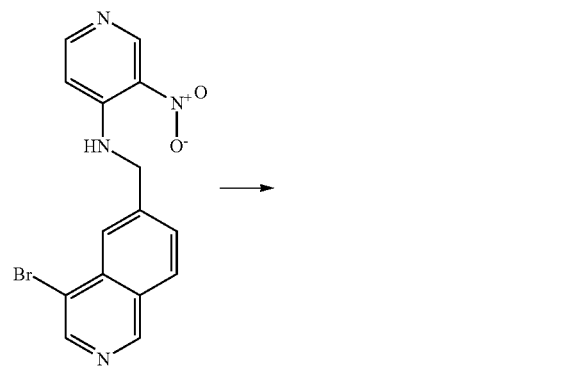

In a sealed tube, to a solution of 246 mg (0.61 mmol) of N-[(4-bromo-6-isoquinolyl)methyl]-N-(3-nitro-4-pyridyl)acetamide in 10 mL of MeOH was added 10 mL of 33% Hydrogen bromide in AcOH. After stirring at 40° C. for 18 h, the reaction mixture was concentrated to dryness. The residue was diluted with EA, washed with saturated aqueous solution of NaHCO₃, water and brine, dried over Na₂SO₄, filtered and concentrated under vacuum to give the crude product as a light yellow solid, which was used directly in the next step.

MS (ESI+): 358.9 [M+H].

¹H NMR (400 MHz, CDCl₃) δ ppm: 9.28 (s, 1H), 9.18 (s, 1H), 8.75 (s, 1H), 8.71 (brs, 1H), 8.29 (d, J=6.0 Hz, 1H), 8.11 (s, 1H), 8.03 (d, J=8.4 Hz, 1H), 7.64 (d, J=8.4 Hz, 1H), 6.69 (d, J=6.0 Hz, 1H), 4.84 (d, J=6.0 Hz, 2H).

N-[[4-(Benzofuran-2-yl)-6-isoquinolyl]methyl]-3-nitro-pyridin-4-amine (Example 75)

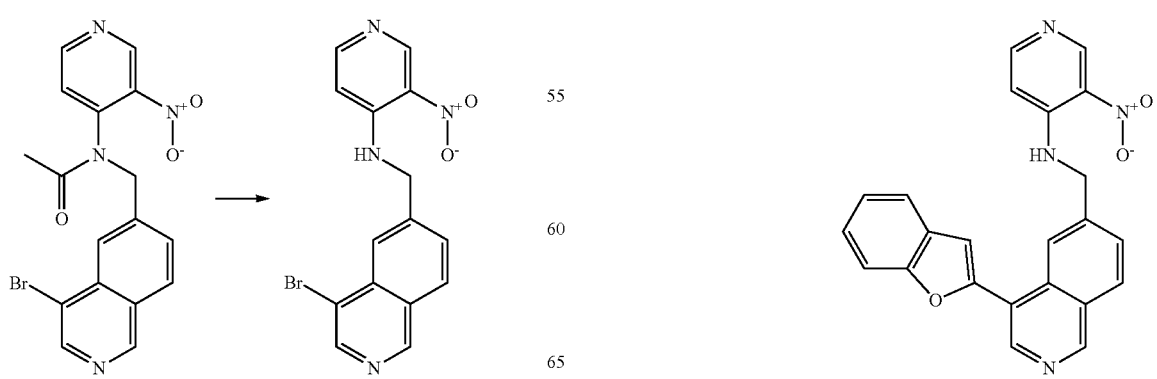

Under argon atmosphere, to a solution of 201 mg (0.56 mmol) of N-[(4-bromo-6-isoquinolyl)methyl]-3-nitro-pyridin-4-amine in 15 mL of dioxane and 3 mL of water were added 110 mg (0.67 mmol) of benzofuran-2-boronic acid, 120 mg (1.12 mmol) of $Na_2CO_3$ and 131 mg (0.11 mmol) of $Pd(PPh_3)_4$. After stirring at 80° C. for 4 h, the mixture was filtered and the filtrate was concentrated under vacuum. The residue was purified by silica gel column chromatography (DCM/MeOH=50/1) to give 197 mg of the product as a yellow solid.

MS (ESI+): 397.2 [M+H].

$^1$H NMR (400 MHz, DMSO-$d_6$+$D_2O$) δ ppm: 9.33 (s, 1H), 9.09 (s, 1H), 8.88 (s, 1H), 8.34 (s, 1H), 8.26 (d, J=8.4 Hz, 1H), 8.17 (d, J=6.0 Hz, 1H), 7.79 (dd, J1=1.2 Hz, J2=8.4 Hz, 1H), 7.71 (d, J=6.0 Hz, 1H), 7.46 (d, J=8.4 Hz, 1H), 7.30-7.42 (m, 3H), 6.90 (d, J=6.0 Hz, 1H), 4.96 (s, 2H).

N4-[[4-(Benzofuran-2-yl)-6-isoquinolyl]methyl] pyridine-3,4-diamine (Example 76)

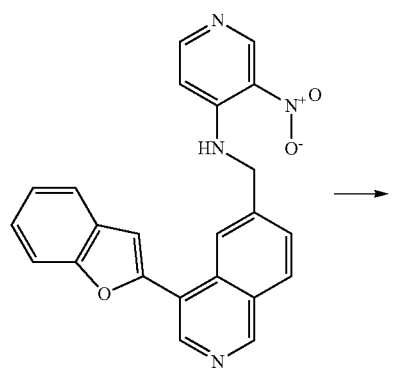

→

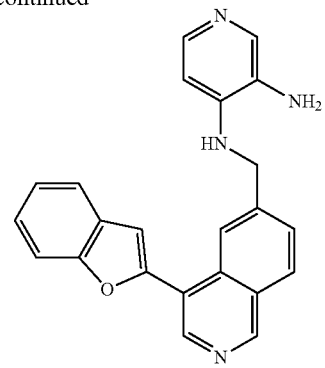

Under argon atmosphere, to a solution of 206 mg (0.52 mmol) of N-[[4-(benzofuran-2-yl)-6-isoquinolyl]methyl]-3-nitro-pyridin-4-amine in 20 mL of EtOH and 10 mL of water were added 1.445 g (5.20 mmol) of $FeSO_4.7H_2O$ and 581 mg (10.39 mmol) of iron powder. After stirring at 80° C. for 3.5 h, the reaction mixture was filtered through Celite and the filtrate was concentrated under vacuum. The residue was purified by preparative HPLC to give 57 mg of the product as a light yellow solid.

MS (ESI+): 367.2 [M+H].

$^1$H NMR (400 MHz, DMSO-$d_6$+$D_2O$) δ ppm: 9.31 (s, 1H), 8.87 (s, 1H), 8.36 (s, 1H), 8.24 (d, J=8.4 Hz, 1H), 7.77 (dd, J1=1.2 Hz, J2=8.4 Hz, 1H), 7.71 (m, 2H), 7.57 (m, 2H), 7.40 (m, 1H), 7.28-7.36 (m, 2H), 6.47 (d, J=6.0 Hz, 1H), 4.77 (s, 2H).

The following example was prepared accordingly to Example 75 by reaction of (4-bromo-6-(bromomethyl)isoquinoline with N-[3-(trifluoromethyl)-4-pyridyl]acetamide followed by depretection of acetyl group and Suzuki-Miyaura reaction with benzofuran-2-boronic acid in the presence of Pd-catalyst:

| Example | | $^1$H NMR (400 MHz) δ ppm | MS (+ESI) [M + H]$^+$ |
|---|---|---|---|
| 77 | ![structure] | (DMSO-$d_6$ + $D_2O$) 9.43 (s, 1H), 8.91 (s, 1H), 8.71 (s, 1H), 8.35 (m, 2H), 8.27 (d, J = 7.2 Hz, 1H), 7.82 (dd, J1 = 1.2 Hz, J2 = 8.4 Hz, 1H), 7.74 (d, J = 7.2 Hz, 1H), 7.54 (d, J = 8.4 Hz, 1H), 7.40-7.46 (m, 2H), 7.35 (m, 1H), 7.12 (d, J = 7.2 Hz, 1H), 5.02 (s, 2H) | 420.2 |

4-(Benzofuran-2-yl)-6-fluoro-isoquinoline

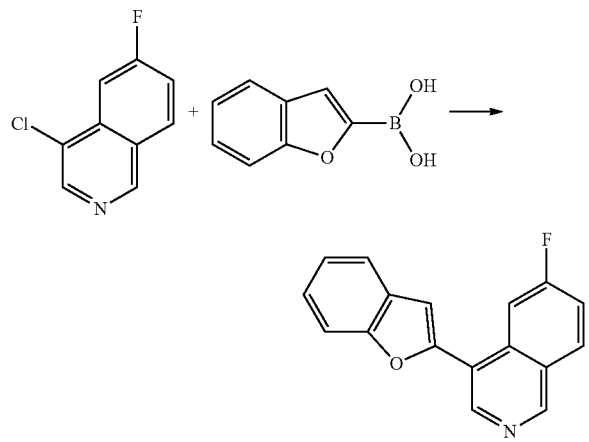

Under argon atmosphere, to a mixture of 500 mg (2.75 mmol) of 4-chloro-6-fluoro-isoquinoline (CAS 918488-55-8), 670 mg (4.13 mmol) of benzofuran-2-ylboronic acid (CAS 98437-24-2) and 1170 mg (5.51 mmol) of $K_3PO_4$ in 20 mL of toluene were added 31 mg (0.14 mmol) of Pd(OAc)$_2$ and 82 mg (0.28 mmol) of Johnphos. The mixture was stirred at 70° C. for 40 h. Then the reaction mixture was diluted with EA, washed with water and brine, dried over $Na_2SO_4$ and filtered. The filtrate is concentrated under reduced pressure and the residue is purified by silica gel column chromatography (PE/EA=3/1) to afford 480 mg of the product as a white solid.

MS (ESI+): 264.1 [M+H].

$^1$H NMR (400 MHz, CDCl$_3$) δ ppm: 9.42 (s, 1H), 8.94 (s, 1H), 8.36 (m, 2H), 7.75-7.30 (m, 6H).

tert-Butyl 4-[[4-(benzofuran-2-yl)-6-isoquinolyl]oxy]piperidine-1-carboxylate

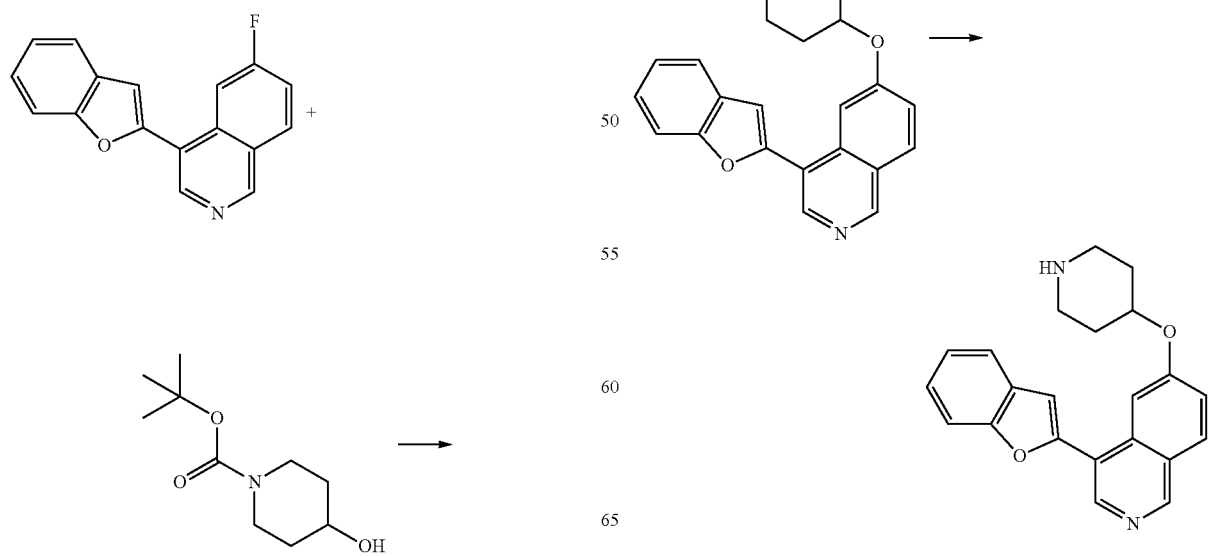

Under argon atmosphere, to a solution of 310 mg (1.52 mmol) of tert-butyl 4-hydroxypiperidine-1-carboxylate (CAS 109384-19-2) in 15 mL of DMAC was added 100 mg (57% dispersion in mineral oil, 2.28 mmol) of NaH at 20° C. After stirring for 0.5 h, 200 mg (0.76 mmol) of 4-(benzofuran-2-yl)-6-fluoro-isoquinoline was added. The mixture was stirred at 80° C. for 4 h. The mixture was diluted with EA, washed with water and brine, dried over $Na_2SO_4$, filtered and concentrated under reduced pressure. The residue is purified by silica gel column chromatography (PE/EA=1/2) to give 430 mg of the product as a white solid.

MS (ESI+): 445.2 [M+H].

$^1$H NMR (400 MHz, CDCl$_3$) δ ppm: 9.18 (s, 1H), 8.79 (s, 1H), 8.09 (d, J=9.2 Hz, 1H), 7.73 (s, 1H), 7.72 (d, J=7.6 Hz, 1H), 7.58 (d, J=8.0 Hz, 1H), 7.44-7.32 (m, 3H), 7.19 (s, 1H), 4.72 (m, 1H), 5.08 (m, 1H), 3.80-3.35 (m, 4H), 2.15-1.80 (m, 4H), 1.46 (s, 9H).

4-(Benzofuran-2-yl)-6-(4-piperidyloxy)isoquinoline (Example 78)

A mixture of 430 mg (0.97 mmol) of tert-butyl 4-[[4-(benzofuran-2-yl)-6-isoquinolyl]oxy]piperidine-1-carboxylate in 10 mL of a 2.0 M HCl in EA was stirred at 10° C. for 1 h. Then the resulting precipitate was collected by filtration to afford 150 mg of the product as a yellow solid.

MS (ESI+): 345.3 [M+H].

$^1$H NMR (400 MHz, DMSO-d$_6$+D$_2$O) δ ppm: 9.51 (s, 1H), 8.90 (s, 1H), 8.47 (d, J=9.2 Hz, 1H), 7.96 (s, 1H), 7.83-7.68 (m, 4H), 7.47-7.35 (m, 2H), 5.08 (m, 1H), 3.32-3.11 (m, 4H), 2.25-1.97 (m, 4H).

4-(2,5-Dimethylpyrrol-1-yl)cyclohexane-1,1-diol

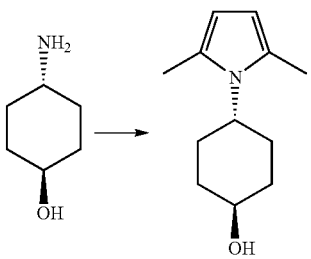

A solution of 1.00 g (8.68 mmol) of trans-4-amino-1-cyclohexanol (CAS 6850-65-3), 360 mg (1.74 mmol) of PTSA and 1.12 mL (0.99 mmol) of hexane-2, 5-dione in 20 mL of methanol was stirred at 65° C. for 4 h. The mixture was concentrated under vacuum and the residue was dissolved in EA. The resulting mixture was washed with water and brine, dried over Na$_2$SO$_4$, filtered and concentrated under reduced pressure to afford 1.05 g of crude product as a brown solid which was used directly in the next step without further purification.

$^1$H NMR (400 MHz, DMSO-d$_6$) δ ppm: 5.52 (s, 2H), 4.63 (d, J=4.0 Hz, 1H), 3.85 (m, 1H), 3.36 (m, 1H), 3.34 (s, 6H), 1.96-1.87 (m, 4H), 1.67-1.25 (m, 4H).

4-[[4-(Benzofuran-2-yl)-6-isoquinolyl]oxy]cyclohexanamine (Example 79)

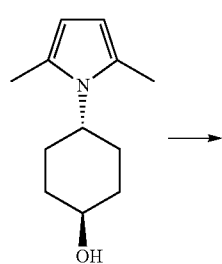

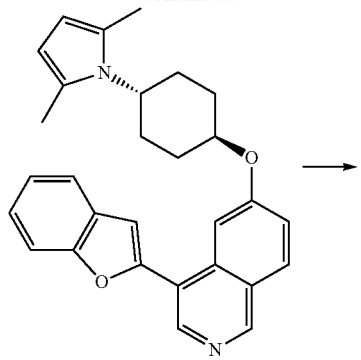

Under argon atmosphere, a solution of 180 mg (0.91 mmol) of 4-(2,5-dimethylpyrrol-1-yl)cyclohexane-1,1-diol, 100 mg (0.91 mmol) of KO$^t$Bu and 120 mg (0.46 mmol) of 4-(benzofuran-2-yl)-6-fluoro-isoquinoline in 10 mL of DMAC was stirred at 80° C. for 4 h. The mixture was diluted with EA, washed with water and brine, dried over Na$_2$SO$_4$, filtered and concentrated under reduced pressure to afford 240 mg of crude 4-(benzofuran-2-yl)-6-[4-(2,5-dimethyl-pyrrol-1-yl)cyclohexoxy]isoquinoline as a brown solid. A mixture of 240 mg (0.55 mmol) of 4-(benzofuran-2-yl)-6-[4-(2,5-dimethylpyrrol-1-yl)cyclohexoxy]isoquinoline, 570 mg (8.25 mmol) of NH$_2$OH.HCl, 0.77 mL (5.50 mmol) of TEA in 10 mL of i-PrOH and 2.5 mL of water was stirred at 85° C. for 16 h. The reaction mixture was concentrated under vacuum. The residue was purified by preparative HPLC to afford 100 mg of the product as a yellow solid.

MS (ESI+): 359.3 [M+H].

$^1$H NMR (400 MHz, DMSO-d$_6$+D$_2$O) δ ppm: 9.41 (s, 1H), 8.88 (s, 1H), 8.36 (d, J=9.2 Hz, 1H), 7.90 (s, 1H), 7.80 (d, J=7.2 Hz, 1H), 8.36 (d, J=8.4 Hz, 1H), 7.63 (s, 1H), 7.59 (d, J=9.2 Hz), 7.46-7.35 (m, 2H), 4.63 (m, 1H), 3.12 (m, 1H), 2.26-2.03 (m, 4H), 1.64-1.46 (m, 4H).

The following example was prepared accordingly to Example 79 by reaction of 4-(benzofuran-2-yl)-6-fluoro-isoquinoline with 4-(2,5-dimethylpyrrol-1-yl)cyclohexane-1,1-diol, followed by the subsequent deprotection:

| Example | | ¹H NMR (400 MHz) δ ppm | MS (+ESI) [M + H]⁺ |
|---|---|---|---|
| 80 | 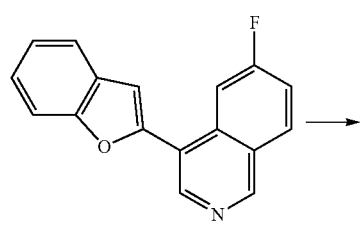 | (DMSO-d₆ + D₂O) δ ppm: 9.42 (s, 1H), 8.88 (s, 1H), 8.40 (d, J = 9.2 Hz, 1H), 7.87 (d, J = 2.0 Hz, 1H), 7.81-7.72 (m, 2H), 7.62-7.30 (m, 2H), 7.47-7.34 (m, 2H), 4.60 (m, 1H), 3.15 (m, 1H), 2.11-1.66 (m, 8H) | 359.2 |

4-(Benzofuran-2-yl)isoquinolin-6-ol

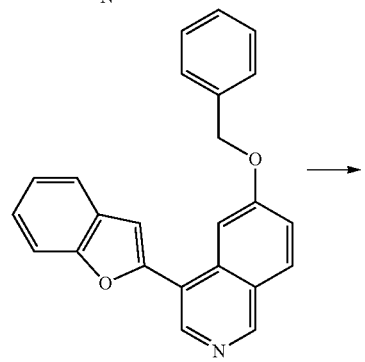

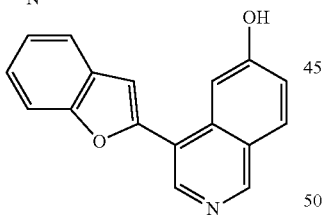

Under argon atmosphere, to a solution of 0.16 mL (1.52 mmol) of BnOH in 15 mL of DMAC was added 100 mg (57%, 2.28 mmol) of NaH at 20° C. The resulting mixture was stirred for 0.5 h at the same temperature. Then 200 mg (0.76 mmol) of 4-(benzofuran-2-yl)-6-fluoro-isoquinoline was added. The mixture was stirred at 80° C. for 4 h. When LCMS indicated the reaction was complete, the reaction mixture was diluted with EA, washed with H₂O and brine successively. The organic phase was dried over anhydrous Na₂SO₄ and concentrated under vacuum to give 270 mg of crude 4-(benzofuran-2-yl)-6-benzyloxy-isoquinoline as a brown solid. Under hydrogen atmosphere (Pressure: 1 Atm.), a mixture of 270 mg (0.76 mmol)) of 4-(benzofuran-2-yl)-6-benzyloxy-isoquinoline and 30 mg of Pd(OH)₂ in 15 mL of MeOH was stirred at 20° C. for 4 h. The mixture was filtered through Celite and the filtrate was concentrated under vacuum to afford 200 mg of the crude product as a yellow oil.

MS (ESI+): 262.1 [M+H].

[4-(Benzofuran-2-yl)-6-isoquinolyl] trifluoromethanesulfonate

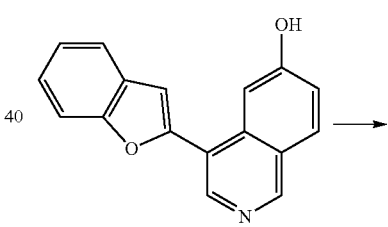

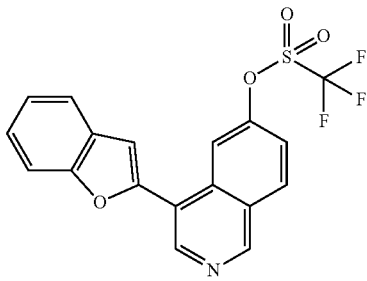

Under argon atmosphere, a mixture of 70 mg (0.25 mmol) of 4-(benzofuran-2-yl)isoquinolin-6-ol, 0.04 mL (0.50 mmol) of pyridine and 0.06 mL (0.38 mmol) of trifluoromethanesulfonic anhydride in 8 mL of DCM was stirred at −50° C. for 2 h. The mixture was diluted with EA, washed with water and brine, dried over Na₂SO₄, filtered and concentrated under reduced pressure. The residue was purified by silica gel column chromatography (PE/EA=3/1) to afford 140 mg of the product as a yellow solid.

MS (ESI+): 394.1 [M+H].

N4-[4-(Benzofuran-2-yl)-6-isoquinolyl]cyclohexane-1,4-diamine (Example 81)

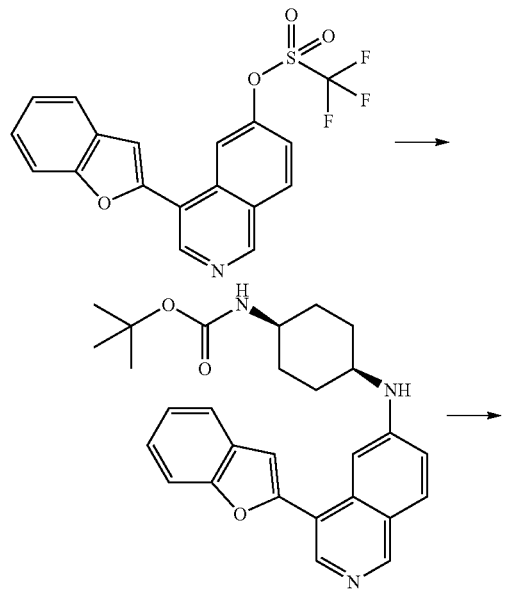

Under argon atmosphere, to a mixture of 70 mg (0.31 mmol) of N-Boc-1,4-cyclohexanediamine (CAS 195314-59-1), 80 mg (0.20 mmol) of [4-(benzofuran-2-yl)-6-isoquinolyl]trifluoromethanesulfonate, 130 mg (0.41 mmol) of $Cs_2CO_3$ in 10 mL of toluene were added 5 mg (0.02 mmol) of $Pd(OAc)_2$ and 20 mg (0.03 mmol) of BINAP. The mixture was stirred at 100° C. for 16 h. Then the reaction mixture was diluted with EA, washed with water and brine, dried over $Na_2SO_4$ and filtered. The filtrate was concentrated under reduced pressure to afford 130 mg of crude tert-butyl N-[4-[[4-(benzofuran-2-yl)-6-isoquinolyl]amino]cyclohexyl]carbamate as a brown solid. 80 mg of crude tert-butyl N-[4-[[4-(benzofuran-2-yl)-6-isoquinolyl]amino]cyclohexyl]carbamate was treated with 8 mL of 2.0 M HCl in EA at 15° C. for 2 h. When LCMS showed that the reaction was complete, the reaction mixture was concentrated under reduced pressure and the residue was purified via preparative HPLC to give 38 mg of the desired product as a brown solid.

MS (ESI+): 358.2 [M+H].

$^1$H NMR (400 MHz, DMSO-$d_6$+$D_2O$) δ ppm: 9.11 (s, 1H), 8.59 (s, 1H), 8.18 (d, J=9.2 Hz, 1H), 7.90 (s, 1H), 7.79 (d, J=7.6 Hz, 1H), 8.70 (d, J=8.4 Hz, 1H), 7.58 (s, 1H), 7.48-7.34 (m, 4H), 3.80 (m, 1H), 3.18 (m, 1H), 1.86-1.66 (m, 8H).

The following example was prepared accordingly to Example 81 by reaction of [4-(benzofuran-2-yl)-6-isoquinolyl]trifluoromethanesulfonate with tert-butyl 4-aminopiperidine-1-carboxylate (CAS 87120-72-7), followed by the subsequent deprotection:

| Example | | $^1$H NMR (400 MHz) δ ppm | MS (+ESI) [M + H]$^+$ |
|---|---|---|---|
| 82 | 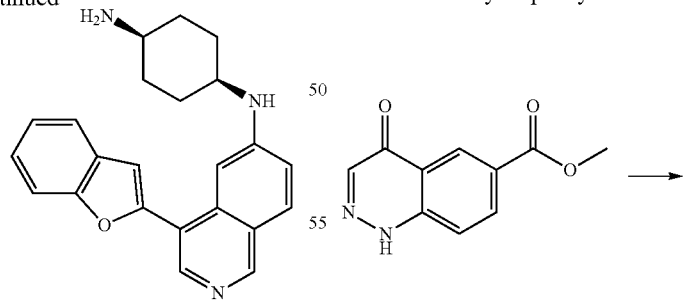 | (DMSO-$d_6$ + $D_2O$) 9.15 (s, 1H), 8.61 (s, 1H), 8.22 (d, J = 9.2 Hz), 7.81-7.71 (m, 2H), 7.60 (s, 1H), 7.47-7.35 (m, 4H), 4.63 (m, 1H), 3.92 (m, 1H), 3.38-3.02 (m, 4H), 2.17-1.65 (m, 4H) | 344.2 |

Methyl 4-phenylcinnoline-6-carboxylate

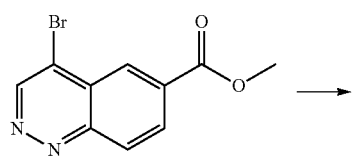

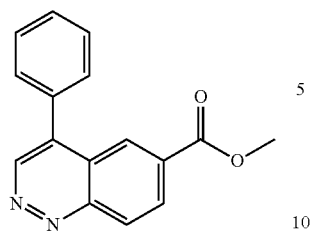

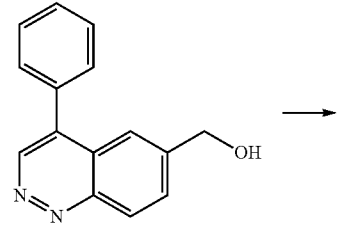

Under nitrogen atmosphere, 1200 mg (5.88 mmol) of methyl 4-oxo-1H-cinnoline-6-carboxylate (CAS 876516-53-9) was dissolved in 50 mL of CHCl₃. Then 6400 mg (22.3 mmol) of POBr₃ was added and the resulting mixture was stirred at 30° C. for 16 h. The reaction mixture was poured on crushed ice and then extracted with EA. The combined organic extracts were washed with saturated aqueous solution of sodium bicarbonate, dried over anhydrous sodium sulfate and concentrated in vacuum to give 1000 mg of methyl 4-bromocinnoline-6-carboxylate as a brown solid. Under argon atmosphere, 550 mg (2.06 mmol) of methyl 4-bromocinnoline-6-carboxylate, 352 mg (2.88 mmol) of Phenylboronic acid (CAS 98-80-6), 151 mg (0.21 mmol) of Pd(dppf)₂Cl₂, 49 mg (0.1 mmol) of X-Phos and 606 mg (6.18 mmol) of KOAc were suspended in 25 mL of dioxane. The mixture was stirred at 110° C. for 16 h. When LCMS showed that the reaction was complete, the reaction mixture was concentrated under vacuum and the residue was purified by silica gel column chromatography (PE/EA=6/1) to give 230 mg of the product as a yellow solid.

MS (ESI+): 265.0 ([M+H], 100%)

$^1$H NMR (400 MHz, CDCl₃) δ ppm: 9.37 (s, 1H), 8.74 (d, J=1.4 Hz, 1H), 8.26 (d, J=9.2 Hz, 1H), 8.43 (dd, J1=1.4 Hz, J2=9.0 Hz, 1H), 7.64-7.58 (m, 5H), 3.98 (s, 3H).

(4-Phenylcinnolin-6-yl)methyl methanesulfonate

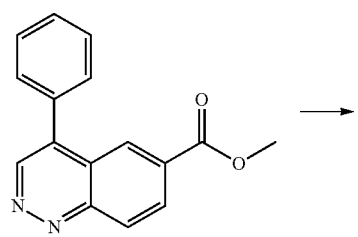

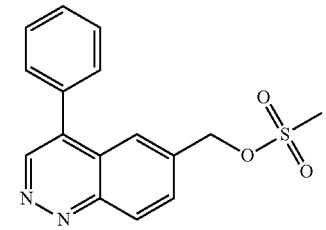

Under nitrogen atmosphere, 230 mg (0.87 mmol) of methyl 4-phenylcinnoline-6-carboxylate was dissolved in 15 mL of THF and the mixture was cooled to 0° C. by an ice bath. Then 50 mg (1.3 mmol) of LiAlH₄ was added, and the resulting mixture was stirring at 0° C. for 1 h. When TLC showed that the reaction was complete, 10 mL of cold water was added dropwise and the resulting mixture was extracted with EA. The combined organic extracts dried over anhydrous sodium sulfate, and concentrated in vacuum to give 200 mg of (4-phenylcinnolin-6-yl)methanol as a brown oil. Under nitrogen atmosphere, 200 mg (0.85 mmol) of (4-phenylcinnolin-6-yl)methanol was dissolved in 20 mL of DCM and the mixture was cooled to 0° C. by an ice bath. Then 0.23 mL (1.69 mmol) of triethylamine and 0.08 mL (1.02 mmol) of MsCl were added in sequence. The resulting mixture was stirred at 0° C. for 1 h. When TLC showed that the reaction was complete, the reaction mixture was concentrated in vacuum to give 260 mg of the crude product as a brown oil which was used directly in the next step without purification.

MS (ESI+): 315.0 ([M+H], 100%)

tert-Butyl 4-[(4-phenylcinnolin-6-yl)methyl]piperazine-1-carboxylate

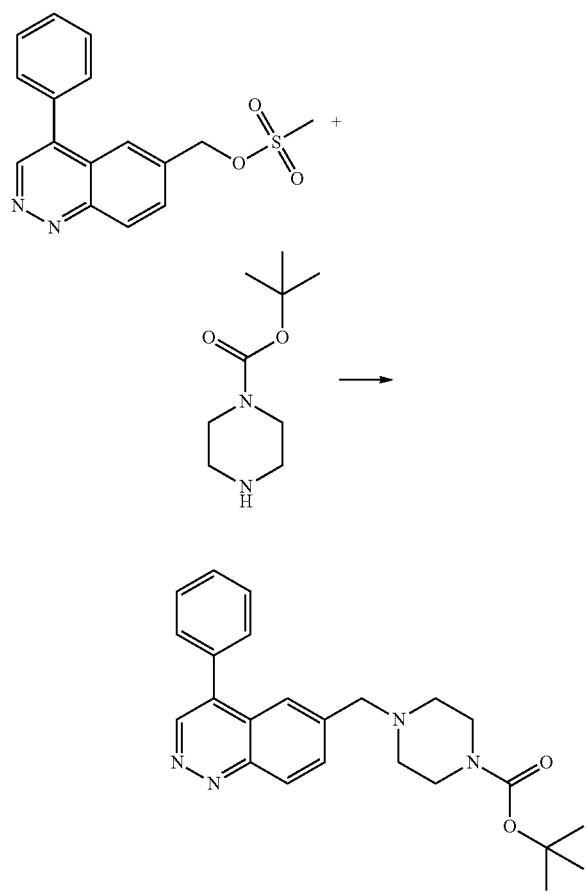

Under nitrogen atmosphere, 110 mg (0.35 mmol) of (4-phenylcinnolin-6-yl)methyl methanesulfonate was dissolved in 5 mL of DMF, then 72 mg (0.38 mmol) of Boc-piperazine (CAS 143238-38-4) and 0.1 mL (0.70 mmol) of TEA were added. The resulting mixture was stirred at 28° C. for 16 h. When TLC showed that the reaction was complete, the solvent was removed under reduced pressure and the residue was purified by preparative TLC (PE/EA=7/2) to give 70 mg of the product as a light yellow oil.

MS (ESI+): 405.2 ([M+H], 100%)

4-Phenyl-6-(piperazin-1-ylmethyl)cinnoline
(Example 83)

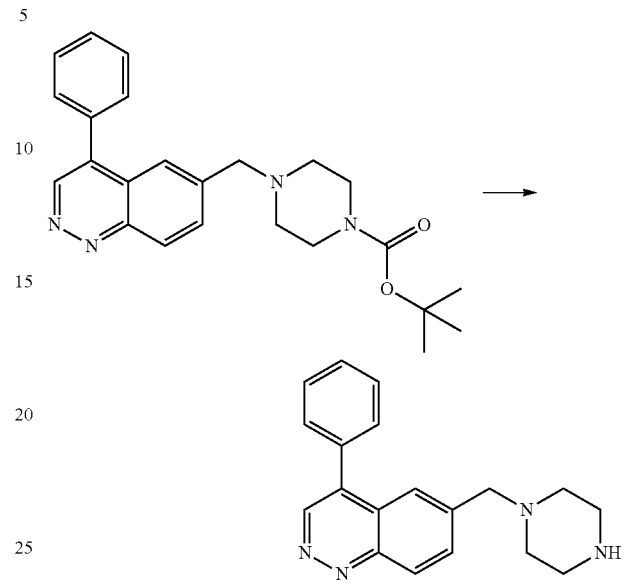

Under nitrogen atmosphere, 70 mg (0.17 mmol) of tert-butyl 4-[(4-phenylcinnolin-6-yl)methyl]piperazine-1-carboxylate was dissolved in 15 mL of 2 M HCl in EA. Then the mixture was stirred at 28° C. for 2 h. When LCMS showed that the reaction was complete, the resulting precipitate was collected by filtration to give 50 mg of the product as a yellow solid.

MS (ESI+): 305.2 [M+H].

$^1$H NMR (400 MHz, DMSO-$d_6$+$D_2O$) δ ppm: 9.41 (s, 1H), 8.63 (d, J=8.8 Hz, 1H), 8.24 (s, 1H), 8.19 (dd, J1=1.6 Hz, J2=8.8 Hz, 1H), 7.76-7.74 (m, 2H), 7.68-7.63 (m, 3H), 4.57 (s, 2H, H-e), 3.37 (m, 8H).

The following example was prepared accordingly to Example 83 by reaction of (4-phenylcinnolin-6-yl)methyl methanesulfonate with 4-N-Boc-amino-piperidine (CAS 73874-95-0) under the condition of $K_2CO_3$/DMF and subsequent deprotection:

| Example | $^1$H NMR (400 MHz) δ ppm | MS (+ESI) [M + H]$^+$ |
|---|---|---|
| 84 | (DMSO-$d_6$ + $D_2O$) 9.41 (s, 1H), 8.65 (d, J = 8.8 Hz, 1H), 8.18 (s, 1H), 8.05 (dd, J1 = 1.6 Hz, J2 = 8.8 Hz, 1H), 7.76-7.71 (m, 2H), 7.68-7.63 (m, 3H), 4.50 (s, 2H), 3.41 + 3.06 (2m, 4H), 3.25 (m, 1H), 2.07 + 1.70 (2m, 4H) | 319.3 |

The following examples were prepared accordingly to Example 83 by reactions of methyl 4-bromocinnoline-6-carboxylate with 4-(2-tetrahydropyranyloxy)phenylboronic acid (CAS 182281-01-2) in the presence of a Pd-catalyst followed by the sequential reactions:

| Example | | ¹H NMR (400 MHz) δ ppm | MS (+ESI) [M + H]⁺ |
|---|---|---|---|
| 85 | (structure: 4-(4-hydroxyphenyl)-6-(piperazin-1-ylmethyl)cinnoline) | (DMSO-d₆ + D₂O) 9.36 (s, 1H), 8.58 (d, J = 8.8 Hz, 1H), 8.27 (s, 1H), 8.13 (dd, J1 = 1.2 Hz, J2 = 8.8 Hz, 1H), 7.61 (m, 2H), 7.04 (m, 2H), 4.52 (s, 2H), 3.35 (m, 8H) | 321.3 |
| 86 | (structure: 4-(4-hydroxyphenyl)-6-((4-aminopiperidin-1-yl)methyl)cinnoline) | (DMSO-d₆ + D₂O) 9.36 (s, 1H), 8.58 (d, J = 8.8 Hz), 8.26 (s, 1H), 8.09 (dd, J1 = 1.4 Hz, J2 = 9.0 Hz, 1H), 7.61-7.53 (m, 2H), 7.06-7.02 (m, 2H), 4.51 (s, 2H), 3.44 + 3.11 (2m, 4H), 3.35 (m, 1H), 2.09 + 1.80 (2m, 4H) | 335.3 |

6-Bromo-4-chloro-2-(2-trimethylsilylethoxymethyl)isoquinolin-1-one tert-Butyl N-[4-[[4-chloro-1-oxo-2-(2-trimethylsilylethoxymethyl)-6-isoquinolyl]amino] cyclohexyl] carbamate Under nitrogen atmosphere, a mixture of 200 mg (0.77 mmol) of 6-bromo-4-chloro-2H-isoquinolin-1-one (CAS 1219130-48-9) and 46 mg (60% dispersion in mineral oil, 1.16 mmol) of NaH in 30 ml of DMF was stirred at 0° C. for 30 minutes. Then 0.21 mL (0.16 mmol) of SEMCl was added dropwise. After stirring at 25° C. for 24 h, the reaction mixture was concentrated under vacuum to dryness. The residue was purified by silica gel column chromatography (PE/EA=10/1) to afford 100 mg of the product as a colorless oil.

MS (ESI+): 388.0 [M+H].

¹H NMR (400 MHz, DMSO-d₆) δ ppm: 8.21 (d, J=8.4Hz, 1H), 7.93 (m, 2H), 7.83 (dd, J1=1.6 Hz, J2=8.4 Hz, 1H), 5.32 (s, 2H), 3.59 (t, J=8.0 Hz, 2H), 0.86 (t, J=8.0Hz, 2H), −0.04 (s, 9H)

Under nitrogen atmosphere, a mixture of 80 mg (0.21 mmol) of 6-bromo-4-chloro-2-(2-trimethylsilylethoxymethyl)isoquinolin-1-one, 44 mg (0.21 mmol) of 1-N-Boc-trans-1, 4-cyclohexyldiamine (CAS 177906-48-8), 21 mg (0.02 mmol) of Pd$_2$(dba)$_3$, 24 mg (0.04 mmol) of XantPhos (CAS 564483-18-7) and 134 mg (0.41 mmol) of Cs$_2$CO$_3$ in 20 ml of toluene was stirred at 80° C. for 18.0 h. The mixture was cooled to 25° C. and then concentrated under vacuum. The residue was purified by silica gel column chromatography (EA/PE=1/2) to get 50 mg of the product as light yellow solid.

MS (ESI+): 522.2 [M+H].

$^1$H NMR (400 MHz, DMSO-d$_6$+D$_2$O) δ ppm: 7.96 (d, J=8.8 Hz, 1H), 7.64 (s, 1H), 7.85 (m, 1H), 6.76 (d, J=7.6Hz, 1H), 6.66 (d, J=1.6Hz, 1H), 5.25 (s, 2H), 3.55 (t, J=8.0 Hz, 2H), 3.20-3.35 (m, 2H), 1.99 (m, 2H), 1.83 (m, 2H), 1.39 (s, 9H), 1.20-1.35 (m, 4H), 0.86 (t, J=8.0Hz, 2H), −0.05 (s, 9H)

tert-Butyl N-[4-[[4-(benzofuran-2-yl)-1-oxo-2-(2-trimethylsilylethoxymethyl)-6-isoquinolyl]amino]cyclohexyl]carbamate

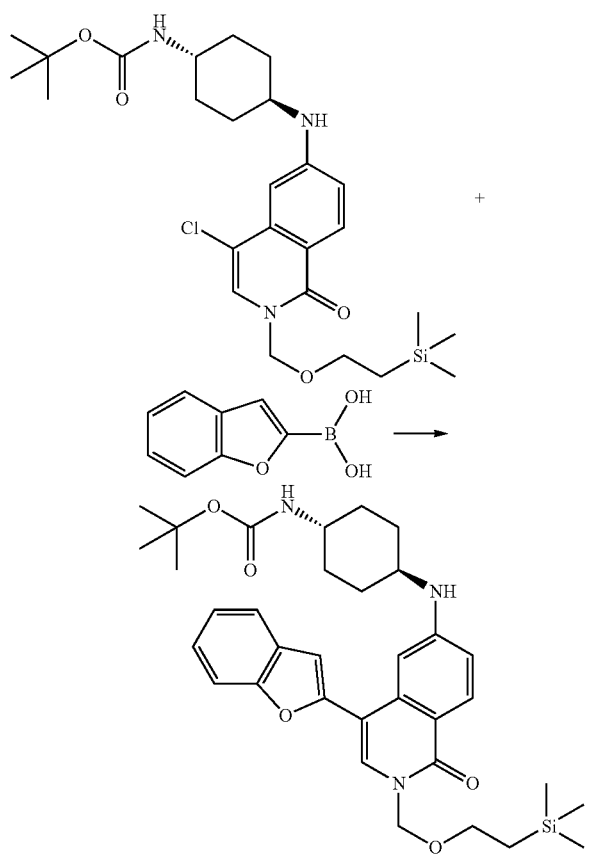

Under argon atmosphere, in a sealed tube equipped with a magnetic stirrer, a mixture of 30 mg (0.06 mmol) of tert-butyl N-[4-[[4-chloro-1-oxo-2-(2-trimethylsilylethoxymethyl)-6-isoquinolyl]amino]cyclohexyl]carbamate, 11 mg (0.07 mmol) of benzofuran-2-boronic acid (CAS 98437-24-2), 5 mg (0.006 mmol) of Pd$_2$(dba)$_3$, 5 mg (0.01 mmol) of S-PHOS (CAS 657486-07-6) and 31 mg (0.11 mmol) of K$_3$PO$_4$·3H$_2$O in 2 mL of dioxane and 0.2 mL of H$_2$O was stirred at 110° C. for 18 h. The mixture was cooled to 25° C. and filtered through Celite. The filtrate was concentrated under vacuum. The residue was purified by preparative HPLC to give 10 mg of the product as a white solid.

MS (ESI+): 604.3 [M+H].

$^1$H NMR (400 MHz, DMSO-d$_6$+D$_2$O) δ ppm: 8.05 (d, J=8.4 Hz, 1H), 7.81 (s, 1H), 7.70 (d, J=8.0 Hz, 1H), 7.61 (d, J=8.0 Hz, 1H), 7.27-7.38 (m, 2H), 7.11 (s, 1H), 7.00 (s, 1H), 7.85 (d, J=8.4 Hz, 1H), 6.79 (d, J=7.6 Hz, 1H), 0.55-0.70 (br, 1H), 5.36 (s, 2H), 3.61 (t, J=8.0 Hz, 2H), 3.15-3.28 (m, 2H), 2.01 (m, 2H), 1.81 (m, 2H), 1.38 (s, 9H), 1.16-1.33 (m, 4H), 0.88 (t, J=8.0 Hz, 2H), −0.04 (s, 9H)

6-[(4-Aminocyclohexyl)amino]-4-(benzofuran-2-yl)-2H-isoquinolin-1-one (Example 87)

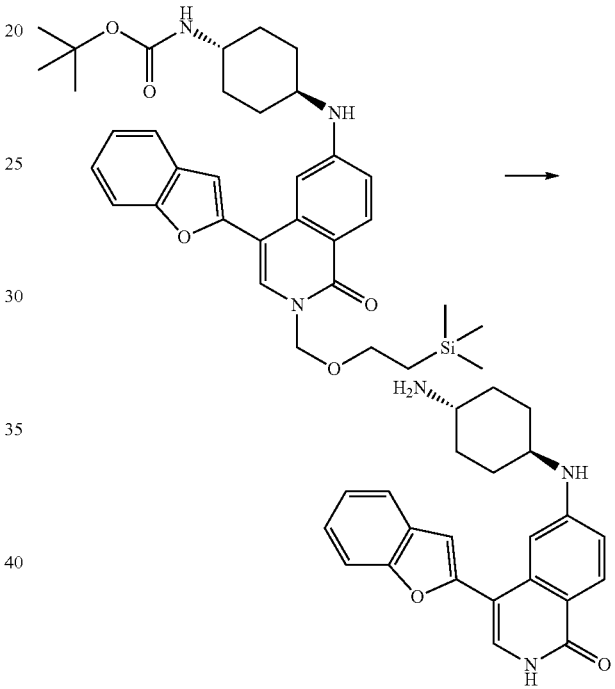

Under nitrogen atmosphere, 290 mg (0.14 mmol) of tert-butyl N-[4-[[4-(benzofuran-2-yl)-1-oxo-2-(2-trimethylsilylethoxymethyl)-6-isoquinolyl]amino]cyclohexyl]carbamate was dissolved in 20 ml of DCM followed by addition of 2 mL of TFA. The mixture was stirred at 25° C. for 2 h. Then the mixture was concentrated under vacuum and the residue was purified by preparative HPLC to give 20 mg of the product as an off-white solid.

MS (ESI+): 374.2 [M+H].

$^1$H NMR (400 MHz, DMSO-d$_6$+D$_2$O) δ ppm: 8.00 (d, J=8.4 Hz, 1H), 7.66 (m, 1H), 7.59 (d, J=8.0 Hz, 1H), 7.47 (s, 1H), 7.25-7.35 (m, 2H), 7.09 (s, 1H), 6.99 (d, J=2.0 Hz, 1H), 6.87 (dd, J1=2.0 Hz, J2=8.4 Hz, 1H), 3.24 (m, 1H), 3.02 (m, 1H), 2.06 (m, 2H), 1.97 (m, 2H), 1.40 (m, 2H), 1.25 (m, 2H)

The following example was prepared accordingly to Example 87 by reaction of tert-butyl N-[4-[[4-(benzofuran-2-yl)-1-oxo-2-(2-trimethylsilylethoxymethyl)-6-isoquinolyl]amino] cyclohexyl]carbamate with phenylboronic acid (CAS 98-80-6) in the presence of a Pd-catalyst and subsequent deprotection:

| Example | | ¹H NMR (400 MHz) δ ppm | MS (+ESI) [M + H]⁺ |
|---|---|---|---|
| 88 | 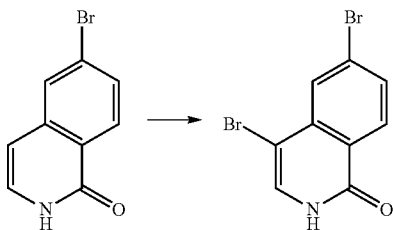 [SMILES: O=c1[nH]ccc2cc(Br)ccc12 ; O=c1[nH]cc(Br)c2cc(Br)ccc12] | (DMSO-d₆ + D₂O) 7.98 (d, J = 8.8 Hz, 1H), 7.35-7.50 (m, 5H), 6.91 (s, 1H), 6.81 (dd, J1 = 2.4 Hz, J2 = 8.8 Hz, 1H), 6.45 (d, J = 2.4 Hz, 1H), 3.05 (m, 1H), 2.95 (m, 1H), 1.90-2.00 (m, 4H), 1.32 (m, 2H), 1.20 (m, 2H) | 334.3 |

4, 6-Dibromo-2H-isoquinolin-1-one

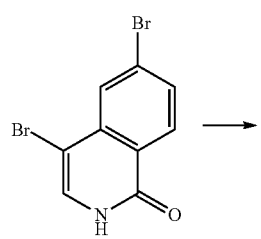

Under nitrogen atmosphere, 200 mg (0.89 mmol) of 6-Bromo-2H-isoquinolin-1-one (CAS 82827-09-6) was dissolved in 30 mL of ACN and the mixture was refluxed at 90° C. Then a solution of 191 mg (1.07 mmol) of NBS in 10 mL of ACN was added dropwise. After addition, the mixture was refluxed at 90° C. for additional 5 h and then cooled to 25° C. The resulting precipitate was collected by filtration to give 200 mg of the product as a light grey solid.

MS (ESI+): 301.8 [M+H].

¹H NMR (400 MHz, CDCl₃+D₂O) δ ppm: 11.75 (brs, 1H), 8.15 (d, J=8.8 Hz, 1H), 7.87 (d, J=2.0 Hz, 1H), 7.78 (dd, J1=2.0 Hz, J2=8.8Hz, 1H), 7.64 (s, 1H).

4,6-Dibromo-2-(2-trimethylsilylethoxymethyl)iso-quinolin-1-one

-continued

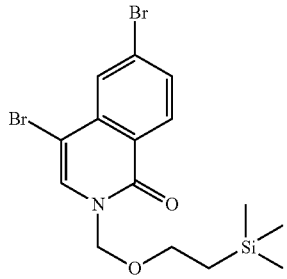

Under nitrogen atmosphere, a mixture of 100 mg (0.66 mmol) of 4, 6-dibromo-2H-isoquinolin-1-one and 26 mg (60% dispersion in mineral oil, 0.66 mmol) of NaH in 10 mL of DMF was stirred at 0° C. for 30 minutes. Then 0.09 mL (0.5 mmol) of SEMCl was added. After stirring at 25° C. for 24 h, the reaction mixture was concentrated under vacuum and the residue was purified by silica gel column chromatography (PE/EA=10/1) to afford 90 mg of the product as a colorless oil.

MS (ESI+): 431.9 [M+H].

¹H NMR (400 MHz, DMSO-d6) δ ppm: 8.20 (d, J=8.4 Hz, 1H), 8.01 (s, 1H), 7.88 (d, J=2.0 Hz, 1H), 7.81 (dd, J1=2.0 Hz, J2=8.4 Hz, 1H), 5.33 (s, 2H), 3.60 (t, J=8.0 Hz, 2H), 0.88 (t, J=8.0 Hz, 2H), -0.05 (s, 9H)

4-Bromo-6-(4-pyridylmethylamino)-2-(2-trimethyl-silylethoxymethyl)isoquinolin-1-one

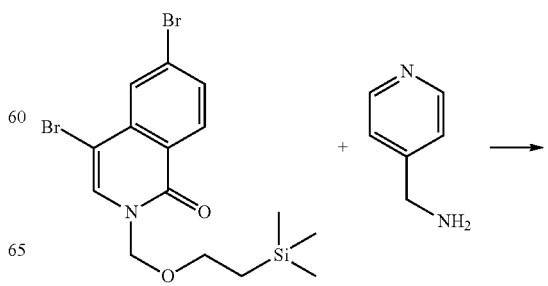

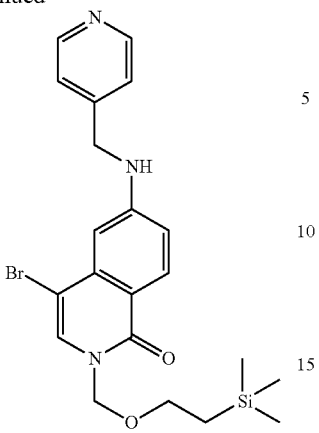

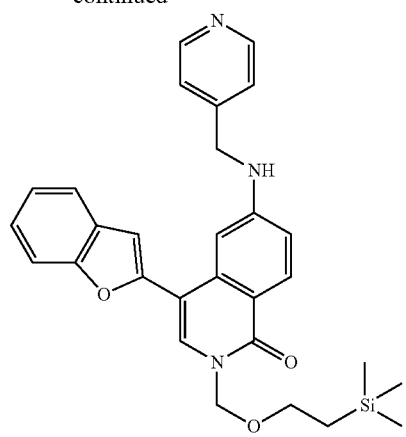

Under nitrogen atmosphere, a mixture of 30 mg (0.07 mmol) of 4,6-dibromo-2-(2-trimethylsilylethoxymethyl)isoquinolin-1-one, 9 mg (0.08 mmol) of 4-Aminomethylpyridine (CAS 3731-53-1), 7 mg (0.007 mmol) of Pd$_2$(dba)$_3$ (CAS 52409-22-0), 8 mg (0.014 mmol) of XantPhos (CAS 564483-18-7) and 45 mg (0.14 mmol) of Cs$_2$CO$_3$ in 10 mL of Toluene was stirred at 80° C. for 16 h. The mixture was cooled to 25° C. and then concentrated under vacuum. The residue was purified by silica gel column chromatography (EA/PE=1/1) to afford 20 mg of the product as a light yellow solid.

MS (ESI+): 460.0/462.0 [M+H].

$^1$H NMR (400 MHz, DMSO-d$_6$) δ ppm: 8.53 (d, J=5.6 Hz, 2H), 7.98 (d, J=8.8 Hz, 1H), 7.73 (s, 1H), 7.56 (t, J=6.0Hz, 1H), 7.38 (d, J=5.6 Hz, 2H), 6.89 (dd, J1=2.0 Hz, J2=8.8 Hz, 1H), 6.64 (s, 1H), 5.26 (s, 2H), 4.49 (d, J=6.0 Hz, 2H), 3.56 (t, J=8.0 Hz, 2H), 0.86 (t, J=8.0 Hz, 2H), −0.05 (s, 9H)

4-(Benzofuran-2-yl)-6-(4-pyridylmethylamino)-2-(2-trimethylsilylethoxymethyl)isoquinolin-1-one

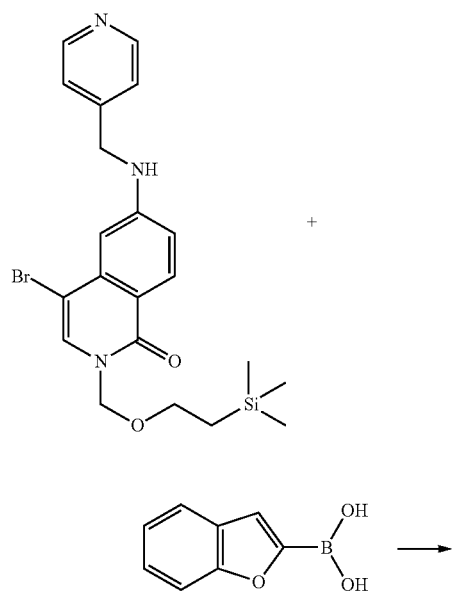

Under argon atmosphere, in a 10 mL sealed tube, a mixture of 20 mg (0.04 mmol) of 4-bromo-6-(4-pyridylmethylamino)-2-(2-trimethylsilylethoxymethyl)isoquinolin-1-one, 14 mg (0.09 mmol) of benzofuran-2-boronic acid (CAS 98437-24-2), 4 mg (0.004 mmol) of Pd$_2$(dba)$_3$, 4 mg (0.009 mmol) of S-PHOS and 23 mg (0.09 mmol) of K$_3$PO$_4$.3H$_2$O in 2 mL of dioxane and 0.2 mL of H$_2$O was stirred at 110° C. for 0.5 h under microwave irradiation. The mixture was cooled to 25° C. and then filtered. The filtrate was concentrated under vacuum and the residue was purified by silica gel column chromatography (EA/PE=1/1) to give 10 mg of the product as a light yellow solid.

MS (ESI+): 498.2 [M+H].

$^1$H NMR (400 MHz, DMSO-d$_6$) δ ppm: 8.50 (m, 2H), 8.06 (d, J=8.8 Hz, 1H), 7.80 (s, 1H), 7.65 (d, J=7.2 Hz, 1H), 7.53 (d, J=7.2 Hz, 1H), 7.25-7.50 (m, 4H), 6.93 (d, J=8.8 Hz, 1H), 6.83 (s, 1H), 6.71 (m, 2H), 5.36 (s, 2H), 4.44 (d, J=4.4Hz, 2H), 3.60 (m, 2H), 0.87 (t, J=8.0 Hz, 2H), −0.05 (s, 9H)

4-(Benzofuran-2-yl)-6-(4-pyridylmethylamino)-2H-isoquinolin-1-one (Example 89)

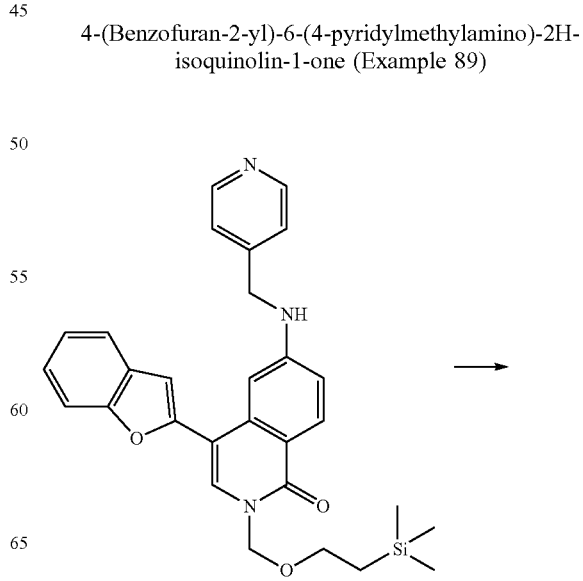

115

-continued

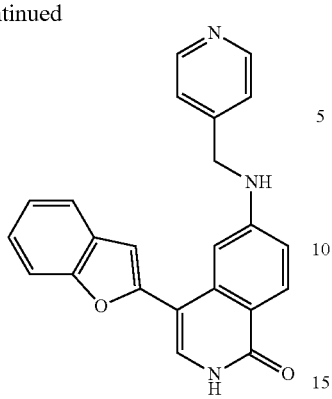

Under nitrogen atmosphere, 180 mg (0.36 mmol) of 4-(benzofuran-2-yl)-6-(4-pyridylmethylamino)-2-(2-trimethylsilylethoxymethyl)isoquinolin-1-one was dissolved in 15 mL of DCM followed by addition of 1.5 mL of TFA. The reaction mixture was stirred at 25° C. for 2 h. Then the mixture was concentrated under vacuum and the residue was purified by preparative HPLC to give 25 mg of the product as a light yellow solid.

MS (ESI+): 368.2 [M+H].

$^1$H NMR (400 MHz, DMSO-d$_6$+D$_2$O) δ ppm: 8.45 (d, J=4.0 Hz, 2H), 8.01 (d, J=8.8Hz, 1H), 7.61 (d, J=7.2 Hz, 1H), 7.47 (d, J=7.2 Hz, 1H), 7.46 (s, 1H), 7.25-7.35 (m, 4H), 6.92 (dd, J1=2.0 Hz, J2=8.8 Hz, 1H), 6.77 (d, J=2.0 Hz, 1H), 6.67 (s, 1H), 4.41 (s, 2H).

The following example was prepared accordingly to Example 89 by reaction of 4-bromo-6-(4-pyridylmethylamino)-2-(2-trimethylsilylethoxymethyl)isoquinolin-1-one with the phenylboronic acid (CAS 98-80-6) in the presence of a Pd-catalyst and subsequent deprotection:

116 tert-Butyl N-(4-bromo-6-methyl-1-isoquinolyl)-N-tert-butoxycarbonyl-carbamate

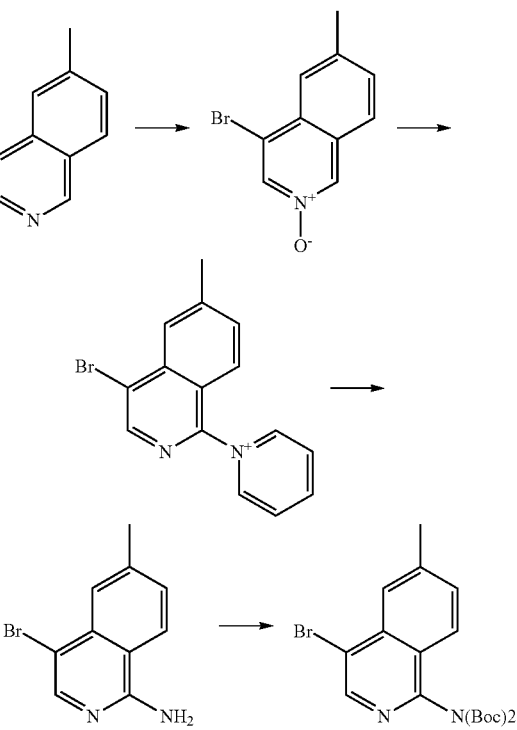

A solution of 220 mg (1.00 mmol) of 4-bromo-6-(bromomethyl)isoquinoline (CAS 98331-27-2) and 513 mg (3.50 mmol) of mCPBA in 4 mL of DCM is stirred at 25° C. for 4 h. The solvent is evaporated and the residue is diluted with EA, washed with saturated NaHCO$_3$ solution and water, dried over Na$_2$SO$_4$, concentrated to give 235 mg of the crude 4-bromo-6-methyl-2-oxido-isoquinolin-2-ium as a grey solid. The crude intermediate is dissolved in 5 mL of pyridine and 376 mg (1.98 mmol) of TsCl is added. The reaction mixture is stirred at 25° C. for 2 h. The pyridine was removed under reduced pressure to afford 285 mg of the crude 4-bromo-6-methyl-1-pyridin-1-ium-1-yl-isoquinoline as a grey solid.

| Example | | $^1$H NMR (400 MHz) δ ppm | MS (+ESI) [M + H]$^+$ |
|---|---|---|---|
| 90 | (structure) | (DMSO-d$_6$ + D$_2$O) 8.44 (d, J = 6.0 Hz, 2H), 7.98 (d, J = 8.8 Hz, 1H), 7.35 (m, 3H), 7.20 (d, J = 6.0 Hz, 2H), 7.14 (m, 2H), 6.89 (s, 1H), 6.84 (dd, J1 = 2.0 Hz, J2 = 8.8 Hz, 1H), 6.29 (d, J = 2.0 Hz, 1H), 4.26 (s, 2H) | 328.1 |

Then the crude intermediate in 10 mL of 2-aminoethanol is stirred at 25° C. for 10 h. The solution is poured onto cracked ice, and the solids are isolated by filtration and dried under vacuum to afford 130 mg of the crude 4-bromo-6-methyl-isoquinolin-1-amine as a grey solid.

This intermediate is dissolved in 5 mL of DCM and 239 mg (1.09 mmol) of Boc$_2$O. 153 µL (1.10 mmol) of TEA, 67 mg (0.55 mmol) of DMAP are added. The resultant solution is stirred at 25° C. for 8 h. The solvent was removed and the residue was purified by silica gel column chromatography (PE/EA=10/1, R$_f$=0.4) to give 111 mg of tert-butyl N-(4-bromo-6-methyl-1-isoquinolyl)-N-tert-butoxycarbonyl-carbamate as a light yellow solid.

MS (ESI+): 437.1 [M+H].

$^1$H NMR (400 MHz, DMSO-d$_6$) δ ppm: 8.65 (s, 1H), 7.95 (s, 1H), 7.84 (d, J=8.8 Hz, 1H), 7.95 (dd, J=1.2 Hz, J2=8.8 Hz, 1H), 2.61 (s, 3H), 1.29 (s, 18H).

tert-Butyl N-[4-bromo-6-(bromomethyl)-1-isoquinolyl]-N-tert-butoxycarbonyl-carbamate

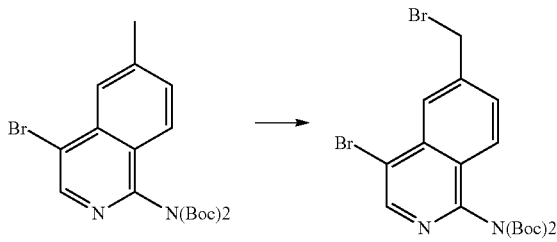

A solution of 4.80 g (11.0 mmol) of tert-butyl N-(4-bromo-6-methyl-1-isoquinolyl)-N-tert-butoxycarbonyl-carbamate, 266 mg (1.10 mmol) of BPO and 1.95 g (11.0 mmol) of NBS in 30 mL of CCl$_4$ is stirred at 100° C. for 8 h. The solvent is evaporated and the residue is purified via silica gel column chromatography (PE/EA=8/1, R$_f$=0.5) to give 2.40 g of tert-butyl N-[4-bromo-6-(bromomethyl)-1-isoquinolyl]-N-tert-butoxycarbonyl-carbamate as a light yellow solid.

MS (ESI+): 515.0 [M+H].

$^1$H NMR (400 MHz, DMSO-d$_6$) δ ppm: 8.73 (s, 1H), 8.26 (s, 1H), 7.84 (d, J=8.8 Hz, 1H), 7.95 (dd, J=8.8 Hz, 1H), 5.01 (s, 2H), 1.29 (s, 18H).

tert-Butyl 4-[[1-[bis(tert-butoxycarbonyl)amino]-4-bromo-6-isoquinolyl]methyl]piperazine-1-carboxylate

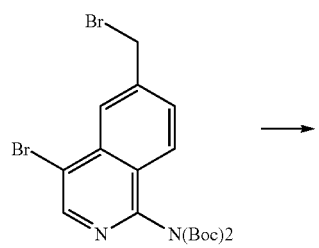

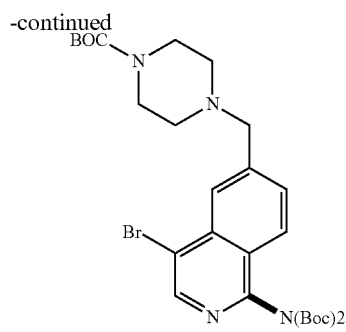

A solution of 1.20 g (2.32 mmol) of tert-butyl N-[4-bromo-6-(bromomethyl)-1-isoquinolyl]-N-tert-butoxycarbonyl-carbamate, 643 mg (4.65 mmol) of K$_2$CO$_3$ and 476 mg (2.56 mmol) of 4-N-Boc-amino-piperidine (CAS 73874-95-0) in 3 mL of DMF is stirred at 25° C. for 2 hours. The solution is diluted with EA, washed with water and brine, dried over Na$_2$SO$_4$, and concentrated. The residue was purified by silica gel column chromatography (PE/EA=4/1, R$_f$=0.4) to give 1.01 g of tert-butyl 4-[[1-[bis(tert-butoxycarbonyl)amino]-4-bromo-6-isoquinolyl]methyl] piperazine-1-carboxylate as a light yellow foam.

MS (ESI+): 621.2 [M+H].

$^1$H NMR (400 MHz, DMSO-d$_6$) δ ppm: 8.68 (s, 1H), 8.08 (s, 1H), 7.91 (d, J=8.4 Hz, 1H), 7.84 (d, J=8.4 Hz, 1H), 3.79 (s, 2H), 3.50-3.20 (m, 4H), 2.46-2.32 (m, 4H), 1.39 (s, 9H), 1.30 (s, 18H).

tert-Butyl 4-[[1-[bis(tert-butoxycarbonyl)amino]-4-phenyl-6-isoquinolyl]methyl]piperazine-1-carboxylate

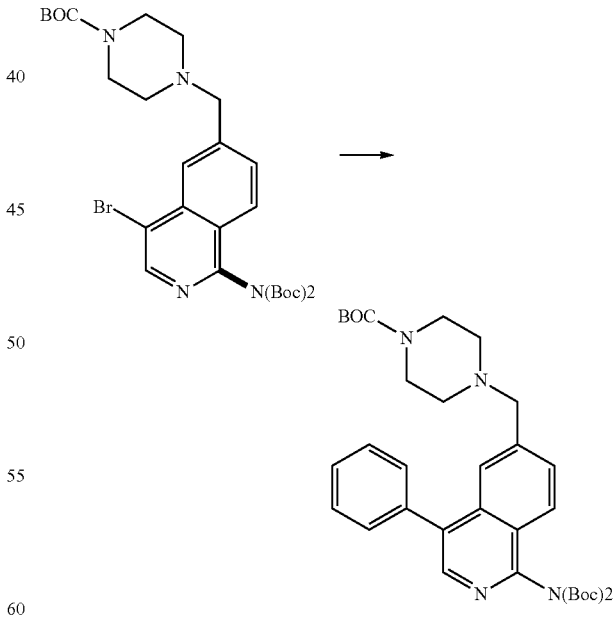

Under argon atmosphere, to a mixture of 300 mg (0.48 mmol) of tert-butyl 4-[[1-[bis(tert-butoxycarbonyl)amino]-4-bromo-6-isoquinolyl]methyl]piperazine-1-carboxylate, 118 mg (0.58 mmol) of 4,4,5,5-tetramethyl-2-phenyl-1,3,2-dioxaborolane (CAS 24388-23-6), 205 mg (0.97 mmol) of K$_3$PO$_4$.H$_2$O in a mixture 5 mL of DMF and 0.5 mL of water, 84 mg (0.07 mmol) of Pd(PPh$_3$)$_4$ are added. The mixture is stirred at 80° C. for 1 h. Then the reaction mixture is diluted with EA, washed with water and brine, dried over Na$_2$SO$_4$ and filtered. The filtrate is concentrated under reduced pressure and the residue is purified by silica gel column chromatography (DCM/MeOH=20/1) to afford 278 mg of the product as a light yellow solid.

MS (ESI+): 619.3 [M+H].

$^1$H NMR (400 MHz, DMSO-d$_6$) δ ppm: 8.34 (s, 1H), 7.91 (d, J=8.8 Hz, 1H), 7.82 (s, 1H), 7.74 (dd, J2=8.8 Hz, 1H), 7.66-7.52 (m, 5H), 3.66 (s, 2H), 3.35 (m, 4H), 2.36-2.28 (m, 4H), 1.38 (s, 9H), 1.37 (s, 18H).

4-Phenyl-6-(piperazin-1-ylmethyl)isoquinolin-1-amine (Example 91)

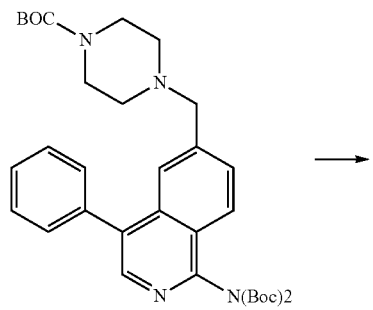

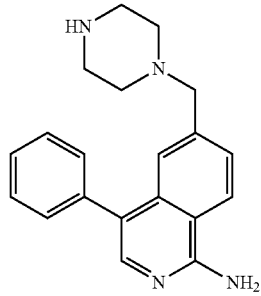

A mixture of 278 mg (0.45 mmol) of tert-butyl 4-[[1-[bis(tert-butoxycarbonyl)amino]-4-phenyl-6-isoquinolyl]methyl]piperazine-1-carboxylate in 10 mL of a 1.7 N solution of HCl in EA is stirred at 25° C. for 2 h. The solvent was evaporated and the residue was washed with EA for 5 times, and then the crude product was purified by preparative HPLC to give 100 mg of the desired product.

MS (ESI+): 319.1 [M+H].

$^1$H NMR (400 MHz, DMSO-d$_6$+D$_2$O) δ ppm: 8.21 (d, J=8.8 Hz, 1H), 7.70 (s, 1H), 7.61 (s, 1H), 7.55-7.35 (m, 6H), 3.61 (s, 2H), 3.03-3.00 (m, 4H), 2.62-2.40 (m, 4H).

The following examples were prepared accordingly to Example 91 by reaction of tert-butyl N-[4-bromo-6-(bromomethyl)-1-isoquinolyl]-N-tert-butoxycarbonyl-carbamate with tert-butyl piperazine-1-carboxylate or tert-butyl N-(4-piperidyl)carbamate and then reaction with the corresponding boronic acid or boronic acid ester in the presence of a Pd-catalyst and subsequent deprotection:

| Example | | $^1$H NMR (400 MHz, DMSO-d$_6$ + D$_2$O) δ ppm | MS (+ESI) [M + H]$^+$ |
|---|---|---|---|
| 92 | (structure) | 8.73 (d, J = 8.8 Hz, 1H), 8.05 (d, J = 8.8 Hz, 1H), 7.91 (d, J = 1.2 Hz, 1H), 7.67 (s, 1H), 7.63-7.45 (m, 5H), 4.45 (s, 2H), 3.45-3.29 (m, 2H), 3.29-3.17 (m, 1H), 3.15-2.02 (m, 2H), 2.16-2.00 (m, 2H), 1.97-1.76 (m, 2H). | 333.3 |
| 93 | (structure) | 8.57 (d, J = 8.8 Hz, 1H), 7.79 (d, J = 8.8 Hz, 1H), 7.74 (s, 1H), 7.54 (s, 1H), 7.33-7.22 (m, 2H), 6.99-6.88 (m, 2H), 3.83 (s, 2H), 3.18-3.00 (m, 4H), 2.76-2.58 (m, 4H). | 335.1 |

| Example | | ¹H NMR (400 MHz, DMSO-d₆ + D₂O) δ ppm | MS (+ESI) [M + H]⁺ |
|---|---|---|---|
| 94 | 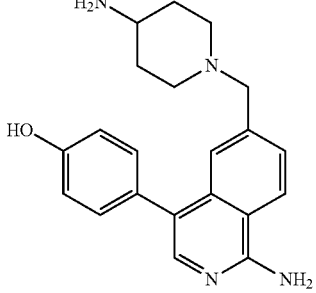 [SMILES: Nc1ncc(-c2ccc(O)cc2)c2cc(CN3CCNCC3)ccc12] | 8.62 (d, J = 8.4 Hz, 1H), 7.89 (s, 1H), 7.88-7.80 (d, J = 8.4 Hz, 1H), 7.57 (s, 1H), 7.29 (dd, J = 6.4 Hz, 2.0 Hz, 2H), 6.93 (dd, J = 6.4 Hz, 2.0 Hz, 2H), 4.37 (s, 2H), 3.42-3.13 (m, 3H), 3.00-2.82 (m, 2H), 2.12-1.95 (m, 2H), 1.80-1.54 (m, 2H). | 349.4 |

2-[[4-(Benzofuran-2-yl)-6-isoquinolyl]oxy]-N,N-dimethyl-ethanamine (Example 95)

Under argon atmosphere, to a solution of 0.14 mL (1.37 mmol) of N,N-dimethylethanolamine in 10 mL of DMF was added 230 mg (5.70 mmol) of NaH at rt.

The mixture was stirred at rt for 0.5 h, followed by the addition of 300 mg (1.14 mmol) of 4-(benzofuran-2-yl)-6-fluoro-isoquinoline. The resulting mixture was stirred at 80° C. for 4 h. LCMS indicated the reaction was complete. The reaction mixture was diluted with EA, washed with H₂O and brine, dried over anhydrous Na₂SO₄ and concentrated to give the crude product, which was further purified by prep-HPLC to give 75 mg of desired product as an orange semisolid.

MS (ESI+): 333.2 [M+H].

¹H NMR (400 MHz, DMSO-d₆+D₂O) δ ppm 9.46 (s, 1H), 8.92 (s, 1H), 8.41 (d, J=8.8 Hz, 1H), 7.91 (d, J=2.0 Hz, 1H), 7.81-7.74 (m, 2H), 7.68-7.62 (m, 2H), 7.47-7.35 (m, 2H), 4.61 (t, J=4.4 Hz, 2H), 3.62 (t, J=4.4 Hz, 2H), 2.89 (s, 6H).

The following compound is prepared in analogy to Example 95, starting from 4-(benzofuran-2-yl)-6-fluoro-isoquinoline and 2-methylpyrazol-3-ol.

| Example | | ¹H NMR (400 MHz) δ ppm | MS (+ESI) [M + H]⁺ |
|---|---|---|---|
| 96 | 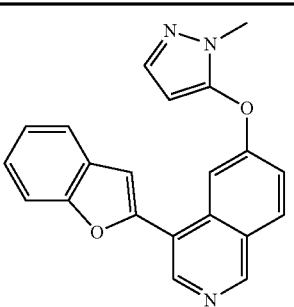 | (DMSO-d₆ + D₂O) 9.39 (s, 1H), 8.98 (s, 1H), 8.37 (d, J = 8.8 Hz, 1H), 8.05 (d, J = 2.4 Hz, 1H), 7.76-7.63 (m, 4H), 7.51 (s, 1H), 7.43-7.32 (m, 2H), 6.10 (d, J = 2.4 Hz, 1H), 3.69 (s, 3H). | 342.2 |

4-Bromo-6-[(2-methylpyrazol-3-yl)oxymethyl]isoquinoline

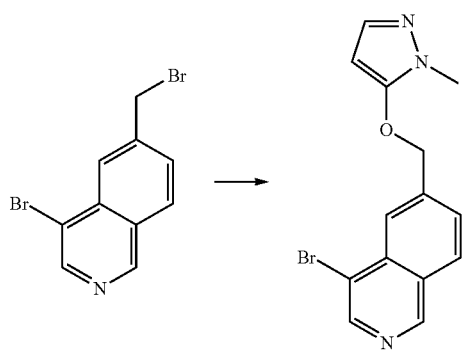 [SMILES: BrCc1ccc2cncc(Br)c2c1 ; Cn1nccc1OCc1ccc2cncc(Br)c2c1]

To a solution of 78 mg (0.80 mmol) of 5-hydroxy-1-methylpyrazole and 220 mg (1.59 mmol) of K₂CO₃ in 10 mL of DMF was added 240 mg (0.80 mmol) of 4-bromo-6-(bromomethyl)isoquinoline and the mixture was stirred at rt for 4 h. LCMS indicated the reaction was complete. The solvent was evaporated under reduced pressure and the residue was dissolved in EA, washed with water and brine, dried over anhydrous Na₂SO₄ and concentrated to dryness. The residue was purified by silica gel chromatography column (PE/EA=1/1, $R_f$=0.3) to give 86 mg of desired product as a white solid.

MS (ESI+): 318.0 [M+H].

¹H NMR (400 MHz, DMSO-d₆) δ ppm 9.35 (s, 1H), 8.79 (s, 1H), 8.27 (d, J=8.8 Hz, 1H), 8.17 (s, 1H), 7.90-7.87 (m, 1H), 7.22 (d, J=2.0 Hz, 1H), 5.76 (d, J=2.0 Hz, 1H), 5.47 (s, 2H), 3.63 (s, 3H).

4-(Benzofuran-2-yl)-6-[(2-methylpyrazol-3-yl)oxymethyl]isoquinoline (Example 97)

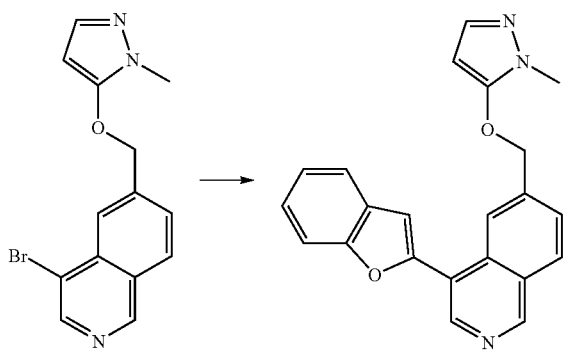 [SMILES: Cn1nccc1OCc1ccc2cncc(Br)c2c1 ; Cn1nccc1OCc1ccc2cncc(-c3cc4ccccc4o3)c2c1]

Under argon atmosphere, to a mixture of 372 mg (1.17 mmol) of 4-bromo-6-[(2-methylpyrazol-3-yl)oxymethyl]isoquinoline, 208 mg (1.29 mmol) of benzofuran-2-boronic acid (CAS 98437-24-2), 529 mg (1.99 mmol) of K₃PO₄·3H₂O in 15 mL of dioxane is added 121 mg (0.12 mmol) of Pd₂(dba)₃ and 79 mg (0.28 mmol) of PCy₃ (CAS 2622-14-2). The mixture was stirred at 100° C. for 16 h. LCMS indicated that the reaction was complete. The solvent was removed and the residue was purified by prep-HPLC to give 105 mg of desired product as a white solid.

MS (ESI+): 356.3 [M+H].

¹H NMR (400 MHz, DMSO-d₆) δ ppm 9.48 (s, 1H), 9.00 (s, 1H), 8.59 (s, 1H), 8.35 (d, J=8.4 Hz, 1H), 7.90 (d, J=8.4 Hz, 1H), 7.81-7.73 (m, 2H), 7.58 (s, 1H), 7.46-7.35 (m, 2H), 7.23 (d, J=2.0 Hz, 1H), 5.77 (d, J=2.0 Hz, 1H), 5.49 (s, 2H), 3.60 (s, 3H).

4-(Benzofuran-2-yl)-N-(2-methylpyrazol-3-yl)isoquinolin-6-amine (Example 98)

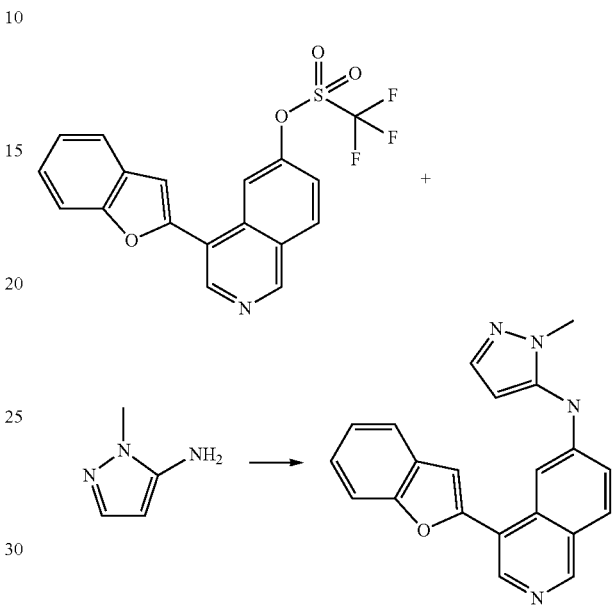

Under argon atmosphere, to a microwave vial equipped with a magnetic stirrer was added 150 mg (0.38 mmol) of [4-(benzofuran-2-yl)-6-isoquinolyl] trifluoromethanesulfonate, 44 mg (0.46 mmol) of 5-amino-1-methylpyrazole (CAS 1192-21-8), 35 mg (0.04 mmol) of Pd₂(dba)₃, 27 mg (0.06 mmol) of X-phos, 240 mg (1.14 mmol) of K₃PO₄·3H₂O and 4 mL of dioxane. The vial was then sealed and the reaction mixture was heated at 100° C. for 30 min using microwave irradiation (230 W). After cooling to rt, the mixture was diluted with 30 mL of EA, filtered through celite. The filtrate was concentrated under vacuum. The residue was purified by prep-HPLC to afford 100 mg of desired product as a yellow solid.

MS (ESI+): 241.5 [M+H].

¹H NMR (400 MHz, DMSO-d6) δ ppm: 9.68 (br, 1H), 9.41 (s, 1H), 8.81 (s, 1H), 8.35 (d, J=9.2 Hz, 1H), 7.79 (d, J=8.0 Hz, 2H), 7.68 (d, J=8.0 Hz, 1H), 7.59-7.54 (m, 3H), 7.48-7.44 (m, 1H), 7.39-7.35 (m, 1H), 6.38 (s, 1H), 3.73 (s, 3H).

N-(4-Chloro-6-isoquinolyl)-N',N'-dimethyl-ethane-1,2-diamine

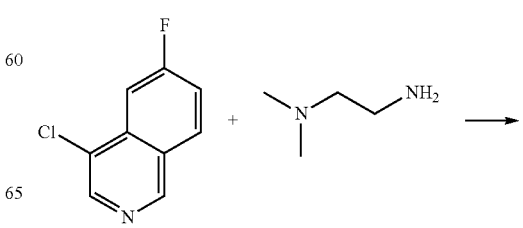

-continued

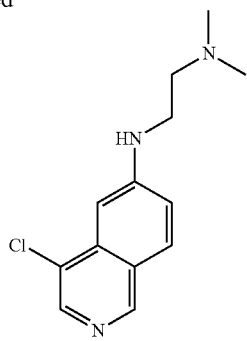

Under argon atmosphere, a microwave vial equipped with a magnetic stirrer was filled with 660 mg (3.63 mmol) of 4-chloro-6-fluoro-isoquinoline and 4 mL (42.79 mmol) of N,N-dimethylethylenediamine. The vial was then sealed and the mixture was heated with stirring at 150° C. using microwave irradiation (230 W) for 30 min. After cooling to rt, the reaction mixture was transferred to a round-bottom flask and concentrated under vacuum. The residue was dissolved in 50 mL of EA, washed with 30 mL of H$_2$O, 30 mL of saturated NH$_4$Cl aqueous solution, 30 mL of brine, dried over Na$_2$SO$_4$ and concentrated to give 670 mg of the desired product as a yellow solid.

MS (ESI+): 250.1 [M+H].

$^1$H NMR (400 MHz, DMSO-d$_6$) δ ppm: 8.82 (s, 1H), 8.31 (s, 1H), 7.83 (d, J=8.8 Hz, 1H), 7.23-7.20 (dd, J=2.0 Hz, 8.8Hz, 1H), 6.79 (m, 1H), 6.74 (d, J=2.0 Hz, 1H), 3.29-3.24 (dd, J=6.4 Hz, 12.0 Hz, 2H), 2.52 (t, J=6.4 Hz, 2H), 2.22 (s, 6H).

N-[4-(Benzofuran-2-yl)-6-isoquinolyl]-N',N'-dimethyl-ethane-1,2-diamine (Example 99)

Under argon atmosphere, to a microwave vial equipped with a magnetic stirrer was filled with 300 mg (1.2 mmol) of N-(4-chloro-6-isoquinolyl)-N',N'-dimethyl-ethane-1,2-diamine, 200 mg (1.26 mmol) of benzofuran-2-boronic acid (CAS 98437-24-2), 250 mg (0.24 mmol) of Pd$_2$(dba)$_3$, 160 mg (0.58 mmol) of PCy$_3$ (CAS 2622-14-2), 640 mg (2.4 mmol) of K$_3$PO$_4$.3H$_2$O and 4 mL of dioxane. The vial was then sealed and the mixture was heated with stirring at 150° C. using microwave irradiation (230 W) for 30 min. After cooling to rt, the reaction mixture was diluted with 50 mL of EA, filtered through celite. The filtrate was concentrated under vacuum. The residue was purified by prep-HPLC to give 190 mg of product (TFA salt) as a yellow solid.

MS (ESI+): 332.2 [M+H].

$^1$H NMR (400 MHz, DMSO-d6) δ ppm: 9.75 (s, 1H), 9.23 (s, 1H), 8.21 (d, J=8.8 Hz, 1H), 7.91 (br, 1H), 7.80-7.73 (m, 2H), 7.65 (s, 1H), 7.47-7.35 (m, 4H), 3.75-3.71 (dd, J=12.0, 6.0 Hz, 2H), 3.37 (t, J=6.4 Hz, 2H), 2.87 (s, 6H).

N'-[4-(Benzofuran-2-yl)-6-isoquinolyl]ethane-1,2-diamine (Example 100)

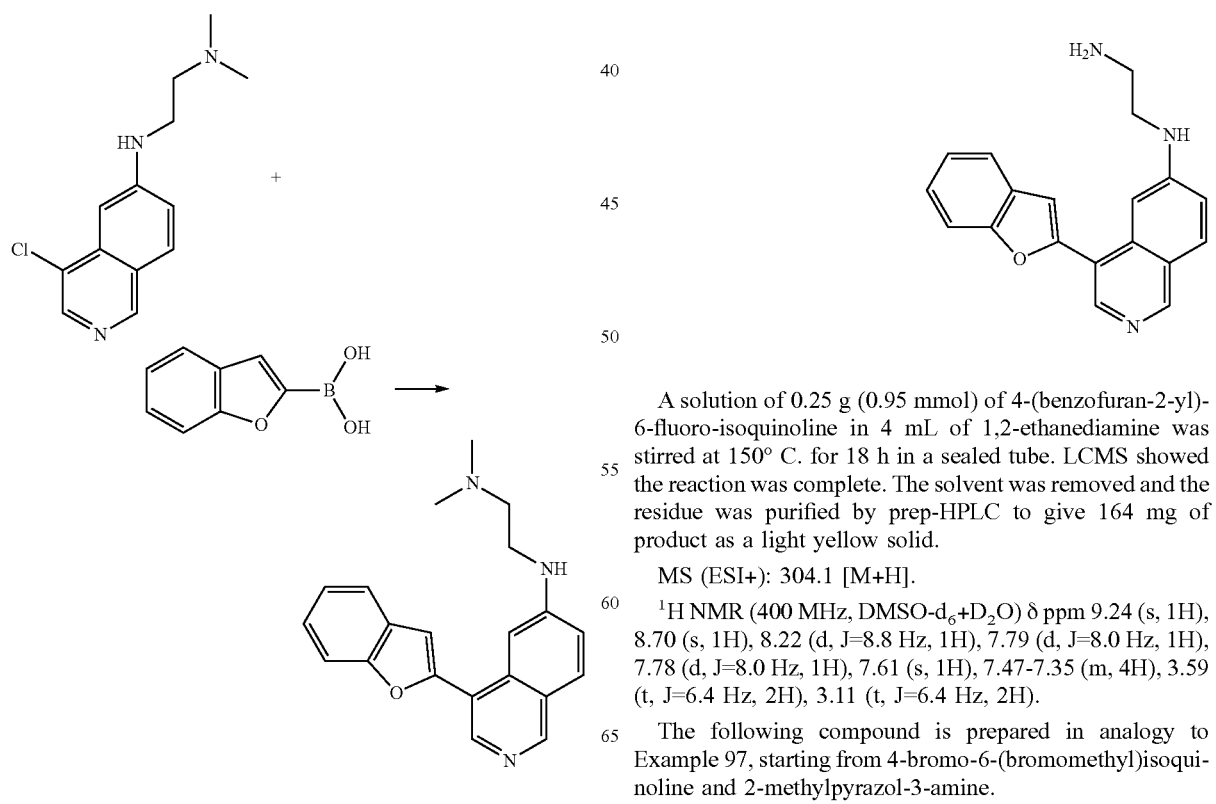

A solution of 0.25 g (0.95 mmol) of 4-(benzofuran-2-yl)-6-fluoro-isoquinoline in 4 mL of 1,2-ethanediamine was stirred at 150° C. for 18 h in a sealed tube. LCMS showed the reaction was complete. The solvent was removed and the residue was purified by prep-HPLC to give 164 mg of product as a light yellow solid.

MS (ESI+): 304.1 [M+H].

$^1$H NMR (400 MHz, DMSO-d$_6$+D$_2$O) δ ppm 9.24 (s, 1H), 8.70 (s, 1H), 8.22 (d, J=8.8 Hz, 1H), 7.79 (d, J=8.0 Hz, 1H), 7.78 (d, J=8.0 Hz, 1H), 7.61 (s, 1H), 7.47-7.35 (m, 4H), 3.59 (t, J=6.4 Hz, 2H), 3.11 (t, J=6.4 Hz, 2H).

The following compound is prepared in analogy to Example 97, starting from 4-bromo-6-(bromomethyl)isoquinoline and 2-methylpyrazol-3-amine.

| Example | ¹H NMR (400 MHz) δ ppm | MS (+ESI) [M + H]⁺ |
|---|---|---|
| 101 | (DMSO-d₆) 9.43 (s, 1H), 8.94 (s, 1H), 8.49 (s, 1H), 8.28 (s, 1H), 7.86-7.69 (m, 3H), 7.49 (s, 1H), 7.46-7.35 (m, 3H), 7.02 (br, 1H), 5.61 (s, 1H), 4.62 (s, 2H), 3.65 (d, J = 5.6 Hz, 3H). | 355.2 | tert-Butyl 2-bromoethylcarbamate

Under argon atmosphere, to a solution of 1.00 g (6.20 mmol) of N-Boc-ethanolamine in 20 mL of DCM was added 2.47 g (7.44 mmol) of CBr₄ and 1.95 g (7.44 mmol) of PPh₃ at 0° C. The resulting mixture was stirred at rt for 1 h. TLC showed the reaction was complete. The solution was removed and the residue was purified by silica gel chromatography column (PE/EA=5/1, $R_f$=0.7) to give 1.39 g of product as a colorless oil.

¹H NMR (400 MHz, CDCl₃) δ ppm: 3.53-3.45 (m, 4H), 1.44 (s, 9H).

2-[[4-(Benzofuran-2-yl)-6-isoquinolyl]oxy]ethanamine (Example 102)

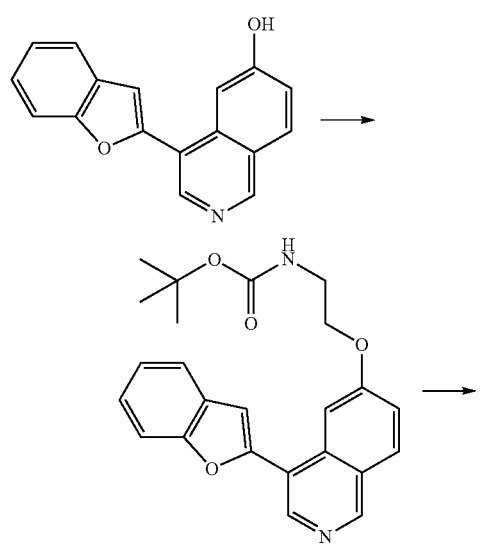

To a mixture of 0.20 g (0.77 mmol) of 4-(benzofuran-2-yl)isoquinolin-6-ol and 0.21 g (1.53 mmol) of K₂CO₃ in 10 mL of DMF was added 0.17 g (0.77 mmol) of tert-butyl 2-bromoethylcarbamate at rt. The resulting mixture was stirred at 80° C. for 4 h. LCMS showed the reaction was complete. The reaction mixture was diluted with EA, washed with H₂O and brine, dried over anhydrous Na₂SO₄ and concentrated to give the crude product, which was further purified by silica gel chromatography (DCM/EA=4/1, $R_f$=0.5) to give 118 mg of the intermediate as a brown semisolid.

A solution of 118 mg (0.29 mmol) of this intermediate in 10 mL 2.0 N solution of HCl in EA was stirred at rt for 1 h, LCMS showed the reaction was complete. The precipitated solid was washed with 20 mL*3 of EA, and collected by filtration to give 100 mg of crude product as a yellow solid, which was further purified by prep-HPLC to give 82 mg of desired product as a light yellow solid.

MS (ESI+): 305.1 [M+H].

¹H NMR (400 MHz, DMSO-d₆+D₂O) δ ppm: 9.42 (s, 1H), 8.89 (s, 1H), 8.38 (d, J=8.8 Hz, 1H), 7.87-7.73 (m, 3H), 7.63-7.59 (m, 2H), 7.47-7.35 (m, 2H), 4.40 (t, J=4.8 Hz, 2H), 3.33 (t, J=4.8 Hz, 2H).

8-(Benzofuran-2-yl)-1, 6-naphthyridine-2-carboxylic acid

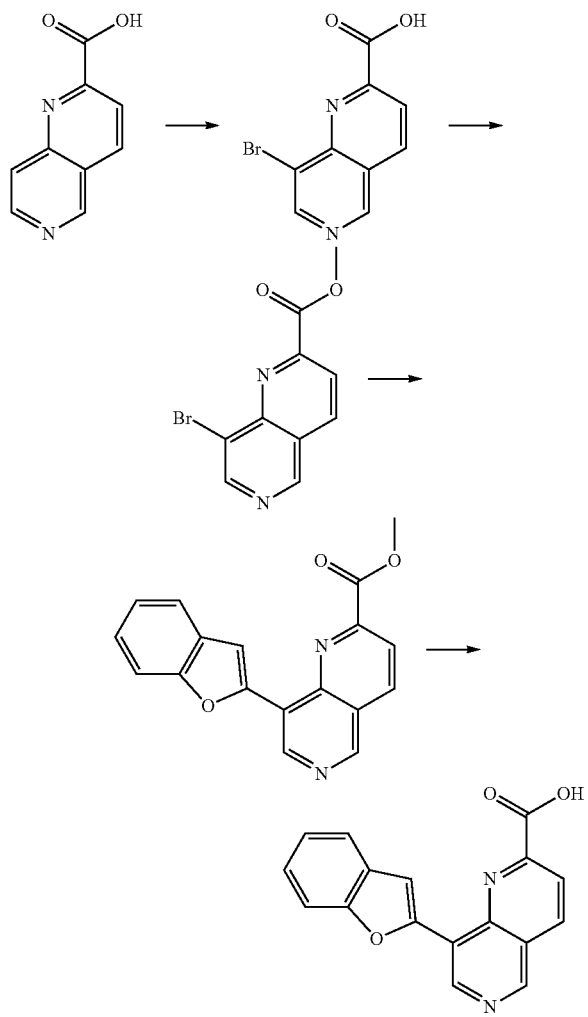

To a stirred solution of 2 g (11.48 mmol) of 1, 6-naphthyridine-2-carboxylic acid (CAS 07-59-8) in 50 mL of AcOH was added 1.18 mL (22.97 mmol) of $Br_2$ dropwise. The resulting mixture was stirred at 80° C. for 4 h. The mixture was concentrated under vacuum. The residue was washed with $Et_2O$ to afford 2.9 g of 8-bromo-1, 6-naphthyridine-2-carboxylic acid as a brown solid.

To a solution of 2.4 g (9.48 mmol) of 8-bromo-1, 6-naphthyridine-2-carboxylic acid in 50 mL of DMF were added 4.64 g (14.2 mmol) of $Cs_2CO_3$ and 0.89 mL (14.2 mmol) of MeI. The resulting mixture was stirred at 30° C. for 5 h. The mixture was diluted with 50 mL of water and extracted with 150 mL (50 mL*3) of EA. The combined organic layers were dried over $Na_2SO_4$, concentrated under vacuum. The residue was purified by silica gel column chromatography (DCM/MeOH=100/2) to afford 2.3 g of methyl 8-bromo-1, 6-naphthyridine-2-carboxylate as a yellow solid.

Under argon atmosphere, to a stirred solution of 3.5 g (13.1 mmol) of methyl 8-bromo-1, 6-naphthyridine-2-carboxylate in 110 mL of DMF/$H_2O$ (v/v=10/1) were added 2.55 g (15.7 mmol) of benzofuran-2-yl boronic acid (CAS 98437-24-2), 5.56 g (26.21 mmol) of $K_3PO_4.3H_2O$ and 2.27 g (1.97 mmol) of $Pd(PPh_3)_4$. After stirring at 80° C. for 3 hours, the mixture was diluted with water and extracted with EA. The separtaed organic layer was dried over $Na_2SO_4$, concentrated under vacuum. The residue was purified by silica gel column chromatography (PE/EA=2/1) to afford 2.11 g of methyl 8-(benzofuran-2-yl)-1, 6-naphthyridine-2-carboxylate as a yellow solid.

To a stirred solution of 1.8 g (5.92 mmol) of methyl 8-(benzofuran-2-yl)-1, 6-naphthyridine-2-carboxylate in 40 mL of THF/$H_2O$ (v/v=1/1) was added 0.99 g (23.66 mmol) of $LiOH.H_2O$. The resulting mixture was stirred at 20° C. for 1 h. The mixture was extracted with 120 mL (40 mL×3) of DCM/i-PrOH (v/v=3/1). The combined organic layers were concentrated under vacuum. The residue was washed with $Et_2O$ to give 1.21 g of 8-(benzofuran-2-yl)-1, 6-naphthyridine-2-carboxylic acid as a yellow solid.

MS (ESI+): 291.0 [M+H].

$^1$H NMR (400 MHz, DMSO-$d_6$) δ ppm: 13.98 (br, 1H), 9.53 (s, 1H), 9.44 (s, 1H), 8.89 (d, J=8.4 Hz, 1H), 8.56 (s, 1H), 8.38 (d, J=8.4 Hz, 1H), 7.82 (d, J=7.6 Hz, 1H), 7.73 (d, J=8.4 Hz, 1H), 7.45-7.41 (m, 1H), 7.35-7.31 (m, 1H).

N-(3-Aminopropyl)-8-(benzofuran-2-yl)-1, 6-naphthyridine-2-carboxamide (Example 103)

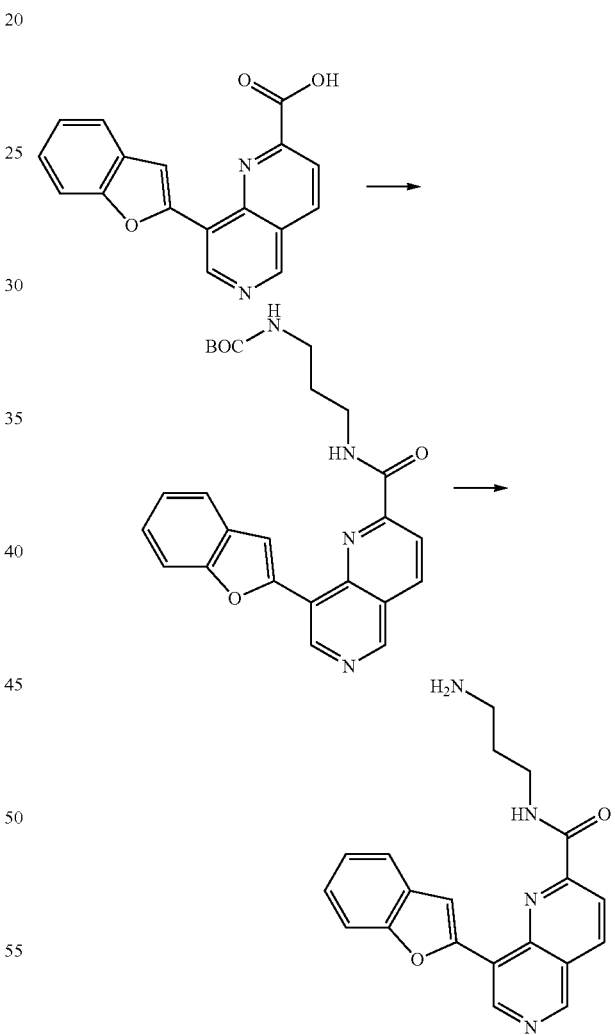

Under nitrogen atmosphere, to a solution of 0.7 g (2.41 mmol) of 8-(benzofuran-2-yl)-1, 6-naphthyridine-2-carboxylic acid and 0.42 g (2.41 mmol) of N-(3-aminopropyl) carbamic acid tert-butyl ester (CAS 75178-96-0) in 20 mL of DMF was added 1.38 g (3.62 mmol) of HATU and 0.5 mL (2.89 mmol) of DIPEA. The resulting solution was stirred at rt for 18 h. The solution was then diluted with 100 mL of EA, washed with 300 mL (100 mL*3) of brine, dried over anhydrous $Na_2SO_4$, concentrated under vacuum. The residue was purified by silica gel column chromatography (EA) to afford 0.15 g of tert-butyl N-[3-[[8-(benzofuran-2-yl)-1,6-naphthyridine-2-carbonyl]amino]propyl]carbamate as a yellow solid. Under nitrogen atmosphere, to a mixture of 0.1 g (0.22 mmol) of tert-butyl N-[3-[[8-(benzofuran-2-yl)-1,6-naphthyridine-2-carbonyl]amino]propyl]carbamate in 3 mL of DCM was added 1.5 mL (20.19 mmol) of TFA dropwise. The resulting solution was stirred at rt for 1 h. The solution was then concentrated under vacuum and the residue was purified by prep-HPLC to afford 0.055 g of N-(3-aminopropyl)-8-(benzofuran-2-yl)-1,6-naphthyridine-2-carboxamide as a yellow solid.

MS (ESI+): 347.0 [M+H].

$^{1}$H NMR (400 MHz, DMSO-$d_6$) δ ppm: 9.48 (s, 1H), 9.41 (s, 1H), 8.89 (d, J=8.8 Hz, 2H), 8.33 (d, J=8.0 Hz, 2H), 7.83 (d, J=7.6 Hz, 1H), 7.72 (d, J=8.0 Hz, 1H), 7.43 (t, J=7.2 Hz, 1H), 7.34 (t, J=7.2 Hz, 1H), 3.54 (t, J=6.4 Hz, 2H), 2.94 (t, J=7.2 Hz, 2H), 1.98-1.91 (m, 2H).

The following example was prepared accordingly to Example 103 by reaction of 8-(benzofuran-2-yl)-1,6-naphthyridine-2-carboxylic acid with the corresponding amine and subsequent deprotection:

To a stirred solution of 1.24 g (16.28 mmol) of 1,3-propandiol (CAS 504-63-2) in 200 mL of DMF at 0° C. was added 0.72 g (17.91 mmol) of 60% NaH and stirred at this temperature for 0.5 h. 4.90 g (16.28 mmol) of 4-bromo-6-(bromomethyl)isoquinoline was added thereto at 0° C. and stirred at 20° C. for 1.5 h. The mixture was diluted with saturated NH$_4$Cl solution at 0° C., extracted with EA, dried over Na$_2$SO$_4$. The solvent was removed under vacuum and the residue was purified by silica gel column chromatography (DCM/MeOH=100/1) to give 2.05 g of the desired product as a light yellow oil.

$^{1}$H NMR (400 MHz, CDCl$_3$) δ ppm: 9.17 (s, 1H), 8.75 (s, 1H), 8.10 (s, 1H), 8.00 (d, 1H, J=8.4 Hz), 7.68 (dd, 1H,

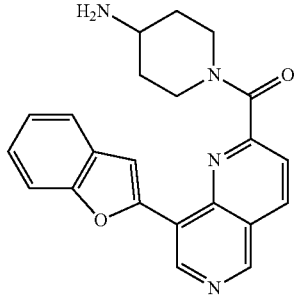 [SMILES: NC1CCN(C(=O)c2ccc3cncc(-c4cc5ccccc5o4)c3n2)CC1]

| Example | | $^{1}$H NMR (400 MHz) δ ppm | MS (+ESI) [M + H]$^{+}$ |
|---|---|---|---|
| 104 | | (DMSO-$d_6$ + D$_2$O) 9.45 (s, 1H), 9.39 (s, 1H), 8.83 (d, J = 8.4 Hz, 1H), 8.16 (s, 1H), 7.93 (d, J = 8.4 Hz, 1H), 7.85 (d, J = 7.6 Hz, 1H), 7.71 (d, J = 8.4 Hz, 1H), 7.44-7.40 (m, 1H), 7.34-7.30 (m, 1H), 4.64 (d, J = 13.6 Hz, 1H), 3.98 (d, J = 14.0 Hz, 1H), 3.37-3.36 (m, 1H), 3.26-3.23 (m, 1H), 3.07-3.01 (m, 1H), 2.12 (d, J = 10.8 Hz, 1H), 1.89 (d, J = 10.8 Hz, 1H), 1.66-1.55 (m, 2H) | 373.2 |

3-[(4-Bromo-6-isoquinolyl)methoxy]propan-1-ol

J=1.2, 8.4 Hz), 4.79 (s, 2H), 3.87 (t, 2H, J=5.6 Hz), 3.77 (t, 2H, J=7.0 Hz), 1.99-1.93 (m, 2H).

2-[3-[(4-Bromo-6-isoquinolyl) methoxy] propyl] isoindoline-1, 3-dione

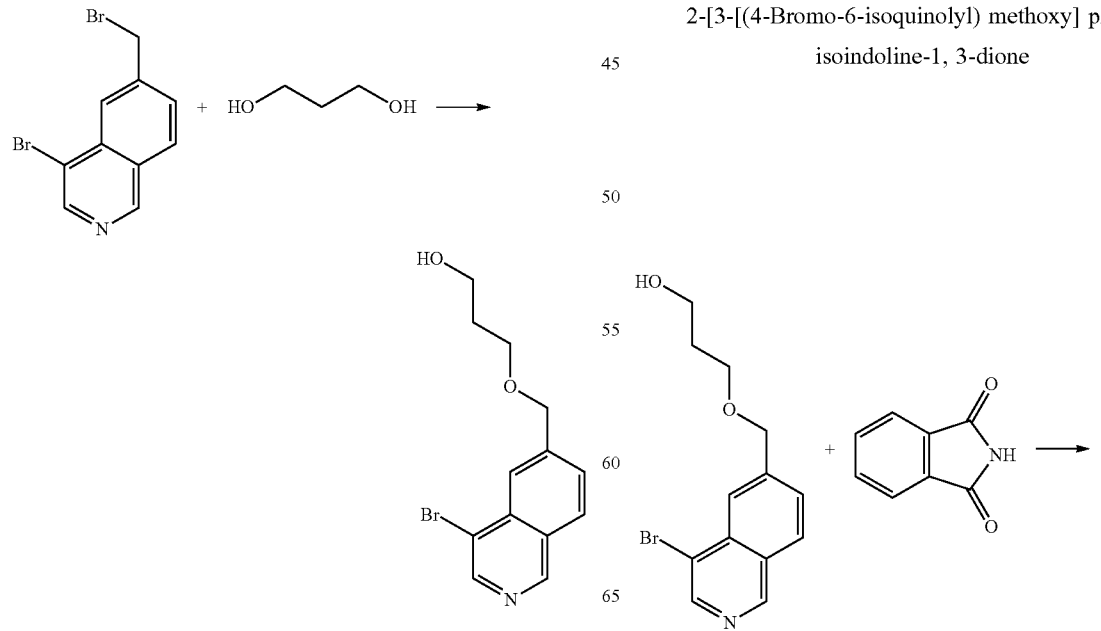

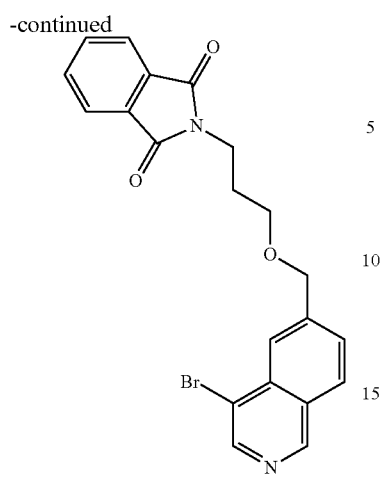

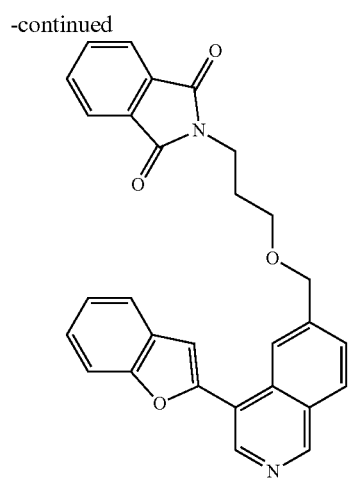

To a solution of 2.81 g (9.49 mmol) of 23-[(4-bromo-6-isoquinolyl)methoxy]propan-1-ol in 150 mL of anhydrous THF were added 4.98 g (18.98 mmol) of PPh₃ and 2.79 g (18.98 mmol) of phthalimide (CAS 85-41-6), followed by the addition of 2.75 mL (18.98 mmol) of DEAD (CAS 1972-28-7) dropwise at 0° C. The mixture was stirred at 20° C. for 18 h. The solvent was removed under vacuum and the residue was purified by silica gel chromatography (PE/EA=2/1) to give 3.59 g of the desired product as a yellow solid.

¹H NMR (400 MHz, CDCl₃) δ ppm: 9.11 (s, 1H), 8.69 (s, 1H), 7.98 (s, 1H), 7.88 (d, 1H, J=8.4 Hz), 7.76-7.70 (m, 2H), 7.59-7.53 (m, 3H), 4.68 (s, 2H), 3.88 (t, 2H, J=6.8 Hz), 3.66 (t, 2H, J=6.0 Hz), 2.09-2.05 (m, 2H).

2-[3-[[4-(Benzofuran-2-yl)-6-isoquinolyl] methoxy] propyl] isoindoline-1, 3-dione

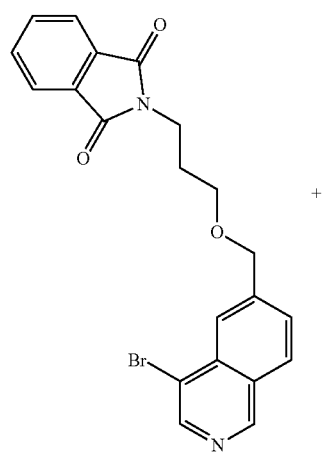

+

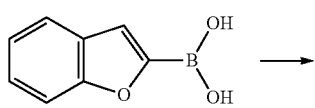

Under argon atmosphere, a microwave vial equipped with a magnetic stirrer were filled with 0.20 g (0.47 mmol) of 2-[3-[(4-bromo-6-isoquinolyl) methoxy] propyl] isoindoline-1, 3-dione, 5 mL of DMF/H₂O (v/v 10/1), 0.09 g (0.56 mmol) of benzofuran-2-yl boronic acid (CAS 98437-24-2), 0.23 g (0.94 mmol) of K₃PO₄.3H₂O and 0.08 g (0.07 mmol) of Pd(PPh₃)₄. The vial was then sealed and the mixture was heated with stirring at 100° C. using microwaves irradiation (30 W) for 0.5 h. After cooling to rt, the mixture was filtered, concentrated under vacuum to give 0.16 g of the crude product, which was used in the next step without further purification.

MS (ESI+): 463.1 [M+H].

3-[[4-(Benzofuran-2-yl)-6-isoquinolyl] methoxy] propan-1-amine (Example 105)

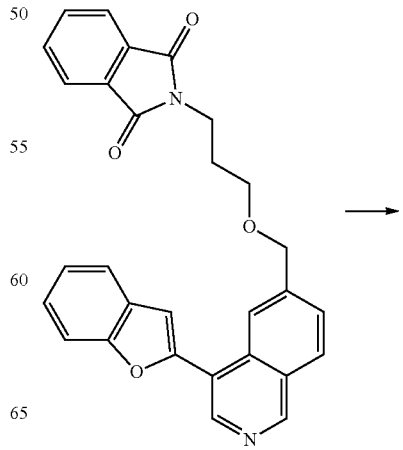

-continued

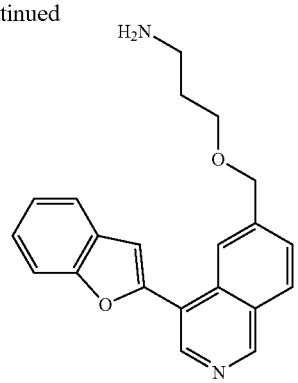

To a stirred solution of 0.16 g (0.35 mmol) of 2-[3-[[4-(benzofuran-2-yl)-6-isoquinolyl] methoxy] propyl] isoindoline-1, 3-dione in 10 mL of MeOH was added 0.09 g (1.73 mmol) of NH$_2$NH$_2$.H$_2$O. The resulting mixture was stirred at 90° C. for 5 hours. The mixture was concentrated to give the crude product, which was purified via preparative HPLC to give 0.08 g of the desired product as a yellow solid.

MS (ESI+): 333.0 [M+H].

$^1$H NMR (400 MHz, DMSO-d6+D2O) δ ppm: 9.34 (s, 1H), 8.87 (s, 1H), 8.37 (s, 1H), 8.25 (d, 1H, J=8.4 Hz), 7.79-7.69 (m, 3H), 7.51 (s, 1H), 7.43-7.32 (m, 2H), 4.73 (s, 2H), 3.58 (t, 2H, J=6.0 Hz), 2.88 (t, 2H, J=7.2 Hz), 1.88-1.82 (m, 2H).

The following examples were prepared accordingly to Example 105 by reaction of 2-[3-[[4-(benzofuran-2-yl)-6-isoquinolyl] methoxy] propyl] isoindoline-1, 3-dione with the corresponding boronic acid in the presence of a Pd-catalyst and subsequent deprotection.

| Example | | $^1$H NMR (400 MHz) δ ppm | MS (+ESI) [M + H]$^+$ |
|---|---|---|---|
| 106 | ![structure] | (DMSO-d$_6$ + D$_2$O) 9.52 (s, 1H), 8.49 (s, 1H), 8.38 (d, 1H, J = 8.8 Hz), 7.83-7.81 (m, 2H), 7.68-7.58 (m, 4H), 4.68 (s, 2H), 3.53 (t, 2H, J = 6.0 Hz), 2.84 (t, 2H, J = 7.2 Hz), 1.84-1.78 (m, 2H) | 327.3 |
| 107 | ![structure] | (DMSO-d$_6$ + D$_2$O) 9.51 (s, 1H), 8.52 (s, 1H), 8.35 (d, 1H, J = 8.8 Hz), 7.86-7.79 (m, 4H), 7.57 (dd, 1H, J = 2.0 Hz, 8.0 Hz), 4.68 (s, 2H), 3.54 (t, 2H, J = 6.0 Hz), 2.86 (t, 2H, J = 7.6 Hz), 1.85-1.79 (m, 2H) | 361.0 |

1-Phenyl-3-[4-(4, 4, 5, 5-tetramethyl-1, 3, 2-dioxaborolan-2-yl) phenyl] urea

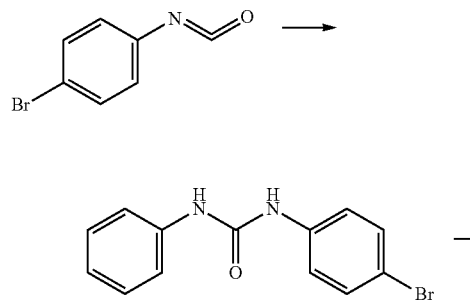

Under nitrogen atmosphere, to a solution of 0.50 g (2.53 mmol) of 4-bromophenyl isocyanate (CAS 2493-02-9) in 20 mL of DCM at 0° C. was added 0.24 g (2.53 mmol) of aniline. The resulting solution was stirred at 20° C. for 3 h. The mixture was filtered, washed with DCM to give 0.46 g of 1-(4-bromophenyl)-3-phenyl-urea as a white solid.

Under nitrogen atmosphere, a solution of 0.20 g (0.69 mmol) of 1-(4-bromophenyl)-3-phenyl-urea, 0.31 g (1.24 mmol) of bis(pinacalato) diboron (CAS 73183-34-3), 0.20 g (2.06 mmol) of KOAc in 10 mL of dioxane was bubbled with argon before 0.08 g (0.10 mmol) of Pd(dppf)Cl$_2$ was added. The mixture was stirred at 100° C. for 7 h. The solution was filtered and concentrated under vacuum to give the crude product, which was purified by silica gel column chromatography (eluent: PE/EA=4/1) to give 0.16 g of the desired product as a light yellow solid.

$^1$H NMR (400 MHz, DMSO-d$_6$) δ ppm: 8.82 (s, 1H), 8.70 (s, 1H), 7.60-7.58 (m, 2H), 7.48-7.44 (m,4H), 7.31-7.27 (m, 2H), 7.00-6.96 (m, 1H), 1.28 (s, 12H).

1-[4-[6-(3-Aminopropoxymethyl)-4-isoquinolyl] phenyl]-3-phenyl-urea (Example 108)

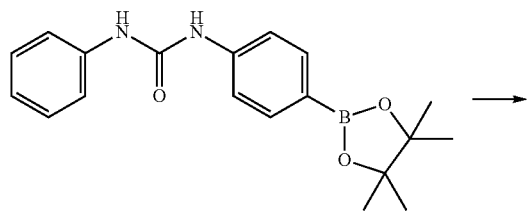

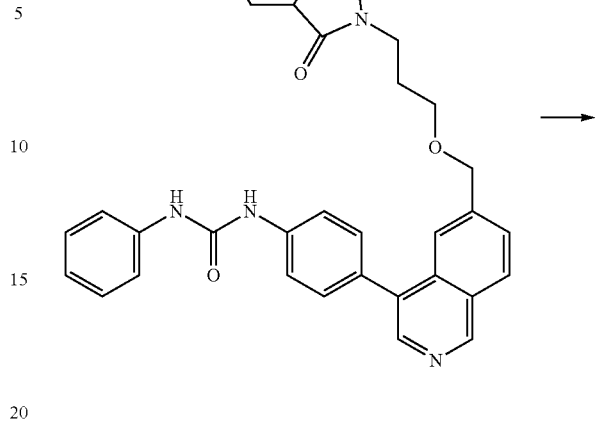

Under argon atmosphere, a microwave vial equipped with a magnetic stirrer was filled with 0.45 g (1.06 mmol) of 2-[3-[(4-bromo-6-isoquinolyl) methoxy] propyl] isoindoline-1, 3-dione, 6 mL of DMF/H$_2$O (v/v 10/1), 0.43 g (1.27 mmol) of 1-phenyl-3-[4-(4, 4, 5, 5-tetramethyl-1, 3, 2-dioxaborolan-2-yl) phenyl] urea, 0.55 g (2.12 mmol) of K$_3$PO$_4$.3H$_2$O and 0.18 g (0.16 mmol) of Pd(PPh$_3$)$_4$. The vial was then sealed and the mixture was heated with stirring at 100° C. using microwaves irradiation (30 W) for 0.5 h. After cooling to rt, the mixture was concentrated under vacuum to give 0.58 g of 1-[4-[6-[3-(1, 3-dioxoisoindolin-2-yl) propoxymethyl]-4-isoquinolyl] phenyl]-3-phenyl-urea. This intermediate is treated with NH$_2$NH$_2$.H$_2$O as described above for Example 105 to provide 65 mg of the desired product as a yellow solid

MS (ESI+): 427.1 [M+H].

$^1$H NMR (400 MHz, DMSO-d$_6$+D$_2$O) δ ppm: 9.27 (s, 1H), 8.41 (s, 1H), 8.19 (d, 1H, J=8.4 Hz), 7.85 (s, 1H), 7.68-7.65 (m, 3H), 7.53-7.45 (m, 4H), 7.31-7.27 (m, 2H), 7.00-6.96 (m, 1H), 4.64 (s, 2H), 3.53 (t, 2H, J=6.0 Hz), 2.85 (t, 2H, J=7.2 Hz), 1.85-1.80 (m, 2H).

6-(3-Aminopropoxymethyl)-4-bromo-isoquinolin-1-amine

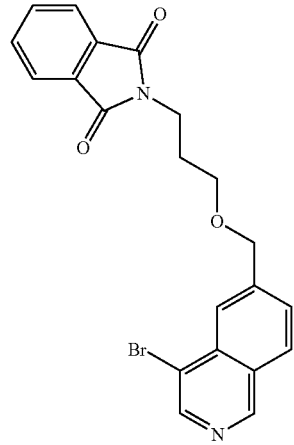

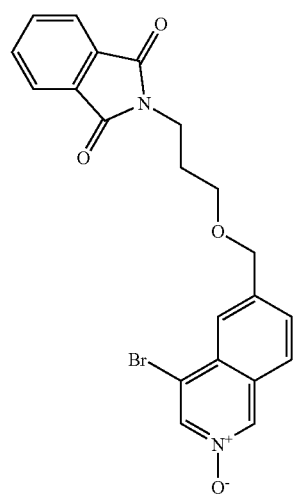

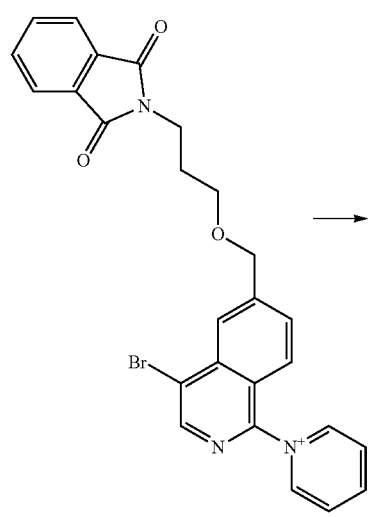

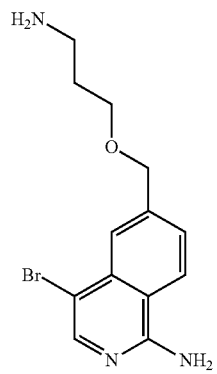

A solution of 0.10 g (0.24 mmol) of 2-[3-[(4-bromo-6 isoquinolyl) methoxy] propyl] isoindoline-1, 3-dione and 0.12 g (0.71 mmol) of m-CPBA in 4 mL of DCM was stirred for 3 hours at 20° C. The reaction was quenched with 2 mL of saturated $Na_2SO_3$ aqueous solution and 2 mL of saturated $Na_2CO_3$ aqueous solution. The mixture was extracted with DCM. The combined organic layers were washed with brine, dried over sodium sulfate, filtered, evaporated under vacuum to give 0.11 g of 2-[3-[(4-bromo-2-oxido-isoquinolin-2-ium-6-yl)methoxy]propyl]isoindoline-1, 3-dione as a yellow solid.

To a solution of 2.28 g (5.17 mmol) of 2-[3-[(4-bromo-2-oxido-isoquinolin-2-ium-6-yl) methoxy] propyl] isoindoline-1, 3-dione in 50 mL of Pyridine was added 1.18 g (6.20 mmol) of TsCl. After stirring the solution at 20° C. for 2 hours, the pyridine was removed under reduced pressure to afford 2.60 g of 2-[3-[(4-bromo-1-pyridin-1-ium-1-yl-6-isoquinolyl)methoxy]propyl]isoindoline-1,3-dione as a yellow oil. A solution of 2.60 g (5.17 mmol) of 2-[3-[(4-bromo-1-pyridin-1-ium-1-yl-6-isoquinolyl) methoxy] propyl] isoindoline-1, 3-dione in 40 mL of 2-aminoethanol was stirred at 20° C. for 16 hours. The solution was poured into cracked ice, extracted with EA, dried over $Na_2SO_4$ and concentrated under vacuum to afford the crude product, which was purified by silica gel column chromatography (DCM/MeOH=100/5) to give 0.97 g of 6-(3-aminopropoxymethyl)-4-bromo-isoquinolin-1-amine as a colorless oil.

MS (ESI+): 310.1 [M+H].

$^1$H NMR (400 MHz, DMSO-$d_6$) δ ppm: 8.22 (d, 1H, J=8.4 Hz), 7.98 (s, 1H), 7.81 (s, 1H), 7.50 (dd, 1H, J=1.2 Hz, 8.4 Hz), 7.05 (s, 2H), 4.67 (s, 2H), 3.56 (t, 2H, J=6.4 Hz), 2.67 (t, 2H, J=6.8 Hz), 1.71-1.64 (m, 2H).

6-(3-Aminopropoxymethyl)-4-(benzofuran-2-yl)isoquinolin-1-amine (Example 109)

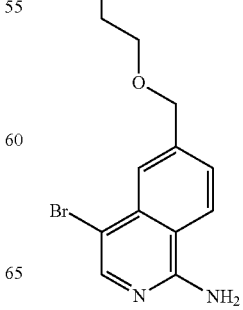

-continued

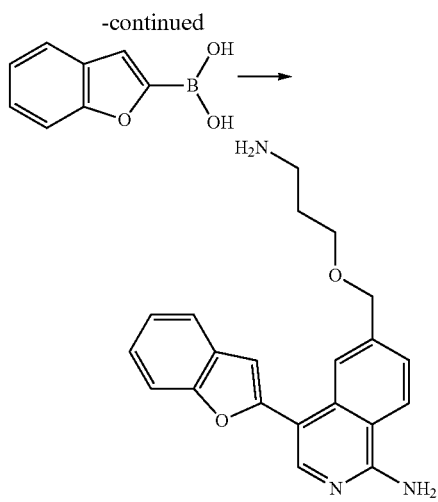

Under argon atmosphere, a microwave vial equipped with a magnetic stirrer were filled with 0.18 g (0.58 mmol) of 6-(3-aminopropoxymethyl)-4-bromo-isoquinolin-1-amine, 5 mL of DMF/H$_2$O (v/v 10/1), 0.11 g (0.70 mmol) of benzofuran-2-yl boronic acid (CAS 98437-24-2), 0.30 g (1.16 mmol) of K$_3$PO$_4$.3H$_2$O and 0.10 g (0.09 mmol) of Pd(PPh$_3$)$_4$. The vial was then sealed and the mixture was heated with stirring at 100° C. using microwaves irradiation (30 W) for 0.5 h. After cooling to rt, the mixture was filtered and the filtrate was purified via Preparative HPLC to give 0.18 g of the desired product as a yellow solid.

MS (ESI+): 348.3 [M+H].

$^1$H NMR (400 MHz, DMSO-d6+D$_2$O) δ ppm: 8.59 (d, 1H, J=8.4 Hz), 8.21 (s, 1H), 8.10 (s, 1H), 7.81-7.66 (m, 3H), 7.42-7.32 (m, 3H), 4.73 (s, 2H), 3.58 (t, 2H, J=6.0 Hz), 2.88 (t, 2H, J=7.2 Hz), 1.88-1.83 (m, 2H).

The following examples were prepared accordingly to Example 109 by reaction of 6-(3-aminopropoxymethyl)-4-bromo-isoquinolin-1-amine with the corresponding boronic acid or boronic acid ester in the presence of a Pd-catalyst and subsequent deprotection:

| Example | | $^1$H NMR (400 MHz) δ ppm | MS (+ESI) [M + H]$^+$ |
|---|---|---|---|
| 110 | (structure) | (DMSO-d$_6$ + D$_2$O) 8.57 (d, 1H, J = 8.4 Hz), 7.77 (d, 1H, J = 7.6 Hz), 7.63-7.61 (m, 4H), 7.50-7.48 (m, 2H), 4.63 (s, 2H), 3.52 (t, 2H, J = 6.0 Hz), 2.83 (t, 2H, J = 7.2 Hz), 1.83-1.77 (m, 2H) | 342.3 |
| 111 | (structure) | (DMSO-d$_6$ + D$_2$O) 8.58 (d, 1H, J = 8.8 Hz), 7.82-7.62 (m, 5H), 7.47 (dd, 1H, J = 2.0, 8.4 Hz), 4.64 (s, 2H), 3.53 (t, 2H, J = 6.0 Hz), 2.85 (t, 2H, J = 7.2 Hz), 1.84-1.78 (m, 2H) | 376.2 |

1-[4-[1-Amino-6-(3-aminopropoxymethyl)-4-isoquinolyl]phenyl]-3-phenyl-urea (Example 112)

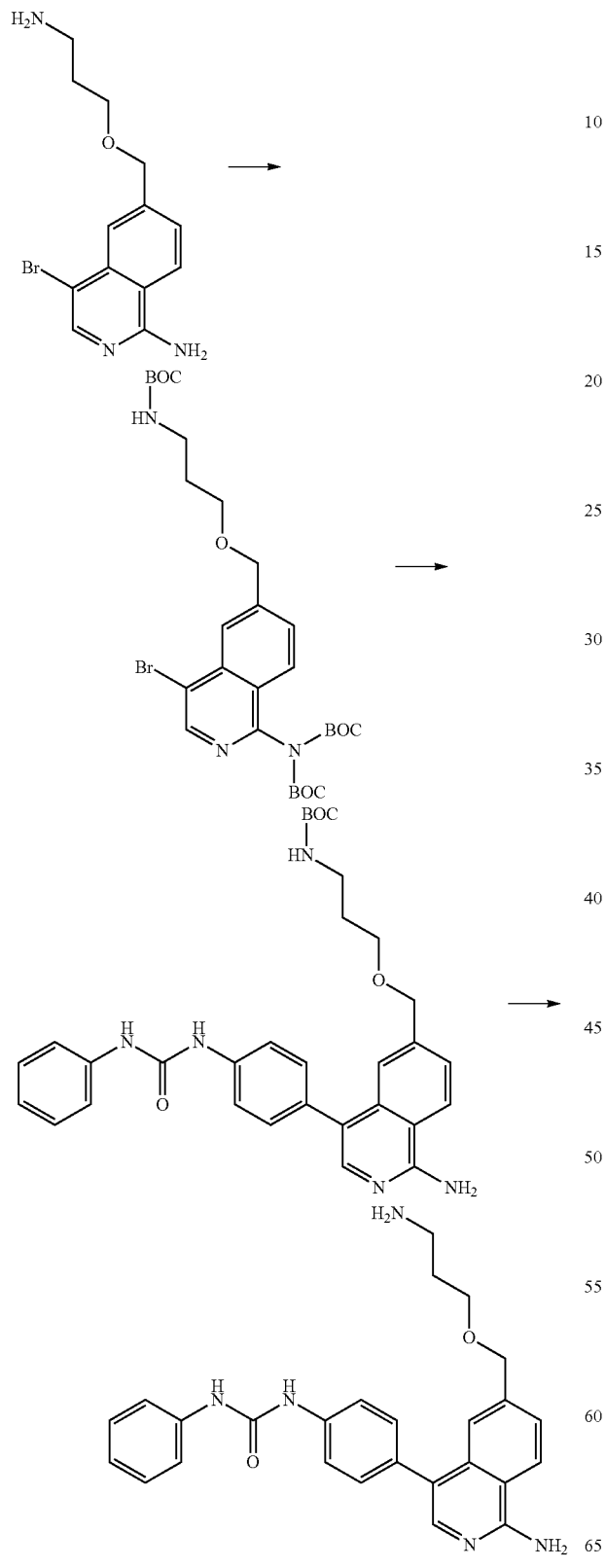

Under argon atmosphere, to a stirred solution of 0.60 g (1.93 mmol) of 6-(3-aminopropoxymethyl)-4-bromo-isoquinolin-1-amine in 40 mL of DCM were added 0.78 g (7.73 mmol) of TEA, 0.04 g (0.29 mmol) of DMAP and 1.35 g (7.73 mmol) of (BOC)$_2$O. The resulting mixture was stirred at 20° C. for 15 hours. The solution was concentrated under vacuum to give the crude product, which was purified by silica gel column chromatography (PE/EA=5/1) to give 0.95 g of tert-butyl N-[4-bromo-6-[3-(tert-butoxycarbonylamino)propoxymethyl]-1-isoquinolyl]-N-tert-butoxycarbonyl-carbamate as a light yellow solid.

Under argon atmosphere, a microwave vial equipped with a magnetic stirrer were filled with 0.60 g (0.98 mmol) of tert-butyl N-[4-bromo-6-[3-(tert-butoxycarbonylamino)propoxymethyl]-1-isoquinolyl]-N-tert-butoxycarbonyl-carbamate, 12 mL of DMF/H$_2$O (v/v 10/1), 0.40 g (1.18 mmol) of 1-phenyl-3-[4-(4,4,5,5-tetramethyl-1,3,2-dioxaborolan-2-yl)phenyl]urea, 0.51 g (1.97 mmol) of K$_3$PO$_4$.3H$_2$O and 0.17 g (0.15 mmol) of Pd(PPh$_3$)$_4$. The vial was then sealed and the mixture was heated with stirring at 100° C. using microwaves irradiation (30 W) for 0.5 h. After cooling to rt, the mixture was concentrated under vacuum to give 0.5 g of tert-butyl N-[3-[[1-amino-4-[4-(phenylcarbamoylamino)phenyl]-6-isoquinolyl]methoxy]propyl]carbamate, which was used in the next step without further purification.

To a stirred solution of 0.50 g (0.92 mmol) of tert-butyl N-[3-[[1-amino-4-[4-(phenylcarbamoylamino) phenyl]-6-isoquinolyl]methoxy]propyl]carbamate in 10 mL of DCM was added 6.80 mL (10.53 mmol) of TFA. The resulting mixture was stirred at 20° C. for 3 hours. The solution was concentrated under vacuum to give the crude product, which was purified via Preparative HPLC to give 0.38 g of the desired product as a white solid.

MS (ESI+): 442.2 [M+H].

$^1$H NMR (400 MHz, DMSO-d6+D$_2$O) δ ppm: 8.56 (d, 1H, J=8.4 Hz), 7.73-7.72 (m, 2H), 7.62-7.60 (m, 3H), 7.47-7.38 (m, 4H), 7.32-7.28 (m, 2H), 7.02-6.99 (m, 1H), 4.65 (s, 2H), 3.53 (t, 2H, J=6.0 Hz), 2.84 (t, 2H, J=7.2 Hz), 1.82-1.79 (m, 2H).

1-[4-[6-[(4-Amino-1-piperidyl)methyl]-4-isoquinolyl]phenyl]-3-(4-chlorophenyl)urea (Example 113)

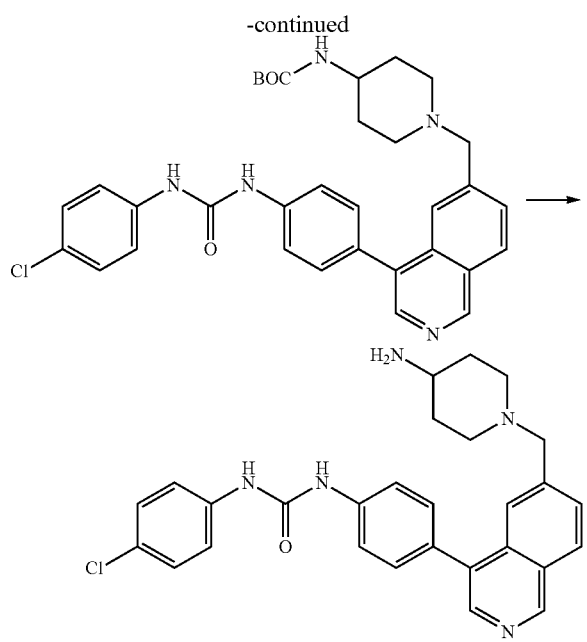

To an ice-cooled solution of 34 μL (0.28 mmol) of diphosgene in 6 mL of anhydrous THF was added a solution of 200 mg (0.46 mmol) of tert-butyl N-[1-[[4-(4-aminophenyl)-6-isoquinolyl]methyl]-4-piperidyl]carbamate and 6 mg (0.046 mmol) of DMAP in 6 mL of anhydrous THF dropwise while keeping the temperature at 0-5° C. Then 193 μL (1.39 mmol) of TEA was added to the solution. The mixture was warmed to rt and stirred for another 40 min before a solution of 59 mg (0.46 mmol) of 4-chloroaniline in 8 mL of anhydrous THF was added dropwise. The reaction mixture was stirred for at rt for 18 h. LCMS showed that the reaction was complete. The reaction mixture was then diluted with EA, washed with water and brine, dried over Na$_2$SO$_4$ and concentrated. The residue was purified via silica gel column chromatography (DCM/MeOH=20/1, R$_f$=0.5) to afford 213 mg of the intermediate as a light yellow semi-solid.

A solution of 200 mg (0.34 mmol) of the above intermediate in 10 mL of a 2N HCl solution in EA was stirred at rt for 2 h. LCMS showed the reaction was complete. The mixture was concentrated to give the crude product, which was purified by prep-HPLC to give 127 mg of product as a light yellow solid.

MS (ESI+): 486.1 [M+H].

$^1$H NMR (400 MHz, DMSO-d$_6$+D$_2$O) δ ppm: 9.48 (s, 1H), 8.52 (s, 1H), 8.40 (d, J=8.8 Hz, 1H), 8.12 (s, 1H), 7.85 (d, J=8.8 Hz, 1H), 7.69-7.53 (m, 4H), 7.52-7.33 (m, 4H), 4.49 (s, 2H), 3.42-3.39 (m, 2H), 3.25 (s, 1H), 3.07 (s, 2H), 2.08-2.05 (m, 2H), 1.70 (s, 2H).

The following compounds are prepared in analogy to Examples 113 by the reactions of tert-butyl N-[1-[[4-(4-aminophenyl)-6-isoquinolyl]methyl]-4-piperidyl] carbamate with different amines to form corresponding ureas, followed with deprotection in acidic conditions;

Note: Elevated temperatures are required during the formation of some isocyanates (50° C. in Example 119, 35° C. in Example 117, 65° C. in Examples 115 and 116).

| Example | | $^1$H NMR (400 MHz) δ ppm | MS (+ESI) [M + H]$^+$ |
|---|---|---|---|
| 114 | (structure) | (DMSO-d$_6$ + D$_2$O) 9.46 (s, 1H), 8.52 (s, 1H), 8.39 (d, J = 8.8 Hz, 1H), 8.12 (s, 1H), 7.84 (d, J = 8.8 Hz, 1H), 7.72-7.67 (m, 3H), 7.56-7.54 (m, 2H), 7.35-7.27 (m, 2H), 7.06-7.03 (m, 1H), 4.48 (s, 2H), 3.42-3.39 (m, 2H), 3.26 (s, 2H), 3.06 (s, 2H), 2.08-2.05 (m, 2H), 1.70 (s, 2H) | 486.1 |
| 115 | (structure) | (DMSO-d$_6$ + D$_2$O) 9.44 (s, 1H), 8.58-8.56 (m, 2H), 8.52 (s, 1H), 8.38 (d, J = 8.4 Hz, 1H), 8.09 (s, 1H), 7.96-7.95 (m, 2H), 7.84 (d, J = 8.4 Hz, 1H), 7.75-7.73 (m, 2H), 7.61-7.59 (m, 2H), 4.48 (s, 2H), 3.41-3.39 (m, 2H), 3.25 (s, 1H), 3.06 (s, 2H), 2.08-2.05 (m, 2H), 1.70-1.69 (m, 2H) | 453.0 |

-continued
| Example | | ¹H NMR (400 MHz) δ ppm | MS (+ESI) [M + H]⁺ |
|---|---|---|---|
| 116 | 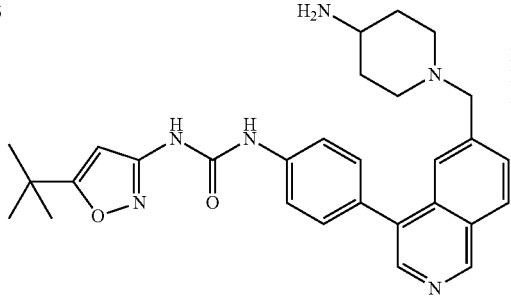 | (DMSO-d₆ + D₂O) 9.46 (s, 1H), 8.51 (s, 1H), 8.40 (d, J = 8.4 Hz, 1H), 8.11 (s, 1H), 7.84 (d, J = 8.4 Hz, 1H), 7.68 (d, J = 8.8 Hz, 2H), 7.56 (d, J = 8.8 Hz, 2H), 6.47 (s, 1H), 4.47 (s, 2H), 3.38 (s, 2H), 3.28-3.26 (m, 1H), 3.09-3.06 (m, 2H), 2.08-2.05 (m, 2H), 1.70 (s, 2H), 1.28 (s, 9H) | 499.2 |
| 117 | 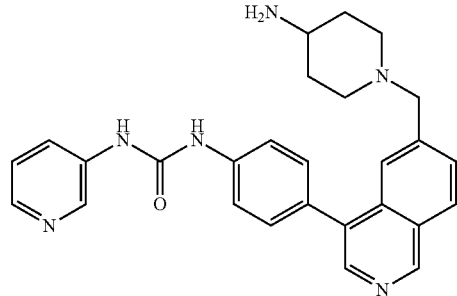 [SMILES: NC1CCN(Cc2ccc3cncc(-c4ccc(NC(=O)Nc5cccnc5)cc4)c3c2)CC1] | (DMSO-d₆ + D₂O) 9.48 (s, 1H), 8.99 (s, 1H), 8.41 (s, 1H), 8.39-8.38 (m, 2H), 8.27-8.24 (m, 1H), 8.11 (s, 1H), 7.86-7.72 (m, 2H), 7.72-7.70 (m, 2H), 7.59-7.56 (m, 2H), 4.48 (s, 2H), 3.39 (s, 2H), 3.25 (s, 1H), 3.07 (s, 2H), 2.08-2.05 (m, 2H), 2.71 (s, 2H) | 453.1 |
| 118 | 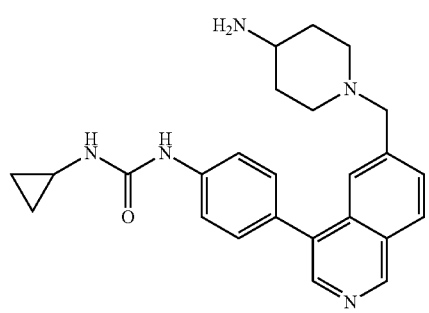 [SMILES: NC1CCN(Cc2ccc3cncc(-c4ccc(NC(=O)NC5CC5)cc4)c3c2)CC1] | (DMSO-d₆ + D₂O) 9.43 (s, 1H), 8.49 (s, 1H), 8.37 (d, J = 8.8 Hz, 1H), 8.10 (s, 1H), 7.82 (d, J = 8.8 Hz, 1H), 7.62 (d, J = 8.8 Hz, 2H), 7.48 (d, J = 8.8 Hz, 2H), 4.47 (s, 2H), 3.39 (s, 2H), 3.24 (s, 1H), 3.05 (s, 2H), 2.59-2.53 (m, 1H), 2.08-2.05 (m, 2H), 1.69 (s, 2H), 0.67-0.65 (m, 2H), 0.43-0.41 (m, 2H) | 416.2 |
| 119 | 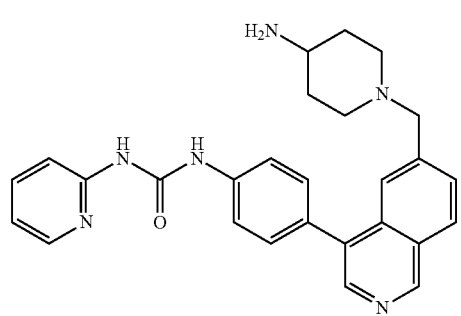 [SMILES: NC1CCN(Cc2ccc3cncc(-c4ccc(NC(=O)Nc5ccccn5)cc4)c3c2)CC1] | (DMSO-d₆ + D₂O) 9.28 (s, 1H), 8.37 (s, 1H), 8.30 (d, J = 4.8 Hz, 1H), 8.21-8.17 (m, 1H), 7.78-7.66 (m, 5H), 7.51-7.45 (m, 3H), 7.06-7.03 (m, 1H), 3.63 (s, 2H), 2.96-2.93 (m, 1H), 2.81-2.78 (m, 2H), 2.05-2.00 (m, 2H), 1.83-1.81 (m, 2H), 1.52-1.46 (m, 2H) | 453.3 |

1-[4-[6-[(4-Amino-1-piperidyl)methyl]-4-isoquinolyl]phenyl]-3-(3-methylisoxazol-5-yl)urea (Example 120)

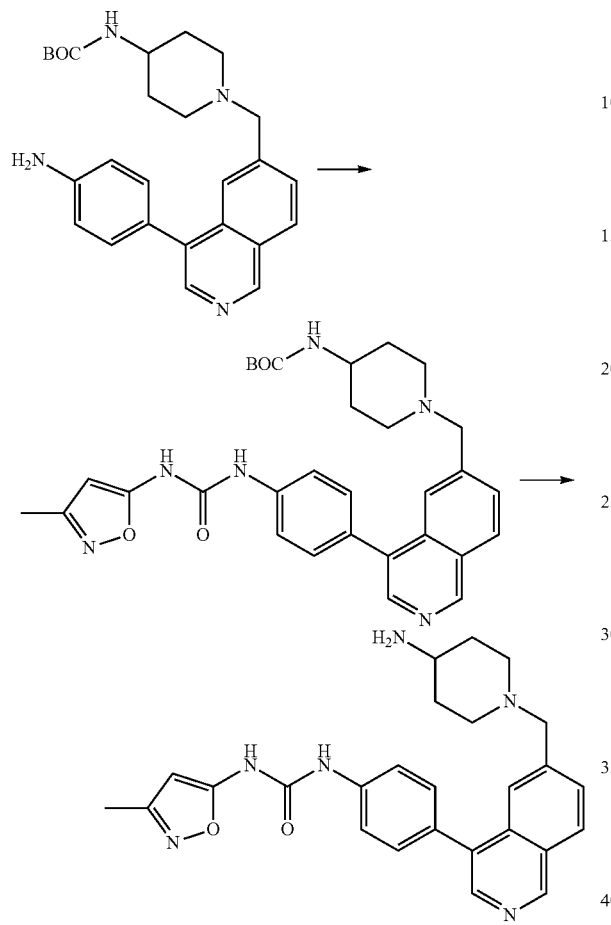

To an ice-cooled solution of 34 μL (0.28 mmol) of diphosgene in 6 mL of anhydrous THF was added a solution of 45 mg (0.46 mmol) of 5-amino-3-methylisoxazole and 6 mg (0.046 mmol) of DMAP in 6 mL of anhydrous THF dropwise keeping the temperature at 0-5° C. Then 193 μL (1.39 mmol) of TEA was added to the solution. The mixture was warmed to rt and stirred for another 40 min before a solution of 200 mg (0.46 mmol) of tert-butyl N-[1-[[4-(4-aminophenyl)-6-isoquinolyl]methyl]-4-piperidyl]carbamate in 8 mL of anhydrous THF was added dropwise. The reaction mixture was stirred at rt for 18 h. LCMS showed that the reaction was complete. Then the reaction mixture was diluted with EA, washed with water and brine, dried over $Na_2SO_4$ and concentrated. The residue was purified via silica gel column (DCM/MeOH=20/1, $R_f$=0.5) to afford 257 mg of the intermediate as a brown semisolid.

A solution of 240 mg (0.43 mmol) of this intermediate in 10 mL of a solution of 2N HCl in EA was stirred at rt for 2 h. LCMS showed the reaction was complete. The mixture was concentrated to give the crude product, which was purified by prep-HPLC to give 118 mg of product as a light yellow solid.

MS (ESI+): 457.1 [M+H].

$^1$H NMR (400 MHz, DMSO-$d_6$+$D_2O$) δ ppm: 9.46 (s, 1H), 8.51 (s, 1H), 8.39 (d, J=8.4 Hz, 1H), 8.10 (s, 1H), 7.84 (d, J=8.4 Hz, 1H), 7.68 (d, J=8.8 Hz, 2H), 7.56 (d, J=8.8 Hz, 2H), 5.99 (s, 1H), 4.48 (s, 2H), 3.39 (s, 2H), 3.25 (s, 1H), 3.06 (s, 2H), 2.17 (s, 3H), 2.08-2.05 (m, 2H), 1.70 (s, 2H).

1-[(4-Bromo-6-isoquinolyl)methyl]pyridin-1-ium-4-amine

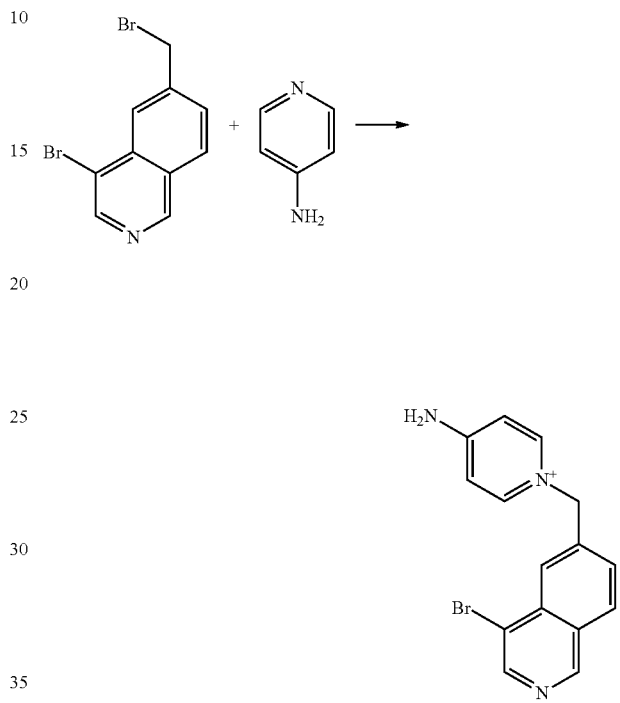

Under argon atmosphere, a microwave vial equipped with a magnetic stirrer filled with the solution of 0.25 g (0.83 mmol) of 4-bromo-6-(bromomethyl)isoquinoline in 3 mL of DMF was added 544 mg (1.66 mmol) of $Cs_2CO_3$ and 156 mg (1.66 mmol) of 4-aminopyridine (CAS 504-24-5). The vial was then sealed and the mixture was heated with stirring at 100° C. using microwaves irradiation (150 W) for 30 min. After cooling to rt, LCMS showed that the starting material was converted into the product. The mixture was used for the next step without further purification.

MS (ESI+): 314.0 [M], 316.0 [M+2]

1-[(4-Phenyl-6-isoquinolyl)methyl]pyridin-1-ium-4-amine (Example 121)

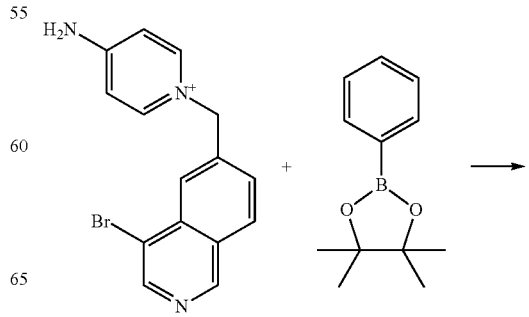

-continued

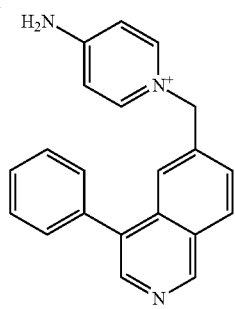

Under argon atmosphere, a microwave vial equipped with a magnetic stirrer was filled with the solution of 1-[(4-bromo-6-isoquinolyl)methyl]pyridin-1-ium-4-amine (0.80 mmol), 3 mL of dioxane, 0.5 mL of H$_2$O, 0.19 g (0.95 mmol) of 4,4,5,5-tetramethyl-2-phenyl-1,3,2-dioxaborolane (CAS 24388-23-6), 0.34 g (0.95 mmol) of K$_3$PO$_4$.3H$_2$O and 138 mg (0.06 mmol) of Pd(PPh$_3$)$_4$. The vial was then sealed and the mixture was heated with stirring at 100° C. using microwave irradiation (150 W) for 30 min. After cooling to rt, LCMS showed that the reaction was complete. The vial content was then transferred to a round-bottom flask, then diluted with 50 mL of EA and filtered through celite pad. The filtrate was concentrated under vacuum and the residue was purified by preparative HPLC. 0.1 mL of conc. hydrochloric acid was added into the collected eluent which was then lyophilized to afford 29 mg of the HCl salt of the product as a yellow solid.

MS (ESI+): 312.27 [M]

$^1$H NMR (400 MHz, DMSO-d$_6$+D$_2$O) δ ppm: 9.58 (s, 1H), 8.56 (d, J=2.0 Hz, 1H), 8.44 (d, J=8.4 Hz, 1H), 8.21-8.20 (m, 2H, H), 7.76 (d, J=8.4 Hz, 1H), 7.72 (s, 1H), 7.61-7.54 (m, 5H, H), 6.84-6.82 (m, 2H), 5.59 (s, 2H).

The following examples were prepared accordingly to Example 121 by reaction 1-[(4-bromo-6-isoquinolyl)methyl]pyridin-1-ium-4-amine with the corresponding boronic acid or boronic acid ester in the presence of a Pd-catalyst:

| Example | | $^1$H NMR (400 MHz) δ ppm | MS (ESI+) [M]$^+$ |
|---|---|---|---|
| 122 | (structure: 4-hydroxyphenyl-substituted isoquinoline with aminopyridinium methyl) | (DMSO-d$_6$ + D$_2$O) 9.50 (s, 1H), 8.48 (s, 1H), 8.41 (d, J = 8.8 Hz, 1H), 8.19 (d, J = 7.2 Hz, 2H), 7.83 (s, 1H), 7.76 (d, J = 8.4 Hz, 1H), 7.38 (d, J = 8.8 Hz, 2H), 6.97 (d. J = 8.8 Hz, 2H, H), 6.84 (d, J = 2.4 Hz, 2H), 5.57 (s, 2H) | 328.3 |
| 123 | (structure: 4-chlorophenyl-substituted isoquinoline with aminopyridinium methyl) | (DMSO-d$_6$ + D$_2$O) 9.56 (s, 1H), 8.56 (d, J = 2.8 Hz, 1H), 8.41 (d, J = 8.4 Hz, 1H), 8.20 (d, J = 7.2 Hz, 2H), 7.76 (d, J = 8.4 Hz, 1H), 7.73 (d, J = 8.4 Hz, 1H), 7.64 (d, J = 8.4 Hz, 2H), 7.58 (d, J = 8.4 Hz, 2H), 6.82 (d, J = 7.6 Hz, 2H), 5.57 (s, 2H) | 346.3 |
| 124 | (structure: phenylurea-phenyl-substituted isoquinoline with aminopyridinium methyl) | (DMSO-d$_6$ + D$_2$O) 9.37 (s, 1H), 8.49 (s, 1H), 8.30 (d, J = 8.4 Hz, 1H), 8.22 (d, J = 7.2 Hz, 2H), 7.91 (s, 1H), 7.67-7.63 (m, 3H), 7.50-7.47 (m, 4H), 7.33-7.29 (m, 2H), 7.00 (t, J = 7.6 Hz, 1H), 6.82 (d, J = 7.6 Hz, 2H), 5.54 (s, 2H) | 446.2 |

1-[(4-Bromo-6-isoquinolyl)methyl]-2-methyl-pyridin-1-ium-4-amine

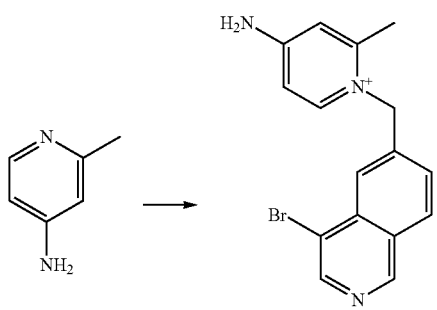

Under argon atmosphere, a microwave vial equipped with a magnetic stirrer was filled with 0.20 g (0.66 mmol) of 4-bromo-6-(bromomethyl)isoquinoline, 3 mL of DMF, 435 mg (1.33 mmol) of $Cs_2CO_3$ and 144 mg (1.33 mmol) of 2-methylpyridin-4-amine (CAS 18437-58-6). The vial was then sealed and the mixture was heated with stirring at 100° C. using microwave irradiation (150 W) for 30 min. After cooling to rt, LCMS showed that the reaction was complete. The mixture was used for the next step without further purification.

MS (ESI+): 328.0 [M], 330.0 [M+2]

1-[[4-(Benzofuran-2-yl)-6-isoquinolyl]methyl]-2-methyl-pyridin-1-ium-4-amine (Example 125)

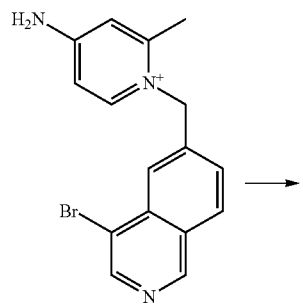

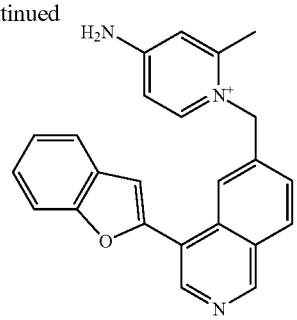

Under argon atmosphere, a microwave vial equipped with a magnetic stirrer was filled with the solution of 1-[(4-bromo-6-isoquinolyl)methyl]-2-methyl-pyridin-1-ium-4-amine (0.61 mmol), 3 mL of dioxane, 0.5 mL of $H_2O$, 0.15 g (0.91 mmol) of benzofuran-2-yl boronic acid (CAS 98437-24-2), 0.26 g (1.22 mmol) of $K_3PO_4 \cdot 3H_2O$ and 106 mg (0.091 mmol) of $Pd(PPh_3)_4$. The vial was then sealed and the mixture was heated with stirring at 100° C. using microwave irradiation (150 W) for 30 min. After cooling to rt, LCMS showed that the reaction was complete. The vial content was then transferred to a round-bottom flask, then diluted with 50 mL of EA and filtered through celite pad. The filtrate was concentrated under vacuum and the residue was purified by preparative HPLC. 0.1 mL of conc. hydrochloric acid was added into the collected eluent which was then lyophilized to give 39 mg of the HCl salt of the product as a yellow solid. The solid was then recrystallized from MeOH/EA to give the pure HCl salt of the product as a yellow solid.

MS (ESI+): 366.33 [M]

$^1$H NMR (400 MHz, DMSO-$d_6$+$D_2O$) δ ppm: 9.42 (s, 1H), 8.97 (s, 1H), 8.34 (d, J=8.4 Hz, 1H), 8.30 (d, J=7.2 Hz, 1H), 7.95 (s, 1H), 7.75 (d, J=7.6 Hz, 1H), 7.68 (d, J=8.0 Hz, 1H), 7.57 (d, J=8.4 Hz, 1H), 7.47 (s, 1H), 7.42 (t, J=7.2 Hz, 1H), 7.35 (t, J=7.2 Hz, 1H), 6.85 (dd, $J_1$=6.8 Hz, $J_2$=2.4 Hz, 1H), 6.81 (s, 1H), 5.73 (s, 2H), 2.39 (s, 3H).

The following examples were prepared accordingly to Example 125 by reaction of benzofuran-2-boronic acid with the corresponding ammonium compound or amine (prepared as described for 1-[(4-bromo-6-isoquinolyl)methyl]-2-methyl-pyridin-1-ium-4-amine) in the presence of a Pd-catalyst:

| Example | | $^1$H NMR (400 MHz) δ ppm | MS (ESI+) [M + H]$^+$ |
|---|---|---|---|
| 126 | (structure) | (DMSO-$d_6$ + $D_2O$) 9.47 (s, 1H), 8.94 (s, 1H), 8.38 (d, J = 7.6 Hz, 1H), 8.35 (s, 1H, H-e), 7.81 (dd, $J_1$ = 8.8 Hz, $J_2$ = 1.6 Hz, 1H), 7.76 (d, J = 7.6 Hz, 1H), 7.56 (d, J = 8.4 Hz, 1H), 7.52 (s, 1H), 7.45 (dd, $J_1$ = 7.2 Hz, $J_2$ = 1.2 Hz, 1H), 7.42-7.35 (m, 1H), 6.72, 6.67 (2s, 2H), 4.85 (s, 2H), 2.37, 2.34 (2s, 6H) | 380.2 |

| Example | | ¹H NMR (400 MHz) δ ppm | MS (ESI+) [M + H]⁺ |
|---|---|---|---|
| 127 | 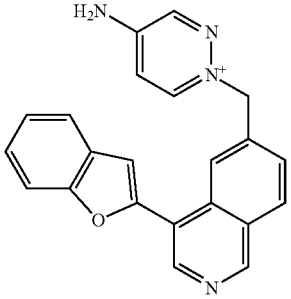 [SMILES: Nc1cc[n+](Cc2ccc3cncc(-c4cc5ccccc5o4)c3c2)nc1] | (DMSO-d₆ + D₂O) 9.39 (s, 1H), 8.97 (s, 1H, H-a), 8.96 (d, J = 7.2 Hz, 1H), 8.52 (d, J = 3.2 Hz, 1H), 8.37 (s, 1H), 8.30 (d, J = 8.4 Hz, 1H), 7.79-7.73 (m, 2H), 7.69-7.67 (m, 1H), 7.55 (s, 1H), 7.43 (m, 1H), 7.38-7.34 (m, 1H), 7.13 (dd, J₁ = 7.2 Hz, J₂ = 3.2 Hz, 1H), 5.82 (s, 2H, H-f), 2.39 (s, 3H) | 353.1 |
| 128 | 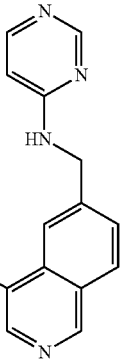 | (DMSO-d₆ + D₂O) 9.46 (s, 1H), 8.97 (s, 1H), 8.76 (s, 1H), 8.42 (s, 1H), 8.32 (d, J = 8.4 Hz, 1H), 8.19 (d, J = 7.2 Hz, 1H), 7.82-7.67 (m, 2H), 7.64 (d, J = 7.6 Hz, 1H), 7.54 (s, 1H), 7.43 (dd, J₁ = 7.2 Hz, J₂ = 0.8 Hz, 1H), 7.41-7.34 (m, 1H), 6.92 (d, J = 7.2 Hz, 1H), 5.01, 4.92 (2s, 2H) | 353.0 |
| 129 | 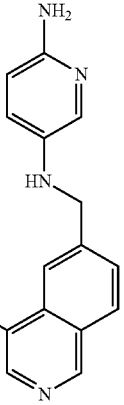 | (DMSO-d₆ + D₂O) 9.29 (s, 1H), 8.86 (s, 1H), 8.37 (s, 1H), 8.21 (d, J = 7.6 Hz, 1H), 7.77-7.74 (m, 2H), 7.65-7.63 (m, 1H), 7.42-7.38 (m, 2H), 7.35-7.28 (m, 1H), 7.28 (s, 1H), 6.93 (dd, J₁ = 8.8 Hz, J₂ = 2.8 Hz, 1H), 6.38 (d, J = 8.8 Hz, 1H), 4.49 (s, 2H) | 367.1 |

2-Azidopyridin-4-amine

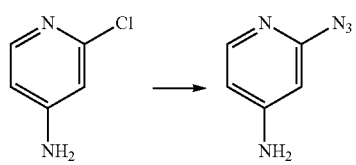 [SMILES: Nc1ccnc(Cl)c1 ; [N-]=[N+]=Nc1cc(N)ccn1]

To a solution of 1.6 g (12.07 mmol) of 4-amino-2-chloropyridine in 25 mL of DMF were added 1.6 g (24.14 mmol) of NaN₃ and 1.3 g (24.14 mmol) of NH₄Cl. The mixture was stirred at 110° C. for 10 h. TLC (DCM/MeOH=10/1, R$_f$=0.2) showed that the reaction was complete. To the mixture were added 150 mL of EA and 100 mL of water. Then the pH value of water phase was adjusted to pH=10 with Na₂CO₃ aqueous solution, followed by extraction with 100 mL×3 of EA. The combined organic phases were concentrated under vacuum and the residue was washed with ether to give 1.31 g of the product as a pale white solid.

¹H NMR (400 MHz, DMSO-d₆+D₂O) δ ppm: 9.58 (s, 1H), 8.55 (s, 1H), 8.47 (d, J=8.8 Hz, 1H), 8.16 (s, 1H), 8.01 (d, J=8.8 Hz, 1H), 7.82-7.55 (m, 5H), 4.50 (s, 2H), 3.41-3.07 (m, 5H), 2.10-1.70 (m, 7H).

2-Azido-N-[(4-bromo-6-isoquinolyl)methyl]pyridin-4-amine

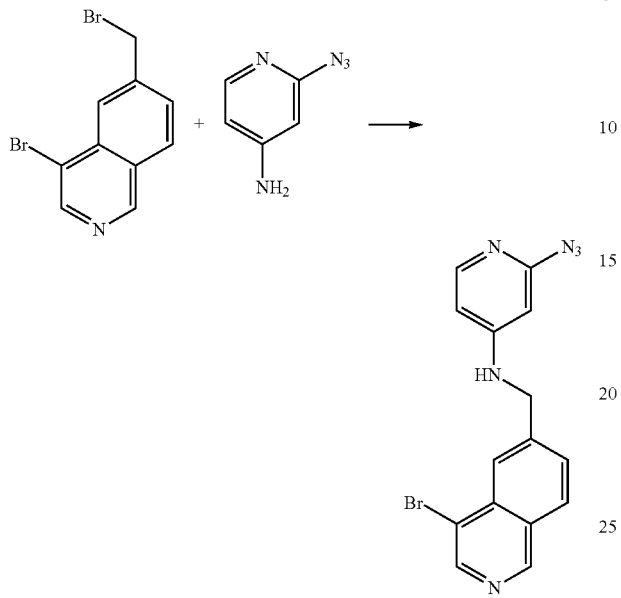

Under argon atmosphere, a microwave vial equipped with a magnetic stirrer was filled with 0.10 g (0.33 mmol) of 4-bromo-6-(bromomethyl)isoquinoline, 2 mL of DMF, 217 mg (0.66 mmol) of $Cs_2CO_3$ and 90 mg (1.33 mmol) of 2-azidopyridin-4-amine. The vial was then sealed and the mixture was heated with stirring at 100° C. using microwave irradiation (150 W) for 30 min. After cooling to rt, LCMS showed that half of the starting material was converted into the product. The mixture was used for the next step without further purification.

MS m/z (ESI+): 355.0 [M]$^+$, 357.0 [M+2]$^+$.

N4-[[4-(Benzofuran-2-yl)-6-isoquinolyl]methyl]pyridine-2,4-diamine (Example 130)

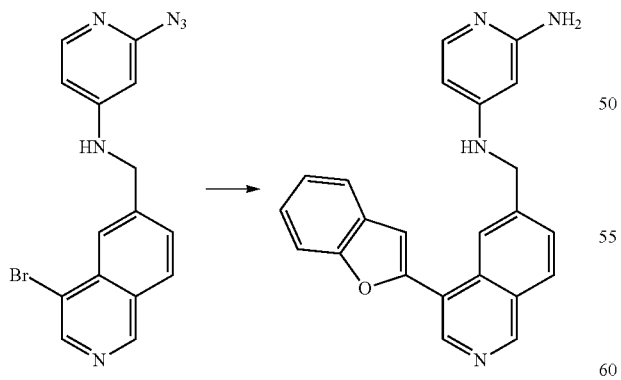

Under argon atmosphere, a microwave vial equipped with a magnetic stirrer was filled with the solution of 2-azidopyridin-4-amine (0.61 mmol), 3 mL of Dioxane, 0.5 mL of $H_2O$, 68 mg (0.42 mmol) of benzofuran-2-yl boronic acid (CAS 98437-24-2), 0.12 g (0.56 mmol) of $K_3PO_4 \cdot 3H_2O$ and 49 mg (0.042 mmol) of $Pd(PPh_3)_4$. The vial was then sealed and the mixture was heated with stirring at 100° C. using microwave irradiation (150 W) for 30 min. After cooling to rt, LCMS showed that the reaction was complete. Meanwhile, most of the azide product was reduced to compound N4-[[4-(benzofuran-2-yl)-6-isoquinolyl]methyl]pyridine-2,4-diamine under this condition. The vial content was then transferred to a round-bottom flask, diluted with 50 mL of EA and filtered through celite pad. The filtrate was concentrated under vacuum and the residue was purified by preparative HPLC to give 17 mg of formic acid salt of product as a yellow solid.

MS (ESI+): 367.2 [M+H]$^+$.

$^1$H NMR (400 MHz, DMSO-$d_6$+$D_2O$) δ ppm: 9.35 (s, 1H), 8.90 (s, 1H), 8.31 (s, 1H), 8.27 (d, J=8.8 Hz, 1H), 7.75 (s, 1H), 7.72 (t, J=1.6 Hz, 1H), 7.59 (dd, $J_1$=12.4 Hz, $J_2$=0.8 Hz, 1H), 7.50 (d, J=7.6 Hz, 1H), 7.42-7.35 (m, 2H), 7.33 (dd, $J_1$=7.2 Hz, $J_2$=0.8 Hz, 1H), 6.24 (dd, $J_1$=7.2 Hz, $J_2$=2.4 Hz, 1H), 5.72 (s, 1H), 4.68 (s, 2H).

tert-Butyl N-pyridazin-4-ylcarbamate

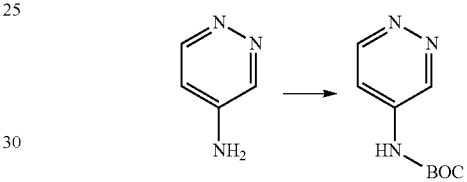

To a solution of 1.0 g (10.5 mmol) of pyridazin-4-amine (CAS 20744-39-2) in 4.8 mL (36.8 mmol) of TEA and 30 mL of DCM was added 5.74 g of $(Boc)_2O$ (26.3 mmol) at 0° C. Then the reaction solution was allowed warming to 25° C. with stirring at 30° C. for 16 h. LCMS showed that the reaction was complete. The solvent was removed under vacuum and the residue was purified by silica gel column chromatography (PE/EA=1/3, $R_f$=0.2) to give 1.5 g of the product as a pale white solid.

$^1$H NMR (400 MHz, DMSO-$d_6$+$D_2O$) δ ppm: 9.14 (dd, $J_1$=2.8 Hz, $J_2$=0.8 Hz, 1H), 8.92 (dd, $J_1$=6.0 Hz, $J_2$=0.8 Hz, 1H), 7.73 (dd, $J_1$=6.0 Hz, $J_2$=2.8 Hz, 1H).

tert-Butyl N-[(4-bromo-6-isoquinolyl)methyl]-N-pyridazin-4-yl-carbamate

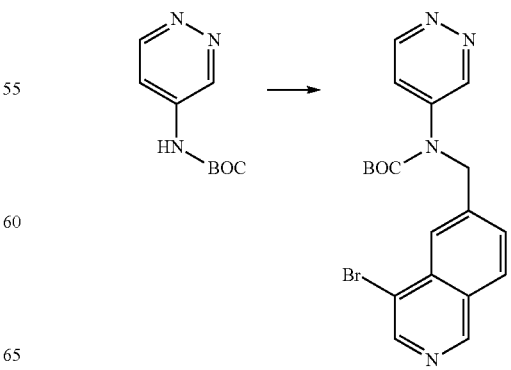

Under nitrogen atmosphere, to a solution of 205 mg (1.0 mmol) of tert-butyl N-pyridazin-4-ylcarbamate in 15 mL of DMF at 0° C. was added 60 mg (1.5 mmol) of NaH. The solution was stirred at that temperature for 1 h, then 300 mg (0.38 mmol) of 4-bromo-6-(bromomethyl)isoquinoline was added. The mixture was stirred at 25° C. for 16 h. LCMS showed that the reaction was complete. The reaction was quenched with 3 mL of water at 0° C., extracted with 30 mL*3 of EA. The combined organic phases were dried over $Na_2SO_4$, concentrated under vacuum and the residue was purified by silica gel column chromatography (PE/EA=1/5, $R_f$=0.3) to give 135 mg of the product as a pale green solid.

$^1$H NMR (400 MHz, $CDCl_3$) δ ppm: 9.31 (d, J=2.8 Hz, 1H), 9.16 (s, 1H), 9.00 (d, J=6.0 Hz, 1H), 8.73 (s, 1H), 8.00 (d, J=8.4 Hz, 1H), 7.97 (s, 1H), 7.53 (dd, $J_1$=8.4 Hz, $J_2$=1.6Hz, 1H), 7.43 (dd, $J_1$=6.0 Hz, $J_2$=3.2 Hz, 1H), 5.22 (s, 2H), 1.52 (s, 9H).

tert-Butyl N-[[4-(benzofuran-2-yl)-6-isoquinolyl]methyl]-N-pyridazin-4-yl-carbamate

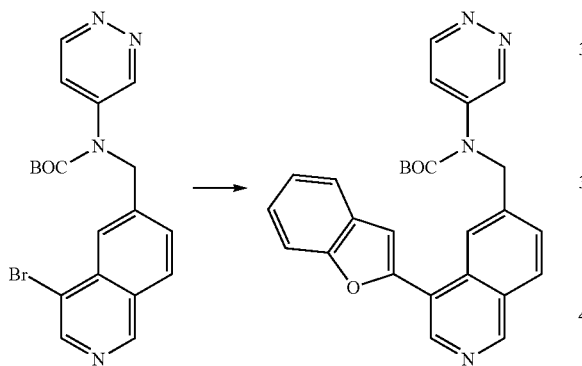

Under Argon atmosphere, to a solution of 0.10 g (0.23 mmol) of tert-butyl N-[(4-bromo-6-isoquinolyl)methyl]-N-pyridazin-4-yl-carbamate in 15 mL of dioxane and 3 mL of $H_2O$ were added 56 mg (0.34 mmol) of benzofuran-2-yl boronic acid (CAS 98437-24-2), 97 mg (0.46 mmol) of $K_3PO_4·3H_2O$ and 40 mg (0.034 mmol) of $Pd(PPh_3)_4$. The mixture was degassed and stirred at 90° C. for 16 h. LCMS showed that the reaction was complete. The solvent was removed under vacuum and the residue was purified by silica gel column chromatography (PE/EA=1/2~1/5, $R_f$=0.3) to give 95 mg of the product as a yellow solid. MS (ESI+): 453.1 [M+H]

$^1$H NMR (400 MHz, DMSO-$d_6$+$D_2O$) δ ppm: 9.48 (d, J=2.0 Hz, 1H), 9.28 (s, 1H), 9.00 (dd, J=6.0 Hz, $J_2$=0.4 Hz, 1H), 8.84 (s, 1H), 8.36 (s, 1H), 8.25 (d, J=8.4 Hz, 1H), 7.98 (s, 1H), 7.73 (dd, J=8.4 Hz, $J_2$=1.6 Hz, 1H), 7.70-7.66 (m, 1H), 7.60-7.53 (m, 1H), 7.46-7.44 (m, 1H), 7.37-7.35 (m, 1H), 7.32 (dd, $J_1$=7.6 Hz, $J_2$=0.8 Hz, 1H), 5.35 (s, 2H), 1.49 (s, 9H).

N-[[4-(benzofuran-2-yl)-6-isoquinolyl]methyl]pyridazin-4-amine (Example 131)

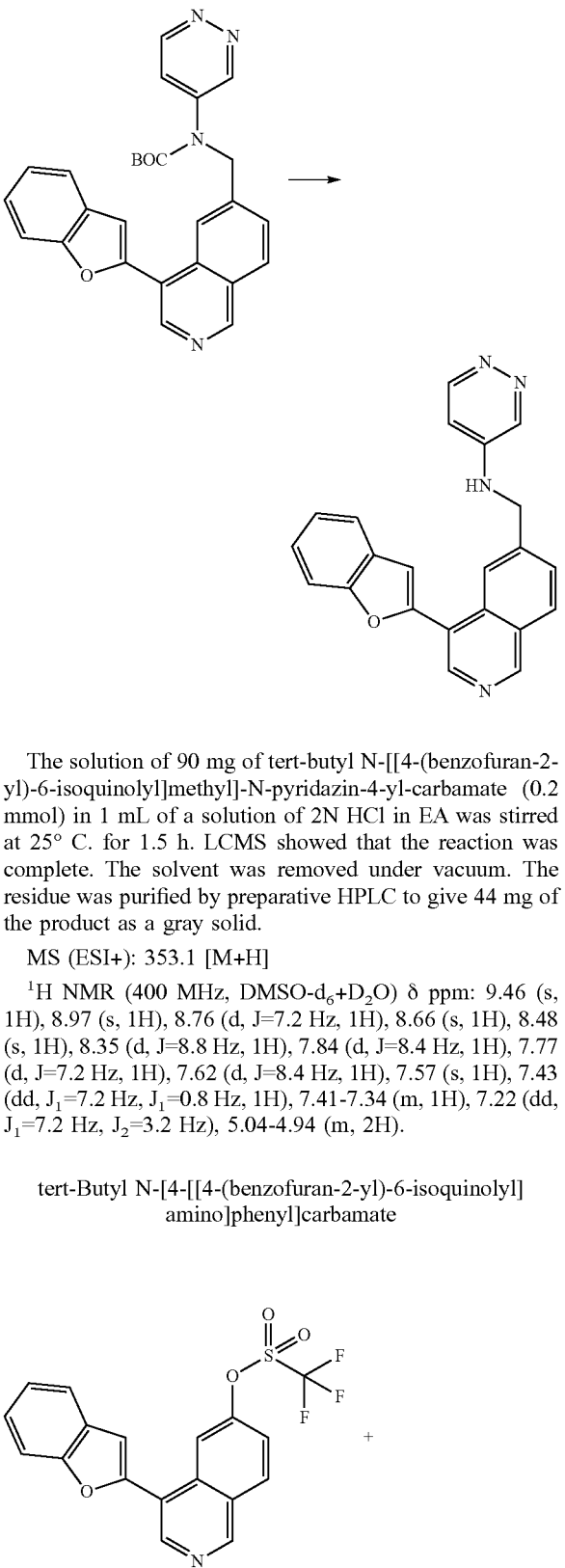

The solution of 90 mg of tert-butyl N-[[4-(benzofuran-2-yl)-6-isoquinolyl]methyl]-N-pyridazin-4-yl-carbamate (0.2 mmol) in 1 mL of a solution of 2N HCl in EA was stirred at 25° C. for 1.5 h. LCMS showed that the reaction was complete. The solvent was removed under vacuum. The residue was purified by preparative HPLC to give 44 mg of the product as a gray solid.

MS (ESI+): 353.1 [M+H]

$^1$H NMR (400 MHz, DMSO-$d_6$+$D_2O$) δ ppm: 9.46 (s, 1H), 8.97 (s, 1H), 8.76 (d, J=7.2 Hz, 1H), 8.66 (s, 1H), 8.48 (s, 1H), 8.35 (d, J=8.8 Hz, 1H), 7.84 (d, J=8.4 Hz, 1H), 7.77 (d, J=7.2 Hz, 1H), 7.62 (d, J=8.4 Hz, 1H), 7.57 (s, 1H), 7.43 (dd, $J_1$=7.2 Hz, $J_1$=0.8 Hz, 1H), 7.41-7.34 (m, 1H), 7.22 (dd, $J_1$=7.2 Hz, $J_2$=3.2 Hz), 5.04-4.94 (m, 2H).

tert-Butyl N-[4-[[4-(benzofuran-2-yl)-6-isoquinolyl]amino]phenyl]carbamate

N1-[4-(Benzofuran-2-yl)-6-isoquinolyl]benzene-1,4-diamine (Example 132)

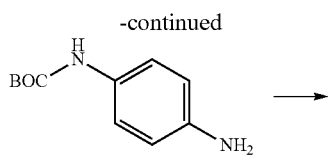

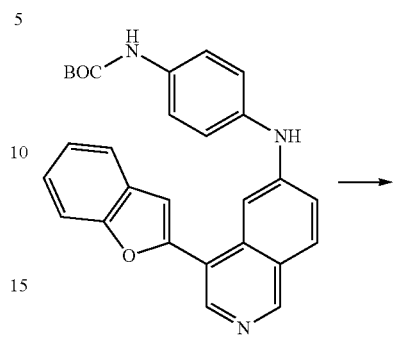

Under argon atmosphere, to a stirred solution of 0.22 g (0.56 mmol) of [4-(benzofuran-2-yl)-6-isoquinolyl] trifluoromethanesulfonate in 6 mL of dioxane were added 0.14 g (0.67 mmol) of N-Boc-p-phenylenediamine (CAS: 71026-66-9), 51 mg (0.06 mmol) of $Pd_2(dba)_3$, 40 mg (0.08 mmol) of X-phos and 0.44 g (1.68 mmol) of $K_3PO_4 \cdot 3H_2O$. After stirring at 90° C. for 15 h, the mixture was concentrated under vacuum to give 200 mg of the crude product, which was used in the next step without further purification.

MS (ESI+): 452.1 [M+H].

To a stirred solution of 0.20 g (0.44 mmol) of tert-butyl N-[4-[[4-(benzofuran-2-yl)-6-isoquinolyl]amino]phenyl] carbamate in 5 mL of DCM was added 3.3 mL (44.3 mmol) of TFA. After stirring at 20° C. for 1.5 h, the mixture was concentrated under vacuum to give the crude product, which was purified via Prep-HPLC to give 150 mg of the desired product as a yellow solid.

MS (ESI+): 352.1 [M+H].

$^1$H NMR (400 MHz, DMSO-d6+D$_2$O) δ ppm: 9.23 (s, 1H), 8.67 (s, 1H), 8.29 (d, J=9.2 Hz, 1H), 7.83 (d, J=2.0 Hz, 1H), 7.78-7.66 (m, 2H), 7.56 (dd, J=2.4, 9.2 Hz, 1H), 7.52 (s, 1H), 7.46-7.33 (m, 4H), 7.14 (d, J=8.4 Hz, 2H).

The following examples were prepared accordingly to Example 132 by reaction of [4-(benzofuran-2-yl)-6-isoquinolyl] trifluoromethanesulfonate with the corresponding amine in the presence of a Pd-catalyst and subsequent deprotection:

| Example | | $^1$H NMR (400 MHz) δ ppm | MS (+ESI) [M + H]$^+$ |
|---|---|---|---|
| 133 | 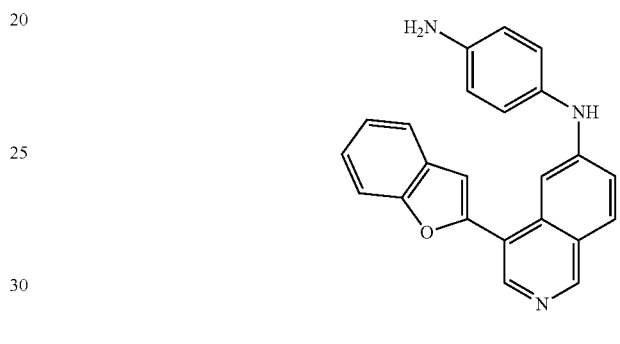 | (DMSO-d$_6$) 9.27 (s, 1H), 8.72 (s, 1H), 8.30 (d, J = 9.2 Hz, 1H), 7.98 (d, J = 2.0 Hz, 1H), 7.80-7.69 (m, 2H), 7.62 (dd, J = 2.4, 9.2 Hz, 1H), 7.55-7.53 (m, 3H), 7.47-7.35 (m, 4H), 4.02 (s, 2H) | 366.1 |

| Example | 1H NMR (400 MHz) δ ppm | MS (+ESI) [M + H]+ |
|---|---|---|
| 134 | (DMSO-d6 + D2O) 9.36 (s, 1H), 8.76 (s, 1H), 8.70 (d, J = 2.8 Hz, 1H), 8.44 (dd, J = 1.6, 5.2 Hz, 1H), 8.39 (d, J = 8.8 Hz, 1H), 8.10-8.07 (m, 1H), 8.02 (d, J = 2.0 Hz, 1H), 7.79 (d, J = 7.2 Hz, 1H), 7.72-7.68 (m, 3H), 7.58 (s, 1H), 7.47-7.34 (m, 2H) | 338.1 |
| 135 | (DMSO-d6 + D2O) 9.26 (s, 1H), 8.68 (s, 1H), 8.31 (d, J = 9.2 Hz, 1H), 7.91 (d, J = 2.0 Hz, 1H), 7.79-7.70 (m, 2H), 7.62 (dd, J = 2.0, 9.2 Hz, 1H), 7.54 (s, 1H), 7.46-7.28 (m, 3H), 6.91-6.84 (m, 2H), 6.68 (dd, J = 1.6, 8.0 Hz, 1H) | 352.1 |
| 136 | (DMSO-d6 + D2O) δ ppm: 9.27 (s, 1H), 8.70 (s, 1H), 8.31 (d, J = 9.2 Hz, 1H), 7.90 (d, J = 2.0 Hz, 1H), 7.77 (d, J = 7.6 Hz, 1H), 7.69-7.65 (m, 2H), 7.57-7.53 (m, 2H), 7.48-7.41 (m, 3H), 7.38-7.34 (m, 1H), 7.25 (d, J = 7.6 Hz, 1H), 4.03 (s, 2H) | 366.1 |

N4-[4-(Benzofuran-2-yl)-6-isoquinolyl]pyridine-2,4-diamine (Example 137)

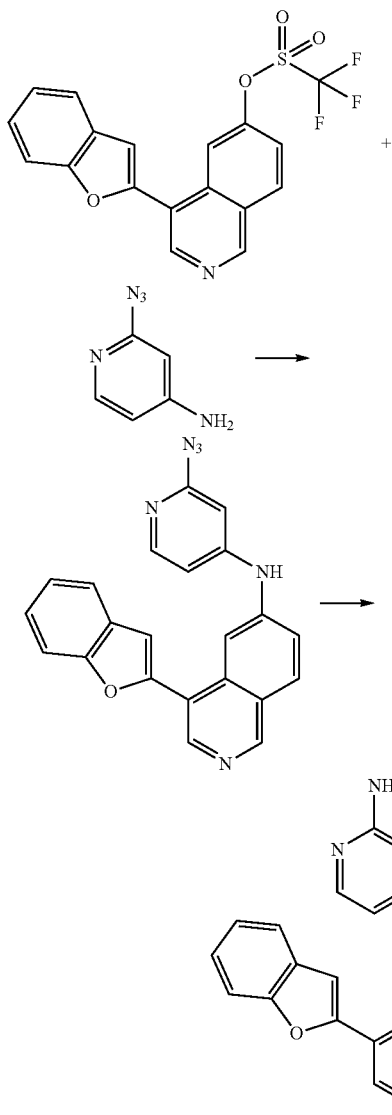

N-(2-azido-4-pyridyl)-4-(benzofuran-2-yl)isoquinolin-6-amine was prepared accordingly to Example 132 by the reaction of [4-(benzofuran-2-yl)-6-isoquinolyl] trifluoromethanesulfonate with 2-azidopyridin-4-amine in the presence of a Pd-catalyst.

To a solution of 0.25 g (0.66 mmol) of the intermediate (N-(2-azido-4-pyridyl)-4-(benzofuran-2-yl)isoquinolin-6-amine) in 20 mL of EtOH was added 1.49 g (6.59 mmol) of $SnCl_2 \cdot 2H_2O$. After refluxing for 3 h, the solution was concentrated under vacuum. The residue was diluted with $H_2O$, adjusted to pH=10 with 6M NaOH aqueous solution, extracted with EA. The combined organic layers were dried over $Na_2SO_4$, filtered through celite and the filtrate was concentrated under vacuum to give the crude product, which was purified via Preparative HPLC to give 208 mg of the desired product as a yellow solid.

MS (ESI+): 353.2 [M+H].

$^1$H NMR (400 MHz, DMSO-$d_6$+$D_2O$) δ ppm: 9.42 (s, 1H), 8.90 (s, 1H), 8.42 (d, J=9.2 Hz, 1H), 8.28 (d, J=2.0 Hz, 1H), 7.80-7.71 (m, 4H), 7.59 (s, 1H), 7.45-7.34 (m, 2H), 6.64-6.59 (m, 2H).

N5-[4-(Benzofuran-2-yl)-6-isoquinolyl]pyridine-2,5-diamine (Example 138)

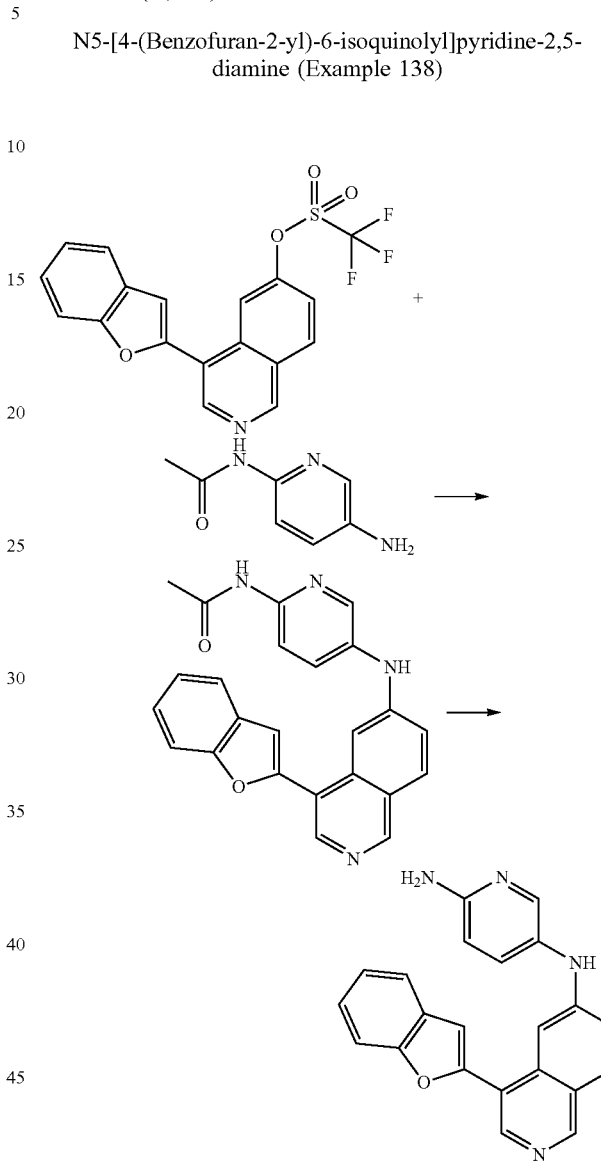

N-[5-[[4-(benzofuran-2-yl)-6-isoquinolyl]amino]-2-pyridyl]acetamide was prepared accordingly to Example 132 by reaction of [4-(benzofuran-2-yl)-6-isoquinolyl] trifluoromethanesulfonate with N-(5-amino-2-pyridyl)acetamide (CAS: 29958-14-3) in the presence of a Pd-catalyst.

To a solution of 0.20 g (0.51 mmol) of the intermediate (N-[5-[[4-(benzofuran-2-yl)-6-isoquinolyl]amino]-2-pyridyl]acetamide) in 8 mL of MeOH was added 4.06 mL of 5 N NaOH solution. After stirring at 90° C. for 3 h, the solution was concentrated to give the crude product, which was purified via Preparative HPLC to give 85 mg of the desired product as a yellow solid.

MS (ESI+): 353.1 [M+H].

$^1$H NMR (400 MHz, DMSO-$d_6$+$D_2O$) δ ppm: 9.29 (s, 1H), 8.72 (s, 1H), 8.30 (d, J=9.2 Hz, 1H), 8.02-7.98 (m, 2H), 7.78 (d, J=7.6 Hz, 1H), 7.68-7.66 (m, 2H), 7.54-7.51 (m, 2H), 7.46-7.34 (m, 2H), 7.10-7.07 (m, 1H).

4-(Benzofuran-2-yl)-N-(4-pyridyl)isoquinolin-6-amine (Example 139)

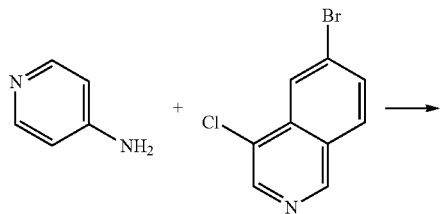

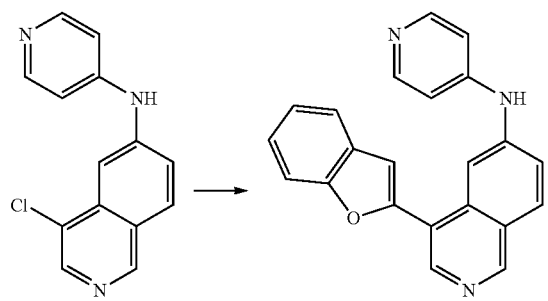

Under argon atmosphere, to a stirred solution of 0.70 g (2.89 mmol) of 6-bromo-4-chloro-isoquinoline in 30 mL of toluene were added 0.30 g (3.18 mmol) of 4-aminopyridine (CAS: 504-24-5), 0.14 g (0.15 mmol) of $Pd_2(dba)_3$, 0.18 g (0.29 mmol) of BINAP and 0.42 g (4.33 mmol) of t-BuONa. After stirring at 80° C. for 5 h, the mixture was concentrated under vacuum to give the crude product, which was purified by silica gel column chromatography (PE/EA=2/1) to give 0.55 g of 4-chloro-N-(4-pyridyl)isoquinolin-6-amine as a white solid.

Under argon atmosphere, to a stirred solution of 0.33 g (1.29 mmol) of 4-chloro-N-(4-pyridyl)isoquinolin-6-amine in 10 mL of dioxane were added 0.42 g (2.58 mmol) of Benzofuran-2-boronic acid (CAS: 98437-24-2), 267 mg (0.26 mmol) of $Pd_2(dba)_3$, 174 mg (0.62 mmol) of $PCy_3$ and 0.58 g (2.19 mmol) of $K_3PO_4 \cdot H_2O$. After stirring at 120° C. for 12 h, the solution was concentrated under vacuum to give the crude product, which was purified via Preparative HPLC to give 310 mg of 4-(benzofuran-2-yl)-N-(4-pyridyl)isoquinolin-6-amine as a yellow solid.

MS (ESI+): 338.1 [M+H].

$^1$H NMR (400 MHz, DMSO-$d_6$+$D_2O$) δ ppm: 9.43 (s, 1H), 8.95 (s, 1H), 8.45-8.37 (m, 4H), 7.84-7.73 (m, 3H), 7.58 (s, 1H), 7.45-7.35 (m, 4H).

(E)-1-(3-Chloro-4-fluoro-phenyl)-N-(2,2-dimethoxy-ethyl)methanimine

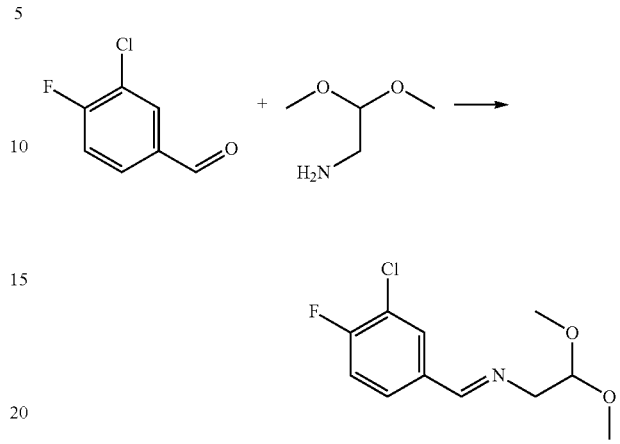

A solution of 5.0 g of 3-chloro-4-fluoro-benzaldehyde (32.4 mmol) and 3.62 g of aminoacetaldehyde dimethyl acetal (34.1 mmol) in 20.0 mL of toluene was stirred at 110° C. for 12 h with a sealed tube, then the reaction mixture was cooled to r.t. and concentrated under vacuum to give 7.8 g of desired product, as yellow oil.

$^1$H NMR (400 MHz, DMSO-d6) δ ppm: 8.30 (s, 1H), 7.89 (d, J=7.2 Hz, 1H), 7.75-7.72 (m, 1H), 7.46 (t, J=8.8 Hz, 1H), 4.62 (t, J=5.2 Hz, 1H), 3.69 (d, J=5.2 Hz, 2H), 3.32-3.27 (m, 6H).

N-[(3-Chloro-4-fluoro-phenyl)methyl]-2,2-dimethoxy-ethanamine

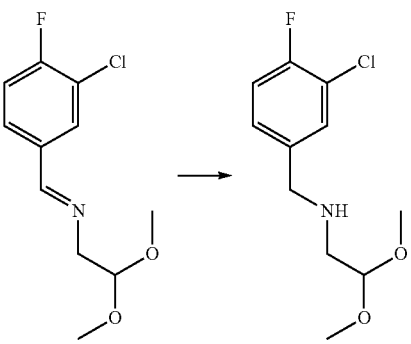 [SMILES: COC(C/N=C/c1ccc(F)c(Cl)c1)OC ; COC(CNCc1ccc(F)c(Cl)c1)OC]

To a solution of 7.5 g of (E)-1-(3-chloro-4-fluoro-phenyl)-N-(2,2-dimethoxyethyl) methan imine (30.5 mmol) in 100.0 mL of EtOH was added 1.7 g of $NaBH_4$ (45.8 mmol) at rt, it was stirred at rt for 3 h, LCMS showed that the desired compound was formed. 50 mL of $H_2O$ was added, the mixture was extracted with EA (100 mL×3), the combined organic phases were washed with brine (25 mL×3), dried over $Na_2SO_4$, filtered and concentrated under vacuum to give the crude product, which was purified by silica gel column chromatography eluting with PE/EA (V/V=3:1) to give 5.0 g of desired compound, as off-white oil.

MS m/z (+ESI): 248.0 ([M+H]$^+$)

N-[(3-Chloro-4-fluoro-phenyl)methyl]-N-(2,2-dimethoxyethyl)-4-methyl-benzenesulfonamide

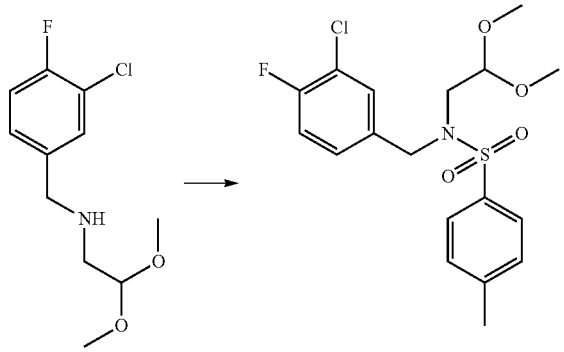 [SMILES: COC(CNCc1ccc(F)c(Cl)c1)OC ; COC(CN(Cc1ccc(F)c(Cl)c1)S(=O)(=O)c1ccc(C)cc1)OC]

To a solution of 5.0 g of N-[(3-chloro-4-fluoro-phenyl)methyl]-2,2-dimethoxy-ethanamine (20.2 mmol) in 100 mL of DCM and 10.0 mL of Py was added 6.2 g of p-Toluenesulfonyl chloride (32.3 mmol) in 50 mL of DCM at 0° C., then it was stirred rt 25 for 5 h, TLC showed that the desired compound was formed. 50 mL of H$_2$O was added, the resulting mixture was extracted with DCM (100 mL*3), the combined organic phases were washed with brine (30 mL*3), dried over Na$_2$SO$_4$, filtered and concentrated under vacuum to give the crude product, which was purified by silica gel column chromatography eluting with PE/EA (V/V=20:1) to give 7.0 g of desired compound, as light yellow oil.

7-Chloro-6-fluoro-isoquinoline

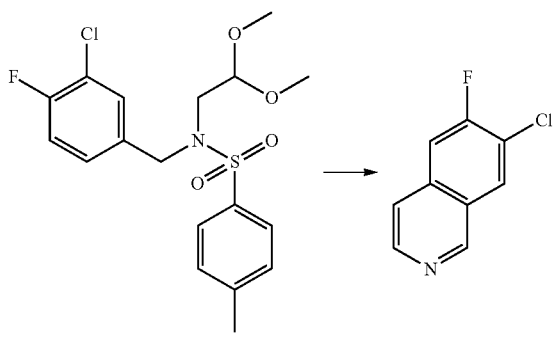 [SMILES: COC(CN(Cc1ccc(F)c(Cl)c1)S(=O)(=O)c1ccc(C)cc1)OC ; Fc1cc2ccncc2cc1Cl]

To a solution of 3 g of N-[(3-chloro-4-fluoro-phenyl)methyl]-N-(2,2-dimethoxyethyl)-4-methyl-benzenesulfonamide (7.5 mmol) in 50 mL of DCM was added 6 g of AlCl$_3$ (44.5 mmol) at rt, it was stirred at rt for 12 h, LCMS showed that the desired compound was formed. The reaction mixture and another batch (RANDY-734-1) were treated with 100 mL of ice water, the resulting mixture was extracted with DCM (50 mL*3), the combined organic phases were washed with aq.NaHCO$_3$ (30 mL), H$_2$O (20 mL*2) and brine (30 mL), dried over Na$_2$SO$_4$, filtered and concentrated under vacuum to give the crude product, which was purified by silica gel column chromatography eluting with PE/EA (V/V=20:1) to give 2.0 g of desired compound, as a light yellow solid. It was recrystallized with PE/EA (V/V=10:1) to give 1.2 g of desired compound, as a yellow solid.
MS m/z (+ESI): 182.0 ([M+H]$^+$).
$^1$H NMR (400 MHz, CDCl$_3$) δ ppm: 9.20 (s, 1H), 8.57 (d, J=6.0 Hz, 1H), 8.08 (d, J=7.6 Hz, 1H), 7.63 (d, J=6.0 Hz, 1H), 7.56 (d, J=9.2 Hz, 1H).

4-Bromo-7-chloro-6-fluoro-isoquinoline

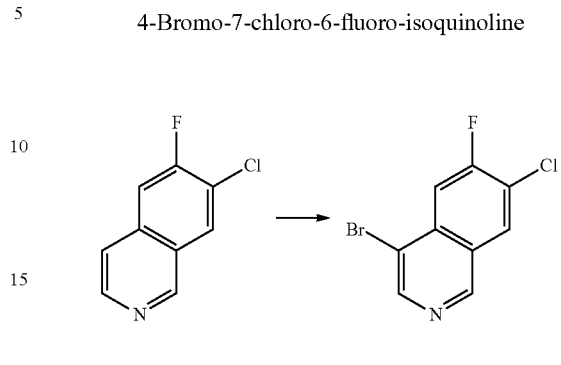

To a solution of 100 mg of 7-chloro-6-fluoro-isoquinoline (0.55 mmol) in 5 mL of AcOH was added 0.5 mL of Br$_2$, it was stirred at 110° C. for 12 h, LCMS showed that the desired compound was formed, the reaction mixture was cooled to r.t. and concentrated under vacuum, the crude product was taken up with 100 mL of DCM, washed with aq. NaHCO$_3$ (20 mL), H$_2$O (20 mL*2) and brine (25 mL), dried over Na$_2$SO$_4$, filtered and concentrated under vacuum to give the crude product, which was purified by silica gel column chromatography (eluent: PE:EA=15:1) to give 40 mg of desired compound, as a yellow solid.
MS m/z (+ESI): 259.9 ([M+H]$^+$).
$^1$H NMR (400 MHz, CDCl$_3$) δ ppm: 9.10 (s, 1H), 8.75 (s, 1H), 8.11 (d, J=7.2 Hz, 1H), 7.92 (d, J=10.0 Hz, 1H).

4-(Benzofuran-2-yl)-7-chloro-6-fluoro-isoquinoline

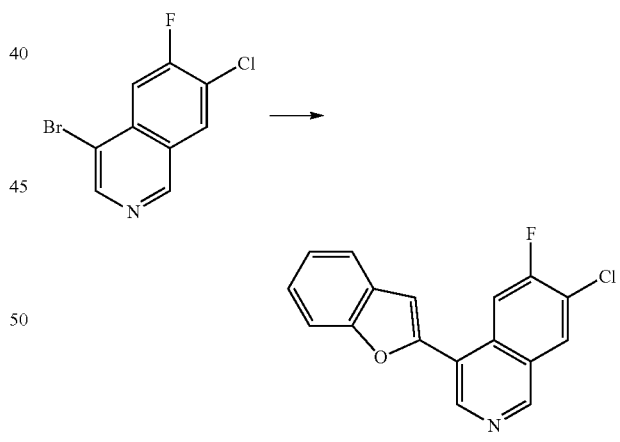

To a solution of 300 mg of 4-bromo-7-chloro-6-fluoro-isoquinoline (0.12 mmol) in 10 mL of dioxane and 1.0 mL of H$_2$O were added 0.21 g of benzofuran-2-ylboronic acid (1.27 mmol), 0.27 g of Pd(PPh$_3$)$_4$ (0.23 mmol) and 0.32 g of K$_2$CO$_3$ (2.3 mmol) at rt, it was stirred at 80° C. for 5 h, LCMS showed that the desired compound was formed. The reaction mixture was cooled to r.t. and concentrated under vacuum, the crude product was purified by silica gel column chromatography (eluent: PE:EA=10:1) to give 240 mg of desired compound, as a yellow solid.
MS m/z (+ESI): 298.0 ([M+H]$^+$)

171 tert-Butyl N-[4-[[4-(benzofuran-2-yl)-7-chloro-6-isoquinolyl]amino]cyclohexyl]carbamate

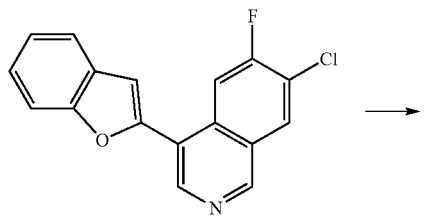

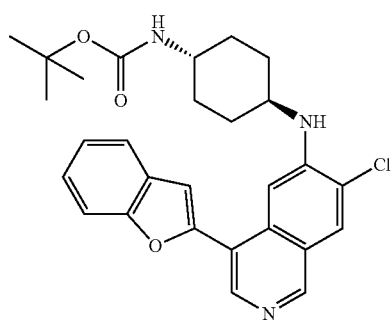

To a solution of 100 mg of 4-(benzofuran-2-yl)-7-chloro-6-fluoro-isoquinoline (0.33 mmol) in 4 mL of DMSO was added 432 mg of N-Boc-1,4-cyclohexanediamine (2.0 mmol) and 97 mg of DIPEA (0.5 mmol), the resulting mixture was stirred at 120° C. for 0.5 h with microwave, LCMS showed that the desired compound was formed, after it was cooled to r.t., the mixture was treated with H₂O (20 mL), then it was extracted with EA (20 mL*3), the combined organic phases were washed with H₂O (10 mL*2) and brine (15 mL), dried over Na₂SO₄, filtered and concentrated under vacuum to give the crude product, which was purified by silica gel column chromatography eluting with DCM/MeOH (V/V=40:1) to give 100 mg of desired compound, as a yellow solid.

MS m/z (+ESI): 492.2 ([M+H]⁺).

N4-[4-(Benzofuran-2-yl)-7-chloro-6-isoquinolyl]cyclohexane-1,4-diamine (Example 140)

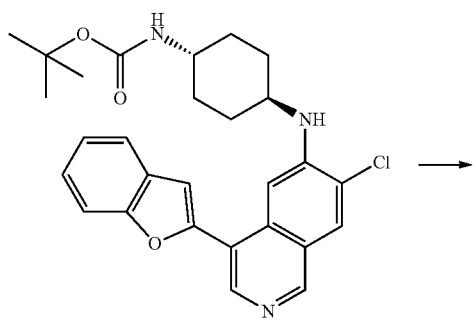

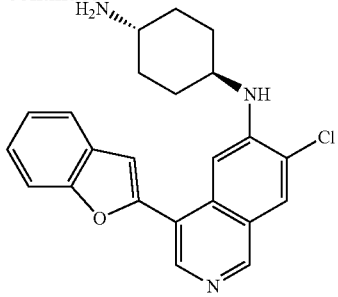

A solution of 150.0 mg of tert-butyl N-[4-[[4-(benzofuran-2-yl)-7-chloro-6-isoquinolyl]amino]cyclohexyl]carbamate (0.3 mmol) in 6.0 mL of 2.5 N of EA/HCl (g) was stirred for 10 h at rt, LCMS showed that the desired compound was formed. It was concentrated under vacuum to give a yellow solid, which was dissolved in H₂O (5.0 mL), adjusting the solution pH=9 with aq. NH₃H₂O, the mixture was extracted with EA (10 mL*3), the combined organic phases were washed with H₂O (5 mL*2), brine (10 mL), dried over Na₂SO₄, filtered and concentrated under vacuum to give the crude product, which was purified by Prep-HPLC to give 30 mg of desired compound, as a yellow solid.

MS m/z (+ESI): 392.2 ([M+H]⁺).

¹H NMR (400 MHz, DMSO-d₆+D₂O) δ ppm: 8.95 (s, 1H), 8.68 (s, 1H), 8.20 (s, 1H), 7.75 (d, J=7.2Hz, 1H), 7.65 (d, J=8.0Hz, 1H), 7.45-7.37 (m, 3H), 7.35-7.31 (m, 1H), 3.33 (t, J=11.2 Hz, 1H), 2.68-2.61 (m, 1H), 2.06 (d, J=11.2 Hz, 2H), 1.88 (d, J=11.2 Hz, 2H), 1.44 (dd, J₁=24.0Hz, J₂=10.4 Hz, 2H), 1.20 (dd, J₁=24.0Hz, J₂=10.4Hz, 2H).

tert-Butyl N-[4-[[4-(benzofuran-2-yl)-7-hydroxy-6-isoquinolyl]amino]cyclohexyl]carbamate

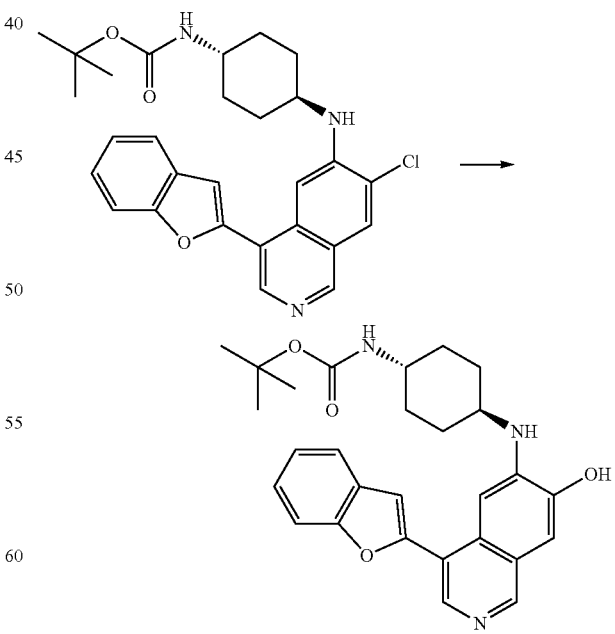

To a solution of 50 mg of tert-butyl N-[4-[[4-(benzofuran-2-yl)-7-chloro-6-isoquinolyl]amino]cyclohexyl]carbamate (0.1 mmol) in 3 mL of Diox. 1 mL of H₂O were added 22 mg of Pd(OAc)₂ (0.1 mmol), 12 mg of x-phos (0.025 mmol) and 57 mg of KOH (1.01 mmol) at rt, it was stirred at 120° C. for 0.5 h with microwave, LCMS showed that the desired compound was formed, after it was cooled to r.t., the resulting mixture and mixture of RANDY-801/803-1 were acidified with 1N of HCl solution to pH=7, then it was extracted with EA (10 mL*3), the combined organic phases were washed with H₂O (10 mL*3), brine (10 mL), dried over Na₂SO₄, filtered and concentrated under vacuum to give the crude product, which was purified by silica gel column chromatography (eluent: DCM/MeOH=30:1) to give 50 mg of desired compound, as a yellow solid.

MS m/z (+ESI): 474.2 ([M+H]⁺).

tert-Butyl N-[4-[[4-(benzofuran-2-yl)-7-methoxy-6-isoquinolyl]amino]cyclohexyl]carbamate

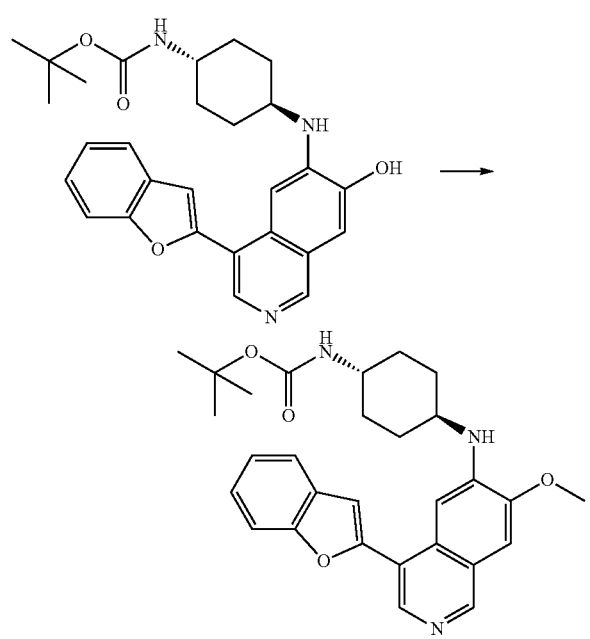

Preparation of diazomethane

To a solution of 1.3 g of KOH (18 mmol) in 10 mL of H₂O and 30 mL of Et₂O was added 1.0 g of N-Methyl-N-Nitrosourea (2.7.0 mmol) in several portions at 0° C., it was stirred at 0° C. for 1 h. Then yellow organic layer was separated and dried over Na₂SO₄ in ice bath. The solution was used directly for next step.

Preparation of tert-butyl N-[4-[[4-(benzofuran-2-yl)-7-methoxy-6-isoquinolyl]amino]cyclohexyl] carbamate To a solution of 50 mg of tert-butyl N-[4-[[4-(benzofuran-2-yl)-7-hydroxy-6-isoquinolyl]amino]cyclohexyl]carbamate (0.1 mmol) in 10 mL of Et₂O and 10 mL of MeOH was added the solution of diazomethane at 0° C., the mixture was stirred at 0° C. for 1 h, LCMS showed that the desired compound was formed, 2 mL of AcOH was added, it was concentrated under vacuum to give the crude product, which was purified by silica gel column chromatography (eluent: DCM/MeOH=50:1) to give 50 mg of desired compound, as a yellow solid.

MS m/z (+ESI): 488.2 ([M+H]⁺).

N4-[4-(Benzofuran-2-yl)-7-methoxy-6-isoquinolyl] cyclohexane-1,4-diamine (Example 141)

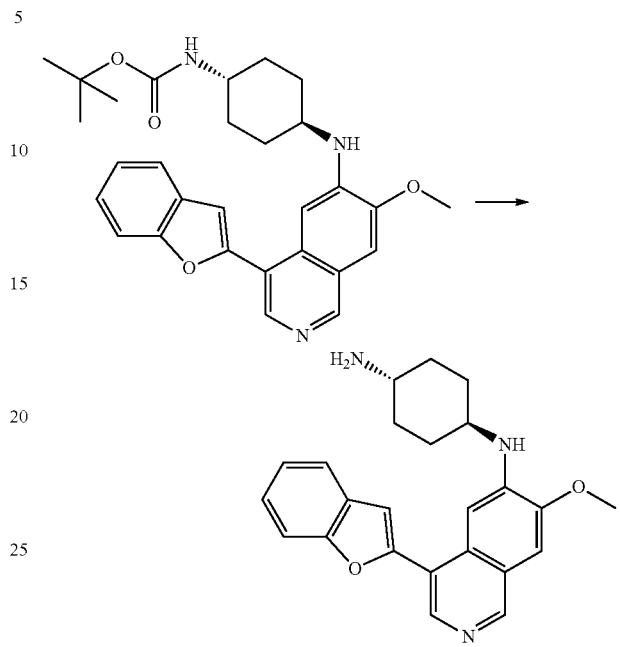

To a solution of 150 mg of tert-butyl N-[4-[[4-(benzofuran-2-yl)-7-methoxy-6-isoquinolyl]amino]cyclohexyl] carbamate (0.3 mmol) in 15 mL of DCM was added 1.0 mL of TFA and 0.2 mL of TES at rt, the reaction mixture was stirred at rt for 2 h, LCMS showed that the desired compound was formed, it was concentrated under vacuum, the crude product was purified with Prep-HPLC to give 30 mg of desired compound, as a light yellow solid. MS m/z (+ESI): 388.3 ([M+H]⁺).

¹H NMR (400 MHz, DMSO-d₆+D₂O) δ ppm: 8.88 (s, 1H), 8.57 (s, 1H), 7.74-7.72 (m, 1H), 7.64 (d, J=8.4Hz, 1H), 7.42-7.29 (m, 5H), 3.97 (s, 3H), 3.33 (br, 1H), 2.95 (br, 1H), 2.11 (d, J=8.0Hz, 2H), 2.00 (br, 2H), 1.47-1.34 (m, 4H).

1-(2-Chloro-4-fluoro-phenyl)-N-(2,2-dimethoxy-ethyl)methanimine

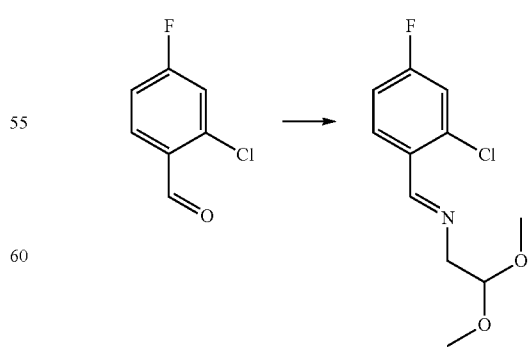

To a solution of 2.5 g of 2-chloro-4-fluorobenzaldehyde (15.7 mmol) and 1.74 g of Aminoacetaldehyde dimethyl acetal (16.6 mmol) in 15 mL of Toluene was added 1.0 g of 4 Å molecular sieves and 0.27 g of PTSA (1.6 mmol) at rt, the mixture was stirred at 100° C. for 10 h, after it was cooled to rt, 50 mL of EA was added, the resulting mixture was washed with saturated NaHCO$_3$ solution (20 mL*2) and H$_2$O (30 mL), the organic phase was dried over Na$_2$SO$_4$, filtered and concentrated under vacuum to give 3.0 g of desired compound, as dark brown oil.

$^1$H NMR (400 MHz, DMSO-d$_6$) δ ppm: 8.62 (s, 1H), 8.00 (dd, J$_1$=8.8Hz, J$_2$=6.4Hz, 1H), 7.53 (dd, J$_1$=8.8Hz, J$_2$=2.4Hz 1H), 7.33-7.28 (m, 1H), 4.64 (t, J=5.2Hz, 1H), 3.76 (dd, J$_1$=5.2Hz, J$_2$=1.2Hz, 2H), 3.34-3.28 (m, 6H).

N-[(2-Chloro-4-fluoro-phenyl)methyl]-2,2-dimethoxy-ethanamine

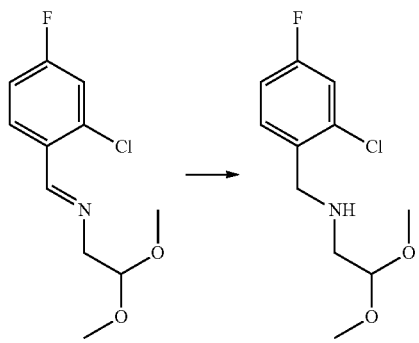 [SMILES: COC(C/N=C/c1ccc(F)cc1Cl)OC ; COC(CNCc1ccc(F)cc1Cl)OC]

To a solution of 0.5 g of 1-(2-chloro-4-fluoro-phenyl)-N-(2,2-dimethoxyethyl)methanimine (2.03 mmol) in 10 mL of EtOH was added 116 mg of NaBH$_4$ at rt, the mixture was stirred at rt for 3 h, LCMS showed that the desired compound was formed, 30 mL of H$_2$O was added, the resulting mixture was extracted with EA (25 mL*3), washed with H$_2$O (15 mL×3) and brine (20 mL). The organic layer was dried over Na$_2$SO$_4$ and concentrated under vacuum to give the crude product, which was purified by silica gel column chromatography eluting with PE/EA (V/V=3:1) to give 300 mg of desired compound, as light yellow oil.

$^1$H NMR (400 MHz, DMSO-d$_6$) δ ppm: 7.55-7.52 (m, 1H), 7.38 (dd, J$_1$=9.2Hz, J$_2$=2.8Hz, 1H), 7.22-7.17 (m, 1H), 4.40 (t, J=5.6Hz, 1H), 3.76 (s, 2H), 3.25 (s, 6H), 2.59 (d, J=5.6Hz, 2H).

N-[(2-Chloro-4-fluoro-phenyl)methyl]-N-(2,2-dimethoxyethyl)-4-methyl-benzenesulfonamide

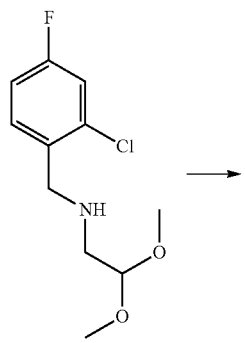

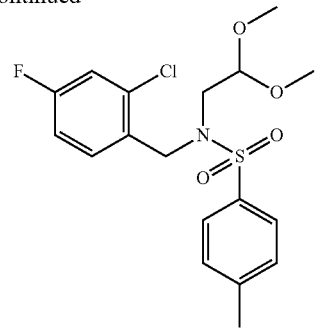

To a solution of 0.3 g of N-[(2-chloro-4-fluoro-phenyl)methyl]-2,2-dimethoxy-ethanamine (1.2 mmol) in 10 mL of DCM and 1 mL of Py was dropped 0.37 g of p-Toluenesulfonyl chloride (1.9 mmol) in 3 mL of DCM at 0° C., it was stirred at rt for 5 h, TLC showed that a new compound was formed. 10 mL of H$_2$O was added, the resulting mixture was extracted with DCM (25 mL*3), the combined organic phases were dried over Na$_2$SO$_4$, filtered and concentrated under vacuum to give the crude product, which was purified by silica gel column chromatography eluting with PE/EA (V/V=20:1) to give 300 mg of desired compound, as off-white oil.

8-Chloro-6-fluoro-isoquinoline

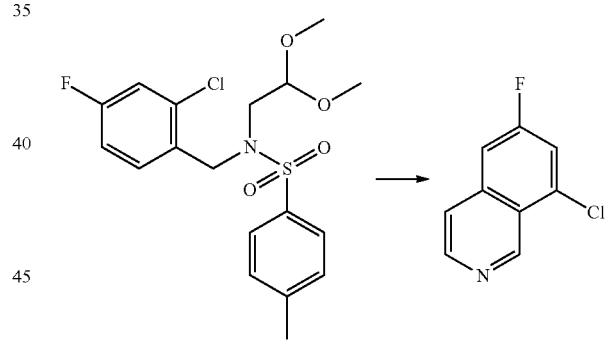

To a solution of 1.0 g of N-[(2-chloro-4-fluoro-phenyl)methyl]-N-(2,2-dimethoxyethyl)-4-methyl-benzenesulfonamide (2.5 mmol) in 50 mL of DCM was added 2.0 g of AlCl$_3$ (15 mmol) at rt, it was stirred at rt for 12 h, LCMS showed that the desired compound was formed. The mixture was poured into 20 mL of ice water, the resulting mixture was extracted with DCM (30 mL*3), the organic phase was washed with aq. NaHCO$_3$, dried over Na$_2$SO$_4$, filtered and concentrated under vacuum to give the crude product, which was purified by silica gel column chromatography eluting with PE/EA (V/V=20:1) to give 0.12 g of desired compound, as a yellow solid. MS m/z (+ESI): 182.0 ([M+H]+).

$^1$H NMR (400 MHz, DMSO-d$_6$) δ ppm: 9.52 (s, 1H), 8.65 (d, J=5.6Hz, 1H), 7.94-7.91 (m, 2H), 7.86 (dd, J$_1$=9.6Hz, J$_2$=2.4Hz, 1H).

177
4-Bromo-8-chloro-6-fluoro-isoquinoline

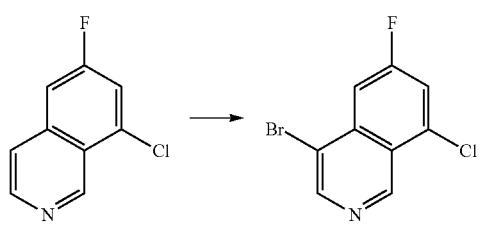 [SMILES: Fc1cc(Cl)c2cnccc2c1 ; Fc1cc(Cl)c2cncc(Br)c2c1]

To a solution of 80 mg of 8-chloro-6-fluoro-isoquinoline (0.44 mmol) in 5 ml of AcOH was added 0.5 mL of $Br_2$, it was stirred at 110° C. for 48 h, LCMS showed that the desired compound was formed, the reaction mixture was cooled to r.t. and concentrated under vacuum to give the crude product, which was purified by silica gel column chromatography eluting with PE/EA (V/V=20:1) to give 30 mg of desired compound, as a yellow solid.

MS m/z (+ESI): 260.0 ([M+H]+).

$^1$H NMR (400 MHz, DMSO-$d_6$) δ ppm: 9.49 (s, 1H), 8.90 (s, 1H), 8.07 (dd, $J_1$=8.8Hz, $J_2$=2.4Hz, 1H), 7.83-7.80 (m, 1H).

4-(Benzofuran-2-yl)-8-chloro-6-fluoro-isoquinoline

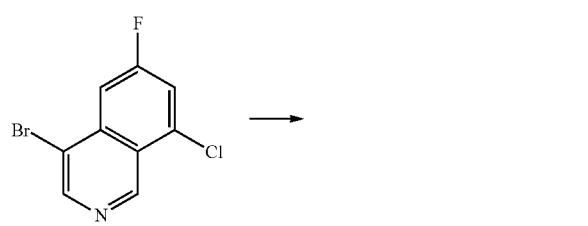

To a solution of 150 mg of 4-bromo-8-chloro-6-fluoro-isoquinoline (0.57 mmol, 1.0 eq., Note1) in 5 mL of dioxane and 2 mL of $H_2O$ were added 103 mg of benzofuran-2-ylboronic acid (0.63 mmol, 1.1 eq.), 66 mg of Pd(PPh$_3$)$_4$ (0.057 mmol, 0.1 eq.) and 159 mg of $K_2CO_3$ (1.15 mmol, 2.0 eq.) at rt, it was stirred at 80° C. for 5 h, LCMS showed that the desired compound was formed, the resulting mixture was concentrated under vacuum to give the crude product, which was purified by silica gel column chromatography (eluent: PE:EA=10:1) to give 100 mg of desired compound, as a yellow solid.

MS m/z (+ESI): 298.0 ([M+H]$^+$).

$^1$H NMR (400 MHz, DMSO-$d_6$) δ ppm: 9.62(s, 1H), 9.09(s, 1H), 8.24(d, J=10.4Hz, 1H), 8.10(d, J=8.0Hz, 1H), 7.79-7.76(m, 2H), 7.66(s, 1H), 7.43(t, J=7.6Hz, 1H), 7.36(t, J=7.6Hz, 1H).

178
tert-Butyl N-[4-[[4-(benzofuran-2-yl)-8-chloro-6-isoquinolyl]amino]cyclohexyl]carbamate

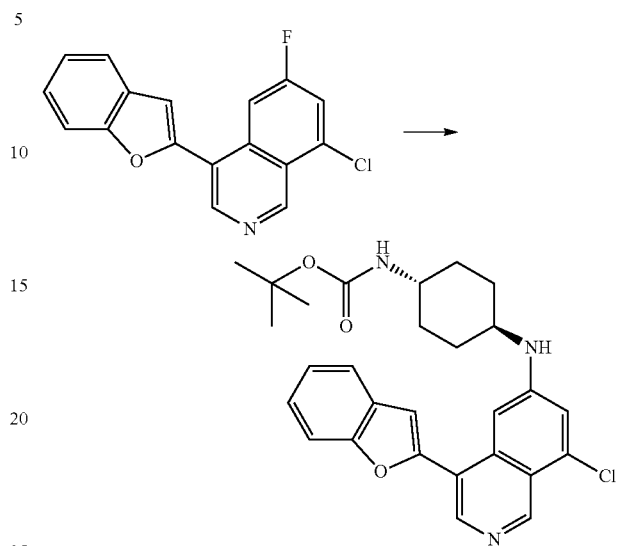

To a solution of 30 mg of 4-(benzofuran-2-yl)-8-chloro-6-fluoro-isoquinoline (0.10 mmol) in 1.0 mL of DMF were added 216 mg of N-Boc-1,4-cyclohexanediamine (0.99 mmol) and 29 mg of DIPEA (0.15 mmol), it was stirred at 130° C. for 0.5 h with microwave, LCMS showed that the desired compound was formed, the reaction mixture was cooled to r.t. and concentrated under vacuum to give the crude product, the crude product was purified by silica gel column chromatography eluting with PE/EA (V/V=10:1) to give 20 mg of desired compound, as a yellow solid.

MS m/z (+ESI): 492.2 ([M+H]$^+$).

N4-[4-(Benzofuran-2-yl)-8-chloro-6-isoquinolyl] cyclohexane-1,4-diamine (Example 142)

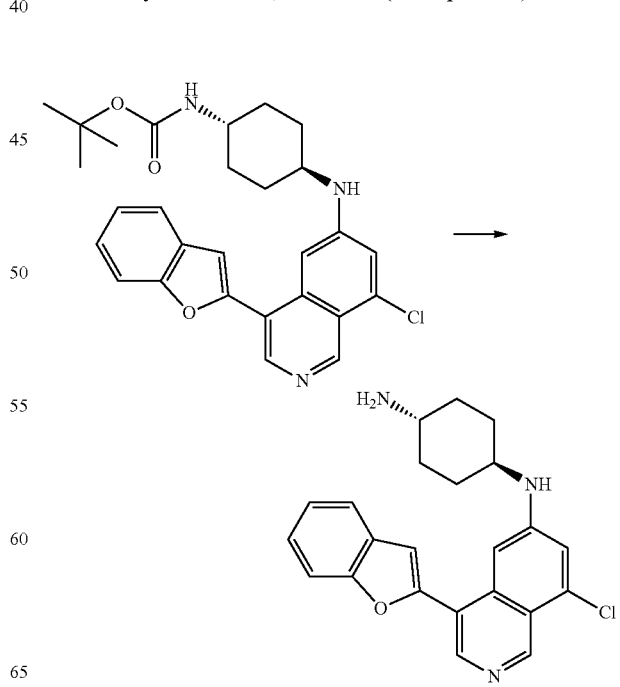

A solution of 40.0 mg of tert-butyl N-[4-[[4-(benzofuran-2-yl)-8-chloro-6-isoquinolyl]amino]cyclohexyl]carbamate (0.08 mmol, 1.0 eq, Note1) in 4.0 mL of 2.5 N of EA/HCl (g) was stirred for 10 h at rt, LCMS showed that the desired compound was formed. It was concentrated under vacuum to give a yellow solid, which was dissolved in 5 mL of $H_2O$. the mixture was adjusted to pH=9 with aq. ammonia, the resulting mixture was extracted with EA (10 mL*3), The combined organic layer was washed with $H_2O$ (5 mL×3) and brine (10 mL), dried over $Na_2SO_4$ and concentrated under vacuum to give the crude product, which was purified by Prep-HPLC to give 25 mg of desired compound, as a yellow solid.

MS m/z (+ESI): 392.3 ([M+H]$^+$).

$^1$H NMR (400 MHz, DMSO-d$_6$+D$_2$O) δ ppm: 9.13(s,1H), 8.65(s,1H), 7.74(d, J=7.2Hz, 1H), 7.64(d, J=8.0Hz, 1H), 7.41-7.28(m, 4H), 7.17(s,1H, H-1), 3.25(s,1H), 2.63-2.52 (m, 1H), 2.02(d, J=10.8Hz, 2H), 1.84(d, J=10.8Hz, 2H), 1.29-1.18(m, 4H).

N4-[4-(benzofuran-2-yl)-8-methoxy-6-isoquinolyl] cyclohexane-1,4-diamine (Example 143)

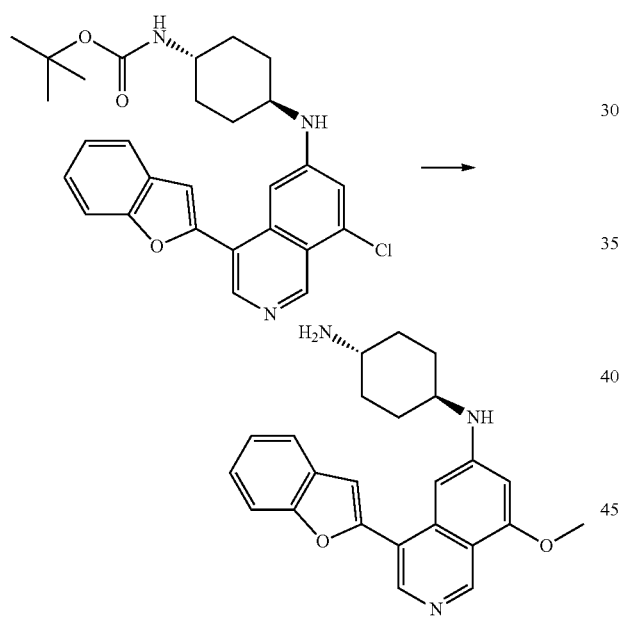

To a solution of 70 mg of tert-butyl N-[4-[[4-(benzofuran-2-yl)-8-chloro-6-isoquinolyl]amino]cyclohexyl]carbamate (0.142 mmol) in 2.5 ml of dioxane were added 16 mg of Pd(PPh$_3$)$_4$ (0.014 mmol), 7 mg of x-phos (0.014 mmol) and 1 mL of NaOMe/MeOH at rt, it was stirred at 120° C. for 0.5 h with microwave, LCMS showed that the desired compound was formed. The reaction mixture was filtered, dried under vacuum to give the crude product, which was purified with Prep-HPLC to give the desired compound as a yellow solid. It was washed with 5% of aq.NH$_3$H$_2$O solution, filtered and dried under vacuum to give 30 mg of desired compound, as a yellow solid.

MS m/z (+ESI): 388.2 ([M+H]$^+$).

$^1$H NMR (400 MHz, DMSO-d$_6$+D$_2$O) δ ppm: 9.04(s, 1H), 8.56(s, 1H), 7.72(d, J=7.6Hz, 1H), 7.63(d, J=7.6Hz, 1H), 7.39-7.29(m, 3H), 6.79(s, 1H), 6.54 (d, J=1.6Hz, 1H), 3.94(s, 3H), 3.26(s, 1H), 2.70-2.67(m, 1H), 2.04(br, 2H), 1.88(br, 2H), 1.24-1.22(m, 4H).

Methyl 4-(benzofuran-2-yl) cinnoline-6-carboxylate

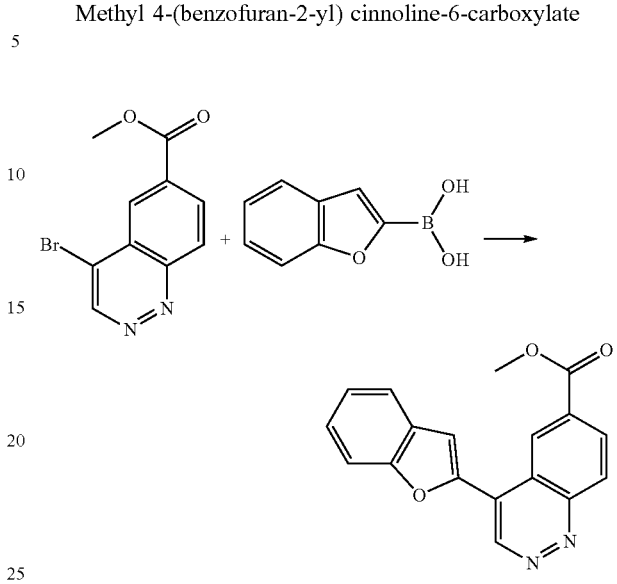

To a mixture of 1.60 g of methyl 4-bromocinnoline-6-carboxylate (5.95 mmol), 1.35 g of benzofuran-2-ylboronic acid (8.32 mmol), 1.75 g of KOAc (17.8 mmol) in 50 mL of dioxane, were added 0.69 g of Pd(PPh$_3$)$_4$ (0.59 mmol) and 0.14 g of X-PHOS (0.3 mmol). The mixture was stirred at 100° C. for 16 h. Then the reaction mixture was diluted with EA, filtered through celite pad. The filtrate was concentrated under vacuum and the residue was purified by silica gel column chromatography (PE/EA=2/1) to afford 1.40 g of the product as a light yellow solid.

MS (ESI+): 305 [M+H].

$^1$H NMR (400 MHz, DMSO-d6) δ ppm: 9.93 (s, 1H), 9.38 (s, 1H), 8.62 (d, J=8.8 Hz, 1H), 8.40 (d, J=8.8 Hz, 1H), 8.09 (s, 1H), 7.86 (d, J=8.0 Hz, 1H), 7.80 (d, J=8.4 Hz, 1H), 7.51 (t, J=7.2 Hz, 1H), 7.40 (t, J=7.2 Hz, 1H), 3.98 (s, 3H).

[4-(Benzofuran-2-yl) cinnolin-6-yl] methanol

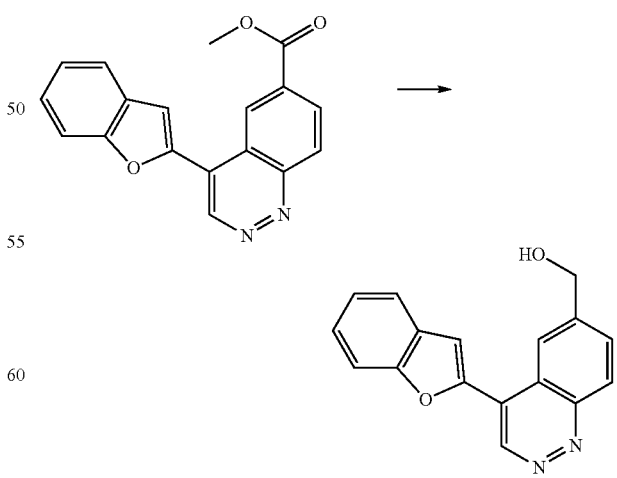

56 mg of LiAlH$_4$ (1.48 mmol) was added to 300 mg of methyl 4-(benzofuran-2-yl)cinnoline-6-carboxylate (0.98 mmol) in 10 mL of THF at 0° C., followed by stirring at RT for 4 hours. Saturated aqueous sodium sulfate solution was added to the reaction mixture and stirred, then concentrated in vacuo. The residue was purified by silica gel column chromatography (PE/EA=1:1) to afford 205 mg of the product as a yellow solid.

MS (ESI+): 277 [M+H].

$^1$H NMR (400 MHz, CDCl$_3$) δ ppm: 9.62 (d, J=3.2 Hz, 1H), 8.61 (s, 1H), 8.52 (dd, J=8.8, 4.0 Hz, 1H), 7.86 (d, J=8.8 Hz, 1H), 7.73 (d, J=7.6 Hz, 1H), 7.66 (d, J=8.4 Hz, 1H), 7.54-7.42 (m, 2H), 7.36 (t, J=7.6 Hz, 1H), 5.03 (d, J=3.6 Hz, 1H), 2.81 (b, 1H).

1-[[4-(Benzofuran-2-yl) cinnolin-6-yl] methyl] piperidin-4-amine (Example 144)

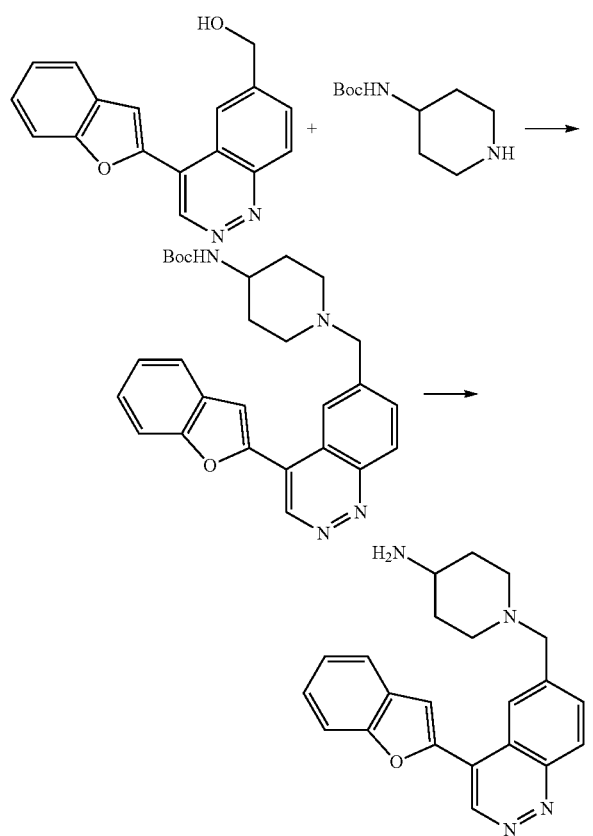

To a solution of 220 mg of [4-(benzofuran-2-yl)cinnolin-6-yl]methanol (0.79 mmol) in 5 mL of CH$_2$Cl$_2$ were added 0.22 mL of TEA (1.59 mmol) and 110 mg of MsCl (0.95 mmol) at 0° C., the resulting mixture was stirred at RT for 1 hour. The solution was concentrated in vacuo to give the residue as brown oil. Then the residue was dissolved in 5 mL of DMF, 0.22 mL of TEA (1.59 mmol) and 189 mg of 4-(N-Boc-Amino)piperidine (0.94 mmol) were added, the reaction mixture was stirred at rt for 16 hours. The solvent was removed in vacuo, the residue was purified by silica gel column chromatography (eluent: acetone/PE=1/3) to give 134 mg of product as light yellow solid. This intermediate was treated with 3.5 mL of a 2 N solution of HCl in EA and stirred at rt for 1 h. Then the suspension was concentrated in vacuo to give the residue, which was purified by preparative HPLC to afford 30 mg of the TFA salt of the product as a light yellow solid.

MS (ESI+): 359[M+H].

$^1$H NMR (400 MHz, DMSO-d6+D$_2$O) δ ppm: 9.87 (s, 1H), 8.87 (dd, J=1.2 Hz, 1H), 8.65 (d, J=8.8 Hz, 1H), 8.09 (dd, J=8.8, 1.2 Hz, 1H), 8.07 (s 1H), 7.86 (d, J=7.6 Hz, 1H), 7.82 (d, J=8.0 Hz, 1H), 7.55-7.53 (m, 1H), 7.51-7.40 (m, 1H), 4.64 (s, 2H), 3.49 (m, 2H), 3.29 (m, 1H), 3.12 (m, 2H), 2.10 (m, 2H), 1.75 (m, 2H).

Methyl 4-(4-chlorophenyl)cinnoline-6-carboxylate

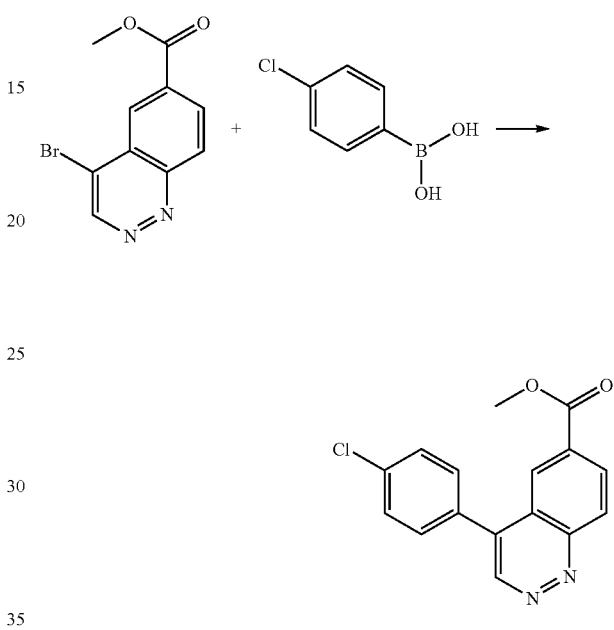

Under argon atmosphere, to a mixture of 0.7 g of methyl 4-bromocinnoline-6-carboxylate (2.62 mmol), 0.57 g of (4-chlorophenyl)boronic acid (3.67 mmol), 0.77 g of KOAc (7.86 mmol) in 15 mL of dioxane, were added 0.3 g of Pd(PPh$_3$)$_4$ (0.26 mmol) and 0.06 g of X-PHOS (0.14 mmol). The mixture was stirred at 100° C. for 16 h. Then the reaction mixture was diluted with EA, filtered through celite pad. The filtrate was concentrated under vacuum and the residue was purified by silica gel column chromatography (PE/EA=2/1) to afford 0.68 g of the product as a light yellow solid.

MS (ESI+): 299 [M+H].

$^1$H NMR (400 MHz, DMSO-d6) δ ppm: 9.51 (s, 1H), 8.69 (d, J=8.8 Hz, 1H), 8.52 (d, J=1.2 Hz, 1H), 8.41 (dd, J=8.8, 1.6 Hz, 1H), 7.76 (m, 4H), 3.92 (s, 3H).

[4-(4-Chlorophenyl) cinnolin-6-yl] methanol

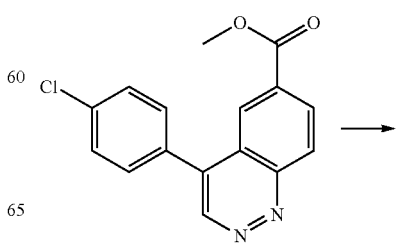

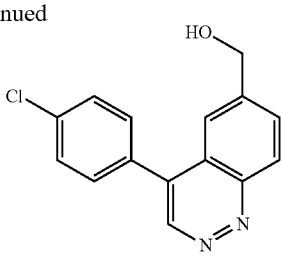

100 mg of LiAlH₄ (2.5 mmol) was added to 500 mg of methyl 4-(4-chlorophenyl)cinnoline-6-carboxylate (1.7 mmol) in 10 mL of THF at 0° C., followed by stirring at RT for 4 hours. Saturated aqueous sodium sulfate was added to the reaction mixture and stirred, then concentrated in vacuum. The residue was purified by silica gel column chromatography (eluent: PE/EA=1:1) to afford 100 mg of the product as a yellow solid.

MS (ESI+): 271 [M+H].

¹H NMR (400 MHz, CDCl₃) δ ppm: 9.19 (s, 1H), 8.56 (d, J=8.8 Hz, 1H), 7.93 (d, J=0.8, Hz, 1H), 7.85 (dd, J=8.8, 1.6 Hz, 1H), 7.56 (dd, J=6.8, 2.0 Hz, 1H), 7.49 (d, J=6.4 Hz, 1H), 4.93 (s, 2H).

1-[[4-(4-Chlorophenyl)cinnolin-6-yl]methyl]piperidin-4-amine (Example 145)

To a solution of 115 mg of [4-(4-chlorophenyl)cinnolin-6-yl]methanol (0.42 mmol) in 4 mL of CH₂Cl₂ were added 0.12 mL of TEA (0.81 mmol) and 57 mg of MsCl (0.48 mmol), the resulting mixture was stirred at rt for 1 hour. The solution was concentrated in vacuum to give the residue as brown oil. Then the residue was dissolved in 4 mL of DMF, 0.12 mL of TEA (0.81 mmol) and 100 mg of 4-(N-Boc-Amino)piperidine (0.48 mmol) were added, followed by stirring at rt for 16 hours. The solvent was removed under vacuum and the residue was purified by silica gel column chromatography (eluent: acetone/PE=1/3) to give 172 mg of product as a light yellow solid. This intermediate was treated with 2 mL of a 2.5 N solution of HCl in EA and stirred at rt for 1 h. Then the suspension was concentrated in vacuum to give the residue, which was purified by preparative HPLC to afford 71 mg of the TFA salt of the product as a light yellow solid.

MS (ESI+): 353[M+H].

¹H NMR (400 MHz, DMSO-d6+D₂O) δ ppm: 9.41 (s, 1H), 8.64 (d, J=8.8 Hz, 1H), 8.12 (s, 1H), 8.04 (dd, J=8.8, 1.2 Hz, 1H), 7.75-7.69 (m, 4H), 4.46 (s, 2H), 3.38 (m, 2H), 3.24 (m, 1H), 3.02 (m, 2H), 2.06 (m, 2H), 1.69 (m, 2H).

4-(Benzofuran-2-yl)-6-(4-pyridylmethoxy)isoquinoline (Example 146)

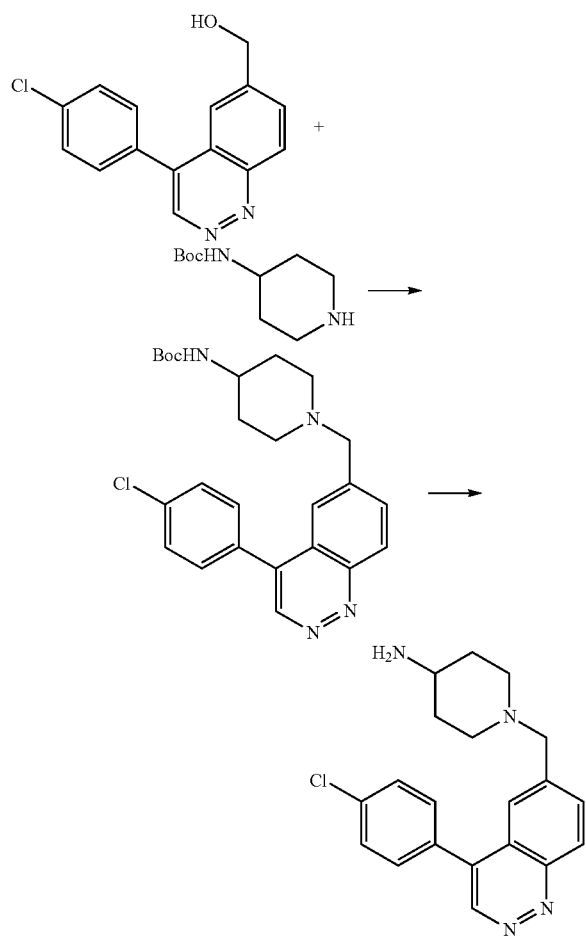

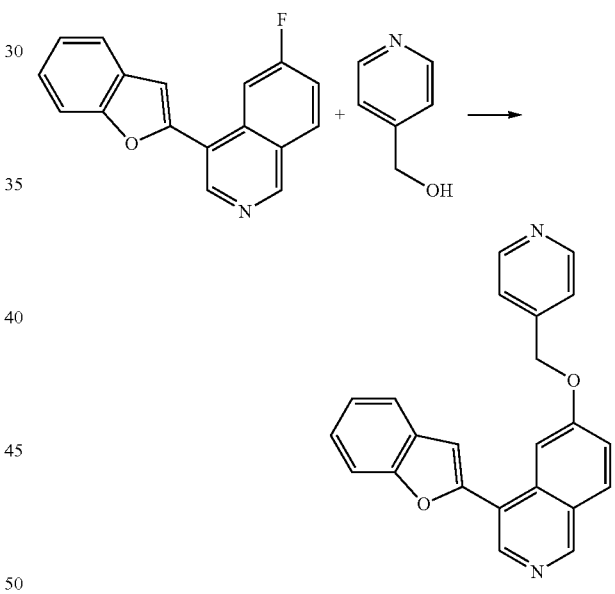

To a solution of 0.12 g (1.14 mmol) of 4-pyridylcarbinol in 3 mL of THF is added 41 mg (1.71 mmol) of NaH, and then the mixture is stirred at rt for 30 min. 0.15 g (0.57 mmol) of 4-(benzofuran-2-yl)-6-fluoro-isoquinoline is added in one portion. The resulting mixture is heated to 100° C. and stirred at this temperature for 2 h. The reaction is quenched with saturated aqueous NH₄Cl solution, and extracted with EA. The combined organic phases are evaporated in vacuo, and the residue is purified by preparative HPLC to yield 105 mg of the desired product as a yellow solid.

MS (ESI+): 353.3 [M+H].

¹H NMR (400 MHz, DMSO-d₆) δ ppm: 9.42 (s, 1H), 8.92 (s, 1H), 8.78 (d, J=6.0 Hz, 2H), 8.37 (d, J=8.8 Hz, 1H), 7.90 (s, 1H), 7.84-7.78 (m, 3H), 7.74-7.67 (m, 2H), 7.54 (s, 1H), 7.47-7.43 (m, 1H), 7.40-7.36 (m, 1H), 5.64 (s, 2H).

4-(Benzofuran-2-yl)-N-(4-pyridylmethyl)isoquinolin-6-amine (Example 147)

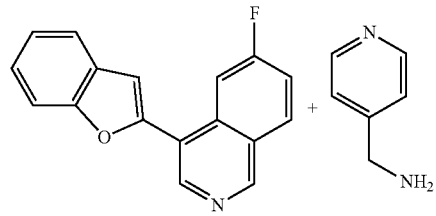

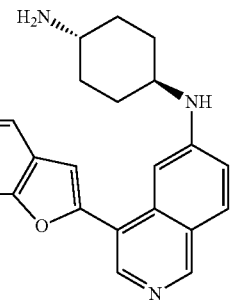

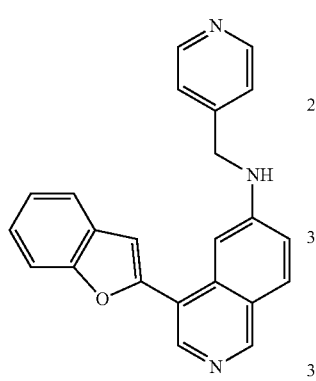

A solution of 0.2 g (0.76 mmol) of 4-(benzofuran-2-yl)-6-fluoro-isoquinoline in 3.86 mL (38.0 mmol) of 4-aminomethylpyridine is heated to 100° C. for 16 h. The reaction mixture is directly purified by preparative HPLC. The desired fractions are collected and 0.5 mL of concentrated HCl is added. The resulting solution is concentrated in vacuo to remove most of acetonitrile and then lyophilized to give 69 mg of the desired product as a yellow solid.

MS (ESI+): 352.4 [M+H].

$^1$H NMR (400 MHz, DMSO-d$_6$+D$_2$O) δ ppm: 9.21 (s, 1H), 8.74 (d, J=5.6 Hz, 2H), 8.62 (s, 1H), 8.25 (d, J=9.2 Hz, 1H), 7.84 (d, J=5.6 Hz, 2H), 7.76 (d, J=9.2 Hz, 1H), 7.59 (d, J=8.3 Hz, 1H), 7.51 (d, J=9.2 Hz, 1H), 7.47-7.43 (m, 1H), 7.39-7.35 (m, 1H), 7.32 (s, 1H), 7.18 (s, 1H), 4.87 (s, 2H).

4-(Benzofuran-2-yl)-N-(4-(trans)aminocyclohexyl)isoquinolin-6-amine (Example 148)

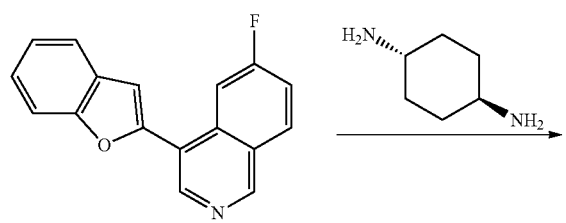

4-(Benzofuran-2-yl)-N-(4-(trans)aminocyclohexyl)isoquinolin-6-amine is prepared in analogy to Example 147 from 4-(benzofuran-2-yl)-6-fluoro-isoquinoline and the corresponding amine.

MS (ESI+): 358.2 [M+H]

$^1$H NMR (400 MHz, DMSO-d$_6$+D$_2$O) δ ppm: 9.11 (s, 1H), 8.57 (s, 1H), 8.18 (brs, 1H), 7.80 (d, J=7.6 Hz, 1H), 7.70 (d, J=8.4 Hz, 1H), 7.59 (s, 1H), 7.47-7.43 (m, 2H), 7.39-7.35 (m, 2H), 3.52 (brs, 1H), 3.10-3.03 (m, 1H), 2.09 (brs, 2H), 2.03 (d, J=10.8 Hz, 2H), 1.55-1.34 (m, 4H)

tert-Butyl N-[6-(aminomethyl)-4-bromo-1-isoquinolyl]-N-tert-butoxycarbonyl-carbamate

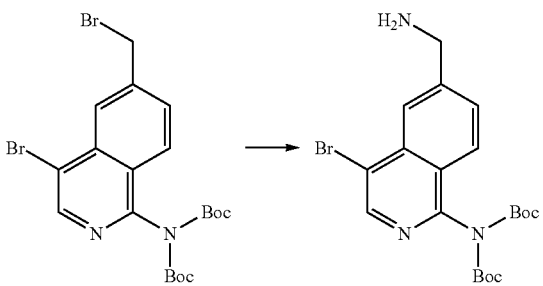 [SMILES: CC(C)(C)OC(=O)N(C(=O)OC(C)(C)C)c1ncc(Br)c2cc(CBr)ccc12 ; CC(C)(C)OC(=O)N(C(=O)OC(C)(C)C)c1ncc(Br)c2cc(CN)ccc12]

A mixture of 1.0 g (1.93 mmol) of tert-butyl N-[4-bromo-6-(bromomethyl)-1-isoquinolyl]-N-tert-butoxycarbonyl-carbamate in 20 mL of 2N ammonia in EtOH was stirred at 30° C. for 16 h. The solvent was removed under vacuum and the residue was purified by column chromatography eluting with DCM/MeOH (v/v=10:1) to yield 0.63 g of the desired product as a yellow semisolid.

$^1$H NMR (400 MHz, DMSO-d6) δ ppm: 8.71 (s, 1H), 8.23 (s, 1H), 7.97-7.93 (m, 1H), 7.90-7.87 (m, 1H), 4.20 (s, 2H), 1.30 (s, 18H).

MS m/z (+ESI): 452.1, 454.1 ([M+H]$^+$)

187
tert-Butyl N-[4-bromo-6-[(4-pyridylamino)methyl]-1-isoquinolyl]-N-tert-butoxycarbonyl-carbamate

188
4-(Benzofuran-2-yl)-6-[(4-pyridylamino)methyl] isoquinolin-1-amine (Example 151)

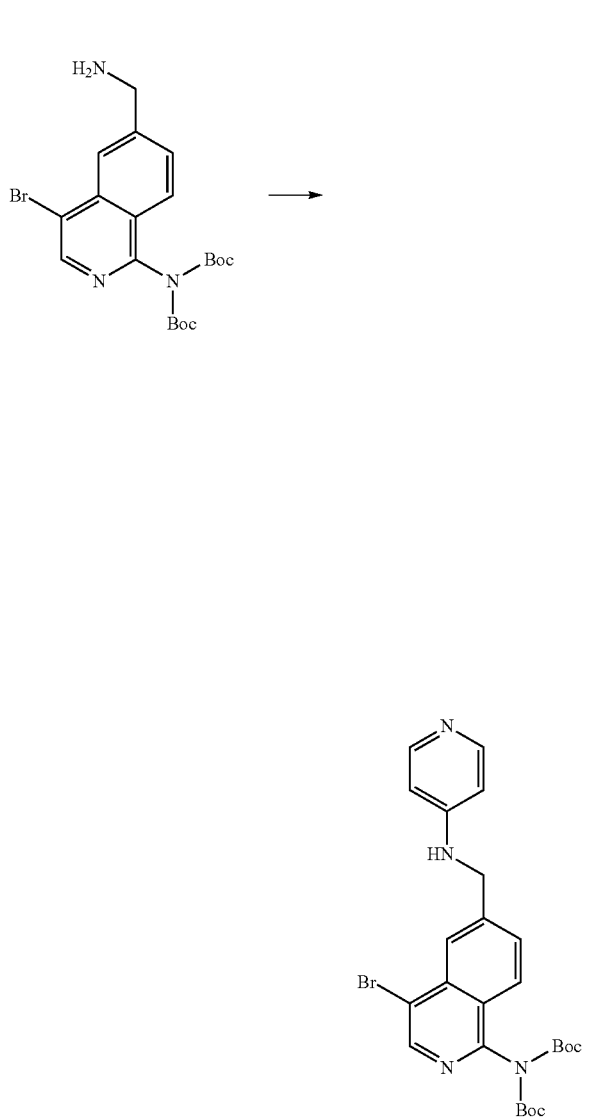

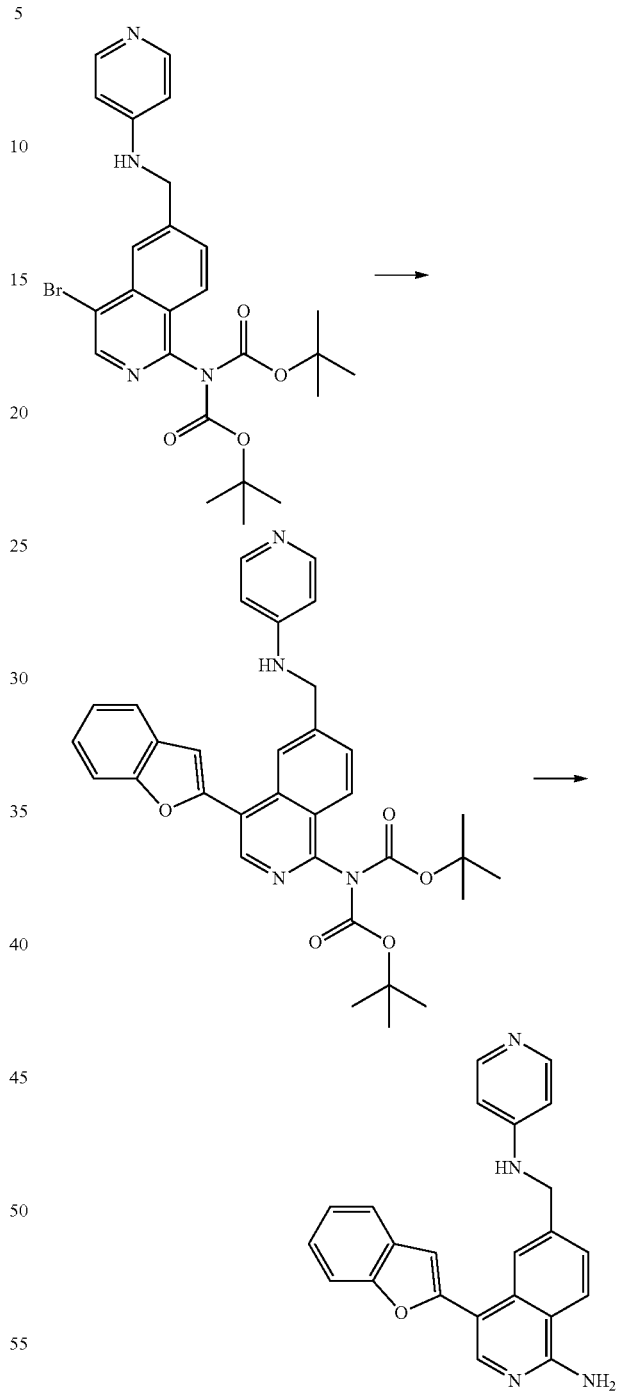

To a solution of 0.6 g (1.32 mmol) of tert-butyl N-[6-(aminomethyl)-4-bromo-1-isoquinolyl]-N-tert-butoxycarbonyl-carbamate in 15 mL of toluene were added 0.42 g (2.65 mol) of 4-bromopyridine, 0.11 g (0.13 mmol) of Pd$_2$(dba)$_3$, 2.16 g (6.63 mmol) of Cs$_2$CO$_3$ and 0.15 g (0.26 mmol) of Xantphos. The mixture was degassed, backfilled with N2, and heated to 100° C. with stirring for 5 h. The undissolved solid was filtered off, and the filtrate was evaporated under vacuum. The residue was purified by column chromatography eluting with DCM/MeOH (v/v=20:1) to yield the 170 mg of the desired product as a colorless oil.

MS (ESI+): 529.1, 531.1 [M+H]$^+$

In analogy to methods described above, tert-butyl N-[4-(benzofuran-2-yl)-6-[(4-pyridylamino)methyl]-1-isoquinolyl]-N-tert-butoxycarbonyl-carbamate is prepared, starting from 170 mg (0.32 mmol) of tert-butyl N-[4-bromo-6-[(4-pyridylamino)methyl]-1-isoquinolyl]-N-tert-butoxycarbonyl-carbamate, the boronic acid, palladium catalyst and base. 170 mg of crude product is obtained as a yellow solid after filtration and concentration, which is used in next step without further purification.

A mixture of 170 mg (0.30 mmol) of this intermediate in 20 mL of 2N HCl in EA is stirred at 30° C. for 2 h. The reaction mixture is concentrated in vacuo and the residue is purified by preparative HPLC to give 31 mg of the desired product as a yellow solid.

MS (ESI+): 367.2 [M+H].

$^1$H NMR (400 MHz, DMSO-$d_6$+$D_2O$) δ ppm: 8.27 (d, J=8.6 Hz, 1H), 8.20 (s, 1H), 8.11 (d, J=1.6 Hz, 1H), 8.06 (d, J=6.8 Hz, 2H), 7.63-7.59 (m, 1H), 7.53 (dd, J=8.6, 1.7 Hz, 1H), 7.50-7.46 (m, 1H), 7.32-7.23 (m, 2H), 6.93 (d, J=0.9 Hz, 1H), 6.68 (d, J=6.8 Hz, 2H), 4.63 (s, 2H).

6-[(4-Aminopyridin-1-ium-1-yl)methyl]-4-(benzofuran-2-yl)isoquinolin-1-amine (Example 152)

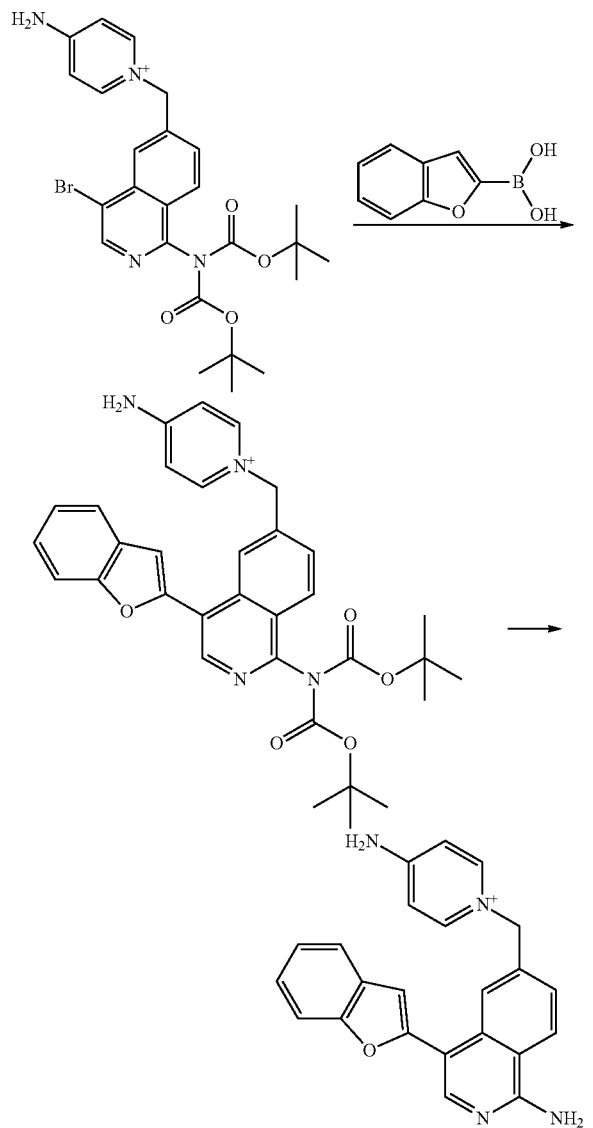

6-[(4-Aminopyridin-1-ium-1-yl)methyl]-4-(benzofuran-2-yl)isoquinolin-1-amine is prepared in analogy to methods described above, starting from tert-butyl N-[6-[(4-aminopyridin-1-ium-1-yl)methyl]-4-bromo-1-isoquinolyl]-N-tert-butoxycarbonyl-carbamate (prepared according to methods described above from tert-butyl N-[4-bromo-6-(bromomethyl)-1-isoquinolyl]-N-tert-butoxycarbonyl-carbamate).

MS (ESI+): 367.1 [M+H].

$^1$H NMR (400 MHz, DMSO-$d_6$+$D_2O$) δ ppm: 8.62 (d, J=8.6 Hz, 1H), 8.31-8.23 (m, 2H), 8.13 (s, 1H), 8.02 (d, J=1.6 Hz, 1H), 7.81-7.70 (m, 2H), 7.59 (dd, J=8.1, 1.0 Hz, 1H), 7.43-7.38 (m, 1H), 7.37-7.29 (m, 2H), 6.91-6.82 (m, 2H), 5.63 (s, 2H).

6-[(4-Amino-1-piperidyl)methyl]-4-(benzofuran-2-yl)isoquinolin-1-amine (Example 153)

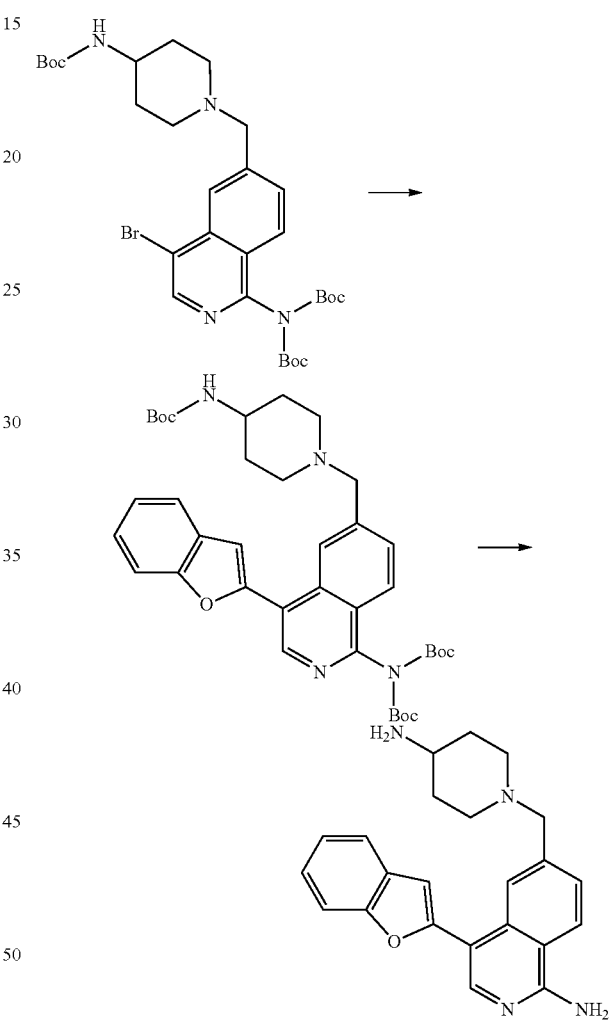

To a solution of 0.4 g (0.62 mmol) of tert-butyl N-[4-bromo-6-[[4-(tert-butoxycarbonylamino)-1-piperidyl]methyl]-1-isoquinolyl]-N-tert-butoxycarbonyl-carbamate in 10 mL of DMF were added 0.15 g (0.94 mmol) of benzofuran-2-boronic acid, 0.11 g (0.094 mmol) of Pd(PPh$_3$)$_4$ and 0.26 g (1.25 mmol) of K$_3$PO$_4$. The mixture was degassed, backfilled with N2, and heated to 90° C. with stirring for 2 h. The reaction mixture was diluted with water and extracted with EA. The combined organic phases were washed with water and brine, dried over Na$_2$SO$_4$, filtered and concentrated under vacuum. The residue was purified by column chromatography eluting with PE/EA (v/v=5:1 to 2:1) to yield 0.38 g of the desired product as a colorless oil.

MS m/z (+ESI): 673.3 [M+H]+

To a solution of 0.38 g of this intermediate in 10 mL of EA was added 20 mL of 2N HCl in EA) and the mixture was stirred at 20° C. for 2 h. The solvent was removed under vacuum, and the residue was washed with EA to give the desired product, which was dissolved in 10 mL of water and lyophilized to give 98 mg of the final compound as a yellow solid.

MS (ESI+): 373.1 [M+H]+

$^1$H NMR (400 MHz, DMSO-d$_6$+D$_2$O) δ ppm: 8.72 (d, J=8.6 Hz, 1H), 8.46 (d, J=1.6 Hz, 1H), 8.16 (s, 1H), 8.05 (dd, J=8.6, 1.6 Hz, 1H), 7.77-7.73 (m, 1H), 7.71-7.66 (m, 1H), 7.53 (s, 1H), 7.43-7.38 (m, 1H), 7.36-7.32 (m, 1H), 4.55 (s, 2H), 3.49-3.35 (m, 2H), 3.34-3.19 (m, 1H), 3.19-3.03 (m, 2H), 2.16-2.03 (m, 2H), 1.97-1.78 (m, 2H).

4-Bromoisoquinoline-6-carboxylic acid

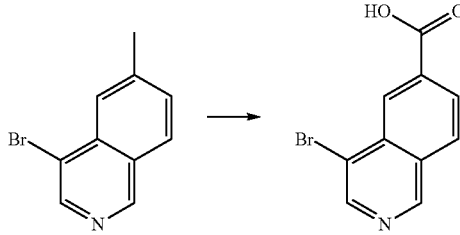

To a solution of 10 g (45.03 mmol) of 4-bromo-6-methylisoquinoline in a mixture of 100 mL of concentrated sulfuric acid and 100 mL of water is added 13.51 g (135.09 mmol) of chromium trioxide at 20° C. The mixture is stirred at this temperature for 48 h. The precipitated solid is collected by filtration, washed with water and dried to give 5.39 g of the desired product as a white solid.

MS (ESI+): 251.9, 253.9 [M+H].

$^1$H NMR (400 MHz, DMSO-d$_6$) δ ppm: 9.44 (s, 1H), 8.86 (s, 1H), 8.68 (d, J=1.5 Hz, 1H), 8.34 (d, J=8.5 Hz, 1H), 8.24 (dd, J=8.5, 1.5 Hz, 1H).

tert-Butyl N-(4-bromo-6-isoquinolyl)carbamate

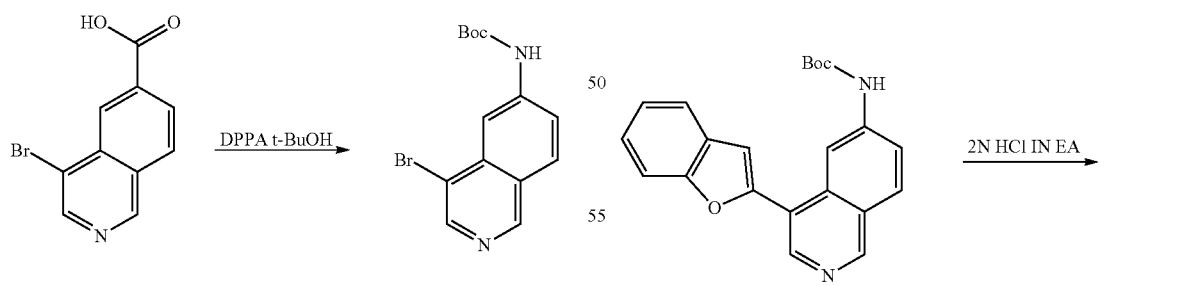

To a solution of 3.6 g (14.28 mmol) 4-bromoisoquinoline-6-carboxylic acid in 50 mL of t-BuOH are added 6.16 mL (28.56 mmol) of diphenylphosphoryl azide and 4.34 g (42.85 mmol) of TEA. The resulting mixture is heated to 80° C. and stirred for 16 h. After concentration by rotary evaporation, the residue is purified by chromatography column over silica gel eluting with PE/EA (5:1) to yield 4.1 g of desired product as a yellow solid.

MS (ESI+): 323.0 [M+H].

$^1$H NMR (400 MHz, DMSO-d6) δ ppm: 10.08 (s, 1H), 9.11 (s, 1H), 8.64 (s, 1H), 8.42 (s, 1H), 8.08 (d, J=8.8 Hz, 1H), 7.71 (dd, J$_1$=8.8 Hz, J$_2$=1.6 Hz, 1H), 1.51 (s, 9H).

tert-Butyl N-[4-(benzofuran-2-yl)-6-isoquinolyl]carbamate

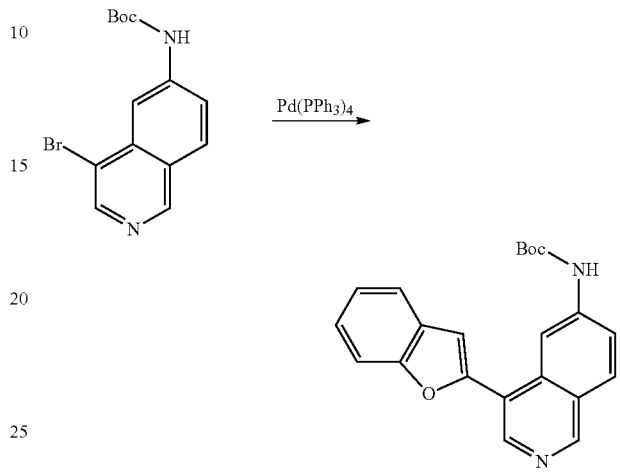

Under argon atmosphere, to a solution of 2.0 g (6.13 mmol) tert-butyl N-(4-bromo-6-isoquinolyl)carbamate in 50 mL of DMF are added 1.49 g (9.19 mmol) of benzofuran-2-boronic acid, 2.6 g (12.25 mmol) of Potassium phosphate and 1.06 g (0.92 mmol) of Pd(PPh$_3$)$_4$. The resulting mixture is heated to 90° C. with stirring for 2 h. The reaction mixture is diluted with EA and washed with water. The organic phase is separated, dried over Na$_2$SO$_4$, and concentrated in vacuo. The residue is purified by chromatography column over silica gel eluting with PE/EA=2:1 to yield 1.7 g of desired product as a yellow solid.

MS (ESI+): 361.1 [M+H].

$^1$H NMR (400 MHz, DMSO-d6) δ ppm: 9.99 (s, 1H), 9.20 (s, 1H), 8.82 (s, 1H), 8.61 (s, 1H), 8.15 (d, J=8.8 Hz, 1H), 7.93 (dd, J$_1$=8.8 Hz, J$_2$=2.0 Hz, 1H), 7.77 (d, J=7.2 Hz, 1H), 7.71 (d, J=8.0 Hz, 1H), 7.45 (s, 1H), 7.43-7.32 (m, 2H), 1.50 (s, 9H).

4-(Benzofuran-2-yl)isoquinolin-6-amine

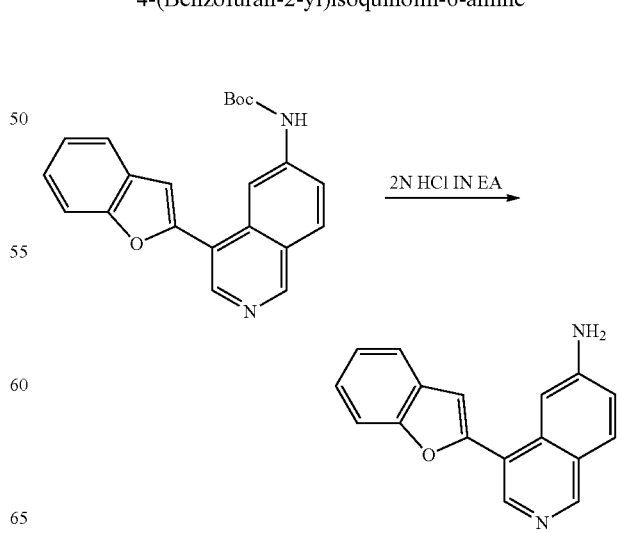

To a solution of 1.7 g (4.72 mmol) tert-butyl N-[4-(benzofuran-2-yl)-6-isoquinolyl]carbamate in 10 mL of EtOH is added 50 mL of 2N HCl in EtOH, and the resulting solution is stirred at 30° C. for 16 h. The solvent was removed in vacuo to give 0.95 g crude product as a yellow solid which is used in next step without further purification.

MS (ESI+): 261.0 [M+H].

$^1$H NMR (400 MHz, DMSO-d6) δ ppm: 9.21 (s, 1H), 8.58 (s, 1H), 8.20 (d, J=9.2 Hz, 1H), 7.79 (d, J=7.6 Hz, 1H), 7.74 (d, J=8.0 Hz, 1H), 7.59 (s, 1H), 7.48-7.43 (m, 2H), 7.39-7.35 (m, 2H)

Alternative Method for the synthesis of 4-(benzofuran-2-yl)isoquinolin-6-amine

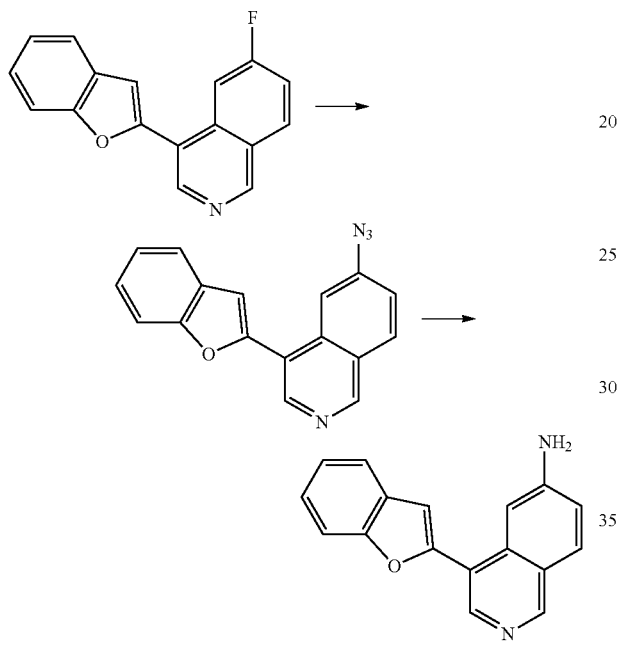

To a solution of 0.9 g (3.42 mmol) of 4-(benzofuran-2-yl)-6-fluoro-isoquinoline in 20 mL of N,N-dimethylformamide is added 0.44 g (6.84 mmol) of sodium azide. And then the mixture is stirred at 120° C. for 16 h. The reaction mixture is poured into 30 mL of water and extracted with 100 mL of EA. The combined organic phases are washed with water and brine, and concentrated under vacuum to give the crude product which is purified by column chromatography eluting with PE/EA (5:1 to 3:1) to yield 0.43 g of 6-azido-4-(benzofuran-2-yl)isoquinoline as a yellow solid.

MS (ESI+): 287.0 [M+H].

$^1$H NMR (400 MHz, CDCl$_3$) δ ppm: 9.22 (s, 1H), 8.93 (s, 1H), 8.16 (d, J=2.1 Hz, 1H), 8.07 (d, J=8.7 Hz, 1H), 7.72 (dd, J=7.6, 0.8 Hz, 1H), 7.65 (dd, J=8.0, 0.8 Hz, 1H), 7.43-7.32 (m, 3H), 7.19 (d, J=0.8 Hz, 1H).

To a solution of 35 mg (0.12 mmol) of 6-azido-4-(benzofuran-2-yl)isoquinoline in a mixture of 1.5 mL of methanol and 1.5 mL of ethyl acetate is added 4 mg of 10% Pd/C and then the mixture is hydrogenated at 20° C. under atmospheric pressure for 16 h. The Pd/C is filtered and the filtrate is evaporated in vacuo to give 30 mg of yellow semisolid, which is used in next step without further purification.

MS (ESI+): 261.1 [M+H].

$^1$H NMR (400 MHz, CDCl$_3$) δ ppm: 9.01 (s, 1H), 8.73 (s, 1H), 7.86 (d, J=8.7 Hz, 1H), 7.69 (d, J=8.0 Hz, 1H), 7.63 (d, J=8.0 Hz 1H), 7.49 (d, J=2.1 Hz, 1H), 7.40-7.29 (m, 2H), 7.10 (s, 1H), 7.07 (dd, J=8.7, 2.2 Hz, 1H).

trans-4-Amino-N-[4-(benzofuran-2-yl)-6-isoquinolyl]cyclohexanecarboxamide (Example 156)

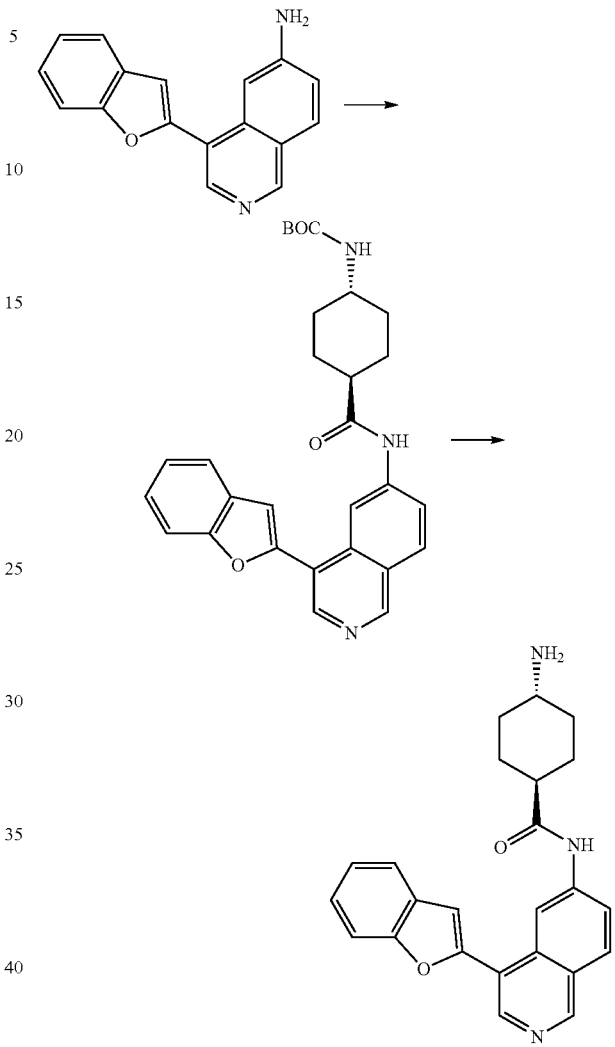

To a solution of 0.28 g (1.15 mmol) trans-4-(Boc-amino) cyclohexanecarboxylic acid in 20 mL of DMF are added 0.4 mL (2.31 mmol) of N,N-Diisopropylethylamine and 0.58 g (1.54 mmol) of HATU. The mixture is stirred at 30° C. for 30 mins, then 0.2 g (0.77 mmol) of 4-(benzofuran-2-yl) isoquinolin-6-amine is added in one portion. After being stirred at 30° C. for 48 h, the reaction mixture is diluted with EA and extracted with water. The organic phase is dried over Na$_2$SO$_4$, and concentrated in vacuo to give 0.36 g crude product, which is used in next step without further purification.

In analogy to methods described above, 70 mg of trans-4-amino-N-[4-(benzofuran-2-yl)-6-isoquinolyl]cyclohexanecarboxamide are obtained as a solid by treatment of 0.37 g of the intermediate with HCl and purification by prep-HPLC.

MS (ESI+): 386.1 [M+H].

$^1$H NMR (400 MHz, DMSO-d$_6$ D$_2$O) δ ppm: 9.38 (s, 1H), 9.00 (s, 1H), 8.85 (s, 1H), 8.33 (d, J=8.8 Hz, 1H), 7.98 (d, J=8.8 Hz, 1H), 7.80 (d, J=7.6 Hz, 1H), 7.71 (d, J=8.4 Hz, 1H), 7.51 (s, 1H), 7.45-7.42 (m, 1H), 7.38-7.34 (m, 1H), 3.03-2.97 (m, 1H), 2.43-2.40 (m, 1H), 2.00-1.92 (m, 4H), 1.56-1.47 (m, 2H), 1.38-1.29 (m, 2H).

The following examples were prepared accordingly to Example 156 by condensation reaction of 4-(benzofuran-2- yl)isoquinolin-6-amine with the corresponding carboxylic acid and subsequent deprotection as required:

| Example | | ¹H NMR (400 MHz) δ ppm | MS (+ESI) [M + H]⁺ |
|---|---|---|---|
| 157 | 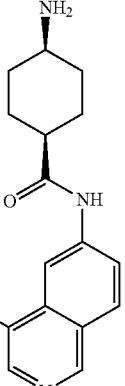 | (DMSO-d₆ + D₂O) 9.40 (s, 1H), 9.00 (s, 1H), 8.86 (s, 1H), 8.34 (d, J = 8.8 Hz, 1H), 8.03 (dd, J₁ = 8.8 Hz, J₂ = 1.6 Hz, 1H), 7.80 (d, J = 7.6 Hz, 1H), 7.72 (d, J = 8.0 Hz, 1H), 7.52 (s, 1H), 7.47-7.43 (m, 1H), 7.40-7.36 (m, 1H), 3.21-3.19 (m, 1H), 2.65-2.64 (m, 1H), 1.96-1.92 (m, 2H), 1.75-1.67 (m, 6H). | 386.2 |

Trans-N-(4-aminocyclohexyl)-4-(benzofuran-2-yl)isoquinoline-6-carboxamide (Example 160)

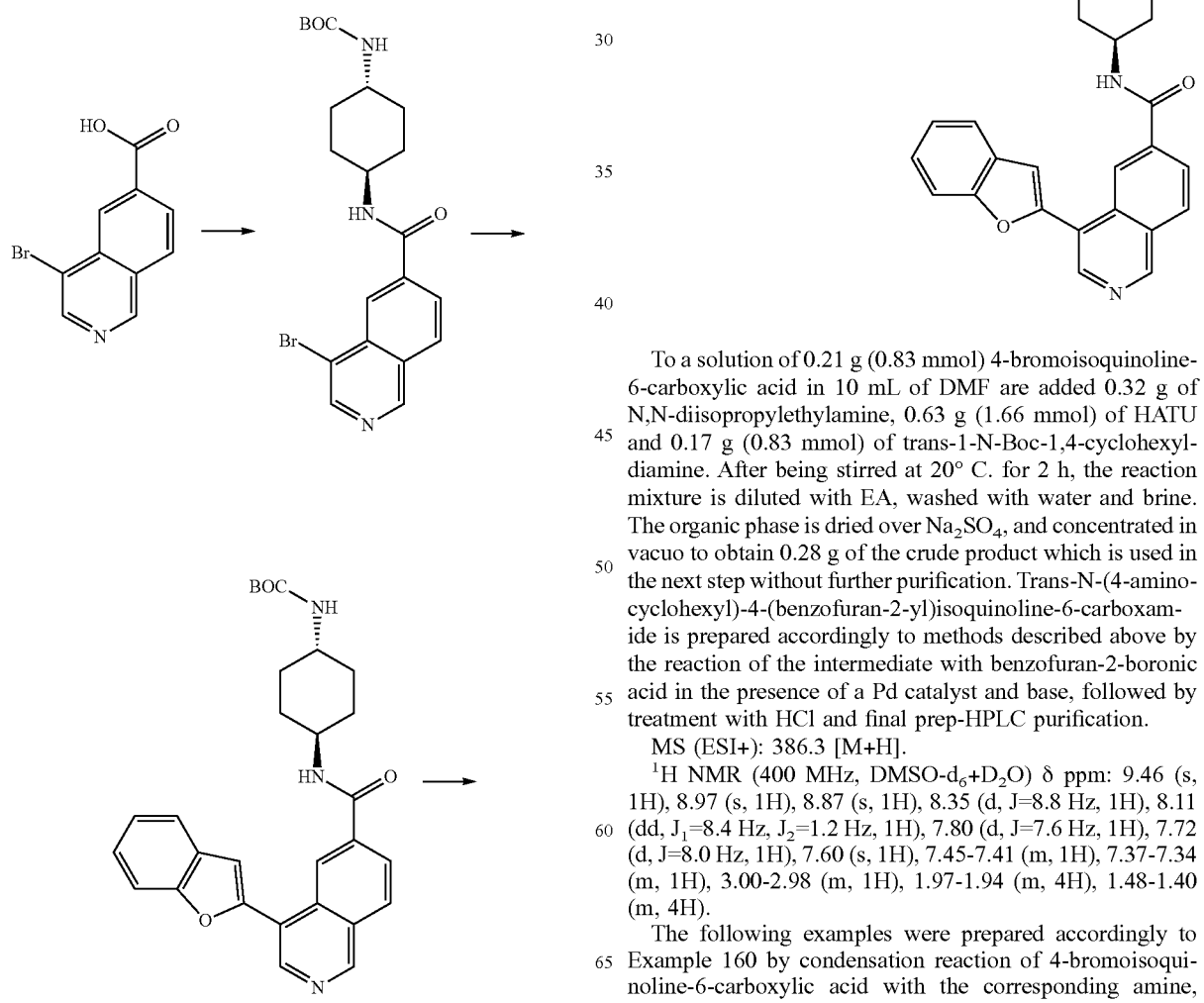

To a solution of 0.21 g (0.83 mmol) 4-bromoisoquinoline-6-carboxylic acid in 10 mL of DMF are added 0.32 g of N,N-diisopropylethylamine, 0.63 g (1.66 mmol) of HATU and 0.17 g (0.83 mmol) of trans-1-N-Boc-1,4-cyclohexyldiamine. After being stirred at 20° C. for 2 h, the reaction mixture is diluted with EA, washed with water and brine. The organic phase is dried over Na₂SO₄, and concentrated in vacuo to obtain 0.28 g of the crude product which is used in the next step without further purification. Trans-N-(4-aminocyclohexyl)-4-(benzofuran-2-yl)isoquinoline-6-carboxamide is prepared accordingly to methods described above by the reaction of the intermediate with benzofuran-2-boronic acid in the presence of a Pd catalyst and base, followed by treatment with HCl and final prep-HPLC purification.

MS (ESI+): 386.3 [M+H].
¹H NMR (400 MHz, DMSO-d₆+D₂O) δ ppm: 9.46 (s, 1H), 8.97 (s, 1H), 8.87 (s, 1H), 8.35 (d, J=8.8 Hz, 1H), 8.11 (dd, J₁=8.4 Hz, J₂=1.2 Hz, 1H), 7.80 (d, J=7.6 Hz, 1H), 7.72 (d, J=8.0 Hz, 1H), 7.60 (s, 1H), 7.45-7.41 (m, 1H), 7.37-7.34 (m, 1H), 3.00-2.98 (m, 1H), 1.97-1.94 (m, 4H), 1.48-1.40 (m, 4H).

The following examples were prepared accordingly to Example 160 by condensation reaction of 4-bromoisoquinoline-6-carboxylic acid with the corresponding amine, Suzuki coupling and final deprotection.

| Example | | ¹H NMR (400 MHz) δ ppm | MS (+ESI) [M + H]⁺ |
|---|---|---|---|
| 161 | 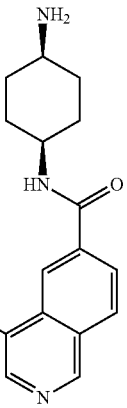 | (DMSO-d₆ + D₂O) 9.47 (s, 1H), 8.98 (s, 1H), 8.87 (s, 1H), 8.37 (d, J = 8.4 Hz, 1H), 8.12 (d, J = 8.4 Hz, 1H), 7.80 (d, J = 7.2 Hz, 1H), 7.73 (d, J = 8.4 Hz, 1H), 7.61 (s, 1H), 7.45-7.41 (m, 1H), 7.38-7.34 (m, 1H), 3.95-3.93 (m, 1H), 3.19-3.17 (m, 1H), 1.86-1.69 (m, 8H). | 386.2 |

4-Bromo-6-methyl-isoquinolin-3-amine

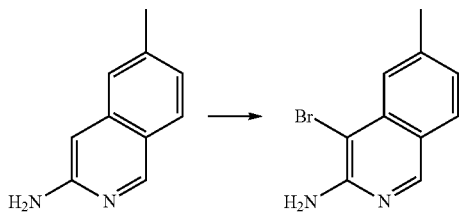

A solution of 51 mg (0.32 mmol) of 6-methylisoquinolin-3-amine (CAS 1192814-93-9) and 69 mg of N-bromosuccinimide (0.39 mmol) in 5 mL of MeOH is stirred at room temperature for 20 min. The reaction solution is concentrated to dryness. The crude product is then purified by silica gel column chromatography (PE/EA=9/1) to give 41 mg of the product as a brown solid.

MS (ESI+): 237.0 [M+H]⁺.

¹H NMR (400 MHz, DMSO-d₆) δ ppm: 8.76 (s, 1H), 7.78 (d, J=8.4 Hz, 1H), 7.50 (s, 1H), 7.11 (d, J=8.4 Hz, 1H), 6.21 (s, 2H), 2.45 (s, 3H).

tert-Butyl N-(4-bromo-6-methyl-3-isoquinolyl)-N-tert-butoxycarbonyl-carbamate

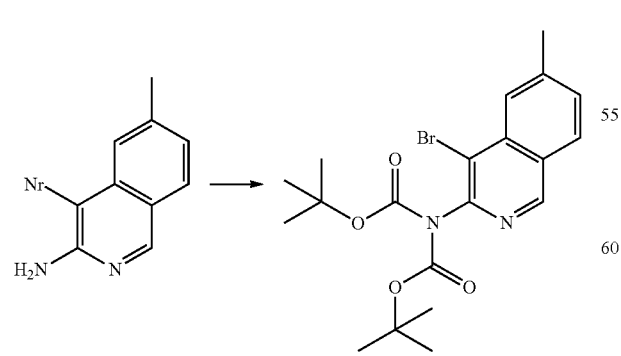

A solution of 41 mg (0.17 mmol) of 4-bromo-6-methyl-isoquinolin-3-amine, 0.12 mL (0.86 mmol) of triethylamine, 4 mg (0.035 mmol) of 4-dimethylaminopyridine and 150 mg (0.69 mmol) of di-tert-butyldicarbonate in 3 mL is stirred at room temperature for 10 h. The reaction solution is concentrated to dryness. The crude product is then purified by silica gel column chromatography (PE/EA=9:1) to give 61 mg of the product as a brown oil.

MS (ESI+): 437.1 [M+H]⁺.

¹H NMR (400 MHz, CDCl₃) δ ppm: 9.03 (s, 1H), 8.01 (s, 1H), 7.90 (d, J=8.4 Hz, 1H), 7.52 (d, J=8.4 Hz, 1H), 2.62 (s, 3H), 1.39 (s, 18H).

tert-Butyl N-[4-bromo-6-(bromomethyl)-3-isoquinolyl]-N-tert-butoxycarbonyl-carbamate

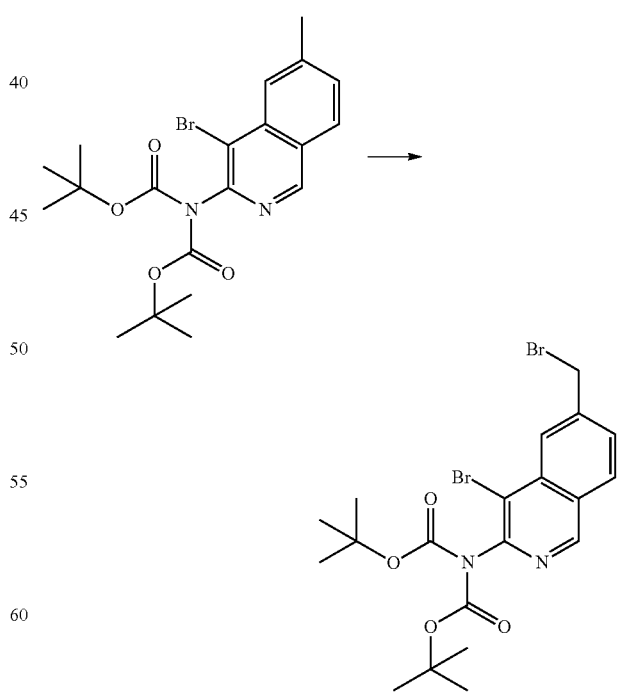

Under N₂ atmosphere, a solution of 182 mg (0.42 mmol) of tert-butyl N-(4-bromo-6-methyl-3-isoquinolyl)-N-tert-butoxycarbonyl-carbamate, 82 mg (0.46 mmol) of N-bromosuccinimide and 20 mg (0.083 mmol) of benzoyl peroxide in 10 mL of CCl₄ is stirred under reflux for 1 h. The reaction solution is concentrated to dryness. The crude product is then purified by silica gel column chromatography (PE/EA=4/1) to give 144 mg of the product as a yellow solid.

MS (ESI+): 517.0 [M+H]⁺.

¹H NMR (400 MHz, CDCl₃) δ ppm: 9.10 (s, 1H), 8.23 (s, 1H), 8.02 (d, J=8.4 Hz, 1H), 7.74 (dd, J=8.4, 1.6 Hz, 1H), 4.70 (s, 2H), 1.39 (s, 18H).

tert-Butyl N-[4-bromo-6-[[4-(tert-butoxycarbonylamino)-1-piperidyl]methyl]-3-isoquinolyl]-N-tert-butoxycarbonyl-carbamate

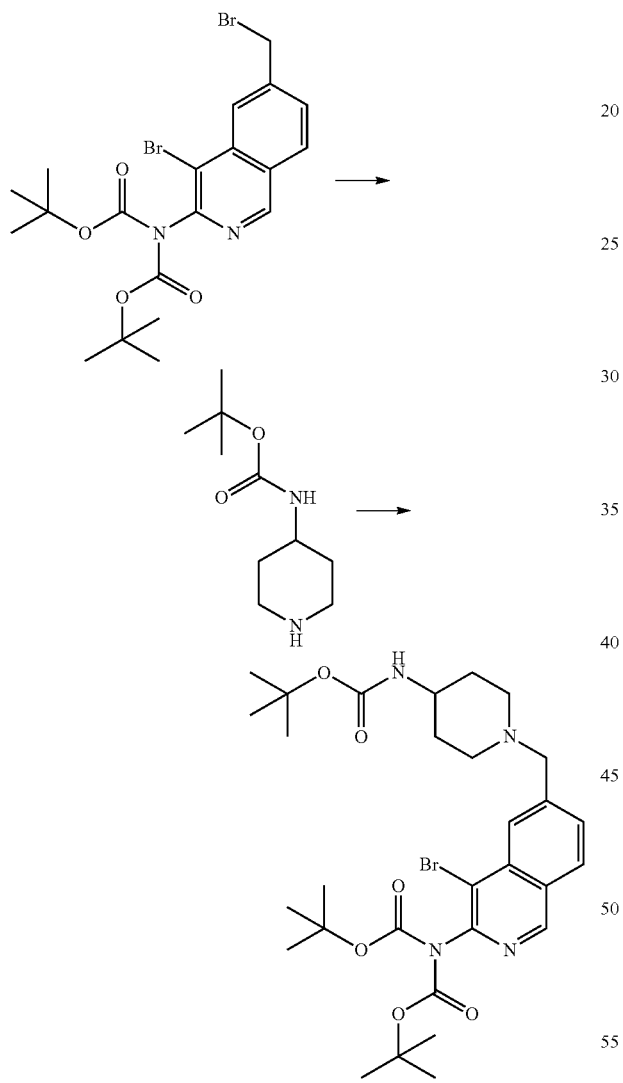

A solution of 140 mg (0.28 mmol) of tert-butyl N-[4-bromo-6-(bromomethyl)-3-isoquinolyl]-N-tert-butoxycarbonyl-carbamate, 83 mg (0.41 mmol) of 1-Boc-4-aminopiperidine (CAS 87120-72-7) and 76 mg (0.55 mmol) of potassium carbonate in 5 mL of DCM is stirred at room temperature for 10 h. The reaction solution is concentrated to dryness. The crude product is then purified by silica gel column chromatography (PE/EA=1/1) to give the product as orange solid.

MS (ESI+): 635.1 [M+H]⁺.

¹H NMR (400 MHz, CDCl₃) δ ppm: 9.08 (s, 1H), 8.13 (s, 1H), 7.97 (d, J=8.4 Hz, 1H), 7.74 (d, J=8.4 Hz, 1H), 4.47 (s, 1H), 3.74 (s, 2H), 3.52 (s, 1H), 2.86-2.84 (m, 2H), 2.25-2.19 (m, 2H), 1.98-1.95 (m, 2H), 1.51-1.46 (m, 2H), 1.46 (s, 9H), 1.42 (s, 18H).

6-[(4-Amino-1-piperidyl)methyl]-4-phenyl-isoquinolin-3-amine (Example 162)

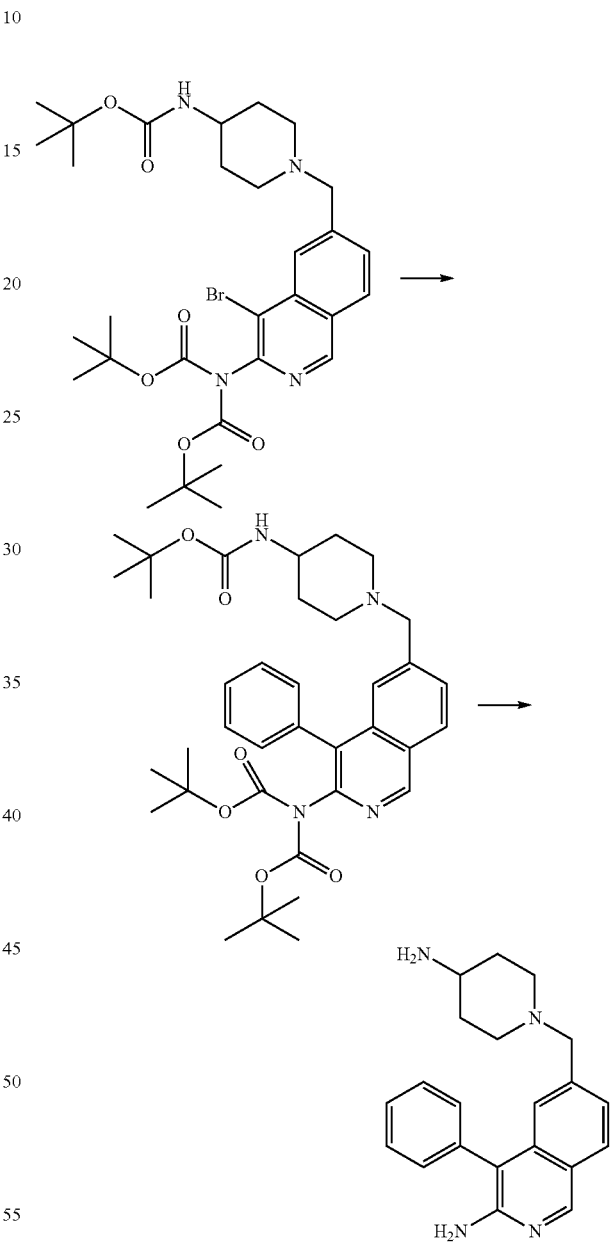

Under N₂ atmosphere, a solution of 93 mg (0.15 mmol) of tert-butyl N-[4-bromo-6-[[4-(tert-butoxycarbonylamino)-1-piperidyl]methyl]-3-isoquinolyl]-N-tert-butoxycarbonyl-carbamate, 27 mg (0.22 mmol) of phenylboronic acid (CAS 98-80-6), 17 mg (0.015 mmol) of tetrakis(triphenylphosphine)palladium and 62 mg (0.29 mmol) of potassium phosphate in a mixed solvent of 5 mL of DMF and 0.3 mL of H₂O is heated to 85° C. and stirred for 10 h. The reaction solution is cooled to r.t. Water (10 mL) is added. The resulting solution is then extracted with EA (3×10 mL). After being washed with water (10 mL), brine (10 mL), and dried with Na₂SO₄, the organics are concentrated to dryness under reduced pressure. The crude is then purified by silica gel column chromatography (PE/EA=1/1) to give 70 mg of tert-butyl N-tert-butoxycarbonyl-N-[6-[[4-(tert-butoxycarbonylamino)-1-piperidyl]methyl]-4-phenyl-3-isoquinolyl]carbamate as a yellow oil.

A solution of 70 mg (0.11 mmol) of this intermediate in 5 mL of 1.0 N solution of HCl in EA is stirred at room temperature for 10 h. The precipitated solid is collected by filtration, washed with EA (10 mL) to give the crude product. The crude product is purified by preparative HPLC to afford 28 mg of the TFA salt of the product as a yellow solid.

MS (ESI+): 333.3 [M+H]⁺.

¹H NMR (400 MHz, DMSO-d₆+D₂O) δ ppm: 9.01 (s, 1H), 8.02 (d, J=8.4 Hz, 1H), 7.62-7.58 (m, 2H), 7.53-7.48 (m, 1H), 7.38-7.35 (m, 2H), 7.29 (dd, J=8.4, 1.6 Hz, 1H), 7.25 (s, 1H), 4.26 (s, 2H), 3.34 (m, 2H), 3.21 (m, 1H), 2.99 (m, 2H), 2.06-2.03 (m, 2H), 1.68-1.66 (m, 2H).

The following example is prepared accordingly to Example 162 by reaction of tert-butyl N-[4-bromo-6-[[4-(tert-butoxycarbonylamino)-1-piperidyl]methyl]-3-isoquinolyl]-N-tert-butoxycarbonyl-carbamate with the corresponding boronic acid in the presence of a Pd-catalyst and subsequent deprotection:

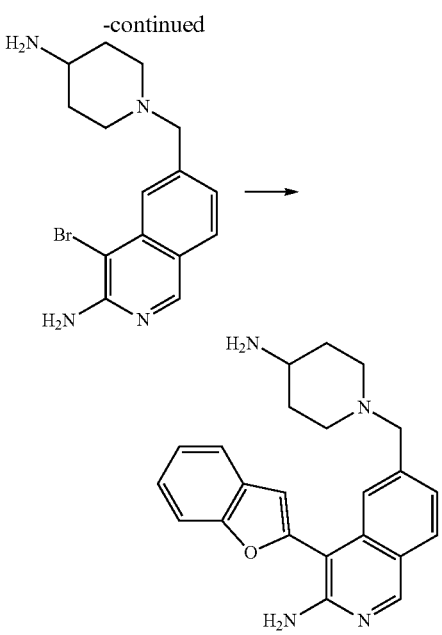

A solution of 140 mg (0.22 mmol) of tert-butyl N-[4-bromo-6-[[4-(tert-butoxycarbonylamino)-1-piperidyl]

| Example | ¹H NMR (400 MHz) δ ppm | MS (+ESI) [M + H]⁺ |
|---|---|---|
| 163 ![structure] | (DMSO-d₆ + D₂O) 8.98 (s, 1H), 8.01 (d, J = 8.4 Hz, 1H), 7.31-7.28 (m, 2H), 7.18-7.15 (m, 2H), 6.99-6.96 (m, 2H), 4.27 (s, 2H), 3.35 (m, 2H), 3.22 (m, 1H), 2.99 (m, 2H), 2.06-2.03 (m, 2H), 1.69-1.67 (m, 2H). | 349.3 |

6-[(4-Amino-1-piperidyl)methyl]-4-(benzofuran-2-yl)isoquinolin-3-amine (Example 164)

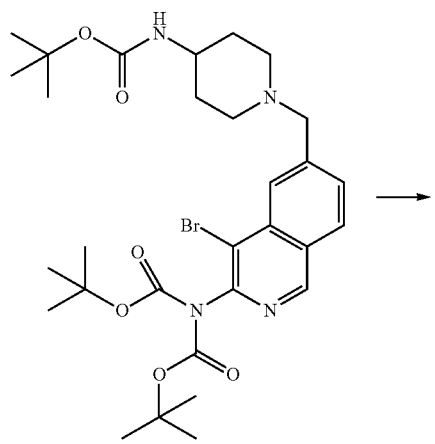

methyl]-3-isoquinolyl]-N-tert-butoxycarbonyl-carbamate in 5 mL of 1.0 N solution of HCl in EA is stirred at room temperature for 10 h. The reaction solution was concentrated to dryness to give 74 mg of the crude HCl salt of 6-[(4-amino-1-piperidyl)methyl]-4-bromo-isoquinolin-3-amine as a yellow solid.

Under N₂ atmosphere, a solution of 150 mg (0.45 mmol) of this intermediate, 140 mg (0.89 mmol) of benzofuran-2-boronic acid (CAS 98437-24-2), 52 mg (0.045 mmol) of tetrakis(triphenylphosphine)palladium and 570 mg (2.68 mmol) of potassium phosphate in a mixture of 5 mL of DMF and 0.3 mL of H₂O is heated to 85° C. and stirred for 2 h. The reaction is filtrated. Water (5.0 mL) and EA (10 mL) are added. The layers are separated. The aqueous layer is extracted with EA (3×10 mL). The combined organics are washed with water (10 mL) and then saturated brine solution (10 mL). The resulting solution is concentrated to dryness. 4.0 N HCl in water (10 mL) is added and the mixture is washed with EA (2×10 mL). The aqueous crude is then purified by preparative HPLC to give 35 mg of the desired product as an orange solid.

MS (+ESI): 373.3 [M+H]⁺.

¹H NMR (400 MHz, DMSO-d₆+D₂O) δ ppm: 9.04 (s, 1H), 8.03 (d, J=8.4 Hz, 1H), 7.75-7.73 (m, 2H), 6.63 (d, J=8.0 Hz, 1H), 7.39-7.20 (m, 3H), 7.20 (s, 1H), 4.34 (s, 2H), 3.40-3.37 (m, 2H), 3.22 (m, 1H), 3.05-2.99 (m, 2H), 2.07-2.04 (m, 2H), 1.68-1.65 (m, 2H).

tert-Butyl N-[6-(aminomethyl)-4-bromo-3-isoquinolyl]-N-tert-butoxycarbonyl-carbamate

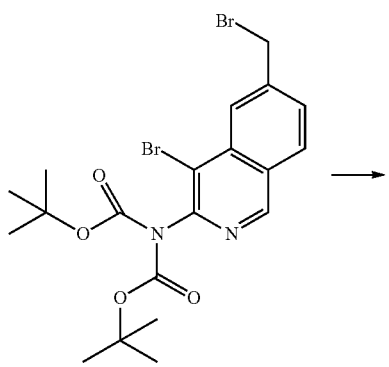

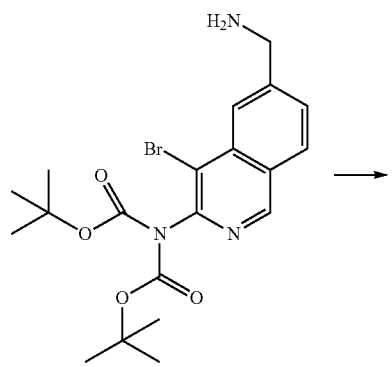

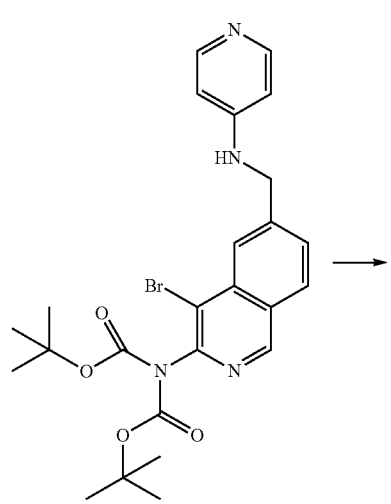

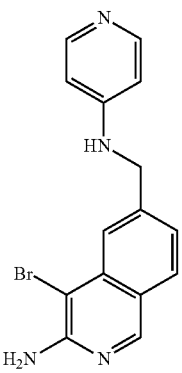

A solution of 350 mg (0.68 mmol) of tert-butyl N-[4-bromo-6-(bromomethyl)-3-isoquinolyl]-N-tert-butoxycarbonyl-carbamate in 15 mL of saturated solution of NH₃ in EtOH is stirred at room temperature for 10 h. The reaction solution is concentrated to dryness and the residue was purified by silica gel column chromatography eluting with EA to give 195 mg of tert-butyl N-[6-(aminomethyl)-4-bromo-3-isoquinolyl]-N-tert-butoxycarbonyl-carbamate as a yellow foam.

Under N₂ atmosphere, a solution of 100 mg (0.22 mmol) of tert-butyl N-[6-(aminomethyl)-4-bromo-3-isoquinolyl]-N-tert-butoxycarbonyl-carbamate, 23 mg (0.022 mmol) of tris(dibenzylideneacetone)dipalladium, 26 mg (0.044 mmol) of XantPhos, 360 mg (1.11 mmol) of cesium carbonate and 172 mg (0.88 mmol) of 4-bromopyridine hydrochloride (CAS 19524-06-2) in 10 mL of toluene is heated to 100° C. and stirred for 4 h. The reaction solution is cooled to r.t. and then filtrated. The mixture is concentrated to dryness. The crude is purified by silica gel column chromatography (DCM/MeOH=10/1) to give 36 mg of tert-butyl N-[4-bromo-6-[(4-pyridylamino)methyl]-3-isoquinolyl]-N-tert-butoxycarbonyl-carbamate as a yellow solid.

This intermediate is treated with HCl in EA as described above for Example 1 to provide 21 mg of the HCl salt of 4-bromo-6-[(4-pyridylamino)methyl]isoquinolin-3-amine as a yellow solid.

¹H NMR (400 MHz, DMSO-d₆+D₂O) δ ppm: 8.88 (s, 1H), 8.17-8.10 (m, 2H), 7.95 (d, J=8.4 Hz, 1H), 7.70 (s, 1H), 7.03 (dd, J=6.8, 2.4 Hz, 1H), 7.04-6.86 (m, 2H), 4.73 (s, 2H).

4-(Benzofuran-2-yl)-6-[(4-pyridylamino)methyl]isoquinolin-3-amine (Example 165)

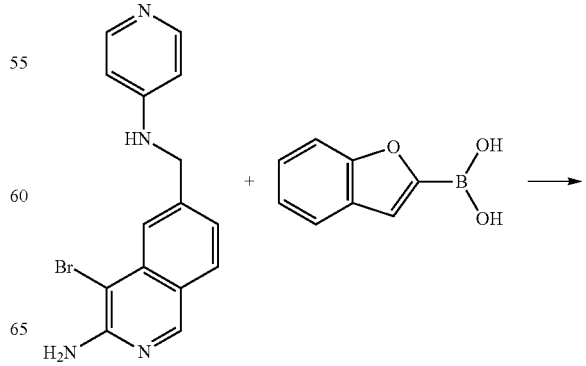

205

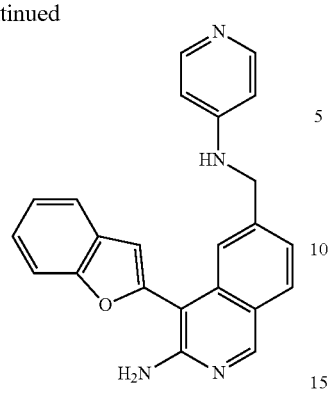

To a solution of 85 mg (0.26 mmol) of the HCl salt of 4-bromo-6-[(4-pyridylamino)methyl]isoquinolin-3-amine, 105 mg (0.65 mmol) of benzofuran-2-boronic acid (CAS 98437-24-2), 30 mg (0.026 mmol) of tetrakis(triphenylphosphine)palladium and 329 mg (1.55 mmol) of potassium phosphate in a mixture of 5 mL of DMF and 0.1 mL of H₂O is heated to 85° C. and stirred for 5 h. The catalyst is removed by filtration and the solvent is evaporated off. The crude product is purified by preparative HPLC to give 23 mg of the desired product as an orange solid.

MS (+ESI): 367.3 [M+H]⁺.

¹H NMR (400 MHz, DMSO-d₆) δ ppm: 8.87 (s, 1H), 8.16-8.05 (m, 2H), 7.95 (d, J=8.4 Hz, 1H), 7.68-7.66 (m, 1H), 7.49-7.46 (m, 2H), 7.37-7.21 (m, 3H), 7.03 (s, 1H), 6.87-6.73 (m, 2H), 4.64 (s, 2H).

6-[(4-Aminopyridin-1-ium-1-yl)methyl]-4-(benzofuran-2-yl)isoquinolin-3-amine trifluoroacetate (Example 166)

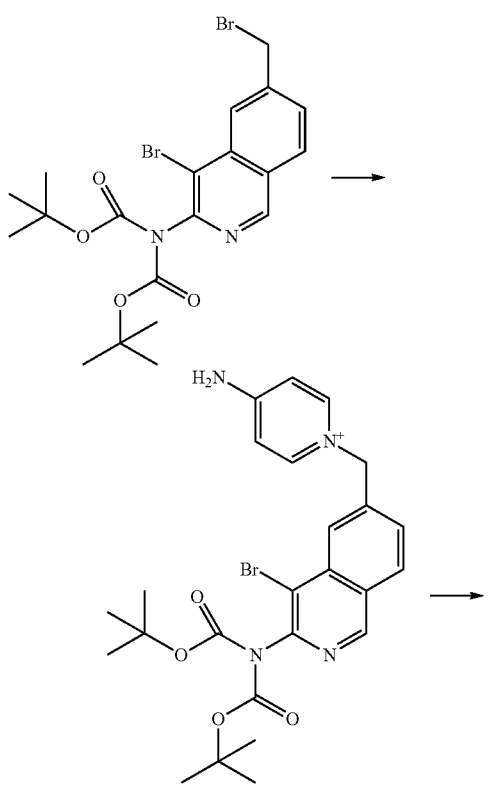

206

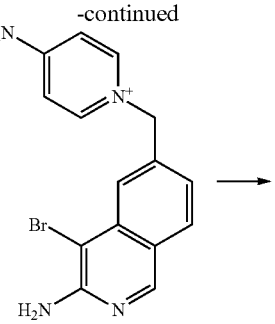

A solution of 190 mg (0.37) of tert-butyl N-[4-bromo-6-(bromomethyl)-3-isoquinolyl]-N-tert-butoxycarbonyl-carbamate and 52 mg (0.55 mmol) of 4-aminopyridine in 10 mL of ACN is stirred at room temperature for 10 h. The reaction solution is concentrated to dryness. The crude product is dissolved in water (10 mL), and washed with EA (10 mL). The crude tert-butyl N-[6-[(4-aminopyridin-1-ium-1-yl)methyl]-4-bromo-3-isoquinolyl]-N-tert-butoxycarbonyl-carbamate trifluoroacetate is obtained as a yellow solid after being dried under reduced pressure.

180 mg of crude tert-butyl N-[6-[(4-aminopyridin-1-ium-1-yl)methyl]-4-bromo-3-isoquinolyl]-N-tert-butoxycarbonyl-carbamate trifluoroacetate is treated with HCl in EA as described above for Example 1 to provide 102 mg of 4-bromo-6-[(4-pyridylamino)methyl]isoquinolin-3-amine chloride as a yellow solid. 150 mg of 4-bromo-6-[(4-pyridylamino)methyl]isoquinolin-3-amine chloride is treated benzofuran-2-boronic acid (CAS 98437-24-2) in the presence of a Pd-catalyst as described above for Example 4 to provide 30 mg of the desired product as a brown solid.

MS (+ESI): 367.3 [M]⁺.

¹H NMR (400 MHz, DMSO-d₆) δ ppm: 8.97 (s, 1H), 8.20-8.18 (m, 2H), 7.95 (d, J=8.4 Hz, 1H), 7.72-7.70 (m, 1H), 7.59-7.57 (m, 1H), 7.42 (s, 1H), 7.38-7.29 (m, 2H), 7.17-7.13 (m, 2H), 6.79 (d, J=7.6 Hz, 2H), 5.42 (s, 2H).

1-[(4-Bromo-6-isoquinolyl)methyl]piperidin-4-amine

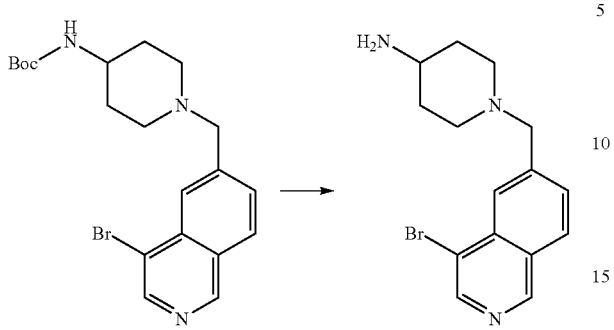

A mixture of 3.4 g (8.08 mmol) of tert-butyl N-[1-[(4-bromo-6-isoquinolyl)methyl]-4-piperidyl]carbamate in 30 mL of a 2.0 N solution of HCl in EA is stirred at rt for 2 h. Then the solvent is evaporated under reduced pressure. The residue is washed five times with EA to afford 2.5 g of the HCl salt of the product as a yellow solid.

MS (ESI+): 320.0 [M+H].

$^1$H NMR (400 MHz, DMSO-d6+D$_2$O) δ ppm: 9.44 (s, 1H), 8.84 (s, 1H), 8.36-8.34 (m, 2H), 8.05 (d, J=8.4 Hz, 1H), 4.59 (s, 2H), 3.45-3.42 (m, 2H), 3.30 (m, 1H), 3.17-3.11 (m, 2H), 2.13-2.10 (m, 2H), 1.96-1.94 (m, 2H).

1-[[4-(5-methyl-2-furyl)-6-isoquinolyl]methyl]piperidin-4-amine (Example 167)

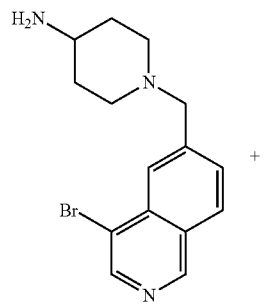

Under argon atmosphere, to a mixture of 100 mg (0.31 mmol) of 1-[(4-bromo-6-isoquinolyl) methyl]piperidin-4-amine, 160 mg (0.78 mmol) of 4,4,5,5-tetramethyl-2-(5-methyl-2-furyl)-1,3,2-dioxaborolane, 400 mg (1.87 mmol) of K$_3$PO$_4$ in a mixture 4 mL of DMF and 0.4 mL of water, 150 mg (0.13 mmol) of Pd(PPh$_3$)$_4$ are added. The mixture is stirred at 90° C. for 3 h. Then the reaction mixture is filtered. The filtrate is concentrated under reduced pressure and the residue is purified via pre-HPLC to afford 85 mg of the product as a yellow solid.

MS (ESI+): 322.1 [M+H].

$^1$H NMR (400 MHz, DMSO-d6+D$_2$O) δ ppm: 9.33 (s, 1H), 8.78 (s, 1H), 8.54 (s, 1H), 8.33 (d, J=8.4 Hz, 1H), 7.83 (dd, J$_1$=8.4 Hz, J$_2$=1.2 Hz, 1H), 7.07 (d, J=3.2 Hz, 1H), 6.39 (d, J=3.2 Hz, 1H), 4.55 (s, 2H), 3.46-3.43 (m, 2H), 3.29-3.27 (m, 1H), 3.13-3.09 (m, 2H), 2.43 (s, 3H), 2.10-2.07 (m, 2H), 1.80-1.65 (m, 2H).

The following examples were prepared accordingly to Example 167 by reaction of 1-[(4-bromo-6-isoquinolyl)methyl]piperidin-4-amine with the corresponding boronic acid or boronic acid ester in the presence of a Pd-catalyst:

| Example | | $^1$H NMR (400 MHz) δ ppm | MS (+ESI) [M + H]$^+$ |
|---|---|---|---|
| 168 | | (DMSO-d$_6$ + D$_2$O) 9.47 (s, 1H), 8.55 (s, 1H), 8.54 (s, 1H), 8.41 (d, J = 8.4 Hz, 1H), 8.15 (s, 1H), 7.84 (dd, J$_1$ = 8.4 Hz, J$_2$ = 1.2 Hz, 1H), 7.76 (d, J = 1.2 Hz, 1H), 7.61 (d, J = 8.4 Hz, 1H), 7.46 (d, J = 3.2 Hz, 1H), 7.30 (dd, J$_1$ = 8.4 Hz, J$_2$ = 1.2 Hz, 1H), 6.56 (dd, J$_1$ = 3.2 Hz, J$_2$ = 0.4 Hz, 1H), 4.45 (s, 2H), 3.39-3.35 (m, 2H), 3.26-3.21 (m, 1H), 3.09-3.00 (m, 2H), 2.06-2.03 (m, 2H), 1.76-1.62 (m, 2H) | 357.2 |

| Example | 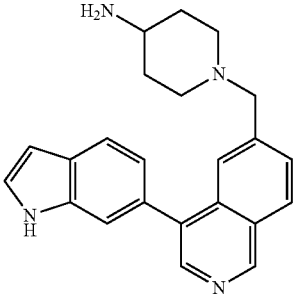 [SMILES: NC1CCN(Cc2ccc3cncc(-c4ccc5cc[nH]c5c4)c3c2)CC1] <br> ¹H NMR (400 MHz) δ ppm | MS (+ESI) [M + H]⁺ |
|---|---|---|
| 169 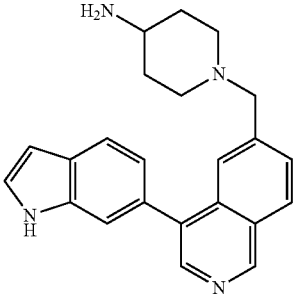 [SMILES: NC1CCN(Cc2ccc3cncc(-c4ccc5cc[nH]c5c4)c3c2)CC1] | (DMSO-d₆ + D₂O) 9.50 (s, 1H), 8.56 (s, 1H), 8.43 (d, J = 8.4 Hz, 1H), 8.16 (s, 1H), 7.86 (dd, J₁ = 8.4 Hz, J₂ = 1.2 Hz, 1H), 7.76 (d, J = 8.4 Hz, 1H), 7.61 (s, 1H), 7.47 (d, J = 3.2 Hz, 1H), 7.21 (dd, J₁ = 8.4 Hz, J₂ = 1.2 Hz, 1H), 6.57 (dd, J₁ = 3.2 Hz, J₂ = 0.4 Hz, 1H), 4.45 (s, 2H), 3.38-3.35 (m, 2H), 3.26-3.21 (m, 1H), 3.07-3.00 (m, 2H), 2.06-2.03 (m, 2H), 1.76-1.62 (m, 2H) | 357.2 |
| 170 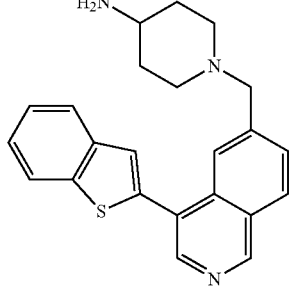 | (DMSO-d₆ + D₂O) 9.48 (s, 1H), 8.74 (s, 1H), 8.41-8.38 (m, 2H), 8.08-8.06 (m, 1H), 8.00-7.98 (m, 1H), 7.86 (dd, J₁ = 8.4 Hz, J₂ = 1.6 Hz, 1H), 7.82 (s, 1H), 7.52-7.45 (m, 2H), 4.52 (s, 2H), 3.42-3.40 (m, 2H), 3.24-3.22 (m, 1H), 3.09-3.06 (m, 2H), 2.08-2.05 (m, 2H), 1.69-1.67 (m, 2H) | 374.2 |
| 171 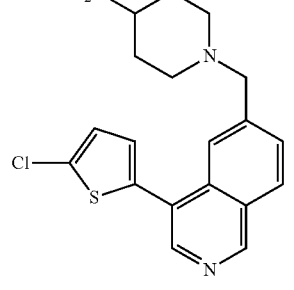 | (DMSO-d₆ + D₂O) 9.43 (s, 1H), 8.62 (s, 1H), 8.37-8.33 (m, 2H), 7.84 (dd, J₁ = 8.4 Hz, J₂ = 1.6 Hz, 1H), 7.38 (d, J = 4.0 Hz, 1H), 7.34 (d, J = 4.0 Hz, 1H), 4.52 (s, 2H), 3.43-3.41 (m, 2H), 3.26-3.24 (m, 1H), 3.09-3.07 (m, 2H), 2.09-2.04 (m, 2H), 1.71-1.68 (m, 2H) | 358.1 |
| 172 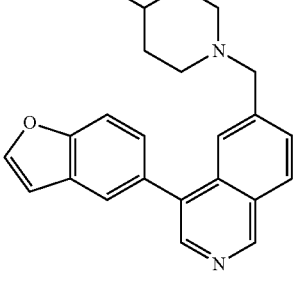 | (DMSO-d₆ + D₂O) 9.63 (s, 1H), 8.62 (s, 1H), 8.49 (d, J = 8.8 Hz, 1H), 8.14 (s, 1H), 8.11 (d, J = 2.4 Hz, 1H), 8.06 (d, J = 8.4 Hz, 1H), 7.94 (d, J = 1.6 Hz, 1H), 7.82 (d, J = 8.4 Hz, 1H), 7.55 (dd, J₁ = 8.4 Hz, J₂ = 1.6 Hz, 1H), 7.09-7.08 (m, 1H), 4.49 (s, 2H), 3.40-3.37 (m, 2H), 3.24-3.22 (m, 1H), 3.07-3.01 (m, 2H), 2.08-2.05 (m, 2H), 1.85-1.82 (m, 2H) | 358.2 |
| 173 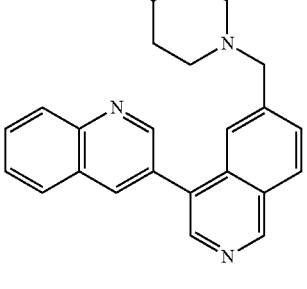 | (DMSO-d₆ + D₂O) 9.74 (s, 1H), 9.30 (d, J = 1.6 Hz, 1H), 9.01 (s, 1H), 8.81 (s, 1H), 8.55 (d, J = 8.4 Hz, 1H), 8.29-8.24 (m, 3H), 8.10 (d, J = 8.4 Hz, 1H), 8.04-8.00 (m, 1H), 7.86-7.83 (m, 1H), 4.50 (s, 2H), 3.42-3.39 (m, 2H), 3.25-3.24 (m, 1H), 3.08-3.02 (m, 2H), 2.09-2.06 (m, 2H), 1.90-1.87 (m, 2H) | 369.2 |

| Example | 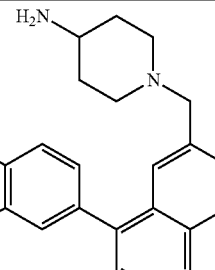 | ¹H NMR (400 MHz) δ ppm | MS (+ESI) [M + H]⁺ |
|---|---|---|---|
| 174 | | (DMSO-d₆ + D₂O) 9.50 (s, 1H), 8.63 (s, 1H), 8.41 (d, J = 8.4 Hz, 1H), 8.15-8.02 (m, 5H), 7.85 (dd, $J_1$ = 8.4 Hz, $J_2$ = 1.6 Hz, 1H), 7.73 (dd, $J_1$ = 8.4 Hz, $J_2$ = 1.6 Hz, 1H), 7.65-7.60 (m, 2H), 4.46 (s, 2H), 3.38-3.36 (m, 2H), 3.23-3.21 (m, 1H), 3.03-3.01 (m, 2H), 2.06-2.03 (m, 2H), 1.68-1.66 (m, 2H) | 368.2 |
| 175 | 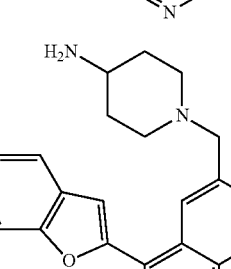 | (DMSO-d₆ + D₂O) 9.46 (s, 1H), 8.97 (s, 1H), 8.61 (s, 1H), 8.38 (d, J = 8.4 Hz, 1H), 7.87 (dd, $J_1$ = 8.4 Hz, $J_2$ = 1.2 Hz, 1H), 7.64 (d, J = 8.8 Hz, 1H), 7.54 (s, 1H), 7.27 (d, J = 2.8 Hz, 1H), 7.02 (dd, $J_1$ = 8.8 Hz, $J_2$ = 2.4 Hz, 1H), 4.58 (s, 2H), 3.82 (s, 3H), 3.46-3.44 (m, 2H), 3.27-3.25 (m, 1H), 3.12-3.10 (m, 2H), 2.10-2.07 (m, 2H), 1.73-1.71 (m 2H) | 388.2 |

6-Methyl-4-(2-quinolyl)isoquinoline

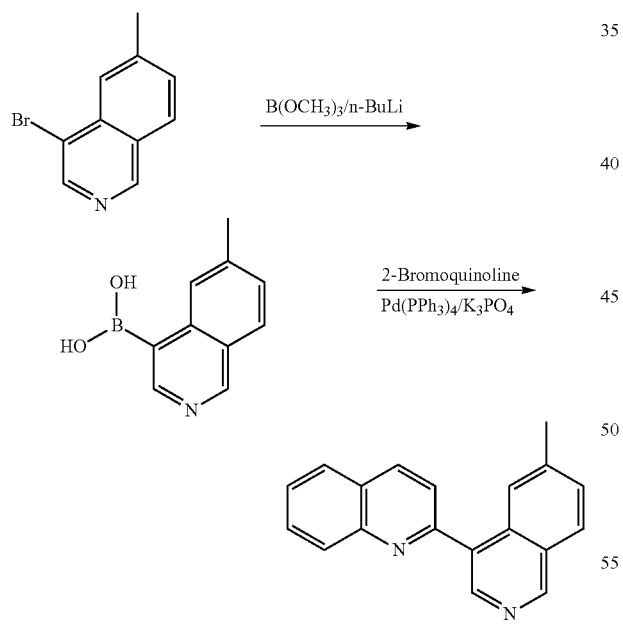

Under Ar, to a cold (−78° C.) stirred solution of 6.8 mL of n-BuLi (10.8 mmol, 1.6M solution in hexane) in 40 ml of THF (dried over sodium) is added dropwise 2 g of 4-bromo-6-methylisoquinoline (9 mmol) in 10 ml of THF (dried over sodium), the rate of addition is adjusted so as to keep the temperature of the reaction mixture below −70° C. After stirring at this temperature for 30 mins, a solution 1.2 mL of trimethyl borate (10.8 mmol) in 5 mL of THF (dried over sodium) is slowly added while the temperature of the mixture is maintained between −70° C. and −65° C. The mixture is allowed to warm to −40° C., and is stirred at this temperature for additional 1 h. The acetone/dry ice bath is removed and the reaction is allowed to warm to −20° C. when an aqueous 2 N hydrogen chloride solution is added. The mixture is allowed to reach room temperature, and the aqueous layer (pH 1) is collected and adjusted to pH 7 with an aqueous 5 N sodium hydroxide solution. The mixture is then saturated with NaCl, and extracted with THF. The combined extracts are dried over Na₂SO₄, concentrated under reduced pressure to provide 1.5 g of (6-methyl-4-isoquinolyl)boronic acid as an off-white solid.

MS (ESI+): 188.1 [M+H].

6-Methyl-4-(2-quinolyl)isoquinoline is prepared accordingly to methods described above by reaction of 0.5 g of 2-bromoquinoline (2.4 mmol) with 0.67 g of (6-methyl-4-isoquinolyl)boronic acid (3.6 mmol) in the presence of a Pd-catalyst to provide 0.34 g of the desired product as a red semisolid.

MS (ESI+): 271.1 [M+H].

¹H NMR (400 MHz, DMSO-d₆) δ ppm: 9.36 (s, 1H), 8.69 (s, 1H), 8.56 (d, J=8.4 Hz, 1H), 8.15-8.10 (m, 3H), 8.03 (s, 1H), 7.91-7.83 (m, 2H), 7.72-7.68 (m, 1H), 7.61 (dd, $J_1$=8.4 Hz, $J_2$=1.2 Hz, 1H), 2.50 (s, 3H).

1-[[4-(2-Quinolyl)-6-isoquinolyl]methyl]piperidin-4-amine (Example 176)

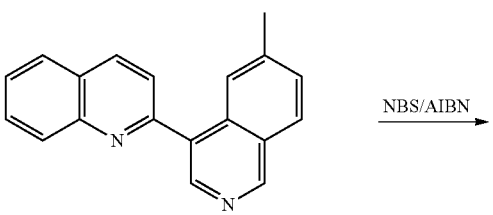

213

-continued

214
tert-Butyl N-[1-[[4-(2-furyl)-6-isoquinolyl]methyl]-4-piperidyl]carbamate

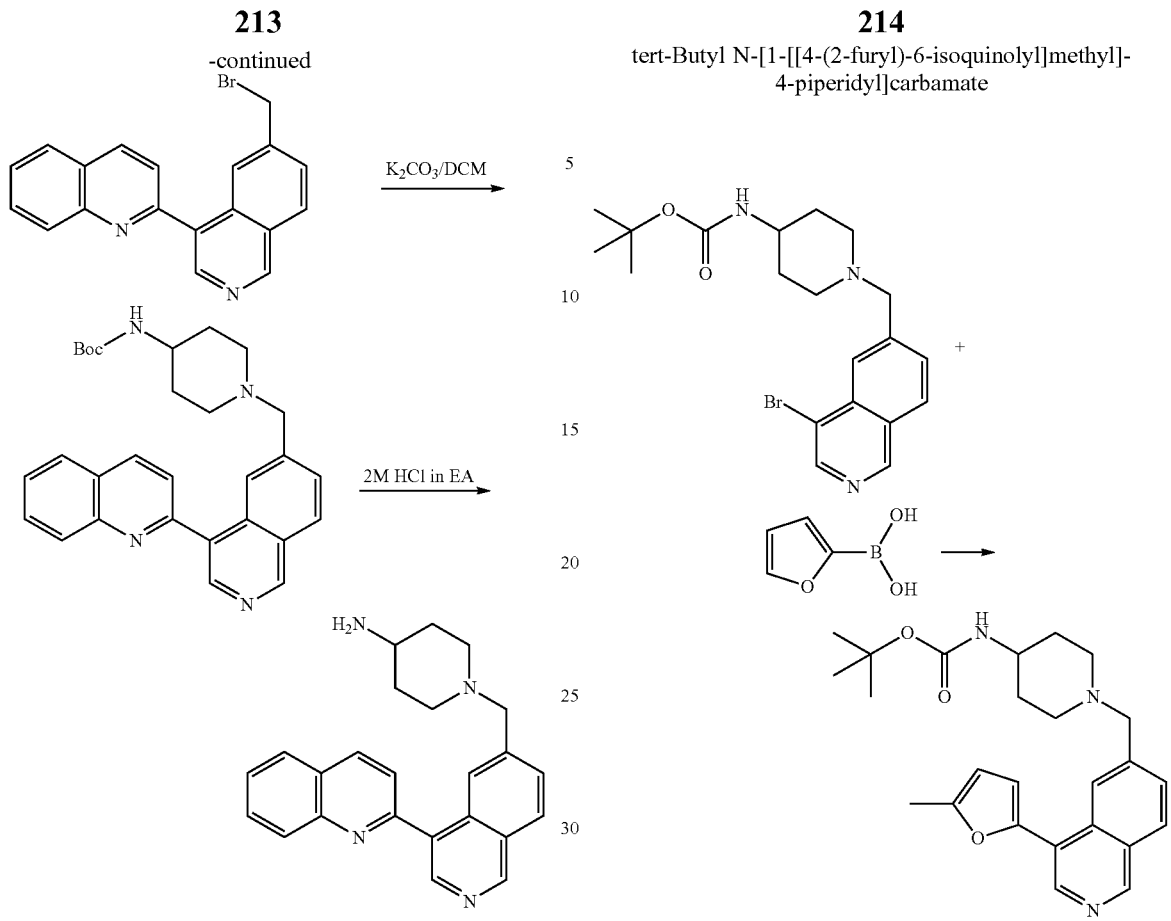

To a stirred solution of 340 mg (1.26 mmol) of 6-methyl-4-(2-quinolyl)isoquinoline in 30 mL of CCl$_4$ are added 31 mg (0.126 mmol) of benzoyl peroxide and 224 mg (1.26 mmol) of NBS. The reaction mixture is heated to 100° C. for 3 h. Then the mixture is cooled down to rt, concentrated to give 300 mg of the crude 6-(bromomethyl)-4-(2-quinolyl) isoquinoline as a yellow solid.

MS (ESI+): 349.0 [M+H].

To a solution of crude 6-(bromomethyl)-4-(2-quinolyl) isoquinoline (0.5 g, 1.43 mmol) in CCl$_4$ (80 mL) and DCM (50 mL) are added K$_2$CO$_3$ (0.4 g, 2.86 mmol) and 4-(Boc-amino) piperidine (0.43 g, 2.15 mmol), and the mixture is stirred at 25° C. for 72 hrs. The solvent is evaporated under reduced pressure and the residue is purified by column chromatography (MeOH/DCM=1/60-1/10) to give 350 mg of tert-butyl N-[1-[[4-(2-quinolyl)-6-isoquinolyl]methyl]-4-piperidyl]carbamate as a yellow solid.

MS (ESI+): 469.2 [M+H].

200 mg of tert-butyl N-[1-[[4-(2-quinolyl)-6-isoquinolyl] methyl]-4-piperidyl]carbamate is treated with HCl in EA as described above for Example 1a to provide 95 mg of 1-[[4-(2-quinolyl)-6-isoquinolyl]methyl]piperidin-4-amine as a yellow solid after purification by preparative HPLC.

MS (ESI+): 369.2 [M+H].

$^1$H NMR (400 MHz, DMSO-d$_6$+D$_2$O) δ ppm: 9.55 (s, 1H), 8.82 (s, 1H), 8.62 (d, J=8.4 Hz, 1H), 8.43-8.41 (m, 2H), 8.13-8.11 (m, 2H), 7.97 (d, J=8.4 Hz, 1H), 7.90-7.85 (m, 2H), 7.74-7.71 (m, 1H), 4.47 (s, 2H), 3.43-3.41 (m, 2H), 3.30-3.21 (m, 1H), 3.10-3.03 (m, 2H), 2.08-2.05 (m, 2H), 1.75-1.63 (m, 2H).

Under argon atmosphere, to a mixture of 200 mg (0.48 mmol) of tert-butyl N-[1-[(4-bromo-6-isoquinolyl)methyl]-4-piperidyl]carbamate, 106 mg (0.95 mmol) of 2-Furanboronic acid, 606 mg (2.85 mmol) of K$_3$PO$_4$ in a mixture 5 mL of DMF and 0.3 mL of water, 55 mg (0.048 mmol) of Pd(PPh$_3$)$_4$ are added. The mixture is stirred at 90° C. for 3 h. Then the reaction mixture is diluted with EA, washed with water and brine, dried over Na$_2$SO$_4$ and filtered. The filtrate is concentrated under reduced pressure and the residue is purified by silica gel column chromatography (PE/EA=2/1) to afford 190 mg of the product as a light yellow oil.

MS (ESI+): 408.2 [M+H].

1-[[4-(2-Furyl)-6-isoquinolyl]methyl]piperidin-4-amine (Example 177)

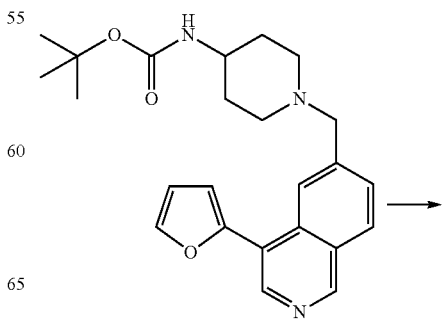

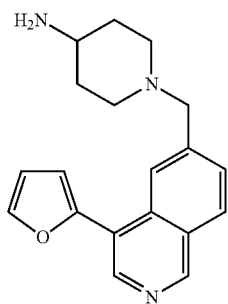

A mixture of 165 mg (0.40 mmol) of tert-butyl N-[1-[[4-(2-furyl)-6-isoquinolyl]methyl]-4-piperidyl]carbamate in 20 mL of a 2.0 N solution of HCl in EA is stirred at rt for 4 h. Then the solvent is evaporated under reduced pressure. The residue is washed five times with EA to afford 110 mg of the HCl salt of the product as a yellow solid.

MS (ESI+): 308.2 [M+H].

$^1$H NMR (400 MHz, DMSO-d6+D$_2$O) δ ppm: 9.45 (d, J=3.4 Hz, 1H), 8.84 (d, J=2 Hz, 1H), 8.64 (s, 1H), 8.40 (dd, J=8.5, 1.8 Hz, 1H), 8.05-7.90 (m, 2H), 7.37-7.26 (m, 1H), 6.85-6.74 (m, 1H), 4.58 (s, 2H), 3.53-3.36 (m, 2H), 3.29 (s, 1H), 3.21-3.02 (m, 2H), 2.18-2.01 (m, 2H), 1.96-1.72 (m, 2H).

The following examples were prepared accordingly to Example 177 by reaction of tert-butyl N-[1-[(4-bromo-6-isoquinolyl)methyl]-4-piperidyl]carbamate with the corresponding boronic acid or boronic acid ester in the presence of a Pd-catalyst and subsequent deprotection

| Example | $^1$H NMR (400 MHz) δ ppm | MS (+ESI) [M + H]$^+$ |
| --- | --- | --- |
| 178 | (DMSO-d$_6$ + D$_2$O) δ ppm: 9.51 (s, 1H), 8.65 (s, 1H), 8.47-8.36 (m, 2H), 8.04-7.93 (m, 1H), 7.83 (dd, J = 5.1, 1.2 Hz, 1H), 7.61 (dd, J = 3.5, 1.2 Hz, 1H), 7.35 (dd, J = 5.1, 3.5 Hz, 1H), 4.54 (s, 2H), 3.51-3.34 (m, 2H), 3.27 (s, 1H), 3.19-2.99 (m, 2H), 2.16-2.01 (m, 2H), 1.93-1.71 (m, 2H). | 324.2 |
| 179 | (DMSO-d$_6$ + D$_2$O) δ ppm: 9.65-9.51 (m, 1H), 8.71-8.63 (m, 1H), 8.54-8.40 (m, 2H), 8.40-8.32 (m, 1H), 8.07-8.02 (m, 1H), 7.99-7.89 (m, 1H), 7.09 (d, J = 4.6 Hz, 1H), 4.57 (s, 2H), 3.55-3.36 (m, 2H), 3.29 (s, 1H), 3.22-3.00 (m, 2H), 2.19-2.02 (m, 2H), 1.89 (s, 2H). | 308.2 |
| 180 | (DMSO-d$_6$ + D$_2$O) δ ppm: 9.47 (s, 1H), 8.62 (s, 1H), 8.40 (d, J = 8.4 Hz, 1H), 8.24 (s, 1H), 7.92 (dd, J = 3.0, 1.4 Hz, 1H), 7.86 (dd, J = 8.4, 1.6 Hz, 1H), 7.82 (dd, J = 5.0, 3.0 Hz, 1H), 7.51 (dd, J = 5.0, 1.4 Hz, 1H), 4.52 (s, 2H), 3.54-3.35 (m, 2H), 3.26 (s, 1H), 3.20-2.98 (m, 2H), 2.18-1.97 (m, 2H), 1.71 (s, 2H). | 324.2 |

| Example | ¹H NMR (400 MHz) δ ppm | MS (+ESI) [M + H]⁺ |
|---|---|---|
| 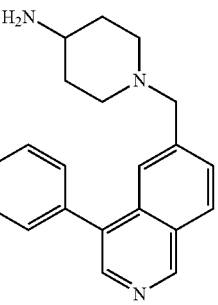<br>181 | (DMSO-d₆ + D₂O) δ ppm: 9.49 (s, 1H), 8.51 (s, 1H), 8.41 (d, J = 8.4 Hz, 1H), 8.08 (s, 1H), 7.85 (dd, J = 8.4, 1.6 Hz, 1H), 7.61-7.50 (m, 4H), 4.62 (s, 2H), 4.47 (s, 2H), 3.49-3.32 (m, 2H), 3.25 (s, 1H), 3.16-2.97 (m, 2H), 2.06 (d, J = 13.3 Hz, 2H), 1.69 (s, 2H). | 348.2 |
| 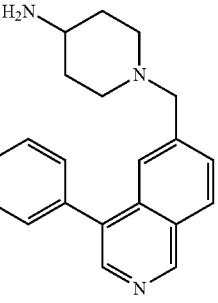<br>182 | (DMSO-d₆ + D₂O) δ ppm: 9.50 (s, 1H), 8.53 (s, 1H), 8.41 (d, J = 8.4 Hz, 1H), 8.07 (s, 1H), 7.85 (dd, J = 8.4, 1.6 Hz, 1H), 7.61-7.42 (m, 4H), 4.62 (s, 2H), 4.48 (s, 2H), 3.52-3.32 (m, 2H), 3.25 (s, 1H), 3.16-2.92 (m, 2H), 2.15-1.98 (m, 2H), 1.70 (s, 2H). | 348.3 |
| 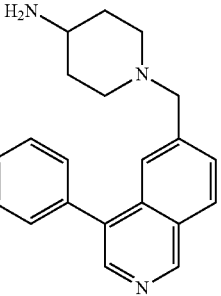<br>183 | (DMSO-d₆ + D₂O) δ ppm: 9.63 (s, 1H), 8.56 (s, 1H), 8.49 (d, J = 8.5 Hz, 1H), 8.13 (s, 1H), 8.09 (dd, J = 8.5, 1.7 Hz, 1H), 7.77-7.64 (m, 4H), 4.49 (s, 2H), 4.16 (s, 2H), 3.47-3.33 (m, 2H), 3.26 (s, 1H), 3.18-2.97 (m, 2H), 2.19-2.01 (m, 2H), 2.01-1.78 (m, 2H). | 347.3 |
| 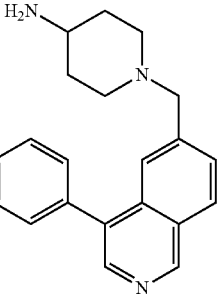<br>184 | (DMSO-d₆ + D₂O) δ ppm: 9.63 (s, 1H), 8.57 (s, 1H), 8.50 (d, J = 8.4 Hz, 1H), 8.26 (s, 1H), 8.02 (d, J = 8.4 Hz, 1H), 7.77 (s, 1H), 7.72-7.59 (m, 3H), 4.55 (s, 2H), 4.17 (s, 2H), 3.50-3.35 (m, 2H), 3.29 (s, 1H), 3.22-3.04 (m, 2H), 2.19-2.02 (m, 2H), 1.95-1.72 (m, 2H). | 347.2 |

-continued
| Example | 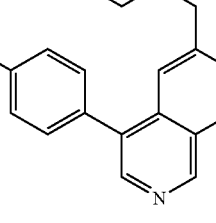<br>185 | ¹H NMR (400 MHz) δ ppm | MS (+ESI) [M + H]⁺ |
|---|---|---|---|
| | | (DMSO-d₆ + D₂O) δ ppm: 9.60 (s, 1H), 8.60 (s, 1H), 8.47 (d, J = 8.4 Hz, 1H), 8.17 (d, J = 4.4 Hz 2H), 8.10 (s, 1H), 8.00 (d, J = 8.4 Hz, 1H), 7.80 (d, J = 8.0 Hz, 2H), 4.49 (s, 2H), 3.48-3.33 (m, 2H), 3.26 (s, 1H), 3.18-2.96 (m, 2H), 2.67 (s, 3H), 2.16-1.99 (m, 2H), 1.95-1.71 (m, 2H). | 360.2 |
| | 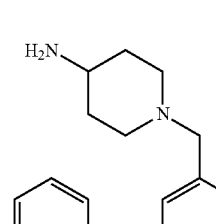<br>186 | (DMSO-d₆ + D₂O) δ ppm: 9.61 (d, J = 2.6 Hz, 1H), 8.61 (d, J = 1.9 Hz, 1H), 8.48 (d, J = 8.4 Hz, 1H) 8.18-8.11 (m, 2H), 8.09 (s, 1H), 8.05-7.95 (m, 1H), 7.95-7.87 (m, 1H), 7.82-7.73 (m, 1H), 4.49 (s, 2H), 3.43-3.40 (m, 2H), 3.27 (s, 1H), 3.19-2.97 (m, 2H), 2.65 (s, 3H), 2.15-1.99 (m, 2H), 1.93-1.69 (m, 2H). | 360.2 |
| | 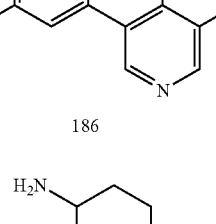<br>187 | (DMSO-d₆ + D₂O) δ ppm: 9.60 (s, 1H), 8.54 (s, 1H), 8.48 (d, J = 8.5 Hz, 1H), 8.15 (s, 1H), 8.03 (dd, J = 8.5, 1.5 Hz, 1H), 7.42 (t, J = 7.8 Hz, 1H), 7.09-6.92 (m, 3H), 4.51 (s, 2H), 3.49-3.33 (m, 2H), 3.26 (s, 1H), 3.18-3.00 (m, 2H), 2.16-2.00 (m, 2H), 1.94-1.69 (m, 2H). | 334.2 |
| | 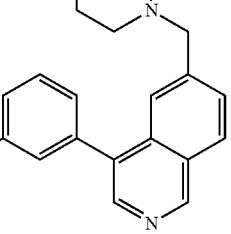<br>188 | (DMSO-d₆ + D₂O) δ ppm: 9.51 (s, 1H), 9.01 (s, 1H), 8.68 (s, 1H), 8.41 (d, J = 8.8 Hz, 1H), 8.00 (dd, J = 8.8, 1.2 Hz, 1H), 7.85 (d, J = 8.8 Hz, 1H), 7.80 (d, J = 8.8 Hz, 1H), 7.5 (d, , J = 6.0 Hz, 1H), 7.45 (dd, J = 7.2, 2.0 Hz, 1H), 4.59 (s, 2H), 3.45 (m, 2H), 3.27 (m, H), 3.12 (m, 2H), 2.15-1.89 (m, 4H) | 392.3 |

4-Bromo-6-(pyrrolo[3,2-c]pyridin-1-ylmethyl)isoquinoline

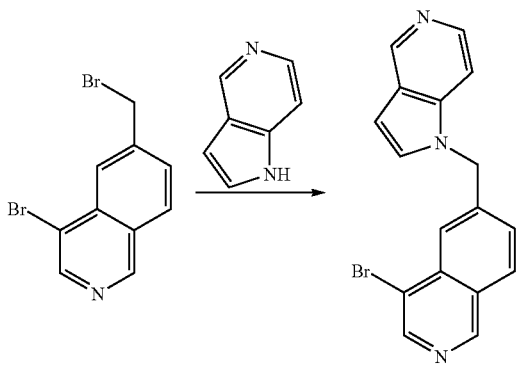

To a solution of 0.05 g of 5-azaindole (CAS: 271-34-1, 0.420 mmol) in 1 mL of THF is added 0.05 g of NaH (60%) (1.27 mmol). The reaction mixture is stirred at 25° C. for 2 h. Then 0.13 g of 4-bromo-6-(bromomethyl)isoquinoline (0.420 mmol) is added, and the reaction mixture was stirred at 25° C. for 16 h. The reaction mixture is quenched with brine and extracted with EA. The combined organic layers are washed with water and brine, and dried over $Na_2SO_4$. After filtration, the filtrate is concentrated in vacuum to give the crude product as light yellow solid. The residue is purified by column chromatography on silica gel eluting with (DCM/MeOH=20/1) to afford the desired product as a yellow solid.

MS (ESI+): 338.0, 340.0 [M+H].

$^1$H NMR (400 MHz, DMSO-$d_6$) δ ppm: 9.28 (s, 1H), 8.88 (d, J=1.2 Hz, 1H), 8.74 (s, 1H), 8.27-8.08 (m, 2H), 7.92-7.78 (m, 1H), 7.71 (d, J=3.2 Hz, 1H), 7.61-7.50 (m, 2H), 6.74 (dd, J=3.2, 0.8 Hz, 1H), 5.79 (d, J=16.2 Hz, 2H).

4-(Benzofuran-2-yl)-6-(pyrrolo[3,2-c]pyridin-1-ylmethyl)isoquinoline (Example 189)

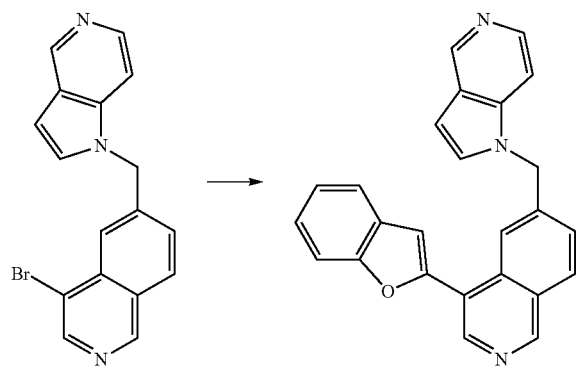 [SMILES: Brc1cncc2ccc(Cn3ccc4cnccc43)cc12 ; c1ccc2oc(-c3cncc4ccc(Cn5ccc6cnccc65)cc34)cc2c1]

To a solution of 0.2 g of 4-bromo-6-(pyrrolo[3,2-c]pyridin-1-ylmethyl)isoquinoline (0.5900 mmol) and 0.29 g of benzofuran-2-boronic acid (CAS: 98437-24-2, 1.77 mmol) in dioxane. (20 mL) and $H_2O$ (1 mL) are added 0.38 g of $K_3PO_4$ (1.77 mmol), 0.061 g of $Pd_2(dba)_3$ (0.0600 mmol), and 0.056 g of 4, 5-bis(diphenylphosphino)-9,9-dimethylxanthene (CAS: 564483-18-7, 0.1200 mmol). The reaction mixture is heated to 90° C. and stirred for 16 h under Ar atmosphere. LCMS shows the desired product is formed. The reaction is diluted with EA, washed with brine and dried over $Na_2SO_4$. After filtration, the filtrate is concentrated in vacuum to give the crude product as a yellow solid. The residue is purified by preparative HPLC to give the product as a light yellow solid.

MS (ESI+): 376.21 [M+H].

$^1$H NMR (400 MHz, DMSO-$d_6$+$D_2O$) δ ppm: 9.40 (s, 1H), 9.28 (s, 1H), 8.91 (s, 1H), 8.43 (d, J=6.8 Hz, 1H), 8.31 (d, J=8.4 Hz, 1H), 8.20 (dd, J=6.8, 1.2 Hz, 1H), 8.13 (d, J=3.2 Hz, 1H), 8.09 (s, 1H), 7.77-7.67 (m, 2H), 7.50 (d, J=8.0 Hz, 1H), 7.46-7.38 (m, 2H), 7.38-7.30 (m, 1H), 7.21 (dd, J=3.6, 0.8 Hz, 1H), 6.00 (s, 2H).

N-[(2-Amino-4-pyridyl)methyl]-4-(benzofuran-2-yl)isoquinolin-6-amine (Example 190)

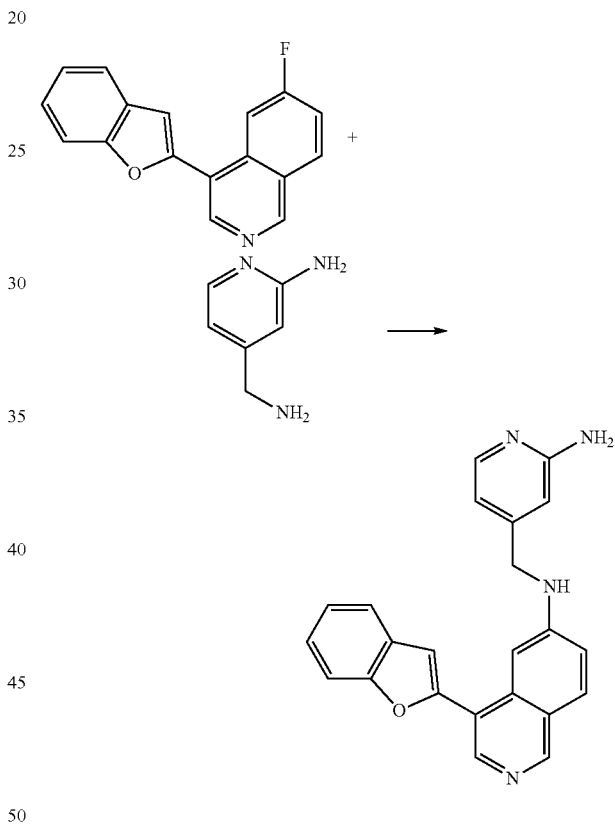

To a solution of 100 mg of 4-(benzofuran-2-yl)-6-fluoroisoquinoline (0.38 mmol) in 1.5 mL of DMSO is added 1.3 g of 4-(aminomethyl)pyridin-2-amine (19 mmol) The mixture is placed in a microwave oven and irradiated under 20 W at 120° C. for 2 hrs. The mixture is diluted with 20 ml EA and washed with 10 ml×10 brine. The organic layer is dried over $Na_2SO_4$, filtered and concentrated to give the crude product which is purified by DCM/MeOH/$NH_3.H_2O$ (30/1/0.01) to give the product as a yellow solid.

MS (ESI+): 367.2 [M+H].

$^1$H NMR (400 MHz, DMSO-$d_6$+$D_2O$) δ ppm: 8.89 (s, 1H), 8.58 (s, 1H), 7.91 (d, J=8.8 Hz, 1H), 7.81 (d, J=5.2 Hz, 1H), 7.73-7.63 (m, 1H), 7.59-7.50 (m, 1H), 7.40-7.25 (m, 2H), 7.21 (dd, J=8.8, 2.4 Hz, 1H), 6.99-6.93 (m, 1H), 6.91 (s, 1H), 6.51 (dd, J=5.3, 1.5 Hz, 1H), 6.45 (s, 1H), 4.28 (s, 2H).

223

4-(Benzofuran-2-yl)-6-(pyrrolo[2,3-c]pyridin-1-ylmethyl)isoquinoline (Example 191)

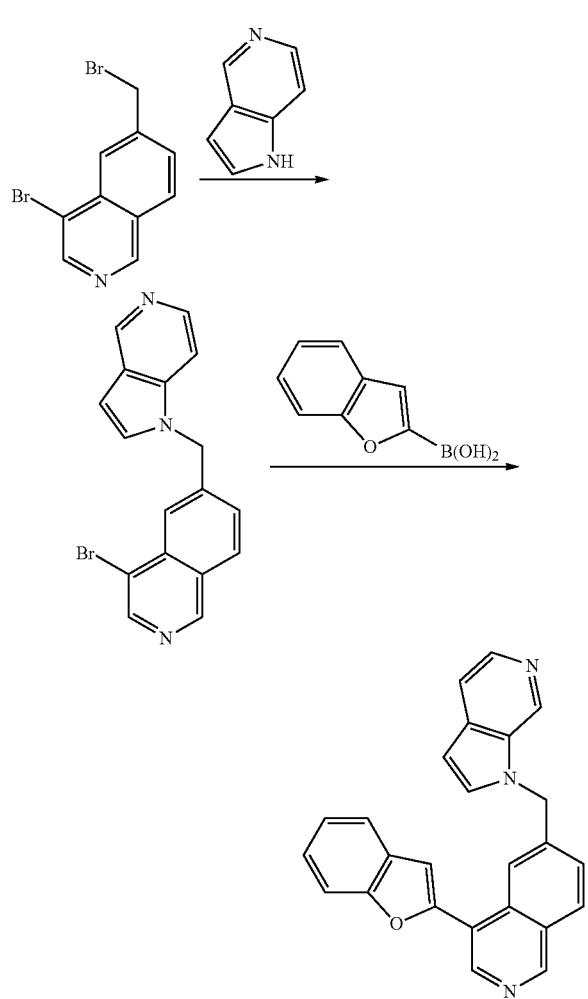

To a suspension of 120 mg of 60% NaH (3 mmol) in 1 mL of anhydrous DMF is added a solution of 118 mg of 6-azaindole (1 mmol) in 2 mL of anhydrous DMF. The mixture is stirred at 30° C. for 3 min. Then a solution of 299 mg of 4-bromo-6-(bromomethyl)isoquinoline (1 mmol) in 2 mL of DMF is added. After being stirred at 30° C. for 1.5 hr., LCMS shows the formation of the product. Water is added to quench the reaction. The mixture is extracted with EA and washed with brine. The organic layer is dried over Na$_2$SO$_4$, filtered and concentrated to give a black brown solid which is purified by column chromatography eluting with PE/EA (1/1) to EA to give 40 mg of 4-bromo-6-(pyrrolo[2,3-c]pyridin-1-ylmethyl)isoquinoline as a white solid.

This intermediate is treated with K$_3$PO$_4$/Pd$_2$(dba)$_3$ in Diox. and H$_2$O as described above to provide 43 mg of 4-(benzofuran-2-yl)-6-(pyrrolo[2,3-c]pyridin-1-ylmethyl) isoquinoline as a light yellow solid.

MS (ESI+): 376.2 [M+H].

$^1$H NMR (400 MHz, DMSO-d$_6$+D$_2$O) δ ppm: 9.36 (d, J=8.0 Hz, 2H), 8.90 (s, 1H), 8.48 (d, J=2.8 Hz, 1H), 8.34-8.24 (m, 2H), 8.20 (d, J=6.4 Hz, 1H), 8.09 (s, 1H), 7.77-7.65 (m, 2H), 7.51 (d, J=8.4 Hz, 1H), 7.46-7.28 (m, 3H), 7.11 (d, J=2.8 Hz, 1H), 6.04 (s, 2H).

224

4-Bromo-6-[(5-nitroindol-1-yl)methyl]isoquinoline

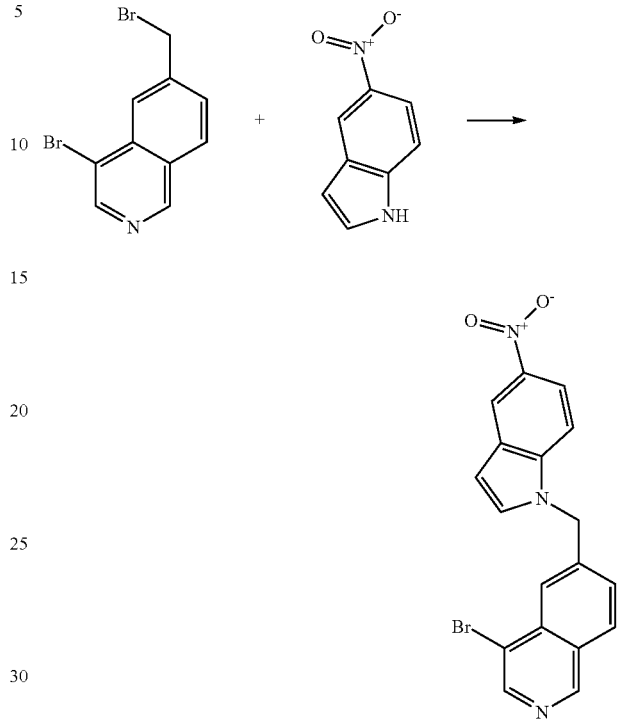

The compound is prepared in analogy to methods described above, starting from 5-nitroindole to give 120 mg of 4-bromo-6-[(5-nitroindol-1-yl)methyl]isoquinoline as a yellow solid.

MS (ESI+): 382.0, 384.0 [M+H].

$^1$H NMR (400 MHz, DMSO-d$_6$) δ 9.24 (s, 1H), 8.69 (s, 1H), 8.62 (d, J=2.4 Hz, 1H), 8.17 (d, J=8.8Hz, 1H), 7.99 (dd, J=9.2, 2.4 Hz, 1H), 7.86-7.75 (m, 2H), 7.66 (d, J=9.0 Hz, 1H), 7.57 (dd, J=8.4, 2.4 Hz, 1H), 6.89 (d, J=3.2 Hz, 1H).

1-[[4-(Benzofuran-2-yl)-6-isoquinolyl]methyl]indol-5-amine (Example 192)

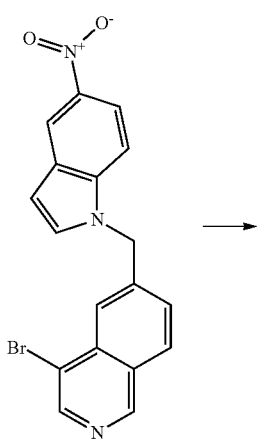

225
-continued

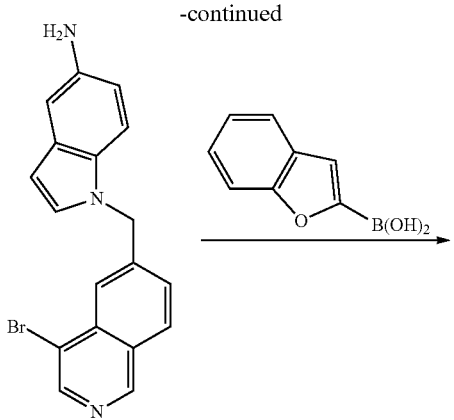

226

To a solution of 145 mg of 4-bromo-6-[(5-nitroindol-1-yl)methyl]isoquinoline (0.38 mmol) in 6 mL of EtOH and 6 mL of $H_2O$ are added 64 mg of Fe powder (1.14 mmol) and 70 mg of $NH_4Cl$ (1.14 mmol). The mixture is stirred at 100° C. for 8 hrs. After filtration to remove the brown solid, the filtrate is concentrated to dryness, taken in EA and washed with saturated $Na_2CO_3$ aq. solution and brine. The organic layer is dried over $Na_2SO_4$ and concentrated to give a brown solid, which is used in the next step without further purification.

This intermediate is treated with $K_3PO_4$/$Pd_2(dba)_3$ in Diox. and $H_2O$ as described above to provide 110 mg of 1-[[4-(benzofuran-2-yl)-6-isoquinolyl]methyl]indol-5-amine as a light yellow solid.

MS (ESI+): 390.2 [M+H].

$^1$H NMR (400 MHz, DMSO-$d_6$+$D_2O$) δ ppm: 9.37 (s, 1H), 8.90 (s, 1H), 8.27 (d, J=8.4 Hz, 1H), 8.02 (s, 1H), 7.78-7.69 (m, 2H), 7.70-7.57 (m, 3H), 7.56-7.49 (m, 1H), 7.47-7.39 (m, 1H), 7.37-7.29 (m, 1H), 7.25 (d, J=0.8 Hz, 1H), 7.07 (dd, J=8.8, 2.4 Hz, 1H), 6.68 (dd, J=3.2, 0.8 Hz, 1H), 5.81 (s, 2H).

The following examples were prepared accordingly to Example 1 by reaction of tert-butyl N-[1-[(4-bromo-6-isoquinolyl)methyl]-4-piperidyl]carbamate with the corresponding boronic acid or boronic acid ester in the presence of a Pd-catalyst and subsequent deprotection:

| Example | $^1$H NMR (400 MHz) δ ppm | MS (+ESI) [M + H]$^+$ |
|---|---|---|
| 193 | ((DMSO-$d_6$ + $D_2O$)) 9.78 (s, 1H), 9.55 (s, 1H), 8.68 (s, 1H), 8.67 (d, J = 6.4 Hz, 1H), 8.59 (d, J = 8.8 Hz, 1H), 8.45 (s, 1H), 8.44 (d, J = 8.4 Hz, 1H), 8.37 (d, J = 6.4 Hz, 1H), 8.14 (d, J = 8.4 Hz, 1H), 8.04 (s, 1H), 7.88 (d, J = 8.4 Hz, 1H), 4.45 (s, 2H), 3.38 (m, 2H), 3.24 (m, 1H), 3.03 (m, 2H), 2.07 (m, 2H), 1.69 (m, 2H) | 369.25 |
| 194 | (DMSO-$d_6$ + $D_2O$) 9.70 (s, 1H), 9.54 (s, 1H), 8.68 (s, 1H), 8.67 (d, J = 5.6 Hz, 1H), 8.59 (s, 1H), 8.44 (d, J = 8.4 Hz, 1H), 8.39-8.34 (m, 2H), 8.26 (d, J = 8.8 Hz, 1H), 8.05 (s, 1H), 7.87 (d, J = 8.4 Hz, 1H), 4.45 (s, 2H), 3.40 (m, 2H), 3.24 (m, 1H), 3.06 (m, 2H), 2.07 (m, 2H), 1.69 (m, 2H). | 369.25 |

-continued

| Example | ¹H NMR (400 MHz) δ ppm | MS (+ESI) [M + H]⁺ |
|---|---|---|
| 195 | (DMSO-d₆ + D₂O) 9.53 (s, 1H), 9.06 (d, J = 4.4 Hz, 1H), 8.66 (s, 1H), 8.64 (d, J = 8.0 Hz, 1H), 8.43 (d, J = 8.4 Hz, 1H), 8.30 (d, J = 8.0 Hz, 1H), 8.26 (s, 1H), 8.08-8.06 (m, 2H), 7.87 (d, J = 8.4 Hz, 1H), 7.76 (m, 1H), 4.46 (s, 2H), 3.37 (m, 2H), 3.23 (m, 1H), 3.03 (m, 2H), 2.07 (m, 2H), 1.68 (m, 2H) | 369.25 |
| 196 | (DMSO-d₆ + D₂O) 9.70 (s, 1H), 9.20 (d, J = 4.8 Hz, 1H), 8.99 (d, J = 8.4 Hz, 1H), 8.75 (s, 1H), 8.54 (d, J = 8.4 Hz, 1H), 8.43 (d, J = 9.6 Hz, 1H), 8.42 (s, 1H), 8.18 (s, 1H), 8.09-8.06 (m, 2H), 7.97 (m, 1H), 4.49 (s, 2H), 3.40 (m, 2H), 3.26 (m, 1H), 3.06 (m, 2H), 2.07 (m, 2H), 1.83 (m, 2H). | 369.25 |
| 197 | (DMSO-d₆ + D₂O) 9.50 (s, 1H), 8.47 (s, 1H), 8.38 (d, J = 8.4 Hz, 1H), 7.89-7.77 (m, 2H), 7.68-7.59 (m, 2H), 7.55 (d, J = 8.4 Hz, 1H), 4.52-4.36 (m, 2H), 3.48-3.19 (m, 3H), 3.13-2.92 (m, 2H), 2.13-1.98 (m, 2H), 1.82-1.57 (m, 2H). | 386.2, 388.1 |
| 198 | (DMSO-d₆ + D₂O) 9.27 (s, 1H), 8.39 (s, 1H), 8.27 (s, 1H, HCOOH), 8.18 (d, J = 8.4 Hz, 1H), 7.75 (s, 1H), 7.66 (dd, J = 8.4 Hz, 1.2 Hz, 1H), 7.49 (dd, J = 8.4 Hz, 8.4 Hz, 1H), 7.13-7.02 (m, 3H), 3.81 (s, 3H), 3.62 (s, 2H), 3.01-2.90 (m, 1H), 2.85-2.75 (m, 2H), 2.09-1.96 (m, 2H), 1.89-1.75 (m, 2H), 1.55-1.39 (m, 2H). | 348.2 |

| Example | ¹H NMR (400 MHz) δ ppm | MS (+ESI) [M + H]⁺ |
|---|---|---|
| 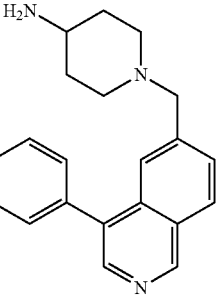<br>199 | (DMSO-d₆ + D₂O) 9.56 (s, 1H), 8.53 (s, 1H), 8.46 (d, J = 8.4 Hz, 1H), 8.16 (s, 1H), 8.00 (d, J = 8.4, 1H), 7.20 (d, J = 1.2 Hz, 1H), 7.17-7.05 (m, 2H), 6.12 (s, 2H), 4.51 (s, 2H), 3.49-3.33 (m, 2H), 3.33-3.21 (m, 1H), 3.19-2.98 (m, 2H), 2.15-1.99 (m, 2H), 1.94-1.71 (m, 2H). | 362.3 |
| 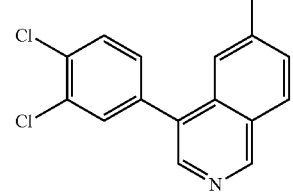<br>200 | (DMSO-d₆ + D₂O) 9.47 (s, 1H), 8.54 (s, 1H), 8.38 (d, J = 8.4 Hz, 1H), 7.99 (s, 1H), 7.91-7.79 (m, 3H), 7.59 (dd, J = 8.4 Hz, 2.0 Hz, 1H), 4.47 (s, 2H), 3.50-3.32 (m, 2H), 3.31-3.19 (m, 1H), 3.16-2.95 (m, 2H), 2.12-1.98 (m, 2H), 1.84-1.60 (m, 2H). | 386.2, 388.1 |
| 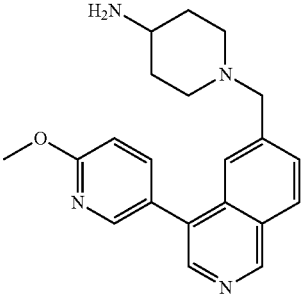<br>201 | (DMSO-d₆ + D₂O) 9.29 (s, 1H), 8.39 (s, 1H), 8.31 (d, J = 2.4 Hz, 1H), 8.27 (s, 1H, HCOOH), 8.19 (d, J = 8.8 Hz, 1H), 7.91 (dd, J = 8.4 Hz, 2.4 Hz, 1H), 7.74-7.63 (m, 2H), 7.03 (d, J = 8.4 Hz, 1H), 3.94 (s, 3H), 3.63 (s, 2H), 3.03-2.89 (m, 1H), 2.82-2.79 (m, 2H), 2.11-1.94 (m, 2H), 1.89-1.75 (m, 2H), 1.57-1.39 (m, 2H). | 349.2 |
| 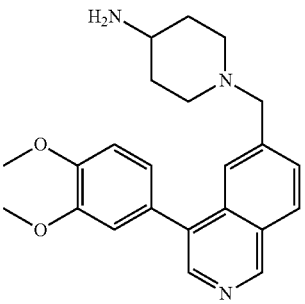<br>202 | (DMSO-d₆ + D₂O) 9.45 (s, 1H), 8.54 (s, 1H), 8.38 (d, J = 8.4 Hz, 1H), 8.13 (s, 1H), 7.83 (dd, J = 8.4 Hz, 1.2 Hz, 1H), 7.23-7.08 (m, 3H), 4.49 (s, 2H), 3.85 (s, 3H), 3.80 (s, 3H), 3.55-3.34 (m, 2H), 3.31-3.19 (m, 1H), 3.18-2.98 (m, 2H), 2.13-1.98 (m, 2H), 1.84-1.59 (m, 2H). | 378.3 |

| Example | ¹H NMR (400 MHz) δ ppm | MS (+ESI) [M + H]⁺ |
|---|---|---|
| 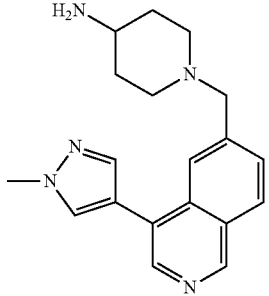<br>203 | (DMSO-d₆ + D₂O) 9.43 (s, 1H), 8.60 (s, 1H), 8.43-8.34 (m, 2H), 8.23 (s, 1H), 7.95 (s, 1H), 7.87 (dd, J = 8.4 Hz, 1.6 Hz, 1H), 4.54 (s, 2H), 3.97 (s, 3H), 3.53-3.35 (m, 2H), 3.34-3.22 (m, 1H), 3.20-3.00 (m, 2H), 2.16-1.98 (m, 2H), 1.84-1.60 (m, 2H). | 322.3 |
| 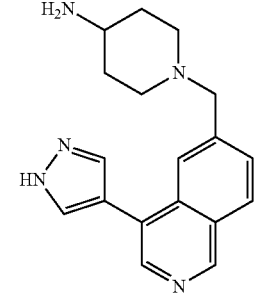<br>204 | (DMSO-d₆ + D₂O) 9.42 (s, 1H), 8.64 (s, 1H), 8.42-8.33 (m, 2H), 8.16 (s, 2H), 7.86 (dd, J = 8.4 Hz, 1.6 Hz, 1H), 7.79 (s, 1H), 4.55 (s, 2H), 3.51-3.36 (m, 2H), 3.33-3.21 (m, 1H), 3.19-3.01 (m, 2H), 2.14-2.04 (m, 2H), 1.80-1.61 (m, 2H). | 308.2 |

The following examples were prepared accordingly to Example 51 by reaction of 4-bromo-6-(bromomethyl)isoquinoline with the corresponding amines followed by coupling with benzofuran-2-boronic acid in the presence of a Pd-catalyst and subsequent deprotection:

| Example | ¹H NMR (400 MHz) δ ppm | MS (+ESI) [M + H]⁺ |
|---|---|---|
| 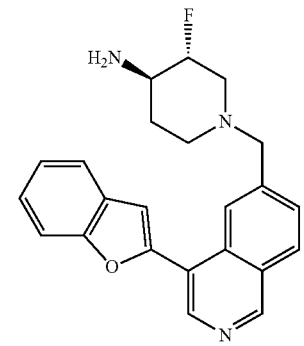<br>205 | (DMSO-d₆ + D₂O) 9.49 (s, 1H), 8.98 (s, 1H), 8.58 (s, 1H), 8.39 (d, J = 8.4 Hz, 1H), 7.89-7.71 (m, 3H), 7.62 (s, 1H), 7.46-7.34 (m, 2H), 4.85-4.66 (m, 1H), 4.41 (s, 2H), 3.61-2.80 (m, 5H), 2.17-1.69 (m, 2H). | 376.3 |

| Example | $^1$H NMR (400 MHz) δ ppm | MS (+ESI) [M + H]$^+$ |
|---|---|---|
| 206 | (DMSO-d$_6$ + D$_2$O) 9.52 (s, 1H), 9.01 (s, 1H), 8.70 (s, 1H), 8.43 (d, J = 8.4 Hz, 1H), 7.98 (d, J = 8.4 Hz, 1H), 7.81-7.74 (m, 2H), 7.69 (s, 1H), 7.46-7.34 (m, 2H), 5.24-5.12 (m, 1H), 4.63 (s, 2H), 3.74-3.20 (m, 5H), 2.08 (m, 2H). | 376.3 |
| 207 | (DMSO-d$_6$ + D$_2$O) 9.42 (s, 1H), 8.90 (s, 1H), 8.39 (s, 1H), 8.32 (d, J = 8.4 Hz, 1H), 7.80 (dd, J = 8.4 Hz, 1.2 Hz, 1H), 7.72 (d, J = 6.8 Hz, 1H), 7.56 (d, J = 8.0 Hz, 1H), 7.42-7.25 (m, 4H), 7.08-7.06 (m, 1H), 6.66-6.57 (m, 2H), 4.84 (ABq, J = 18.0 Hz, 2H), 4.42 (t, J = 4.4 Hz, 1H), 3.55-3.49 (m, 2H), 2.14-2.11 (m, 2H). | 406.1 |

The following examples were prepared accordingly to Example 60 by reaction of (4-bromo-6-(bromomethyl)isoquinoline with the corresponding Boc-protected amino-pyridine derivatives, Suzuki-Miyaura reaction with the corresponding boronic acid and deprotection:

| Example | $^1$H NMR (400 MHz) δ ppm | MS (+ESI) [M + H]$^+$ |
|---|---|---|
| 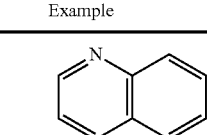 208 | (DMSO-d$_6$ + D$_2$O) 9.45 (s, 1H), 8.77 (s, 1H), 8.59 (d, J = 8.0 Hz, 1H), 8.49 (s, 1H), 8.43 (d, J = 7.2 Hz, 1H), 8.38 (d, J = 8.4 Hz, 1H), 8.01 (m, 1H), 7.91 (m, 2H), 7.80 (m, 1H), 7.67 (d, J = 1.6 Hz, 1H), 7.11 (d, J = 3.6 Hz, 1H), 6.85 (d, J = 7.2 Hz, 1H), 6.66 (dd, J$_1$ = 3.6 Hz, J$_2$ = 1.6 Hz, 1H), 5.14 (s, 2H). | 352.1 |

| Example | ¹H NMR (400 MHz) δ ppm | MS (+ESI) [M + H]⁺ |
|---|---|---|
| 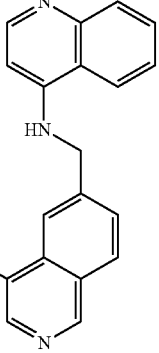<br>209 | (DMSO-d₆ + D₂O) 9.33 (s, 1H), 8.69 (s, 1H), 8.56 (d, J = 8.4 Hz, 1H), 8.41 (m, 2H), 8.32 (d, J = 8.8 Hz, 1H), 8.00 (m, 1H), 7.92 (d, J = 8.0 Hz, 1H), 7.87 (dd, J₁ = 8.4 Hz, J₂ = 1.6 Hz, 1H), 7.80 (m, 1H), 6.90 (d, J = 3.2 Hz, 1H), 6.78 (d, J = 7.2 Hz, 1H), 6.20 (dd, J₁ = 3.2 Hz, J₂ = 0.8 Hz, 1H), 5.12 (s, 2H), 1.92 (s, 3H). | 366.2 |

The following examples were prepared accordingly to Example 81 by reaction of [4-(benzofuran-2-yl)-6-isoquinolyl]trifluoromethanesulfonate with the corresponding amine, followed by the subsequent deprotection:

| Example | ¹H NMR (400 MHz) δ ppm | MS (+ESI) [M + H]⁺ |
|---|---|---|
| 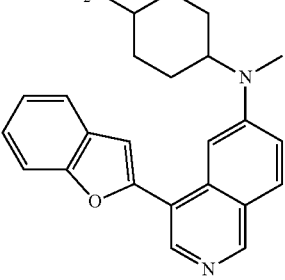<br>210 | (DMSO-d₆ + D₂O) 9.11 (s, 1H), 8.61 (s, 1H), 8.20 (d, J = 9.6 Hz, 1H), 7.79 (d, J = 7.2 Hz, 1H), 7.71 (d, J = 8.8 Hz, 1H), 7.68 (dd, J₁ = 9.6 Hz, J₂ = 2.4 Hz, 1H), 7.60 (s, 1H), 7.45-7.34 (m, 3H), 3.99-3.98 (m, 1H), 3.08-3.07 (m, 1H), 3.01 (s, 3H), 2.05-2.03 (m, 2H), 1.81-1.73 (m, 4H), 1.58-1.48 (m, 2H). | 372.4 |
| 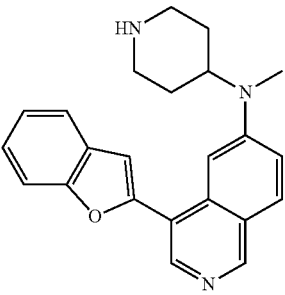<br>211 | (DMSO-d₆ + D₂O) 9.18 (s, 1H), 8.64 (s, 1H), 8.27 (d, J = 9.6 Hz, 1H), 7.81-7.79 (m, 2H), 7.72 (d, J = 8.4 Hz, 1H), 7.66 (s, 1H), 7.49-7.34 (m, 3H), 4.44-4.39 (m, 1H), 3.44-3.40 (m, 2H), 3.11-3.08 (m, 2H), 3.03 (s, 3H), 2.07-1.90 (m, 4H). | 358.3 |

| Example | ¹H NMR (400 MHz) δ ppm | MS (+ESI) [M + H]⁺ |
|---|---|---|
| 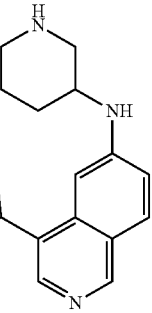 212 | (DMSO-d₆ + D₂O) 9.18 (s, 1H), 8.63 (s, 1H), 8.25 (d, J = 9.6 Hz, 1H), 7.80 (d, J = 8.0 Hz, 1H), 7.72 (d, J = 8.0 Hz, 1H), 7.60 (s, 1H), 7.48-7.35 (m, 4H), 3.98-3.93 (m, 1H), 3.45-3.41 (m, 1H), 3.27-3.22 (m, 1H), 2.94-2.83 (m, 2H), 2.12-1.94 (m, 2H), 1.78-1.55 (m, 2H). | 344.3 |
| 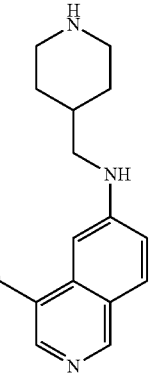 213 | (DMSO-d₆ + D₂O) 9.08 (s, 1H), 8.58 (s, 1H), 8.16 (d, J = 9.6 Hz, 1H), 7.79 (d, J = 7.2 Hz, 1H), 7.70 (d, J = 8.8 Hz, 1H), 7.58 (s, 1H), 7.46-7.32 (m, 4H), 3.30-3.23 (m, 4H), 2.90-2.83 (m, 2H), 1.92-1.89 (m, 3H), 1.43-1.34 (m, 2H). | 358.3 |
| 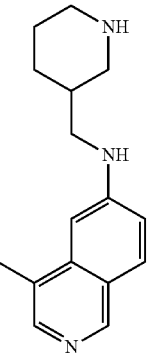 214 | (DMSO-d₆ + D₂O) 9.15 (s, 1H), 8.61 (s, 1H), 8.20 (d, J = 9.6 Hz, 1H), 7.79 (d, J = 7.2 Hz, 1H), 7.72 (d, J = 8.8 Hz, 1H), 7.61 (s, 1H), 7.46-7.35 (m, 4H), 3.34-3.22 (m, 4H), 2.82-2.68 (m, 2H), 2.10-2.08 (m, 1H), 1.85-1.82 (m, 2H), 1.61-1.58 (m, 1H), 1.30-1.26 (m, 1H). | 358.3 |

The following examples were prepared accordingly to Example 91 by reaction of tert-butyl N-[4-bromo-6-(bromomethyl)-1-isoquinolyl]-N-tert-butoxycarbonyl-carbamate with tert-butyl piperazine-1-carboxylate or tert-butyl N-(4-piperidyl)carbamate and then reaction with the corresponding boronic acid or boronic acid ester in the presence of a Pd-catalyst and subsequent deprotection:

| Example | ¹H NMR (400 MHz, DMSO-d₆ + D₂O) δ ppm | MS (+ESI) [M + H]⁺ |
|---|---|---|
| 215 (4-(4-chlorophenyl)-7-((4-aminopiperidin-1-yl)methyl)isoquinolin-1-amine) | 8.69 (d, J = 8.6 Hz, 1H), 7.99 (dd, J = 8.6 Hz, 1.7 Hz, 1H), 7.87 (d, J = 1.6 Hz, 1H), 7.67 (s, 1H), 7.62-7.50 (m, 2H), 7.56-7.54 (m, 2H), 4.43 (s, 2H), 3.38-3.36 (m, 2H), 3.26-3.24 (m, 1H), 3.04-3.02 (m, 2H), 2.09-2.06 (m, 2H), 1.86-1.83 (m, 2H). | 367.3, 369.3 |
| 216 (4-(3-chlorophenyl) analog) | 8.71 (d, J = 8.6 Hz, 1H), 8.02 (d, J = 8.8 Hz, 1H), 7.86 (s, 1H), 7.72 (s, 1H), 7.64-7.55 (m, 3H), 7.56-7.46 (m, 1H), 4.44 (s, 2H), 3.38-3.37 (m, 2H), 3.24 (m, 1H), 3.03-3.01 (m, 2H), 2.07 (m, 2H), 1.87-1.85 (m, 2H). | 367.3, 369.2 |
| 217 (4-(3,4-dichlorophenyl) analog) | 8.64 (d, J = 8.4 Hz, 1H), 7.89-7.77 (m, 4H), 7.72 (s, 1H), 7.49 (dd, J₁ = 8.4 Hz, J₂ = 2.1 Hz, 1H), 4.40 (s, 2H), 3.36-3.34 (m, 2H), 3.25-3.23 (m, 1H), 3.00-2.98 (m, 2H), 2.07-2.04 (m, 2H), 1.71-1.68 (m, 2H). | 401.3, 403.3 |
| 218 (4-(3,5-dichlorophenyl) analog) | 8.64 (d, J = 8.8 Hz, 1H), 7.85 (dd, J = 8.8 Hz, 1.6 Hz, 1H), 7.79 (d, J = 1.6 Hz, 1H), 7.75-7.74 (m, 2H), 7.57 (d, J = 1.6 Hz, 2H), 4.42 (s, 2H), 3.38-3.36 (m, 2H), 3.26-3.24 (m, 1H), 3.01-3.00 (m, 2H), 2.07-2.03 (m, 2H), 1.72-1.69 (m, 2H). | 401.3, 403.3 |

-continued
| Example | $^1$H NMR (400 MHz, DMSO-d$_6$ + D$_2$O) δ ppm | MS (+ESI) [M + H]$^+$ |
|---|---|---|
| 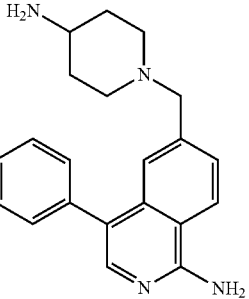<br>219 | 8.64 (d, J = 8.4 Hz, 1H), 7.85 (d, J = 8.8 Hz, 1H), 7.82 (s, 1H), 7.66 (s, 1H), 7.55-7.52 (m, 2H), 7.40-7.36 (m, 2H), 4.37 (s, 2H), 3.31-3.23 (m, 3H), 2.97-2.95 (m, 2H), 2.06-2.03 (m, 2H), 1.69-1.67 (m, 2H). | 351.3 |
| 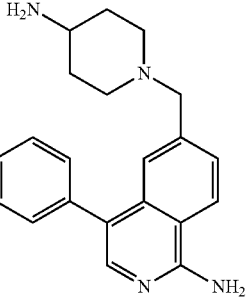<br>220 | 8.67 (d, J = 8.8 Hz, 1H), 7.89-7.87 (m, 2H), 7.70 (s, 1H), 7.63-7.58 (m, 1H), 7.39-7.33 (m, 3H), 4.44 (s, 2H), 3.38-3.36 (m, 2H), 3.26-3.24 (m, 1H), 3.03-3.01 (m, 2H), 2.07-2.05 (m, 2H), 1.71-1.69 (m, 2H). | 351.3 |
| 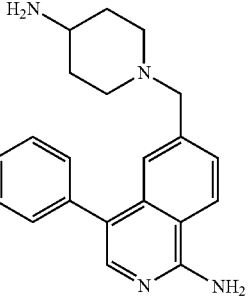<br>221 | 8.63 (d, J = 7.6 Hz, 1H), 7.86-7.83 (m, 2H), 7.68 (d, J = 2.4 Hz, 1H), 7.62-7.55 (m, 2H), 7.35-7.31 (m, 1H, 4.39 (s, 2H), 3.33-3.31 (m, 2H), 3.35-3.23 (m, 1H), 2.99-2.97 (m, 2H), 2.07-2.04 (m, 2H), 1.71-1.68 (m, 2H). | 369.3 |
| 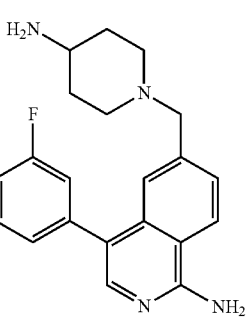<br>222 | 8.66 (d, J = 8.8 Hz, 1H), 7.89-7.86 (m, 2H), 7.74 (s, 1H), 7.41-7.35 (m, 1H), 7.30-7.25 (m, 2H), 4.44 (s, 2H), 3.38-3.36 (m, 2H), 3.26-3.24 (m, 1H), 3.03-3.01 (m, 2H), 2.07-2.04 (m, 2H), 1.72-1.70 (m, 2H). | 369.4 |

| Example | ¹H NMR (400 MHz, DMSO-d₆ + D₂O) δ ppm | MS (+ESI) [M + H]⁺ |
|---|---|---|
| 223 | 8.60 (d, J = 8.6 Hz, 1H), 8.28 (s, 1H), 8.06 (s, 1H), 7.89 (d, J = 8.8 Hz, 1H), 7.75 (d, J = 8.0 Hz, 1H), 7.66 (d, J = 8.0 Hz, 1H), 7.42 (s, 1H), 7.42-7.32 (m, 2H), 4.07 (s, 2H), 3.17 (brs, 4H), 2.88 (brs, 4H). | 359.2 | tert-Butyl 4-[[4-(benzofuran-2-yl)-6-isoquinolyl]methyl]piperazine-1-carboxylate

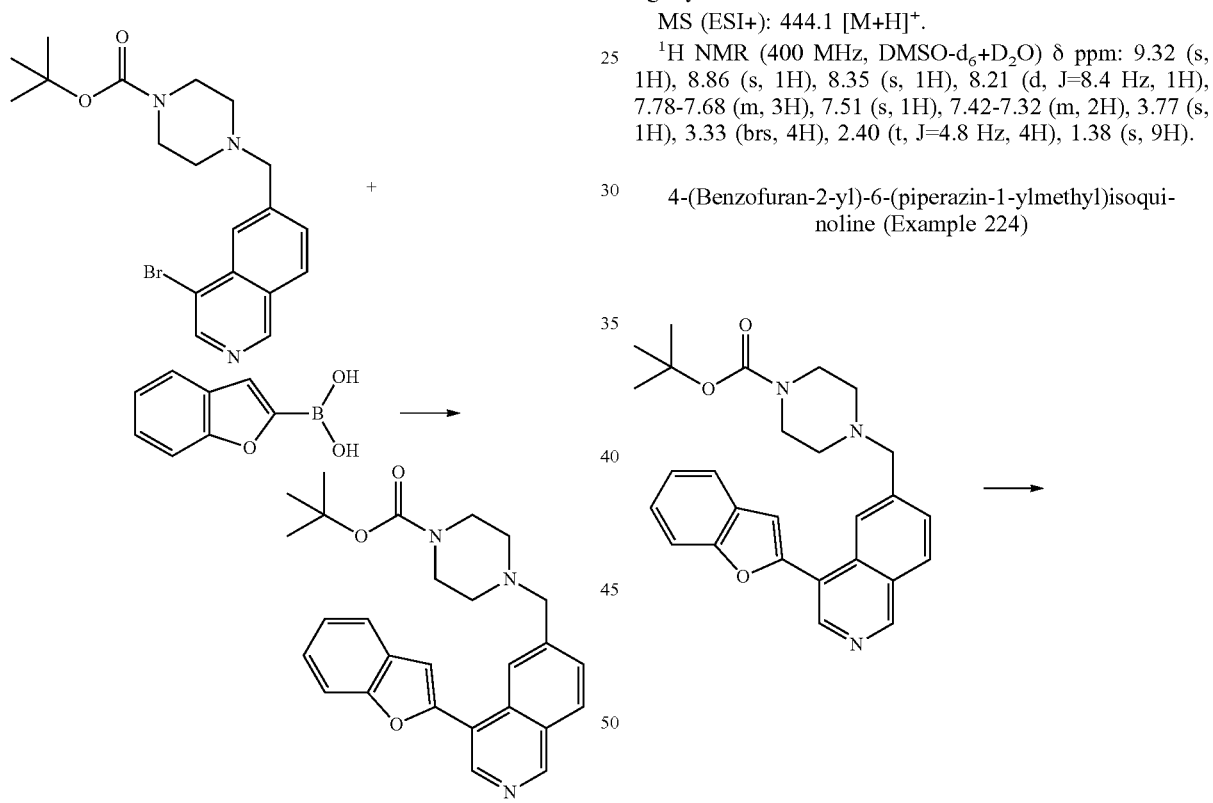

Under argon atmosphere, to a mixture of 390 mg (0.76 mmol) of tert-butyl 4-[(4-bromo-6-isoquinolyl)methyl]piperazine-1-carboxylate (prepared as described for tert-butyl N-[1-[(4-bromo-6-isoquinolyl)methyl]-4-piperidyl]carbamate), 185 mg (1.14 mmol) of benzofuran-2-boronic acid, 323 mg (1.52 mmol) of K₃PO₄ in a mixture of 5 mL of dioxane and 0.6 mL of water, 70 mg (0.076 mmol) of Pd(PPh₃)₄ were added. The mixture was stirred at 90° C. for 18 h. Then the reaction mixture was diluted with EtOAc, washed with water and brine, dried over Na₂SO₄ and filtered. The filtrate was concentrated under reduced pressure and the residue was purified by silica gel column chromatography (PE/EA=2/1) to afford 350 mg of tert-butyl 4-[[4-(benzofuran-2-yl)-6-isoquinolyl]methyl]piperazine-1-carboxylate as a light yellow oil.

MS (ESI+): 444.1 [M+H]⁺.

¹H NMR (400 MHz, DMSO-d₆+D₂O) δ ppm: 9.32 (s, 1H), 8.86 (s, 1H), 8.35 (s, 1H), 8.21 (d, J=8.4 Hz, 1H), 7.78-7.68 (m, 3H), 7.51 (s, 1H), 7.42-7.32 (m, 2H), 3.77 (s, 1H), 3.33 (brs, 4H), 2.40 (t, J=4.8 Hz, 4H), 1.38 (s, 9H).

4-(Benzofuran-2-yl)-6-(piperazin-1-ylmethyl)isoquinoline (Example 224)

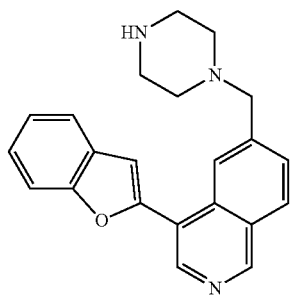

353 mg (0.745 mmol) of tert-butyl 4-[[4-(benzofuran-2-yl)-6-isoquinolyl]methyl]piperazine-1-carboxylate was suspended in a solution of 20 mL of 1N HCl in EtOAc. The mixture was stirred at 25° C. for 18 h. The yellow solid was collected by centrifugation and dried under vacuum to give 360 mg of 4-(benzofuran-2-yl)-6-(piperazin-1-ylmethyl)isoquinoline as a yellow solid.

MS (ESI+): 344.2 [M+H]+.

$^1$H NMR (400 MHz, DMSO-d$_6$+D$_2$O) δ ppm: 9.58 (s, 1H), 9.04 (s, 1H), 8.74 (s, 1H), 8.47 (d, J=8.8 Hz, 1H), 8.05 (d, J=8.4 Hz, 1H), 7.84-7.78 (m, 3H), 7.50-7.38 (m, 2H), 4.60 (s, 2H), 3.37 (m, 8H).

The following examples were prepared accordingly to Example 224 by reaction of tert-butyl 4-[(4-bromo-6-isoquinolyl)methyl]piperazine-1-carboxylate with the corresponding boronic acid in the presence of a Pd-catalyst and subsequent deprotection:

| Example | $^1$H NMR (400 MHz) δ ppm | MS (+ESI) [M + H]+ |
|---|---|---|
| 225 | (DMSO-d$_6$ + D$_2$O) 9.47 (s, 1H), 8.81 (s, 1H), 8.60 (s, 1H), 8.41 (d, J = 8.4 Hz, 1H), 7.96 (m, 2H), 7.28 (s, J = 3.2 Hz, 1H), 6.79 (dd, J = 3.2 Hz, 1.6 Hz, 1H), 4.38 (s, 2H), 3.28 (brs, 4H), 3.16 (brs, 4H). | 294.1 |
| 226 | (DMSO-d$_6$ + D$_2$O) 9.51 (s, 1H), 8.81 (s, 1H), 8.69 (s, 1H), 8.45 (d, J = 8.4 Hz, 1H), 8.03 (d, J = 8.4 Hz, 1H), 7.28 (d, J = 3.6 Hz, 1H), 6.43 (dd, J = 3.2 Hz, 0.8 Hz, 1H), 4.53 (s, 2H), 3.35 (brs, 4H), 3.27 (brs, 4H), 2.45 (s, 3H). | 308.2 |

1-[[4-(1,3-Benzothiazol-2-yl)-6-isoquinolyl]methyl]piperidin-4-amine (Example 227)

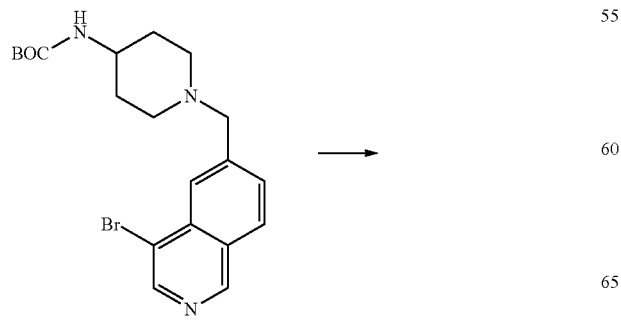

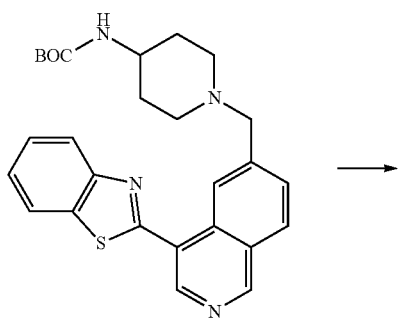

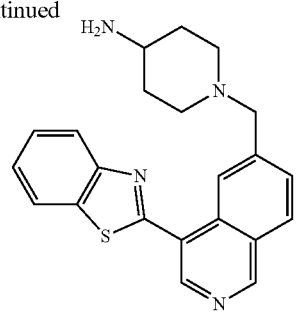

To a solution of 0.42 g (1.01 mmol) of tert-butyl N-[1-[(4-bromo-6-isoquinolyl)methyl]-4-piperidyl]carbamate in 10 mL of toluene were added 0.232 g (1.68 mmol) of K$_2$CO$_3$, 2 mg (0.008 mmol) of Pd(OAc)$_2$, 34 mg (0.168 mmol) of copper(II) acetate monohydrate, 114 mg (0.84 mmol) of 1,3-benzothiazole and 110 mg (0.420 mmol) of PPh₃. The resulting mixture was stirred at 110° C. for 24 h under air atmosphere. The undissolved solid was filtered off and the filtrate was concentrated to dryness. The residue was purified by column chromatography over silica gel eluting with PE/EA (1:1, R$_f$=0.12) to give 264 mg of tert-butyl N-[1-[[4-(1,3-benzothiazol-2-yl)-6-isoquinolyl]methyl]-4-piperidyl]carbamate as a light yellow solid.

To a solution of 0.12 g (0.25 mmol) of this intermediate in 10 mL of EtOAc was added 20 mL of 2N HCl in EtOAc, and then the mixture was stirred at 25° C. for 4 h. The solid was collected by filtration, dried under vacuum and purified by preparative HPLC (TFA) to give 160 mg of 1-[[4-(1,3-benzothiazol-2-yl)-6-isoquinolyl]methyl]piperidin-4-amine as a yellow solid.

MS (ESI+): 375.2 [M+H]⁺.

¹H NMR (400 MHz, DMSO-d₆+D₂O) δ ppm: 9.56 (s, 1H), 9.03 (2s, 2H), 8.42 (d, J=8.4 Hz, 1H), 8.22 (2d, J=7.2 Hz, 2H), 7.90 (d, J=8.4 Hz, 1H), 7.68-7.57 (m, 2H), 4.55 (s, 2H), 3.54-3.38 (m, 2H), 3.34-3.22 (m, 1H), 3.21-3.01 (m, 2H), 2.15-2.00 (m, 2H), 1.84-1.57 (m, 2H).

The following examples were prepared accordingly to Example 227 by reaction of tert-butyl N-[1-[(4-bromo-6-isoquinolyl)methyl]-4-piperidyl]carbamate with 1,3-benzoxazole in the presence of a Pd-catalyst and subsequent deprotection:

¹H NMR (400 MHz, CDCl₃) δ ppm: 9.16 (s, 1H), 8.75 (s, 1H), 8.04 (dd, J=8.8 Hz, 5.6 Hz, 1H), 7.82 (dd, J=10.0 Hz, 2.4 Hz, 1H), 7.46 (ddd, J=10.0 Hz, 8.8 Hz, 2.4 Hz, 1H).

trans-N4-(4-phenyl-6-isoquinolyl)cyclohexane-1,4-diamine (Example 229)

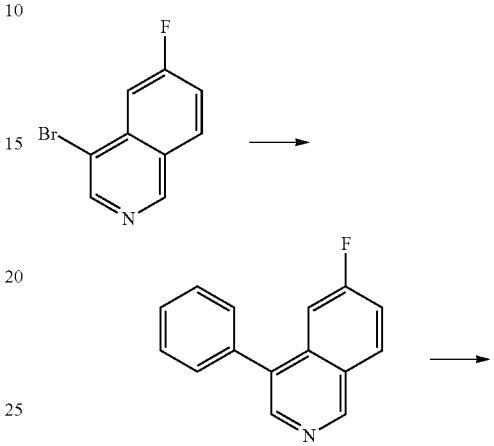

| Example | ¹H NMR (400 MHz) δ ppm | MS (+ESI) [M + H]⁺ |
|---|---|---|
| 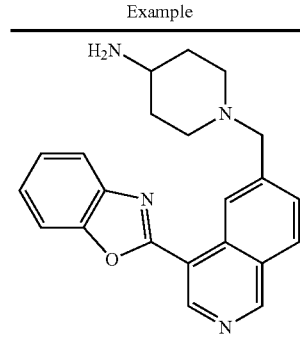 228 | (DMSO-d₆ + D₂O) 9.60 (s, 1H), 9.39 (s, 1H), 9.36 (s, 1H), 8.43 (d, J = 8.4 Hz, 1H), 7.97-7.86 (m, 3H), 7.59-7.46 (m, 2H), 4.62 (s, 2H), 3.59-3.39 (m, 2H), 3.35-3.23 (m, 1H), 3.23-3.07 (m, 2H), 2.16-2.03 (m, 2H), 1.86-1.63 (m, 2H). | 359.2 |

4-Bromo-6-fluoro-isoquinoline

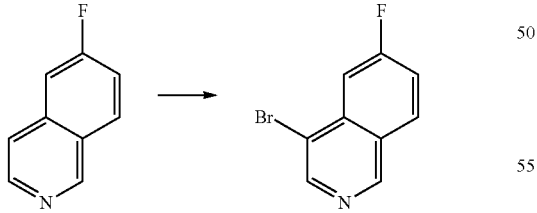

To a solution of 30.0 g (197.76 mmol) of 6-fluoroisoquinoline in 200 mL of AcOH was added 53.9 g (296.64 mmol) of N-bromosuccinimide. Then the mixture was heated to 60° C. for 16 h. The solvent was removed under unreduced pressure and the residue was dissolved in EtOAc, washed with saturated aqueous NaHCO₃ solution, water and brine, dried over anhydrous sodium sulfate and concentrated to dryness. The residue was purified by silica gel column chromatography (PE:EA=5:1, R$_f$=0.3) to give 15.5 g of 4-bromo-6-fluoro-isoquinoline as a white solid.

MS (ESI+): 226.1, 228.1 [M+H]⁺.

-continued

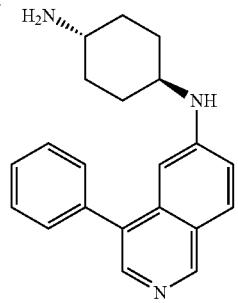

To a solution of 2.0 g (8.85 mmol) of 4-bromo-6-fluoro-isoquinoline in 20 mL of DMF and 2 mL of H₂O were added 1.62 g (13.27 mmol) of phenylboronic acid, 1.53 g (1.33 mmol) of Pd(PPh₃)₄ and 3.76 g (17.7 mmol) of K₃PO₄. The mixture was stirred at 90° C. for 3 h. The mixture was diluted with 500 mL of EtOAc and washed with 100 mL of brine. The organic layer was dried over Na₂SO₄, filtered and concentrated to give the product as a black solid which was purified by column chromatography over silica gel eluting with PE/EA (5/1) to give 1.48 g of 6-fluoro-4-phenyl-isoquinoline as a light yellow solid. The mixture of 0.5 g (2.24 mmol) of 6-fluoro-4-phenyl-isoquinoline and 15.82 mL (134.38 mmol) of trans-1,4-cyclohexanediamine in 100 mL sealable tube was heated to 110° C. for 2 days. The mixture was diluted with EtOAc and washed with water. The aqueous layer was extracted with EtOAc and the combined EA layers were washed with brine, dired over $Na_2SO_4$, filtered and concentrated to give the product as a black brown semisolid which was purified by column chromatography over silica gel eluting with DCM/MeOH (50/1-5/1) to give 0.7 g of the product as a light yellow solid. 100 mg of the above solid was dissolved in EtOAc and acidified with 1N HCl in EtOAc. The yellow solid was collected by centrifugation and dissolved in ACN and $H_2O$. After lyophilization, 60 mg of N4-(4-phenyl-6-isoquinolyl)cyclohexane-1,4-diamine was obtained as a yellow solid.

MS (ESI+): 318.2 [M+H]$^+$.

$^1$H NMR (400 MHz, DMSO-d$_6$+D$_2$O) δ ppm: 9.14 (s, 1H), 8.18 (d, J=9.2 Hz, 1H), 8.11 (s, 1H), 7.62-7.54 (m, 5H), 7.38 (d, J=9.2 Hz, 1H), 6.67 (br, 1H), 3.26 (br, 1H), 3.05-2.98 (m, 1H), 2.00-1.93 (m, 4H), 1.41-1.25 (m, 4H).

trans-N-[4-(Aminomethyl)cyclohexyl]acetamide

To a solution of 0.6 g (2.58 mmol) of tert-butyl trans-4-aminocyclohexylmethylcarbamate in 20 mL of DCM was added 0.53 g (5.15 mmol) of TEA. The resulting solution was stirred for 10 mins. And then 0.28 mL (3.86 mmol) of acetyl chloride was added dropwise in 10 mins. The mixture was stirred at 20° C. for 16 h. LC-MS showed the reaction was complete, and the mixture was quenched with water, extracted with DCM, dried over anhydrous $Na_2SO_4$, filtered and concentrated to dryness to give 0.6 g of tert-butyl N-[(4-acetamidocyclohexyl) methyl] carbamate as a white solid which was used in the next step without further purification.

To a solution of 0.6 g (2.0 mmol) of this intermediate in 10 mL of DCM was added 0.76 mL (9.99 mmol) of TFA. The mixture was stirred at 20° C. for 3 h. And then the mixture was concentrated to dryness to give 0.3 g of N-[4-(aminomethyl)cyclohexyl]acetamide as a yellow oil which was used in the next step without further purification.

MS (ESI+): 171.1 [M+H]$^+$.

trans-N-[(4-Aminocyclohexyl) methyl]-4-(benzofuran-2-yl) isoquinolin-6-amine (Example 230)

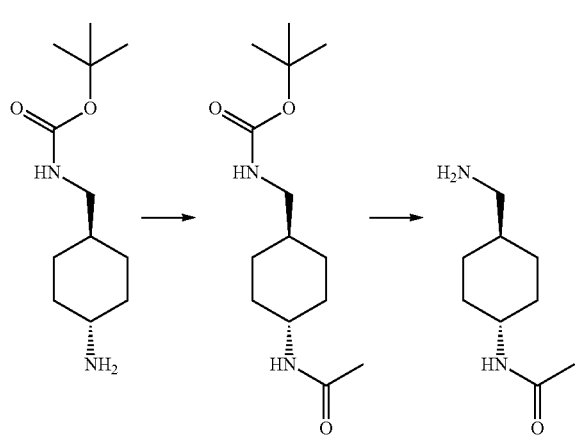 [SMILES: CC(C)(C)OC(=O)NC[C@H]1CC[C@H](N)CC1 ; CC(=O)N[C@H]1CC[C@H](CNC(=O)OC(C)(C)C)CC1 ; CC(=O)N[C@H]1CC[C@H](CN)CC1]

To a solution of 0.2 g (0.72 mmol) of 4-(benzofuran-2-yl)-6-fluoro-isoquinoline in 2 mL of NMP were added 0.31 g (1.44 mmol) of trans-N-[4-(aminomethyl)cyclohexyl]acetamide and 0.66 mL (3.61 mmol) of DIPEA. The mixture was heated to 160° C. under microwave irradiation for 30 mins. Then the mixture was quenched with water, extracted with EtOAc, dried over anhydrous $Na_2SO_4$, filtered and concentrated to dryness. The crude product was purified by Biotage flash chromatography to give 0.24 g of trans-N-[4-[[[4-(benzofuran-2-yl)-6-isoquinolyl]amino]methyl]cyclohexyl]-acetamide as a yellow oil.

To a solution of 0.22 g (0.51 mmol) of this intermediate in 1 mL of MeOH, 1 mL of $H_2O$ and 1 mL of THF was added 0.28 g (5.05 mmol) of sodium methoxide. The mixture was stirred at 100° C. for 16 h. And then the reaction mixture was filtered and concentrated to dryness. The crude product was purified by Biotage flash chromatography using acidic condition (TFA) to give 89 mg of trans-N-[(4-aminocyclohexyl) methyl]-4-(benzofuran-2-yl) isoquinolin-6-amine as a yellow solid.

MS (ESI+): 372.2 [M+H]$^+$.

$^1$H NMR (400 MHz, DMSO-d$_6$+D$_2$O) δ ppm: 9.09 (s, 1H), 8.57 (s, 1H), 8.15 (d, J=9.2 Hz, 1H), 7.79 (d, J=8.4 Hz, 1H), 7.69 (d, J=8.4 Hz, 1H), 7.57 (s, 1H), 7.47-7.29 (m, 4H), 3.17-3.15 (m, 2H), 2.98-2.92 (m, 1H), 1.96-1.93 (m, 2H), 1.87-1.84 (m, 2H), 1.61-1.59 (m, 1H), 1.33-1.23 (m, 2H), 1.15-1.05 (m, 2H).

The following compound was prepared in analogy to Example 230, starting from tert-butyl cis-4-aminocyclohexylmethylcarbamate.

| Example | ¹H NMR (400 MHz) δ ppm | MS (+ESI) [M + H]⁺ |
|---|---|---|
| 231 (structure shown) | (DMSO-d₆ + D₂O) 9.09 (s, 1H), 8.58 (s, 1H), 8.15 (d, J = 9.2 Hz, 1H), 7.79 (d, J = 8.4 Hz, 1H), 7.69 (d, J = 8.4 Hz, 1H), 7.57 (s, 1H), 7.47-7.29 (m, 4H), 3.24-3.22(m, 3H), 1.88-1.86 (m, 1H), 1.71-1.47 (m, 8H). | 372.1 |

4-Bromo-6-[(4-quinolylamino)methyl]isoquinolin-1-amine

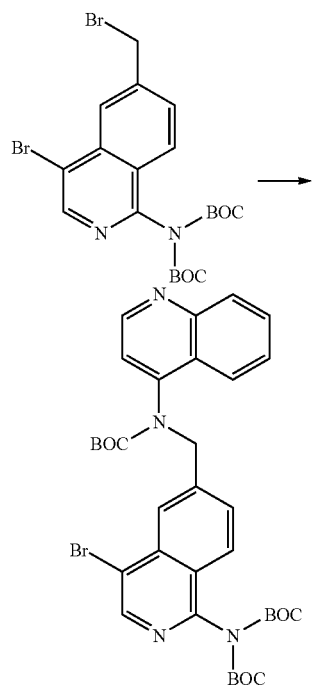

To a solution of 56 mg (2.33 mmol) of NaH in 2 mL of DMF was added 0.19 g (0.78 mmol) of tert-butyl N-(4-quinolyl)carbamate. The resulting mixture was stirred at 25° C. for 3 h and cooled to −20° C. before addition of a solution of 0.4 g (0.78 mmol) of tert-butyl N-[4-bromo-6-(bromomethyl)-1-isoquinolyl]-N-tert-butoxycarbonyl-carbamate in 2 mL of DMF. The mixture was stirred at −20° C. for 2 h. The reaction was quenched with 3 mL of saturated aqueous NH₄Cl solution and extracted with 30 mL of EtOAc. The organic layer was dried over Na₂SO₄, filtered and concentrated to give a yellow oil which was purified by flash column chromatography over silica gel eluting with PE/EA (3/1) to give 0.25 g of tert-butyl N-[[1-[bis(tert-butoxycarbonyl)amino]-4-bromo-6-isoquinolyl]methyl]-N-(4-quinolyl)carbamate as a yellow oil. A suspension of 0.25 g (0.37 mmol) of this intermediate in 5 mL of a solution of 1N HCl in EtOAc was stirred at 25° C. for 18 h. The solvent was evaporated off under vacuum. The yellow solid was collected by centrifugation, washed with EtOAc and dried under reduced pressure to give 173 mg of 4-bromo-6-[(4-quinolylamino)methyl]isoquinolin-1-amine.

MS (ESI+): 379.3, 381.3 [M+H]⁺.

¹H NMR (400 MHz, DMSO-d₆+D₂O) δ ppm: 8.55 (d, J=8.4 Hz, 1H), 8.48 (d, J=8.4 Hz, 1H), 8.42 (d, J=6.0 Hz, 1H), 8.03 (s, 1H), 7.98 (m, 2H), 7.92-7.76 (m, 3H), 6.77 (d, J=7.2 Hz, 1H), 5.06 (s, 2H).

4-Phenyl-6-(piperazin-1-ylmethyl)isoquinolin-1-amine (Example 232)

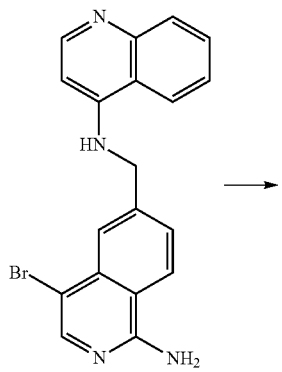

-continued

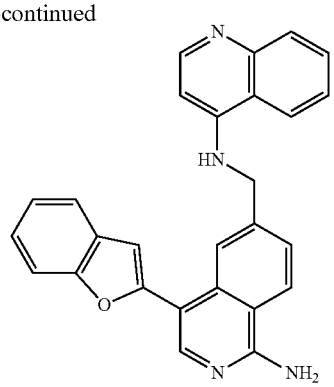

To a solution of 0.17 g (0.46 mmol) of 4-bromo-6-[(4-quinolylamino)methyl]isoquinolin-1-amine and 0.22 g (1.37 mmol) of benzofuran-2-boronic acid in 20 mL of dioxane and 2 mL of H$_2$O were added 0.05 g (0.05 mmol) of Pd$_2$(dba)$_3$, 0.05 g (0.09 mmol) of Xantphos and 0.45 g (1.37 mmol) of Cs$_2$CO$_3$. The reaction mixture was heated to 90° C. and stirred for 2 h at this temperature under argon atmosphere. The solid was filtered off and the filtrate was purified by preparative HPLC to give 18 mg of 4-phenyl-6-(piperazin-1-ylmethyl)isoquinolin-1-amine as a light yellow powder.

MS (ESI+): 417.2 [M+H]$^+$.

$^1$H NMR (400 MHz, DMSO-d$_6$+D$_2$O) δ ppm: 8.53 (d, J=8.4 Hz, 1H), 8.46 (d, J=8.4 Hz, 1H), 8.40 (d, J=6.8 Hz, 1H), 8.11 (s, 1H), 8.03 (s, 1H), 8.01 (m, 1H), 7.92 (d, J=8.0 Hz, 1H), 7.84 (d, J=8.8 Hz, 1H), 7.74 (m, 1H), 7.51 (m, 1H), 7.20 (m, 2H), 7.08 (s, 1H), 6.94 (d, J=7.2 Hz, 1H), 6.77 (d, J=6.8 Hz, 1H), 5.08 (s, 2H).

4-Chloro-6-fluoro-isoquinolin-1-amine

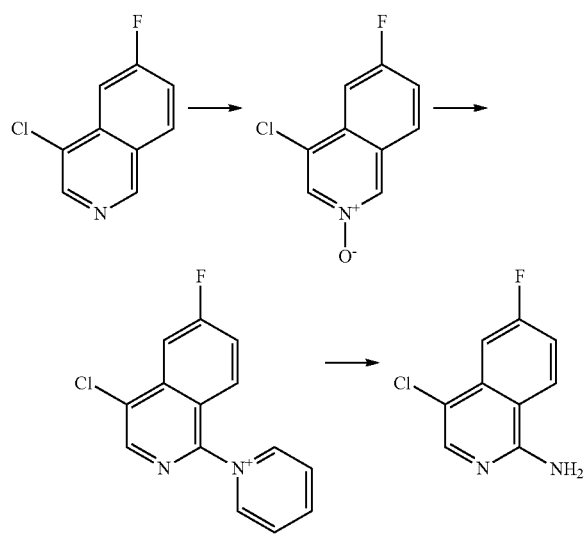

To a solution of 1.0 g (5.5 mmol) of 4-chloro-6-fluoro-isoquinoline (CAS: 918488-55-8) in 15 mL of DCM was added 2.85 g (16.5 mmol) of mCPBA. The mixture was stirred at 30° C. for 16 h. The reaction was quenched with saturated aqueous Na$_2$SO$_3$ solution and saturated aqueous NaHCO$_3$ solution and extracted with DCM. The organic phase was separated, dried over Na$_2$SO$_4$, filtered and concentrated to give 1.0 g of the crude 4-chloro-6-fluoro-2-oxido-isoquinolin-2-ium as a grey solid.

The crude 4-chloro-6-fluoro-2-oxido-isoquinolin-2-ium was dissolved in 10 mL of pyridine and 1.9 g (10.1 mmol) of TsCl was added. The reaction mixture was stirred at 30° C. for 4 h. The pyridine was removed under reduced pressure to afford 1.2 g of the crude 4-chloro-6-fluoro-1-pyridin-1-ium-1-yl-isoquinoline as a brown solid.

A suspension of 1.2 g of 4-chloro-6-fluoro-1-pyridin-1-ium-1-yl-isoquinoline in 9 mL of 2-aminoethanol was stirred at 30° C. for 16 h. The solution was poured onto crushed ice, and the solids were isolated by filtration and dried under vacuum to afford 400 mg of the crude 4-chloro-6-fluoro-isoquinolin-1-amine as a light brown solid.

MS (ESI+): 197.0, 199.0 [M+H]$^+$.

$^1$H NMR (400 MHz, DMSO-d$_6$) δ ppm: 8.38 (dd, J=9.2 Hz, 2.0 Hz, 1H), 7.92 (s, 1H), 7.52 (m, 2H), 7.16 (brs, 2H).

4-(Benzofuran-2-yl)-6-fluoro-isoquinolin-1-amine

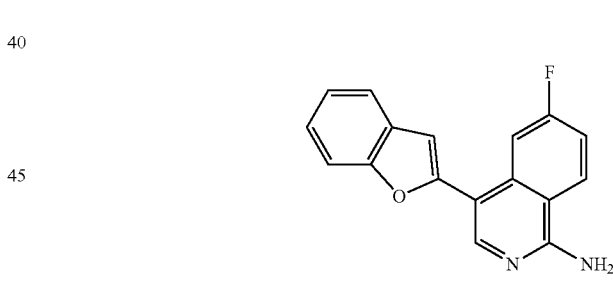

To a solution of 4 g (20 mmol) of 4-chloro-6-fluoro-isoquinolin-1-amine and 4.86 g (30 mmol) of benzofuran-2-boronic acid in 10 mL of dioxane and 1 mL of water were added 4.24 g (40 mmol) of K$_3$PO$_4$, 1.83 g (2.0 mmol) of Pd$_2$(dba)$_3$ and 1.9 g (4.0 mmol) of X-phos. The reaction mixture was heated to 90° C. and stirred for 3 h under Ar atmosphere. The mixture was diluted with EtOAc, washed with brine. The organic layer was dried over Na$_2$SO$_4$, filtered and concentrated to give a black semisolid which was purified by column chromatography eluting with PE/EA (2/1) to give 1.5 g of 4-(benzofuran-2-yl)-6-fluoro-isoquinolin-1-amine as a light yellow solid.

MS (ESI+): 279.0 [M+H]$^+$.

$^1$H NMR (400 MHz, DMSO-d$_6$) δ ppm: 8.44 (dd, J$_1$=9.2 Hz, J$_2$=2.0 Hz, 1H), 8.23 (s, 1H), 7.84 (d, J=2.4 Hz, 1H), 7.66 (m, 2H), 7.45 (m, 1H), 7.28 (m, 2H), 7.16 (s, 1H).

4-(Benzofuran-2-yl)-N6-(4-pyridylmethyl)isoquinoline-1,6-diamine (Example 233)

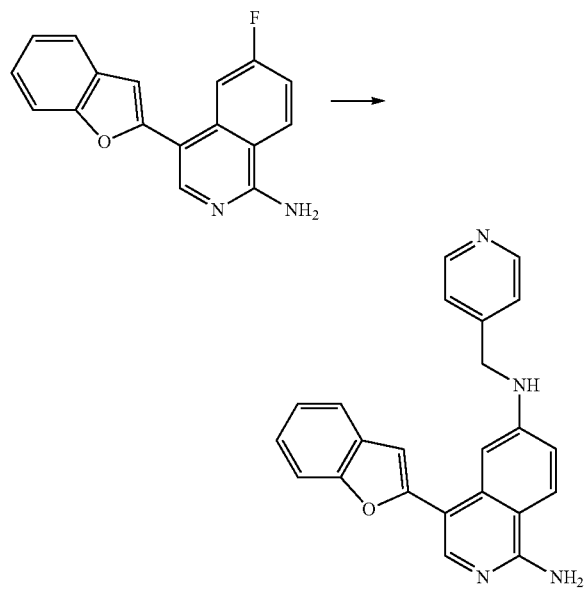

A solution of 0.78 g (7.19 mmol) of 4-aminomethylpyridine, 0.2 g (0.72 mmol) of 4-(benzofuran-2-yl)-6-fluoroisoquinolin-1-amine and 0.46 g (3.59 mmol) of DIPEA in 2 mL of NMP was heated in a microwave reactor at 180° C. for 4 h. The volatiles were evaporated and the residue was purified by preparative HPLC (TFA) to give 107 mg of 4-(benzofuran-2-yl)-N6-(4-pyridylmethyl)isoquinoline-1,6-diamine as a light brown solid.

MS (ESI+): 367.2 [M+H]$^+$.

$^1$H NMR (400 MHz, DMSO-$d_6$+$D_2O$) δ ppm: 8.71 (d, J=6.4 Hz, 2H), 8.30 (d, J=9.2 Hz, 1H), 7.87 (s, 1H), 7.78 (d, J=6.4 Hz, 2H), 7.69 (d, J=7.2 Hz, 1H), 7.53 (d, J=8.0 Hz, 1H), 7.41-7.30 (m, 2H), 7.18 (d, J=9.2 Hz, 1H), 7.04-6.94 (m, 2H), 4.74 (s, 2H).

The following examples were prepared accordingly to Example 233 by reaction of 4-(benzofuran-2-yl)-6-fluoroisoquinolin-1-amine with the corresponding amines:

| Example | | $^1$H NMR (400 MHz) δ ppm | MS (+ESI) [M + H]$^+$ |
|---|---|---|---|
| 234 | ![structure] | (DMSO-$d_6$ + $D_2O$) 8.30 (d, J = 9.2 Hz, 1H), 7.88 (s, 1H), 7.83 (d, J = 6.4 Hz, 1H), 7.69 (d, J = 7.2 Hz, 1H), 7.51 (d, J = 8.0 Hz, 1H), 7.40-7.29 (m, 2H), 7.16 (d, J = 9.2 Hz, 1H), 7.04 (s, 1H), 6.97 (s, 1H), 6.82 (s, 1H), 6.78 (dd, J = 6.4 Hz, 1.6 Hz, 1H), 4.52 (s, 2H). | 382.2 |
| 235 | ![structure] | (DMSO-$d_6$ + $D_2O$) 8.23 (d, J = 10.0 Hz, 1H), 7.84 (s, 1H), 7.72 (d, J = 7.2 Hz, 1H), 7.62 (d, J = 8.0 Hz, 1H), 7.42-7.28 (m, 2H), 7.25 (s, 1H), 7.13-7.09 (m, 2H), 3.33-3.29 (m, 1H), 3.06-2.98 (m, 1H), 2.08-1.94 (m, 4H), 1.47-1.24 (m, 4H). | 373.3 |

1-(2-Chloro-4-methyl-phenyl)-N-(2,2-dimethoxy-ethyl)methanimine

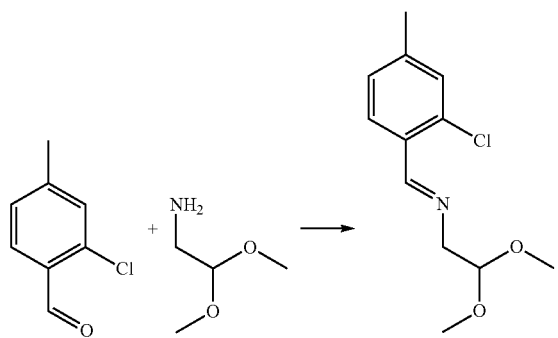

20.4 g (194.0 mmol) of aminoacetaldehyde dimethyl acetal (CAS: 22483-09-6) and 25.0 g (161.7 mmol) of 2-chloro-4-methyl-benzaldehyde (CAS: 50817-80-6) were dissolved in 150 mL toluene. The mixture was heated with a Dean-Stark trap at reflux for 1 h. The mixture was allowed to cool to room temperature and concentrated to give 39.08 g of the desired product as a light yellow oil.

$^1$H NMR (400 MHz, DMSO-$d_6$) δ ppm: 8.62 (s, 1H), 7.85 (d, J=8.0 Hz, 1H), 7.35 (s, 1H), 7.22 (d, J=8.0 Hz, 1H), 4.63 (t, J=5.4 Hz, 1H), 3.74 (dd, J=5.4 Hz, 1.4 Hz, 2H), 3.30 (s, 6H), 2.34 (s, 3H).

N-[(2-Chloro-4-methyl-phenyl)methyl]-2,2-dimethoxy-ethanamine

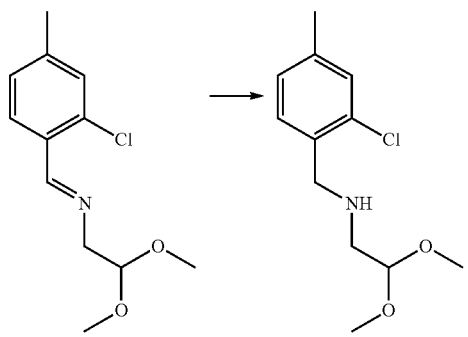 [SMILES: COC(C/N=C/c1ccc(C)cc1Cl)OC ; COC(CNCc1ccc(C)cc1Cl)OC]

To a solution of 39 g (161.35 mmol) of 1-(2-chloro-4-methyl-phenyl)-N-(2,2-dimethoxyethyl)methanimine in 300 mL of ethanol was added 9.16 g (242.03 mmol) sodium borohydride portionwise. The resulting mixture was stirred at 20° C. for 2 h. 10 mL of acetone was slowly added into the flask to quench the reaction. The volatiles were removed under vacuum. The residue was dissolved with DCM and absorbed on silica gel, and then loaded on a silica gel column and eluted with PE-EA (10:1 to 3:1, $R_f$=0.1) to produce 24.2 g of the desired product as a light yellow oil.

MS m/z (+ESI): 244.0, 246.0 [M+H]$^+$ $^1$H NMR (400 MHz, CDCl$_3$) δ ppm: 7.26 (d, J=7.8 Hz, 1H), 7.19 (s, 1H), 7.05 (d, J=7.4 Hz, 1H), 4.51 (t, J=5.5 Hz, 1H), 3.88 (s, 2H), 3.38 (s, 6H), 2.75 (d, J=5.5 Hz, 2H), 2.33 (s, 3H).

N-[(2-Chloro-4-methyl-phenyl)methyl]-N-(2,2-dimethoxyethyl)-4-methyl-benzenesulfonamide

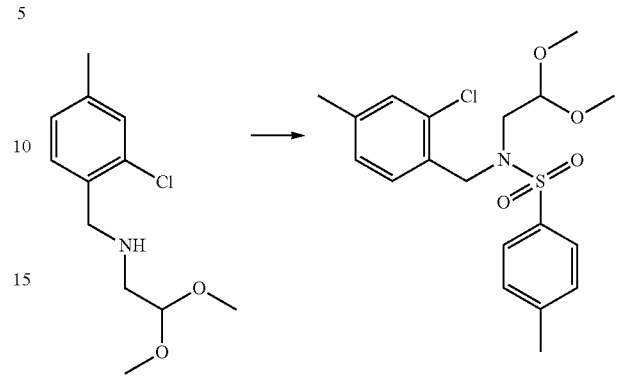

To a solution of 24.2 g (99.29 mmol) of N-[(2-chloro-4-methyl-phenyl)methyl]-2,2-dimethoxy-ethanamine and 24.0 mL (297.9 mmol) of pyridine in 300 mL of DCM was added a solution of 22.7 g (119.15 mmol) of p-toluenesulfonyl chloride in 100 mL of DCM dropwise. The resulting mixture was stirred at 20° C. for 16 h. 250 mL of water was added to quench the reaction, and the aqueous phase was extracted with DCM (150 mL×2). The combined organic phases were washed with water and brine, dried over Na$_2$SO$_4$, filtered and concentrated under vacuum to give the crude product. The crude product was purified by column chromatography on silica gel with PE-EA (20:1 to 10:1, $R_f$=0.2) to produce 38.5 g of the desired product as a light yellow oil.

MS m/z (+ESI): 366.1, 368.1 [M-MeO+H]$^+$.

$^1$H NMR (400 MHz, CDCl$_3$) δ ppm: 7.73 (d, J=8.3 Hz, 2H), 7.28-7.38 (m, 3H), 7.14 (s, 1H), 7.05 (d, J=8.0 Hz, 1H), 4.54 (s, 2H), 4.37 (t, J=5.4 Hz, 1H), 3.30 (d, J=5.3 Hz, 2H), 3.23 (s, 6H), 2.45 (s, 3H), 2.32 (s, 3H).

8-Chloro-6-methyl-isoquinoline

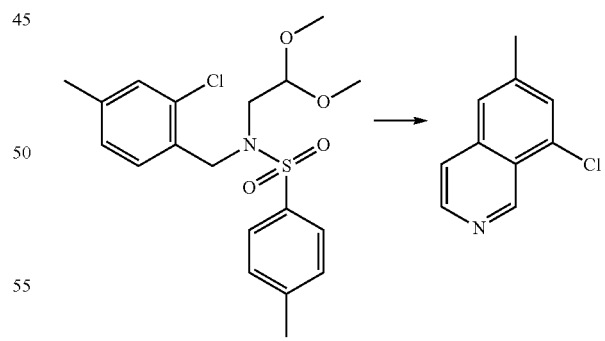

To a solution of 2.01 g (15.08 mmol) of AlCl$_3$ in 20 mL of DCM was added a solution of 1.0 g (2.51 mmol) of N-[(2-chloro-4-methyl-phenyl) methyl]-N-(2,2-dimethoxyethyl)-4-methyl-benzenesulfonamide 4-methyl-benzenesulfonamide in 5 mL of DCM dropwise at 0° C. The resulting mixture was allowed to warm to 20° C. and stirred at this temperature for 16 h. The reaction mixture was poured into 50 mL of cold water, and the aqueous phase was extracted with DCM (20 mL×2). The combined organic phases were washed with water and brine, dried over Na$_2$SO$_4$, filtered and concentrated under vacuum to give the crude product. The crude product was purified by column chromatography on silica gel with PE-EA (10:1 to 3:1, R$_f$=0.5) to produce 400 mg of the desired product as a yellow solid.

MS m/z (+ESI): 178.1, 180.1 [M+H]$^+$.

$^1$H NMR (400 MHz, CDCl$_3$) δ ppm: 9.60 (s, 1H), 8.58 (d, J=5.8 Hz, 1H), 7.58 (d, J=5.5 Hz, 1H), 7.54-7.50 (m, 2H), 2.55 (s, 3H).

4-Bromo-8-chloro-6-methyl-isoquinoline

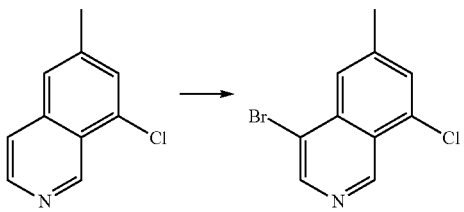

To a stirred solution of 1.0 g (5.62 mmol) of 8-chloro-6-methyl-isoquinoline in 10 mL of acetic acid was added 1.50 (8.44 mmol) of N-bromosuccinimide and the reaction mixture was heated to 100° C. for 16 h. The solvent was removed under vacuum and the residual brown oil was treated with EtOAc and aqueous Na$_2$CO$_3$, and filtered. The separated aqueous phase was extracted with EtOAc. The combined organic phases were washed with water and brine, and concentrated under vacuum. The crude product was purified by column chromatography on silica gel with PE-EA (30:1 to 10:1, R$_f$=0.6) to produce 360 mg of the desired product as a light yellow solid.

MS m/z (+ESI): 256.0, 258.0, 260.0 [M+H]$^+$.

$^1$H NMR (400 MHz, DMSO-d$_6$) δ ppm: 9.53 (s, 1H), 8.77 (s, 1H), 7.89 (s, 1H), 7.58 (s, 1H), 2.61 (s, 3H).

tert-Butyl N-[1-[(4-bromo-8-chloro-6-isoquinolyl)methyl]-4-piperidyl]carbamate

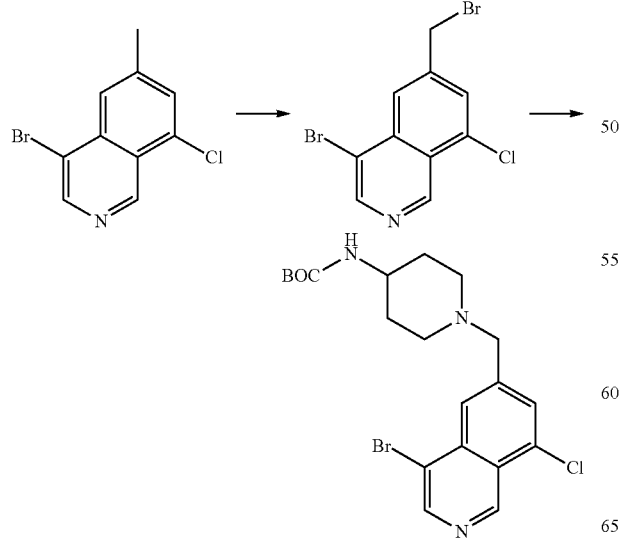

To a stirred solution of 0.6 g (2.34 mmol) of 4-bromo-8-chloro-6-methyl-isoquinoline in 25 mL of CCl$_4$ were added 417 mg (2.34 mmol) of N-bromosuccinimide and 36 mg (0.23 mmol) of 2,2-azobis(2-methylpropionitrile). The reaction mixture was heated to 100° C. for 3 h under argon atmosphere. The reaction mixture was purified by flash chromatography (PE-EA, 3:1) to give 0.58 g of 4-bromo-6-(bromomethyl)-8-chloro-isoquinoline as an off-white solid.

To a stirred solution of 0.58 g (1.73 mmol) of this intermediate in 40 mL of CCl$_4$ were added 20 mL of DCM, 0.42 g (2.08 mmol) of 4-N-Boc-amino-piperidine and 0.72 g (5.19 mmol) of K$_2$CO$_3$. The reaction mixture was stirred at 20° C. for 16 h and filtered through Celite. The filtrate was concentrated under vacuum. The crude product was purified by column chromatography on silica gel with PE-EA (10:1 to 1:1, R$_f$=0.5) to produce 440 mg of the desired product as an off-white solid.

MS m/z (+ESI): 454.1, 456.1, 458.1 [M+H]$^+$ $^1$H NMR (400 MHz, CDCl$_3$) δ ppm: 9.55 (s, 1H), 8.80 (s, 1H), 7.98 (s, 1H), 7.80 (s, 1H), 4.47 (br s, 1H), 3.69 (s, 2H), 3.60-3.45 (m, 1H), 2.88-2.76 (m, 2H), 2.16-2.27 (m, 2H), 2.01-1.91 (m, 2H), 1.55-1.48 (m, 2H), 1.46 (s, 9H).

tert-Butyl N-[1-[[4-(benzofuran-2-yl)-8-chloro-6-isoquinolyl]methyl]-4-piperidyl]carbamate

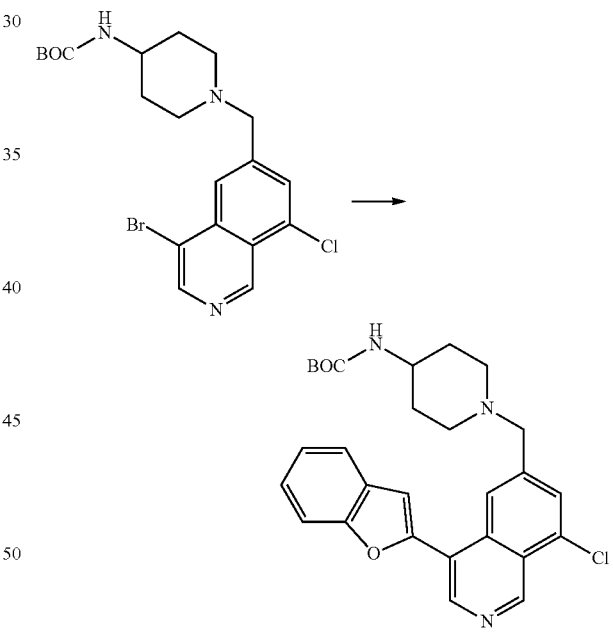

To a stirred solution of 0.44 g (0.97 mmol) of tert-butyl N-[1-[(4-bromo-8-chloro-6-isoquinolyl)methyl]-4-piperidyl]carbamate in 15 mL of dioxane and 1 mL of H$_2$O were added 0.47 g (2.90 mmol) of benzofuran-2-boronic acid, 112 mg (0.097 mmol) of Pd(PPh$_3$)$_4$ and 0.616 g (2.90 mmol) of K$_3$PO$_4$. The reaction mixture was stirred for 3 h at 95° C. under argon. The volatiles were removed under vacuum. The crude product was purified by column chromatography on silica gel with PE-EA (5:1 to 2:1, R$_f$=0.2) to produce 355 mg of the desired product as a light yellow solid.

MS m/z (+ESI): 492.2, 494.2 [M+H]$^+$ $^1$H NMR (400 MHz, DMSO-d$_6$) δ ppm: 9.69 (s, 1H), 8.97 (s, 1H), 8.27 (s, 1H), 7.81 (s, 1H), 7.73 (d, J=7.0 Hz, 1H), 7.64 (d, J=8.3 Hz, 1H), 7.44-7.33 (m, 2H), 7.16 (s, 1H), 4.45 (br s, 1H), 3.68 (s, 2H), 3.58-3.46 (m, 1H), 2.88-2.78 (m, 2H), 2.25-2.16 (m, 2H), 1.95 (m, 2H), 1.53-1.47 (m, 2H), 1.46 (s, 9H).

1-[[4-(Benzofuran-2-yl)-8-chloro-6-isoquinolyl]methyl]piperidin-4-amine (Example 236)

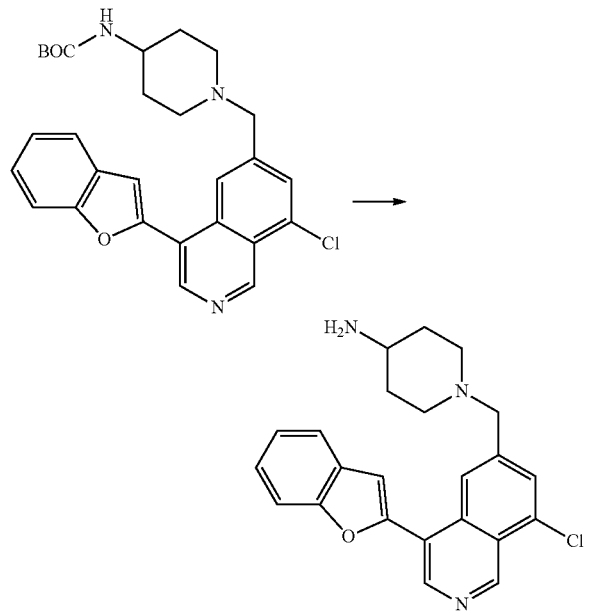

To a stirred solution of 2.0 g (4.06 mmol) of tert-butyl N-[1-[[4-(benzofuran-2-yl)-8-chloro-6-isoquinolyl]methyl]-4-piperidyl]carbamate in 30 mL of DCM was added 15 mL (201.94 mmol) of TFA, and the resulting solution was stirred at 20° C. for 2 h. The volatiles were removed under vacuum and the residue was purified by preparative HPLC using acidic conditions (TFA). The desired fractions were concentrated to remove most of ACN and to the residue was added 2 mL of 37% aqueous HCl. After lyophilisation, 1.3 g of 1-[[4-(benzofuran-2-yl)-8-chloro-6-isoquinolyl]methyl]piperidin-4-amine as HCl salt was obtained as a yellow solid.

MS m/z (+ESI): 392.4, 394.3 [M+H]+

$^1$H NMR (400 MHz, DMSO-$d_6$+$D_2O$) δ ppm: 9.67 (s, 1H), 9.09 (s, 1H), 8.63 (s, 1H), 8.14 (s, 1H), 7.79 (d, J=7.6 Hz, 1H), 7.74 (d, 1H, J=8.4 Hz), 7.69 (d, J=1.6 Hz, 1H), 7.45-7.41 (m, 1H), 7.37-7.33 (m, 1H), 4.56 (s, 2H), 3.55-3.38 (m, 2H), 3.35-3.21 (m, 1H), 3.20-3.03 (m, 2H), 2.15-2.04 (m, 2H), 1.93-1.73 (m, 2H).

The following examples were prepared accordingly to Example 236 by reaction of tert-butyl N-[1-[[4-(benzofuran-2-yl)-8-chloro-6-isoquinolyl]methyl]-4-piperidyl]carbamate with the corresponding boronic acid by Suzuki coupling in the presence of a Pd-catalyst and subsequent deprotection:

| Example | | $^1$H NMR (400 MHz) δ ppm | MS (+ESI) [M + H]+ |
|---|---|---|---|
| 237 | | (DMSO-$d_6$ + $D_2O$) 9.66 (s, 1H), 8.65 (s, 1H), 8.00 (s, 1H), 7.94 (s, 1H), 7.71-7.58 (m, 4H), 4.45 (s, 2H), 3.51-3.34 (m, 2H), 3.31-3.15 (m, 1H), 3.13-2.99 (m, 2H), 2.14-2.00 (m, 2H), 1.80-1.60 (m, 2H). | 386.1, 388.1 |
| 238 | | (DMSO-$d_6$ + $D_2O$) 9.67 (s, 1H), 8.67 (s, 1H), 8.00 (s, 1H), 7.96 (s, 1H), 7.78-7.59 (m, 2H), 7.49-7.39 (m, 1H), 4.46 (s, 2H), 3.49-3.37 (m, 2H), 3.31-3.19 (m, 1H), 3.11-2.96 (m, 2H), 2.12-2.01 (m, 2H), 1.80-1.61 (m, 2H). | 388.1, 390.1 |

| Example | 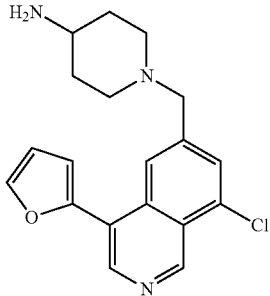 | ¹H NMR (400 MHz) δ ppm | MS (+ESI) [M + H]⁺ |
|---|---|---|---|
| 239 | 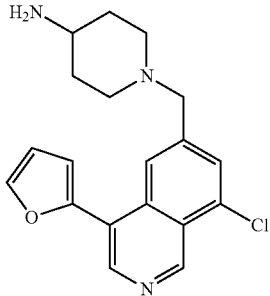 | (DMSO-d₆ + D₂O) 9.59 (s, 1H), 8.95 (s, 1H), 8.52 (s, 1H), 8.03-7.98 (m, 2H), 7.21 (d, J = 3.2 Hz, 1H), 6.80 (dd, J = 2.0 Hz, 3.2 Hz, 1H), 4.54 (s, 2H), 3.53-3.39 (m, 2H), 3.34-3.22 (m, 1H), 3.18-3.04 (m, 2H), 2.14-2.05 (m, 2H), 1.80-1.64 (m, 2H). | 342.1, 344.1 |
| 240 | 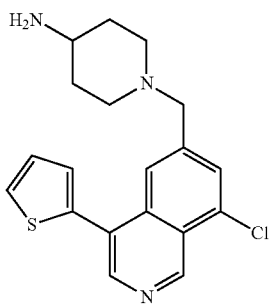 [SMILES: NC1CCN(Cc2cc(Cl)c3cncc(-c4cccs4)c3c2)CC1] | (DMSO-d₆ + D₂O) 9.63 (s, 1H), 8.76 (s, 1H), 8.32 (s, 1H), 8.02 (s, 1H), 7.84 (dd, J = 1.2 Hz, 5.2 Hz, 1H), 7.53 (dd, J = 1.2 Hz, 3.6 Hz, 1H), 7.34 (dd, J = 3.6 Hz, 5.2 Hz, 1H), 4.51 (s, 2H), 3.51-3.37 (m, 2H), 3.33-3.19 (m, 1H), 3.16-3.02 (m, 2H), 2.13-2.03 (m, 2H), 1.79-1.63 (m, 2H). | 358.1, 360.1 |
| 241 | 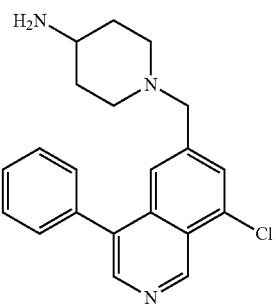 [SMILES: NC1CCN(Cc2cc(Cl)c3cncc(-c4ccccc4)c3c2)CC1] | (DMSO-d₆ + D₂O) 9.64 (s, 1H), 8.63 (s, 1H), 7.98 (s, 2H), 7.63-7.54 (m, 5H), 4.44 (s, 2H), 3.48-3.34 (m, 2H), 3.31-3.18 (m, 1H), 3.13-2.97 (m, 2H), 2.11-2.02 (m, 2H), 1.80-1.59 (m, 2H). | 352.4, 354.3 |

1-[[4-(Benzofuran-2-yl)-8-methoxy-6-isoquinolyl]methyl]piperidin-4-amine (Example 242)

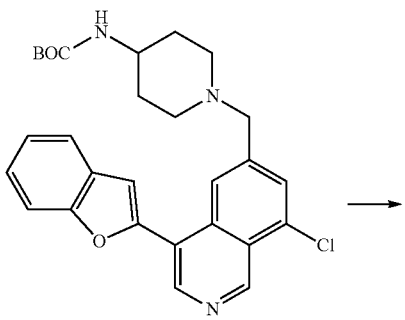

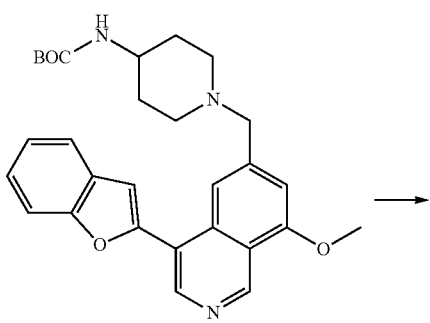

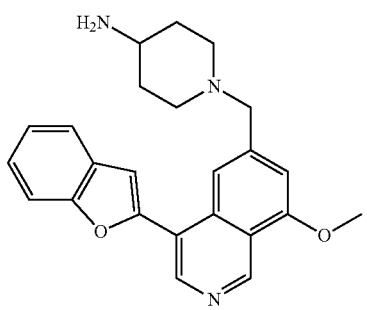

To a solution of 1.5 g (3.05 mmol) of tert-butyl N-[1-[[4-(benzofuran-2-yl)-8-chloro-6-isoquinolyl]methyl]-4-piperidyl]carbamate in 21 mL of MeOH and 21 mL of dioxane were added 0.29 g (0.61 mmol) of X-phos, 0.82 g (15.24 mmol) of sodium methoxide, and 0.35 g (0.30 mmol) of Pd(PPh$_3$)$_4$. The reaction mixture was heated under argon in a sealable vial at 60° C. for 1 h. The reaction mixture was diluted with water, extracted with EtOAc, dried over Na$_2$SO$_4$, filtered and concentrated to give 1.35 g of tert-butyl N-[1-[[4-(benzofuran-2-yl)-8-methoxy-6-isoquinolyl]methyl]-4-piperidyl]carbamate as a yellow oil.

To a stirred solution of 1.35 g (2.77 mmol) of this intermediate in DCM (12 mL) was added 6.0 mL (80.78 mmol) of TFA and the resulting solution was stirred at 20° C. for 2 h until LC-MS showed the reaction was complete. The volatiles were removed under vacuum and the residue was purified by preparative HPLC using acidic conditions. The desired fractions were concentrated to remove most of ACN and to the residue was added 2 mL of 37% aqueous HCl. After lyophilization, 1.06 g of 1-[[4-(benzofuran-2-yl)-8-methoxy-6-isoquinolyl]methyl]piperidin-4-amine HCl salt was obtained as a yellow solid.

MS m/z (+ESI): 388.3 [M+H]$^+$ $^1$H NMR (400 MHz, DMSO-d$_6$+D$_2$O) δ ppm: 9.62 (s, 1H), 9.00 (s, 1H), 8.20 (s, 1H), 7.79 (d, J=7.6 Hz, 1H), 7.74 (d, J=8.4 Hz, 1H), 7.71 (s, 1H), 7.60 (s, 1H), 7.45-7.42 (m, 1H), 7.37-7.34 (m, 1H), 4.55 (s, 2H), 4.12 (s, 3H), 3.47-3.44 (m, 2H), 3.31-3.23 (m, 1H), 3.15-3.09 (m, 2H), 2.11-2.08 (m, 2H), 1.95-1.86 (m, 2H).

The following compounds were prepared in analogy to Example 242 by reaction of tert-butyl N-[1-[(4-bromo-8-chloro-6-isoquinolyl)methyl]-4-piperidyl]carbamate with the corresponding boronic acid by Suzuki coupling in the presence of a Pd-catalyst, then methoxylation with sodium methoxide in the presence of a Pd-catalyst and subsequent deprotection:

| Example | | $^1$H NMR (400 MHz) δ ppm | MS (+ESI) [M + H]$^+$ |
|---|---|---|---|
| 243 | ![structure] | (DMSO-d$_6$ + D$_2$O) 9.60 (s, 1H), 8.55 (s, 1H), 7.72-7.59 (m, 2H), 7.52 (s, 1H), 7.45-7.39 (m, 1H), 7.30 (s, 1H), 4.43 (s, 2H), 4.10 (s, 3H), 3.50-3.35 (m, 2H), 3.32-3.17 (m, 1H), 3.13-2.96 (m, 2H), 2.18-2.00 (m, 2H), 1.81-1.61 (m, 2H). | 384.1 |

-continued

| Example | | $^1$H NMR (400 MHz) δ ppm | MS (+ESI) [M + H]$^+$ |
|---|---|---|---|
| 244 | 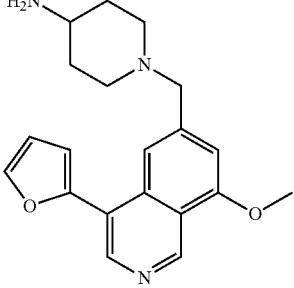 | (DMSO-d$_6$ + D$_2$O) 9.52 (s, 1H), 8.84 (s, 1H). 8.07 (s, 1H), 7.97 (d, J = 1.2 Hz, 1H), 7.31 (s, 1H), 7.17 (d, J = 3.2 Hz, 1H), 6.78 (dd, J = 1.2 Hz, 3.2 Hz, 1H), 4.51 (s, 2H), 4.09 (s, 3H), 3.54-3.39 (m, 2H), 3.35-3.19 (m, 1H), 3.19-3.03 (m, 2H), 2.16-2.08 (m, 2H), 1.82-1.63 (m, 2H). | 338.2 |
| 245 | 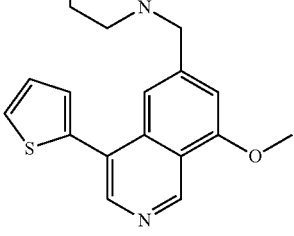 | (DMSO-d$_6$ + D$_2$O) 9.43 (s, 1H), 8.53 (s, 1H), 8.13 (s, 1H, HCOOH), 7.76 (dd, J = 1.2 Hz, 5.2 Hz, 1H), 7.68 (s, 1H), 7.41 (dd, J = 1.2 Hz, 3.6 Hz, 1H), 7.29 (dd, J = 3.6 Hz, 5.2 Hz, 1H), 7.13 (s, 1H), 4.03 (s, 3H), 3.68 (s, 2H), 3.07-2.94 (m, 1H), 2.91-2.81 (m, 2H), 2.15-2.05 (m, 2H), 1.90-1.81 (m, 2H), 1.60-1.47 (m, 2H). | 354.2 |
| 246 | 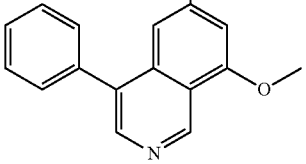 | (DMSO-d$_6$ + D$_2$O) 9.60 (s, 1H), 8.52 (s, 1H), 7.59-7.54 (m, 6H), 7.31 (s, 1H), 4.41 (s, 2H), 4.09 (s, 3H), 3.44-3.35 (m, 2H), 3.28-3.20 (m, 1H), 3.11-2.99 (m, 2H), 2.10-2.03 (m, 2H), 1.77-1.64 (m, 2H). | 348.3 |

The following compound was prepared in analogy to Example 236, starting from 2, 2-dimethoxyethanamine and the corresponding substituted benzaldehyde:

| Example | | $^1$H NMR (400 MHz) δ ppm | MS (+ESI) [M + H]$^+$ |
|---|---|---|---|
| 247 | 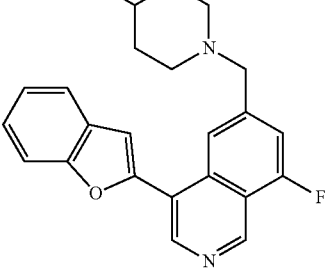 | (DMSO-d$_6$ + D$_2$O) 9.60 (s, 1H), 9.12 (s, 1H), 8.51 (s, 1H), 7.90 (d, J$_{HF}$ = 10.8 Hz, 1H), 7.78 (m, 3H), 7.43 (m, 2H), 4.58 (s, 2H), 3.48 (m, 2H), 3.26 (m, 1H), 3.11 (m, 2H), 2.10 (m, 2H), 1.90 (m, 2H). | 376.3 |

-continued

| Example | ¹H NMR (400 MHz) δ ppm | MS (+ESI) [M + H]⁺ |
|---|---|---|
| 248 | (DMSO-d₆ + D₂O) 9.62 (s, 1H), 9.11 (s, 1H), 8.70 (d, J = 5.6 Hz, 1H), 7.84 (s, 1H), 7.78 (m, 2H), 7.43 (m, 2H), 4.66 (s, 2H), 3.56 (m, 2H), 3.24 (m, 3H), 2.11 (m, 2H), 1.89 (m, 2H). | 394.3 |
| 249 | (DMSO-d₆ + D₂O) 9.43 (s, 1H), 8.98 (s, 1H), 8.82 (d, J$_{HF}$ = 6.8 Hz, 1H), 8.06 (d, J$_{HF}$ = 9.6 Hz, 1H), 7.80-7.71 (m, 3H), 7.45-7.34 (m, 2H), 4.61 (s, 2H), 3.52 (m, 3H), 3.25 (m, 2H), 2.11 (m, 2H), 1.81 (m, 2H). | 376.3 |
| 250 | (DMSO-d₆ + D₂O) 9.44 (s, 1H), 9.03 (s, 1H), 8.81 (s, 1H), 8.58 (s, 1H), 7.80 (d, J = 7.2 Hz, 1H), 7.74 (m, 1H), 7.66 (d, J = 0.4 Hz, 1H), 7.45 (m, 1H), 7.37 (m, 1H), 4.68 (s, 2H), 3.53 (m, 2H), 3.27 (m, 3H), 2.09 (m, 2H), 1.76 (m, 2H). | 392.3, 394.3 |

1-[(7-Chloro-4-phenyl-6-isoquinolyl)methyl]piperidin-4-amine (Example 251)

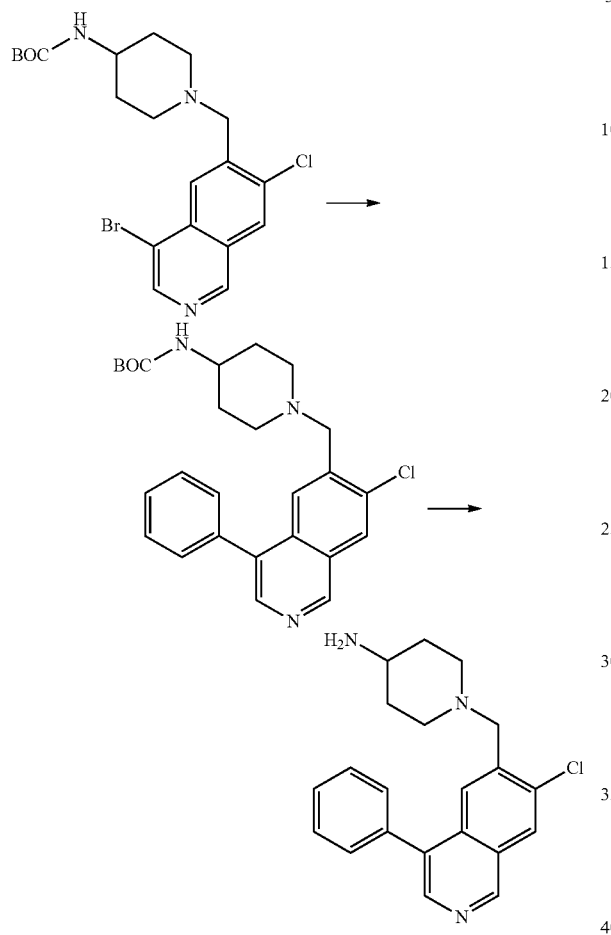

To a stirred solution of 0.09 g (0.20 mmol) of tert-butyl N-[1-[(4-bromo-7-chloro-6-isoquinolyl)methyl]-4-piperidyl]carbamate (prepared in analogy to tert-butyl N-[1-[(4-bromo-8-chloro-6-isoquinolyl)methyl]-4-piperidyl]carbamate, starting from 2,2-dimethoxyethanamine and 3-chloro-4-methyl-benzaldehyde via 7 steps) and 0.07 g (0.59 mmol) of phenylboronic acid in 15 mL of dioxane and 1 mL of H$_2$O were added 0.13 g (0.59 mmol) of K$_3$PO$_4$ and 0.02 g (0.02 mmol) of Pd(PPh$_3$)$_4$. The reaction mixture was stirred under argon at 95° C. for 3 h. The volatiles were removed under vacuum. The crude product was purified by column chromatography on silica gel with PE-EA (5:1 to 2:1, R$_f$=0.2) to give 48 mg of tert-butyl N-[1-[(7-chloro-4-phenyl-6-isoquinolyl)methyl]-4-piperidyl]carbamate as a colorless semi-solid.

To a solution of 48 mg (0.11 mmol) of tert-butyl N-[1-[(7-chloro-4-phenyl-6-isoquinolyl)methyl]-4-piperidyl]carbamate in 2 mL of DCM was added 1 mL of TFA. The solution was stirred at 10° C. for 2 h. The solvent was evaporated and the residue was purified by preparative HPLC to give 45 mg of 1-[(7-chloro-4-phenyl-6-isoquinolyl)methyl]piperidin-4-amine as light brown solid.

MS (ESI+): 352.3, 354.3 [M+H]$^+$.

$^1$H NMR (400 MHz, DMSO-d$_6$+D$_2$O) ppm: 9.41 (s, 1H), 8.55-8.54 (m, 2H), 8.24 (s, 1H), 7.63-7.61 (m, 4H), 7.59-7.54 (m, 1H), 4.56 (s, 2H), 3.49-3.39 (m, 2H), 3.34-3.21 (m, 1H), 3.23-3.11 (m, 2H), 2.10-2.01 (m, 2H), 1.80-1.61 (m, 2H).

tert-Butyl N-[1-[[4-(benzofuran-2-yl)-8-nitro-6-isoquinolyl]methyl]-4-piperidyl]carbamate

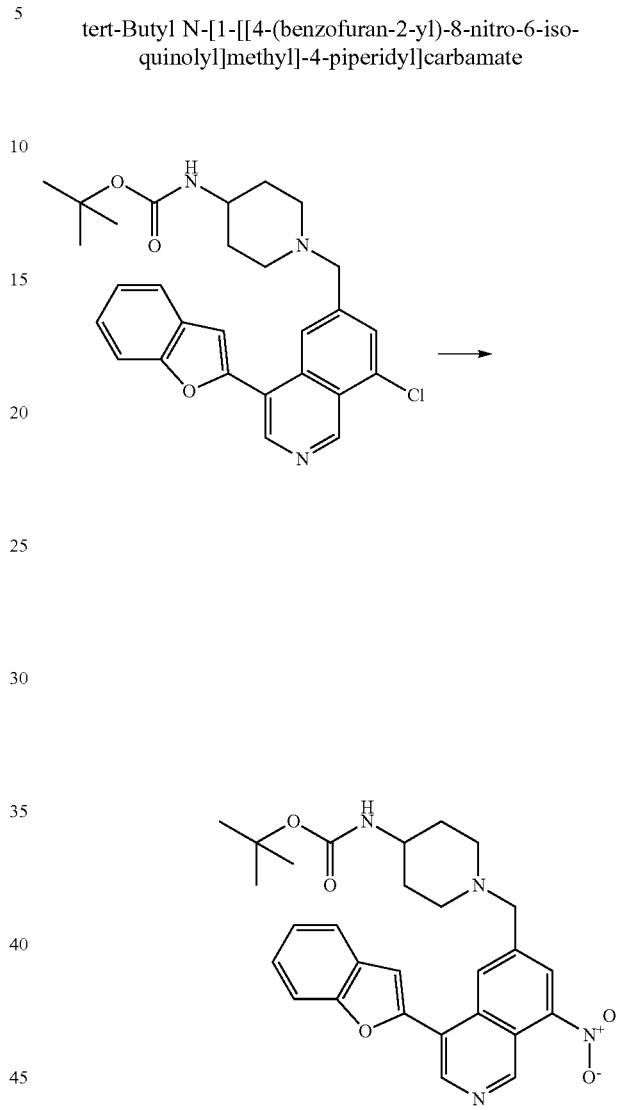

To a 10 mL pressure vessel charged with a magnetic stir bar were added 0.04 g (0.51 mmol) of NaNO$_2$, 0.0016 g (0.005 mmol) of tris[2-(2-methoxyethoxy)ethyl]amine, 0.05 g (0.1 mmol) of tBuBrettPhos, 0.05 g (0.1 mmol) of tert-butyl N-[1-[[4-(benzofuran-2-yl)-8-chloro-6-isoquinolyl]methyl]-4-piperidyl] carbamate, 0.04 g (0.04 mmol) of Pd$_2$(dba)$_3$ and 2.0 mL of t-BuOH. The reaction mixture was reacted under microwave irradiation at 120° C. (MW power 90 W) for 30 mins. The reaction solution was purified by preparative HPLC to give 0.03 g of tert-butyl N-[1-[[4-(benzofuran-2-yl)-8-nitro-6-isoquinolyl]methyl]-4-piperidyl]carbamate as an orange solid.

MS (ESI+): 503.2 [M+H]$^+$.

$^1$H NMR (400 MHz, DMSO-d$_6$+D$_2$O) δ ppm: 9.84 (s, 1H), 9.14 (s, 1H), 8.94 (s, 1H), 8.65 (s, 1H), 7.82 (d, J=7.6 Hz, 1H), 7.75 (d, J=8.4 Hz, 1H), 7.65 (s, 1H), 7.44 (m, 2H), 4.63 (s, 2H), 3.46-3.07 (m, 5H), 1.94 (m, 2H), 1.54 (m, 2H), 1.35 (s, 9H).

1-[[4-(Benzofuran-2-yl)-8-nitro-6-isoquinolyl]methyl]piperidin-4-amine (Example 252)

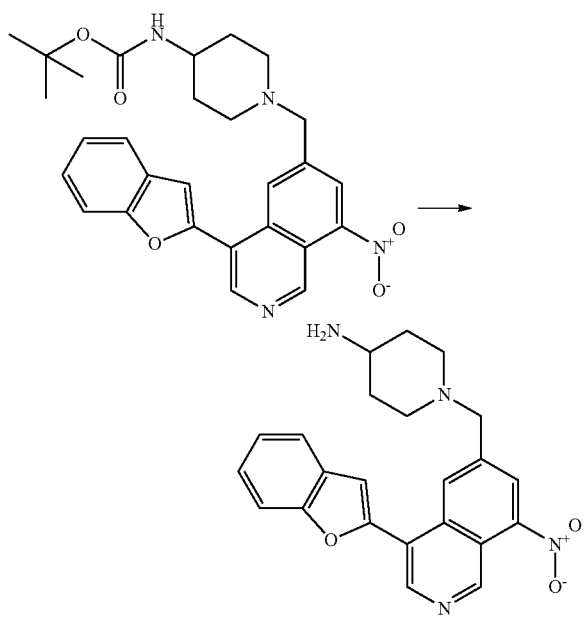

To a solution of 0.06 g (0.12 mmol) of tert-butyl N-[1-[[4-(benzofuran-2-yl)-8-nitro-6-isoquinolyl] methyl]-4-piperidyl]carbamate in 2.0 mL of EtOAc was added 2.0 mL of a solution of 4N HCl in EtOAc. The mixture was stirred at 20° C. for 1 h. The solid was collected by filtration and washed with EtOAc three times to afford 0.043 g of 1-[[4-(benzofuran-2-yl)-8-nitro-6-isoquinolyl]methyl]piperidin-4-amine as an orange solid.

MS (ESI+): 403.3 [M+H]$^+$.

$^1$H NMR (400 MHz, DMSO-d$_6$+D$_2$O) δ ppm: 9.84 (s, 1H), 9.16 (s, 1H), 9.00 (s, 1H), 8.75 (s, 1H), 7.76 (m, 3H), 7.42 (m, 2H), 4.67 (s, 2H), 3.51 (m, 2H), 3.12 (m, 2H), 2.11 (m, 2H), 1.85 (m, 2H).

6-Methyl-7-nitro-isoquinoline

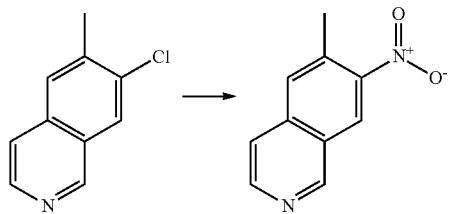

A sealable vial was charged with 0.05 g (0.14 mmol) of tris[2-(2-methoxyethoxy)ethyl]amine, 0.68 g (1.41 mmol) of 2-(di-tert-butylphosphino)-2',4',6'-triisopropyl-3,6-dimethoxybiphenyl, 0.5 g (2.81 mmo) of 7-chloro-6-methyl-isoquinoline (prepared from 3-chlorobenzylaldehyde and 2,2-dimethoxyethanamine via four steps in analogy to the preparation of 8-chloro-6-methyl-isoquinoline), 0.52 g (0.56 mmol) of Pd$_2$(dba)$_3$, 0.97 g (14.07 mmol) of NaNO$_2$ and 15 mL of t-BuOH (15 mL). The vessel was evacuated and backfilled with argon. The reaction mixture was stirred at 135° C. for 20 h. The solvent was removed under vacuum to give the residue which was purified by column chromatography (PE/EA: 10/1-4/1, R$_f$=0.4) to afford 0.47 g of 6-methyl-7-nitro-isoquinoline as a yellow solid.

MS (ESI+): 189.1 [M+H]$^+$.

$^1$H NMR (400 MHz, DMSO-d$_6$) δ ppm: 9.52 (s, 1H), 8.94 (s, 1H), 8.67 (d, J=6.0 Hz, 1H), 8.08 (s, 1H), 7.89 (d, J=5.6 Hz, 1H), 2.68 (s, 3H).

4-Bromo-6-methyl-7-nitro-isoquinoline

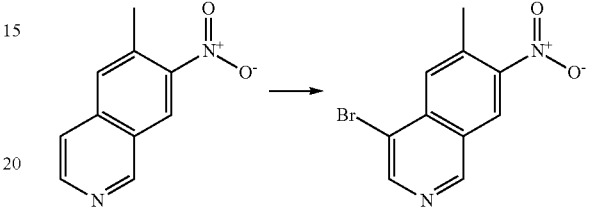

To a solution of 0.2 g (1.06 mmol) of 6-methyl-7-nitro-isoquinoline in 5.0 mL of AcOH was added 0.28 g (1.59 mmol) of NBS and the reaction mixture was stirred at 60° C. for 2 h. The solvent was removed under vacuum to give the residue which was dissolved in DCM, washed with saturated aqueous Na$_2$CO$_3$ and brine, dried over Na$_2$SO$_4$, filtered and concentrated to afford the crude product. The crude product was purified by column chromatography (PE/EA: 10/1-6/1, R$_f$=0.5) to afford 0.14 g of 4-bromo-6-methyl-7-nitro-isoquinoline as a light yellow solid.

MS (ESI+): 267.0, 269.0 [M+H]$^+$.

$^1$H NMR (400 MHz, DMSO-d$_6$) δ ppm: 9.51 (s, 1H), 9.03 (s, 1H), 8.93 (s, 1H), 8.14 (s, 1H), 2.75 (m, 3H).

4-Bromo-6-(bromomethyl)-7-nitro-isoquinoline

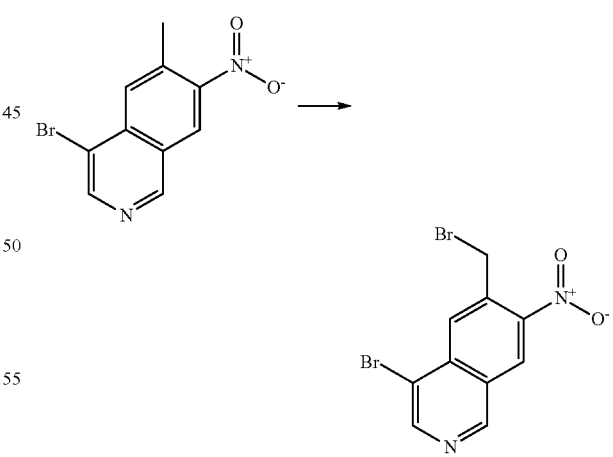

To a stirred solution of 0.23 g (0.86 mmol) of 4-bromo-6-methyl-7-nitro-isoquinoline in 10 mL of CCl$_4$ were added 0.17 g (0.95 mmol) of NBS and 0.13 g (0.52 mmol) of BPO. The reaction mixture was heated to 110° C. for 2 h. TLC (EA/PE=1/4, R$_{f\ SM}$=0.4, R$_{fpro.}$=0.3) indicated that about 50% of starting material remained, so additional 0.085 g (0.48 mmol) of NBS and 0.065 g (0.26 mmol) of BPO were added into the reaction and the stirring was continued for another 2 h at 110° C. The solvent was removed under vacuum to give crude product. The crude product was purified by column chromatography (EA/PE: 20/1-10/1) to afford 0.16 g of 4-bromo-6-(bromomethyl)-7-nitro-isoquinoline as a yellow solid.

MS (ESI+): 344.9, 346.9, 348.9 [M+H]⁺.

¹H NMR (400 MHz, DMSO-$d_6$) δ ppm: 9.58 (s, 1H), 9.15 (s, 1H), 9.02 (s, 1H), 8.49 (s, 1H), 5.26 (s, 2H).

tert-Butyl N-[1-[(4-bromo-7-chloro-6-isoquinolyl)methyl]-4-piperidyl]carbamate

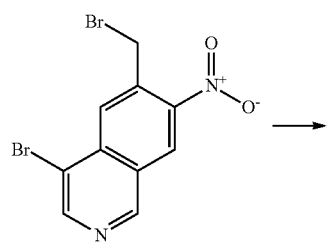

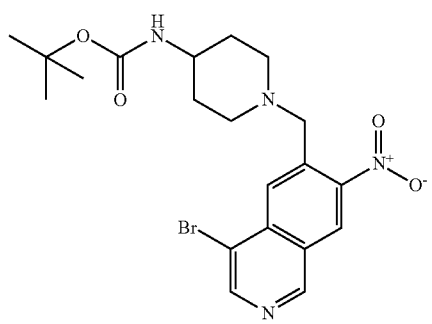

To a stirred solution of 0.11 g (0.32 mmol) of 4-bromo-6-(bromomethyl)-7-chloro-isoquinoline in 2.0 mL of DMF and 2.0 mL of THF were added 0.08 g (0.38 mmol) of 4-N-Boc-amino-piperidine and 0.13 g (0.95 mmol) of $K_2CO_3$. The reaction mixture was stirred at 50° C. for 3 h. The mixture was cooled and filtered through Celite. The filtrate was concentrated under vacuum to give the crude product which was purified by column chromatography (PE/EA: 10/1-4/1, $R_f$=0.3) to afford 0.11 g of tert-butyl N-[1-[(4-bromo-7-chloro-6-isoquinolyl)methyl]-4-piperidyl]carbamate as an off-white solid.

MS (ESI+): 465.1, 467.1 [M+H]⁺.

¹H NMR (400 MHz, DMSO-$d_6$) δ ppm: 9.49 (s, 1H), 8.95 (s, 1H), 8.89 (s, 1H), 8.24 (s, 1H), 6.78 (d, J=7.2 Hz, 1H), 3.93 (s, 2H), 3.20 (m, 1H), 2.65 (m, 2H), 2.11 (m, 2H), 1.62 (m, 2H), 1.36 (s, 9H), 1.26 (m, 2H).

tert-Butyl N-[1-[[4-(benzofuran-2-yl)-7-chloro-6-isoquinolyl]methyl]-4-piperidyl]carbamate

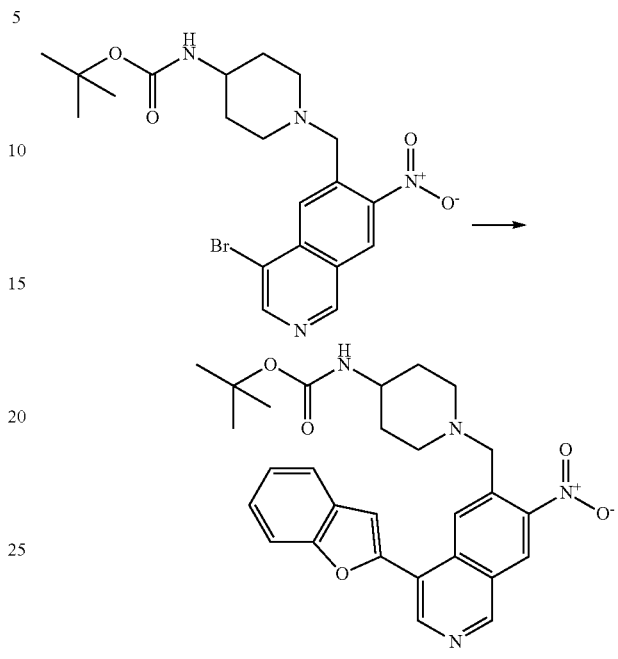

To a stirred solution of 0.1 g (0.21 mmol) of tert-butyl N-[1-[(4-bromo-7-chloro-6-isoquinolyl) methyl]-4-piperidyl] carbonate in 4.0 mL of dioxane and 0.4 mL of $H_2O$ were added 0.1 g (0.64 mmol) of benzofuran-2-ylboronic acid, 0.02 g (0.02 mmol) of Pd(PPh₃)₄ and 0.14 g (0.64 mmol) of $K_3PO_4$. The reaction mixture was stirred under argon at 95° C. for 1.5 h. The volatiles were removed under vacuum. The residue was then purified by flash column chromatography (PE/EA: 6/1-4/1) to afford 0.1 g of tert-butyl N-[1-[[4-(benzofuran-2-yl)-7-chloro-6-isoquinolyl]methyl]-4-piperidyl]carbamate as a yellow solid.

MS (ESI+): 503.3 [M+H]⁺.

¹H NMR (400 MHz, DMSO-$d_6$) δ ppm: 9.56 (s, 1H), 9.13 (s, 1H), 8.91 (s, 1H), 8.67 (s, 1H), 7.80 (m, 2H), 7.65 (s, 1H), 7.47-7.36 (m, 2H), 6.80 (d, J=7.6 Hz, 1H, NH), 3.94 (s, 2H), 3.18 (m, 1H), 2.67 (m, 2H), 2.10 (m, 2H), 1.63 (m, 2H), 1.36 (s, 9H), 1.28 (m, 2H).

1-[[4-(Benzofuran-2-yl)-8-nitro-6-isoquinolyl]methyl]piperidin-4-amine (Example 253)

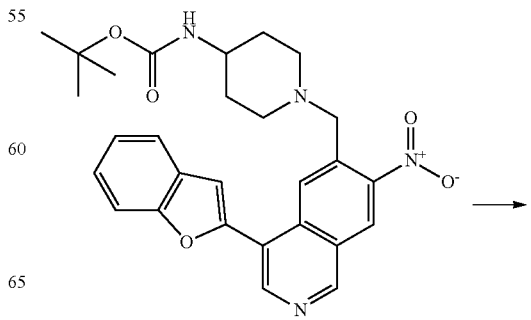

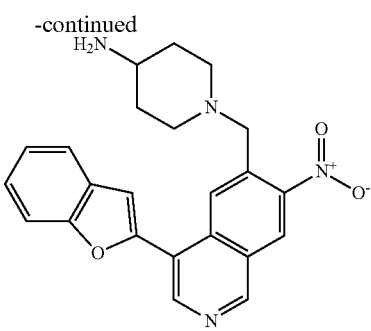

A suspension of 0.06 g (0.12 mmol) of tert-butyl N-[1-[[4-(benzofuran-2-yl)-8-nitro-6-isoquinolyl] methyl]-4-piperidyl]carbamate in 2.0 mL of a solution of 4N HCl in EtOAc was stirred at 20° C. for 1 h. The solid was collected by filtration and washed with EtOAc three times to afford 50 mg of 1-[[4-(benzofuran-2-yl)-8-nitro-6-isoquinolyl] methyl]piperidin-4-amine as an orange solid.

MS (ESI+): 403.3 [M+H]⁺.

¹H NMR (400 MHz, DMSO-d₆+D₂O) δ ppm: 9.71 (s, 1H), 9.38 (s, 1H), 9.23 (s, 1H), 8.85 (s, 1H), 7.82 (d, J=7.2 Hz, 1H), 7.76 (m, 2H), 7.47-7.37 (m, 2H), 4.86 (s, 2H), 3.62 (m, 2H), 3.32 (m, 3H), 2.15 (m, 2H), 1.86 (m, 2H).

tert-Butyl N-[1-[[7-amino-4-(benzofuran-2-yl)-6-isoquinolyl]methyl]-4-piperidyl]carbamate

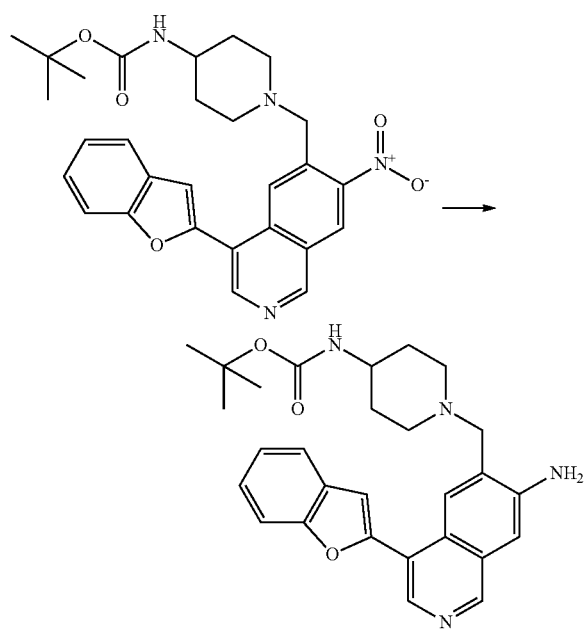

To a solution of 0.14 g (0.28 mmol) of tert-butyl N-[1-[[4-(benzofuran-2-yl)-7-nitro-6-isoquinolyl] methyl]-4-piperidyl]carbamate in 23 mL of EtOH and 7.0 mL of H₂O were added 0.09 g (1.67 mmol) of iron powder and 0.09 g of NH₄Cl. The suspension was stirred at 80° C. for 2 h. The solid was filtered off and the filtrate was concentrated to give the residue which was purified by column chromatography (DCM/MeOH=100/1-20/1) to afford 0.11 g of tert-butyl N-[1-[[7-amino-4-(benzofuran-2-yl)-6-isoquinolyl]methyl]-4-piperidyl]carbamate as a light yellow solid.

MS (ESI+): 473.2 [M+H]⁺.

¹H NMR (400 MHz, DMSO-d₆) δ ppm: 9.00 (s, 1H), 8.55 (s, 1H), 8.13 (s, 1H), 7.74 (m, 2H), 7.45 (s, 1H), 7.41-7.31 (m, 2H), 7.16 (s, 1H), 6.80 (d, J=8.0 Hz, 1H, NH), 6.06 (br s, 2H, NH₂), 3.65 (s, 2H), 3.23 (m, 1H), 2.79 (m, 2H), 2.03 (m, 2H), 1.71 (m, 2H), 1.37 (m, 11H).

6-[(4-Amino-1-piperidyl)methyl]-4-(benzofuran-2-yl)isoquinolin-7-amine (Example 254)

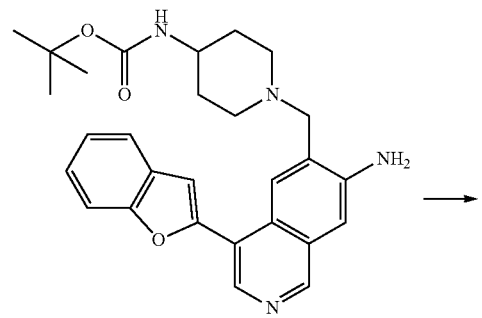

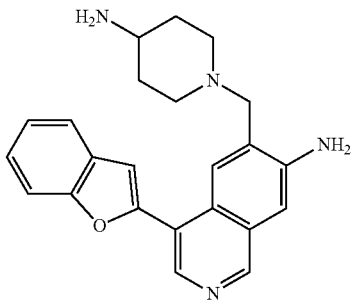 [SMILES: Nc1cc(CN2CCC(N)CC2)cc2c(-c3cc4ccccc4o3)cncc12]

A suspension of 0.11 g (0.23 mmol) of tert-butyl N-[1-[[7-amino-4-(benzofuran-2-yl)-6-isoquinolyl]methyl]-4-piperidyl]carbamate in 2.0 mL of a solution of 4N HCl in EtOAc was stirred at 20° C. for 1 h. The solid was collected by filtration and washed with EtOAc three times to afford 0.11 g of 6-[(4-amino-1-piperidyl)methyl]-4-(benzofuran-2-yl)isoquinolin-7-amine as a yellow solid.

MS (ESI+): 373.3 [M+H]⁺.

¹H NMR (400 MHz, DMSO-d₆+D₂O) δ ppm: 9.32 (s, 1H), 8.63 (s, 1H), 7.84 (s, 1H), 7.80 (d, J=7.6 Hz, 1H), 7.75 (d, J=8.4 Hz, 1H), 7.46 (m, 2H), 7.38 (m, 1H), 4.58 (s, 2H), 3.50 (m, 3H), 3.22 (m, 2H), 2.11 (m, 2H), 1.89 (m, 2H).

The following compound was prepared in analogy to Example 254 by reaction of tert-butyl N-[1-[[4-(benzofuran-2-yl)-8-nitro-6-isoquinolyl] methyl]-4-piperidyl]carbamate with iron powder and subsequent deprotection:

| Example | | ¹H NMR (400 MHz) δ ppm | MS (+ESI) [M + H]⁺ |
|---|---|---|---|
| 255 | 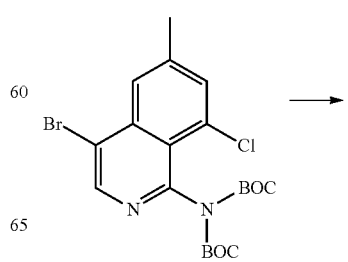 | (DMSO-d₆ + D₂O) 9.62 (s, 1H), 8.82 (s, 1H), 7.78 (d, J = 7.2 Hz, 1H), 7.71 (d, J = 8.0 Hz, 1H), 6.65 (s, 1H), 6.55 (s, 1H), 7.45-7.34 (m, 2H), 6.93 (s, 1H), 4.37 (s, 2H), 3.44 (m, 2H), 3.25 (m, 1H), 3.08 (m, 2H), 2.09 (m, 2H), 1.72 (m, 2H). | 473.3 |

4-Bromo-8-chloro-6-methyl-isoquinolin-1-amine

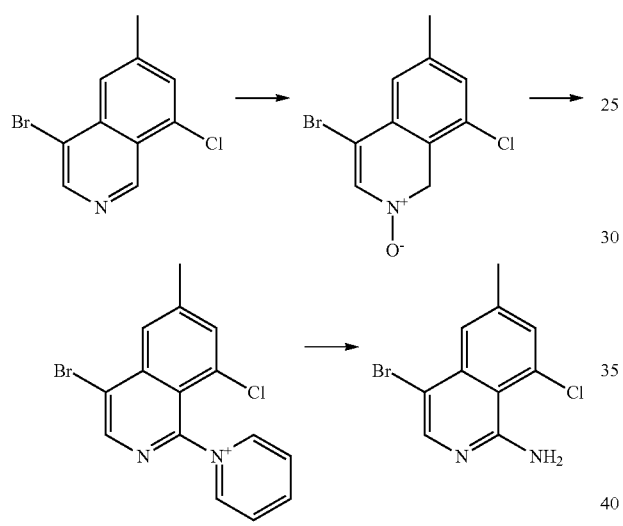

To a solution of 0.26 g (1.01 mmol) of 4-bromo-8-chloro-6-methyl-isoquinoline in 50 mL of DCM was added 0.68 g (3.04 mmol) of 3-chloroperoxybenzoic acid and the reaction mixture was stirred at 20° C. for 16 h. The reaction was quenched with aqueous Na₂SO₃ solution and aqueous NaHCO₃ solution and extracted with DCM. The organic phases were washed with water, dried over Na₂SO₄, filtered and concentrated under vacuum to give 0.27 g of 4-bromo-8-chloro-6-methyl-2-oxido-isoquinolin-2-ium as a yellow solid which was used in the next step without further purification.

To a solution of 0.27 g (0.99 mmol) of 4-bromo-8-chloro-6-methyl-2-oxido-isoquinolin-2-ium in 10 mL of pyridine was added 0.38 g (1.98 mmol) of p-toluenesulfonyl chloride and then the mixture was stirred at 20° C. for 2 h. The solvent was removed under vacuum to give 0.3 g of 4-bromo-8-chloro-6-methyl-1-pyridin-1-ium-1-yl-isoquinoline as a brown semisolid which was used in the next step without further purification.

A solution of 0.3 g (0.90 mmol) of 4-bromo-8-chloro-6-methyl-1-pyridin-1-ium-1-yl-isoquinoline in 2 mL (33.14 mmol) of ethanolamine was stirred at 20° C. for 16 h. The reaction mixture was poured into ice water and extracted with DCM. The organic layer was dried over Na₂SO₄ and evaporated to give the crude product which was purified by column chromatography on silica gel with PE-EA (3:1, R$_f$=0.4) to afford 0.12 g of 4-bromo-8-chloro-6-methyl-isoquinolin-1-amine product as a yellow solid.

MS m/z (+ESI): 271.1, 273.1, 275.1 [M+H]⁺.
¹H NMR (400 MHz, DMSO-d₆) δ ppm: (s, 1H), 7.68 (s, 1H), 7.55 (d, J=1.5 Hz, 1H), 7.12 (s, 2H), 2.47 (s, 3H).

tert-Butyl N-(4-bromo-8-chloro-6-methyl-1-isoquinolyl)-N-tert-butoxycarbonyl-carbamate

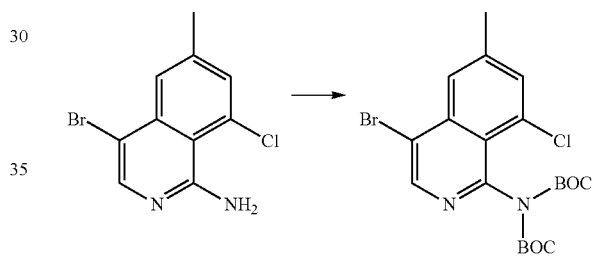

To a solution of 0.1 g (0.37 mmol) of 4-bromo-8-chloro-6-methyl-isoquinolin-1-amine in 20 mL of DCM were added 0.32 g (1.47 mmol) of Boc₂O, 14 mg (0.11 mmol) of DMAP and 0.1 mL (0.74 mmol) of TEA and then the mixture was stirred at 35° C. for 16 h. The solvent was removed under vacuum and the residue was purified by column chromatography eluting with PE/EA=8:1 (R$_f$=0.2) to yield 0.13 g of the desired product as a yellow solid.

MS m/z (+ESI): 471.4, 473.4, 475.4 [M+H]⁺.
¹H NMR (400 MHz, DMSO-d6) δ ppm: 8.76 (s, 1H), 8.02 (s, 1H), 7.91 (d, J=1.2 Hz, 1H), 2.58 (s, 3H), 1.28 (s, 18H).

tert-Butyl N-[4-(benzofuran-2-yl)-6-[[4-(tert-butoxycarbonylamino)-1-piperidyl]methyl]-8-chloro-1-isoquinolyl]-N-tert-butoxycarbonyl-carbamate

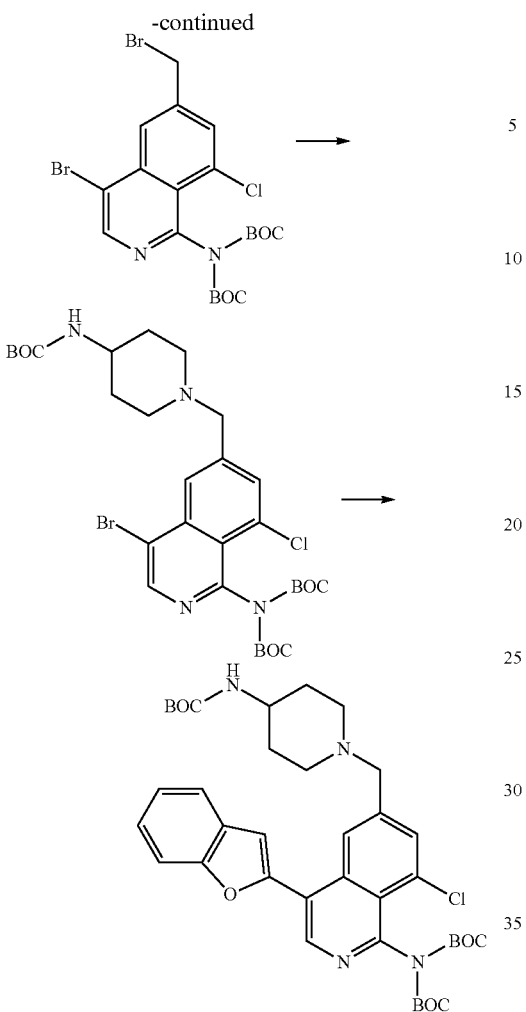

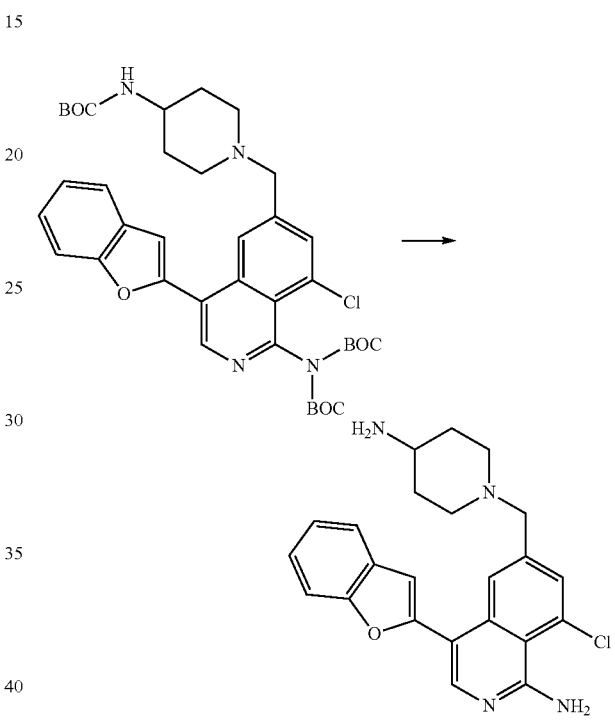

To a stirred solution of 0.3 g (0.64 mmol) of tert-butyl N-(4-bromo-8-chloro-6-methyl-1-isoquinolyl)-N-tert-butoxycarbonyl-carbamate and 0.11 g (0.64 mmol) of NBS in 30 mL of $CCl_4$ was added 10 mg (0.064 mmol) of AIBN. The reaction mixture was heated to 100° C. for 2 h. The reaction mixture was used in the next step directly without any work-up.

To the above stirred solution of 0.35 g (0.64 mmol) of tert-butyl N-[4-bromo-6-(bromomethyl)-8-chloro-1-isoquinolyl]-N-tert-butoxycarbonyl-carbamate in 30 mL of $CCl_4$ were added 20 mL of DCM, 0.26 g (1.91 mmol) of $K_2CO_3$ and 0.15 g (0.76 mmol) of 4-N-Boc-amino-piperidine. The reaction mixture was stirred at 20° C. for 16 h and filtered through Celite. The filtrate was concentrated under vacuum. The crude product was purified by column chromatography on silica gel with PE-EA (5:1 to 1:1, $R_f$=0.6) to afford 0.14 g of tert-butyl N-[4-bromo-6-[[4-(tert-butoxycarbonylamino)-1-piperidyl]methyl]-8-chloro-1-isoquinolyl]-N-tert-butoxycarbonyl-carbamate as a yellow oil.

To a stirred solution of 0.14 g (0.21 mmol) of tert-butyl N-[4-bromo-6-[[4-(tert-butoxycarbonylamino)-1-piperidyl]methyl]-8-chloro-1-isoquinolyl]-N-tert-butoxycarbonyl-carbamate and 0.1 g (0.63 mmol) of benzofuran-2-boronic acid in 8 mL of dioxane and 0.5 mL of $H_2O$ were added 0.18 g (0.84 mmol) of $K_3PO_4$ and 48 mg (0.042 mmol) of $Pd(PPh_3)_4$. The reaction mixture was stirred for 3 h at 95° C. under Argon. The volatiles were removed under vacuum. The crude product was purified by column chromatography on silica gel with PE-EA (3:1 to 4:3, $R_f$=0.2) to produce 130 mg of the desired product as a yellow foam.

MS m/z (+ESI): 707.8, 709.8 [M+H]$^+$ $^1$H NMR (400 MHz, CDCl$_3$) δ ppm: 8.85 (s, 1H), 8.37 (s, 1H), 7.90 (d, J=1.3 Hz, 1H), 7.82 (d, J=7.3 Hz, 1H), 7.76 (d, J=8.5 Hz, 1H), 7.57 (s, 1H), 7.48-7.42 (m, 1H), 7.41-7.35 (m, 1H), 6.79 (br d, J=7.8 Hz, 1H), 3.70 (s, 2H), 3.29-3.16 (m, 1H), 2.83-2.73 (m, 2H), 2.13-2.01 (m, 2H), 1.76-1.64 (m, 2H), 1.48-1.40 (m, 2H), 1.37 (s, 9H), 1.32 (s, 18H).

6-[(4-Amino-1-piperidyl)methyl]-4-(benzofuran-2-yl)-8-chloro-isoquinolin-1-amine (Example 256)

A mixture of 2.1 g (2.97 mmol) of tert-butyl N-[4-(benzofuran-2-yl)-6-[[4-(tert-butoxycarbonylamino)-1-piperidyl]methyl]-8-chloro-1-isoquinolyl]-N-tert-butoxycarbonyl-carbamate in a solution of 50 mL of 2 N solution of HCl in EtOAc was stirred at 20° C. for 2 h until LC-MS showed the reaction was complete. The volatiles were removed under vacuum and the residue was purified by Biotage flash chromatography using acidic conditions (TFA). The desired fractions were concentrated to remove most of ACN and to the residue was added 2 mL of 37% aqueous HCl. After lyophilisation, 1.1 g of 6-[(4-amino-1-piperidyl)methyl]-4-(benzofuran-2-yl)-8-chloro-isoquinolin-1-amine as HCl salt was obtained as a yellow solid.

MS m/z (+ESI): 407.3, 409.3 [M+H]$^+$ $^1$H NMR (400 MHz, DMSO-d$_6$+D$_2$O) δ ppm: 8.31 (d, J=1.2 Hz, 1H), 8.24 (s, 1H), 8.10 (d, J=1.6 Hz, 1H), 7.74 (d, J=7.2 Hz, 1H), 7.66 (d, J=8.0 Hz, 1H), 7.41 (s, 1H), 7.40-7.31 (m, 2H), 4.49 (s, 2H), 3.50-3.36 (m, 2H), 3.35-3.18 (m, 1H), 3.17-3.02 (m, 2H), 2.16-2.05 (m, 2H), 1.95-1.77 (m, 2H).

The following compounds were prepared in analogy to Example 256 by reaction of tert-butyl N-[4-bromo-6-[[4-(tert-butoxycarbonylamino)-1-piperidyl]methyl]-8-chloro-1-isoquinolyl]-N-tert-butoxycarbonyl-carbamate with phenylboronic acid by Suzuki coupling in the presence of a Pd-catalyst and subsequent deprotection:

| Example | 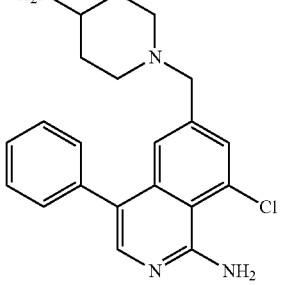 | ¹H NMR (400 MHz) δ ppm | MS (+ESI) [M + H]⁺ |
|---|---|---|---|
| 257 | | (DMSO-d₆ + D₂O) 8.18 (s, 1H), 7.79 (d, J = 1.2 Hz, 1H), 7.77 (s, 1H), 7.59-7.47 (m, 5H), 4.40 (s, 2H), 3.41-3.34 (m, 2H), 3.29-3.20 (m, 1H), 3.08-2.99 (m, 2H), 2.10-2.05 (m, 2H), 1.92-1.81 (m, 2H). | 367.4, 369.3 |

(4-Bromo-8-chloro-6-isoquinolyl)methanol

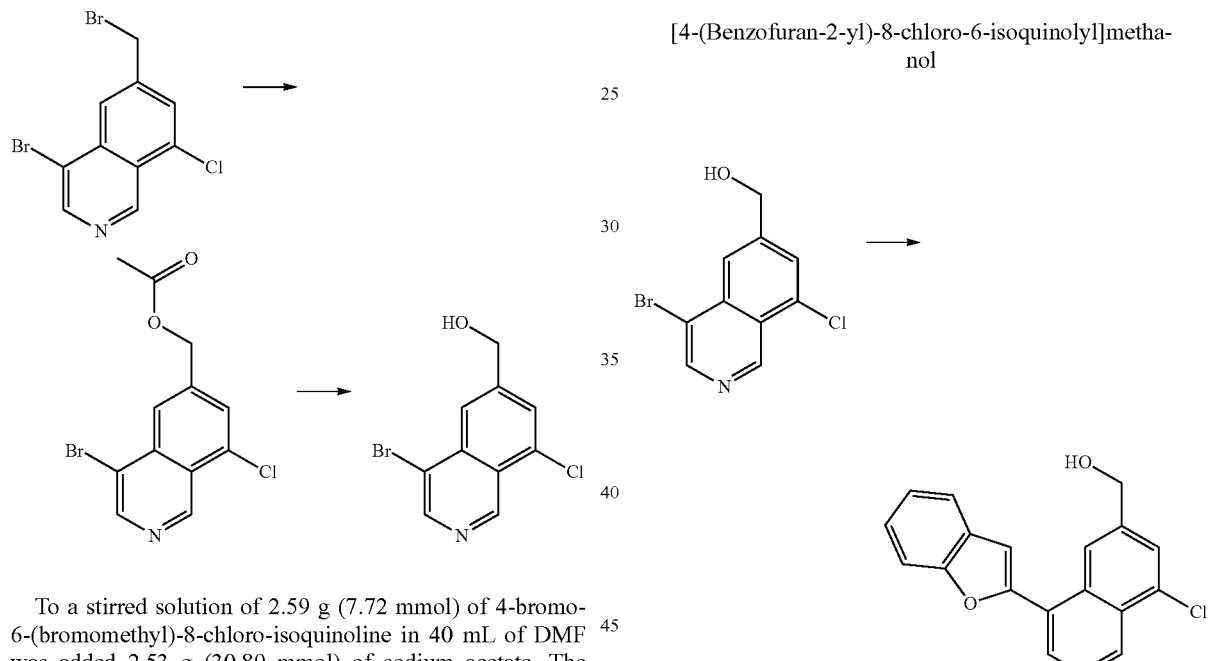

To a stirred solution of 2.59 g (7.72 mmol) of 4-bromo-6-(bromomethyl)-8-chloro-isoquinoline in 40 mL of DMF was added 2.53 g (30.89 mmol) of sodium acetate. The reaction mixture was heated to 70° C. for 1 h under argon. The reaction mixture was cooled to room temperature and diluted with EtOAc and water. The aqueous phase was extracted with EtOAc. The combined EtOAc phases were washed with water and brine, dried over Na₂SO₄, filtered and concentrated to dryness to give 2.42 g of (4-bromo-8-chloro-6-isoquinolyl)methyl acetate as a yellow semisolid.

To a stirred solution of 2.42 g (7.69 mmol) of 4-bromo-8-chloro-6-isoquinolyl)methyl acetate in 20 mL of MeOH, 40 mL of THF and 2 mL of H₂O was added 1.61 g (38.47 mmol) of lithium hydroxide monohydrate. The reaction mixture was stirred for 16 h at 10° C. under argon. The reaction mixture was diluted with DCM and dried with Na₂SO₄. The desiccant was filtered off and the filtrate was concentrated to dryness. The crude product was purified by column chromatography on silica gel with PE-EA (10:1), DCM-EA (10:1, R$_f$=0.4) to produce 1.06 g of (4-bromo-8-chloro-6-isoquinolyl)methanol as a light yellow solid.

MS m/z (+ESI): 271.9, 274.0, 275.9 [M+H]⁺

¹H NMR (400 MHz, CDCl₃) δ ppm: 9.57 (s, 1H), 8.81 (s, 1H), 8.09 (s, 1H), 7.76 (s, 1H), 4.96 (d, J=5.5 Hz, 2H), 2.18 (t, J=5.5 Hz, 1H).

[4-(Benzofuran-2-yl)-8-chloro-6-isoquinolyl]methanol

To a stirred solution of 1.06 g (3.89 mmol) of (4-bromo-8-chloro-6-isoquinolyl)methanol in 20 mL of dioxane and 2 mL of H₂O were added 1.26 g (7.78 mmol) of benzofuran-2-boronic acid, 0.45 g (0.39 mmol) of Pd(PPh₃)₄, and 2.48 g (11.67 mmol) of K₃PO₄. The reaction mixture was stirred under Argon at 90° C. for 3 h and LC-MS showed the reaction was complete. The volatiles were removed under vacuum. The crude product was purified by column chromatography on silica gel with DCM, DCM-EA (20:1, R$_f$=0.15) to produce 0.78 g of the desired product as a light yellow solid.

MS m/z (+ESI): 310.1, 312.1 [M+H]⁺.

¹H NMR (400 MHz, DMSO-d₆+D₂O) δ ppm: 9.54 (s, 1H), 8.95 (s, 1H), 8.33 (s, 1H), 7.82 (s, 1H), 7.77 (d, J=7.0 Hz, 1H), 7.70 (d, J=8.3 Hz, 1H), 7.51 (s, 1H), 7.40 (dd, J=8.3 Hz, 1.3 Hz, 1H), 7.35 (dd, J=7.6 Hz, 0.9 Hz, 1H), 4.73 (s, 2H).

[4-(Benzofuran-2-yl)-8-methoxy-6-isoquinolyl]methanol

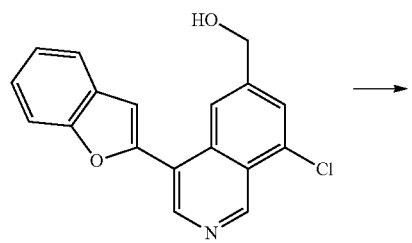

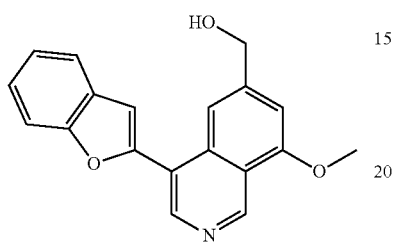

To a solution of 0.78 g (1.76 mmol) of 4-(benzofuran-2-yl)-8-chloro-6-isoquinolyl]methanol in 10 mL of dioxane and 10 mL of MeOH were added 0.24 g (0.53 mmol) of X-phos, 306 mg (0.26 mmol) of Pd(PPh$_3$)$_4$ and 1.90 g (35.3 mmol) of NaOMe. The reaction mixture was heated in a sealable vial at 100° C. for 3 h. The reaction was diluted with DCM and filtered through Celite. The filtrate was concentrated to dryness and purified by column chromatography eluting with DCM-MeOH (100:1, R$_f$=0.1) to 320 mg of the desired product as a yellow solid.

MS m/z (+ESI): 306.1 [M+H]$^+$.

$^1$H NMR (400 MHz, DMSO-d$_6$+D$_2$O) δ ppm: 9.48 (s, 1H), 8.86 (s, 1H), 7.92 (s, 1H), 7.77 (d, J=7.3 Hz, 1H), 7.70 (d, J=8.0 Hz, 1H), 7.47 (s, 1H), 7.43-7.37 (m, 1H), 7.37-7.31 (m, 1H), 7.15 (s, 1H), 4.72 (s, 2H), 4.04 (s, 3H).

[4-(Benzofuran-2-yl)-8-methoxy-2-oxido-isoquinolin-2-ium-6-yl]methanol

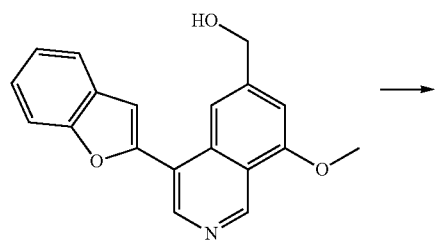

To a solution of 0.29 g (0.62 mmol) of [4-(benzofuran-2-yl)-8-methoxy-6-isoquinolyl]methanol in 10 mL of DCM was added 415 mg (1.85 mmol) of 3-chloroperoxybenzoic acid and then the reaction mixture was stirred at 15° C. for 16 h. The precipitated solid was collected by filtration and rinsed with aqueous Na$_2$CO$_3$ and water. After drying under vacuum, 160 mg of [4-(benzofuran-2-yl)-8-methoxy-2-oxido-isoquinolin-2-ium-6-yl]methanol was obtained as a yellow solid.

MS m/z (+ESI): 322.1 [M+H]$^+$ $^1$H NMR (400 MHz, DMSO-d$_6$+D$_2$O) δ ppm: 8.87 (s, 1H), 8.54 (d, J=1.8 Hz, 1H), 7.90 (s, 1H), 7.79 (d, J=7.5 Hz, 1H), 7.72 (d, J=8.3 Hz, 1H), 7.62 (s, 1H), 7.47-7.40 (m, 1H), 7.40-7.33 (m, 1H), 7.18 (s, 1H), 4.69 (s, 2H), 4.01 (s, 3H).

1-Amino-4-(benzofuran-2-yl)-8-methoxy-6-isoquinolyl]methanol

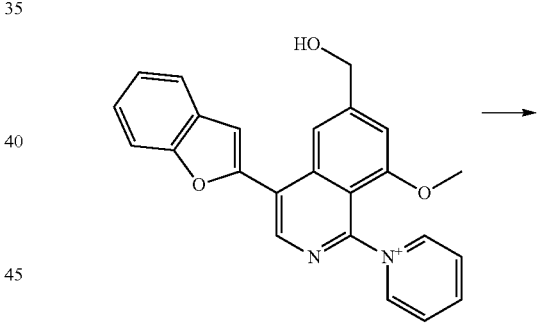

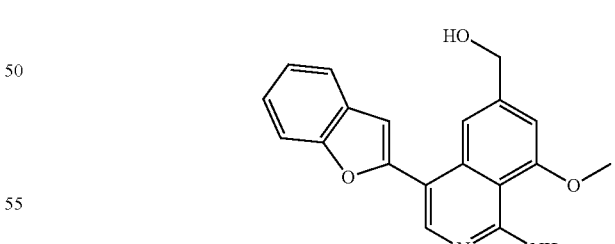

To a stirred solution of 0.16 g (0.49 mmol) of [4-(benzofuran-2-yl)-8-methoxy-2-oxido-isoquinolin-2-ium-6-yl]methanol in 3 mL of pyridine was added 0.19 g (0.98 mmol) of TsCl and the reaction mixture was stirred at 15° C. for 1 h. The mixture was concentrated to dryness to give 0.18 g of 4-(benzofuran-2-yl)-8-methoxy-1-pyridin-1-ium-1-yl-6-isoquinolyl]methanol as a light brown semisolid which was used in the next step directly.

To a solution of 0.18 g (0.46 mmol) of [4-(benzofuran-2-yl)-8-methoxy-1-pyridin-1-ium-1-yl-6-isoquinolyl]methanol in 2 mL of DCM was added 1.13 mL (18.59 mmol) of ethanolamine. The mixture was stirred at 20° C. for 16 h. The reaction was quenched with water, extracted with DCM, dried over anhydrous Na₂SO₄, filtered and concentrated to dryness. The crude product was purified by flash column chromatography (DCM:MeOH=100:1 to 50:1) to give 100 mg of 1-amino-4-(benzofuran-2-yl)-8-methoxy-6-isoquinolyl]methanol as a yellow solid.

MS m/z (+ESI): 321.0 [M+H]⁺

¹H NMR (400 MHz, DMSO-d₆+D₂O) δ ppm: 8.06 (s, 1H), 7.65 (dd, J=7.6 Hz, 1.1 Hz, 1H), 7.61 (s, 1H), 7.57 (d, J=7.6 Hz), 7.31-7.23 (m, 2H), 7.06 (s, 1H), 6.98 (s, 1H), 4.59 (s, 2H), 3.98 (s, 3H).

6-[(4-Amino-1-piperidyl)methyl]-4-(benzofuran-2-yl)-8-methoxy-isoquinolin-1-amine (Example 258)

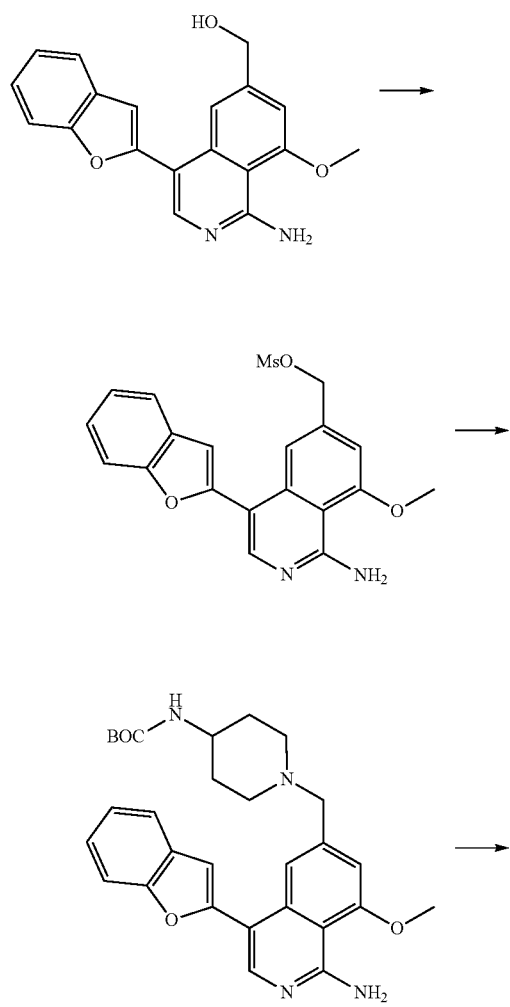

-continued

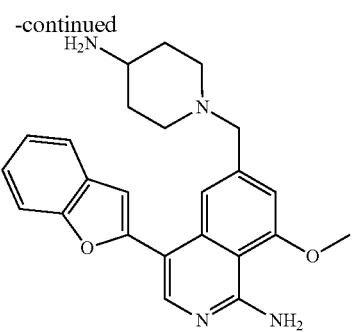

To a solution of 0.4 g (1.22 mmol) of [1-amino-4-(benzofuran-2-yl)-8-methoxy-6-isoquinolyl]methanol in 5 mL of DCM were added 0.25 g (2.45 mmol) of TEA and 0.21 g (1.84 mmol) of MsCl at 0° C. The mixture was stirred at 20° C. for 2 h. LC-MS showed most of the starting materials was consumed, and the mixture was quenched with water, extracted with DCM, dried over anhydrous Na₂SO₄, filtered and concentrated to dryness to give 0.48 g of [1-amino-4-(benzofuran-2-yl)-8-methoxy-6-isoquinolyl]methyl methanesulfonate as a yellow solid which was used in next step directly without further purification. To a solution of 0.48 g (1.18 mmol) of [1-amino-4-(benzofuran-2-yl)-8-methoxy-6-isoquinolyl]methyl methanesulfonate in 10 mL of THF were added 0.33 g (2.36 mmol) of K₂CO₃ and 0.36 g (1.77 mmol) of 4-(N-Boc-amino)piperidine. The mixture was stirred at 20° C. for 16 h. LC-MS showed the reaction was complete, and the mixture was quenched with water, extracted with DCM, dried over anhydrous Na₂SO₄, filtered and concentrated to dryness. The crude product was purified by flash column chromatography (DCM:MeOH=100:1 to 50:1) to give 0.4 g of tert-butyl N-[1-[[1-amino-4-(benzofuran-2-yl)-8-methoxy-6-isoquinolyl]methyl]-4-piperidyl]carbamate as a yellow solid.

To a stirred solution of 3.3 g (6.24 mmol) of tert-butyl N-[1-[[1-amino-4-(benzofuran-2-yl)-8-methoxy-6-isoquinolyl]methyl]-4-piperidyl]carbamate in 30 mL of DCM was added 9.46 mL (124.75 mmol) of TFA. The reaction mixture was stirred at 15° C. for 2 h. The volatiles were evaporated and the residue was purified by preparative HPLC to give the product as TFA salt. To the fractions was added 10 mL of 37% aqueous HCl, followed by lyophilization to give 1.86 g of 6-[(4-amino-1-piperidyl)methyl]-4-(benzofuran-2-yl)-8-methoxy-isoquinolin-1-amine HCl salt as a yellow solid.

MS m/z (+ESI): 403.5 [M+H]

¹H NMR (400 MHz, DMSO-d₆+D₂O) δ ppm: 8.08 (s, 1H), 7.86 (s, 1H), 7.73 (d, J=7.8 Hz, 1H), 7.66-7.64 (m, 2H), 7.40-7.36 (m, 2H), 7.34-7.30 (m, 1H), 4.46 (s, 2H), 4.13 (s, 3H), 3.44-3.39 (m, 2H), 3.28-3.23 (m, 1H), 3.10-3.04 (m, 2H), 2.10-2.07 (m, 2H), 1.93-1.84 (m, 2H).

The following compound was prepared in analogy to Example 258, starting from (4-bromo-8-chloro-6-isoquinolyl)methanol and phenylboronic acid.
and 2-methylpyrazol-3-amine.

| Example | 1H NMR (400 MHz) δ ppm | MS (+ESI) [M + H]+ |
|---|---|---|
| 259 | (DMSO-d6 + D2O) δ ppm: 7.67 (s, 1H), 7.59 (s, 1H), 7.54-7.33 (m, 5H), 7.32 (d, J = 0.8 Hz, 1H), 4.35 (s, 2H), 4.13 (s, 3H), 3.40-3.31 (m, 2H), 3.28-3.21 (m, 1H), 3.07-2.97 (m, 2H), 2.11-2.03 (m, 2H), 1.94-1.82 (m, 2H). | 363.4 |

4-(Benzofuran-2-yl)-6-(piperazin-1-ylmethyl)isoquinolin-3-amine (Example 260)

4-Bromo-6-[(4-quinolylamino)methyl]isoquinolin-3-amine

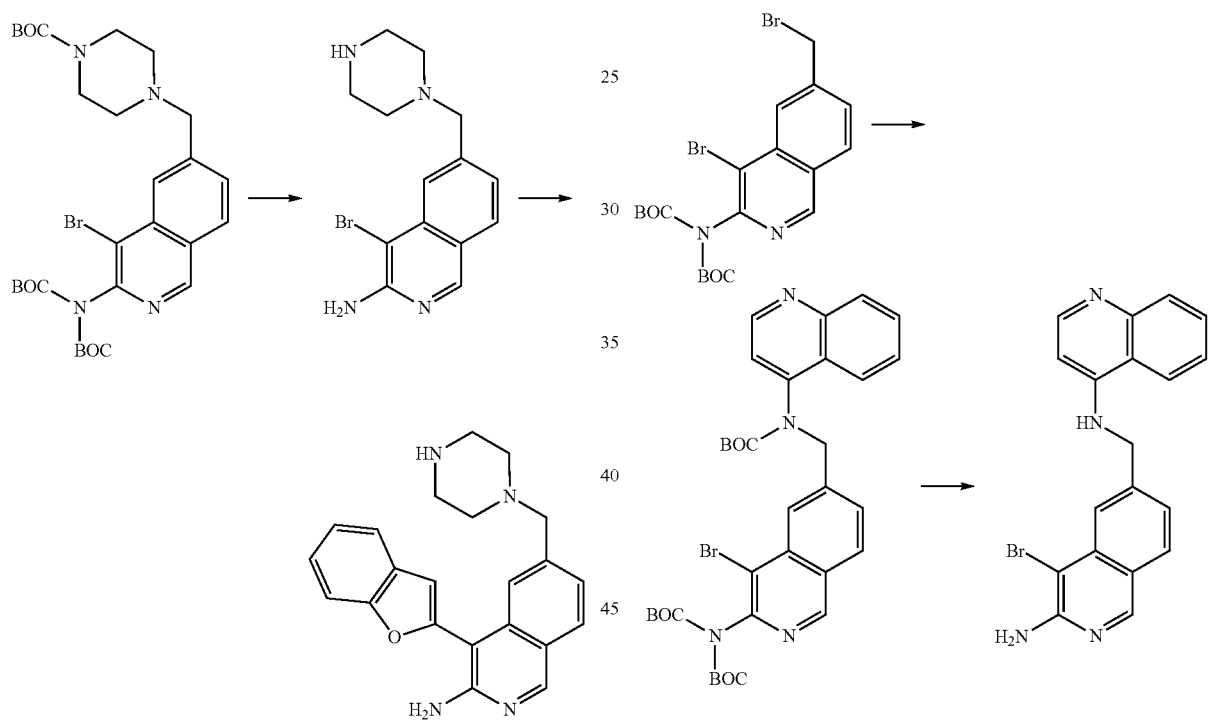

A suspension of 460 mg (0.74 mmol) of tert-butyl 4-[[3-[bis(tert-butoxycarbonyl)amino]-4-bromo-6-isoquinolyl]methyl]piperazine-1-carboxylate (prepared as described for tert-butyl N-[4-bromo-6-[[4-(tert-butoxycarbonylamino)-1-piperidyl]methyl]-3-isoquinolyl]-N-tert-butoxycarbonyl-carbamate) in 20 mL of 1.0 N solution of HCl in EtOAc was stirred at 25° C. for 18 h. The yellow precipitate was collected by centrifugation and dried in vacuo to give 220 mg of 4-bromo-6-(piperazin-1-ylmethyl)isoquinolin-3-amine as a yellow solid.

MS (+ESI): 359.2 [M+H]+.

1H NMR (400 MHz, DMSO-d6+D2O) δ ppm: 9.01 (s, 1H), 8.01 (d, J=8.4 Hz, 1H), 7.74 (dd, J=7.2 Hz, 1.2 Hz, 1H), 7.68 (s, 1H), 7.62 (dd, J=7.2 Hz, 1.2 Hz, 1H), 7.39-7.29 (m, 3H), 7.19 (s, 1H), 4.11 (s), 3.19 (brs, 4H), 3.04 (brs).

To a suspension of 98 mg (4.08 mmol) of NaH in 2 mL of DMF was added 0.17 g (0.68 mmol) of tert-butyl N-(4-quinolyl)carbamate. The mixture was stirred at 25° C. for 3 h and cooled to −20° C. before addition of a solution of 0.35 g (0.68 mmol) of tert-butyl N-[4-bromo-6-(bromomethyl)-3-isoquinolyl]-N-tert-butoxycarbonyl-carbamate in 2 mL of DMF. The reaction was stirred at −20° C. for 2 h until LC-MS showed the reaction was complete. The reaction was quenched with 3 mL of saturated aqueous NH4Cl solution and extracted with 30 mL of EtOAc. The EtOAc layer was dried over Na2SO4, filtered and concentrated to give a yellow oil which was purified by flash column chromatography over silica gel eluting with PE/EA (3/1) to give 40 mg of tert-butyl N-[[3-[bis(tert-butoxycarbonyl)amino]-4-bromo-6-isoquinolyl]methyl]-N-(4-quinolyl)carbamate as a yellow oil.

A suspension of 40 mg (0.059 mmol) of this intermediate in 5 mL of a solution of 1N HCl in EtOAc was stirred at 25°

C. for 18 h. The solvent was evaporated off in vacuo. The yellow solid was collected by centrifugation, washed with EtOAc and dried under reduced pressure to give 53 mg of 4-bromo-6-[(4-quinolylamino)methyl]isoquinolin-3-amine.

MS (+ESI): 379.3, 381.3 [M+H]$^+$.

$^1$H NMR (400 MHz, DMSO-d$_6$+D$_2$O) δ ppm: 8.80 (s, 1H), 8.53 (d, J=8.4 Hz, 1H), 8.39 (d, J=6.8 Hz, 1H), 7.98 (d, J=8.0 Hz, 1H), 7.91 (m, 2H), 7.75 (m, 1H), 7.72 (s, 1H), 7.29 (d, J=8.4 Hz, 1H), 6.76 (d, J=8.4 Hz, 1H), 4.94 (s, 2H).

4-(Benzofuran-2-yl)-6-[(4-quinolylamino)methyl]isoquinolin-3-amine (Example 261)

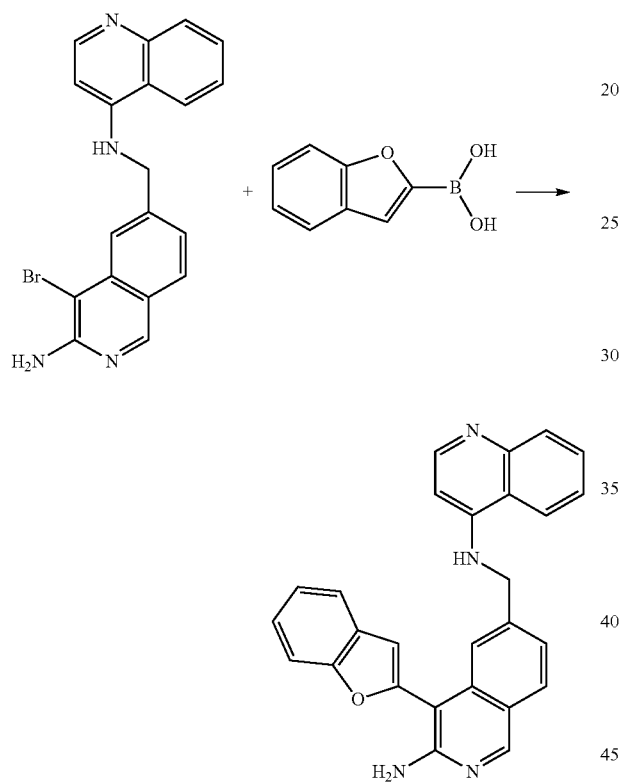

To a solution of 53 mg (0.14 mmol) of 4-bromo-6-[(4-quinolylamino)methyl]isoquinolin-3-amine and 68 mg (0.42 mmol) of benzofuran-2-boronic acid in 10 mL of dioxane and 1 mL of H$_2$O were added 0.01 g (0.01 mmol) of Pd$_2$(dba)$_3$, 0.02 g (0.03 mmol) of Xantphos and 0.14 g (0.42 mmol) of Cs$_2$CO$_3$. The reaction mixture was heated to 90° C. for 2 h under Argon atmosphere. The volatiles were evaporated under reduced pressure and the residue was purified by preparative HPLC to give 19 mg of 4-(benzofuran-2-yl)-6-[(4-quinolylamino)methyl]isoquinolin-3-amine as an orange powder.

MS (+ESI): 417.2 [M+H]$^+$.

$^1$H NMR (400 MHz, DMSO-d$_6$+D$_2$O) δ ppm: 8.95 (s, 1H), 8.38 (d, J=7.2 Hz, 1H), 8.33 (d, J=8.0 Hz, 1H), 7.96 (m, 2H), 7.87 (d, J=8.0 Hz, 1H), 7.65 (m, 1H), 7.44 (m, 2H), 7.32 (dd, J$_1$=8.4 Hz, J$_2$=1.6 Hz, 1H), 7.17 (m, 2H), 7.06 (m, 1H), 6.91 (d, J=0.8 Hz, 1H), 6.70 (d, J=7.2 Hz, 1H), 4.90 (s, 2H).

tert-Butyl N-[1-[(4-bromo-6-isoquinolyl)methyl]-1,8-naphthyridin-1-ium-4-yl]carbamate

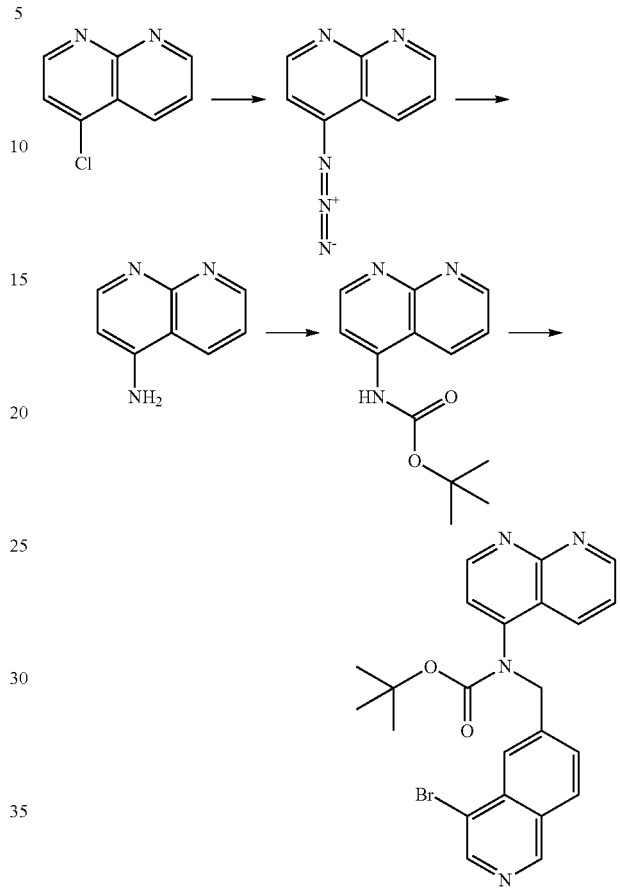

To a solution of 0.5 g (3.04 mmol) of 4-chloro-[1,8]naphthyridine in 10 mL of DMF was added 0.39 g (6.08 mmol) of NaN$_3$. The mixture was stirred for 5 h at 60° C. The reaction was allowed to cool to room temperature and diluted with 300 mL of EtOAc, washed with water, brine and dried over Na$_2$SO$_4$. The desiccant was filtered off and the solvents were evaporated under vacuum to give 0.5 g of 4-azido-1,8-naphthyridine as a light brown solid.

To a solution of 0.5 g (2.92 mmol) of 4-azido-1,8-naphthyridine in 30 mL of THF was added 100 mg of 10% Pd/C. The mixture was hydrogenated at 30° C. under atmospheric pressure for 5 h. The catalyst was removed by filtration. The solvent was evaporated to give 420 mg of 1,8-naphthyridin-4-amine a crude product as a light brown solid.

To a solution of 0.42 g (2.89 mmol) of 1,8-naphthyridin-4-amine in 50 mL of DCM were added 0.64 g (2.89 mmol) of Boc$_2$O, 0.11 g (0.87 mmol) of DMAP and 1.43 mL (8.68 mmol) of DIPEA and then the mixture was stirred at 30° C. for 16 h. The solvent was removed under vacuum and the residue was purified by column chromatography eluting with DCM/MeOH (20/1, R$_f$=0.4) to give 350 mg of tert-butyl N-(1,8-naphthyridin-4-yl)carbamate as a brown solid.

A suspension of 280 mg (1.14 mmol) of tert-butyl N-(1,8-naphthyridin-4-yl)carbamate and 164 mg (0.12 mmol) of NaH in 2 mL of THF was stirred at 40° C. for 16 h. A solution of 0.04 g (0.13 mmol) of 4-bromo-6-(bromomethyl)isoquinoline in 2 mL of THF was added thereto at 35° C. The mixture was stirred at 35° C. for additional 0.5 h. The reaction was quenched with saturated aqueous NH₄Cl solution. The mixture was diluted with EtOAc and washed with brine. The organic layer was dried over Na₂SO₄, filtered and concentrated to give the product as a light brown semisolid which was purified by preparative HPLC to give 140 mg of tert-butyl N-[1-[(4-bromo-6-isoquinolyl)methyl]-1,8-naphthyridin-1-ium-4-yl]carbamate as a light brown solid.

MS (+ESI): 465.0, 467.0 [M+H]⁺.

¹H NMR (400 MHz, DMSO-d₆+D₂O) δ ppm: 9.23 (s, 1H), 9.04 (m, 2H), 8.68 (s, 1H), 8.25 (d, J=8.0 Hz, 1H), 8.13 (d, J=8.8 Hz, 1H), 7.94 (s, 1H), 7.66 (m, 2H), 7.55 (d, J=4.8 Hz, 1H), 5.25 (br s, 2H), 1.27 (s, 9H).

tert-Butyl N-[[4-(benzofuran-2-yl)-6-isoquinolyl]methyl]-N-(1,8-naphthyridin-4-yl)carbamate

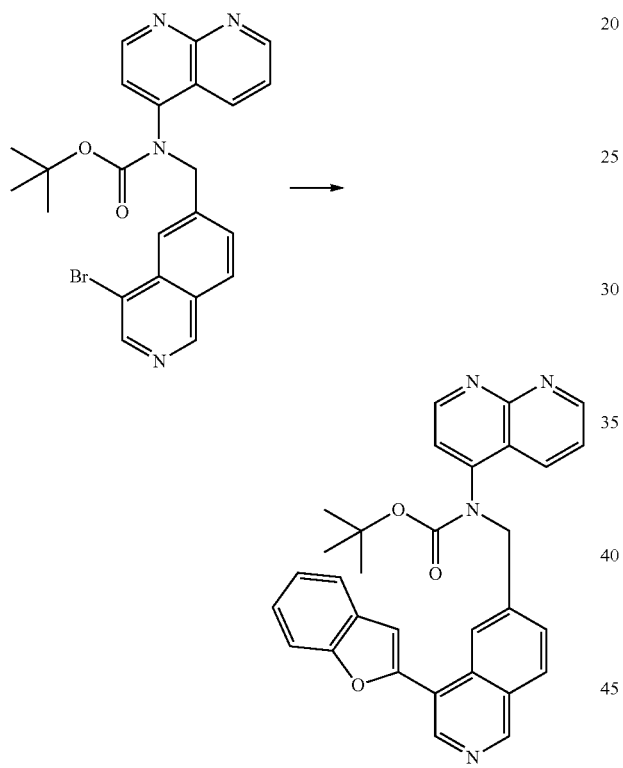

To a solution of 0.11 g (0.24 mmol) of tert-butyl N-[(4-bromo-6-isoquinolyl)methyl]-N-(1,8-naphthyridin-4-yl)carbamate and 0.06 g (0.35 mmol) of benzofuran-2-boronic acid in 10 mL of dioxane and 1 mL of H₂O were added 0.04 g (0.05 mmol) of Pd₂(dba)₃, 0.02 g (0.05 mmol) of X-Phos and 117 mg (0.35 mmol) of Cs₂CO₃. The mixture was stirred at 100° C. for 18 h. The mixture was diluted with 50 mL of EtOAc and washed with 30 mL of brine. The organic layer was dried over Na₂SO₄, filtered and concentrated to give a brown solid which was purified by column chromatography over silica gel eluting with DCM:MeOH (50:1 to 20:1) to give 120 mg of tert-butyl N-[[4-(benzofuran-2-yl)-6-isoquinolyl]methyl]-N-(1,8-naphthyridin-4-yl)carbamate as a light red foam.

MS (+ESI): 503.2 [M+H]⁺.

¹H NMR (400 MHz, DMSO-d₆) δ ppm: 9.35 (s, 1H), 9.08 (d, J=4.8 Hz, 1H), 9.01 (dd, J₁=4.0 Hz, J₂=1.6 Hz, 1H), 8.87 (s, 1H), 8.28 (s, 1H), 8.19 (m, 2H), 7.74 (m, 2H), 7.61 (m, 2H), 7.47 (m, 1H), 7.41 (m, 1H), 7.35 (m, 1H), 7.31 (s, 1H), 5.27 and 5.22 (br d, 2H), 1.17 (s, 9H).

N-[[4-(Benzofuran-2-yl)-6-isoquinolyl]methyl]-1,8-naphthyridin-4-amine (Example 262)

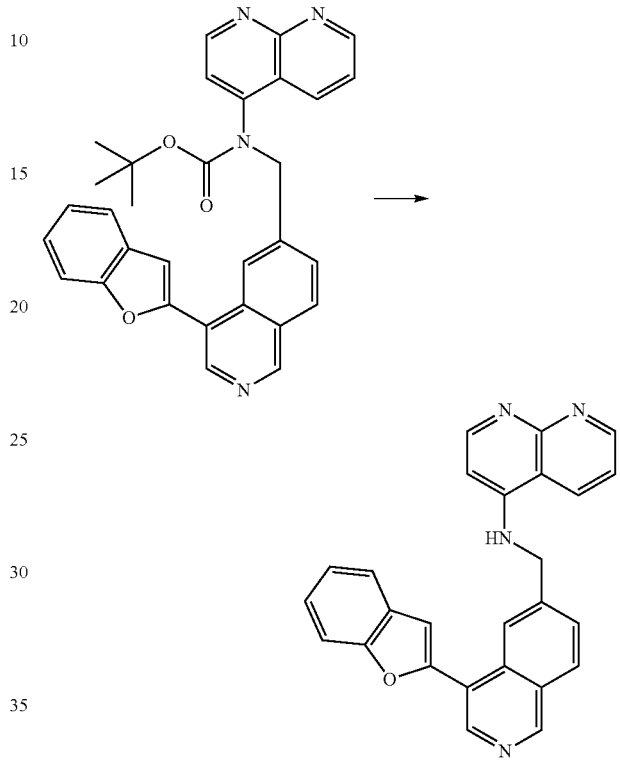

A suspension of 0.14 g (0.28 mmol) of tert-butyl N-[[4-(benzofuran-2-yl)-6-isoquinolyl]methyl]-N-(1,8-naphthyridin-4-yl)carbamate in 5 mL of a solution of 1N HCl in EtOAc was stirred at 15° C. for 5 h. The solid was collected by centrifugation, washed with EtOAc and concentrated to dryness to give 120 mg of N-[[4-(benzofuran-2-yl)-6-isoquinolyl]methyl]-1,8-naphthyridin-4-amine as a yellow solid.

MS (+ESI): 403.2 [M+H]⁺.

¹H NMR (400 MHz, DMSO-d₆+D₂O) δ ppm: 9.63 (br s, 1H), 9.12 (m, 2H), 8.99 (br s, 1H), 8.49 (m, 3H), 8.00 (dd, J₁=8.8 Hz, J₂=1.2 Hz, 1H), 7.84 (dd, J₁=8.8 Hz, J₂=4.8 Hz, 1H), 7.69 (m, 1H), 7.57 (d, J=0.4 Hz, 1H), 7.36-7.30 (m, 2H), 7.23 (m, 1H), 6.92 (d, J=7.2 Hz, 1H), 5.21 (s, 2H).

tert-Butyl 4-(benzylamino)-3,3-difluoro-piperidine-1-carboxylate

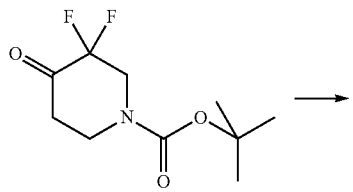

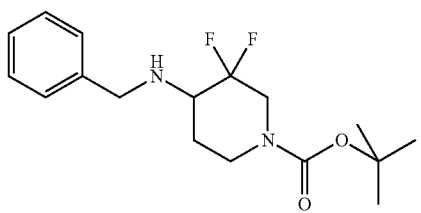

To a suspension of 0.235 g (1.0 mmol) of tert-butyl 3,3-difluoro-4-oxo-piperidine-1-carboxylate in 10 mL of DCM were added 0.13 g (1.2 mmol) of benzylamine and 0.42 g (2.0 mmol) of sodium triacetoxyborohydride. The reaction was stirred at 15° C. for 16 h. The reaction was quenched with saturated aqueous NaHCO₃ solution. The organic layer was separated, washed with brine, dried over Na₂SO₄, filtered and concentrated to give the crude product which was purified by column chromatography on silica gel (EA-PE=1:4, R$_f$=0.4) to produce 85 mg of tert-butyl 4-(benzylamino)-3,3-difluoro-piperidine-1-carboxylate as a colorless oil.

MS (+ESI): 327.2 [M+H]$^+$.

$^1$H NMR (400 MHz, DMSO-d₆) δ 7.36-7.29 (m, 4H), 7.24-7.20 (m, 1H), 3.94-3.81 (m, 3H), 3.65-3.62 (m, 1H), 3.36 (m, 1H), 3.08 (m, 1H), 2.92-2.88 (m, 1H), 2.39 (m, 1H), 1.83-1.77 (m, 1H), 1.48 (m, 1H), 1.39 (s, 9H).

N-[1-[(4-Bromo-6-isoquinolyl)methyl]-3,3-difluoro-4-piperidyl]acetamide

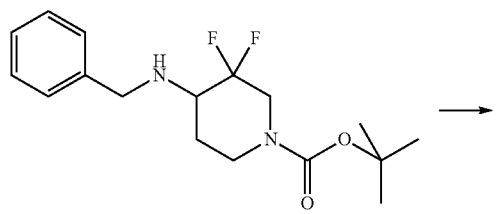

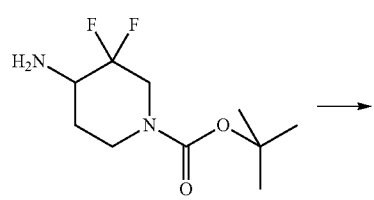

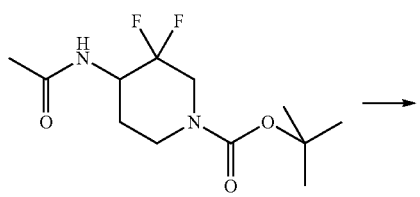

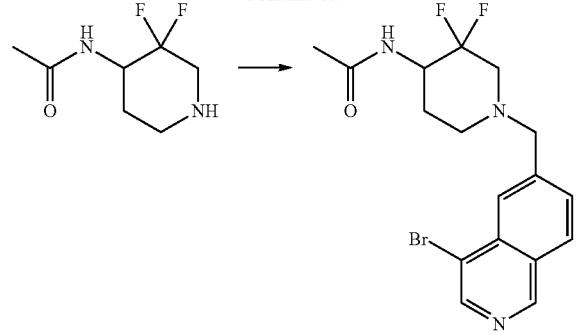

To a solution of 0.6 g (1.84 mmol) of tert-butyl 4-(benzylamino)-3,3-difluoro-piperidine-1-carboxylate in 50 mL of MeOH was added 300 mg of 10% Pd/C. The reaction mixture was hydrogenated at 15° C. under normal atmosphere for 16 h. The reaction was filtered through Celite and the filtrate was evaporated to afford 0.38 g of tert-butyl 4-amino-3,3-difluoro-piperidine-1-carboxylate as a colorless oil.

To a solution of 0.38 g (1.61 mmol) of tert-butyl 4-amino-3,3-difluoro-piperidine-1-carboxylate and 0.33 g (3.22 mmol) of TEA in 20 mL of DCM was added 0.17 mL (2.41 mmol) of acetyl chloride. The reaction was stirred at 15° C. for 16 h. LC-MS showed the reaction was complete, and the mixture was quenched by water, extracted with DCM, dried over anhydrous Na₂SO₄, filtered and concentrated to dryness to give 0.40 g of tert-butyl 4-acetamido-3,3-difluoro-piperidine-1-carboxylate the crude product as a yellow solid.

To a solution of 0.4 g (1.44 mmol) of tert-butyl 4-acetamido-3,3-difluoro-piperidine-1-carboxylate in 8 mL of DCM was added 4 mL (53.85 mmol) of TFA. The reaction mixture was stirred at 15° C. for 2 h. The reaction mixture was evaporated to give 0.25 g of N-(3,3-difluoro-4-piperidyl)acetamide as a yellow oil. To a solution of 0.43 g (1.43 mmol) of 4-bromo-6-(bromomethyl)isoquinoline in 10 mL of DMF and 10 mL of THF were added 0.25 g (1.43 mmol) of N-(3,3-difluoro-4-piperidyl)acetamide and 0.79 g (5.71 mmol) of K₂CO₃ and then the mixturewas stirred at 50° C. for 3 h. The reaction mixture was evaporated to give the crude product which was purified by column chromatography on silica gel (EA-PE=2:1, then EA-MeOH=15:1 R$_f$=0.3) to produce 0.42 g of N-[1-[(4-bromo-6-isoquinolyl)methyl]-3,3-difluoro-4-piperidyl]acetam the product as a white solid.

MS (+ESI): 398.1, 400.1 [M+H]$^+$.

$^1$H NMR (400 MHz, DMSO-d₆) δ ppm: 9.30 (s, 1H), 8.74 (s, 1H), 8.19 (d, J=8.4 Hz, 1H), 8.11 (d, J=8.8 Hz, 1H), 8.03 (s, 1H), 7.75 (dd, J=8.4 Hz, 1.6 Hz, 1H), 4.21-4.11 (m, 1H), 3.88 (s, 2H), 3.12-2.30 (m, 4H), 1.87 (s, 3H), 1.75-1.63 (m, 2H).

297
N-[1-[[4-(Benzofuran-2-yl)-6-isoquinolyl]methyl]-3,3-difluoro-4-piperidyl]acetamide

298
1-[[4-(Benzofuran-2-yl)-6-isoquinolyl]methyl]-3,3-difluoro-piperidin-4-amine (Example 263)

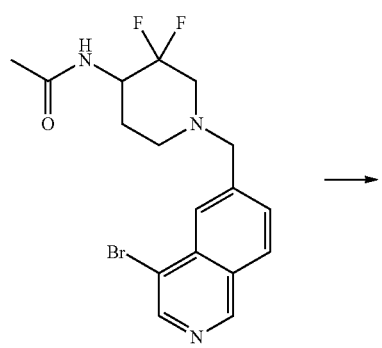

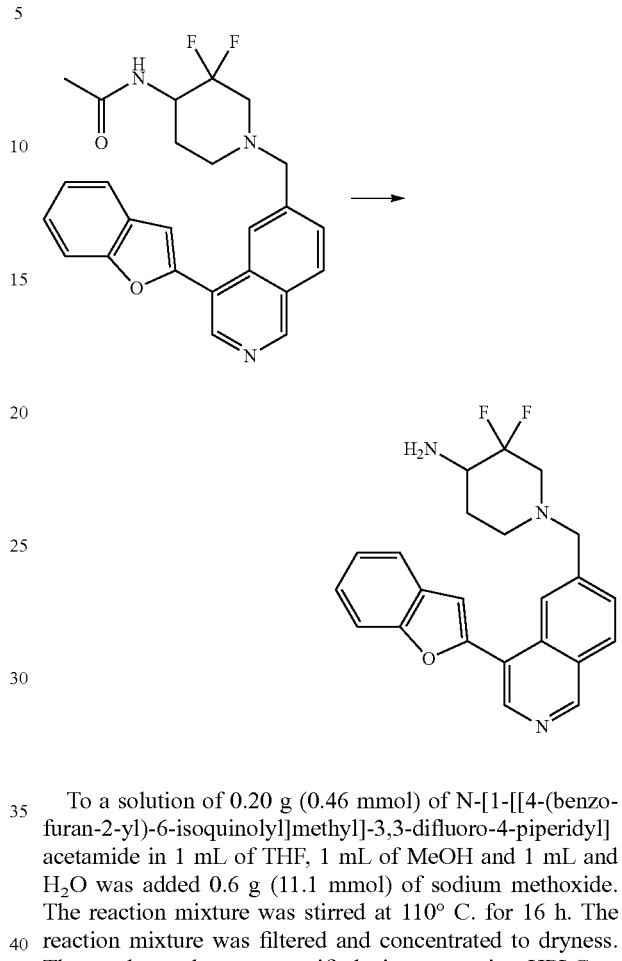

To a stirred solution of 0.4 g (1.0 mmol) of N-[1-[(4-bromo-6-isoquinolyl)methyl]-3,3-difluoro-4-piperidyl]acetamide in 20 mL of dioxane and 1.2 mL of H₂O were added 0.23 g (0.2 mmol) of Pd(PPh₃)₄, 0.85 g (4.0 mmol) of K₃PO₄ and 0.49 g (3.0 mmol) of benzofuran-2-boronic acid. The reaction mixture was stirred for 2 h at 95° C. under Argon. LC-MS showed the reaction was complete. The reaction mixture was evaporated to give the crude product which was purified by column chromatography on silica gel (EA-PE=2:1 to EA to EA-MeOH=15:1, R$_f$=0.2) to produce 0.40 g of N-[1-[[4-(benzofuran-2-yl)-6-isoquinolyl]methyl]-3,3-difluoro-4-piperidyl]acetamide as a yellow solid.

MS (+ESI): 436.2 [M+H]⁺.

¹H NMR (400 MHz, DMSO-d₆) δ ppm: 9.37 (s, 1H), 8.93 (s, 1H), 8.41 (s, 1H), 8.24 (d, J=8.4 Hz, 1H), 8.10 (d, J=8.8 Hz, 1H), 7.79-7.72 (m, 3H), 7.54 (s, 1H), 7.44-7.33 (m, 2H), 4.18-4.12 (m, 1H), 3.88 (s, 2H), 3.12-2.29 (m, 4H), 1.87 (s, 3H), 1.72-1.65 (m, 2H).

To a solution of 0.20 g (0.46 mmol) of N-[1-[[4-(benzofuran-2-yl)-6-isoquinolyl]methyl]-3,3-difluoro-4-piperidyl]acetamide in 1 mL of THF, 1 mL of MeOH and 1 mL and H₂O was added 0.6 g (11.1 mmol) of sodium methoxide. The reaction mixture was stirred at 110° C. for 16 h. The reaction mixture was filtered and concentrated to dryness. The crude product was purified via preparative HPLC to afford 0.12 g of 1-[[4-(benzofuran-2-yl)-6-isoquinolyl]methyl]-3,3-difluoro-piperidin-4-amine as a yellow solid.

MS (+ESI): 394.3 [M+H]⁺.

¹H NMR (400 MHz, DMSO-d₆+D₂O) δ ppm: 9.47 (s, 1H), 8.94 (s, 1H), 8.49 (s, 1H), 8.35 (d, J=8.4 Hz, 1H), 7.83-7.70 (m, 3H), 7.59 (s, 1H), 7.45-7.34 (m, 2H), 4.01-3.92 (m, 2H), 3.71-3.63 (m, 1H), 3.26-2.36 (m, 4H), 2.04-1.73 (m, 2H).

tert-Butyl N-(4-bromo-7-chloro-6-methyl-1-isoquinolyl)-N-tert-butoxycarbonyl-carbamate

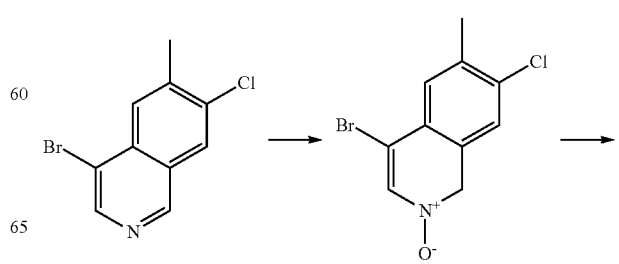

-continued

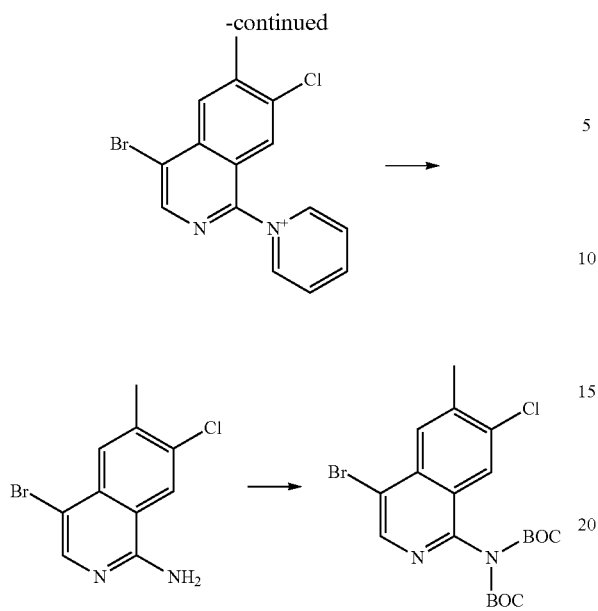

To a solution of 1.3 g (5.07 mmol) of 4-bromo-7-chloro-6-methyl-isoquinoline in 15 mL of DCM was added 2.62 g (15.2 mmol) of mCPBA. The reaction mixture was stirred at 10° C. for 16 h. LC-MS showed that the reaction was complete. The reaction was treated with 60 mL of saturated aqueous $Na_2SO_3$ solution and 40 mL of saturated aqueous $Na_2CO_3$, extracted with DCM, and washed with brine. The organic layer was dried over sodium sulfate, filtered, and evaporated to give 1.3 g of 4-bromo-7-chloro-6-methyl-2-oxido-isoquinolin-2-ium as a grey solid.

To a solution of 1.3 g (4.77 mmol) of 4-bromo-7-chloro-6-methyl-2-oxido-isoquinolin-2-ium in 20 mL of pyridine was added 1.11 g (5.72 mmol) of TsCl and then the mixture was stirred at 10° C. for 2 h. The solvent was removed under vacuum to give 1.5 g of 4-bromo-7-chloro-6-methyl-1-pyridin-1-ium-1-yl-isoquinoline as a yellow oil which was used in the next step without further purification.

A solution of 1.5 g (4.48 mmol) of 4-bromo-7-chloro-6-methyl-1-pyridin-1-ium-1-yl-isoquinoline in 10.51 mL (174.17 mmol) of 2-aminoethanol was stirred at 20° C. for 16 h. LC-MS showed that the reaction was complete. The solution was poured onto cracked ice, and the precipitates were collected by filtration and dried to provide 1.2 g of 4-bromo-7-chloro-6-methyl-isoquinolin-1-amine product as a pink solid.

To a solution of 1.2 g (4.42 mmol) of 4-bromo-7-chloro-6-methyl-isoquinolin-1-amine in 40 mL of DCM were added 3.86 g (17.68 mmol) of $Boc_2O$ and 0.05 g (0.44 mmol) of DMAP and then the mixture was stirred at 10° C. for 16 h. LC-MS showed the staring material was consumed, and the desired product was formed. The solvent was removed under vacuum and the residue was purified by column chromatography eluting with PE/EA (20:1 to 10:1) to yield 1.4 g of tert-butyl N-(4-bromo-7-chloro-6-methyl-1-isoquinolyl)-N-tert-butoxycarbonyl-carbamate as a white solid.

MS (+ESI): 471.0, 473.0, 475.0 [M+H]$^+$.

$^1$H NMR (400 MHz, DMSO-$d_6$) δ ppm: 8.71 (s, 1H), 8.17 (s, 1H), 7.94 (s, 1H), 2.63 (s, 3H), 1.31 (s, 18H).

tert-Butyl N-[4-bromo-6-[[4-(tert-butoxycarbonylamino)-1-piperidyl]methyl]-7-chloro-1-isoquinolyl]-N-tert-butoxycarbonyl-carbamate

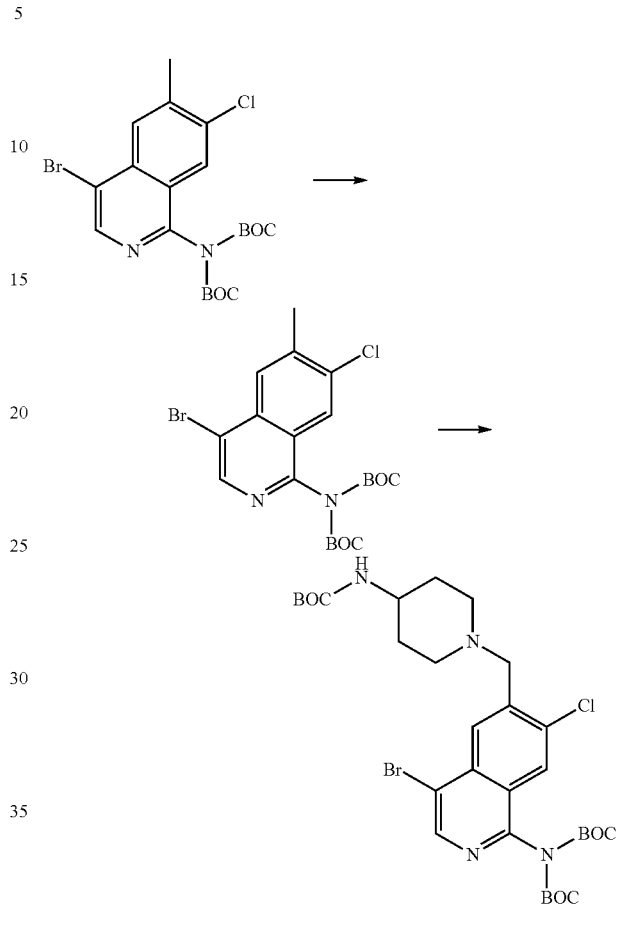

To a stirred mixture of 0.8 g (1.7 mmol) of tert-butyl N-(4-bromo-7-chloro-6-methyl-1-isoquinolyl)-N-tert-butoxycarbonyl-carbamate and 0.3 g (1.7 mmol) of NBS in 40 mL of $CCl_4$ was added 0.12 g (0.51 mmol) of benzoyl peroxide. The reaction mixture was heated to 110° C. for 2 h. After cooled to room temperature, the solvent was removed under reduced pressure. The residue was purified by column chromatography on silica gel with PE-EA (10:1, $R_f$=0.4) to afford 0.55 g of tert-butyl N-[4-bromo-6-(bromomethyl)-7-chloro-1-isoquinolyl]-N-tert-butoxycarbonyl-carbamate as a white solid.

To a stirred solution of 0.55 g (1.0 mmol) of tert-butyl N-[4-bromo-6-(bromomethyl)-7-chloro-1-isoquinolyl]-N-tert-butoxycarbonyl-carbamate in 20 mL of THF were added 0.24 g (1.2 mmol) of 4-N-Boc-amino-piperidineand 0.41 g (3.0 mmol) of $K_2CO_3$. The reaction mixture was stirred at 50° C. for 3 h and filtered through Celite. The filtrate was concentrated under vacuum. The residue was purified by column chromatography (PE/EA=5/1~3/1, $R_f$=0.5) to afford 0.49 g of the desired product as a colorless semisolid.

MS (+ESI): 669.1, 671.1 673.1 [M+H]$^+$.

$^1$H NMR (400 MHz, DMSO-$d_6$) δ ppm: 8.74 (s, 1H), 8.30 (s, 1H), 7.94 (s, 1H), 6.82 (d, J=7.2 Hz, 1H, NH), 3.79 (s, 2H), 3.30 (m, 1H, overlapped), 2.92-2.81 (m, 2H), 2.27-2.15 (m, 2H), 1.82-1.70 (m, 2H), 1.56-1.43 (m, 2H), 1.38 (s, 9H), 1.32 (s, 18H).

301
tert-Butyl N-tert-butoxycarbonyl-N-[6-[[4-(tert-butoxycarbonylamino)-1-piperidyl]methyl]-7-chloro-4-phenyl-1-isoquinolyl]carbamate

302
6-[(4-Amino-1-piperidyl)methyl]-7-chloro-4-phenyl-isoquinolin-1-amine (Example 264)

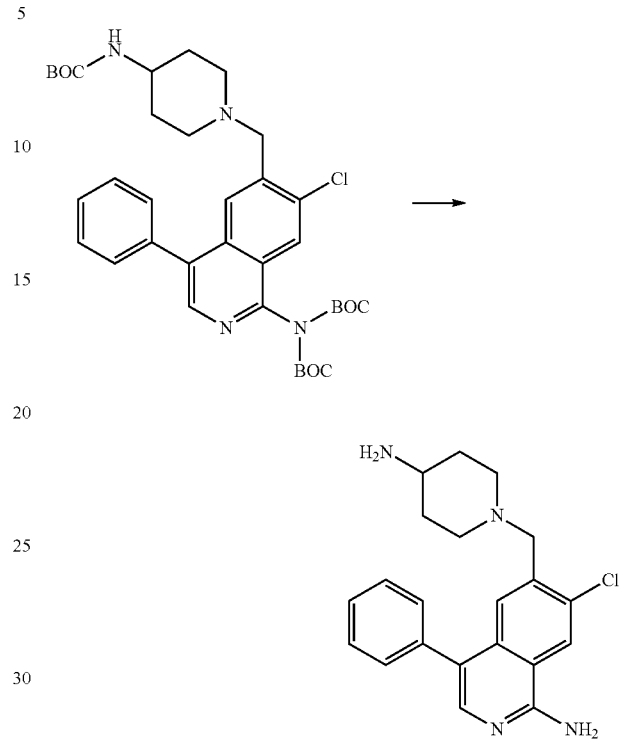

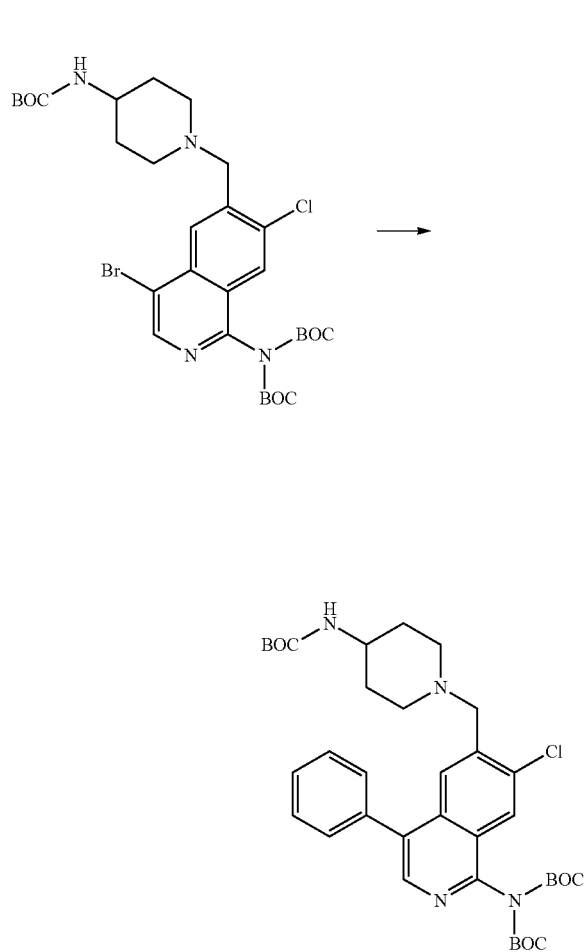

To a stirred solution of 0.49 g (0.73 mmol) of tert-butyl N-[4-bromo-6-[[4-(tert-butoxycarbonylamino)-1-piperidyl]methyl]-7-chloro-1-isoquinolyl]-N-tert-butoxycarbonyl-carbamate and 0.27 g (2.19 mmol) of phenylboronic acid in 15 mL of dioxane and 1 mL of H$_2$O were added 0.47 g (2.19 mmol) of K$_3$PO$_4$ and 0.08 g (0.07 mmol) of Pd(PPh$_3$)$_4$. The reaction mixture was stirred under argon at 95° C. for 3 h and LC-MS showed the reaction was complete. The volatiles were removed under vacuum. The residue was purified by column chromatography on silica gel with PE-EA (7:1 to 5:1, R$_f$=0.55) to produce 0.26 g of the desired product as a white solid.

MS (+ESI): 667.3, 669.3 [M+H]$^+$.

$^1$H NMR (400 MHz, DMSO-d$_6$) δ ppm: 8.39 (s, 1H), 8.07 (s, 1H), 7.87 (s, 1H), 7.66-7.53 (m, 5H), 6.81 (br s, 1H, NH), 3.65 (s, 2H), 3.30 (m, 1H), 2.82-2.75 (m, 2H), 2.15-2.05 (m, 2H), 1.70-1.54 (m, 2H), 1.36 (s, 27H), 1.33 (m, 2H, overlapped).

To a solution of 0.26 g (0.39 mmol) of tert-butyl N-tert-butoxycarbonyl-N-[6-[[4-(tert-butoxycarbonylamino)-1-piperidyl]methyl]-7-chloro-4-phenyl-1-isoquinolyl]carbamate in 5 mL of DCM was added 2.5 mL of TFA. The solution was stirred at 18° C. for 2 h. The solvent was evaporated and the residue was purified by preparative HPLC to give 68 mg of 6-[(4-amino-1-piperidyl)methyl]-7-chloro-4-phenyl-isoquinolin-1-amine as a light yellow powder.

MS (+ESI): 367.4, 369.4 [M+H]$^+$.

$^1$H NMR (400 MHz, DMSO-d$_6$+D$_2$O) δ ppm: 8.84 (s, 1H), 8.02 (s, 1H), 7.65 (s, 1H), 7.58-7.46 (m, 5H), 4.33 (s, 2H), 3.36-3.14 (m, 3H), 3.05-2.82 (m, 2H), 2.05-1.94 (m, 2H), 1.70-1.54 (m, 2H).

tert-Butyl N-[1-[(7-chloro-4-phenyl-6-isoquinolyl)methyl]-4-piperidyl]carbamate

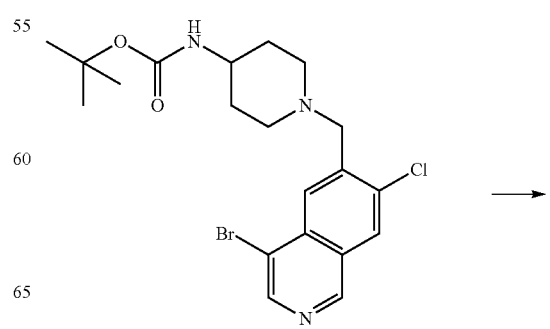

-continued

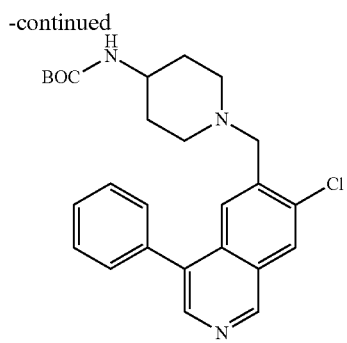

To a solution of 0.38 g (0.84 mmol) of tert-butyl N-[1-[(4-bromo-7-chloro-6-isoquinolyl)methyl]-4-piperidyl]carbamate in 10 mL of dioxane and 1 mL of H$_2$O were added 0.154 g (1.26 mmol) of phenylboronic acid, 97 mg (0.084 mmol) of Pd(PPh$_3$)$_4$ and 0.54 g (2.52 mmol) of K$_3$PO$_4$. The mixture was stirred at 95° C. for 2 h. The mixture was diluted with EtOAc and washed with brine. The organic layer was dried over Na$_2$SO$_4$, filtered and concentrated to give the black oil which was purified by column chromatography over silica gel eluting with PE/EA (4/1) to give 0.28 g of the desired product as a white solid.

MS (+ESI): 452.1, 454.1 [M+H]$^+$.

$^1$H NMR (400 MHz, DMSO-d$_6$) δ ppm: 9.30 (s, 1H), 8.47 (s, 1H), 8.37 (s, 1H), 8.02 (s, 1H), 7.62-7.47 (m, 5H), 6.82 (d, J=8.4 Hz, 1H, NH), 3.65 (s, 2H), 3.22 (m, H), 2.81 (m, 2H), 2.90 (m, 2H), 1.69 (m, 2H), 1.30 (m, 2H), 1.38 (s, 9H).

tert-Butyl N-[1-[(7-hydroxy-4-phenyl-6-isoquinolyl)methyl]-4-piperidyl]carbamate

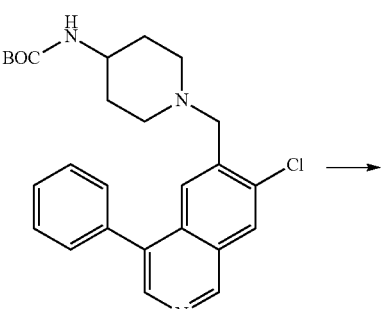

To a solution of 0.22 g (0.49 mmol) of tert-butyl N-[1-[(7-chloro-4-phenyl-6-isoquinolyl)methyl]-4-piperidyl]carbamate in 1.5 mL of H$_2$O and 4 mL of dioxane were added 0.05 g (0.10 mmol) of X-Phos, 0.14 g (2.44 mmol) of KOH and 0.09 g (0.10 mmol) of Pd$_2$(dba)$_3$. The mixture was stirred at 120° C. under microwave irradiation for 30 mins.

additional 0.05 g (0.10 mmol) of X-Phos, 0.09 g (0.10 mmol) of Pd$_2$(dba)$_3$ and 0.14 g (2.44 mmol) of KOH were added. After another 30 mins, the mixture was diluted with 50 mL of EtOAc and washed with 20 mL of brine. The organic layer was dried over Na$_2$SO$_4$, filtered and concentrated to dryness. The residue was purified by preparative HPLC to give 20 mg of the desired product as a light yellow solid.

6-[(4-Amino-1-piperidyl)methyl]-4-phenyl-isoquinolin-7-ol (Example 265)

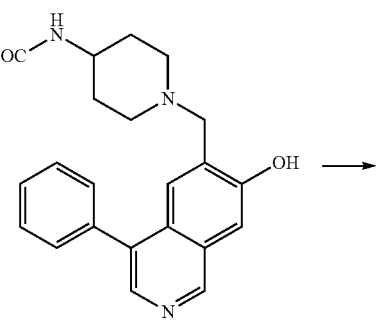

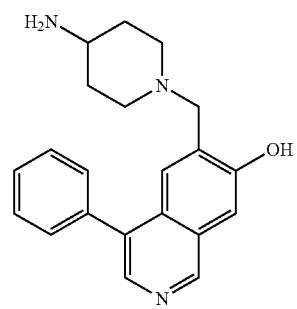

A suspension of 0.07 g (0.15 mmol) of tert-butyl N-[1-[(7-hydroxy-4-phenyl-6-isoquinolyl)methyl]-4-piperidyl]carbamate in 5 mL of a solution of 1N HCl in EtOAc was stirred at 20° C. for 1 h. The yellow solid was collected by centrifugation and washed with EtOAc. After drying in vacuo, 62 mg of the desired product was obtained as a light brown solid.

MS (+ESI): 334.2 [M+H]$^+$.

$^1$H NMR (400 MHz, DMSO-d$_6$+D$_2$O) δ ppm: 9.33 (s, 1H), 8.32 (s, 1H), 8.08 (s, 1H), 7.66 (s, 1H), 7.61-7.55 (m, 5H), 4.42 (s, 2H), 3.39-3.13 (m, 5H), 2.08-2.01 (m, 2H), 1.79-1.64 (m, 2H).

1-[(7-Methoxy-4-phenyl-6-isoquinolyl)methyl]piperidin-4-amine (Example 266)

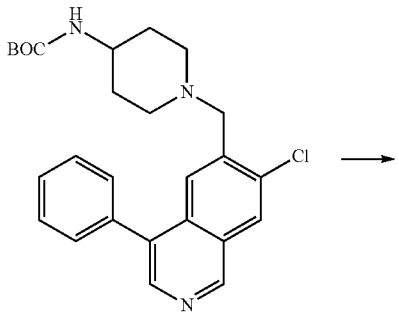

305

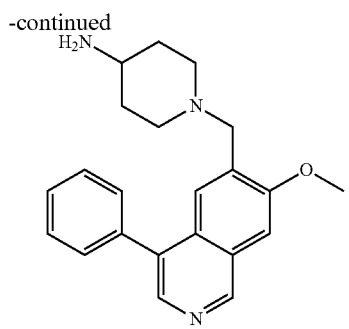

To a solution of 0.06 g (0.13 mmol) of tert-butyl N-[1-[(7-chloro-4-phenyl-6-isoquinolyl)methyl]-4-piperidyl]carbamate in 2 mL of dioxane and 4 mL of MeOH were added 143 mg (2.65 mmol) of sodium methoxide, 0.01 g (0.01 mmol) of Pd$_2$(dba)$_3$ and 0.01 g (0.01 mmol) of tBu-BrettPhos. The mixture was stirred at 120° C. under microwave irradiation for 2 h. The black solid was filtered off and the filtrate was purified by preparative HPLC to give 52 mg of 1-[(7-methoxy-4-phenyl-6-isoquinolyl)methyl]piperidin-4-amine as a white solid.

MS (+ESI): 348.2 [M+H]$^+$.

$^1$H NMR (400 MHz, DMSO-d$_6$+D$_2$O) δ ppm: 9.37 (s, 1H), 8.39 (s, 1H), 8.08 (s, 1H), 7.85 (s, 1H), 7.61-7.53 (m, 5H), 4.44 (s, 2H), 4.03 (s, 3H), 3.46-3.07 (m, 5H), 2.08-2.01 (m, 2H), 1.75-1.64 (m, 2H).

(7-Chloro-4-phenyl-6-isoquinolyl)methanol

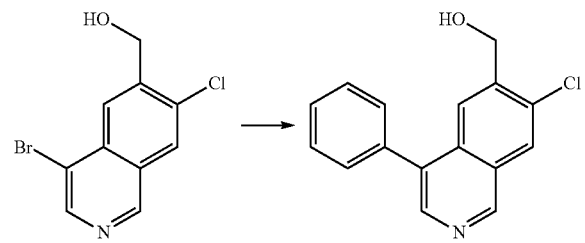 [SMILES: OCc1cc2c(Br)cncc2cc1Cl ; OCc1cc2c(-c3ccccc3)cncc2cc1Cl]

To a solution of 1.0 g (3.67 mmol) of (4-bromo-7-chloro-6-isoquinolyl)methanol in 50 mL of THF) and 5 mL of H$_2$O were added 0.45 g (3.67 mmol) of phenylboronic acid, 0.42 g (0.37 mmol) of Pd(PPh$_3$)$_4$ and 2.34 g (11.01 mmol) of K$_3$PO$_4$. The mixture was stirred at 100° C. for 2 h. The mixture was diluted with DCM and washed with brine. The organic layer was dried over Na$_2$SO$_4$, filtered and concentrated to give a brown solid which was purified by column chromatography eluting with PE/EA (10/1 to 5/1) then THF/MeOH (3/1) to give 0.8 g of the desired product as a light yellow solid.

MS (+ESI): 270.0, 272.0 [M+H]$^+$.

$^1$H NMR (400 MHz, DMSO-d$_6$+D$_2$O) δ ppm: 9.28 (s, 1H), 8.41 (s, 1H), 8.33 (s, 1H), 8.04 (s, 1H), 7.58-7.52 (m, 5H), 4.67 (s, 2H).

306

(7-Methoxy-4-phenyl-6-isoquinolyl)methanol

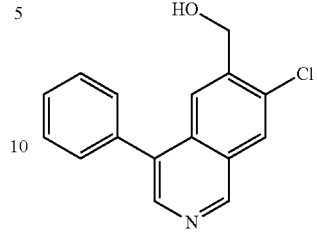

To a solution of 0.15 g (0.56 mmol) of (7-chloro-4-phenyl-6-isoquinolyl)methanol in 2 mL of dioxane and 2 mL of MeOH were added 0.05 g (0.06 mmol) of Pd$_2$(dba)$_3$, 127 mg (2.78 mmol) of sodium methoxide, and 0.05 g (0.11 mmol) of tBuBrettPhos. The mixture was stirred at 120° C. for 5 mins. The solvents were evaporated and the residue was purified by column chromatography eluting with PE/EA (3:1) to give 70 mg of (7-methoxy-4-phenyl-6-isoquinolyl)methanol as a white solid.

MS (+ESI): 266.1 [M+H]$^+$.

$^1$H NMR (400 MHz, DMSO-d$_6$) δ ppm: 9.21 (s, 1H), 8.28 (s, 1H), 7.93 (s, 1H), 7.59-7.51 (m, 6H), 5.28 (t, J=5.6 Hz, 1H, OH), 4.62 (d, J=5.2 Hz, 2H), 3.97 (s, 3H).

(1-Amino-7-methoxy-4-phenyl-6-isoquinolyl)methanol

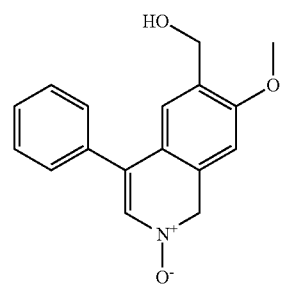

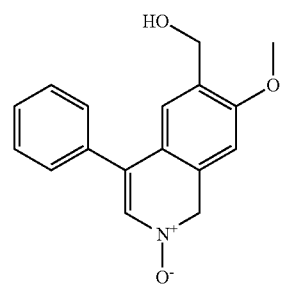

308 tert-Butyl N-[1-[(1-amino-7-methoxy-4-phenyl-6-isoquinolyl)methyl]-4-piperidyl]carbamate

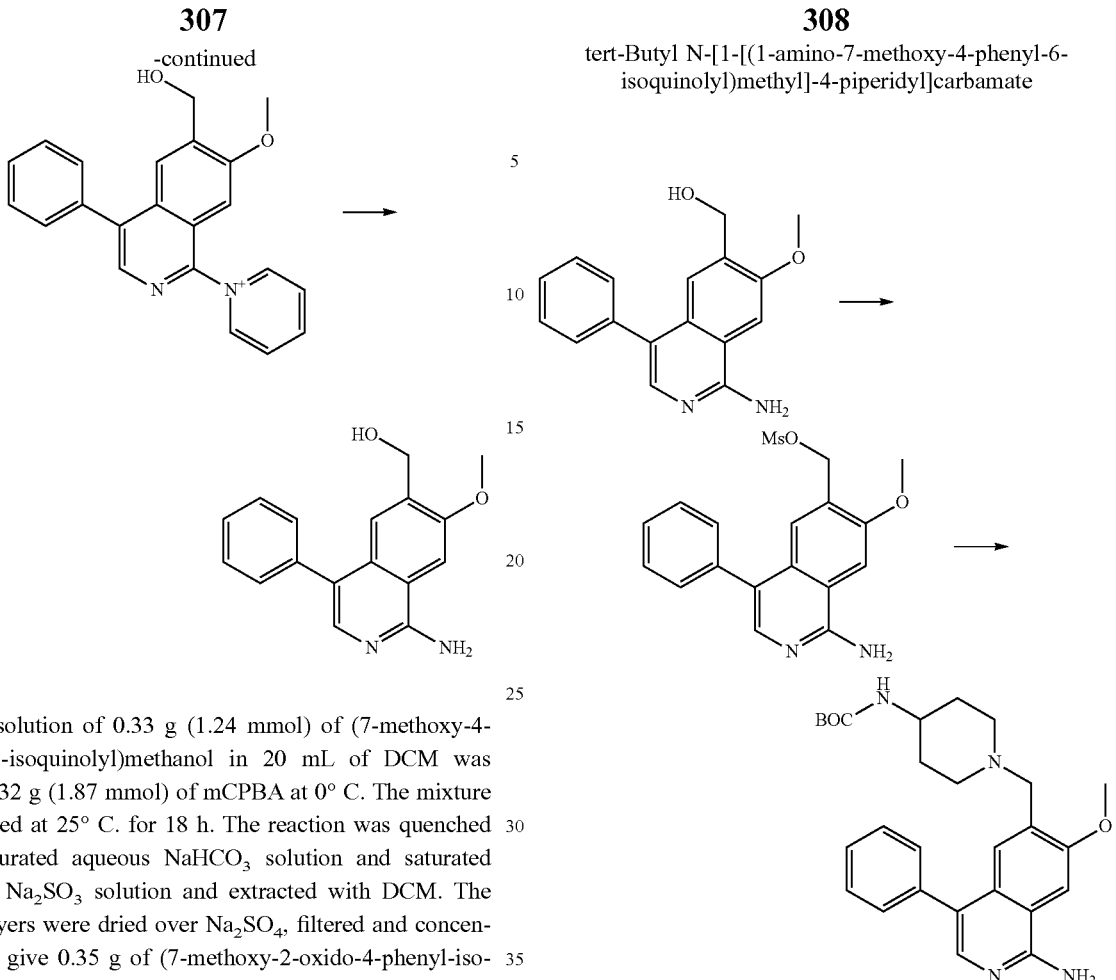

To a solution of 0.33 g (1.24 mmol) of (7-methoxy-4-phenyl-6-isoquinolyl)methanol in 20 mL of DCM was added 0.32 g (1.87 mmol) of mCPBA at 0° C. The mixture was stirred at 25° C. for 18 h. The reaction was quenched with saturated aqueous NaHCO$_3$ solution and saturated aqueous Na$_2$SO$_3$ solution and extracted with DCM. The DCM layers were dried over Na$_2$SO$_4$, filtered and concentrated to give 0.35 g of (7-methoxy-2-oxido-4-phenyl-isoquinolin-2-ium-6-yl)methanol the product as a light yellow solid which was used in the next step without further purification.

To a solution of 0.35 g (1.24 mmol) of (7-methoxy-2-oxido-4-phenyl-isoquinolin-2-ium-6-yl)methanol in 5 mL of pyridine was added 0.28 g (1.49 mmol) of TsCl at 25° C. The mixture was stirred at 25° C. for 2 h. The solvent was evaporated under vacuum to give 0.42 g of (7-methoxy-4-phenyl-1-pyridin-1-ium-1-yl-6-isoquinolyl)methanol as a light yellow solid which was used in the next step without further purification.

To a solution of 0.4 g (1.17 mmol) of (7-methoxy-4-phenyl-1-pyridin-1-ium-1-yl-6-isoquinolyl)methanol in 5 mL of DCM was added 5.0 mL (84.46 mmol) of 2-aminoethanol at 25° C. The mixture was stirred at 25° C. for 18 h. The mixture was diluted with ice water and extracted with DCM. The DCM layers were dried over Na$_2$SO$_4$, filtered and concentrated to give crude product as a black red solid which was purified by column chromatography over silica gel eluting with DCM/MeOH (100/1 to 30/1) to give 0.16 g of (1-amino-7-methoxy-4-phenyl-6-isoquinolyl)methanol as a yellow solid.

$^1$H NMR (400 MHz, DMSO-d$_6$) δ ppm: 7.81 (s, 1H), 7.61 (s, 2H), 7.51-7.39 (m, 5H), 6.85 (brs, 2H, NH$_2$), 5.17 (t, J=5.6 Hz, 1H, OH), 4.57 (d, J=4.8 Hz, 2H), 3.93 (s, 3H).

To a solution of 0.16 g (0.57 mmol) of (1-amino-7-methoxy-4-phenyl-6-isoquinolyl)methanol in 10 mL of DCM was added 0.12 g (1.14 mmol) of triethylamine followed by 0.07 g (0.57 mmol) of MsCl. The mixture was stirred at 25° C. for 18 h before quenched by aqueous NH$_4$Cl solution. Then the mixture was extracted with DCM. The organic layers were dried over Na$_2$SO$_4$, filtered and concentrated to give 0.19 g of (1-amino-7-methoxy-4-phenyl-6-isoquinolyl)methyl methanesulfonate as a yellow foam.

To a solution of 0.19 g (0.53 mmol) of (1-amino-7-methoxy-4-phenyl-6-isoquinolyl)methyl methanesulfonate in 15 mL of THF were added 0.16 g (0.80 mmol) of 4-(N-Boc-amino)piperidine and 0.15 g (1.06 mmol) of K$_2$CO$_3$. The mixture was stirred at 25° C. for 18 h. The solvent was evaporated under vacuum and the residue was purified by preparative HPLC to give 56 mg of tert-butyl N-[1-[(1-amino-7-methoxy-4-phenyl-6-isoquinolyl)methyl]-4-piperidyl]carbamate as a white solid.

MS (+ESI): 463.2 [M+H]$^+$.

$^1$H NMR (400 MHz, DMSO-d$_6$+D$_2$O) δ ppm: 8.11 (s, 1H), 7.92 (s, 1H), 7.59-7.49 (m, 6H), 4.38 (s, 2H), 4.03 (s, 3H), 3.45 (s, 1H), 3.32-3.05 (m, 4H), 1.91-1.52 (m, 4H), 1.36 (s, 9H).

6-[(4-Amino-1-piperidyl)methyl]-7-methoxy-4-phenyl-isoquinolin-1-amine (Example 267)

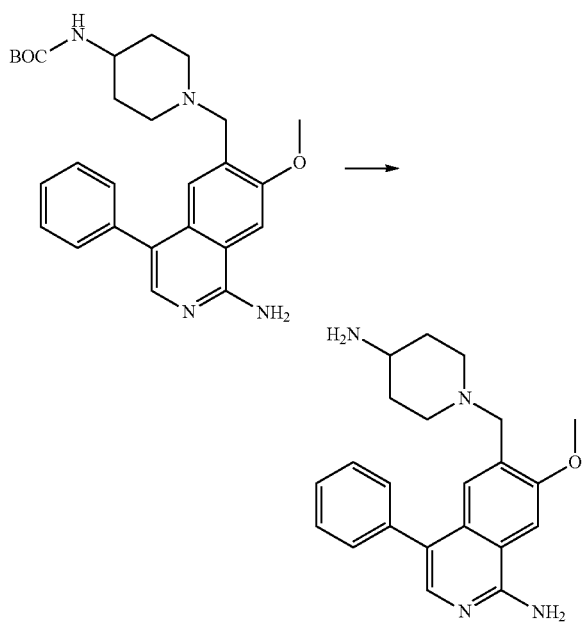

A suspension of 56 mg (0.12 mmol) of tert-butyl N-[1-[(1-amino-7-methoxy-4-phenyl-6-isoquinolyl)methyl]-4-piperidyl]carbamate in 2 mL of a solution of 1N HCl solution in EtOAc. The mixture was stirred at 25° C. for 0.5 h. The white solid was collected by centrifugation and dissolved in ACN and H$_2$O. After lyophilization, 30 mg of 6-[(4-Amino-1-piperidyl)methyl]-7-methoxy-4-phenyl-isoquinolin-1-amine was obtained as a yellow solid.

MS (+ESI): 363.2 [M+H]$^+$.

$^1$H NMR (400 MHz, DMSO-d$_6$+D$_2$O) δ ppm: 8.17 (s, 1H), 7.96 (s, 1H), 7.58-7.49 (m, 6H), 4.37 (brs, 2H), 4.04 (s, 3H), 3.42-3.03 (m, 5H), 2.10-2.02 (m, 2H), 1.89-1.77 (m, 2H).

tert-Butyl 7-oxa-4-azabicyclo[4.1.0]heptane-4-carboxylate

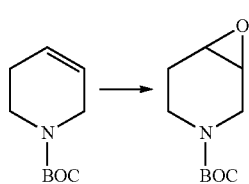 [SMILES: CC(C)(C)OC(=O)N1CC=CCC1 ; CC(C)(C)OC(=O)N1CCC2OC2C1]

To a solution of 0.50 g (2.73 mmol) of tert-butyl 3,6-dihydro-2H-pyridine-1-carboxylate in 30 mL of DCM was added 0.92 g (4.09 mmol) of mCPBA. The resultant solution was stirred at 20° C. for 18 h. TLC indicated that the reaction was complete. The reaction was diluted with DCM, washed with aq. NaHCO$_3$, aq. Na$_2$S$_2$O$_3$ and brine, dried over Na$_2$SO$_4$, filtered and concentrated. The residue was purified by column chromatography (PE/EA, 5/1, R$_f$=0.2) to give 0.43 g of tert-butyl 7-oxa-4-azabicyclo[4.1.0]heptane-4-carboxylate as a colorless oil.

MS (+ESI): 144.1 [M+H]$^+$.

$^1$H NMR (400 MHz, CDCl$_3$) δ ppm: 4.09-3.58 (m, 2H), 3.57-3.02 (m, 4H), 2.18-1.84 (m, 2H), 1.47 (s, 9H).

tert-Butyl (3R,4R/3S,4S)-4-azido-3-hydroxy-piperidine-1-carboxylate

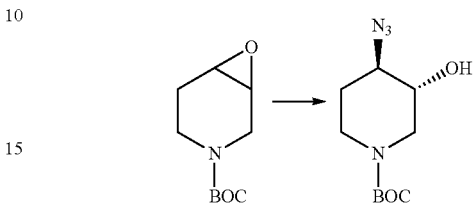

To a solution of 0.43 g (2.16 mmol) of tert-butyl 7-oxa-4-azabicyclo[4.1.0]heptane-4-carboxylate in 7 mL of DMF was added a solution of 0.21 g (3.24 mmol) of NaN$_3$ in 6 mL of acetone-water (2:1, v/v). The mixture was stirred at 80° C. for 20 h. The solution was diluted with EtOAc, washed with water, 10% aq. LiCl and brine, dried over Na$_2$SO$_4$, filtered and concentrated. The residue was purified by column chromatography (PE/EA, 5/1, R$_f$=0.13) to give 368 mg of tert-butyl (3R,4R/3S,4S)-4-azido-3-hydroxy-piperidine-1-carboxylate as a white semisolid.

MS (+ESI): 243.1 [M+H]$^+$.

$^1$H NMR (400 MHz, DMSO-d$_6$+D$_2$O) δ ppm: 4.03-3.74 (m, 2H), 3.46-3.15 (m, 2H), 3.00-2.57 (m, 2H), 1.93-1.73 (m, 1H), 1.37 (s, 9H), 1.27-1.09 (m, 1H).

(3R,4R/3S,4S)-4-Azidopiperidin-1-ium-3-ol; 2,2,2-trifluoroacetate

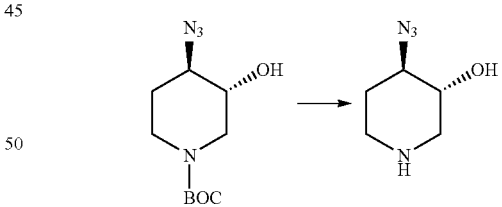

To a solution of 0.37 g (1.51 mmol) of tert-butyl (3R,4R/3S,4S)-4-azido-3-hydroxy-piperidine-1-carboxylate in 5 mL of DCM was added 5 mL of TFA. The resultant solution was stirred at 20° C. for 3 h. The solvent was evaporated to give 389 mg of the desired product as a yellow semisolid.

MS (+ESI): 243.1 [M+H]$^+$.

$^1$H NMR (400 MHz, DMSO-d$_6$+D$_2$O) δ ppm: 3.70-3.52 (m, 2H), 3.26-3.09 (m, 2H), 2.98-2.67 (m, 2H), 2.14-1.99 (m, 1H), 1.62-1.44 (m, 1H).

(3R,4R/3S,4S)-4-Azido-1-[(4-bromo-6-isoquinolyl)methyl]piperidin-3-ol

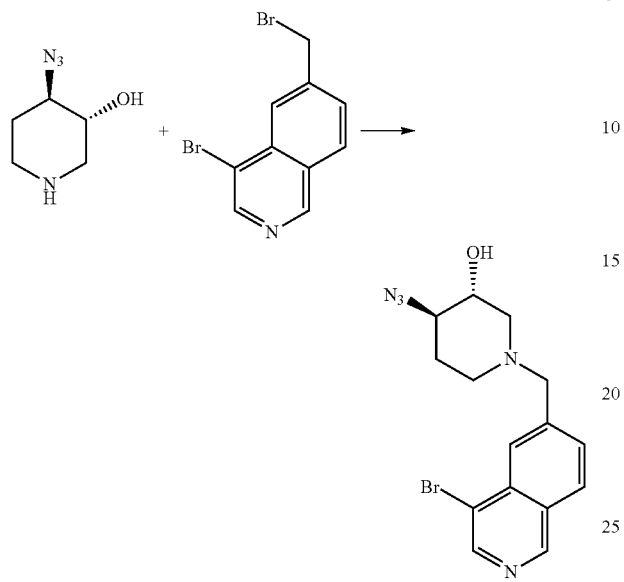

To a solution of 0.39 g (1.5 mmol) of (3R,4R/3S,4S)-4-azidopiperidin-1-ium-3-ol; 2,2,2-trifluoroacetate, in dry 5 mL of DMF was added 0.94 g (6.83 mmol) of $K_2CO_3$ and 0.41 g (1.37 mmol) of 4-bromo-6-(bromomethyl)isoquinoline. The mixture was stirred at 20° C. for 5 h. Then the solution was taken into EtOAc, washed with water, dried over $Na_2SO_4$, filtered and concentrated under reduced pressure. The residue was purified by column chromatography (PE/EA, 3:1 to 1:1, $R_f$=0.23) to yield 493 mg the desired product as a colorless oil.

MS (+ESI): 362.0, 364.0 [M+H]$^+$.

$^1$H NMR (400 MHz, DMSO-d$_6$+D$_2$O) δ ppm: 9.25 (s, 1H), 8.70 (s, 1H), 8.16 (d, J=8.4 Hz, 1H), 7.96 (s, 1H), 7.74 (dd, J=8.4 Hz, 0.8 Hz, 1H), 3.76 (ABq, 2H, overlapped), 3.48-3.16 (m, 2H), 2.92-2.70 (m, 2H), 2.13-1.78 (m, 3H), 1.46-1.29 (m, 1H).

(3R,4R/3S,4S)-4-Azido-1-[[4-(benzofuran-2-yl)-6-isoquinolyl]methyl]piperidin-3-ol

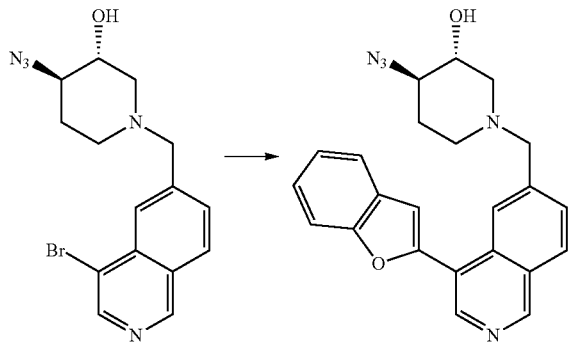 [SMILES: [N-]=[N+]=N[C@@H]1CCN(Cc2ccc3cncc(Br)c3c2)C[C@H]1O ; [N-]=[N+]=N[C@@H]1CCN(Cc2ccc3cncc(-c4cc5ccccc5o4)c3c2)C[C@H]1O]

To a solution of 0.1 g (0.28 mmol) of (3R,4R/3S,4S)-4-azido-1-[(4-bromo-6-isoquinolyl)methyl]piperidin-3-ol in a mixture of 5 mL of dioxane and 0.30 mL of $H_2O$ were added 0.35 g (1.66 mmol) of $K_3PO_4$, 0.03 g (0.03 mmol) of Pd(PPh$_3$)$_4$ and 0.09 g (0.55 mmol) of benzofuran-2-ylboronic acid. The resulting mixture was stirred at 90° C. for 16 h under argon atmosphere. The solvent was evaporated and the residue was purified by Biotage flash chromatography (ACN-H$_2$O-TFA) and lyophilized. The obtained TFA salt was dissolved in EtOAc and washed with aq. NaHCO$_3$, dried over Na$_2$SO$_4$, filtered and concentrated under reduced pressure to give 56 mg of (3R,4R/3S,4S)-4-azido-1-[[4-(benzofuran-2-yl)-6-isoquinolyl]methyl]piperidin-3-ol as a colorless oil.

MS (+ESI): 400.0[M+H]$^+$.

$^1$H NMR (400 MHz, DMSO-d$_6$+D$_2$O) δ ppm: 9.34 (s, 1H), 8.89 (s, 1H), 8.36 (s, 1H), 8.22 (d, J=8.4 Hz, 1H), 7.78-7.69 (m, 3H), 7.52 (s, 1H), 7.43-7.33 (m, 2H), 3.76 (ABq, J=14.0 Hz, 2H), 3.45-3.38 (m, 1H), 3.24-3.17 (m, 1H), 2.91-2.87 (m, 1H), 2.80-2.76 (m, 1H), 2.10-2.04 (m, 1H), 1.96-1.89 (m, 1H), 1.87-1.82 (m, 1H), 1.42-1.33 (m, 1H).

(3R,4R/3S,4S)-4-Amino-1-[[4-(benzofuran-2-yl)-6-isoquinolyl]methyl]piperidin-3-ol (Example 268)

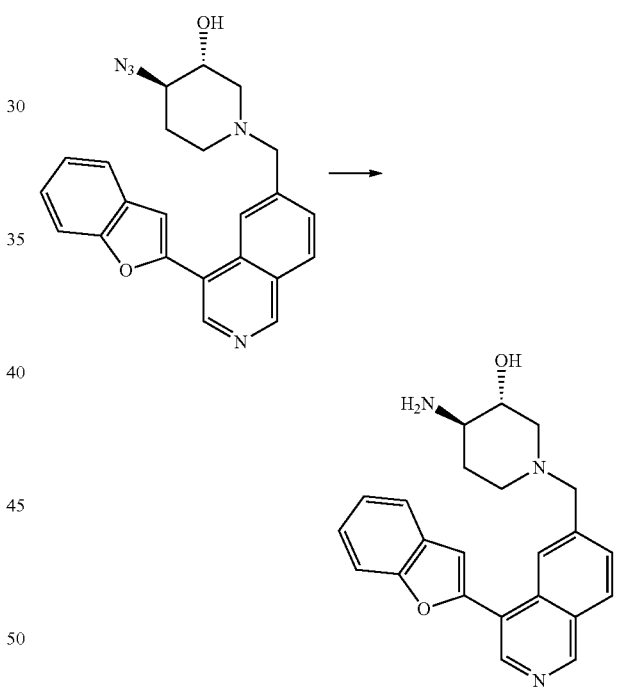

To a solution of 0.2 g (0.50 mmol) of (3R,4R/3S,4S)-4-azido-1-[[4-(benzofuran-2-yl)-6-isoquinolyl]methyl]piperidin-3-ol in 13.5 mL of ACN and 1.5 mL of H$_2$O was added 0.26 g (1.0 mmol) of PPh$_3$. The mixture was stirred at 20° C. for 16 h, and LC-MS showed the formation of the desired product. The residue was purified by preparative HPLC to give 183 mg of (3R,4R/3S,4S)-4-amino-1-[[4-(benzofuran-2-yl)-6-isoquinolyl]methyl]piperidin-3-ol as a light yellow solid.

MS (+ESI): 374.2 [M+H]$^+$.

$^1$H NMR (400 MHz, DMSO-d$_6$+D$_2$O) δ ppm: 9.47 (s, 1H), 8.99 (s, 1H), 8.62 (s, 1H), 8.39 (d, J=8.4 Hz, 1H), 7.87 (dd, J=8.4 Hz, 1.2 Hz, 1H), 7.78 (d, J=7.2 Hz, 1H), 7.73 (dd, J=8.4 Hz, 0.4 Hz, 1H), 7.60 (s, 1H), 7.45-7.34 (m, 2H), 4.60

(s, 2H), 3.49-3.27 (m, 2H), 3.17-2.99 (m, 2H), 2.95-2.89 (m, 1H), 2.14-2.12 (m, 1H), 1.76-1.65 (m, 1H).

(3S,4R/3R,4S)-4-Azido-1-[[4-(benzofuran-2-yl)-6-isoquinolyl]methyl]piperidin-3-ol

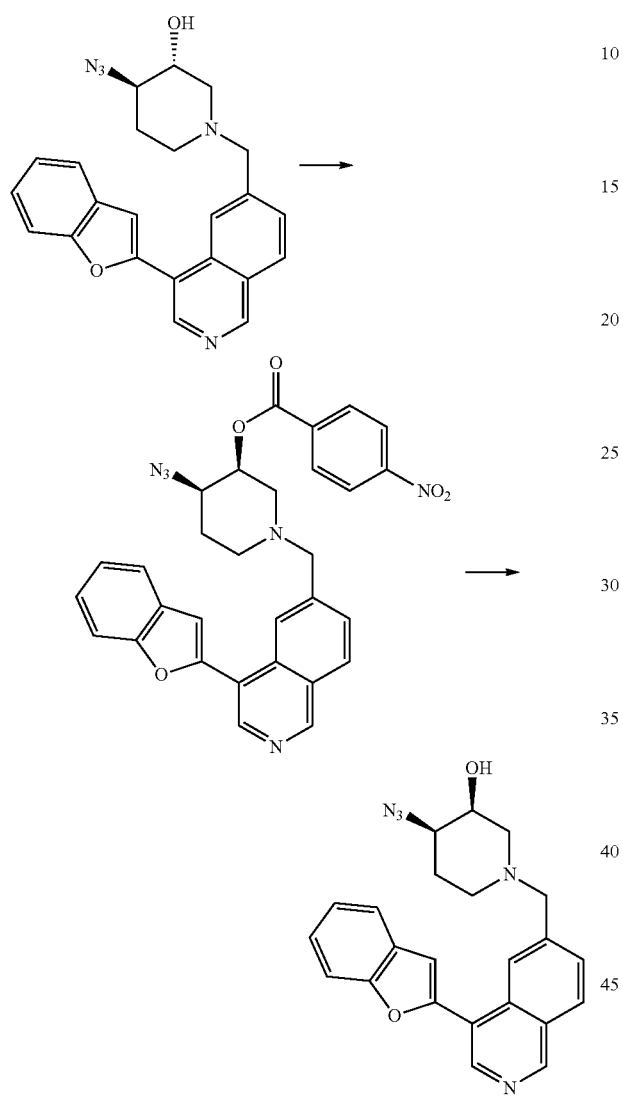

To a stirred, cooled (0° C.) mixture of 0.8 g (2.00 mmol) of (3R,4R/3S,4S)-4-azido-1-[[4-(benzofuran-2-yl)-6-isoquinolyl]methyl]piperidin-3-ol, 2.0 g (7.61 mmol) of PPh$_3$, and 1.34 g (8.01 mmol) of 4-nitrobenzoic acid in 20 mL of THF was added 1.42 mL (9.01 mmol) of DEAD dropwise. The resulting mixture was stirred at room temperature for 16 h. The mixture was diluted with Et$_2$O, washed with brine, dried over Na$_2$SO$_4$, filtered and concentrated. The residue was purified by column chromatography over silica gel eluting with PE-DCM-EA (5:5:2, R$_f$=0.22) to give 1 g of [(3S,4R/3R,4S)-4-azido-1-[[4-(benzofuran-2-yl)-6-isoquinolyl]methyl]-3-piperidyl] 4-nitrobenzoate as a light yellow oil.

To 1.6 g (2.92 mmol) of this intermediate in a mixture of 25 mL DCM and 50 mL of MeOH was added 1.58 g (29.17 mmol) of sodium methoxide. The mixture was stirred at 20° C. for 16 h. The mixture was diluted with DCM and washed with brine, dried over Na$_2$SO$_4$, filtered and concentrated. The crude product was purified by column chromatography over silica gel eluting with PE-EA (1:1), DCM-EA-PE (1:1:1), DCM-EA (1:1) to give 0.7 g of (3S,4R/3R,4S)-4-azido-1-[[4-(benzofuran-2-yl)-6-isoquinolyl]methyl]piperidin-3-ol as a yellow semisolid.

MS (+ESI): 400.3 [M+H]$^+$.

$^1$H NMR (400 MHz, DMSO-d$_6$+D$_2$O) δ ppm: 9.32 (s, 1H), 8.88 (s, 1H), 8.37 (s, 1H), 8.19 (d, J=8.4 Hz, 1H), 7.78-7.74 (m, 2H), 7.70 (d, J=8.0 Hz, 1H), 7.52 (s, 1H), 7.42-7.40 (m, 1H), 7.39-7.32 (m, 1H), 4.00 (ABq, J=14.0 Hz, 2H), 4.05-3.92 (m, 1H), 3.49-3.45 (m, 1H), 3.33-3.27 (m, 1H), 2.83-2.78 (m, 1H), 2.69-2.65 (m, 1H), 2.49-2.42 (m, 1H), 2.00-1.95 (m, 1H), 1.73-1.67 (m, 1H).

(3S,4R/3R,4S)-4-Amino-1-[[4-(benzofuran-2-yl)-6-isoquinolyl]methyl]piperidin-3-ol (Example 269)

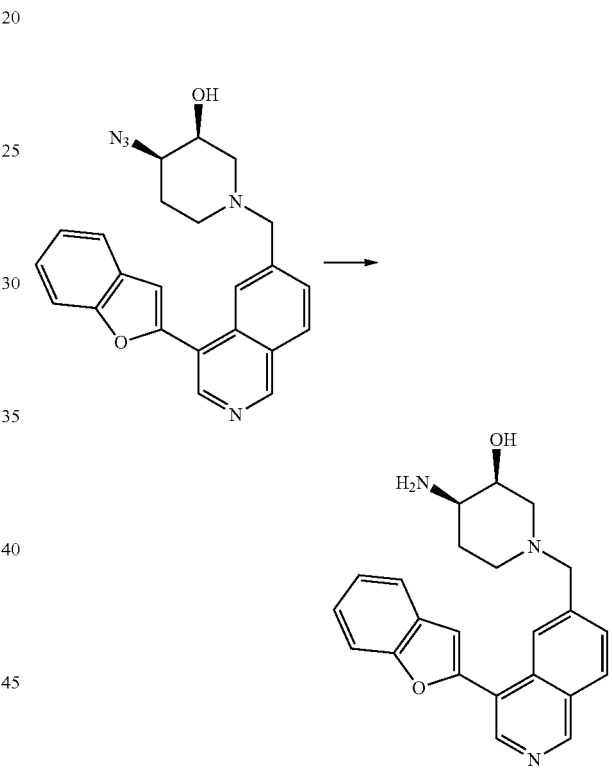

To a solution of 0.07 g (0.18 mmol) of (3S,4R/3R,4S)-4-azido-1-[[4-(benzofuran-2-yl)-6-isoquinolyl]methyl]piperidin-3-ol in a mixture of 9 mL of ACN and 1 mL of H$_2$O was added 0.09 g (0.35 mmol) of PPh$_3$. The mixture was stirred at 20° C. for 16 h until LC-MS show the formation of the desired product. The solution was purified by preparative HPLC to give 51 mg of (3S,4R/3R,4S)-4-amino-1-[[4-(benzofuran-2-yl)-6-isoquinolyl]methyl]piperidin-3-ol as a yellow solid.

MS (+ESI): 374.4 [M+H]$^+$.

$^1$H NMR (400 MHz, DMSO-d$_6$+D$_2$O) δ ppm: 9.46 (s, 1H), 8.98 (s, 1H), 8.62 (s, 1H), 8.39 (d, J=8.4 Hz, 1H), 7.90 (d, J=8.4 Hz, 1H), 7.78 (d, J=7.6 Hz, 1H), 7.72 (d, J=8.4 Hz, 1H), 7.60 (s, 1H), 7.45-7.34 (m, 2H), 4.70 (ABq, J=13.2 Hz, 2H), 3.67-3.62 (m, 4H), 3.47-3.35 (m, 2H), 2.27-2.17 (m, 1H), 2.12-2.05 (m, 1H).

6-[[(3S,4R/3R,4S)-4-Azido-3-methoxy-1-piperidyl]methyl]-4-(benzofuran-2-yl)isoquinoline

(3S,4R/3R,4S)-1-[[4-(Benzofuran-2-yl)-6-isoquinolyl]methyl]-3-methoxy-piperidin-4-amine (Example 270)

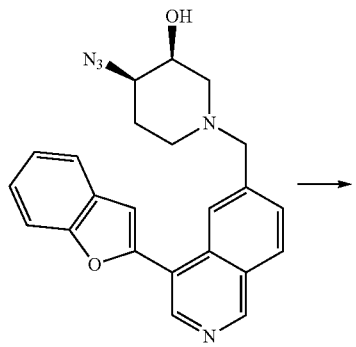

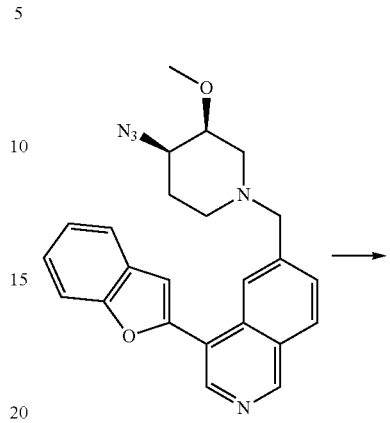

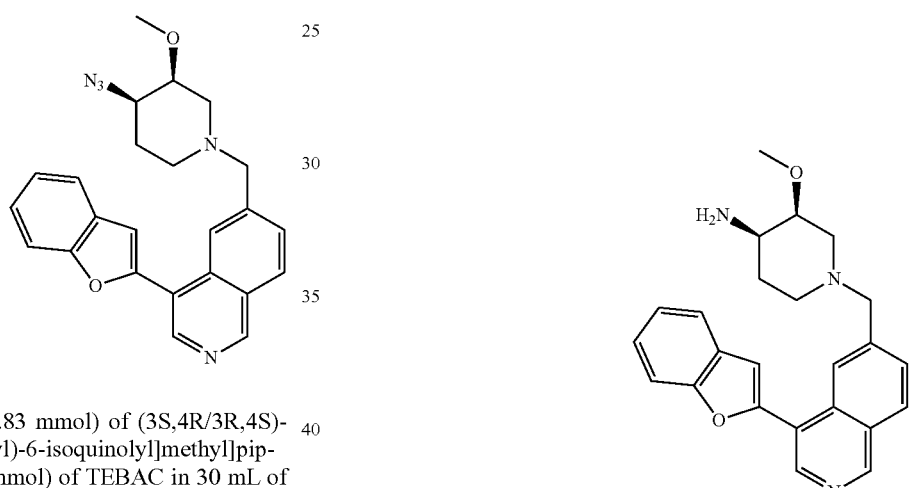

To a solution of 0.33 g (0.83 mmol) of (3S,4R/3R,4S)-4-azido-1-[[4-(benzofuran-2-yl)-6-isoquinolyl]methyl]piperidin-3-ol and 75 mg (0.33 mmol) of TEBAC in 30 mL of DCM was added 7.5 mL of 50% aq. NaOH at 0° C., followed by the addition of 0.07 mL (0.91 mmol) of dimethyl sulfate. The reaction mixture was stirred at 0° C. for 4 h. TLC and LC-MS showed around 40% of the starting material was consumed. The reaction was quenched by the addition of 4 mL of ammonia. After stirring for 2 h, the reaction mixture was diluted with water and extracted with DCM. The combined organic phases were washed with water and concentrated to give crude product as a light brown viscous oil. The crude product was purified by preparative HPLC. The desired fractions were neutralized with aqueous $NaHCO_3$ and concentrated to remove most of acetonitrile. The residue was extracted with DCM, dried over $Na_2SO_4$, filtered and concentrated to give 70 mg of 6-[[(3S,4R/3R,4S)-4-azido-3-methoxy-1-piperidyl]methyl]-4-(benzofuran-2-yl)isoquinoline as a light brown viscous oil.

MS (+ESI): 414.2 [M+H]$^+$.

$^1$H NMR (400 MHz, DMSO-d$_6$+D$_2$O) δ ppm: 9.32 (s, 1H), 8.88 (s, 1H), 8.36 (s, 1H), 8.20 (d, J=8.4 Hz, 1H), 7.78-7.68 (m, 3H), 7.51 (s, 1H), 7.43-7.32 (m, 2H), 4.01 (ABq, J=14.0 Hz, 2H), 4.00-3.88 (m, 1H), 3.44-3.40 (m, 1H), 3.30-3.26 (m, 1H), 3.22 (s, 3H), 2.83-2.74 (m, 2H), 2.48-2.41 (m, 1H), 2.05-1.95 (m, 1H), 1.73-1.67 (m, 1H).

To a solution of 0.07 g (0.17 mmol) of 6-[[(3S,4R/3R,4S)-4-azido-3-methoxy-1-piperidyl]methyl]-4-(benzofuran-2-yl)isoquinoline in 4.5 mL of ACN and 0.5 mL of H$_2$O was added 0.17 g (0.34 mmol) of PPh$_3$. The resulting solution was stirred at 28° C. for 16 h. The mixture was concentrated to give a volume of 2 mL and purified by flash chromatography (ACN-H$_2$O-TFA) to give 40 mg of (3S,4R/3R,4S)-1-[[4-(benzofuran-2-yl)-6-isoquinolyl]methyl]-3-methoxy-piperidin-4-amine as a yellow solid.

MS (+ESI): 388.2 [M+H]$^+$.

$^1$H NMR (400 MHz, DMSO-d$_6$+D$_2$O) δ ppm: 9.48 (s, 1H), 9.00 (s, 1H), 8.59 (s, 1H), 8.39 (d, J=8.4 Hz, 1H), 7.90 (dd, J=8.4 Hz, 1.6 Hz, 1H), 7.81-7.73 (m, 2H), 7.62 (s, 1H), 7.46-7.35 (m, 2H), 4.65 (ABq, J=13.2 Hz, 2H), 3.71-3.60 (m, 4H), 3.36-3.31 (m, 2H), 3.26 (s, 3H), 2.27-2.18 (m, 1H), 2.10-2.01 (m, 1H).

The following examples were prepared accordingly to Example 270 by reaction of (3R,4R/3S,4S)-4-azido-1-[[4-(benzofuran-2-yl)-6-isoquinolyl]methyl]piperidin-3-ol with dimethyl sulfate and subsequent reduction of azide with PPh$_3$:

| Example | | ¹H NMR (400 MHz) δ ppm | MS (+ESI) [M + H]⁺ |
|---|---|---|---|
| 271 | 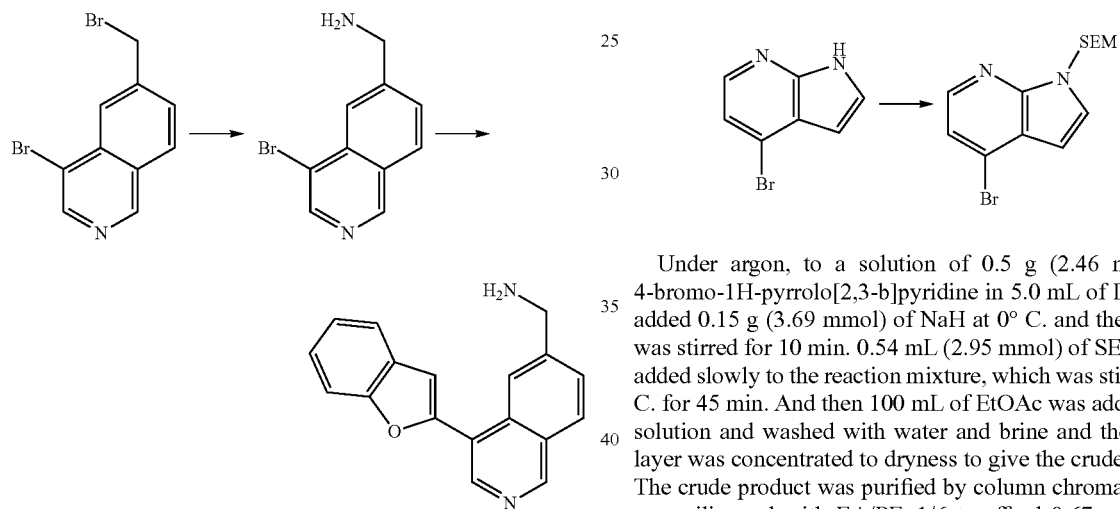 | (DMSO-d₆ + D₂O) 9.46 (s, 1H), 8.98 (s, 1H), 8.59 (s, 1H), 8.38 (d, J = 8.4 Hz, 1H), 7.87 (dd, J = 8.4 Hz, 1.2 Hz), 7.78 (d, J = 7.2 Hz, 1H), 7.72 (d, J = 7.6 Hz, 1H), 7.60 (s, 1H), 7.47-7.31 (m, 2H), 4.54 (ABq, J = 13.2 Hz, 2H), 3.84-3.76 (m, 1H), 3.52-3.46 (m, 1H), 3.33 (s, 3H), 3.31-3.28 (m, 1H), 3.20-3.16 (m, 1H), 3.04-2.96 (m, 1H), 2.88-2.83 (m, 1H), 2.13-2.08 (m, 1H), 1.74-1.65 (m, 1H). | 388.3 |

[4-(Benzofuran-2-yl)-6-isoquinolyl]methanamine 1 g (3.32 mmol) of 4-bromo-6-(bromomethyl)isoquinoline was added portionwise to 100 mL of a solution of NH₃ in MeOH at −20° C. The mixture was stirred at this temperature for 16 h. The solution was concentrated and then washed with 30 mL of i-PrOH to give 0.78 g of (4-bromo-6-isoquinolyl)methanamine as a pink solid.

To a solution of 0.2 g (0.84 mmol) of (4-bromo-6-isoquinolyl)methanamine and 0.41 g (2.53 mmol) of benzofuran-2-boronic acid in 30 mL of dioxane and 2.0 mL of H₂O were added 0.54 g (2.53 mmol) of K₃PO₄, 0.09 g (0.08 mmol) of Pd₂(dba)₃ and 0.1 g (0.17 mmol) of Xantphos. The reaction mixture was heated to 90° C. and stirred for 2 h under argon atmosphere. The reaction was concentrated under vacuum to give the crude product which was purified by column chromatography over silica gel (DCM/MeOH=50/1, R$_f$=0.2) to afford 0.18 g of [4-(benzofuran-2-yl)-6-isoquinolyl]methanamine as a yellow powder.

MS (ESI+): 275.0 [M+H]⁺.

¹H NMR (400 MHz, DMSO-d₆) δ ppm: 9.36 (s, 1H), 8.92 (s, 1H), 8.44 (s, 1H), 8.22 (d, J=8.4 Hz, 1H), 7.81-7.74 (m, 3H), 7.59 (s, 1H), 7.44-7.34 (m, 2H), 4.06 (s, 2H).

2-[(4-Bromopyrrolo[2,3-b]pyridin-1-yl)methoxy]ethyl-trimethyl-silane

Under argon, to a solution of 0.5 g (2.46 mmol) of 4-bromo-1H-pyrrolo[2,3-b]pyridine in 5.0 mL of DMF was added 0.15 g (3.69 mmol) of NaH at 0° C. and the reaction was stirred for 10 min. 0.54 mL (2.95 mmol) of SEMCl was added slowly to the reaction mixture, which was stirred at 0° C. for 45 min. And then 100 mL of EtOAc was added to the solution and washed with water and brine and the organic layer was concentrated to dryness to give the crude product. The crude product was purified by column chromatography over silica gel with EA/PE=1/6 to afford 0.67 g of 2-[(4-bromopyrrolo[2,3-b]pyridin-1-yl)methoxy]ethyl-trimethyl-silane as a light yellow oil.

MS (ESI+): 327.0 [M+H]⁺.

¹H NMR (400 MHz, DMSO-d₆) δ ppm: 8.16 (d, J=5.2 Hz, 1H), 7.79 (d, J=3.6 Hz, 1H), 7.43 (d, J=5.2 Hz, 1H), 6.53 (d, J=3.6 Hz, 1H), 5.64 (s, 2H), 3.51 (t, J=8.0 Hz, 2H), 0.81 (t, J=8.0 Hz, 2H), 0.11 (s, 9H).

N-[[4-(Benzofuran-2-yl)-6-isoquinolyl]methyl]-1-(2-trimethylsilylethoxymethyl)pyrrolo[2,3-b]pyridin-4-amine

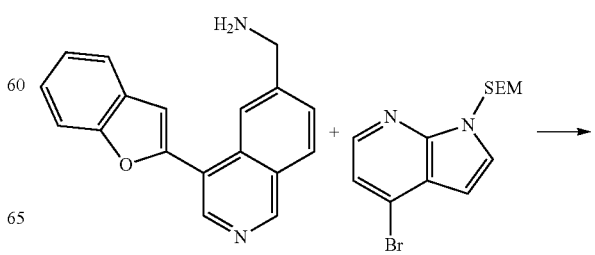

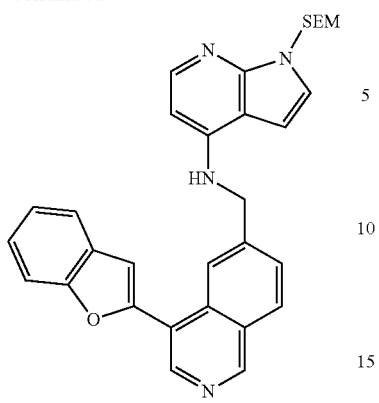

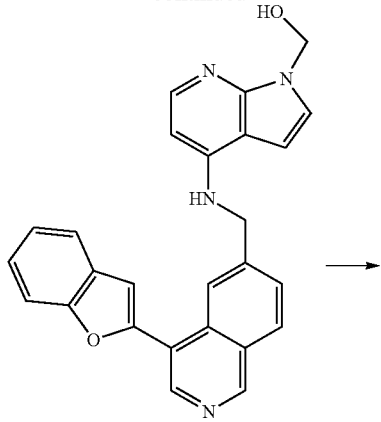

To a solution of 0.12 g (0.44 mmol) of 2-[(4-bromopyrrolo[2,3-b]pyridin-1-yl)methoxy]ethyl-trimethyl-silane and 0.12 g (0.37 mmol) of [4-(benzofuran-2-yl)-6-isoquinolyl]methanamine in 2.0 mL of dioxane were added 0.02 g (0.02 mmol) of $Pd_2(dba)_3$, 0.02 g (0.04 mmol) of Xantphos and 0.18 g (0.55 mmol) of $Cs_2CO_3$. The reaction mixture was heated to 100° C. and stirred for 2.5 h under Ar atmosphere. The reaction was concentrated under vacuum to give the crude product which was purified by column chromatography over silica gel (DCM/MeOH=100/1-40/1, $R_f$=0.3) to afford N-[[4-(benzofuran-2-yl)-6-isoquinolyl]methyl]-1-(2-trimethylsilylethoxymethyl)pyrrolo[2,3-b]pyridin-4-amine as a brown solid.

MS (ESI+): 521.1 [M+H]+.

$^1$H NMR (400 MHz, DMSO-$d_6$) δ ppm: 9.34 (s, 1H), 8.91 (s, 1H), 8.49 (s, 1H), 8.23 (d, J=8.4 Hz, 1H), 7.82-7.80 (m, 2H), 7.63-7.25 (m, 6H), 6.73 (d, J=3.6 Hz, 1H), 6.18 (d, J=5.6 Hz, 1H), 5.55 (s, 2H), 4.81 (d, J=6.4 Hz, 2H), 3.49 (t, J=8.0 Hz, 2H), 0.87-0.78 (m, 2H), 0.14 (s, 9H).

N-[[4-(Benzofuran-2-yl)-6-isoquinolyl]methyl]-1H-pyrrolo[2,3-b]pyridin-4-amine (Example 272)

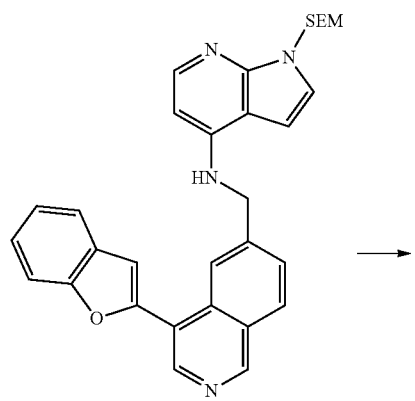

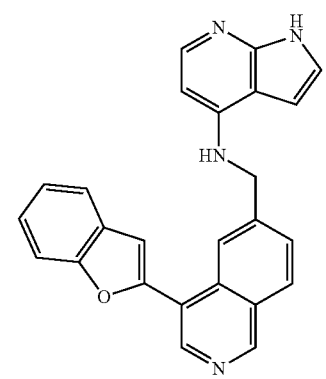

A solution of 110 mg (0.21 mmol) of N-[[4-(benzofuran-2-yl)-6-isoquinolyl]methyl]-1-(2-trimethylsilylethoxymethyl)pyrrolo[2,3-b]pyridin-4-amine in 10 mL of TFA was stirred for 2 h at 25° C. The solvent was evaporated off to give 0.09 g of [4-[[4-(benzofuran-2-yl)-6-isoquinolyl]methylamino]pyrrolo[2,3-b]pyridin-1-yl]methanol as a yellow solid which was used in the next step without further purification.

To a solution of 88 mg of this intermediate in 10 mL of MeOH and 5.0 mL of DCM was added 1.5 mL of 25% ammonia. The reaction solution was stirred for 20 h at 25° C. The solvent was removed under vacuum and the residue was purified by chromatography column over silica with DCM/MeOH/$NH_3 \cdot H_2O$=100/1/0.1-30/1/0.1 to afford 0.06 g of N-[[4-(benzofuran-2-yl)-6-isoquinolyl]methyl]-1H-pyrrolo[2,3-b]pyridin-4-amine as an off-white solid.

MS (ESI+): 391.2[M+H]+.

$^1$H NMR (400 MHz, DMSO-$d_6$) δ ppm: 9.30 (s, 1H), 8.86 (s, 1H), 8.40 (s, 1H), 8.24 (d, J=8.4 Hz, 1H), 7.80-7.77 (m, 2H), 7.59-7.57 (m, 1H), 7.33-7.25 (m, 3H), 7.23-7.15 (m, 2H), 6.68 (d, J=3.2 Hz, 1H), 6.22 (d, J=6.0 Hz, 1H), 4.85 (s, 2H).

321 tert-Butyl N-[1-[(4-trimethylsilylacetylenyl-6-iso-quinolyl)methyl]-4-piperidyl]carbamate

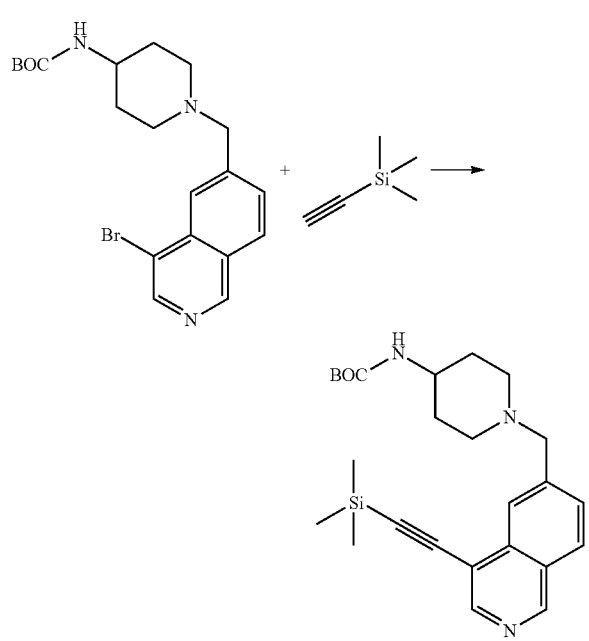

In a sealed tube, to a suspension of 2.00 g (4.76 mmol) of tert-butyl N-[1-[(4-bromo-6-isoquinolyl)methyl]-4-piperidyl]carbamate, 334 mg (0.48 mmol) of Pd(PPh$_3$)$_2$Cl$_2$ and 181 mg (0.95 mmol) of CuI in 30 mL of DIPEA was added 6.72 mL (47.58 mmol) of trimethylsilylacetylene under an inert atmosphere. The mixture was stirred at 80° C. for 16 h. The solvent was removed under reduced pressure and the residue was dissolved in EA. The organic layer was washed with water, brine, dried over anhydrous Na$_2$SO$_4$, and concentrated in vacuo to give the crude product, which was purified via silica gel (PE/EA=1/1) to give 1.67 g of product as a light yellow semisolid.

MS (+ESI): 438.3 [M+H].

$^1$H NMR (400 MHz, CDCl$_3$) δ ppm: 9.17 (s, 1H), 8.71 (s, 1H), 8.11 (s, 1H), 7.94 (d, J=8.0 Hz), 7.69 (d, J=8.0 Hz, 1H), 3.73 (s, 2H), 3.53 (m, 1H), 2.84 (m, 2H), 2.22 (m, 2H), 1.94 (m, 2H), 1.61 (m, 2H), 1.46 (s, 9H), 0.37 (s, 9H).

tert-Butyl N-[1-[(4-acetylenyl-6-isoquinolyl)methyl]-4-piperidyl]carbamate

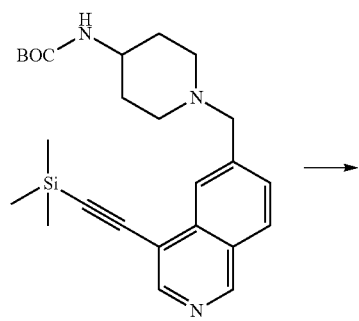

322

-continued

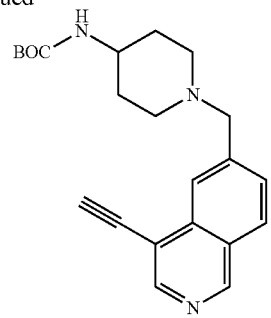

A mixture of 1670 mg (3.82 mmol) tert-butyl N-[1-[(4-trimethylsilylacetylenyl-6-isoquinolyl)methyl]-4-piperidyl]carbamate of in 15 mL of 2 N TBAF in THF was stirred at rt for 2 h. The solvent was removed under reduced pressure and the residue was extracted with EA/H$_2$O. The organic layer was washed with brine, dried over anhydrous Na$_2$SO$_4$, and concentrated in vacuo to give 1400 mg of crude product as a dark brown semisolid.

MS (+ESI): 366.3 [M+H]

$^1$H NMR (400 MHz, CDCl$_3$) δ ppm: 9.19 (s, 1H), 8.73 (s, 1H), 8.12 (s, 1H), 7.96 (d, J=8.4 Hz), 7.72 (d, J=8.4 Hz, 1H), 3.72 (s, 2H), 3.51 (s, 1H), 3.50 (m, 1H), 2.82 (m, 2H), 2.19 (m, 2H), 1.93 (m, 2H), 1.51 (m, 2H), 1.46 (s, 9H).

tert-Butyl N-[1-[(4-furo{2,3-b}pyridin-2-yl)-6-iso-quinolyl)methyl]-4-piperidyl]carbamate

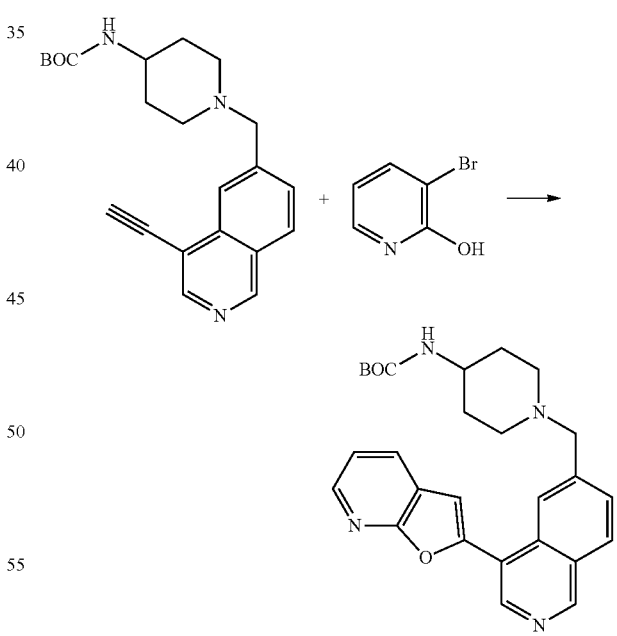

In a sealed tube, a suspension of 400 mg (1.09 mmol) of tert-butyl N-[1-[(4-acetylenyl-6-isoquinolyl)methyl]-4-piperidyl]carbamate, 240 mg (1.38 mmol) of 3-bromo-2-hydroxypyridine, 77 mg (0.11 mmol) of Pd(PPh$_3$)$_2$Cl$_2$ and 535 mg (1.64 mmol) of Cs$_2$CO$_3$ in 10 mL of DMF under an inert atmosphere was stirred at 110° C. for 16 h. The mixture was extracted with EA/H$_2$O. The organic layer was washed with brine, dried over anhydrous Na$_2$SO$_4$, and concentrated in vacuo to give the crude product, which was purified via silica gel (pure EA) to give 107 mg of product as a light yellow semisolid.

MS (+ESI): 459.3 [M+H].

¹H NMR (400 MHz, DMSO-d6+D₂O) δ ppm: 9.35 (s, 1H), 8.88 (s, 1H), 8.36 (d, J=4.8 Hz, 1H), 8.30 (s, 1H), 8.22-8.20 (m, 2H), 7.65 (d, J=8.0 Hz, 1H), 7.56 (s, 1H), 7.44 (m, 1H), 3.66 (s, 2H), 3.19 (m, 1H), 2.73 (m, 2H), 2.05 (m, 2H), 1.66 (m, 2H), 1.37 (m, 2H), 1.32 (s, 9H).

1-[(4-Furo{2,3-b}pyridin-2-yl-6-isoquinolyl)methyl]piperidin-4-amine (Example 273)

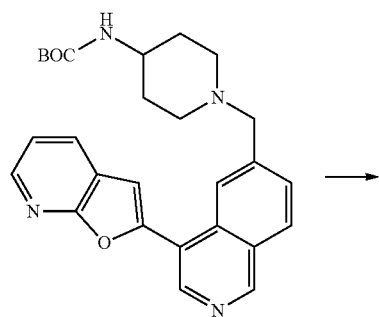

→

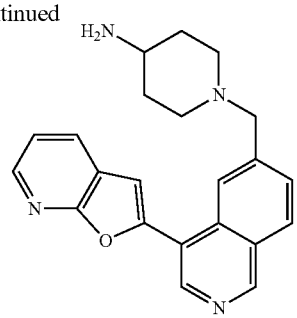

A mixture of 100 mg (0.22 mmol) of tert-butyl N-[1-[(4-furo{2,3-b}pyridin-2-yl)-6-isoquinolyl)methyl]-4-piperidyl]carbamate in 8 mL of DCM and 2 mL of TFA was stirred at rt for 1 h. The solvent was removed and the residue was purified by prep-HPLC to give 70 mg of product as colorless semisolid.

MS (+ESI): 359.20 [M+H].

¹H NMR (400 MHz, DMSO-d6+D₂O) δ ppm: 9.52 (s, 1H), 9.00 (s, 1H), 8.61 (s, 1H), 8.43-8.39 (m, 2H), 8.26 (dd, J=7.6 Hz, 1.6 Hz, 1H), 7.90 (dd, J=8.4 Hz, 1.2 Hz, 1H), 7.65 (s, 1H), 7.47 (dd, J=8.0 Hz, 4.8 Hz, 1H), 4.57 (s, 2H), 3.44 (m, 2H), 3.27 (m, 1H), 3.12 (m, 2H), 2.07 (m, 2H), 1.70 (m, 2H).

The following examples were prepared accordingly to Example 273 by reaction of tert-butyl N-[1-[(4-acetylenyl-6-isoquinolyl)methyl]-4-piperidyl]carbamate with corresponding iodo-hydroxypyridines followed by Boc removal under acidic conditions:

| Example | | ¹H NMR (400 MHz) δ ppm | MS (+ESI) [M + H]⁺ |
|---|---|---|---|
| 274 | (structure) | (DMSO-d₆ + D₂O): 9.58 (s, 1H), 9.37 (s, 1H), 9.12 (s, 1H), 8.62 (d, J = 5.6 Hz, 1H), 8.61 (s, 1H), 8.44 (d, J = 8.4 Hz, 1H), 8.17 (d, J = 5.6 Hz, 1H), 7.92 (d, J = 8.4 Hz, 1H), 7.91 (s, 1H), 4.58 (s, 2H), 3.45 (m, 2H), 3.27 (m, 1H), 3.11 (m, 2H), 2.07 (m, 2H), 1.71 (m, 2H) | 359.20 |
| 275 | (structure) | (DMSO-d₆ + D₂O): 9.54 (s, 1H), 9.35 (s, 1H), 9.05 (s, 1H), 8.76 (d, J = 6.4 Hz, 1H), 8.56 (s, 1H), 8.42 (d, J = 8.4 Hz, 1H), 8.27 (d, J = 6.4 Hz, 1H), 7.93 (s, 1H), 7.90 (d, J = 8.4 Hz, 1H), 4.55 (s, 2H), 3.44 (m, 2H), 3.28 (m, 1H), 3.10 (m, 2H), 2.07 (m, 2H), 1.75 (m, 2H) | 359.20 |

| Example | <sup></sup> | ¹H NMR (400 MHz) δ ppm | MS (+ESI) [M + H]⁺ |
|---|---|---|---|
| 276 | 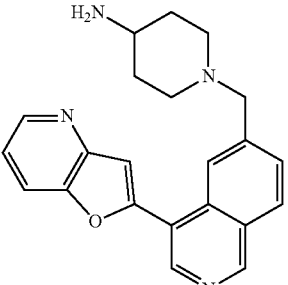 | (DMSO-d₆ + D₂O): 9.52 (s, 1H), 9.06 (s, 1H), 8.64 (d, J = 5.6 Hz, 1H), 8.63 (s, 1H), 8.41 (d, J = 8.4 Hz, 1H), 8.18 (d, J = 8.4 Hz, 1H), 7.89 (d, J = 8.4 Hz, 1H), 7.83 (s, 1H), 7.49 (m, 1H), 4.59 (s, 2H), 3.45 (m, 2H), 3.27 (m, 1H), 3.11 (m, 2H), 2.07 (m, 2H), 1.72 (m, 2H) | 359.24 |

Methyl 4-(benzofuran-2-yl) cinnoline-6-carboxylate

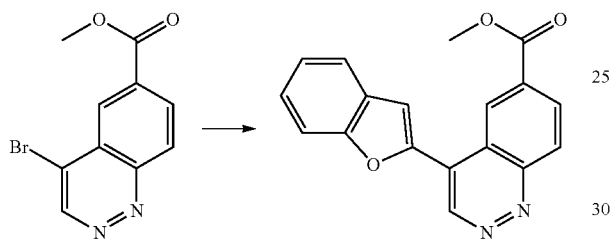

A solution of 1.60 g (5.95 mmol) of methyl 4-bromocinnoline-6-carboxylate, 1.35 g (8.32 mmol) of benzofuran-2-ylboronic acid (CAS 98437-24-2), 1.75 g (17.8 mmol) of KOAc, 0.69 g (0.59 mmol) of Pd(PPh₃)₄ and 0.14 g (0.30 mmol) of X-Phos in 50 mL of dioxane is stirred at 90° C. for 16 h under N₂ atmosphere. The mixture is diluted with EA, washed with water and brine, dried over Na₂SO₄, filtered and concentrated under reduced pressure. The residue is purified by silica gel column chromatography (PE/EA=1/4) to give 1.4 g of the product as a yellow solid.

MS (ESI+): 305.1 [M+H].

¹H NMR (400 MHz, DMSO-d₆) δ ppm: 9.93 (s, 1H), 9.38 (s, 1H), 8.62 (d, J=8.8 Hz, 1H), 8.40 (d, J=8.8 Hz, 1H), 8.09 (s, 1H), 7.86 (d, J=8.0 Hz, 1H), 7.80 (d, J=8.4 Hz, 1H), 7.51 (t, J=7.2 Hz, 1H), 7.40 (t, J=7.2 Hz, 1H), 3.98 (s, 3H).

4-(Benzofuran-2-yl)cinnoline-6-carboxylic acid

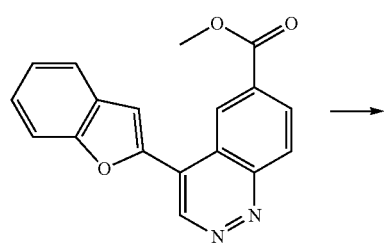

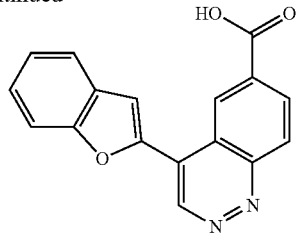

A solution of 1.30 g (4.27 mmol) of methyl 4-(benzofuran-2-yl)cinnoline-6-carboxylate and 0.34 g (8.54 mmol) of NaOH in 20 mL of THF and 20 mL of H₂O is stirred at 28° C. for 12 h. The suspension is concentrated under vacuum to remove THF. Then 1 N HCl is added to adjust pH=6, and a lot of solid precipitated. The solid is filtered and washed with EA to give 1.0 g of product as a yellow solid.

MS (ESI+): 291.0 [M+H].

¹H NMR (400 MHz, DMSO-d₆) δ ppm: 9.73 (s, 1H), 9.14 (s, 1H), 8.49 (d, J=8.8 Hz, 1H), 8.42 (d, J=8.8 Hz, 1H), 7.93 (s, 1H), 7.85 (d, J=7.6 Hz, 1H), 7.77 (d, J=8.4 Hz, 1H), 7.48 (t, J=7.6 Hz, 1H), 7.38 (t, J=7.2 Hz, 1H).

4-(Benzofuran-2-yl)-N-(4-pyridyl)cinnoline-6-carboxamide

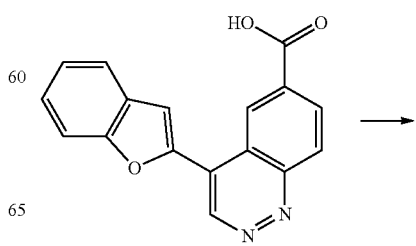

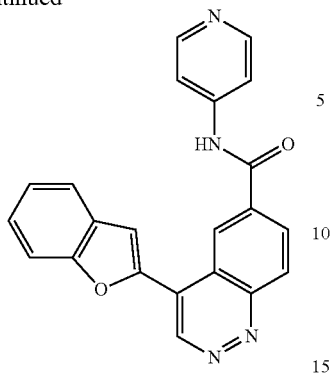

A solution of 0.82 g (2.83 mmol) of 4-(benzofuran-2-yl)cinnoline-6-carboxylic acid, 0.40 g (4.24 mmol) of 4-aminopyridine (CAS 504-24-5), 0.95 g (11.3 mmol) of NaHCO$_3$ and 1.29 g (3.39 mmol) of HATU in 20 mL of DMF is stirred at 30° C. for 12 h. The mixture is diluted with EA, washed with water and brine, dried over Na$_2$SO$_4$, filtered and concentrated under reduced pressure. The residue is purified by silica gel column chromatography (MeOH/EA=1/10) to give 0.8 g of the product as a yellow solid.

MS (ESI+): 367.1 [M+H].

$^1$H NMR (400 MHz, DMSO-d$_6$) δ ppm: 11.1 (s, 1H), 9.93 (s, 1H), 9.26 (s, 1H), 8.69 (d, J=9.2 Hz, 1H), 8.52 (d, J=5.2 Hz, 2H), 8.43 (d, J=9.2 Hz, 1H), 8.19 (s, 1H), 7.87 (d, J=7.6 Hz, 1H), 7.82-7.81 (m, 3H), 7.51 (t, J=7.2 Hz, 1H), 7.40 (t, J=7.2 Hz, 1H).

N-[[4-(Benzofuran-2-yl)-1,2,3,4-tetrahydrocinnolin-6-yl]methyl]pyridin-4-amine (Example 277)

To a solution of 0.40 g (1.09 mmol) of 4-(benzofuran-2-yl)-N-(4-pyridyl)cinnoline-6-carboxamide in 10 mL of THF at 0° C. is added 1.1 mL (11 mmol) of borane dimethyl sulfide complex. The reaction mixture is warmed to 70° C. and stirred for 8 h. After cooling to 0° C., 5 mL of MeOH is added and the mixture is stirred at 20° C. under air atmosphere for 120 h. The reaction mixture is concentrated under reduced pressure and the residue is purified by preparative HPLC to give 15 mg of the desired product as a yellow solid.

MS (ESI+): 353.1 [M+H].

$^1$H NMR (400 MHz, DMSO-d$_6$+D$_2$O) δ ppm: 9.78 (s, 1H), 8.65 (s, 1H), 8.56 (d, J=8.8 Hz, 1H), 8.16 (d, J=7.2 Hz, 2H), 7.99 (dd, J$_1$=8.8 Hz, J$_2$=1.6 Hz, 1H), 7.95 (s, 1H), 7.82 (d, J=8.0 Hz, 1H), 7.62 (d, J=8.4 Hz, 1H), 7.50 (m, 1H), 7.39 (t, J=7.6 Hz, 1H), 7.09 (dd, J$_1$=6.8 Hz, J$_2$=2.0 Hz, 1H), 6.95 (dd, J$_1$=7.2 Hz, J$_2$=2.8 Hz, 1H), 4.93 (s, 2H).

4-(Benzofuran-2-yl)cinnoline-6-carboxamide

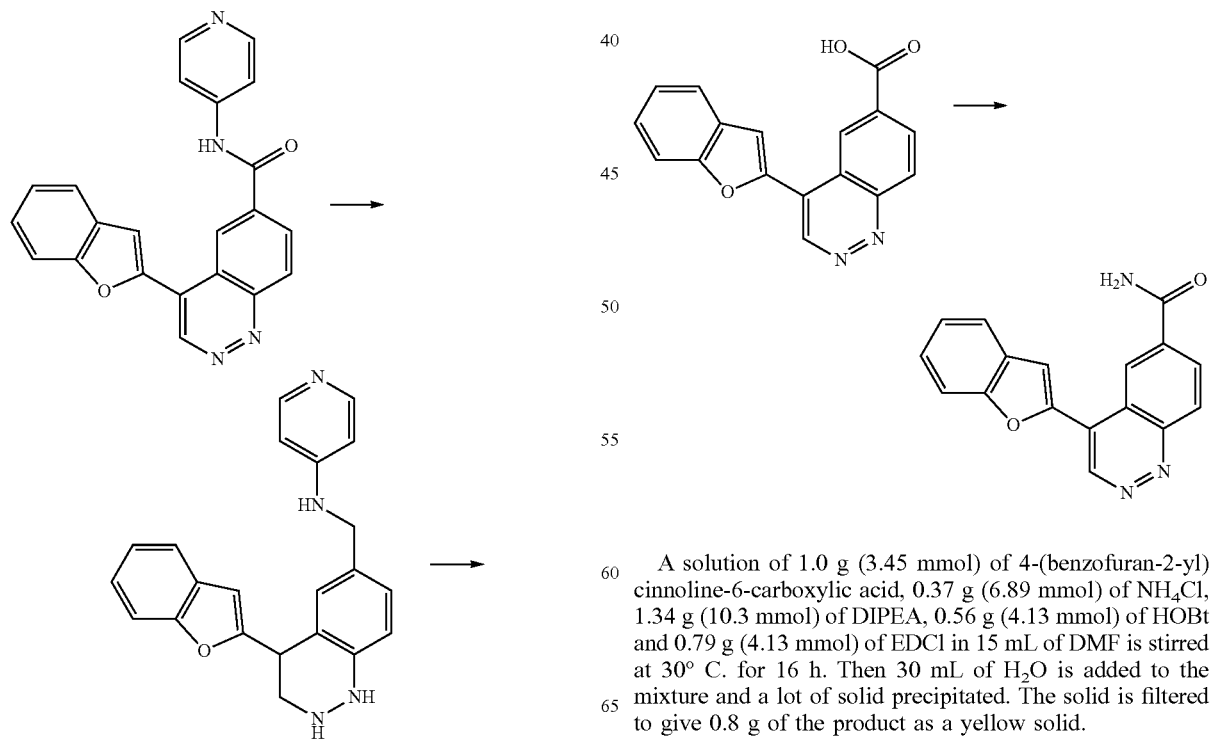

A solution of 1.0 g (3.45 mmol) of 4-(benzofuran-2-yl)cinnoline-6-carboxylic acid, 0.37 g (6.89 mmol) of NH$_4$Cl, 1.34 g (10.3 mmol) of DIPEA, 0.56 g (4.13 mmol) of HOBt and 0.79 g (4.13 mmol) of EDCl in 15 mL of DMF is stirred at 30° C. for 16 h. Then 30 mL of H$_2$O is added to the mixture and a lot of solid precipitated. The solid is filtered to give 0.8 g of the product as a yellow solid.

MS (ESI+): 290.0 [M+H].

329

$^1$H NMR (400 MHz, DMSO-d$_6$) δ ppm: 9.87 (s, 1H), 9.14 (s, 1H), 8.62 (d, J=8.8 Hz, 1H), 8.51 (s, 1H), 8.40 (d, J=8.8 Hz, 1H), 8.13 (s, 1H), 7.89-7.82 (m, 3H), 7.52 (t, J=7.6 Hz, 1H), 7.41 (t, J=7.6 Hz, 1H).

N-(2-Amino-4-pyridyl)-4-(benzofuran-2-yl)cinnoline-6-carboxamide

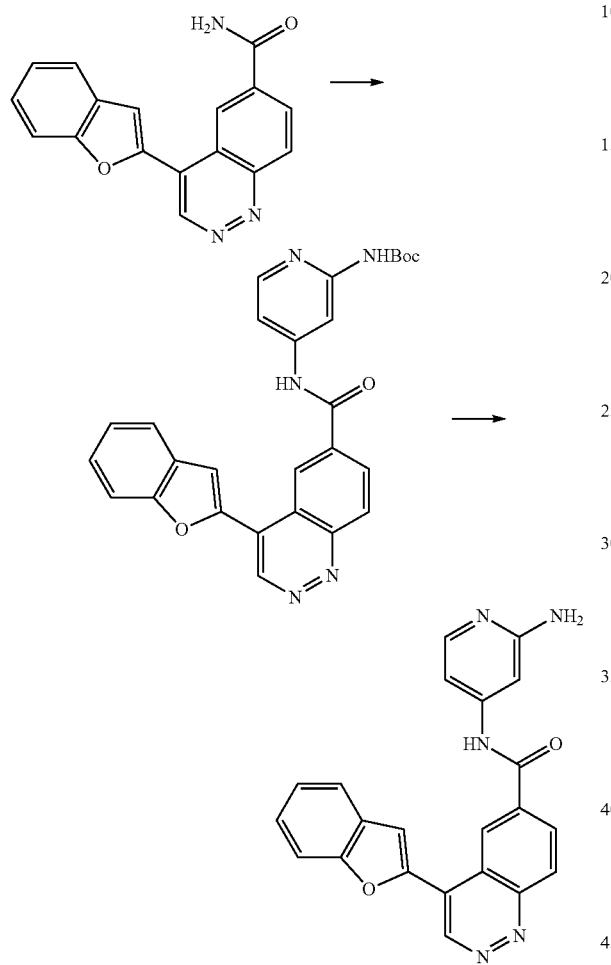

A solution of 350 mg (1.21 mmol) of 4-(benzofuran-2-yl)cinnoline-6-carboxamide, 277 mg (1.21 mmol) of 2-Boc-Amino-4-chloropyridine (CAS 130721-78-7), 251 mg (0.24 mmol) of Pd$_2$(dba)$_3$, 231 mg (0.48 mmol) of X-Phos and 349 mg (3.63 mmol) of t-BuONa in 35 mL of Dioxane is stirred at 120° C. under N$_2$ atmosphere for 16 h. The reaction mixture is concentrated under vacuum to afford the residue, which is purified by silica gel column chromatography (MeOH/DCM=1/20) to afford 160 mg of tert-butyl N-[4-[[4-(benzofuran-2-yl)cinnoline-6-carbonyl]amino]-2-pyridyl]carbamate as a yellow solid. This intermediate is dissolved in 3 mL of a 1.0 N solution of HCl in EA and the mixture is stirred at rt for 1 h. Then the solvent is evaporated under reduced pressure to afford the residue, which is dissolved in 5 mL of MeOH and NH$_4$OH is added until the pH value is up to 8. Then the mixture is concentrated in vacuo to afford the residue, which is purified by silica gel column chromatography (MeOH/DCM=1/10) to give 100 mg of the product as a yellow solid.

MS (ESI+): 382.1 [M+H].

330

$^1$H NMR (400 MHz, DMSO-d$_6$) δ ppm: 11.0 (s, 1H), 9.94 (s, 1H), 9.24 (d, J=1.6 Hz, 1H), 8.69 (d, J=8.8 Hz, 1H), 8.43 (dd, J$_1$=8.8 Hz, J$_2$=1.6 Hz), 8.21 (d, J=0.8 Hz), 7.89 (d, J=6.0 Hz, 1H), 7.88 (d, J=8.4 Hz, 1H), 7.83 (d, J=8.4 Hz, 1H), 7.53 (m, 1H), 7.43 (m, 1H), 7.29 (d, J=1.6 Hz, 1H), 6.96 (dd, J$_1$=6.0 Hz, J$_2$=1.6 Hz, 1H), 5.76 (s, 2H).

N4-[[4-(Benzofuran-2-yl)cinnolin-6-yl]methyl]pyridine-2,4-diamine (Example 278)

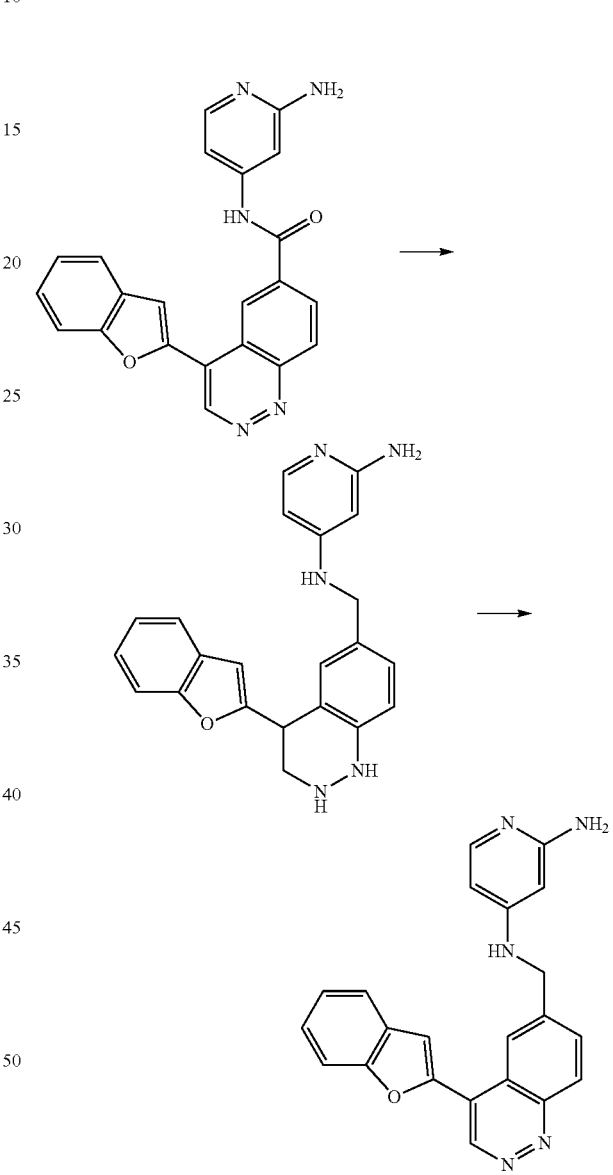

To a solution of 0.10 g (0.26 mmol) of N-(2-amino-4-pyridyl)-4-(benzofuran-2-yl)cinnoline-6-carboxamide in 5 mL of THF at 0° C. is added 2.6 mL (2.6 mmol) of borane dimethyl sulfide complex. The reaction mixture is warmed to 70° C. and stirred for 8 h. After cooling to 0° C., 5 mL of MeOH is added and the mixture is stirred at 20° C. under air atmosphere for 120 h. The reaction mixture is concentrated under reduced pressure and the residue is purified by preparative HPLC to give 5 mg of the desired product as a yellow solid.

MS (ESI+): 368.3 [M+H].

¹H NMR (400 MHz, DMSO-d₆+D₂O) δ ppm: 9.77 (s, 1H), 8.60 (s, 1H), 8.54 (d, J=8.8Hz, 1H), 7.97 (dd, J₁=8.8 Hz, J₂=1.6 Hz, 1H), 7.92 (s, 1H), 7.82 (d, J=7.6 Hz, 1H), 7.63 (d, J=8.4 Hz, 1H), 7.54 (d, J=7.2 Hz, 1H), 7.50 (m, 1H), 7.39 (m, 1H), 6.38 (m, 1H), 5.69 (s, 1H), 4.76 (s, 2H).

N-[(2,3-Dichloro-4-methyl-phenyl)methyl]-2,2-dimethoxy-ethanamine

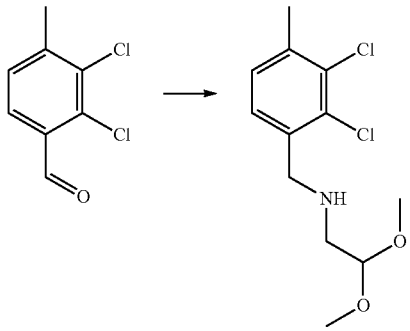 [SMILES: Cc1ccc(C=O)c(Cl)c1Cl ; COC(CNCc1ccc(C)c(Cl)c1Cl)OC]

A solution of 13.0 g (68.8 mmol) of 2,3-dichloro-4-methyl-benzaldehyde and 8.76 g (82.5 mmol) of aminoacetaldehyde dimethyl acetal (CAS 22483-09-6) in 100 mL of toluene is stirred with a Dean-Stark trap under reflux for 2 h. The mixture is concentrated under vacuum to give the residue, which is dissolved in 100 mL of EtOH and 2.71 g (70.4 mmol) of NaBH₄ is added slowly at 0° C. The reaction mixture is stirred at 20° C. for 2 h. 50 mL of H₂O was added and the mixture is extracted with EA. The combined organic layers are dried over Na₂SO₄ and then concentrated under vacuum to afford 13.0 g of the residue as a yellow oil.
MS (ESI+): 278.0 [M+H].

N-[(2,3-Dichloro-4-methyl-phenyl)methyl]-N-(2,2-dimethoxyethyl)-4-methyl-benzenesulfonamide

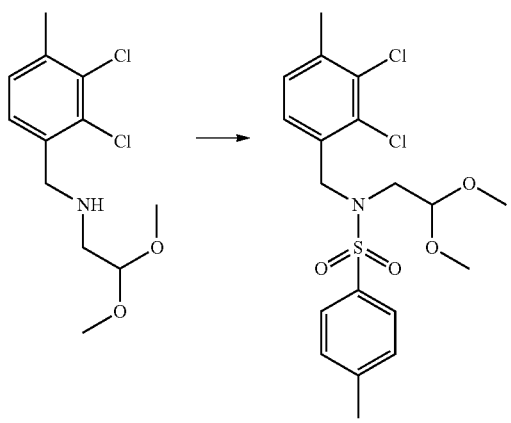 [SMILES: COC(CNCc1ccc(C)c(Cl)c1Cl)OC ; COC(CN(Cc1ccc(C)c(Cl)c1Cl)S(=O)(=O)c1ccc(C)cc1)OC]

A solution of 6.0 g (21.1 mmol) of N-[(2,3-dichloro-4-methyl-phenyl)methyl]-2,2-dimethoxy-ethanamine, 5.1 mL (63.4 mmol) of pyridine and 4.88 g (25.4 mmol) of TsCl in 100 mL of DCM is stirred at 20° C. for 16 h. The mixture is diluted with DCM, washed with water and brine, dried over Na₂SO₄, filtered and concentrated under reduced pressure. The residue is purified by silica gel column chromatography (EA/PE=1/10) to give 7.2 g of the product as a yellow oil.

¹H NMR (400 MHz, DMSO-d₆) δ ppm: 7.72 (d, J=8.4 Hz, 2H), 7.42 (d, J=8.4 Hz, 2H), 7.35 (m, 2H), 4.42 (s, 2H), 4.27 (t, J=5.2Hz, 1H), 3.23 (d, J=5.2Hz, 2H), 3.11 (s, 6H), 2.40 (s, 3H), 2.37 (s, 3H).

7,8-Dichloro-6-methyl-isoquinoline

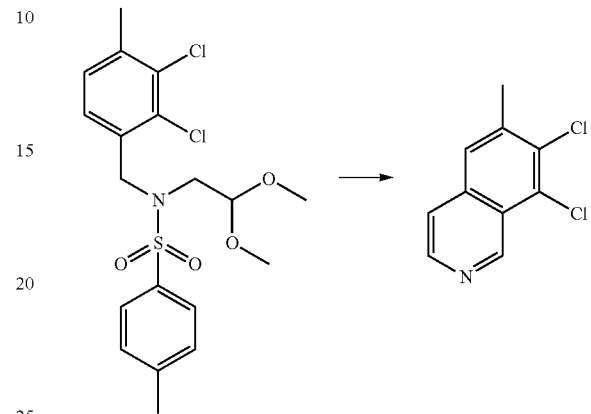

To a solution of 13.3 g (94.9 mmol) of AlCl₃ in 50 mL of DCM is added 7.20 g (15.8 mmol) of N-[(2,3-dichloro-4-methyl-phenyl)methyl]-N-(2,2-dimethoxyethyl)-4-methyl-benzene sulfon-amide in 50 mL of DCM at 0° C. The resulting mixture is allowed to warm to 20° C. and stirred at this temperature for 16 h. The reaction mixture is poured into 100 mL of cold water, and the aqueous phase is extracted with DCM. The combined organic layers are dried over Na₂SO₄ and then concentrated under vacuum to afford the residue, which is purified by silica gel column chromatography (EA/PE=1/10) to give 1.48 g of the product as a yellow solid.
MS (ESI+): 212.0 [M+H].
¹H NMR (400 MHz, DMSO-d₆) δ ppm: 9.46 (s, 1H), 8.61 (d, J=5.6 Hz, 1H), 7.95 (s, 1H), 7.82 (d, J=5.2 Hz, 1H), 2.55 (s, 3H).

4-Bromo-7,8-dichloro-6-methyl-isoquinoline

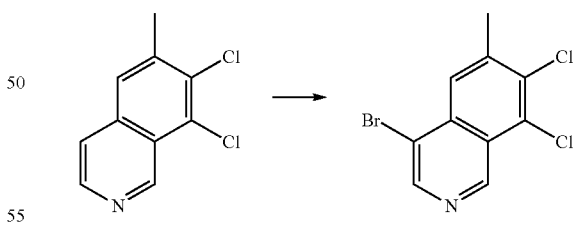

A solution of 2.10 g (9.43 mmol) of 7,8-dichloro-6-methyl-isoquinoline and 2.54 g (14.1 mmol) of NBS in 30 mL of AcOH is stirred at 60° C. for 3 h. The mixture is diluted with DCM, washed with sat. aqueous Na₂CO₃ solution and brine, dried over Na₂SO₄, filtered and concentrated under reduced pressure. The residue is purified by silica gel column chromatography (EA/PE=1/20) to give 1.80 g of the product as a white solid.
MS (ESI+): 289.9 [M+H].
¹H NMR (400 MHz, DMSO-d₆) δ ppm: 9.46 (s, 1H), 8.87 (s, 1H), 8.06 (s, 1H), 2.64 (s, 3H).

333 tert-Butyl N-[1-[(4-bromo-7, 8-dichloro-6-isoquinolyl)methyl]-4-piperidyl]carbamate

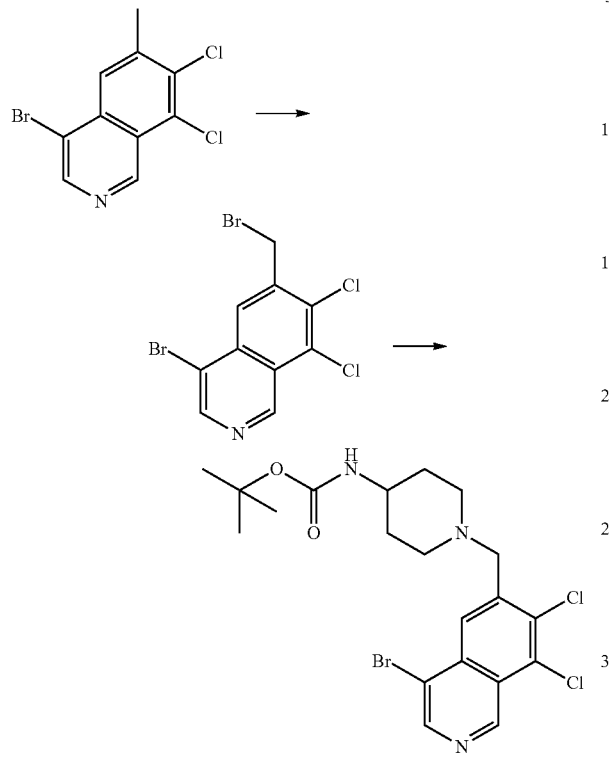

A solution of 1.80 g (5.57 mmol) of 4-bromo-7,8-dichloro-6-methyl-isoquinoline, 1.21 g (6.68 mmol) of NBS and 0.09 g (0.56 mmol) of AIBN in 30 mL of CC4 is stirred at 85° C. for 3 h. The mixture is concentrated under reduced pressure to give the residue, which is dissolved in 50 mL of DCM. 1.06 g (7.30 mmol) of $K_2CO_3$ and 0.77 g (3.65 mmol) of 4-N-Boc-amino-piperidine (CAS 73874-95-0) are added and the mixture is stirred at 20° C. for 16 h. The reaction mixture is diluted with EA, washed with water and brine, dried over $Na_2SO_4$, filtered and concentrated under reduced pressure. The residue is purified by silica gel column chromatography (EA/PE=1/2) to give 0.60 g of the product as a white solid.

MS (ESI+): 488.0 [M+H].

tert-Butyl N-[1-[[4-(benzofuran-2-yl)-7, 8-dichloro-6-isoquinolyl]methyl]-4-piperidyl]carbamate

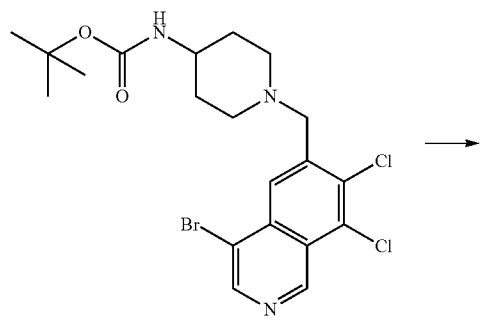

334

-continued

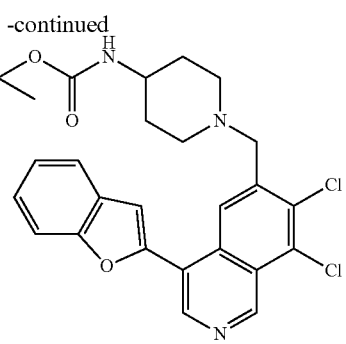

A solution of 0.60 g (1.17 mmol) of tert-Butyl N-[1-[(4-bromo-7,8-dichloro-6-isoquinolyl)methyl]-4-piperidyl]carbamate, 0.57 g (3.50 mmol) of benzofuran-2-ylboronic acid (CAS 98437-24-2), 0.75 g (3.50 mmol) of $K_3PO_4$ and 0.14 g (0.12 mmol) of Pd(PPh$_3$)$_4$ in 10 mL of Dioxane and 1 mL of $H_2O$ is stirred at 95° C. under $N_2$ atmosphere for 16 h. The mixture is diluted with EA, washed with water and brine, dried over $Na_2SO_4$, filtered and concentrated under reduced pressure. The residue is purified by silica gel column chromatography (PE/EA=1/2) to give 0.5 g of the product as a yellow solid.

MS (ESI+): 526.1 [M+H].

1-[[4-(Benzofuran-2-yl)-7,8-dimethoxy-6-isoquinolyl]methyl]piperidin-4-amine (Example 279)

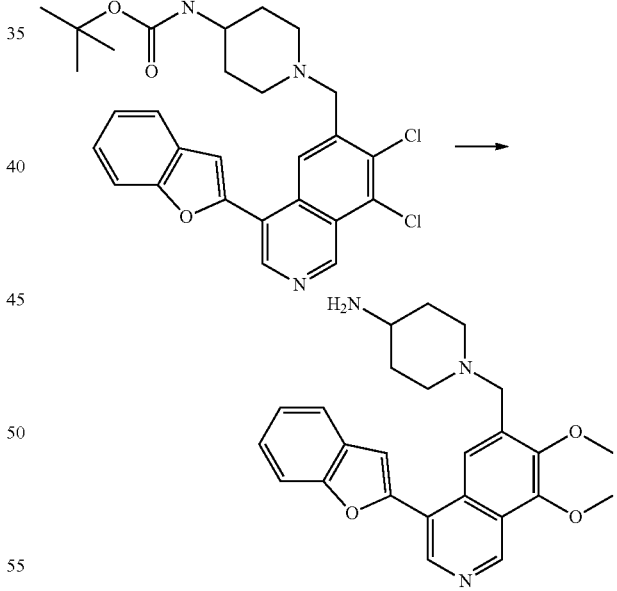

A solution of 40 mg (0.07 mmol) of tert-butyl N-[1-[[4-(benzofuran-2-yl)-7,8-dichloro-6-isoquinolyl]methyl]-4-piperidyl]carbamate, 7 mg (0.01 mmol) of 2-(di-tert-butylphosphino)-2',4',6'-triisopropyl-3,6-dimethoxybiphenyl (CAS 1160861-53-9), 1.0 mL (5.78 mmol) of 30% NaOMe, and 12 mg (0.01 mmol) of tBuBrettPhos Pd G3 ([(2-Di-tert-butylphosphino-3,6-dimethoxy-2',4',6'-triisopropyl-1,1'-biphenyl)-2-(2'-amino-1,1'-biphenyl)]palladium(II) methanesulfonate) in 3 mL of dioxane is stirred at 120° C. for 0.25 h under microwave irradiation. The mixture is concentrated under reduced pressure to afford the residue, which is purified by preparative HPLC to give 3 mg of the product as a yellow solid.

MS (ESI+): 418.2 [M+H].

$^1$H NMR (400 MHz, DMSO-d$_6$+D$_2$O) δ ppm: 9.54 (s, 1H), 8.94 (s, 1H), 8.41 (s, 1H), 7.80-7.72 (m, 2H), 7.60 (s, 1H), 7.44 (m, 1H), 7.36 (m, 1H), 4.54 (s, 2H), 4.08 (s, 3H), 4.06 (s, 3H), 3.49 (m, 2H), 3.27 (m, 1H), 3.18 (m, 2H), 2.06 (m, 2H), 1.71 (m, 2H).

1-[[4-(Benzofuran-2-yl)-7,8-dichloro-6-isoquinolyl]methyl]piperidin-4-amine (Example 280)

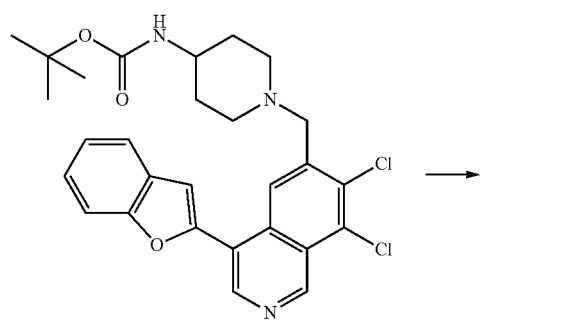

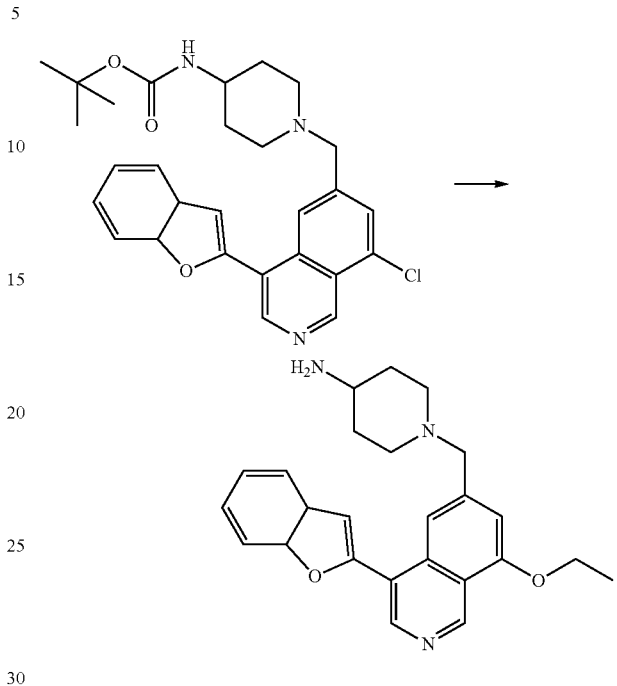

1-[[4-(Benzofuran-2-yl)-8-ethoxy-6-isoquinolyl]methyl]piperidin-4-amine (Example 281)

To a solution of 0.10 g (0.19 mmol) of tert-butyl N-[1-[[4-(benzofuran-2-yl)-7,8-dichloro-6-isoquinolyl]methyl]-4-piperidyl]carbamate in 5 mL of EA is added 0.8 mL of a 2.5 N solution of HCl in EA at 0° C. The reaction mixture is stirred at 20° C. for 16 h. The reaction mixture is concentrated under reduced pressure and the residue is purified by preparative HPLC to give 60 mg of the desired product as a yellow solid.

MS (ESI+): 426.1 [M+H].

$^1$H NMR (400 MHz, DMSO-d$_6$+D$_2$O) δ ppm: 9.70 (s, 1H), 9.14 (s, 1H), 8.76 (s, 1H), 7.82-7.73 (m, 2H), 7.67 (s, 1H), 7.46 (m, 1H), 7.39 (m, 1H), 4.62 (s, 2H), 3.47 (m, 2H), 3.27 (m, 2H), 3.12 (m, 2H), 2.07 (m, 2H), 1.72 (m, 2H).

To a solution of 70 mg (0.14 mmol) of tert-butyl N-[1-[[4-(benzofuran-2-yl)-8-chloro-6-isoquinolyl]methyl]-4-piperidyl]carbamate in 2 mL of dioxane were added 1 mL (2.85 mmol) of 20% NaOEt/EtOH solution, 14 mg (0.029 mmol) of X-Phos and 6 mg (0.029 mmol) of Pd(OAc)$_2$. The reaction mixture was stirred at 120° C. for 15 min using microwave irradiation, LCMS indicated that ca. 10% of the desired product and ca. 70% of the dechlorination by-product were formed. The reaction mixture was filtered, the filtrate was concentrated under vacuum, the residue was purified by prep-HPLC to afford 2 mg of the desired product as a light yellow solid.

MS (ESI+): 402.3 [M+H].

$^1$H NMR (400 MHz, DMAO-d$_6$+D$_2$O) δ ppm: 9.49 (s, 1H); 8.87 (s, 1H); 8.36 (s, 1H); 7.86 (s, 1H); 7.76 (d, J=7.6Hz, 1H); 7.69 (d, J=8.0Hz, 1H); 7.47 (s, 1H); 7.40~7.33 (m, 2H); 7.15 (s, 1H); 4.29 (q, J=6.8Hz, 2H); 3.69 (s, 2H); 2.96 (m, 1H); 2.86 (m, 2H); 2.07 (m, 2H); 1.85 (m, 2H); 1.50 (m, 5H).

(4-Bromo-7-chloro-6-isoquinolyl) methanol

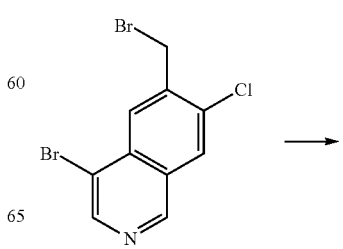

-continued

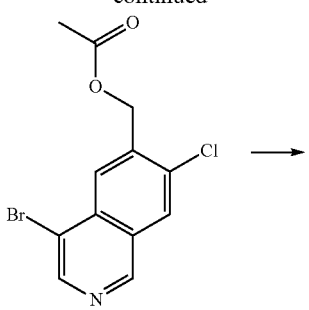

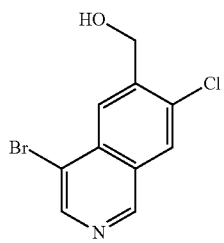

To a stirred solution of 0.60 g (1.8 mmol) of 4-bromo-6-(bromomethyl)-7-chloro-isoquinoline (prepared according to procedures described above) in 20 mL of DMF was added 0.60 g (7.2 mmol) of NaOAc. The reaction mixture was stirred at 60° C. under argon atmosphere for 1 h. The reaction mixture was taken up with water (60 mL), extracted with EA (50 mL×2). The combined organic layers were washed with water and brine, dried over anhydrous Na$_2$SO$_4$, and concentrated under vacuum to dryness. The crude product was purified by silica gel column chromatography (eluent: PE/EA=5:1) to afford (4-bromo-7-chloro-6-isoquinolyl)methyl acetate as a light yellow solid.

MS (ESI+): 313.9 [M+H].

To a stirred solution of 0.38 g (1.25 mmol) of (4-bromo-7-chloro-6-isoquinolyl) methyl acetate in 5 mL of MeOH, 10 mL of THF and 2 mL of H$_2$O was added 0.25 g (6.0 mmol) of LiOH.H$_2$O. The reaction mixture was stirred at 20° C. for 16 h. The reaction mixture was taken up with DCM and dried over anhydrous Na$_2$SO$_4$. The desiccant was filtered off, the filtrate was concentrated under vacuum to dryness. The crude product was purified by column chromatography on silica gel (eluent: PE/EA=10:1) to give (4-bromo-7-chloro-6-isoquinolyl) methanol as a light yellow solid.

MS (ESI+): 271.9 [M+H].

[4-(Benzofuran-2-yl)-7-chloro-6-isoquinolyl] methanol

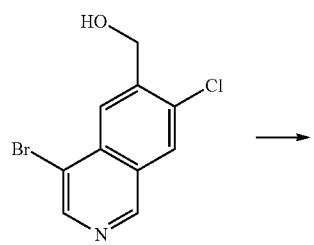

-continued

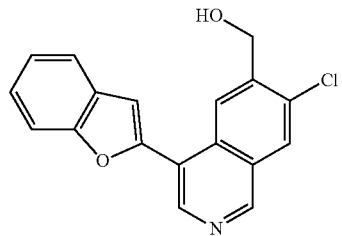

To a stirred solution of 1.1 g (4.0 mmol) of (4-bromo-7-chloro-6-isoquinolyl) methanol in 30 mL of dioxane and 3 mL of H$_2$O were added 2.0 g (12.1 mmol) of benzofuran-2-ylboronic acid, 0.40 g (0.4 mmol) of Pd(PPh$_3$)$_4$ and 3.2 g (12.1 mmol) of K$_3$PO$_4$. The reaction mixture was stirred at 90° C. for 3 h under argon atmosphere. The solvents were removed under vacuum, the residue was purified by column chromatography on silica gel (eluent: DCM/EA=20:1) to give the desired product as a yellow solid.

MS (ESI+): 310.0 [M+H].

[4-(Benzofuran-2-yl)-7-methoxy-6-isoquinolyl] methanol

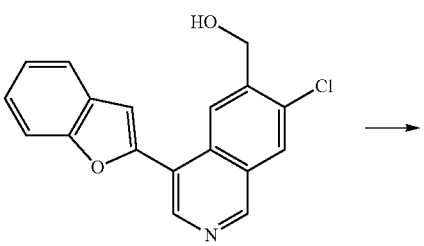

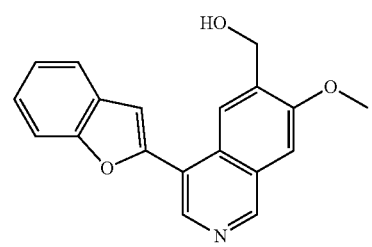

To a stirred solution of 100 mg (0.32 mmol) of [4-(benzofuran-2-yl)-7-chloro-6-isoquinolyl]-methanol in dioxane (3 mL) were added 30% NaOMe/MeOH solution (0.6 mL, 3.22 mmol), Pd$_2$(dba)$_3$ (33 mg, 0.032 mmol) and t-BuBrettPhos (16 mg, 0.032 mmol). The reaction mixture was heated at 120° C. using microwave irradiation for 5 min, LC-MS showed that the desired product and a dechlorination by-product (ca. 3:1) were formed. The mixture was acidified with aq. 1N HCl solution to pH=7, then extracted with EA (20 ml×3), the combined organic layers were washed with brine, and dried with Na$_2$SO$_4$, then filtered and concentrated under vacuum to give the crude product. The crude product was purified by column chromatography on silica gel (DCM/MeOH=70:1) to give 65 mg of the desired compound as a yellow solid.

MS (ESI+): 306.1 [M+H].

339
tert-Butyl N-[1-[[4-(benzofuran-2-yl)-7-methoxy-6-isoquinolyl]methyl]-4-piperidyl]carbamate

340
1-[[4-(Benzofuran-2-yl)-7-methoxy-6-isoquinolyl]methyl]piperidin-4-amine (Example 282)

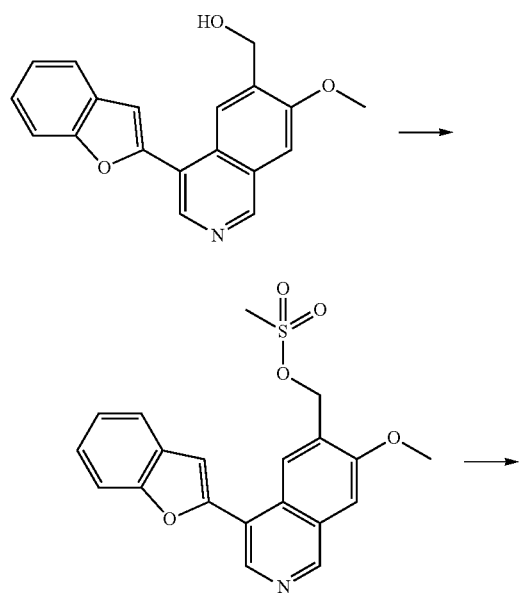

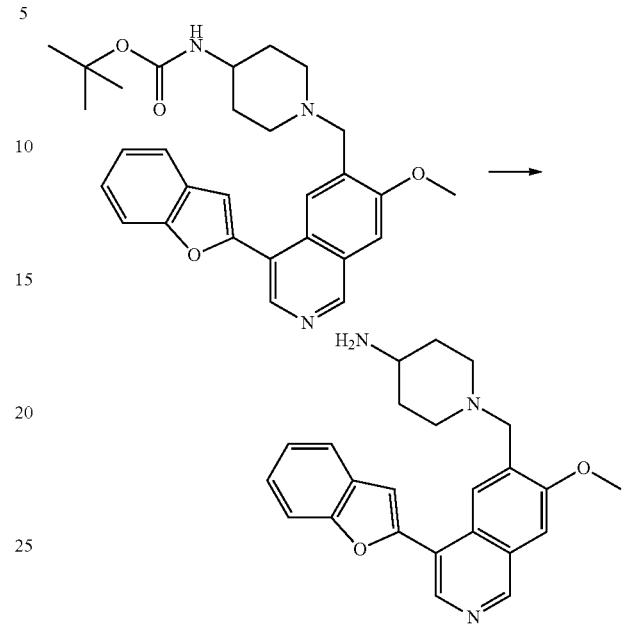

To a solution of 80 mg (0.16 mmol) of tert-butyl N-[1-[[4-(benzofuran-2-yl)-7-methoxy-6-isoquinolyl]methyl]-4-piperidyl]carbamate in 2 mL of DCM was added 0.5 mL (6.5 mmol) of TFA, the reaction mixture was stirred at 25° C. for 2 h, the mixture was concentrated under vacuum to give the crude product, which was purified by prep-HPLC to give the title compound as a yellow solid.

MS (ESI+): 388.2 [M+H].

$^1$H NMR (400 MHz, DMSO-$d_6$+$D_2O$) δ ppm: 9.37 (s, 1H); 8.86 (s, 1H); 8.63 (s, 1H); 7.85 (s, 1H); 7.80~7.73 (m, 2H); 7.61 (s, 1H); 7.46~7.34 (m, 2H); 4.55 (s, 2H); 4.05 (s, 3H); 3.50 (m, 2H); 3.27 (m, 1H); 3.17 (m, 2H); 2.07 (m, 2H); 1.72 (m, 2H).

To a solution of 130 mg (0.43 mmol) of [4-(benzofuran-2-yl)-7-methoxy-6-isoquinolyl] methanol and 129 mg (1.28 mmol) of TEA in 5 mL of DCM was added 73 mg (0.64 mmol) of MsCl at 0° C. The reaction mixture was stirred at 20° C. for 3 h, the mixture was diluted with DCM, washed with water and brine, dried over anhydrous $Na_2SO_4$, the volatiles were removed under vacuum to afford 160 mg of the crude [4-(benzofuran-2-yl)-7-methoxy-6-isoquinolyl] methyl methanesulfonate, which was used for next step without further purification.

MS (ESI+): 384.0 [M+H].

To a solution of 160 mg (0.42 mmol) of [4-(benzofuran-2-yl)-7-methoxy-6-isoquinolyl]methyl methanesulfonate in 5 mL of DCM were added 127 mg (1.25 mmol) of TEA and 167 mg (0.83 mmol) of 4-(N-Boc-amino) piperidine. The reaction mixture was stirred at 20° C. for 18 h, LC-MS indicated that the reaction was complete, the mixture was concentrated under vacuum to dryness, the residue was purified by column chromatography on silica gel (eluent: PE/EA=2:1~1:1) to give the desired product as an off-white solid.

MS (ESI+): 488.2 [M+H].

4-(Benzofuran-2-yl)-6-(hydroxymethyl) isoquinolin-8-ol

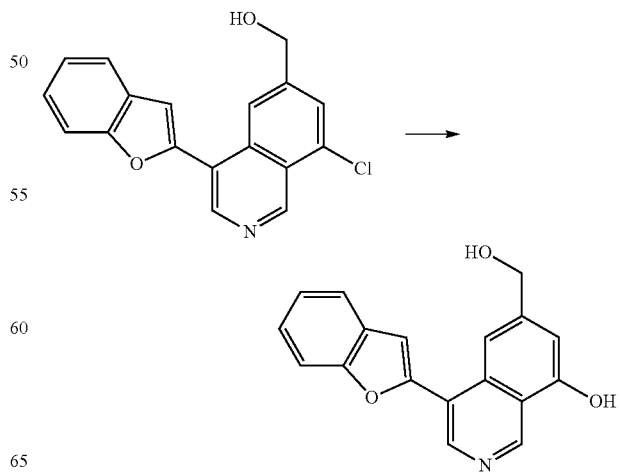

To a stirred solution of 50 mg (0.16 mmol) of [4-(benzofuran-2-yl)-8-chloro-6-isoquinolyl]-methanol (prepared according to procedures described above) in 3.0 mL of dioxane and of 1.0 mL of H$_2$O were added 63 mg (1.13 mmol) of KOH, 15 mg (0.065 mmol) of Pd(OAc)$_2$ and 15 mg (0.032 mmol) of x-Phos. The reaction mixture was stirred at 120° C. using microwave irradiation for 5 min, LCMS showed that the reaction was complete, the mixture was acidified with 1N HCl solution to pH=7, then extracted with EA, the combined organic layers were washed with brine, dried over anhydrous Na$_2$SO$_4$, filtered and concentrated under vacuum to give the crude product, which was purified by column chromatography on silica gel (eluent: DCM/MeOH=30:1) to give 25 mg of the desired compound as an orange solid.

MS (ESI+): 292.2 [M+H].

tert-Butyl N-[1-[[4-(benzofuran-2-yl)-8-isopropoxy-6-isoquinolyl]methyl]-4-piperidyl]carbamate

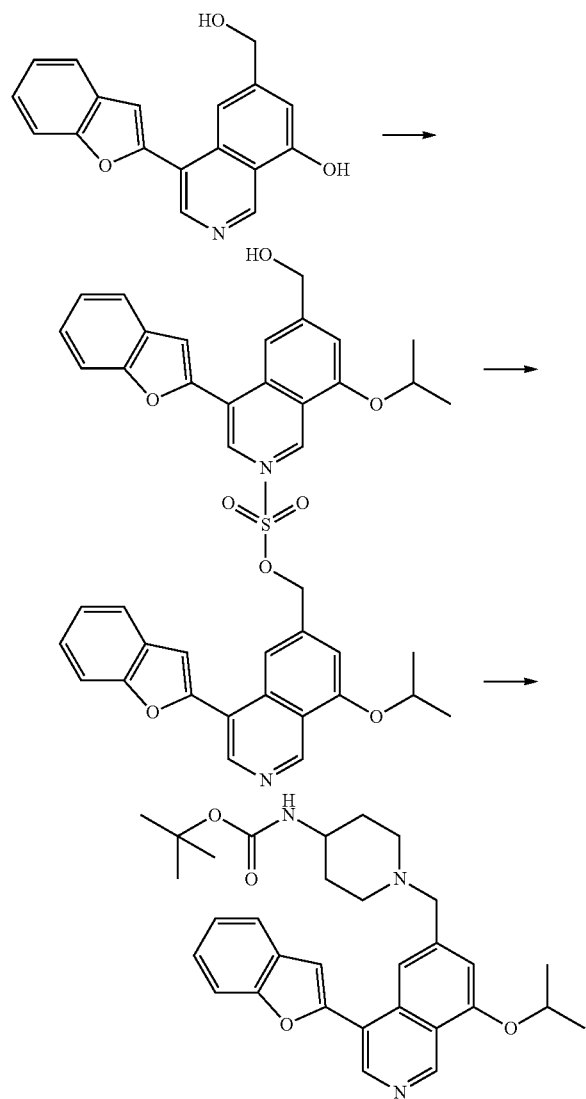

To a stirred solution of 180 mg (0.62 mmol) of 4-(benzofuran-2-yl)-6-(hydroxymethyl)-isoquinolin-8-ol in 6 mL of DMF were added 171 mg (1.24 mmol) of K$_2$CO$_3$ and 114 mg (0.93 mmol) of 2-bromopropane. The reaction mixture was stirred at 65° C. for 4 h. 30 ml of H$_2$O was added, the resulting mixture was extracted with EA, the combined organic phases were washed with water and brine, dried over anhydrous Na$_2$SO$_4$, filtered and concentrated under vacuum to give 200 mg of the crude [4-(benzofuran-2-yl)-8-isopropoxy-6-isoquinolyl]-methanol as a yellow solid, which was used directly for next step without further purification.

MS (ESI+): 334.2 [M+H].

To a solution of 130 mg (0.39 mmol) of [4-(benzofuran-2-yl)-8-isopropoxy-6-isoquinolyl]-methanol and 118 mg (1.17 mmol) of TEA in 5 mL of DCM was added 73 mg (0.64 mmol) of MsCl at 0° C. The reaction mixture was stirred at 20° C. for 3 h, the mixture was diluted with DCM, then washed with water and brine, dried over anhydrous Na$_2$SO$_4$, the volatiles were removed under vacuum to afford 160 mg of the crude [4-(benzofuran-2-yl)-8-isopropoxy-6-isoquinolyl]methyl methanesulfonate as a yellow solid, which was used for next step without further purification.

MS (ESI+): 412.1 [M+H].

To a solution of 160 mg (0.39 mmol) of [4-(benzofuran-2-yl)-8-isopropoxy-6-isoquinolyl]methyl methanesulfonate in 10 mL of DCM were added 118 mg (1.17 mmol) of TEA and 117 mg (0.58 mmol) of 4-(N-Boc-amino)piperidine. The reaction mixture was stirred at 20° C. for 3 h, the mixture was concentrated under vacuum to dryness, the residue was purified by column chromatography on silica gel (eluent: PE/EA=2:1~1:1) to give the desired product as an off-white solid.

MS (ESI+): 516.2 [M+H].

1-[[4-(benzofuran-2-yl)-8-isopropoxy-6-isoquinolyl]methyl]piperidin-4-amine (Example 283)

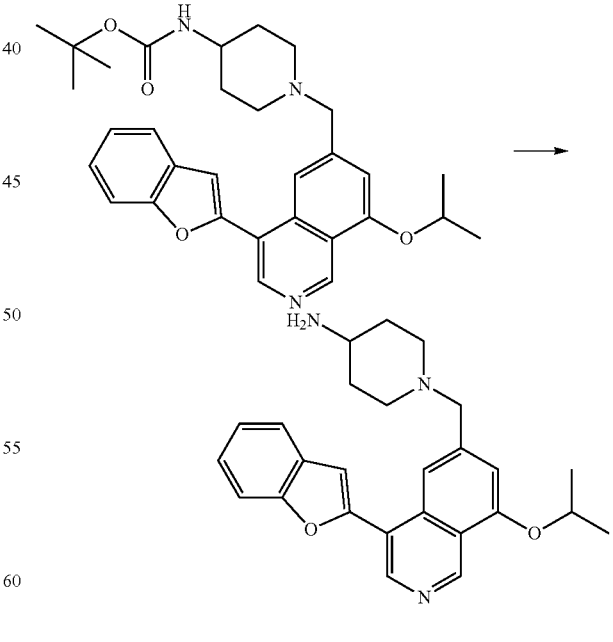

To a solution of 75 mg (0.15 mmol) of tert-butyl N-[1-[[4-(benzofuran-2-yl)-8-isopropoxy-6-isoquinolyl]methyl]-4-piperidyl]carbamate in 3 mL of DCM was added 0.54 mL (7.27 mmol) of TFA, the reaction mixture was stirred at 25° C. for 3 h, the mixture was concentrated under vacuum to give the crude product, which was purified by prep-HPLC to give the desired product as a yellow solid.

MS (ESI+): 416.2 [M+H].

¹H NMR (400 MHz, DMSO-d₆+D₂O) δ ppm: 9.58 (s, 1H); 8.97 (s, 1H); 8.08 (s, 1H); 7.78~7.71 (m, 2H); 7.57 (s, 1H); 7.45~7.33 (m, 3H); 4.94 (m, 1H); 4.52 (s, 2H); 3.45 (m, 2H); 3.25 (m, 1H); 3.09(m, 2H); 2.09 (m, 2H); 1.71 (m, 2H); 1.46 (d, J=6.0Hz, 6H).

The following compounds were prepared in analogy to Example 256 by reaction of tert-butyl N-[4-bromo-6-[[4-(tert-butoxycarbonylamino)-1-piperidyl]methyl]-8-chloro-1-isoquinolyl]-N-tert-butoxycarbonyl-carbamate with the corresponding boronic acid by Suzuki-Miyaura coupling reaction in the presence of a Pd-catalyst and subsequent deprotection:

| Example | | ¹H NMR (400 MHz) δ ppm | MS (+ESI) [M + H]⁺ |
|---|---|---|---|
| 284 | 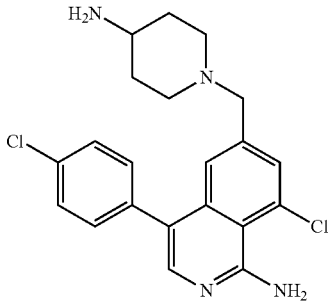 [SMILES: Nc1ncc(-c2ccc(Cl)cc2)c2cc(CN3CCC(N)CC3)cc(Cl)c12] | (DMSO-d₆ + D₂O) 7.88 (s, 1H), 7.78 (s, 1H), 7.70 (s, 1H), 7.60-7.57 (m, 2H), 7.48-7.46 (m, 2H), 4.33 (s, 2H), 3.36-3.33 (m, 2H), 3.28-3.20 (m, 1H), 3.01-2.91 (m, 2H), 2.07-2.04 (m, 2H), 1.70-1.67 (m, 2H). | 401.1, 403.1 |
| 285 | 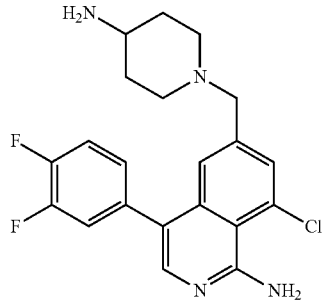 [SMILES: Nc1ncc(-c2ccc(F)c(F)c2)c2cc(CN3CCC(N)CC3)cc(Cl)c12] | (DMSO-d₆ + D₂O) 7.89 (s, 1H), 7.82 (s, 1H), 7.71 (s, 1H), 7.62-7.54 (m, 2H), 7.32-7.29 (m, 1H), 4.36 (s, 2H), 3.39-3.36 (m, 2H), 3.28-3.20 (m, 1H), 3.01-2.91 (m, 2H), 2.07-2.04 (m, 2H), 1.71-1.68 (m, 2H). | 403.1, 405.1 |
| 286 | 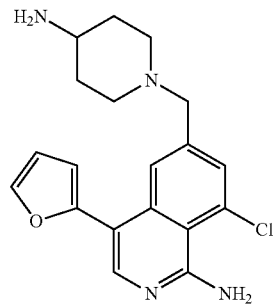 [SMILES: Nc1ncc(-c2ccco2)c2cc(CN3CCC(N)CC3)cc(Cl)c12] | (DMSO-d₆ + D₂O) 8.15 (s, 1H), 8.06 (s, 1H), 7.89 (s, 1H), 7.86 (d, 1H, J = 2.0 Hz, 1H), 6.86 (d, 1H, J = 3.2 Hz, 1H), 6.70 (dd, 1H, J = 2.0 Hz, 3.2 Hz, 1H), 4.44 (s, 2H), 3.44-3.39 (m, 2H), 3.31-3.25 (m, 1H), 3.10-3.06 (m, 2H), 2.09-2.06 (m, 2H), 1.73-1.70 (m, 2H). | 357.1, 359.1 |
| 287 | 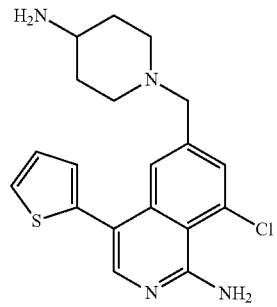 | (DMSO-d₆ + D₂O) 8.02 (s, 1H), 7.92 (s, 1H), 7.87 (s, 1H), 7.71 (dd, 1H, J = 1.2 Hz, 5.2 Hz, 1H), 7.30 (dd, 1H, J = 1.2 Hz, 3.6 Hz, 1H), 7.25 (dd, 1H, J = 3.6 Hz, 5.2 Hz, 1H), 4.38 (s, 2H), 3.39-3.36 (m, 2H), 3.28-3.22 (m, 1H), 3.04-2.96 (m, 2H), 2.08-2.05 (m, 2H), 1.71-1.68 (m, 2H). | 373.1, 375.1 |

The following compound was prepared in analogy to Example 242 by reaction of tert-butyl N-[1-[(4-bromo-8-chloro-6-isoquinolyl)methyl]-4-piperidyl]carbamate with 4-chlorophenylboronic acid by Suzuki-Miyaura coupling reaction in the presence of a Pd-catalyst, then methoxylation with sodium methoxide in the presence of a Pd-catalyst and subsequent deprotection:

| Example | | $^1$H NMR (400 MHz) δ ppm | MS (+ESI) [M + H]$^+$ |
|---|---|---|---|
| 288 | 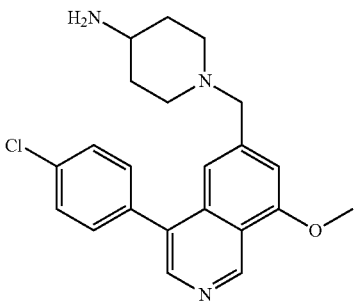 [SMILES: COc1cc(CN2CCC(N)CC2)cc2c(-c3ccc(Cl)cc3)cncc12] | (DMSO-d$_6$ + D$_2$O) 9.60 (s, 1H), 8.54 (s, 1H), 7.65-7.58 (m, 4H), 7.51 (s, 1H), 7.30 (s, 1H), 4.42 (s, 2H), 4.10 (s, 3H), 3.44-3.40 (m, 2H), 3.30-3.24 (m, 1H), 3.10-3.03 (m, 2H), 2.09-2.06 (m, 2H), 1.79-1.68 (m, 2H). | 382.1, 384.1 |

The following examples were prepared accordingly to Example 91 by reaction of tert-butyl N-[4-bromo-6-(bromomethyl)-1-isoquinolyl]-N-tert-butoxycarbonyl-carbamate with tert-butyl N-(4-piperidyl)carbamate and then reaction with the corresponding boronic acid in the presence of a Pd-catalyst and subsequent deprotection:

| Example | | $^1$H NMR (400 MHz) δ ppm | MS (+ESI) [M + H]$^+$ |
|---|---|---|---|
| 289 | 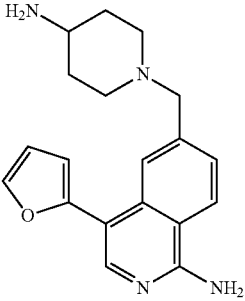 [SMILES: Nc1ncc(-c2ccco2)c2cc(CN3CCC(N)CC3)ccc12] | (DMSO-d$_6$ + D$_2$O) 8.62 (d, J = 8.4 Hz, 1H), 8.30 (s, 1H), 7.94 (s, 1H), 7.90-7.84 (m, 2H), 6.94 (d, J = 3.2 Hz, 1H), 6.72 (dd, J = 1.6 Hz, 3.2 Hz, 1H), 4.49 (s, 2H), 3.49-3.34 (m, 2H), 3.32-3.21 (m, 1H), 3.16-2.90 (m, 2H), 2.15-1.99 (m, 2H), 1.85-1.61 (m, 2H). | 323.1 |
| 290 | 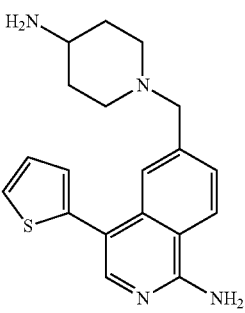 | (DMSO-d$_6$ + D$_2$O) 8.65 (d, J = 8.4 Hz, 1H), 8.14 (s, 1H), 7.88 (dd, J = 1.2 Hz, 8.4 Hz, 1H), 7.81 (s, 1H), 7.75 (dd, J = 0.8 Hz, 5.2 Hz, 1H), 7.38 (dd, J = 1.2 Hz, 3.6 Hz, 1H), 7.28 (dd, J = 3.6 Hz, 5.2 Hz, 1H), 4.45 (s, 2H), 3.44-3.30 (m, 2H), 3.30-3.19 (m, 1H), 3.11-2.94 (m, 2H), 2.11-2.01 (m, 2H), 1.79-1.61 (m, 2H). | 339.1 |

The following compounds were prepared in analogy to Example 100 by reaction of 4-(benzofuran-2-yl)-6-fluoro-isoquinoline with the corresponding amines:

| Example | | ¹H NMR (400 MHz) δ ppm | MS (+ESI) [M + H]⁺ |
|---|---|---|---|
| 291 | 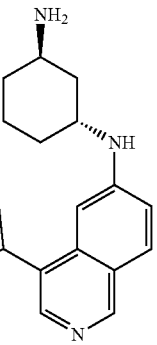 | (DMSO-d₆ + D₂O) 9.14 (s, 1H), 8.62 (s, 1H), 8.20 (d, J = 8.8 Hz, 1H), 7.80 (d, J = 7.2 Hz, 1H), 7.72 (d, J = 8.4 Hz, 1H), 7.59 (s, 1H), 7.48-7.35 (m, 4H), 4.09 (s, 1H), 3.38-3.36 (m, 1H), 2.08-1.45 (m, 8H). | 358.2 |
| 292 | 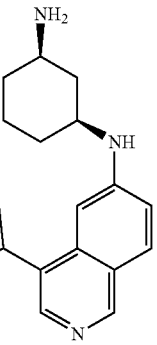 | (DMSO-d₆ + D₂O) 9.13 (s, 1H), 8.61 (s, 1H), 8.20 (d, J = 8.8 Hz, 1H), 7.80 (d, J = 7.8 Hz, 1H), 7.72 (d, J = 8.4 Hz, 1H), 7.59 (s, 1H), 7.47-7.35 (m, 4H), 3.71 (s, 1H), 3.22-3.16 (m, 1H), 2.28-1.84 (m, 4H), 1.45-1.16 (m, 4H). | 358.3 |

The following compound was prepared in analogy to Example 1 by reaction of 4-bromo-6-(bromomethyl)isoquinoline with 3-(tert-butoxycarbonylamino)piperidine, followed by Suzuki-Miyaura coupling with benzofuran-2-yl-boronic acid in the presence of a Pd-catalyst and subsequent deprotection:

| Example | | ¹H NMR (400 MHz) δ ppm | MS (+ESI) [M + H]⁺ |
|---|---|---|---|
| 293 | 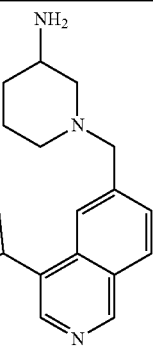 | (DMSO-d₆ + D₂O) 9.48 (s, 1H), 9.01 (s, 1H), 8.62 (s, 1H), 8.41 (d, J = 8.4 Hz, 1H), 7.89 (d, J = 8.4 Hz, 1H), 7.81-7.73 (m, 2H), 7.61 (s, 1H), 7.47-7.35 (m, 2H), 4.71-4.56 (m, 2H), 3.41-2.84 (m, 5H), 2.01-1.45 (m, 4H). | 358.2 |

The following example was prepared accordingly to Example 46 by reaction of 4-bromo-6-(bromomethyl)isoquinoline with piperidine followed by coupling with benzofuran-2-ylboronic acid in the presence of Pd-catalyst:

| Example | | ¹H NMR (400 MHz) δ ppm | MS (+ESI) [M + H]⁺ |
|---|---|---|---|
| 294 | 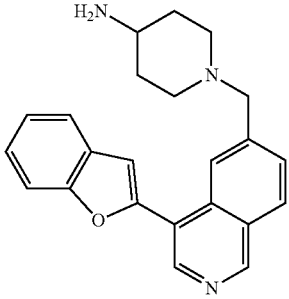 | (DMSO-d₆ + D₂O) 9.48 (s, 1H), 9.00 (s, 1H), 8.63 (s, 1H), 8.39 (d, J = 8.4 Hz, 1H), 7.90 (d, J = 8.4 Hz, 1H), 7.81-7.74 (m, 2H), 7.63 (s, 1H), 7.46-7.35 (m, 2H), 4.58 (s, 2H), 3.37-2.94 (m, 4H), 1.84-1.35 (m, 6H). | 343.3 |

4-Bromo-8-methoxy-6-methyl-isoquinoline

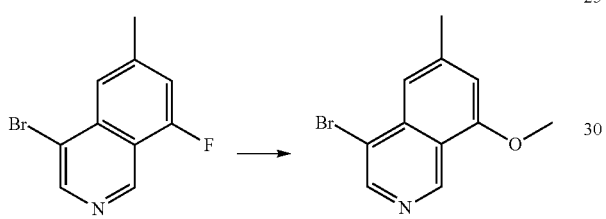

To a solution of 100 mg (0.42 mmol) of 4-bromo-8-fluoro-6-methyl-isoquinoline in 2 mL of DMF was added 0.11 g (2.08 mmol) of sodium methoxide. The reaction mixture was stirred at 25° C. for 10 min. The reaction mixture was extracted with EA and evaporated to give crude product. The crude product was purified by column chromatography on silica gel with PE-EA (5:1, R$_f$=0.2) to produce 80 mg of 4-bromo-8-methoxy-6-methyl-isoquinoline as a white solid.

MS (ESI+): 252.0, 254.0 [M+H]⁺.

4-Bromo-8-methoxy-6-methyl-isoquinolin-1-amine

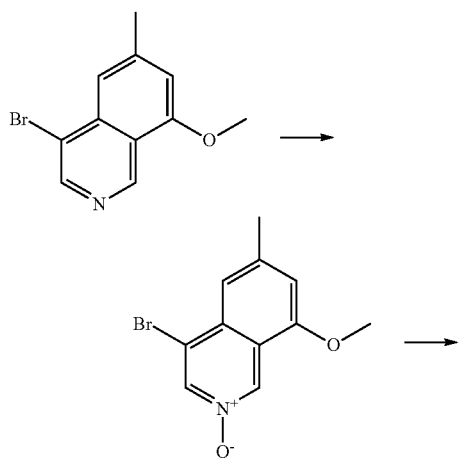

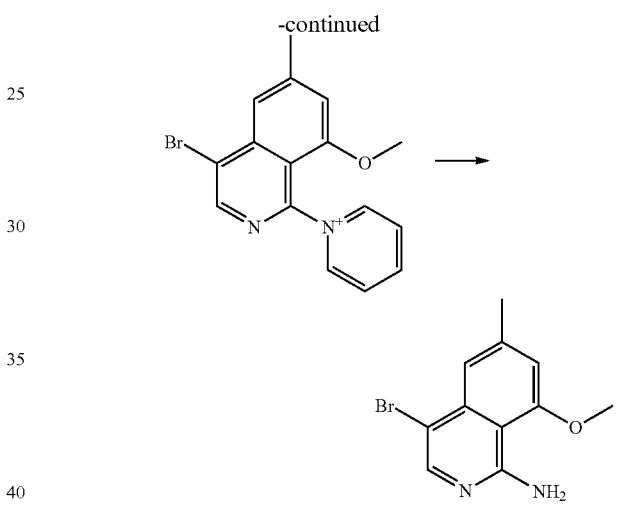

To a solution of 650 mg (2.58 mmol) of 4-bromo-8-methoxy-6-methyl-isoquinoline in 100 mL of DCM was added 1.44 g (6.45 mmol) of mCPBA and the mixture was stirred at 25° C. for 16 h. The reaction was quenched with aq. Na₂SO₃ solution and aq. NaHCO₃ solution and extracted with DCM. The organic phase was separated, and dried over Na₂SO₄. The solvent was removed under vacuum to give 650 mg of 4-bromo-8-methoxy-6-methyl-2-oxido-isoquinolin-2-ium as a yellow solid.

To a solution of 0.65 g (2.42 mmol) of 4-bromo-8-methoxy-6-methyl-2-oxido-isoquinolin-2-ium in pyridine (15 mL) was added 0.51 g (2.67 mmol) of p-toluenesulfonyl chloride and then the mixture was stirred at 28° C. for 2 h. The solvent was removed under vacuum to give 0.7 g of 4-bromo-8-methoxy-6-methyl-1-pyridin-1-ium-1-yl-isoquinoline as a brown semisolid.

A solution of 0.7 g (2.12 mmol) of 4-bromo-8-methoxy-6-methyl-1-pyridin-1-ium-1-yl-isoquinoline in 4 mL (66.3 mmol) of ethanolamine was stirred at 20° C. for 16 h. The reaction mixture was poured into ice water and the solid was collected by filtration and washed with water, dried to afford 0.38 g of 4-bromo-8-methoxy-6-methyl-isoquinolin-1-amine as a yellow solid.

MS (ESI+): 267.0, 269.0 [M+H]⁺.

351 tert-Butyl N-(4-bromo-8-methoxy-6-methyl-1-iso-quinolyl)-N-tert-butoxycarbonyl-carbamate

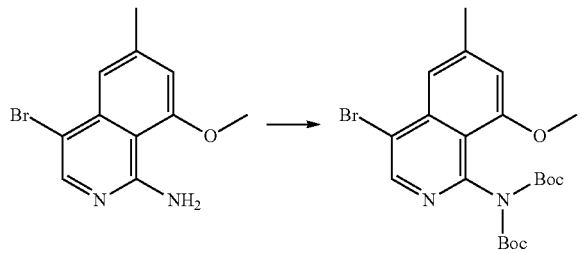 [SMILES: COc1cc(C)cc2c(Br)cnc(N)c12 ; COc1cc(C)cc2c(Br)cnc(N(C(=O)OC(C)(C)C)C(=O)OC(C)(C)C)c12]

To a solution of 1.5 g (5.62 mmol) of 4-bromo-8-methoxy-6-methyl-isoquinolin-1-amine in DCM (150 mL) were added 4.9 g (22.46 mmol) of Boc$_2$O, 0.21 g (1.68 mmol) of DMAP and 1.56 mL (11.23 mmol) of TEA. And then the mixture was stirred at 25° C. for 16 h. The solvent was removed under vacuum and the residue was purified by column chromatography eluting with PE/EA (10:1~6:1) to yield 2.6 g of the desired product as a yellow solid.

MS (ESI+): 467.0, 469.0 [M+H]$^+$.

tert-Butyl N-[4-bromo-6-[[4-(tert-butoxycarbonylamino)-1-piperidyl]methyl]-8-methoxy-1-isoquinolyl]-N-tert-butoxycarbonyl-carbamate

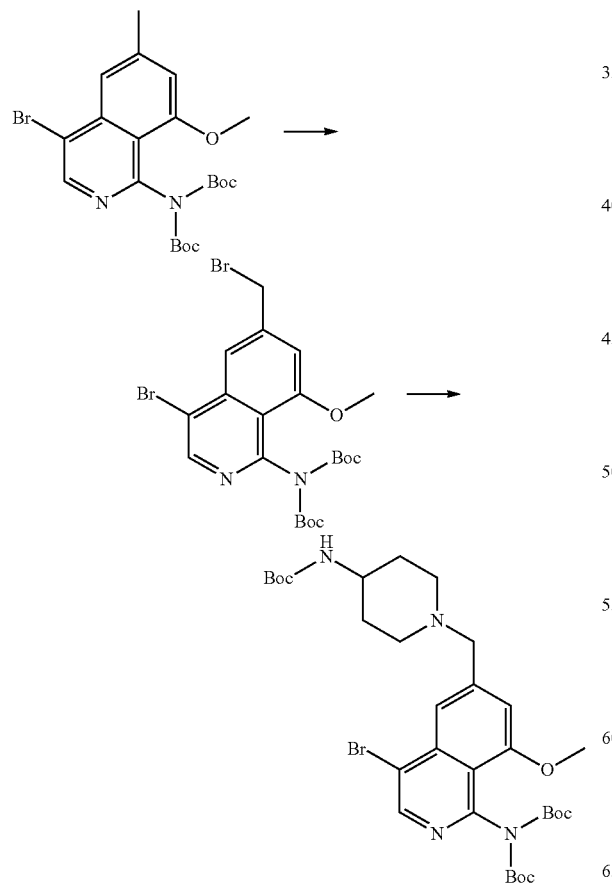

352

To a stirred solution of 0.6 g (1.28 mmol) of tert-butyl N-(4-bromo-8-methoxy-6-methyl-1-isoquinolyl)-N-tert-butoxycarbonyl-carbamate in CCl$_4$ (50 mL) were added 0.23 g (1.28 mmol) of NBS and 0.09 g (0.39 mmol) of benzoyl peroxide. The reaction mixture was heated to 100° C. for 2 h under argon atmosphere. The solvent was removed under vacuum and the residue was purified by column chromatography eluting with PE/EA (3:1) to yield 0.5 g of tert-butyl N-[4-bromo-6-(bromomethyl)-8-methoxy-1-isoquinolyl]-N-tert-butoxycarbonyl-carbamate as a yellow solid.

To a stirred solution of 0.5 g (0.92 mmol) of tert-butyl N-[4-bromo-6-(bromomethyl)-8-methoxy-1-isoquinolyl]-N-tert-butoxycarbonyl-carbamate in DCM (50 mL) were added 0.38 g (2.75 mmol) of K$_2$CO$_3$ and 0.22 g (1.1 mmol) of 4-N-Boc-amino-piperidine. The reaction mixture was stirred at 20° C. for 16 h and filtered through Celite. The filtrate was concentrated under vacuum. The crude product was purified by column chromatography on silica gel with (PE-EA=4:1 to 1:1, R$_f$=0.4) to afford 0.35 g of tert-butyl N-[4-bromo-6-[[4-(tert-butoxycarbonylamino)-1-piperidyl]methyl]-8-methoxy-1-isoquinolyl]-N-tert-butoxycarbonyl-carbamate as a yellow solid.

MS (ESI+): 665.2, 667.2 [M+H]$^+$.

tert-Butyl N-tert-butoxycarbonyl-N-[6-[[4-(tert-butoxycarbonylamino)-1-piperidyl] methyl]-4-(4-chlorophenyl)-8-methoxy-1-isoquinolyl]carbamate

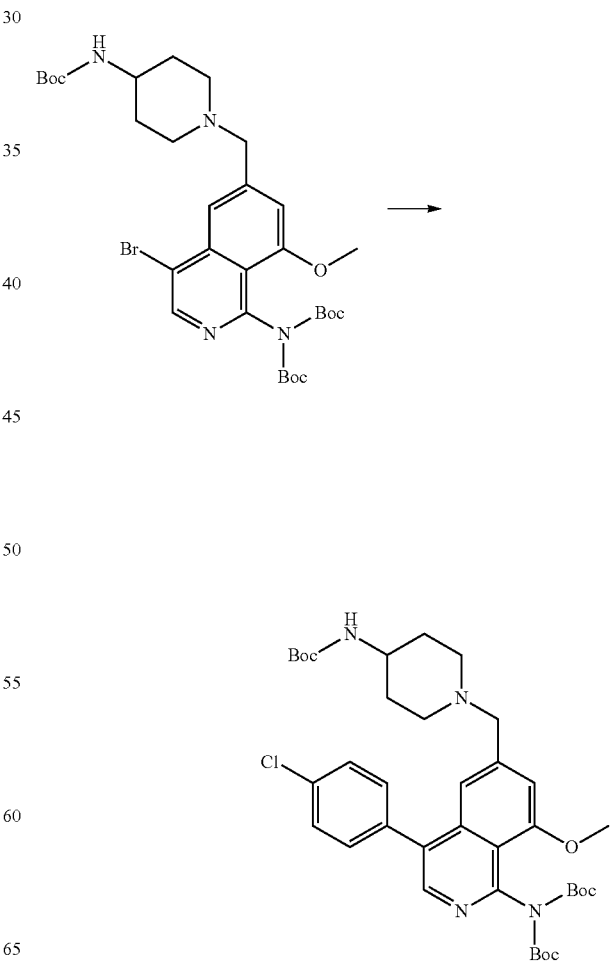

353

To a stirred solution of 0.07 g (0.45 mmol) of 4-chlorophenylboronic acid and 0.19 g (0.90 mmol) of $K_3PO_4$ in dioxane (10 mL) and $H_2O$ (1 mL) were added 0.05 g (0.05 mmol) of $Pd(PPh_3)_4$ and 0.15 g (0.23 mmol) of tert-butyl N-[4-bromo-6-[[4-(tert-butoxycarbonylamino)-1-piperidyl]methyl]-8-methoxy-1-isoquinolyl]-N-tert-butoxycarbonyl-carbamate. The reaction mixture was stirred under argon at 95° C. for 3 h and LC-MS showed the reaction was complete. The volatiles were removed under vacuum. The crude product was purified by column chromatography on silica gel with PE-EA (2:1 to 1:1, $R_f$=0.2) to produce 0.13 g of the desired product as a yellow oil.

MS (ESI+): 697.3, 699.3 $[M+H]^+$.

6-[(4-Amino-1-piperidyl)methyl]-4-(4-chlorophenyl)-8-methoxy-isoquinolin-1-amine (Example 295)

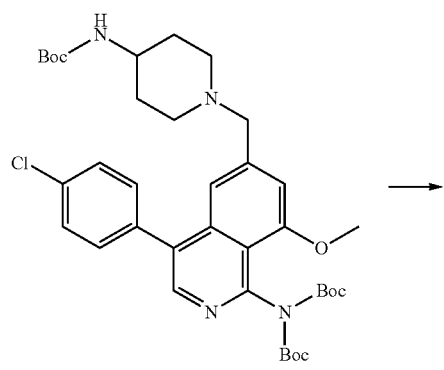

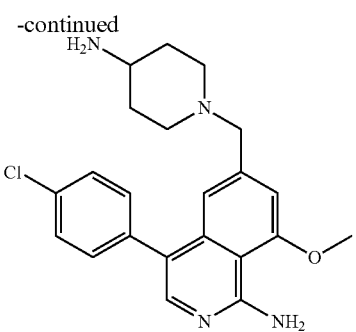

To a solution of 0.13 g (0.19 mmol) of tert-butyl N-tert-butoxycarbonyl-N-[6-[[4-(tert-butoxycarbonylamino)-1-piperidyl]methyl]-4-(4-chlorophenyl)-8-methoxy-1-isoquinolyl]carbamate in DCM (2 mL) was added 1 mL (13.46 mmol) of TFA. The reaction mixture was stirred at 25° C. for 2 h. The volatiles were removed under vacuum and the residue was purified by preparative HPLC to give 0.07 g of 6-[(4-amino-1-piperidyl)methyl]-4-(4-chlorophenyl)-8-methoxy-isoquinolin-1-amine as a yellow solid.

MS (ESI+): 397.1, 399.1 $[M+H]^+$.

$^1$H NMR (400 MHz, DMSO-$d_6$+$D_2O$) ppm: 7.62-7.58 (m, 3H), 7.49-7.45 (m, 2H), 7.39 (s, 1H), 7.27 (s, 1H), 4.30 (s, 2H), 4.10 (s, 3H), 3.38-3.31 (m, 2H), 3.24-3.19 (m, 1H), 3.01-2.92 (m, 2H), 2.06-2.03 (m, 2H), 1.70-1.67 (m, 2H).

The following compounds were prepared in analogy to Example 295 by reaction of tert-butyl N-[4-bromo-6-[[4-(tert-butoxycarbonylamino)-1-piperidyl] methyl]-8-methoxy-1-isoquinolyl]-N-tert-butoxycarbonyl-carbamate with the corresponding boronic acid by Suzuki-Miyaura coupling reaction in the presence of a Pd-catalyst and subsequent deprotection:

| Example | $^1$H NMR (400 MHz) δ ppm | MS (+ESI) [M + H]$^+$ |
| --- | --- | --- |
| 296 | (DMSO-$d_6$ + $D_2O$) 7.62 (s, 1H), 7.59-7.53 (m, 2H), 7.39 (s, 1H), 7.31-7.28 (m, 2H), 4.32 (s, 2H), 4.10 (s, 3H), 3.39-3.32 (m, 2H), 3.28-3.22 (m, 1H), 3.01-2.92 (m, 2H), 2.07-2.04 (m, 2H), 1.71-1.68 (m, 2H). | 399.1 |
| 297 | (DMSO-$d_6$ + $D_2O$) 7.89 (s, 1H), 7.86 (d, 1H, J = 2.0 Hz, 1H), 7.75 (s, 1H), 7.43 (s, 1H), 6.89 (d, 1H, J = 3.2 Hz, 1H), 6.70 (dd, 1H, J = 2.0 Hz, 3.2 Hz, 1H), 4.43 (s, 2H), 4.10 (s, 3H), 3.44-3.39 (m, 2H), 3.30-3.25 (m, 1H), 3.10-3.02 (m, 2H), 2.09-2.06 (m, 2H), 1.74-1.70 (m, 2H). | 353.1 |

| Example | $^1$H NMR (400 MHz) δ ppm | MS (+ESI) [M + H]$^+$ |
|---|---|---|
| 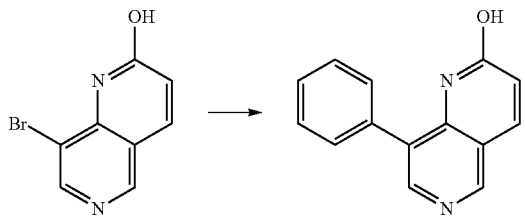 [SMILES: Oc1ccc2cncc(Br)c2n1 ; Oc1ccc2cncc(-c3ccccc3)c2n1]  298 | (DMSO-d$_6$ + D$_2$O) 7.75 (s, 1H), 7.73 (dd, 1H, J = 1.2 Hz, 5.2 Hz, 1H), 7.62 (s, 1H), 7.44 (s, 1H), 7.33 (dd, 1H, J = 1.2 Hz, 3.6 Hz, 1H), 7.25 (dd, 1H, J = 3.6 Hz, 5.2 Hz, 1H), 4.41 (s, 2H), 4.11 (s, 3H), 3.41-3.39 (m, 2H), 3.30-3.24 (m, 1H), 3.10-3.04 (m, 2H), 2.09-2.06 (m, 2H), 1.74-1.70 (m, 2H). | 369.1 |

8-Phenyl-1, 6-naphthyridin-2-ol

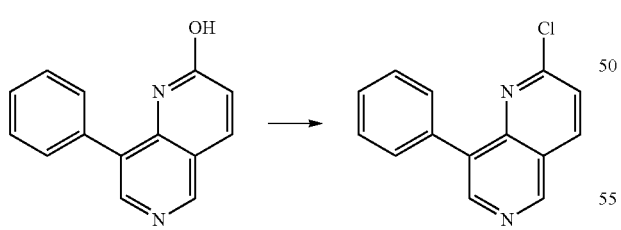

To a stirred solution of 1.5 g (6.67 mmol) of 8-bromo-1,6-naphthyridin-2-ol in 75 mL of dioxane and 5 mL of H$_2$O were added 1.06 g (8.67 mmol) of phenylboronic acid, 1.16 g (1 mmol) of Pd(PPh$_3$)$_4$ and 4.24 g (20 mmol) of K$_3$PO$_4$. Then the reaction was stirred at 90° C. for 3 h. The solvents were removed under reduced pressure. The residue was purified by column chromatography on silica gel (EA, R$_f$=0.4) to produce the desired product as a yellow solid.

MS (ESI+): 223.0 [M+H]$^+$.

$^1$H NMR (400 MHz, CDCl$_3$) δ ppm: 8.81 (s, 1H), 8.78 (br s, 1H), 8.51 (s, 1H), 7.89 (d, J=9.8 Hz, 1H), 7.62-7.53 (m, 3H), 7.48-7.42 (m, 2H), 6.73 (d, J=9.5 Hz, 1H).

2-Chloro-8-phenyl-1, 6-naphthyridine

A solution of 0.6 g (2.67 mmol) of 8-phenyl-1, 6-naphthyridin-2-ol in 15 mL of POCl$_3$ was stirred at 70° C. for 16 h. The reaction was cooled to rt, poured to ice water mixture, neutralized with 3 M aq. NaOH to pH=10, and then extracted with EA. The combined organic layers were washed with brine, dried over anhydrous Na$_2$SO$_4$, filtered and concentrated to afford 0.64 g of 2-chloro-8-phenyl-1, 6-naphthyridine as a yellow solid which was used in the next step without purification.

MS (ESI+): 241.0, 243.0 [M+H]$^+$.

$^1$H NMR (400 MHz, CDCl$_3$) δ ppm: 9.26 (s, 1H), 8.87 (s, 1H), 8.30 (d, J=8.5 Hz, 1H), 7.80-7.75 (m, 2H), 7.57-7.52 (m, 2H), 7.51-7.43 (m, 2H).

8-Phenyl-2-vinyl-1, 6-naphthyridine

To a stirred solution of 0.49 g (2.04 mmol) of 2-chloro-8-phenyl-1, 6-naphthyridine in 30 mL of dioxane and 2 mL of H$_2$O were added 0.35 g (0.31 mmol) of Pd(PPh$_3$)$_4$, 0.45 mL (2.65 mmol) of pinacol vinylboronate and 1.3 g (6.11 mmol) of K$_3$PO$_4$. Then the reaction was stirred at 90° C. for 3 h. LC-MS showed the reaction was complete. The solvent was removed under reduced pressure, and the residue was purified by flash chromatography (EA/PE=1:5, R$_f$=0.2) to give 0.46 g of 8-phenyl-2-vinyl-1, 6-naphthyridine as a yellow oil.

MS (ESI+): 233.1 [M+H]$^+$.

$^1$H NMR (400 MHz, CDCl$_3$) δ ppm: 9.19 (s, 1H), 8.79 (s, 1H), 8.28 (d, J=8.4 Hz, 1H), 7.82 (d, J=7.2 Hz, 2H), 7.66 (d, J=8.4 Hz, 1H), 7.60-7.40 (m, 3H), 6.90 (dd, J=17.2 Hz, 10.8 Hz, 1H), 6.39 (d, J=17.6 Hz, 1H), 5.70 (d, J=10.8 Hz, 1H).

8-Phenyl-1, 6-naphthyridine-2-carbaldehyde

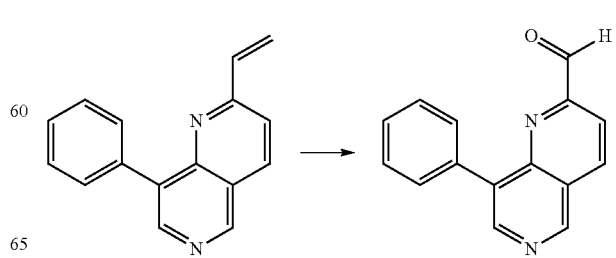

To a cooled (−78° C.) solution of 0.03 g (0.13 mmol) of 8-phenyl-2-vinyl-1, 6-naphthyridine in 4 mL of DCM and 1 mL of MeOH was bubbled with ozone for 2 min. Then the reaction was quenched with Me₂S. The solvent was removed under reduced pressure to afford 0.26 g of 8-phenyl-1, 6-naphthyridine-2-carbaldehyde as a yellow solid which was used in the next step without purification.

MS (ESI+): 235.0 [M+H]⁺.

¹H NMR (400 MHz, CDCl₃) δ ppm: 10.16 (s, 1H), 9.38 (s, 1H), 8.93 (s, 1H), 8.54 (d, J=8.4 Hz, 1H), 8.17 (d, J=8.4 Hz, 1H), 7.82 (d, J=8.0 Hz, 2H), 7.60-7.40 (m, 3H).

tert-Butyl N-[1-[(8-phenyl-1, 6-naphthyridin-2-yl)methyl]-4-piperidyl]carbamate

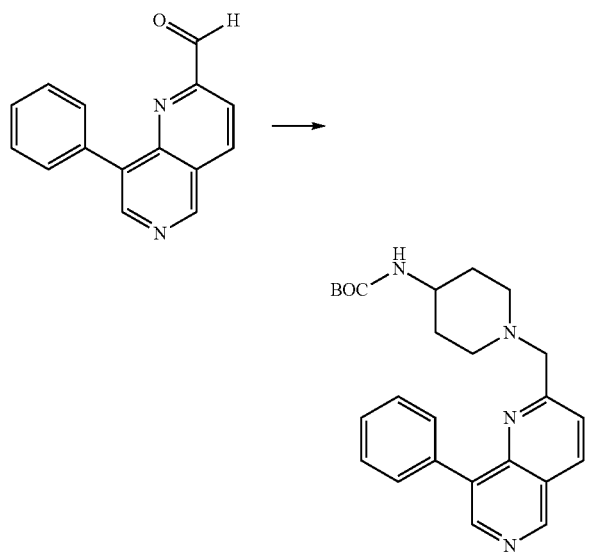

To a solution of 0.2 g (0.43 mmol) of 8-phenyl-1, 6-naphthyridine-2-carbaldehyde and 0.09 g (0.43 mmol) of 4-(Boc-amino)piperidine in 3 mL of DCM was added 0.11 g (0.51 mmol) of NaBH(OAc)₃. The reaction was stirred at 25° C. for 3 h, and then the reaction was quenched with H₂O and extracted with DCM. The combined organic layers were washed with brine, dried over anhydrous Na₂SO₄, filtered and concentrated. The residue was purified by flash chromatography (EA, R_f=0.2) to give 0.14 g of tert-butyl N-[1-[(8-phenyl-1, 6-naphthyridin-2-yl)methyl]-4-piperidyl]carbamate as a yellow oil.

MS (ESI+): 419.2 [M+H]⁺.

¹H NMR (400 MHz, CDCl₃) δ ppm: 9.23 (s, 1H), 8.80 (s, 1H), 8.31 (d, J=8.5 Hz, 1H), 7.81-7.71 (m, 3H), 7.60-7.43 (m, 3H), 4.51 (br d, J=7.8 Hz, 1H), 3.86 (s, 2H), 3.60-3.45 (m, 1H), 2.95-2.85 (m, 2H), 2.37-2.27 (m, 2H), 2.00-1.90 (m, 2H), 1.54-1.48 (m, 2H), 1.46 (s, 9H).

1-[(8-Phenyl-1, 6-naphthyridin-2-yl)methyl]piperidin-4-amine (Example 299)

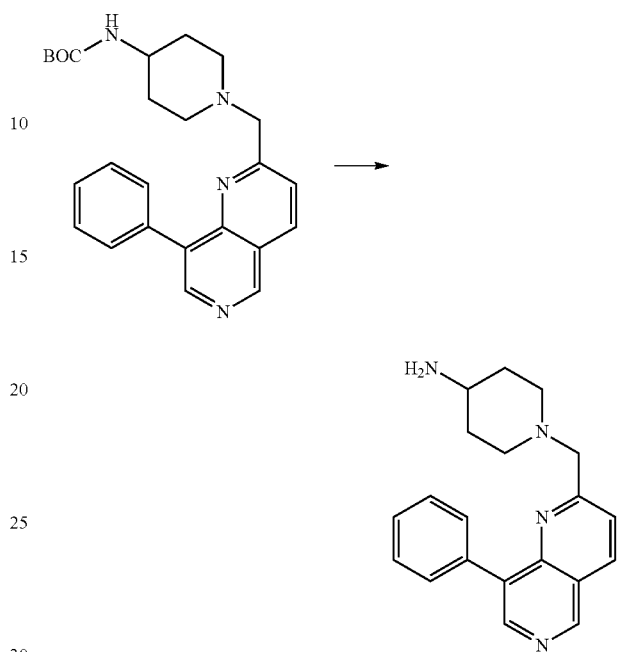

To a solution of 0.14 g (0.30 mmol) of tert-butyl N-[1-[(8-phenyl-1, 6-naphthyridin-2-yl)methyl]-4-piperidyl]carbamate in 5 mL of DCM was added 1.2 mL of TFA. The reaction was stirred at 25° C. for 2 h. Then the solution was concentrated under reduced pressure. The residue was purified by prep-HPLC to afford 55 mg of 1-[(8-phenyl-1, 6-naphthyridin-2-yl)methyl]piperidin-4-amine as a light yellow solid.

MS (ESI+): 319.2 [M+H]⁺.

¹H NMR (400 MHz, DMSO-d₆+D₂O) δ ppm: 9.39 (s, 1H), 8.77 (s, 1H), 8.66 (d, J=8.3 Hz, 1H), 7.80-7.72 (m, 3H), 7.56-7.43 (m, 3H), 4.70-3.00 (m, 7H), 2.05-1.85 (m, 2H), 1.75-1.52 (m, 2H).

1-[8-(Benzofuran-2-yl)-1, 6-naphthyridin-2-yl]ethane-1,2-diol

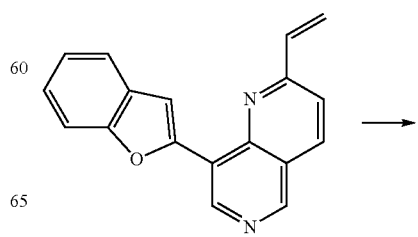

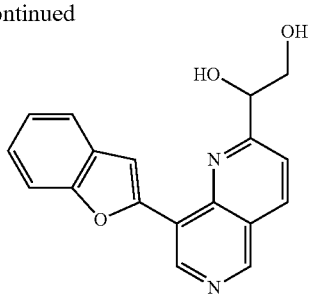

To a solution of 0.4 g (1.45 mmol) of 8-(benzofuran-2-yl)-2-vinyl-1,6-naphthyridine (Prepared in analogy to 8-phenyl-2-vinyl-1, 6-naphthyridine, starting from 8-bromo-1, 6-naphthyridin-2-ol via 3 steps) in 30 mL of THF and 2 mL of H$_2$O were added 0.34 g (2.91 mmol) of NMO and 0.03 g (0.07 mmol) of K$_2$OsO$_4$.2H$_2$O. The reaction was stirred at 25° C. for 3 h. Then the reaction was quenched with saturated Na$_2$SO$_3$ and extracted with EA. The combined organic layers were washed with brine, dried over anhydrous Na$_2$SO$_4$, filtered and concentrated to give 0.44 g of 1-[8-(benzofuran-2-yl)-1, 6-naphthyridin-2-yl]ethane-1,2-diol as a brown solid which was used in the next step without purification.

MS (ESI+): 307.1 [M+H]$^+$.

8-(Benzofuran-2-yl)-1, 6-naphthyridine-2-carbaldehyde

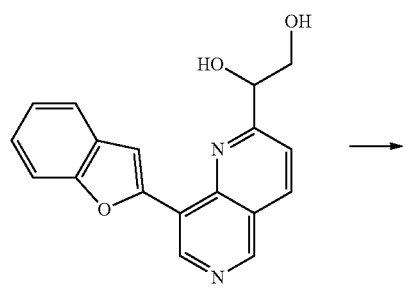

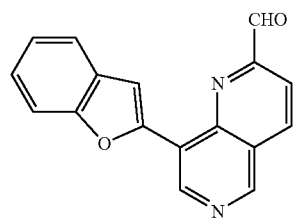

To a solution of 0.44 g (1.44 mmol) of 1-[8-(benzofuran-2-yl)-1, 6-naphthyridin-2-yl]ethane-1,2-diol in 30 mL of THF and 6 mL of H$_2$O was added 0.93 g (4.31 mmol) of NaIO$_4$. The reaction was stirred at 25° C. for 2 h. Then the reaction was diluted with EA and washed with H$_2$O. The combined organic layer was washed with brine, dried over anhydrous Na$_2$SO$_4$, filtered and concentrated. The residue was purified by flash chromatography (EA/PE=1/1, R$_f$=0.7) to give 0.25 g of 8-(benzofuran-2-yl)-1, 6-naphthyridine-2-carbaldehyde as a yellow solid.

MS (ESI+): 275.1 [M+H]$^+$.

$^1$H NMR (400 MHz, CDCl$_3$) δ ppm: 10.43 (s, 1H), 9.62 (s, 1H), 9.34 (s, 1H), 8.56 (d, J=8.3 Hz, 1H), 8.46 (s, 1H), 8.25 (d, J=8.5 Hz, 1H), 7.76 (d, J=7.8 Hz, 1H), 7.64 (d, J=8.3 Hz, 1H), 7.45-7.38 (m, 1H), 7.36-7.29 (m, 1H).

tert-Butyl N-[1-[[8-(benzofuran-2-yl)-1, 6-naphthyridin-2-yl]methyl]-4-piperidyl]carbamate

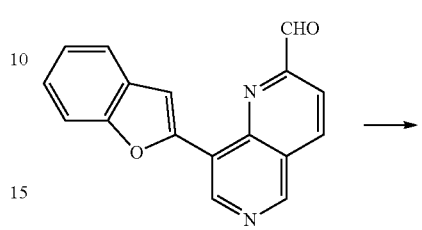

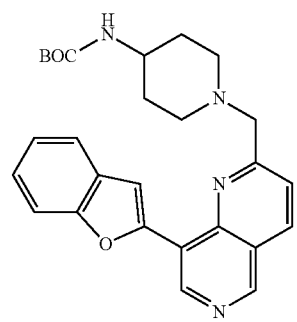

To a solution of 0.2 g (0.72 mmol) of 8-(benzofuran-2-yl)-1, 6-naphthyridine-2-carbaldehyde and 0.14 g (0.72 mmol) of 4-(Boc-amino)piperidine in 20 mL of DCM was added 0.18 g (0.87 mmol) of NaBH(OAc)$_3$. The reaction was stirred at 25° C. for 3 h, and then the reaction was quenched with H$_2$O and extracted with DCM. The combined organic layers were washed with brine, dried over anhydrous Na$_2$SO$_4$, filtered and concentrated. The residue was purified by flash chromatography (EA, R$_f$=0.2) to give 0.22 g of tert-butyl N-[1-[[8-(benzofuran-2-yl)-1, 6-naphthyridin-2-yl]methyl]-4-piperidyl]carbamate as a yellow solid.

MS (ESI+): 459.2 [M+H]$^+$.

$^1$H NMR (400 MHz, CDCl$_3$) δ ppm: 9.49 (s, 1H), 9.19 (s, 1H), 8.38 (s, 1H), 8.31 (d, J=8.5 Hz, 1H), 7.86 (d, J=8.5 Hz, 1H), 7.73 (d, J=7.3 Hz, 1H), 7.61 (d, J=7.8 Hz, 1H), 7.40-7.34 (m, 1H), 7.33-7.27 (m, 1H), 4.50 (br s, 1H), 4.02 (s, 2H), 3.65-3.50 (m, 1H), 2.95 (br d, J=11.8 Hz, 2H), 2.39 (br t, J=10.5 Hz, 2H), 2.01 (br d, J=11.0 Hz, 2H), 1.65-1.50 (m, 2H), 1.47 (s, 9H).

1-[[8-(Benzofuran-2-yl)-1, 6-naphthyridin-2-yl]methyl]piperidin-4-amine (Example 300)

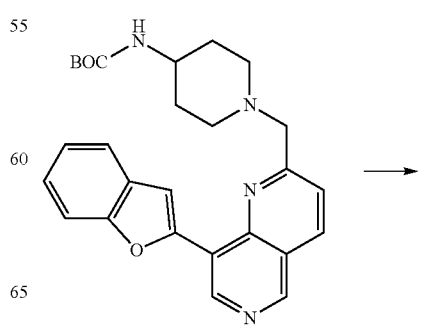

-continued

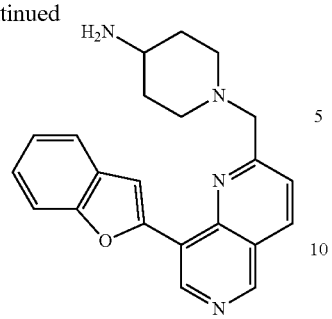

To a solution of 0.2 g (0.43 mmol) of tert-butyl N-[1-[[8-(benzofuran-2-yl)-1, 6-naphthyridin-2-yl]methyl]-4-piperidyl]carbamate in 5 mL of DCM was added 1.2 mL of TFA. The reaction was stirred at 25° C. for 2 h. Then the solution was concentrated under reduced pressure. The residue was purified by Prep-HPLC to afford 0.15 g of 1-[[8-(benzofuran-2-yl)-1, 6-naphthyridin-2-yl]methyl]piperidin-4-amine as a yellow solid.

MS (ESI+): 359.2 [M+H]$^+$.

$^1$H NMR (400 MHz, DMSO-d$_6$+D$_2$O) δ ppm: 9.47 (s, 1H), 9.38 (s, 1H), 8.80 (d, J=8.5 Hz, 1H), 8.26 (s, 1H), 7.90-7.82 (m, 2H), 7.73 (d, J=8.0 Hz, 1H), 7.46-7.42 (m, 1H), 7.37-7.33 (m, 1H), 4.90 (s, 2H), 4.00-3.80 (m, 2H), 3.46-3.23 (m, 3H), 2.19 (br d, J=12.8 Hz, 2H), 2.06-1.87 (m, 2H).

The following compounds were prepared in analogy to Example 301 by reaction of 8-(benzofuran-2-yl)-1, 6-naphthyridine-2-carbaldehyde with the corresponding amine by reductive amination reaction. If necessary, functional groups of some compounds were protected as required, and were finally deprotected:

trans-N4-(8-phenyl-1, 6-naphthyridin-2-yl)cyclohexane-1,4-diamine (Example 303)

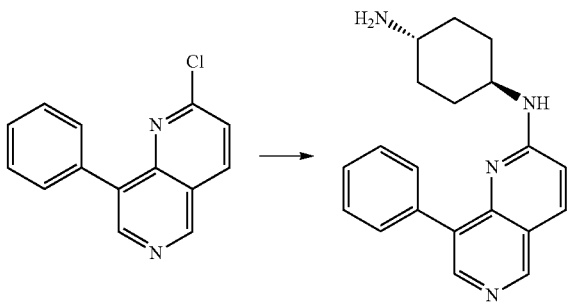 [SMILES: Clc1ccc2cncc(-c3ccccc3)c2n1 ; N[C@H]1CC[C@H](Nc2ccc3cncc(-c4ccccc4)c3n2)CC1]

To a solution of 0.1 g (0.42 mmol) of 2-chloro-8-phenyl-1, 6-naphthyridine and 0.09 g (0.83 mmol) of trans-1, 4-diaminocyclohexane in 3 mL of DMF was added 0.29 mL (2.08 mmol) of TEA. The reaction was stirred at 100° C. for 16 h. LC-MS showed the desired product was formed. Then the solvent was removed under reduced pressure, and the residue was purified by Prep-HPLC to afford 60 mg of N4-(8-phenyl-1, 6-naphthyridin-2-yl)cyclohexane-1,4-diamine as a yellow solid.

MS (ESI+): 319.2 [M+H]$^+$.

$^1$H NMR (400 MHz, DMSO-d$_6$+D$_2$O) δ ppm: 9.11 (s, 1H), 8.57 (s, 1H), 8.20 (d, J=9.3 Hz, 1H), 7.85-7.78 (m, 2H), 7.57-7.44 (m, 3H), 7.03 (d, J=9.3 Hz, 1H), 3.77-3.67 (m, 1H), 3.10-2.95 (m, 1H), 2.10-1.90 (m, 4H), 1.41-1.23 (m, 4H).

| Example | $^1$H NMR (400 MHz) δ ppm | MS (+ESI) [M + H]$^+$ |
|---|---|---|
| 301 | (DMSO-d$_6$ + D$_2$O) 9.45 (s, 1H), 9.35 (s, 1H), 8.78 (d, J = 8.4 Hz, 1H), 8.27 (s, 1H), 8.86 (d, J = 8.4 Hz, 1H), 7.77 (d, J = 7.6 Hz, 1H), 7.71 (d, J = 8.4 Hz, 1H), 7.44-7.40 (m, 1H), 7.36-7.32 (m, 1H), 4.86 (s, 2H), 3.78-3.75 (m, 2H), 3.22-3.14 (m, 2H), 1.89-1.75 (m, 5H), 1.47-1.43 (m, 1H). | 344.2 |
| 302 | (DMSO-d$_6$ + D$_2$O) 9.41 (s, 1H), 9.33 (s, 1H), 8.71 (d, J = 8.4 Hz, 1H), 8.35 (s, 1H), 7.90 (d, J = 8.4 Hz, 1H), 7.79 (d, J = 7.2 Hz, 1H), 7.71 (d, J = 8.4 Hz, 1H), 7.43-7.39 (m, 1H), 7.34-7.30 (m, 1H), 4.34 (s, 2H), 3.27-3.24 (m, 4H), 3.06-3.03 (m, 4H). | 345.2 | trans-N4-[8-(benzofuran-2-yl)-1, 6-naphthyridin-2-yl]cyclohexane-1,4-diamine (Example 304)

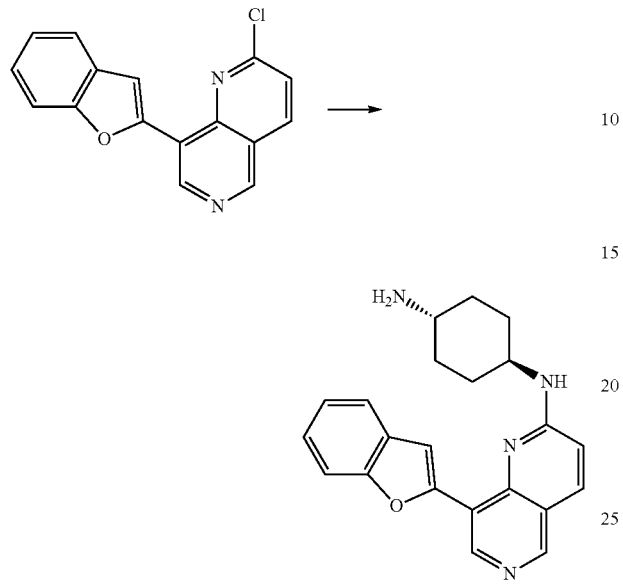

To a solution of 0.1 g (0.36 mmol) of 8-(benzofuran-2-yl)-2-chloro-1,6-naphthyridine (prepared in analogy to 2-chloro-8-phenyl-1, 6-naphthyridine starting from 8-bromo-1, 6-naphthyridin-2-ol via 2 steps) and 0.08 g (0.71 mmol) of trans-1,4-diaminocyclohexane in 4 mL of DMF was added 0.25 mL (1.78 mmol) of TEA. The reaction was stirred at 100° C. for 16 h. Then the solvent was removed under reduced pressure, and the residue was purified by prep-HPLC to afford 80 mg of N4-[8-(benzofuran-2-yl)-1, 6-naphthyridin-2-yl]cyclohexane-1,4-diamine as a yellow solid.

MS (ESI+): 359.2 [M+H]$^+$.

$^1$H NMR (400 MHz, DMSO-d$_6$+D$_2$O) δ ppm: 9.07 (s, 1H), 9.05 (s, 1H), 8.22 (s, 1H), 8.20 (d, J=9.3 Hz, 1H), 7.82 (d, J=7.5 Hz, 1H), 7.71 (d, J=8.5 Hz, 1H), 7.48-7.41 (m, 1H), 7.39-7.32 (t, J=8.0 Hz, 1H), 7.09 (d, J=9.0 Hz, 1H), 4.11-3.99 (m, 1H), 3.23-3.10 (m, 1H), 2.36-2.25 (m, 2H), 2.17-2.07 (m, 2H), 1.73-1.58 (m, 2H), 1.55-1.38 (m, 2H).

The following compounds were prepared in analogy to previously described methods by reaction of 8-bromo-1,6-naphthyridine-2-carboxylic acid with the corresponding amine under standard amide coupling conditions (e.g. HATU, DIPEA), followed by Suzuki-Miyaura coupling with corresponding boronic acid in the presence of a Pd-catalyst. If necessary, functional groups of some compounds were protected as required, and were finally deprotected:

| Example | $^1$H NMR (400 MHz) δ ppm | MS (+ESI) [M + H]$^+$ |
|---|---|---|
| 305 | (DMSO-d$_6$ + D$_2$O) 9.46 (s, 1H), 9.37 (s, 1H), 8.84 (d, J = 8.4 Hz, 1H), 8.18 (s, 1H), 8.00 (d, J = 8.4 Hz, 1H), 7.81 (d, J = 7.6 Hz, 1H), 7.71 (d, J = 8.0 Hz, 1H), 7.44-7.39 (m, 1H), 7.34-7.31 (m, 1H), 4.00-3.97 (m, 2H), 3.83-3.80 (m, 2H), 3.36-3.33 (m, 2H), 3.16-3.13 (m, 2H). | 359.2 |

4-Bromo-6-methyl-isoquinoline-8-carbonitrile

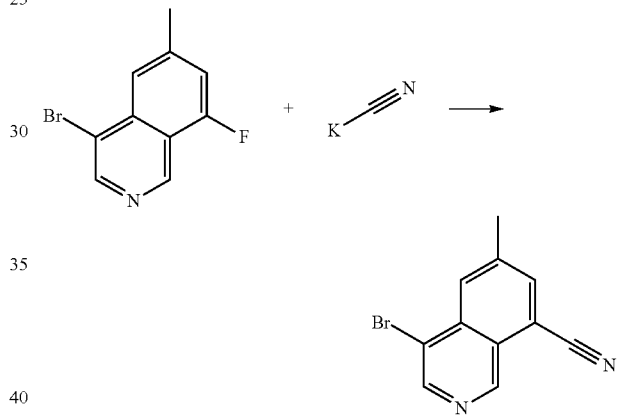

To a solution of 1.01 g (4.17 mmol) of 4-bromo-8-fluoro-6-methyl-isoquinoline in 15 mL of DMF were added 1.36 g (20.8 mmol) of potassium cyanide, 0.86 g (6.25 mmol) of potassium carbonate and 1.04 g (6.25 mmol) of potassium iodide. The mixture was stirred at 130° C. for 10 h. The reaction was quenched with water and diluted with EA. Two layers were separated and the organic phase was extracted by EA. The combined extracts were washed with water, saturated brine solution, and dried over Na$_2$SO$_4$ before concentration to dryness. The crude product was then purified by flash column chromatography (PE/EA=10/1) to give 150 mg of 4-bromo-6-methyl-isoquinoline-8-carbonitrile as a white solid.

MS (ESI+): 247.0, 249.0 [M+H]$^+$.

$^1$H NMR (400 MHz, CDCl$_3$+D$_2$O) δ ppm: 9.52 (s, 1H), 8.87 (s, 1H), 8.21 (s, 1H), 7.93 (d, J=1.2 Hz, 1H), 2.68 (s, 3H).

365
tert-Butyl N-[1-[(4-bromo-8-cyano-6-isoquinolyl)methyl]-4-piperidyl]carbamate

366
tert-Butyl N-[1-[[4-(benzofuran-2-yl)-8-cyano-6-isoquinolyl]methyl]-4-piperidyl]carbamate

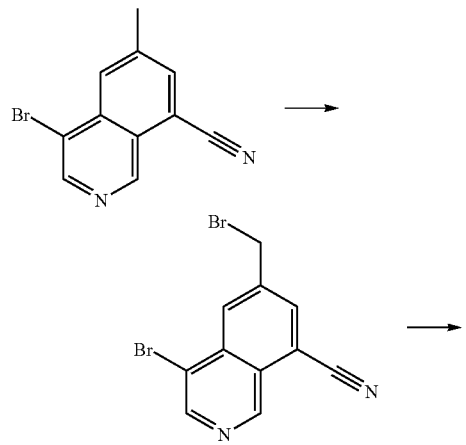

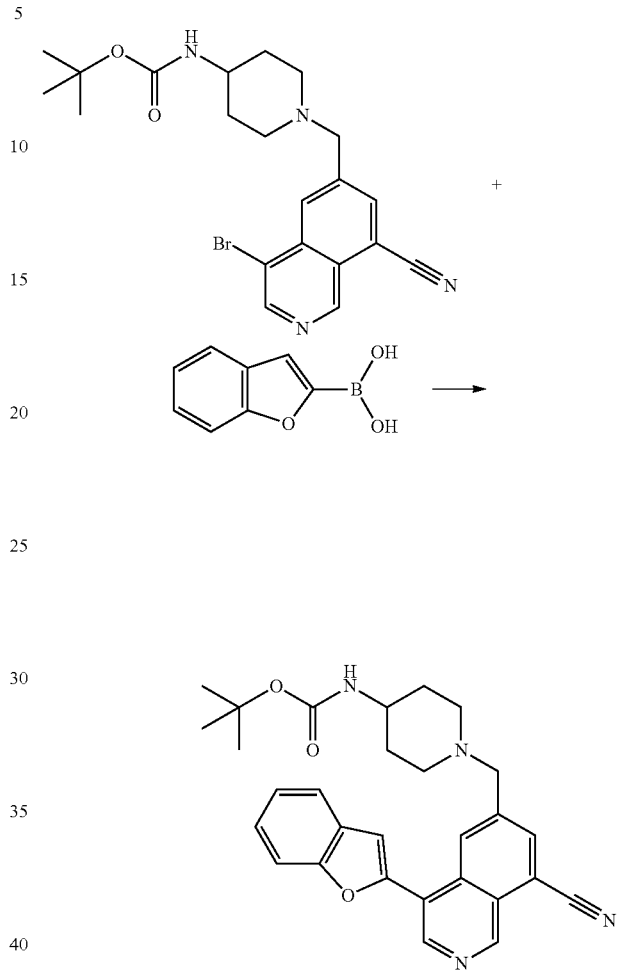

To a solution of 0.2 g (0.81 mmol) of 4-bromo-6-methyl-isoquinoline-8-carbonitrile in 10 mL of carbon tetrachloride were added 0.02 g (0.08 mmol) of benzoyl peroxide (wet with 25% water) and 0.17 g (0.97 mmol) of N-bromosuccinimide. The mixture was stirred at 90° C. for 2 h. The reaction solution was concentrated to dryness. The crude product as a yellow oil was then used in the next step without further purification.

To a solution of 0.13 g (0.40 mmol) of crude 4-bromo-6-(bromomethyl)isoquinoline-8-carbonitrile in 15 mL DCM were added 0.10 g (0.48 mmol) of 4-(N-Boc-amino)piperidine and 0.07 g (0.52 mmol) of $K_2CO_3$. The mixture was stirred at 25° C. for 10 h. The reaction solution was filtrated and the filtrate was concentrated to dryness and then purified by flash column chromatography (PE/EA=2/1) to give 130 mg of tert-butyl N-[1-[(4-bromo-8-cyano-6-isoquinolyl)methyl]-4-piperidyl]carbamate as a yellow solid.

MS (ESI+): 445.1, 447.1 [M+H]+.

Under argon atmosphere, to a solution of 0.13 g (0.29 mmol) of tert-butyl N-[1-[(4-bromo-8-cyano-6-isoquinolyl)methyl]-4-piperidyl]carbamate in 5 mL DMF and 0.3 mL of $H_2O$ were added 0.09 g (0.58 mmol) of benzofuran-2-boronic acid, 0.03 g (0.03 mmol) of tetrakis(triphenylphosphine)palladium and 0.19 g (0.88 mmol) of potassium phosphate. The mixture was stirred at 85° C. for 10 h. The reaction was quenched with water and diluted with EA. Two layers were separated and the organic phase was extracted by EA. The organic phases were combined and washed with water, saturated brine solution, and dried over $Na_2SO_4$ before concentration to dryness. The crude product was then purified by flash column chromatography (PE/EA=1/1) to give 62 mg of tert-butyl N-[1-[[4-(benzofuran-2-yl)-8-cyano-6-isoquinolyl]methyl]-4-piperidyl]carbamate as a yellow solid.

MS (ESI+): 483.2 [M+H]+.

6-[(4-Amino-1-piperidyl)methyl]-4-(benzofuran-2-yl)isoquinoline-8-carbonitrile (Example 306)

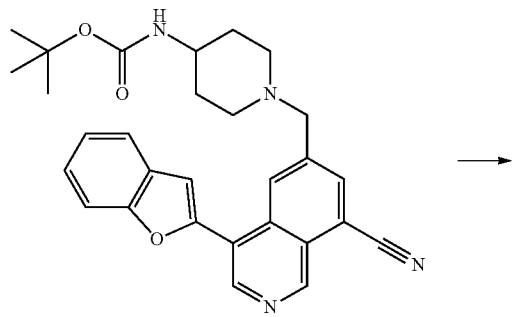

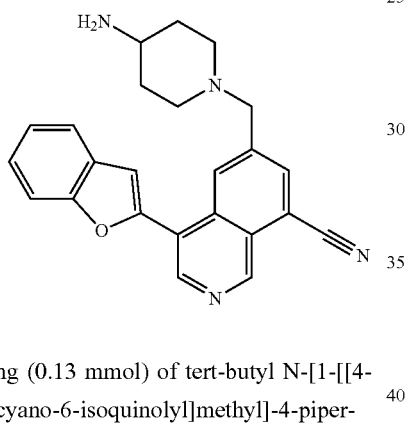

A mixture of 63 mg (0.13 mmol) of tert-butyl N-[1-[[4-(benzofuran-2-yl)-8-cyano-6-isoquinolyl]methyl]-4-piperidyl]carbamate in a solution of 1.7 N HCl in EA (8.0 mL) was stirred at 20° C. for 10 h. The reaction solution was concentrated to dryness. The crude product was then purified by Prep-HPLC to afford 45 mg of 6-[(4-amino-1-piperidyl)methyl]-4-(benzofuran-2-yl)isoquinoline-8-carbonitrile as a light yellow solid.

MS (ESI+): 383.2 [M+H]+.

$^1$H NMR (400 MHz, DMSO-d$_6$+D$_2$O) δ ppm: 9.58 (s, 1H), 9.19 (s, 1H), 8.93 (s, 1H), 8.46 (d, J=0.8 Hz, 1H), 7.81 (d, J=7.6 Hz, 1H), 7.75 (d, J=8.4 Hz, 1H), 7.48-7.44 (m, 1H), 7.40-7.36 (m, 1H), 4.59 (s, 2H), 3.48-3.45 (m, 2H), 3.27-3.26 (m, 1H), 3.09-3.08 (m, 2H), 2.10-2.07 (m, 2H), 1.72-1.70 (m, 2H).

The following example was prepared accordingly to Example 306 by reaction of tert-butyl N-[1-[(4-bromo-8-cyano-6-isoquinolyl)methyl]-4-piperidyl]carbamate with phenylboronic acid in the presence of a Pd-catalyst and subsequent deprotection:

| Example | $^1$H NMR (400 MHz) δ ppm | MS (+ESI) [M + H]+ |
|---|---|---|
| 307 | (DMSO-d$_6$ + D$_2$O) 9.54 (s, 1H), 8.71 (s, 1H), 8.39 (s, 1H), 8.30 (s, 1H), 7.64-7.56 (m, 5H), 7.44-7.41 (m, 2H), 7.01 (d, J = 8.4 Hz, 2H), 4.42 (s, 2H), 3.35-3.22 (m, 3H), 2.97-2.96 (m, 2H), 2.05-2.02 (m, 2H), 1.67-1.65 (m, 2H). | 343.2 |

The following example was prepared accordingly to Example 229 by Suzuki coupling reaction of 4-bromo-8-chloro-6-fluoro-isoquinoline with phenylboronic acid in the presence of a Pd-catalyst and subsequent substitution with trans-1,4-cyclohexanediamine:

| Example | $^1$H NMR (400 MHz) δ ppm | MS (+ESI) [M + H]+ |
|---|---|---|
| 308 | (DMSO-d$_6$ + D$_2$O) 9.09 (s, 1H), 8.15 (s, 1H), 7.55-7.46 (m, 5H), 7.22 (d, J = 2.0 Hz, 1H), 6.51 (d, J = 1.2 Hz, 1H), 2.99 (m, 1H), 2.50 (m, 1H), 1.87 (m, 2H), 1.75 (m, 2H), 1.17-1.01 (m, 4H). | 352.1, 354.1 |

The following example was prepared accordingly to Example 79 by reaction of 6-fluoro-4-phenyl-isoquinoline with 4-(2,5-dimethylpyrrol-1-yl)cyclohexanol, followed by the subsequent deprotection:

| Example | $^1$H NMR (400 MHz) δ ppm | MS (+ESI) [M + H]+ |
|---|---|---|
| 309 | (DMSO-d$_6$ + D$_2$O) 9.53 (s, 1H), 8.46 (m, 2H), 7.67-7.57 (m, 6H), 7.19 (d, J = 2.4 Hz, 1H), 4.46-4.41 (m, 1H), 3.10-3.05 (m, 1H), 2.12-2.10 (m, 2H), 1.99-1.97 (m, 2H), 1.54-1.38 (m, 4H). | 319.2 |

The following example was prepared accordingly to Example 79 by reaction of 4-(benzofuran-2-yl)-8-chloro-6-fluoro-isoquinoline with 4-(2,5-dimethylpyrrol-1-yl)cyclohexanol, followed by the subsequent deprotection:

| Example | ¹H NMR (400 MHz) δ ppm | MS (+ESI) [M + H]⁺ |
|---|---|---|
| 310 | (DMSO-d₆ + D₂O) 9.44 (s, 1H), 8.92 (s, 1H), 7.78-7.64 (m, 4H), 7.54 (s, 1H), 7.44-7.34 (m, 2H), 4.55 (m, 1H), 3.04 (m, 1H), 2.20 (m, 2H), 1.99 (m, 2H), 1.56-1.44 (m, 4H). | 393.1, 395.1 |

The following example was prepared accordingly to Example 79 by reaction of 8-chloro-6-fluoro-4-phenyl-isoquinoline (prepared from 4-bromo-8-chloro-6-fluoro-isoquinoline and phenylboronic acid by Suzuki coupling reaction in analogy to the preparation of 4-(benzofuran-2-yl)-8-chloro-6-fluoro-isoquinoline) with 4-(2,5-dimethylpyrrol-1-yl)cyclohexanol, followed by the subsequent deprotection:

| Example | ¹H NMR (400 MHz) δ ppm | MS (+ESI) [M + H]⁺ |
|---|---|---|
| 311 | (DMSO-d₆ + D₂O) 9.49 (s, 1H), 8.47 (s, 1H), 7.73 (d, J = 2.0 Hz, 1H), 7.62-7.53 (m, 5H), 7.08 (d, J = 2.0 Hz, 1H), 4.41-4.36 (m, 1H), 3.09-3.03 (m, 1H), 2.09-2.07 (m, 2H), 1.98-1.95 (m, 2H), 1.50-1.37 (m, 4H). | 353.0, 355.0 |

8-Chloro-6-fluoro-4-phenyl-isoquinoline

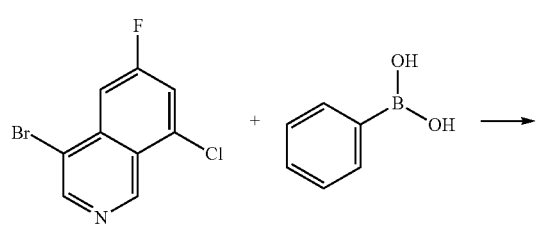

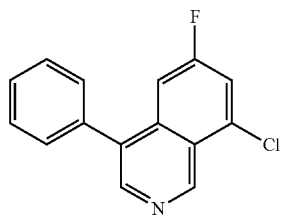

To a solution of 4.11 g (14.97 mmol) of 4-bromo-8-chloro-6-fluoro-isoquinoline in THF (250 mL) and H₂O (25 mL) were added 2.01 g (16.47 mmol) of phenylboronic acid, 1.73 g (1.5 mmol) of tetrakis(triphenylphosphine)palladium (0) and 9.53 g (44.92 mmol) of potassium phosphate. The mixture was stirred at 100° C. for 2 h. The mixture was diluted with 500 mL of EA and washed with of brine (100 mL×3). The organic layer was dried over Na₂SO₄, filtered and concentrated to give the product as a black solid which was purified by column chromatography over silica gel eluting with PE/EA (30/1) to give 3.07 g of 8-chloro-6-fluoro-4-phenyl-isoquinoline as a light yellow solid.

MS (ESI+): 258.0, 260.0 [M+H]⁺.

¹H NMR (400 MHz, DMSO-d₆) ppm: 9.56 (s, 1H), 8.59 (s, 1H), 8.01 (m, 1H), 7.61-7.54 (m, 5H), 7.43 (d, J=6.0 Hz, 1H).

8-Chloro-6-fluoro-4-phenyl-isoquinolin-1-amine

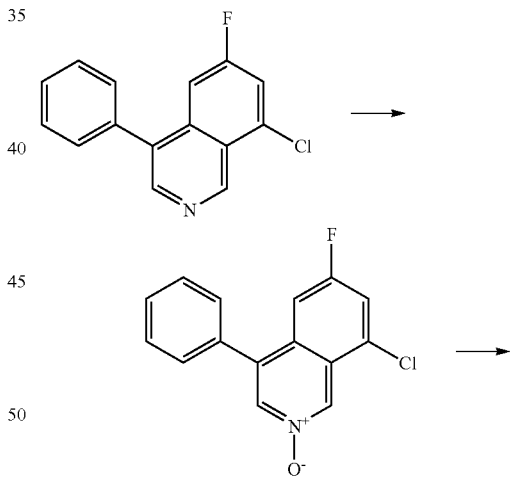

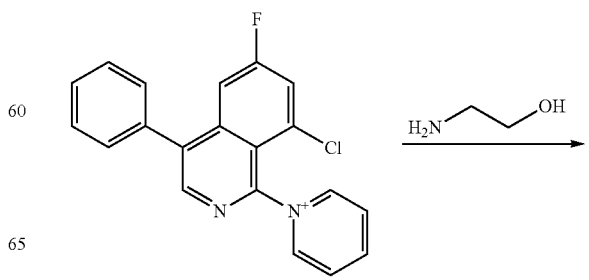

-continued

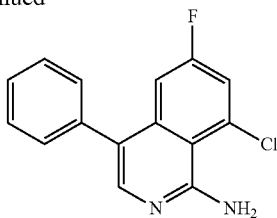

To a solution of 0.32 g (1.16 mmol) of 8-chloro-6-fluoro-4-phenyl-isoquinoline in DCM (10 mL) was added 0.3 g (1.75 mmol) of m-chloroperbenzoic acid. The mixture was stirred at 30° C. for 18 h. The mixture was quenched with saturated aq. $Na_2SO_3$ solution and saturated aq. $NaHCO_3$ solution, and then extracted with DCM. The organic layers were dried over $Na_2SO_4$, filtered and concentrated to give 0.32 g of 8-chloro-6-fluoro-2-oxido-4-phenyl-isoquinolin-2-ium as a yellow solid which was used in the next step without further purification.

To a solution of 0.34 g (1.17 mmol) of 8-chloro-6-fluoro-2-oxido-4-phenyl-isoquinolin-2-ium in pyridine (10 mL) was added 0.27 g (1.4 mmol) of p-toluenesulfonyl chloride. The mixture was stirred at 25° C. for 2 h. The solvent was removed under vacuum to give 0.39 g of 8-chloro-6-fluoro-4-phenyl-1-pyridin-1-ium-1-yl-isoquinoline as a yellow oil which was used into the next step without further purification.

To a solution of 0.39 g (1.05 mmol) of 8-chloro-6-fluoro-4-phenyl-1-pyridin-1-ium-1-yl-isoquinoline in dichloromethane (5 mL) was added 5 mL of 2-aminoethanol. The mixture was stirred at 30° C. for 18 h. The mixture was diluted with DCM and washed with brine, dried over $Na_2SO_4$, filtered and concentrated to give 0.28 g of 8-chloro-6-fluoro-4-phenyl-isoquinolin-1-amine as a yellow oil.

MS (ESI+): 273.0, 275.0 $[M+H]^+$.

$^1$H NMR (400 MHz, DMSO-$d_6$) ppm: 7.82 (s, 1H), 7.65 (dd, J=8.0 Hz, 2.4 Hz, 1H), 7.53-7.40 (m, 5H), 7.20 (dd, J=8.4 Hz, 2.8 Hz, 1H), 7.12 (s, 2H).

Trans-N6-(4-aminocyclohexyl)-8-chloro-4-phenyl-isoquinoline-1,6-diamine (Example 312)

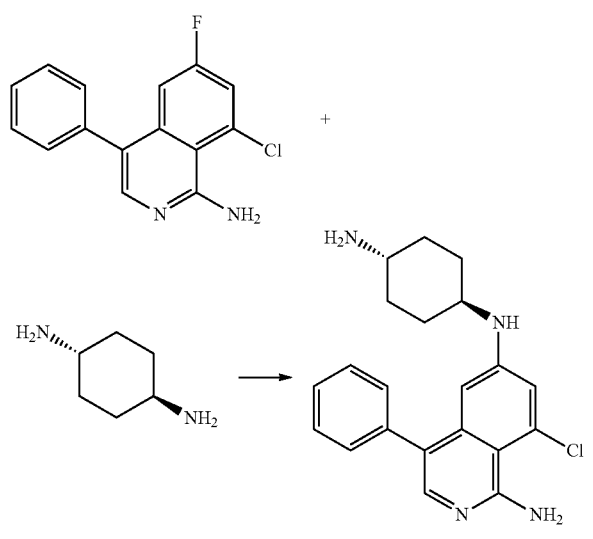

To a suspension of 0.12 g (0.43 mmol) of 8-chloro-6-fluoro-4-phenyl-isoquinolin-1-amine in NMP (3 mL) was added 0.05 g (0.43 mmol) of trans-1,4-diaminocyclohexane. The mixture was stirred at 160° C. for 40 min under microwave irradiation. The mixture was diluted with 10 mL of brine and extracted with DCM (10 mL×2). The DCM layers were dried over $Na_2SO_4$, filtered and concentrated to give the residue which was purified by prep-HPLC to give 124 mg of N6-(4-aminocyclohexyl)-8-chloro-4-phenyl-isoquinoline-1,6-diamine as an off-white solid.

MS (ESI+): 367.1, 369.1 $[M+H]^+$.

$^1$H NMR (400 MHz, DMSO-$d_6$+$D_2O$) ppm: 7.54-7.39 (m, 6H), 7.17 (s, 1H), 6.46 (s, 1H), 3.13 (br, 1H), 3.01-2.93 (m, 1H), 1.96-1.86 (m, 4H), 1.38-1.16 (m, 4H).

The following example was prepared accordingly to Example 312 by substitution reaction of 4-(benzofuran-2-yl)-8-chloro-6-fluoro-isoquinolin-1-amine (prepared from 4-(benzofuran-2-yl)-8-chloro-6-fluoro-isoquinoline via 3 steps in analogy to the preparation of 8-chloro-6-fluoro-4-phenyl-isoquinolin-1-amine) with trans-1,4-cyclohexanediamine:

| Example | $^1$H NMR (400 MHz) δ ppm | MS (+ESI) $[M + H]^+$ |
|---|---|---|
| 313 | (DMSO-$d_6$ + $D_2O$) δ ppm: 7.97 (s, 1H), 7.64 (dd, J = 7.2 Hz, 1.2 Hz, 1H), 7.55 (d, J = 8.0 Hz, 1H), 7.32-7.24 (m, 2H), 7.03-6.99 (m, 3H), 3.11 (m, 1H), 2.61 (m, 1H), 2.04 (m, 2H), 1.81 (m, 2H), 1.25-1.09 (m, 4H). | 407.2, 409.1 |

Trans-4-[[4-(Benzofuran-2-yl)-8-methoxy-6-isoquinolyl]oxy]cyclohexanamine (Example 314)

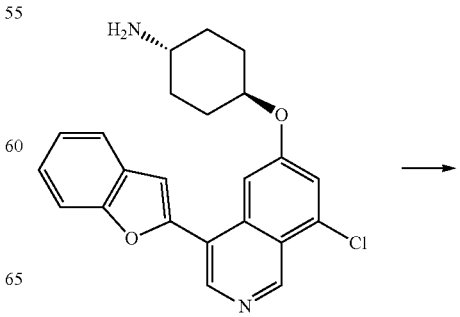

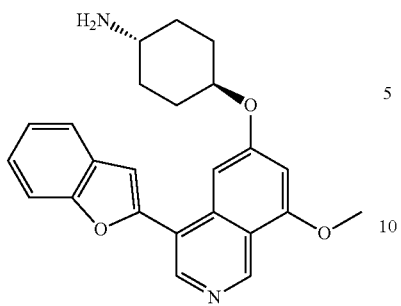

To a solution of 0.1 g (0.24 mmol) of 4-[[4-(benzofuran-2-yl)-8-chloro-6-isoquinolyl]oxy]cyclohexanamine in dioxane (1 mL) and methanol (1 mL) were added 65 mg (1.21 mmol) of sodium methoxide, 12 mg (0.02 mmol) of 2-(di-tert-butylphosphino)-2',4',6'-triisopropyl-3,6-dimethoxybiphenyl and 22 mg (0.02 mmol) of $Pd_2(dba)_3$. The mixture was stirred under microwave irradiation at 120° C. for 30 min. The mixture was filtered through Celite pad. The solvents were evaporated under vacuum and the residue was purified by preparative HPLC to give 65 mg of 4-[[4-(benzofuran-2-yl)-8-methoxy-6-isoquinolyl]oxy]cyclohexanamine as a yellow solid.

MS (ESI+): 389.2 [M+H]$^+$.

$^1$H NMR (400 MHz, DMSO-$d_6$+$D_2O$) ppm: 9.44 (s, 1H), 8.83 (s, 1H), 7.80 (d, J=7.6 Hz, 1H), 7.70 (d, J=8.4 Hz, 1H), 7.63 (s, 1H), 7.50 (s, 1H), 7.47-7.43 (m, 1H), 7.39-7.35 (m, 1H), 6.98 (d, J=2.0 Hz, 1H), 4.69-4.64 (m, 1H), 4.08 (s, 3H), 3.14-3.09 (m, 1H), 2.26-2.23 (m, 2H), 2.06-2.03 (m, 2H), 1.61-1.48 (m, 4H).

The following example was prepared accordingly to Example 314 by reaction of trans-N4-(8-chloro-4-phenyl-6-isoquinolyl)cyclohexane-1,4-diamine with sodium methoxide:

| Example | $^1$H NMR (400 MHz) δ ppm | MS (+ESI) [M + H]$^+$ |
|---|---|---|
| 315 | (DMSO-$d_6$ + $D_2O$) δ ppm: 9.00 (s, 1H), 8.01 (s, 1H), 7.60-7.53 (m, 5H), 6.67 (s, 1H), 6.28 (s, 1H), 4.02 (s, 3H), 3.01 (m, 1H), 2.51 (m, 1H), 1.96-1.94 (m, 4H), 1.30-1.27 (m, 4H). | 348.2 |

The following example was prepared accordingly to Example 314 by reaction of trans-4-[(8-chloro-4-phenyl-6-isoquinolyl)oxy]cyclohexanamine with sodium methoxide:

| Example | $^1$H NMR (400 MHz) δ ppm | MS (+ESI) [M + H]$^+$ |
|---|---|---|
| 316 | (DMSO-$d_6$ + $D_2O$) δ ppm: 9.45 (s, 1H), 8.39 (s, 1H), 7.61-7.57 (m, 5H), 6.98 (d, J = 2.0 Hz, 1H), 6.76-6.75 (d, J = 1.2 Hz, 1H), 4.43-4.38 (m, 1H), 4.09 (s, 3H), 3.08-3.04 (m, 1H), 2.11-2.08 (m, 2H), 1.99-1.96 (m, 2H), 1.52-1.49 (m, 2H), 1.39-1.36 (m, 2H). | 349.2 | trans-N6-(4-aminocyclohexyl)-4-phenyl-isoquinoline-1,6-diamine (Example 317)

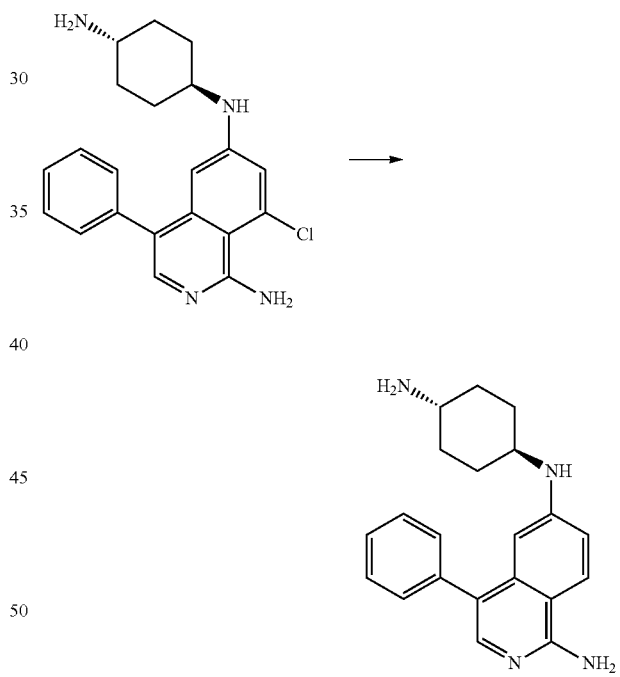

To a solution of 0.07 g (0.17 mmol) of N6-[(4R)-4-aminocyclohexyl]-8-chloro-4-phenyl-isoquinoline-1,6-diamine in MeOH (5 mL) was added 10% Pd/C (20 mg). The mixture was stirred under $H_2$ atmosphere for 30 min at 30° C. The solid was filtered off and the filtrate was concentrated and lyophilized to give 47 mg of N6-(4-aminocyclohexyl)-4-phenyl-isoquinoline-1,6-diamineas as an off-white solid.

MS (ESI+): 333.0, 335.0 [M+H]$^+$.

$^1$H NMR (400 MHz, DMSO-$d_6$+$D_2O$) ppm: 8.25 (d, J=9.2 Hz, 1H), 7.55-7.42 (m, 5H), 7.36 (s, 1H), 7.07 (d, J=9.2 Hz, 1H), 6.54 (s, 1H), 3.15 (br, 1H), 3.03-2.95 (m, 1H), 1.97-1.90 (m, 4H), 1.38-1.18 (m, 4H).

375

Trans-tert-Butyl N-[4-[[4-(benzofuran-2-yl)-8-chloro-6-isoquinolyl]oxy]cyclohexyl]carbamate

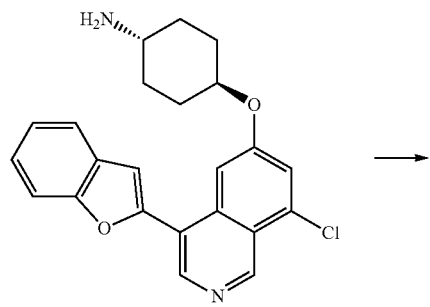

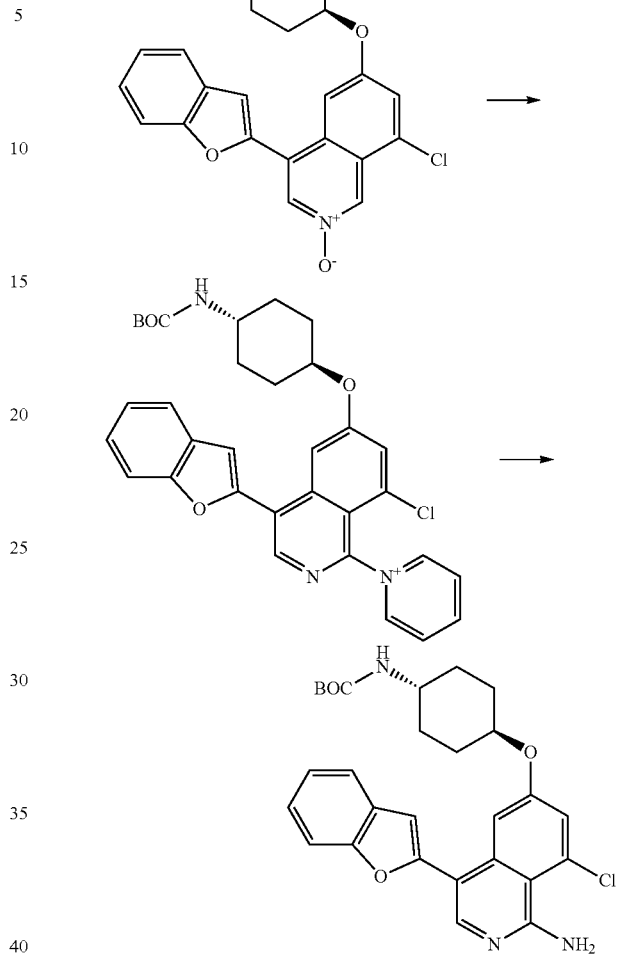

To a solution of 2.0 g (5.09 mmol) of 4-[[4-(benzofuran-2-yl)-8-chloro-6-isoquinolyl]oxy]cyclohexanamine in DCM (30 mL) were added 0.73 g (7.25 mmol) of TEA and 1.33 g (6.11 mmol) of Boc$_2$O. The mixture was stirred at 20° C. for 24 h. The volatiles were evaporated and the residue was purified by column chromatography on silica gel (PE-EA=10:1 to 2:1, R$_f$=0.6) to afford 2.2 g of tert-butyl N-[4-[[4-(benzofuran-2-yl)-8-chloro-6-isoquinolyl]oxy]cyclohexyl]carbamate as a light yellow solid.

MS (ESI+): 493.5, 495.4 [M+H]$^+$.

Trans-tert-Butyl N-[4-[[1-amino-4-(benzofuran-2-yl)-8-chloroisoquinolyl]oxy]cyclohexyl]carbamate

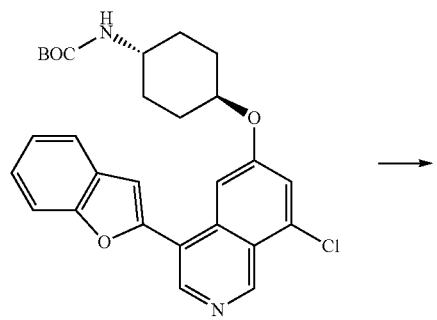

To a solution of 0.4 g (0.77 mmol) of tert-butyl N-[4-[[4-(benzofuran-2-yl)-8-chloro-6-isoquinolyl]oxy]cyclohexyl]carbamate in DCM (10 mL) was added 0.35 g (1.54 mmol) of mCPBA and the mixture was stirred at 25° C. for 16 h. The reaction was quenched with aq. Na$_2$SO$_3$ solution and aq. NaHCO$_3$ solution and extracted with DCM. The organic phases were dried over Na$_2$SO$_4$. The solvent was removed under vacuum to give 0.39 g of tert-butyl N-[4-[4-(benzofuran-2-yl)-8-chloro-2-oxido-isoquinolin-2-ium-6-yl]oxy-cyclohexyl]carbamate as a yellow solid which was used in the next step without further purification.

To a solution of 0.39 g (0.73 mmol) of tert-butyl N-[4-[4-(benzofuran-2-yl)-8-chloro-2-oxido-isoquinolin-2-ium-6-yl]oxycyclohexyl]carbamate in pyridine (5 mL) was added 0.17 g (0.88 mmol) of p-toluenesulfonyl chloride and then the mixture was stirred at 25° C. for 2 h. The solvent was removed under vacuum to give 0.42 g of tert-butyl N-[4-[[4-(benzofuran-2-yl)-8-chloro-1-pyridin-1-ium-1-yl-6-isoquinolyl]oxy]cyclohexyl]carbamate as a brown solid which was used in the next step without further purification.

To a solution of 0.42 g (0.70 mmol) of tert-butyl N-[4-[[4-(benzofuran-2-yl)-8-chloro-1-pyridin-1-ium-1-yl-6-isoquinolyl]oxy]cyclohexyl]carbamate in DCM (5 mL) was added 1.4 mL (22.96 mmol) of ethanolamine. The resulting mixture was stirred at 15° C. for 16 h. The DCM was removed under vacuum and the residue was purified by preparative HPLC to give 0.14 g of tert-butyl N-[4-[[1-amino-4-(benzofuran-2-yl)-8-chloro-6-isoquinolyl]oxy]cyclohexyl]carbamate as a yellow solid.

MS (ESI+): 508.5, 510.5 [M+H]+.

1H NMR (400 MHz, DMSO-d6+D2O) ppm: 8.14 (s, 1H), 7.68 (dd, J=6.8 Hz, 1.6 Hz, 1H), 7.59 (d, J=8.4 Hz, 1H), 7.48 (d, J=2.4 Hz, 1H), 7.34-7.26 (m, 3H), 7.13 (d, J=0.8 Hz, 1H), 6.78 (d, J=8.4 Hz, 1H), 4.39-4.34 (m, 1H), 3.30-3.28 (m, 1H), 2.11-2.08 (m, 2H), 1.84-1.81 (m, 2H), 1.52-1.37 (m, 2H), 1.37 (s, 9H), 1.37-1.23 (m, 2H).

trans-6-(4-Aminocyclohexoxy)-4-(benzofuran-2-yl)-8-chloro-isoquinolin-1-amine (Example 318)

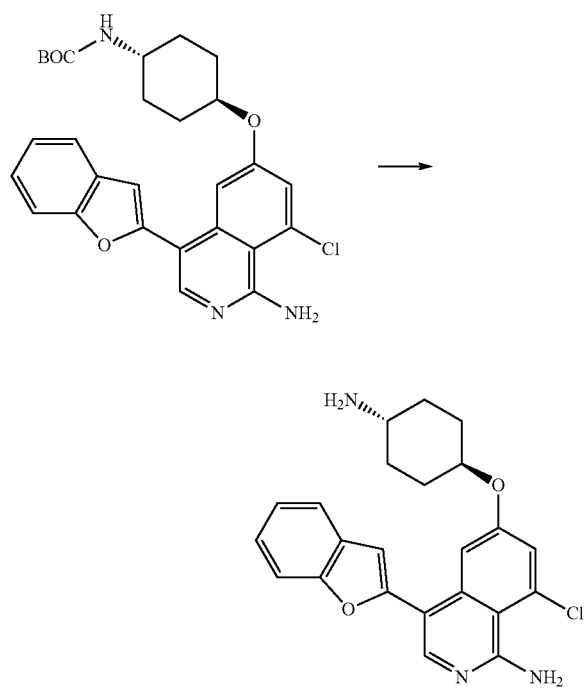

To a solution of 0.14 g (0.27 mmol) of tert-butyl N-[4-[[1-amino-4-(benzofuran-2-yl)-8-chloro-6-isoquinolyl]oxy]cyclohexyl]carbamate in DCM (10 mL) was added 0.67 mL (9 mmol of TFA. The resulting mixture was stirred at 15° C. for 4 h. The DCM was removed under vacuum and the residue was purified by preparative HPLC to afford 46 mg of 6-(4-aminocyclohexoxy)-4-(benzofuran-2-yl)-8-chloro-isoquinolin-1-amine as a yellow solid.

MS (ESI+): 408.2, 410.1 [M+H]+.

1H NMR (400 MHz, DMSO-d6+D2O) ppm: 8.09 (s, 1H), 7.74 (dd, J=7.6 Hz, 0.8 Hz, 1H), 7.65-7.63 (m, 2H), 7.49 (d, J=2.4 Hz, 1H), 7.41-7.32 (m, 2H), 7.31 (d, J=2.0 Hz, 1H), 4.58-4.53 (m, 1H), 3.11-3.05 (m, 1H), 2.16-2.14 (m, 2H), 2.01-1.98 (m, 2H), 1.54-1.41 (m, 4H).

The following example was prepared in analogy to Example 318, starting from 4-[(8-chloro-4-phenyl-6-isoquinolyl)oxy]cyclohexanamine via 5 steps:

| Example | 1H NMR (400 MHz) δ ppm | MS (+ESI) [M + H]+ |
|---|---|---|
| 319 | (DMSO-d6 + D2O) 7.66 (d, J = 3.0 Hz, 2H), 7.58-7.49 (m, 3H), 7.44-7.42 (m, 2H), 6.87 (d, J = 3.0 Hz, 1H), 4.40-4.35 (m, 1H), 3.06-3.01 (m, 1H), 2.05-1.94 (m, 4H), 1.50-1.34 (m, 4H). | 368.0, 370.0 |

The following example was prepared in analogy to Example 318, starting from 4-[[4-(Benzofuran-2-yl)-6-isoquinolyl]oxy]cyclohexanamine via 5 steps:

| Example | 1H NMR (400 MHz) δ ppm | MS (+ESI) [M + H]+ |
|---|---|---|
| 320 | (DMSO-d6 + D2O) 8.53 (d, J = 9.2 Hz, 1H), 8.03 (s, 1H), 8.40 (dd, J = 7.2 Hz, 0.8 Hz, 1H), 7.64 (m, 1H), 7.60 (d, J = 2.4 Hz, 1H), 7.52-7.49 (dd, J = 9.2 Hz, 2.4 Hz, 1H), 7.41-7.31 (m, 3H), 4.58-4.53 (m, 1H), 3.12-3.06 (m, 1H), 2.19-2.17 (m, 2H), 2.03-2.00 (m, 2H), 1.56-1.44 (m, 4H). | 374.2 |

The following example was prepared in analogy to Example 318, starting from 4-[(8-methoxy-4-phenyl-6-isoquinolyl)oxy]cyclohexanamine via 5 steps:

| Example | 1H NMR (400 MHz) δ ppm | MS (+ESI) [M + H]+ |
|---|---|---|
| 321 | (DMSO-d6 + D2O) 7.54-7.47 (m, 4H), 7.44-7.41 (m, 2H), 6.86 (d, J = 2.0 Hz, 1H), 6.51 (d, J = 2.4 Hz, 1H), 4.34-4.29 (m, 1H), 4.06 (s, 3H), 3.07-3.01 (m, 1H), 2.06-2.04 (m, 2H), 1.97-1.95 (m, 2H), 1.50-1.32 (m, 4H). | 364.1 |

The following example was prepared in analogy to Example 318, starting from 4-[(4-phenyl-6-isoquinolyl)oxy]cyclohexanamine via 5 steps:

| Example | $^1$H NMR (400 MHz) δ ppm | MS (+ESI) [M + H]$^+$ |
|---|---|---|
| 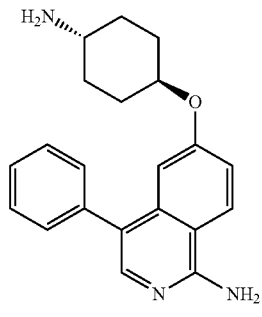 322 | (DMSO-d$_6$ + D$_2$O) 8.54 (d, J = 1.2 Hz, 1H), 7.58-7.46 (m, 7H), 6.97 (d, J = 2.4 Hz, 1H), 4.40-4.35 (m, 1H), 3.08-3.03 (m, 1H), 2.09-2.06 (m, 2H), 1.98-1.95 (m, 2H), 1.49-1.37 (m, 4H). | 334.2 | trans-tert-Butyl N-[4-[[4-(benzofuran-2-yl)-8-methoxy-6-isoquinolyl]oxy]cyclohexyl]carbamate

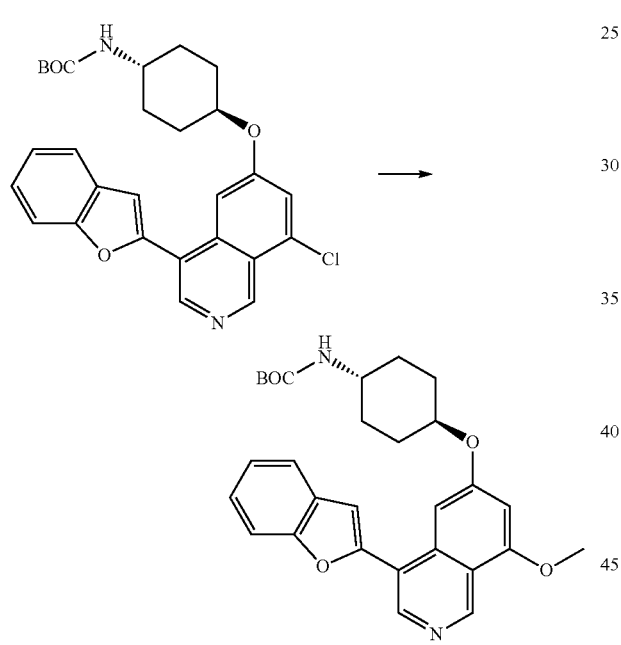

To a solution of 0.9 g (1.73 mmol) of tert-butyl N-[4-[[4-(benzofuran-2-yl)-8-chloro-6-isoquinolyl]oxy]cyclohexyl]carbamate in dioxane (6 mL) and MeOH (6 mL) were added 0.47 g (8.67 mmol) of sodium methoxide, 0.1 g (0.21 mmol) of 2-(Di-tert-butylphosphino)-2',4',6'-triisopropyl-3,6-dimethoxybiphenyl and 0.16 g (0.17 mmol) of Pd$_2$(dba)$_3$. The mixture was stirred at 90° C. for 1 h. The mixture was cooled to rt and the precipitates were collected by filtration, washed with water and dried under vacuum to give 0.49 g of tert-butyl N-[4-[[4-(benzofuran-2-yl)-8-methoxy-6-isoquinolyl]oxy]cyclohexyl]carbamate as an off-white solid.

MS (ESI+): 489.5 [M+H]$^+$.

$^1$H NMR (400 MHz, CDCl$_3$) ppm: 9.49 (s, 1H), 8.82 (s, 1H), 7.71 (d, J=7.2 Hz, 1H), 7.58 (d, J=8.0 Hz, 1H), 7.39-7.34 (m, 3H), 7.10 (s, 1H), 7.58 (d, J=2.0 Hz, 1H), 4.49-4.41 (m, 1H), 4.04 (s, 3H), 3.65-3.53 (m, 1H), 2.31-2.24 (m, 2H), 2.20-2.13 (m, 2H), 1.70-1.63 (m, 2H), 1.48 (s, 9H), 1.36-1.30 (m, 2H).

trans-tert-Butyl N-[4-[[1-amino-4-(benzofuran-2-yl)-8-methoxy-6-isoquinolyl]oxy]cyclohexyl]carbamate

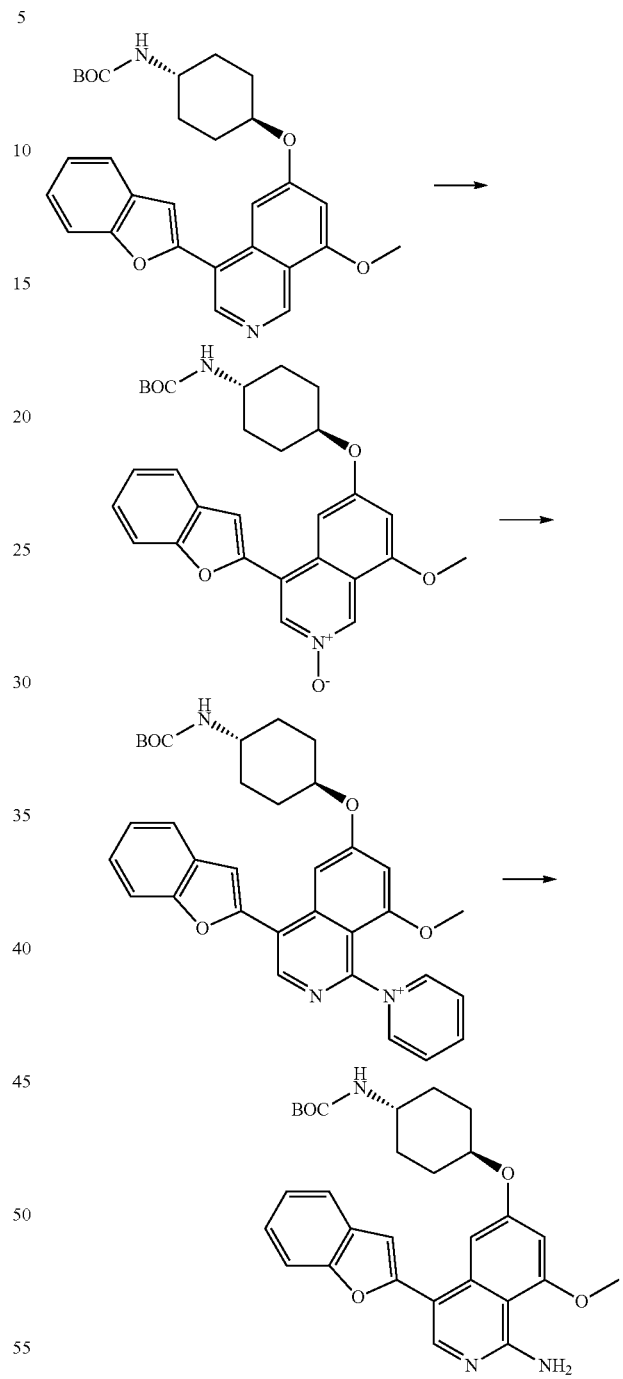

To a solution of 0.49 g (0.95 mmol) of tert-butyl N-[4-[[4-(benzofuran-2-yl)-8-methoxy-6-isoquinolyl]oxy]cyclohexyl]carbamate in DCM (20 mL) was added 0.43 g (1.91 mmol) of mCPBA and the mixture was stirred at 15° C. for 16 h. The reaction was quenched with aq. Na$_2$SO$_3$ solution and aq. NaHCO$_3$ solution and extracted with DCM. The organic phases were dried over Na$_2$SO$_4$. The solvent was removed under vacuum to give 0.51 g of tert-butyl N-[4-[4-(benzofuran-2-yl)-8-methoxy-2-oxido-isoquinolin-2- ium-6-yl]oxycyclohexyl]carbamate as a brown solid which was used in the next step without further purification.

To a solution of 0.51 g (0.91 mmol) of tert-butyl N-[4-[4-(benzofuran-2-yl)-8-methoxy-2-oxido-isoquinolin-2-ium-6-yl]oxycyclohexyl]carbamate in pyridine (7 mL) was added 0.21 g (1.09 mmol) of p-toluenesulfonyl chloride and then the mixture was stirred at 25° C. for 2 h. The solvent was removed under vacuum to give 0.57 g of tert-butyl N-[4-[[4-(benzofuran-2-yl)-8-methoxy-1-pyridin-1-ium-1-yl-6-isoquinolyl]oxy]cyclohexyl]carbamate as a brown solid which was used in the next step without further purification.

To a solution of 0.57 g (0.91 mmol) of tert-butyl N-[4-[[4-(benzofuran-2-yl)-8-methoxy-1-pyridin-1-ium-1-yl-6-isoquinolyl]oxy]cyclohexyl]carbamate in DCM (5 mL) was added 1.82 mL (29.87 mmol) of ethanolamine. The resulting mixture was stirred at 15° C. for 16 h. The DCM was removed under vacuum and the residue was purified by preparative HPLC to give 113 mg of tert-butyl N-[4-[[1-amino-4-(benzofuran-2-yl)-8-methoxy-6-isoquinolyl]oxy]cyclohexyl]carbamate as a yellow solid.

MS (ESI+): 504.5 [M+H]+.

$^1$H NMR (400 MHz, DMSO-$d_6$+$D_2O$) ppm: 7.96 (s, 1H), 7.74 (d, J=7.2 Hz, 1H), 7.63 (d, J=8.4 Hz, 1H), 7.41-7.31 (m, 2H), 7.28 (s, 1H), 7.14 (d, J=2.0 Hz, 1H), 6.90 (d, J=2.0 Hz, 1H), 4.51-4.46 (m, 1H), 4.06 (s, 3H), 3.33-3.25 (m, 1H), 2.12-2.10 (m, 2H), 1.82-1.82 (m, 2H), 1.53-1.43 (m, 2H), 1.36 (s, 9H), 1.30-1.21 (m, 2H).

trans-6-(4-Aminocyclohexoxy)-4-(benzofuran-2-yl)-8-methoxy-isoquinolin-1-amine (Example 323)

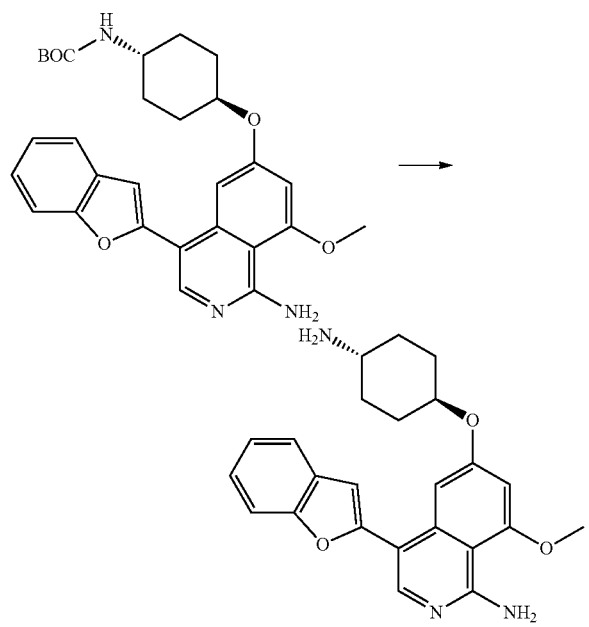

To a solution of 113 mg (0.21 mmol) of tert-butyl N-[4-[[1-amino-4-(benzofuran-2-yl)-8-methoxy-6-isoquinolyl]oxy]cyclohexyl]carbamate in DCM (10 mL) was added 0.52 mL (7.03 mmol) of TFA. The resulting mixture was stirred at 15° C. for 4 h. The DCM was removed under vacuum and the residue was purified by preparative HPLC to give 120 mg of 6-(4-aminocyclohexoxy)-4-(benzofuran-2-yl)-8-methoxy-isoquinolin-1-amine as a brown solid.

MS (ESI+): 404.2 [M+H]+.

$^1$H NMR (400 MHz, DMSO-$d_6$+$D_2O$) ppm: 7.97 (s, 1H), 7.72 (d, J=7.2 Hz, 1H), 7.62 (d, J=8.0 Hz, 1H), 7.40-7.30 (m, 2H), 7.29 (s, 1H), 7.13 (d, J=2.0 Hz, 1H), 6.90 (d, J=2.0 Hz, 1H), 4.55-4.50 (m, 1H), 4.07 (s, 3H), 3.10-3.05 (m, 1H), 2.18-2.15 (m, 2H), 2.01-1.98 (m, 2H), 1.54-1.40 (m, 4H).

MNK Inhibition Assay:

For the measurement of the activity of the MNK1 kinase the Z-Lyte kinase assay system was used. The kinase activity of MNK1 can be quantified with the Z-Lyte kinase assay kit Ser/Thr 7 peptide (Life Technologies PV3180). The kit was utilized according to the instructions of the provider. A recombinant GST-MNK1 fusion protein produced in and purified from baculovirus infected insect cells was used as enzyme source (GST-MNK1 Life Technologies PV6023 or Carna Biosciences 02-145). It was verified that both sources of the MNK1 enzyme gave similar IC50 values with several compounds. The MNK1 enzyme assay was performed in 384 well round bottom black microtiter plates (Corning 3676). The kinase reaction was performed for 3 hours at 31° C. As instructed by the provider of the kit the amount of enzyme was chosen such that ~30% of the substrate peptide was phosphorylated in control wells containing buffer only. The MNK1 inhibiting activity of compounds was tested by adding the compounds to the kinase reaction at a concentration of 10000, 5000, 2000, 1000, 500, 200, 100, 50 nM. Compounds with strong MNK1 inhibition were tested at 20, 10, 5, 2, 1 and 0.5 nM in addition. Each compound concentration was tested at least in duplicate. The % phosphorylation of the substrate peptide at each compound concentration was calculated as described in the assay manual. The fluorescent signals were recorded on Biotek Cytation 3 microplate reader. The IC50, the concentration that reduced substrate phosphorylation by 50% if compared to buffer only wells, was calculated with the Grafit 6 software (Erythacus software).

The activity of MNK2 and its inhibition by compounds can be measured as described for MNK1, for example by using GST-MNK2 Life technologies PV5607 as enzyme source.

Cell Growth Assay:

The inhibition of cell growth by the compounds was tested by exposing the human pancreatic cancer cell line MiaPaCa2 (ATCC CRL-1420) to the compounds. The assay was performed in 384 well clear bottom white microtiter plates (Greiner #781098). Each well was seeded with $10^3$ cells in 20 µl of Dulbecco's modified Eagle's medium (Sigma D6796) supplied with 10% fetal calf serum (Sigma F7524), 2.5% horse serum (Sigma H0146), 1% Penicillin-Streptomycin (Sigma P0781), 1% MEM nonessential amino acid solution 100× (Sigma M71459) and 1% 200 mM L-Glutamine (Sigma G7513) culture medium. After overnight incubation at 37° C. in 5% $CO_2$ the compounds were added in the following concentrations: 100, 50, 20, 10, 5, 2, 1, 0.5, 0.2 and 0.1 µM. Each compound concentration was tested in quadruplicate. The incubation was then continued for 72 hours. After 72 hours the growth of the cells was assessed by the addition of the CellTiterGlo reagent (Promega G9242) as instructed by the provider. The luminescent signal was recorded on a SpectraMax M2 microplate reader. The signal obtained in wells containing cells cultivated in the absence of compound was set to 100% growth after subtracting the signal obtained in medium only wells. The % growth in each well was calculated by subtracting the medium only value and dividing through the 100% growth value. The IC50 for cell growth, the concentration of compound at which cell growth was reduced to 50%, was calculated with the GraFit6 software (Erythacus software). Results are shown in the Tables below.

TABLE 1

| Example | IC50 MNK1 nM | Inhibition of MNK1 activity at indicated concentration | IC50 MiaPaCa μM | Inhibition of MiaPaCa growth at indicated concentration |
|---|---|---|---|---|
| 1 | 109.5 | | 3.54 | |
| 2 | 93 | | 34.58 | |
| 3 | 847 | | 20.63 | |
| 4 | 334 | | 25.96 | |
| 5 | | 39% at 1 μM | 32.58 | |
| 6 | 917 | | 6.05 | |
| 7 | 744 | | 17.47 | |
| 8 | | 95% at 10 μM | n.d. | |
| 9 | 258 | | 10.79 | |
| 10 | 325 | | 11.68 | |
| 11 | | 33% at 1 μM | 10.08 | |
| 12 | | 92% at 10 μM | | 60% at 100 μM |
| 13 | 285 | | 24.28 | |
| 14 | | 34% at 1 μM | | 52% at 50 μM |
| 15 | 3964 | | | |
| 16 | 1909 | | | 67% at 100 μM |
| 17 | | 100% at 10 μM | | 61% at 50 μM |
| 18 | 459 | | 30.37 | |
| 19 | | 39% at 1 μM | 29.66 | |
| 20 | | 45% at 1 μM | | 62% at 100 μM |
| 21 | | 49% at 1 μM | | 64% at 100 μM |
| 22 | 662 | | | 69% at 100 μM |
| 23 | 2359 | | 30.62 | |
| 24 | 926 | | 45.51 | |
| 25 | 166 | | 14.61 | |
| 26 | | 40% at 1 μM | 54.27 | |
| 28 | 353 | | 47.61 | |
| 29 | | 43% at 1 μM | n.d. | |
| 30 | | 34% at 1 μM | n.d. | |
| 31 | 484 | | 2.19 | |
| 32 | 2408 | | 8.4 | |
| 33 | 866 | | n.d. | |
| 34 | 1091 | | n.d. | |
| 35 | | 56% at 1 μM | 11.82 | |
| 36 | 99 | | 20.21 | |
| 37 | 336 | | | 57% at 50 μM |
| 38 | 351 | | 25 | |
| 39 | 496 | | n.d. | |
| 40 | 263 | | | 48% at 100 μM |
| 41 | 254 | | | 67% at 100 μM |
| 42 | 496 | | | 44% at 50 μM |
| 43 | 219 | | 32.25 | |
| 44 | 61 | | 20.55 | |
| 46 | 618 | | 8.21 | |
| 47 | 1120 | | 10.93 | |
| 48 | 1150 | | 25.02 | |
| 50 | 384 | | 5.59 | |
| 51 | 4217 | | 6.34 | |
| 52 | 163 | | 14.06 | |
| 53 | 580 | | 18.59 | |
| 54 | 15 | | 2.85 | |
| 55 | 14 | | 1.83 | |
| 56 | 143 | | | 85% at 100 μM |
| 57 | 7.9 | | 3.37 | |
| 58 | 50 | | 13.61 | |
| 59 | 90 | | 47 | |
| 60 | 135 | | n.d. | |
| 61 | 3 | | 5.25 | |
| 62 | 2138 | | n.d. | |
| 63 | 68 | | n.d. | |
| 64 | | 41% at 10 μM | 14.8 | |
| 65 | 157 | | n.d. | |
| 66 | 5.4 | | 1.37 | |
| 67 | 57 | | 5.58 | |
| 68 | 45 | | 6.19 | |
| 69 | 17 | | 7 | |
| 70 | 32 | | 12.21 | |
| 71 | 128 | | 10.33 | |
| 72 | 12 | | 5.08 | |
| 73 | 5 | | 15 | |
| 74 | 5.3 | | 19.23 | |
| 75 | 2128 | | 18 | |
| 76 | 5.9 | | 4.75 | |
| 77 | 1130 | | 10 | |
| 78 | 208 | | 3.46 | |
| 79 | 401 | | 4.72 | |
| 80 | 675 | | 3.55 | |
| 81 | n.d. | | 2.21 | |
| 82 | n.d. | | 2.17 | |
| 83 | | 54% at 10 μM | | 31% at 100 μM |
| 84 | 3734 | | | 33% at 100 μM |
| 85 | 318 | | | 33% at 100 μM |
| 86 | 174 | | | 50% at 100 μM |
| 87 | 1980 | | 4.47 | |
| 88 | 171 | | n.d. | |
| 89 | | 35% at 10 μM | n.d. | |
| 90 | 1065 | | n.d. | |
| 91 | 476 | | 11.3 | |
| 92 | 577 | | 7.2 | |
| 93 | 197 | | | 27% at 50 μM |
| 94 | 221 | | | 27% at 50 μM |
| 95 | 1734 | | 8.38 | |
| 96 | 3986 | | 6.14 | |
| 97 | 397 | | 10.76 | |
| 98 | | 40% at 1 μM | 9.88 | |
| 99 | | 60% at 1 μM | 4.39 | |
| 100 | | 51% at 10 μM | 4.01 | |
| 101 | 180 | | 18.95 | |
| 102 | 1048 | | 7 | |
| 103 | 88 | | 4.12 | |
| 104 | n.d. | | 18.49 | |
| 105 | 89 | | 12.8 | |
| 106 | | 34% at 1 μM | 20.71 | |
| 107 | 1117 | | 20.97 | |
| 108 | 3507 | | 14.95 | |
| 109 | 687 | | 8.54 | |
| 110 | 395 | | 11.32 | |
| 111 | 1153 | | 8.32 | |
| 112 | | 19% at 1 μM | 43.83 | |
| 113 | 3151 | | 9.21 | |
| 114 | 1211 | | 3.83 | |
| 115 | 490 | | | 52% at 100 μM |
| 116 | 887 | | 3.07 | |
| 117 | 603 | | | 34% at 100 μM |
| 118 | 422 | | | 48% at 100 μM |
| 119 | 388 | | 2.56 | |
| 120 | 683 | | 18.65 | |
| 121 | 165 | | 21.82 | |
| 122 | 28 | | | 37% at 100 μM |
| 123 | 132 | | 7.92 | |
| 124 | 2084 | | 45.77 | |
| 125 | 52 | | 4.04 | |
| 126 | 363 | | 5.5 | |
| 127 | 21 | | 8.48 | |
| 128 | 84 | | 15.83 | |
| 129 | 143 | | 23.14 | |
| 130 | 21 | | 0.58 | |
| 131 | 24 | | n.d. | |
| 132 | 3118 | | | 53% at 100 μM |
| 133 | 152 | | 11.53 | |
| 134 | 4679 | | | 45% at 100 μM |
| 135 | 4679 | | 10.93 | |
| 136 | 558 | | 20.58 | |
| 137 | 1086 | | 3.25 | |
| 138 | 1596 | | 12.11 | |
| 139 | 903 | | 10.41 | |
| 140 | 10 | | 1.87 | |
| 141 | 187 | | 2.26 | |
| 142 | 180 | | 3.79 | |
| 143 | 474 | | 1.96 | |
| 144 | 1891 | | 4.61 | |
| 145 | 2716 | | 29 | |
| 146 | 268 | | 19.98 | |
| 147 | 92 | | 7.14 | |
| 148 | 58 | | 1.745 | |
| 151 | 11 | | 2.51 | |

TABLE 1-continued

| Example | IC50 MNK1 nM | Inhibition of MNK1 activity at indicated concentration | IC50 MiaPaCa μM | Inhibition of MiaPaCa growth at indicated concentration |
|---|---|---|---|---|
| 152 | 17 | | 1.56 | |
| 153 | 131 | | 3.5 | |
| 156 | 371 | | 10.44 | |
| 157 | 50 | | 7.88 | |
| 160 | 284 | | 12.19 | |
| 161 | 465 | | 23.98 | |
| 162 | | 54% at 1 μM | 9.88 | |
| 163 | 142 | | 13.75 | |
| 164 | 847 | | 6.62 | |
| 165 | 6 | | 5.7 | |
| 166 | 57 | | n.d. | |
| 167 | 1039 | | 0.8 | |
| 168 | 760 | | 12.37 | |
| 169 | 247 | | 10.3 | |
| 170 | 361 | | 2.6 | |
| 171 | 189 | | 11.15 | |
| 172 | 270 | | 11.94 | |
| 173 | 958 | | 9.87 | |
| 174 | 465 | | 4.7 | |
| 175 | 1074 | | 7.72 | |
| 176 | 3701 | | 29 | |
| 177 | 125 | | 3.65 | |
| 178 | 154 | | 4.98 | |
| 179 | 276 | | 4.97 | |
| 180 | 177 | | 12.12 | |
| 181 | 522 | | 22.8 | |
| 182 | 1177 | | 38 | |
| 183 | 306 | | 8.64 | |
| 184 | | 35% at 1 μM | 7.89 | |
| 185 | 849 | | 22 | |
| 186 | 1244 | | 24 | |
| 187 | 266 | | 13 | |
| 188 | 340 | | 5.63 | |
| 189 | 11 | | 8.39 | |
| 190 | 87 | | 7.44 | |
| 191 | 437 | | 19 | |
| 192 | 1550 | | 26 | |
| 193 | 1048 | | 11.53 | |
| 194 | 797 | | 16.33 | |
| 195 | 797 | | 16.2 | |
| 196 | 331 | | 20.35 | |
| 197 | 1392 | | 9.86 | |
| 198 | 882 | | 11.1 | |
| 199 | 212 | | 8.67 | |
| 200 | 245 | | 16.4 | |
| 201 | 803 | | 25.16 | |
| 202 | 1271 | | 19.41 | |
| 203 | 624 | | | 48% at 50 μM |
| 204 | 4703 | | | 55% at 50 μM |
| 205 | 2145 | | 4.52 | |
| 206 | 17 | | 8.06 | |
| 207 | 606 | | 8.04 | |
| 208 | 56 | | 8.17 | |
| 209 | 56 | | 7.5 | |
| 210 | 22 | | 1.76 | |
| 211 | 425 | | 5.57 | |
| 212 | 418 | | 1.7 | |
| 213 | 113 | | 3.48 | |
| 214 | 534 | | 1.42 | |
| 215 | 473 | | 3.3 | |
| 216 | 1106 | | 2.52 | |
| 217 | 3006 | | 3.06 | |
| 218 | 5720 | | 2.47 | |
| 219 | 1018 | | 5.31 | |
| 220 | 1465 | | 4.28 | |
| 221 | 351 | | 5.03 | |
| 222 | 1910 | | 3.5 | |
| 223 | 1137 | | 3.94 | |
| 224 | 222 | | 11.56 | |
| 225 | 96 | | | 65% at 50 μM |
| 226 | 229 | | 20.45 | |
| 227 | 1019 | | 4.43 | |
| 228 | 483 | | 4.98 | |
| 229 | 225 | | 4.5 | |
| 230 | 2194 | | 6.02 | |
| 231 | | 54% at 10 μM | 3.24 | |
| 232 | 21 | | 1.23 | |
| 233 | 4302 | | 6.8 | |
| 234 | 74 | | 0.9 | |
| 235 | 871 | | 4.52 | |
| 236 | 579 | | 4.4 | |
| 237 | 426 | | 7.8 | |
| 238 | 234 | | 9.08 | |
| 239 | 100 | | 3.2 | |
| 240 | 145 | | 5.76 | |
| 241 | 213 | | 10.44 | |
| 242 | 164 | | 2.74 | |
| 243 | 347 | | 5.73 | |
| 244 | 116 | | 14.2 | |
| 245 | 24 | | 3.33 | |
| 246 | 432 | | 5.73 | |
| 247 | 228 | | 8.4 | |
| 248 | 147 | | 10.04 | |
| 249 | 44 | | 7.86 | |
| 250 | 64 | | 4.94 | |
| 251 | 55 | | 4.55 | |
| 252 | 308 | | 20.53 | |
| 253 | 50 | | 2.67 | |
| 254 | 57 | | 6.99 | |
| 255 | 18 | | 5.27 | |
| 256 | 216 | | 1.22 | |
| 257 | 159 | | 4.87 | |
| 258 | 149 | | 3.57 | |
| 259 | 66 | | 1.3 | |
| 260 | 1588 | | 17.51 | |
| 261 | 54 | | 3.99 | |
| 262 | 28 | | 6.8 | |
| 263 | 703 | | 9.97 | |
| 264 | 194 | | 5.93 | |
| 265 | 308 | | 21.87 | |
| 266 | 59 | | 14.41 | |
| 267 | 340 | | 3.93 | |
| 268 | 53 | | 5.33 | |
| 269 | 141 | | 9.03 | |
| 270 | 934 | | 13.67 | |
| 271 | 288 | | 4.29 | |
| 272 | 5.4 | | 7.25 | |
| 273 | 767 | | 30.37 | |
| 274 | 624 | | 3.98 | |
| 275 | 175 | | 5.07 | |
| 276 | 161 | | 15.52 | |
| 277 | 131 | | 5.76 | |
| 278 | 43 | | 3.57 | |
| 279 | 116 | | 5.63 | |
| 280 | 536 | | 5.66 | |
| 281 | 297 | | 2.81 | |
| 282 | 152 | | 4.63 | |
| 283 | 750 | | 2.55 | |
| 284 | 160 | | 4.23 | |
| 285 | 150 | | 6.77 | |
| 286 | 27 | | 1.64 | |
| 287 | 142 | | 4.74 | |
| 288 | 241 | | 4.61 | |
| 289 | 418 | | 10.26 | |
| 290 | 183 | | 5.21 | |
| 291 | 638 | | 4.75 | |
| 292 | 161 | | 5.09 | |
| 293 | 2081 | | 14.45 | |
| 294 | 1515 | | 35.26 | |
| 295 | 300 | | 1.68 | |
| 296 | 453 | | 5.34 | |
| 297 | 290 | | 1.21 | |
| 298 | 282 | | 3.58 | |
| 299 | 237 | | | 85% at 100 μM |
| 300 | 89 | | 8.36 | |
| 301 | 1717 | | 51.74 | |
| 302 | 142 | | 18.04 | |
| 303 | 31 | | 9.52 | |
| 304 | 10 | | 1.96 | |
| 305 | 1299 | | 28.02 | |

TABLE 1-continued

| Example | IC50 MNK1 nM | Inhibition of MNK1 activity at indicated concentration | IC50 MiaPaCa μM | Inhibition of MiaPaCa growth at indicated concentration |
|---|---|---|---|---|
| 306 | 179 | | 9.13 | |
| 307 | 256 | | 47.73 | |
| 308 | 28 | | 2.34 | |
| 309 | 61 | | 4.43 | |
| 310 | 135 | | 2.37 | |
| 311 | 105 | | 5.76 | |
| 312 | 171 | | 1.3 | |
| 313 | 282 | | 2.06 | |
| 314 | 302 | | 4.74 | |
| 315 | 87 | | 2.55 | |
| 316 | 55 | | 5.57 | |
| 317 | 312 | | 4.58 | |
| 318 | 296 | | 3.8 | |
| 319 | 38 | | 2.85 | |
| 320 | 94 | | 2.27 | |
| 321 | 175 | | 1.31 | |
| 322 | 153 | | 2.17 | |
| 323 | 211 | | 3.2 | | n.d. = not determined.

It was not possible to determine meaningful results of MNK1 inhibition for Examples 81, 82 and 104 due to fluorescence interfering with the assay system.

The invention claimed is:

1. A compound of formula I:

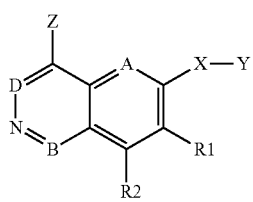

(I)

wherein:
A is N,
B is CR; and
D is CR;
R represents, independently at each occurrence, hydrogen, OH or NH$_2$;
R1 and R2, independently of each other, represent hydrogen, N(R3)$_2$, halogen, cyano, nitro, R4-C1-C4alkyl, R4-C1-C4halogenoalkyl, OH, R4-C1-C4alkoxy, R4-C1-C4halogenoalkoxy, SH, R4-C1-C4alkythio, R4-C1-C4halogenoalkylthio;
R3 represents, independently at each occurrence, hydrogen, R4-C1-C4alkyl or R4-C1-C4halogenoalkyl;
R3a represents, independently at each occurrence, hydrogen or C1-C4 alkyl;
R4 represents, independently at each occurrence, hydrogen, halogen, cyano, OH, SH, NH$_2$, NH(CH$_3$) or N(CH$_3$)$_2$;
X represents a group of formula -E- or -E-F—, wherein E and F are different from each other and represent a group selected from —C(R3a)$_2$-, —(C═O)—, —NR3a- and —O— and F is linked to Y, with the proviso that if X represents -E-F— one of E or F represents —C(R3a)$_2$- or —(C═O)—;
Y represents a group selected from mono- or bicyclic C3-C11cycloalkyl, which may be partially unsaturated, mono- or bicyclic 3 to 11-membered heterocycloalkyl, which may be partially unsaturated, a mono- or bicyclic group comprising at least one heteroaryl cycle, wherein said heterocycloalkyl group and said mono- or bicyclic group comprising at least one heteroaryl cycle comprise one or more heteroatoms selected from nitrogen, oxygen and sulfur and Y is either unsubstituted or substituted by one or more substituents and comprises including its substituents one or more than one nitrogen atom having a lone electron pair; and
Z represents a mono- or bicyclic group comprising at least one aryl or heteroaryl cycle, said heteroaryl cycle comprising one or more heteroatoms selected from nitrogen, oxygen and sulfur, which aryl or heteroaryl group is unsubstituted or substituted by one or more substituents;
including tautomers of said compound, mixtures of two tautomeric forms of said compound, or a pharmaceutically acceptable salt of said compound, including tautomers thereof or mixtures of two tautomeric forms thereof;
with the proviso that Y comprises one or more primary amino group —NH$_2$ when X represents —(C═O)— or —(C═O)—NR3a-, wherein R3a represents hydrogen or C1-C4alkyl.

2. The compound according to claim 1 or a pharmaceutically acceptable salt thereof, wherein Y comprises one or more primary amino group —NH$_2$.

3. The compound according to claim 1 or a pharmaceutically acceptable salt thereof, wherein X represents a group of formula -E- or -E-F—, wherein E and F are different from each other and represent a group selected from —C(R3a)$_2$-, —NR3a- and —O— and F is linked to Y, with the proviso that if X represents -E-F— one of E or F represents —C(R3a)$_2$-.

4. The compound according to claim 1 or a pharmaceutically acceptable salt thereof, wherein A is N, B is CR and D is CH.

5. The compound according to claim 1 or a pharmaceutically acceptable salt thereof, wherein:
X represents a spacer group of formula -E-, wherein
E represents —C(R3a)$_2$-, —NR3a- or —O—, and
R3a represents hydrogen or methyl.

6. The compound according to claim 5 or a pharmaceutically acceptable salt thereof, wherein:
X represents —CH$_2$—, —NH— or —O—.

7. The compound according to claim 1 or a pharmaceutically acceptable salt thereof, wherein:
X represents —CH$_2$—, —NH— or —O—; and
Y comprises one or more primary amino group —NH$_2$.

8. The compound according to claim 1 or a pharmaceutically acceptable salt thereof, wherein Y comprises one or more structural element of formula:

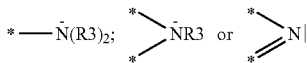

wherein R3 has the meaning as defined in claim 1 and «—» indicates a lone electron pair at the nitrogen atom and «*» indicates a chemical bond to a further atom.

9. The compound according to claim 1 or a pharmaceutically acceptable salt thereof, wherein:
Y is unsubstituted or substituted by one, two or more substituents selected from halogen, cyano, nitro, —(C═O)—R3, —(C═O)—OR3, —N(R3)$_2$, —(C═O)—N(R3)$_2$, —NR3—(C═O)—R3, —NR3—

(C=O)—OR3, R4-C1-C4alkyl, R4-C1-C4halogenoalkyl, OH, SH, R4-C1-C4alkoxy, R4-C1-C4halogenoalkoxy, R4-C1-C4alkylthio and R4-C1-C4halogenoaklthio, as well as oxo in case that the substituent is not located at an aryl or heteroaryl cycle.

10. The compound according to claim 1 or a pharmaceutically acceptable salt thereof, wherein:

Z is unsubstituted or substituted by one, two or more substituents selected from halogen, cyano, nitro, R4-C1-C4alkyl, R4-C1-C4halogenoalkyl, OH, SH, R4-C1-C4alkoxy, R4-C1-C4halogenoalkoxy, R4-C1-C4alkyithio, R4-C1-C4halogenoalkylthio, —(C=O)—R3, —(C=O)—OR3, —N(R3)$_2$, —(C=O)—(R3)$_2$, —N(R3)—(C=O)—R3, —N(R3)—(C=O)—N(R3)$_2$— and —N(R3)—(C=O)—NR3—Z1, wherein Z1 represents C3-C6cycloalkyl, phenyl or 5- to 6-membered heteroaryl comprising one or more heteroatoms selected from nitrogen, oxygen and sulfur and is unsubstituted or substituted by one, two or more substituents selected from halogen, cyano, R4-C1-C4alkyl, R4-C1-C4halogenoalkyl, OH, R4-C1-C4alkoxy and R4-C1-C4halogenoalkoxy.

11. The compound according to claim 1 or a pharmaceutically acceptable salt thereof, wherein:

Y is selected from:

(B) a group, which is unsubstituted or substituted by one, two or more substituents selected from halogen, cyano, nitro, —(C=O)—R3, —(C=O)—OR3, —N(R3)$_2$, —(C=O)—N(R3)$_2$, —NR3—(C=O)—R3, —NR3—(C=O)—OR3, R4-C1-C4alkyl, R4-C1-C4halogenoalkyl, OH, SH, R4-C1-C4alkoxy, R4-C1-C4halogenoalkoxy, R4-C1-C4alkylthio and R4-C1-C4halogenoalkylthio, as well as oxo, and which is saturated or partially unsaturated and selected from the groups of formula:

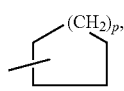
(Ba)

wherein p is 0, 1, 2 or 3;

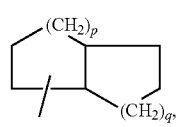
(Bb)

wherein p and q are independently selected from 0, 1, 2 and 3 so that (p+q) is 0 to 4 and the linking bond may be located at both cycles of the group;

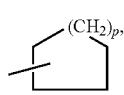
(Bc)

wherein p is 0, 1, 2 or 3 and wherein 1, 2 or 3 ring carbon atoms are replaced by nitrogen atoms and one ring carbon ring atom may furthermore be replaced by a sulfur or an oxygen atom and the number of remaining ring carbon atoms is at least 2;

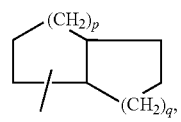
(Bd)

wherein p and q are independently selected from 0, 1, 2 and 3 so that (p+q) is 0 to 4, the linking bond may be located at both cycles of the group and wherein 1 to 4 ring carbon atom of the group are replaced by nitrogen atoms and one ring carbon ring atom per cycle of the group may furthermore be replaced by a sulfur or an oxygen atom so that the number of remaining ring carbon atoms per cycle of the group is at least 2;

(D) a heteroaryl group, which is unsubstituted or substituted and selected from the groups of formula:

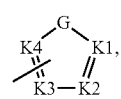
(Da)

wherein G is selected from NR3, O and S and one or two of K1, K2, K3 and K4 may be nitrogen and all others are selected from CH and C substituted by a substituent selected from halogen, cyano, nitro, —(C=O)—R3, —(C=O)—OR3, —N(R3)$_2$, —(C=O)—N(R3)$_2$, —NR3—(C=O)—R3, —NR3—(C=O)—OR3, R4-C1-C4alkyl, R4-C1-C4halogenoalkyl, OH, SH, R4-C1-C4alkoxy, R4-C1-C4halogenoalkoxy, R4-C1-C4alkylthio and R4-C1-C4ha- logenoalkylthio;

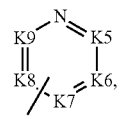
(Db)

wherein one or two of K5, K6, K7, K8 and K9 may be nitrogen and all others are selected from CH and C substituted by a substituent selected from halogen, cyano, nitro, —(C=O)—R3, —(C=O)—OR3, —N(R3)$_2$, —(C=O)—N(R3)$_2$, —NR3—(C=O)—R3, —NR3—(C=O)OR3, R4-C1-C4alkyl, R4-C1-C4halogenoalkyl, OH, SH, R4-C1-C4alkoxy, R4-C1-C4halogenoalkoxy, R4-C1-C4alkylthio and R4-C1-C4halogenoalkylthio;

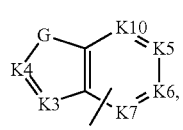
(Dc)

wherein G is selected from NR3, O and S and one of K3 and K4 may be nitrogen, CH or C substituted by a substituent selected from halogen, cyano, nitro, —(C=O)—R3, —(C=O)—OR3, —N(R3)$_2$, —(C=O)—N(R3)$_2$, —NR3—(C=O)—R3, NR3—(C=O)—OR3, R4-C1-C4alkyl, R4-C1-C4halogenoalkyl, OH, SH, R4-C1-C4alkoxy, R4-C1-C4halogenoalkoxy, R4-C1-C4alkylthio and R4-C1-C4halogenoalkylthio, and the other is CH or C substituted by a substituent selected from halogen, cyano, nitro, —(C=O)—R3, —(C=O)—OR3, —N(R3)$_2$, —(C=O)—N(R3)$_2$, —NR3—(C=O)—R3, —NR3—(C=O)—OR3, R4-C1-C4alkyl, R4-C1-C4halogenoalkyl, OH, SH, R4-C1-C4alkoxy, R4-C1-C4halogenoalkoxy, R4-C1-C4alkylthio and R4-C1-C4halogenoalkylthio, and one or two of K5, K6, K7, and K10 may be nitrogen and all others are selected from CH and C substituted by a substituent selected from halogen, cyano, nitro, —(C=O)—R3, —(C=O)—OR3, —N(R3)$_2$, —(C=O)—N(R3)$_2$, —NR3—(C=O)—R3, —NR3—(C=O)—OR3, R4-C1-C4alkyl, R4-C1-C4halogenoalkyl, OH, SH, R4-C1-C4alkoxy, R4-C1-C4halogenoalkoxy, R4-C1-C4alkylthio and R4-C1-C4halogenoalkylthio, and the linking bond may be located at both cycles of the group; and

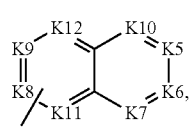

(Dd)

wherein one of K5, K6, K7, K8, K9, K10, K11 and K12 is nitrogen and one of the others in the same cycle and two of the others in the other cycle may also be nitrogen and all others in both cycles are selected from CH and C substituted by a stibstituent selected from halogen, cyano, nitro, —(O=O)—R3, —(C=O)—OR3, —N(R3)$_2$, —(C=O)—N(R3)$_2$, —NR3—(C=O)—R3, —NR3—(C=O)—OR3, R4-C1-C4alkyl, R4-C1-C4halogenoalkyl, OH, SH, R4-C1-C4alkoxy, R4-C1-C4halogenoalkoxy, R4-C1-C4alkylthio and R4-C1-C4halogenoalkylthio, and the linking bond may be located at both cycles of the group.

12. The compound according to claim 1 or a pharmaceutically acceptable salt thereof wherein:

Y is selected from substituted monocyclic saturated 5-, 6- or 7-membered cycloalkyl, which comprise at least one substituent selected from NH$_2$, NH(CH$_3$)and N(CH$_3$)$_2$; unsubstituted or substituted, monocyclic saturated 5-, 6- or 7-membered heterocycloalkyl, which comprises 1 or 2 nitrogen heteroatoms and optionally at least one substituent selected from NH$_2$, NH(CH$_3$) and N(CH$_3$)$_2$; and an unsubstituted or substituted mono- or bicyclic heteroaryl group, which comprises 1 or 2 nitrogen heteroatoms per cycle present in said heteroaryl group and optionally at least one substituent selected from NH$_2$, NH(CH$_3$) and N(CH$_3$)$_2$.

13. The compound according to claim 1 or a pharmaceutically acceptable salt thereof, wherein:

Z is selected from a monocycle aryl group or a bicycle group comprising at least one aryl cycle having 6 to 10 ring atoms; as well as a monocycle heteroaryl group and a bicyclic group comprising at least one heteroaryl group and having 5 to 10 ring atoms, wherein a heteroaryl cycle comprises 1 to 3 heteroatoms and said groups Z are unsubstituted or substituted by one or more substituents selected from halogen, cyano, nitro, R4-C1-C4alkyl, R4-C1-C4halogenoalkyl, OH, SH, R4-C1-C4alkoxy, R4-C1-C4halogenoalkoxy, R4-C1-C4alkylthio, R4-C1-C4halogenoalkylthio, —(C=O)—R3, —(C=O)—OR3, —N(R3)$_2$, —(C=O)—N(R3)$_2$, —N(R3)—(C=O)—R3, —N(R3)—(C=O)—N(R3)$_2$ and —N(R3)—(C=O)—NR3—Z1, wherein Z1 represents C3-C6cycloalkyl, phenyl or 5- to 6-membered heteroaryl comprising one or more heteroatoms selected from nitrogen, oxygen and sulfur and is unsubstituted or substituted by one, two or more substituents selected from halogen, cyano, R4-C1-C4alkyl, R4-C1-C4halogenoalkyl, OH, R4-C1-C4alkoxy and R4-C1C4halogenoalkoxy.

14. The compound according to claim 1 or a pharmaceutically acceptable salt thereof, wherein:

Z is selected from:

(E) an unsubstituted aryl group or an aryl group substituted by one, two or more substituents selected from halogen, cyano, nitro, R4-C1-C4alkyl, R4-C1-C4halogenoalkyl, OH, SH, R4-C1-C4alkoxy, R4-C1-C4halogenoalkoxy, R4-C1-C4alkylthio, R4-C1-C4halogenoalkylthio, —(C=O)—R3, —(C=O)—OR3, —N(R3)$_2$, —(C=O)—N(R3)$_2$, —N(R3)—(C=O)—R3, —N(R3)—(C=O)—N(R3)$_2$ and —N(R3)—(C=O)—NR3—Z1, wherein Z1 represents C3-C6cycloalkyl, phenyl or 5- to 6-membered heteroaryl comprising one or more heteroatoms selected from nitrogen, oxygen and sulfur and is unsubstituted or substituted by one, two or more substituents selected from halogen, cyano, R4-C1-C4alkyl, R4-C1-C4halogenoalkyl, OH, R4-C1-C4alkoxy and R4-C1-C4halogenoalkoxy, said aryl group being selected from (Ea): phenyl and (Eb): naphthyl; and (F) an unsubstituted heteroaryl group or a heteroaryi group substituted by one, two or more substituents selected from halogen, cyano, nitro, R4-C1-C4alkyl, R4-C1-C4halogenoalkyl, OH, SH, R4-C1-C4alkoxy, R4-C1-C4halogenoalkoxy, R4-C1-C4alkylthio, R4-C1-C4halogenoalkylthio, —(C=O)—R3, —(C=O)—OR3, —N(R3)$_2$, —(C=O)—N(R3)$_2$, —N(R3)$_2$, —(C=O)—R3, —N(R3)—(C=O)—N(R3)$_2$ and —N(R3)—(C=O)—NR3—Z1, wherein Z1 represents C3-C6cycloalkyl, phenyl or 5- to 6-membered heteroaryl comprising one or more heteroatoms selected from nitrogen, oxygen and sulfur and is unsubstituted or substituted by one, two or more substituents selected from halogen, cyano, R4-C1-C4alkyl, R4-C1-C4halogenoalkyl, OH, R4-C1-C4alkoxy and R4-C1-C4halogenoalkoxy, said heteroaryl group being selected from the groups of formula:

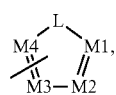

(Fa)

wherein L is selected from NR3, O and S and one or two of M1, M2, M3 and M4 may be nitrogen and all others are selected from CH and C substituted by a substituent selected from halogen, cyano, nitro, R4-C1-C4alkyl, R4-C1-C4halogenoalkyl, OH,SH, R4-C1-C4alkoxy, R4-C1-C4halogenoalkoxy, R4-C1-C4aklylthio, R4-C1-C4halogenoalkythio, —(C=O)—R3, —(C=O)—OR3, —N(R3)$_2$, —(C=O)—N(R3)$_2$, —N(R3)—(C=O)—R3, —N(R3)—(C=O)—N(R3)$_2$ and —N(R3)—(C=O)—NR3—Z1, wherein Z1 represents C3-C6cycloakyl, phenyl or 5- to 6-membered heteroaryl comprising one or more heteroatoms selected from nitrogen, oxygen and sulfur and is unsubstituted or substituted bv one two or more substituents selected from halogen, cyano, R4-C1-C4alkyl, R4-C1-C4halogenoalkyl, OH, R4-C1C4alkoxy and R4-C1-C4halogenoalkoxy;

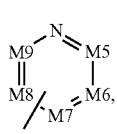

(Fb)

wherein one or two of M5, M6, M7, M8 and M9 may be nitrogen and all others are selected from CH and C substituted by a substituent selected from halogen, cyano, nitro, R4-C1-C4alkyl, R4-C1-C4halogenoalkyl, OH, SH, R4-C1-C4alkoxy, R4-C1-C4halogenoalkoxy, R4-C1-C4alkylthio, R4-C1-C4halogeno alkylthio, —(C=O)—R3, —(C=O)—OR3, —N(R3)$_2$, —(C=O)—N(R3)$_2$, —N(R3)—(C=O)—R3, —N(R3)—(C=O)—N(R3)$_2$ and —N(R3)—(C=O)—NR3—Z1, wherein Z1 represents C3-C6cycloalkyl, phenyl or 5- to 6-membered heteroaryl comprising one or more heteroatoms selected from nitrogen, oxygen and sulthr and is unsubstituted or substituted by one, two or more substituents selected from halogen, cyano, R4-C1-C4alkyl, R4-C1-C4halogenoalkyl, OH, R4-C1-C4alkoxy and R4-C1-C4halogenoalkoxy;

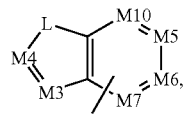

(Fc)

wherein L is selected from NR3, O and S, one of M3 and M4 may be nitrogen, CH or C substituted by a substituent selected from halogen, cyano, nitro, R4-C1-C4alkyl, R4-C1-C4halogenoalkyl, OH, SH, R4-C1-C4alkoxy, R4-C1-C4halogenoalkoxy, R4-C1-C4alkylthio, R4-C1-C4halogenoalkylthio, —(C=O)—R3, —(C=O)—OR3, —N(R3)$_2$, —(C=O)—N(R3)$_2$, —N(R3)—(C=O)—R3, —N(R3), —(C=O)—N(R3)$_2$ and —N(R3)—(C=O)—NR3—Z1, wherein Z1 represents C3-C6cycloalkyl, phenyl or 5 to 6-membered heteroaryl comprising one or more heteroatoms selected from nitrogen, oxygen and sulfur and is unsubstituted or substituted by one, two or more substituents selected from halogen, cyano, R4-C1-C4alkyl, R4-C1-C4halogenoalkyl, OH, R4-C1-C4alkoxy and R4-C1-C4halegenoalkoxy, the other is CH and C substituted by a substituent selected from halogen, cyano, nitro, R4-C1-C4alkyl, R4-C1-C4halogenoalkyl, OH, SH, R4-C1-C4alkoxy, R4-C1-C4halogenoalkoxy, R4-C1-C4alkylthio, R4-C1-C4halogenoalkylthio, —(C=O)—R3, —(C=O)—OR3, —N(R3)$_2$, —(C=O)—N(R3)$_2$, —N(R3)—(C=O)—R3, —N(R3)—(C=O)—N(R3)$_2$ and —N(R3)—(C=O)—NR3—Z1, wherein Z1 represents C3-C6cycloalkyl, phenyl or 5- to 6-membered heteroaryl comprising one or more heteroatoms selected from nitrogen, oxygen and sulfur and is unsubstituted or substituted by one, two or more substituents selected from halogen, cyano, R4-C1-C4alkyl, R4-C1-C4halogenoalkyl, OH, R4-C1-C4alkoxy and R4-C1-C4halogenoalkoxy, and one or two of M5, M6, M7, and M10 may be nitrogen and all others are selected from CH and C substituted by a substituent selected from halogen, cyano, nitro, R4-C1-C4alkyl, R4-C1-C4halogenoalkyl, OH, SH, R4-C1-C4alkoxy, R4-C1-C4halogenoalkoxy, R4-C1-C4alkylthio, R4-C1-C4halogenoalkylthio, —(C=O)—R3, —(C=O)—OR3, —N(R3)$_2$, —(C=O)—N(R3)$_2$, —N(R3)—(C=O)—R3, —N(R3)—(C=O)—N(R3)$_2$ and —N(R3)—(C=O)—NR3—Z1, wherein Z1 represents C3-C6cycloalkyl, phenyl or 5- to 6-membered heteroaryl comprising one or more heteroatoms selected from nitrogen, oxygen and sulfur and is unsubstituted or substituted by one, two or more substituents selected from halogen, cyano, R4-C1-C4alkyl, R4-C1-C4halogenoalkyl, OH, R4-C1-C4alkoxy and R4-C1-C4halogenoalkoxy, and the linking bond may be located at both cycles of the group; and

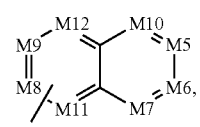

(Fd)

wherein one of M5, M6, M7, M8, M9, M10, M11 and M12 may be nitrogen and one of the others in the same cycle and two of the others in the other cycle may also be nitrogen and all others in both cycles are selected from CH and C substituted by a substituent selected from halogen, cyano, nitro, R4-C1-C4alkyl, R4-C1-C4halogenoalkyl, OH, SH, R4-C1-C4alkoxy, R4-C1-C4halogenoalkoxy, R4-C1-C4alkylthio, R4-C1-C4halogenoalkylthio, —(C=O)—R3, —(C=O)—OR3, —N(R3)$_2$, —(C=O)—N(R3)$_2$, —N(R3)—(C=O)—R3, —N(R3)—(C=O)—N(R3)$_2$ and —N(R3)—(C=O)—NR3—Z1, wherein Z1 represents C3-C6cycloalkyl, phenyl or 5- to 6-membered heteroaryl comprising one or more heteroatoms selected from nitrogen, oxygen and sulfur and is unsubstituted or substituted by one, two or more substituents selected from halogen, cyano, R4-C1-C4alkyl, R4-C1-C4halogenoalkyl, OH, R4-C1-C4alkoxy and R4-C1-C4halogenoalkoxy, and the linking bond may be located at both cycles of the group.

15. The compound according to claim 1 or a pharmaceutically acceptable salt thereof, wherein:

Y is selected from cyclopentyl, cyclohexyl, pyrrolidinyl, piperidinyl, piperazinyl, morpholinyl, pyrazolyl, pyridinyl, pyrirnidinyl, pyridazinyl, 1-H-pyrrolo[3,2-c]

pyridine, 3H-pyrrolo[2,3-c]pyridin-1-yl, which are unsubstituted or substituted by one or two groups selected from fluoro, chloro, cyano, nitro, C1-C2alkyl, C1-C2fluoroalkyl, C1-C2alkoxy, C1-C2fluoroalkoxy, —NH₂, —NH(CH₃), —N(CH₃)₂, H₂N—C1-C2 alkyl, H₂N—C1-C2fluoro-alkyl, —OH and oxo, wherein when Y is not substituted by oxo when aromatic or heteroaromatic.

16. The compound according to claim 1 or a pharmaceutically acceptable salt thereof, wherein:
Y is selected from 3-aminocyclopentyl, 3- or 4-aminocyclohexyl and 4-aminopiperidin-1-yl.

17. The compound according to claim 1 or a pharmaceutically acceptable salt thereof, wherein:
Z is selected from phenyl, naphthyl and a group of one of the formulae;

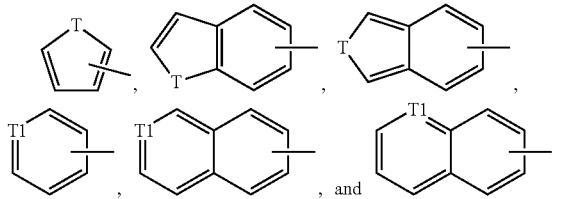

wherein T represents a group selected from NH and N(CH₃), or an O — or S-atom; T1 represents a N-atom; the free valence can be located at any of the ring carbon atoms of the entire group Z; and
wherein one to three of the ring carbon atoms can furthermore be replaced by a N-atom, and wherein group Z is unsubstituted or substituted by one to three groups selected from halogen, C1-C4alkyl and C1-C4alkoxy.

18. The compound according to claim 1 or a pharmaceutically acceptable salt thereof; wherein:
Z is selected from phenyl, which is unsubstituted or substituted by Cl or F, and benzofuran-2-yl.

19. The compound according to claim 1 or a pharmaceutically acceptable salt thereof, wherein:
X-Y is selected from

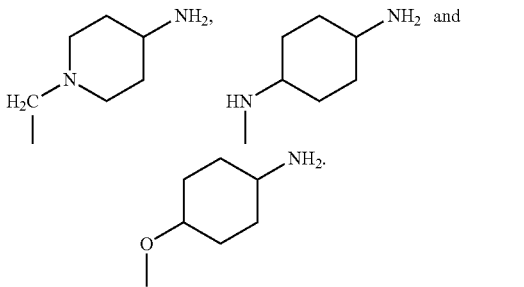

20. The compound according to claim 1 or a pharmaceutically acceptable salt thereof, wherein:
A is N, B is CR and D is CH;
R represents hydrogen, OH or NH₂;
R1 and R2, independently of each other, represent hydrogen, N(R3)₂, halogen, cyano, nitro, R4-C1-C4alkyl, R4-C1-C4halogenoalkyl, OH, R4-C1-C4alkoxy, R4-C1-C4halogenoalkoxy;
R3 represents, independently at each occurrence, hydrogen, R4-C1-C4alkyl or R4-C1-C4halogenoalkyl;
R3a represents, independently at each occurrence, hydrogen or methyl;
R4 represents, independently at each occurrence, hydrogen, halogen, cyano, OH, NH₂, NH(CH₃) or N(CH₃)₂;
X represents C(R3a)₂-, —NR3a- or —O—;
Y is selected from substituted monocyclic saturated 5-, 6- or 7-membered cycloalkyl, which comprise at least one substituent selected from NH₂, NH(CH₃) and N(CH₃)₂, unsubstituted or substituted, monocyclic saturated 5-, 6- or 7-membered heterocycloalkyl, which comprises 1 or 2 nitrogen heteroatoms and optionally at least one substituent selected from NH₂, NH(CH₃) and N(CH₃)₂, and an unsubstituted or substituted mono- or bicyclic heteroaryl group, which comprises 1 or 2 nitrogen heteroatoms per cycle present in said heteroaryl group and optionally at least one substituent selected from NH₂, NH(CH₃) and N(CH₃)₂;
Z is selected from:
(E) an unsubstituted aryl group or an aryl group substituted as defined below, said aryl group being selected from
(Ea): phenyl and
(Eb): naphthyl; and
(F) an unsubstituted heteroaryl group or a heteroaryl group substituted as defined below, said heteroaryl group being selected from the groups of formula:

(Fa)

wherein L is selected from NR3, O and S and one or two of M1, M2, M3 and M4 may be nitrogen and all others are selected from CH and C substituted as defined below;

(Fb)

wherein one or two of M5, M6, M7, M8 and M9 may be nitrogen and all others are selected from CH and C substituted as defined below;

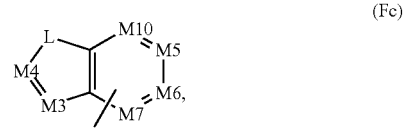
(Fc)

wherein L is selected from NR3, O and S, one of M3 and M4 may be nitrogen, CH or C substituted as defined below, the other is CH or C substituted as defined below and one or two of M5, M6, M7, and M10 may be nitrogen and all others are selected from CH and C substituted as defined below, and the linking bond may be located at both cycles of the grow; and

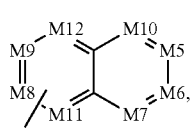
(Fd)

wherein one of M5, M6, M7, M8, M9, M10, M11 and M12 may be nitrogen and one of the others in the same cycle and two of the others in the other cycle may also be nitrogen and all others in both cycles are selected from CH and C substituted as defined below, and the linking bond may be located at both cycles of the group; and when substituted group Z is substituted by one, two or more substituents selected from halogen, cyano, nitro, R4-C1-C4alkyl, R4-C1-C4halogenoalkyl, OH, R4-C1-C4alkoxy, R4-C1-C4halogenoalkoxy, R4-C1-C4alkylthio, R4-C1-C4halogenoalkylthio, —(C=O)—R3; —(C=O)—OR3, —N(R3)2, —(C=O)—N(R3)$_2$, —N(R3)—(C=O)—R3, —N(R3)—(C=O)—N(R3)$_2$ or a group —N(R3)—(C=O)—NR3—Z1; wherein Z1 represents C3-C6cycloalkyl, phenyl or 5- to 6-membered heteroaryl comprising one or more heteroatoms selected from nitrogen, oxygen and sulfur, and is unsubstituted or substituted by one, two or more substituents selected from halogen, cyano, nitro, R4-C1-C4alkyl, R4-C1-C4halogenoalkyl, OH, R4-C1-C4alkoxy and R4-C1-C4halogenoalkoxy.

21. The compound according to claim 1 or a pharmaceutically acceptable salt thereof, having the formula I-3;

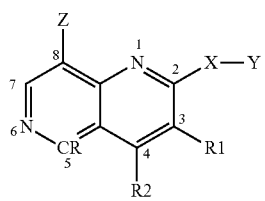
(I-3)

wherein

R represents hydrogen, OH or NH$_2$;

R1 and R2, independently of each other, represent hydrogen, halogen, NH$_2$, C1-C4alkyl, C1-C4halogenalkyl, C1-C4alkoxy, or C1-C4halogenalkoxy;

R3 represents, independently at each occurrence, hydrogen or methyl;

R3a represents, independently at each occurrence, hydrogen or methyl;

R4 represents independently at each occurrence hydrogen, halogen, cyano, OH, NH$_2$, NH(CH$_3$) or N(CH$_3$)$_2$;

X represents C(R3a)$_2$-, —NR3a- or —O—;

Y is selected from substituted monocyclic saturated 5-, 6- or 7-membered cycloalkyl, which comprise at least one substituent selected from NH$_2$, NH(CH$_3$) and N(CH$_3$)$_2$, unsubstituted or substituted, monocyclic saturated 5-, 6- or 7-membered heterocycloalkyl, which comprises 1 or 2 nitrogen heteroatoms and optionally at least one substituent selected from NH$_2$, NH(CH$_3$) and N(CH$_3$)$_7$, and an unsubstituted or substituted mono- or bicyclic heteroaryl group, which comprises 1 or 2 nitrogen heteroatoms per cycle present in said heteroaryl group and optionally at least one substituent selected from NH$_2$, NH(CH$_3$) and N(CH$_3$)$_2$;

and wherein group Y may be additionally substituted by one group selected from C1-C4alkyl, hydroxy, nitro, C1-C4alkoxy, C1-C4fluoroalkyl, cyano, halogen, and C1-C4alkoxycarbonyl:

Z is selected from:

(E) an unsubstituted aryl group or an aryl group substituted as defined below, said aryl group being selected from (Ea): phenyl: and (F) an unsubstituted heteroaryl group or a heteroaryl group substituted as defined below, said heteroaryl group being selected from the groups of formula:

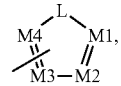
(Fa)

wherein L is selected from NH, O and S and one or two of M1, M2, M3 and M4 may be nitrogen and all others are selected from CH and C substituted as defined below;

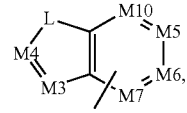
(Fc)

wherein L is selected from NH, O and S, one of M3 and M4 may be nitrogen, CH or C substituted as defined below, the other is CH or C substituted as defined below and one or two of M5, M6, M7, and M10 may he nitrogen and all others are selected from CH and C substituted as defined below, and the linking bond may be located at both cycles of the group; and when substituted group Z is substituted by one, two or more substituents selected from halogen, cyano, nitro, R4-C1-C4alkyl, R4-C1-C4halogenoalkyl, OH, N(R3)$_2$, and R4-C1-C4alkoxy.

22. The compound according to claim 1 or a pharmaceutically acceptable salt thereof, having the formula I-3

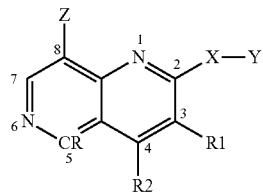
(I-3)

wherein:

R represents hydrogen or NH$_2$;

R1 and R2, independently of each other, represent hydrogen, N(R3)$_2$, halogen, cyano, nitro, C1-C4halogenoalkyl, OH, C1-C4alkoxy or C1-C4halogenoalkoxy;

R3 represents, independently at each occurrence, hydrogen or C1-C4alkyl;

X represents —CH₂—, —NH— or —O—;

Y is selected from substituted monocyclic saturated 5-, 6- or 7-membered cycloalkyl, which comprise one substituent selected from NH₂, NH(CH₃) and N(CH₃)₂, unsubstituted or substituted, monocyclic saturated 5-, 6- or 7-membered heterocycloalkyl, which comprises 1 or 2 nitrogen heteroatoms and, when substituted, one substituent selected from NH₂, NH(CH₃) and N(CH₃)₂, and an unsubstituted or substituted 5 or 6-membered monocyclic heteroaryl group, which comprises 1 or 2 nitrogen heteroatoms and, when substituted, one substituent selected from NH₂, NH(CH₃) and N(CH₃)₂;

Z is selected from phenyl and a group of one of the formulae:

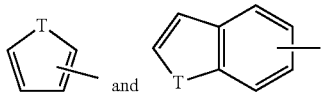

wherein T represents a group selected from NH and N(CH₃), or an O- or S-atom, the free valence can be located at any of the ring atoms of the entire group Z including the group T if T is not an O- or S-atom; and wherein one to three of the ring carbon atoms can furthermore be replaced by a N-atom, and wherein group Z is unsubstituted or substituted by one to three groups selected from halogen, C1-C4alkyl and C1-C4alkoxy.

23. A pharmaceutical composition, comprising a compound according to claim 1, tautomers of said compound, mixtures of two tautomeric forms of said compound, a pharmaceutically acceptable salt of said compound, tautomers thereof or mixtures of two tautomeric forms thereof, and a pharmaceutically acceptable carrier.

24. A compound of formula I-3:

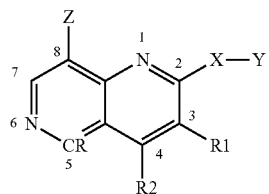

(I-3)

wherein:

R represents hydrogen or —NH₂;

R1 and R2, independently of one another, represent hydrogen, fluoro, chloro, hydroxy, methoxy, ethoxy, propoxy, —NH₂ or nitro;

X—Y is selected from

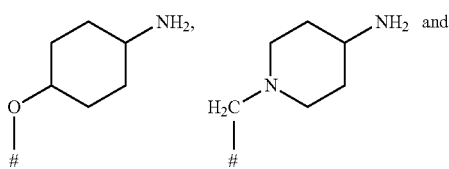

-continued

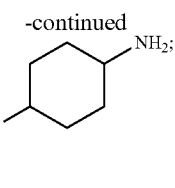

Z is selected from phenyl, which is unsubstituted of substituted by one or two substituents selected from fluoro and chloro; and a group of one of the formulae

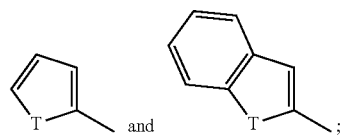

T is selected from an O- or S-atom, including tautomers of said compound, mixtures of two tautomeric forms of said compound, or a pharmaceutically acceptable salt of said compound, including tautomers thereof or mixtures of two tautomeric forms thereof.

25. The compound according to claim 24 or a pharmaceutically acceptable salt thereof, having the formula I-3 and wherein Z is an unsubstituted group selected from phenyl, furan-2-yl, thiophen-2yl and benzofuran-2-yl.

26. The compound according to claim 7 or a pharmaceutically acceptable salt thereof, wherein there are at least three concatenated atoms between at least one of said primary amino groups and the X—Y bond.

27. The compound according to claim 9 or a pharmaceutically acceptable salt thereof; wherein Y is unsubstituted or substituted by one substituent.

28. The compound according to claim 10 or a pharmaceutically acceptable salt thereof, wherein Z is unsubstituted or substituted by one substituent and Z1 represents C3-C6cycloalkyl, phenyl or 5- to 6-membered heteroaryl comprising one or two heteroatoms selected from nitrogen, oxygen and sulfur, and is unsubstituted or substituted by one, two or more substituents selected from halogen, cyano, R4-C1-C4alkyl, R4-C1-C4halogenoalkyl, OH, R4-C1-C4alkoxy and R4-C1-C4halogenoalkoxy.

29. The compound according to claim 11 or a pharmaceutically acceptable salt thereof, wherein NR3 is NH.

30. The compound according to claim 13 or a pharmaceutically acceptable salt thereof, wherein Z is selected from a monocyclic aryl group or a bicyclic group comprising two aryl cycles, and having 6 to 10 ring atoms, as well as a monocyclic heteroaryl group and a bicyclic group comprising at least one heteroaryl group fused with a further aryl or heteroaryl group, and having 5 to 10 ring atoms, wherein a heteroaryl cycle comprises 1 or 2 heteroatoms, and said groups Z are unsubstituted or substituted by one or more substituents selected from halogen, cyano, nitro, R4-C1-C4alkyl, R4-C1-C4halogenoalkyl, OH, SB, R4-C1-C4alkoxy, R4-C1-C4halogenoalkoxy, R4-C1-C4alkylthio, R4-C1-C4halogenoalkythio, —(C═O)—R3, —(C═O)—OR3, —N(R3)₂, —(C═O)—N(R3)₂, —N(R3)—(C═O)—R3, —N(R3)—(C═O)—N(R3)₂ and —N(R3)—(C═O)—NR3—Z1, wherein Z1 represents C3-C6cycloalkyl, phenyl or 5- to 6-membered heteroaryl comprising one or more heteroatoms selected from nitrogen, oxygen and sulfur and is substituted or substituted by one, two or more substituents selected from halogen, cyano, R4-C1-C4alkyl, R4-C1-C4halogenoalkyl, OH, R4-C1-C4alkoxy and R4-C1-C4halogenoalkoxy.

31. The compound according to claim 14 or a pharmaceutically acceptable salt thereof, wherein NR3 is NH.

32. The compound according to claim 15 or a pharmaceutically acceptable salt thereof, wherein Y is pyrrolidin-1-yl, pyrrolidin-3, piperidin-1-yl, piperidin-3-yl, piperidin 4-yl, piperazin-1-yl, morpholin-4-yl, pyrazol-5-yl, pyridinium-1-yl, pyridin-3-yl, pyridin-4-yl, or pyridazinium-1-yl.

33. The compound according to claim 20 or a pharmaceutically acceptable salt thereof, wherein NR3 is NH and when substituted group Z is substituted by one substituent selected from halogen, cyano, nitro, R4-C1-C4alkyl, R4-C1-C4halogenoalkyl, OH, R4-C1-C4alkoxy, R4-C1-C4halogenoalkoxy, R4-C1-C4alkylthio, R4-C1-C4halogem- alkylthio, —(C=O)—R3; —(C=O)—OR3, —N(R3)$_2$, —(C=O)—N(R3)$_2$, —N(R3)—(C=O)—R3, —N(R3)—(C=O)—N(R3)$_2$ or a group —N(R3)—(C=O)—NR3-Z1, wherein Z1 represents C3-C6cycloalkyl, phenyl or 5- to 6-membered heteroaryl comprising one or two heteroatoms selected from nitrogen, oxygen and sulfur and is unsubstituted or substituted by one, two or more substituents selected from halogen, cyano, nitro, R4-C1-C4alkyl, R4-C1-C4halogenoalkyl, OH, R4-C1-C4alkoxy and R4-C1-C4halogenoalkoxy.

34. The compound according to claim 21 or a pharmaceutically acceptable salt thereof, wherein substituted group Z is substituted by one, substituent selected from halogen, cyano, nitro, R4-C1-C4alkyl, R4-C1-C4halogenoalkyl, OH, N(R3)$_2$, and R4-C1-C4alkoxy.

35. The compound according to claim 16 or a pharmaceutically acceptable salt thereof, wherein Y is selected from 4-aminocyclohexyl and 4-aminopiperidin-1-yl.

36. The compound according to claim 17 or a pharmaceutically acceptable salt thereof, wherein Z is selected from furan-2-yl, furan-3-yl, thiophen-2, thiophen-3-yl, benzofuran-2-yl, benzooxazol-2-yl, benzothiazol-2-yl, furo[3,2-c]pyridin-2yl, furo[2,3-c]pyridin-2yl, benzo[b]thiophen-2yl, 1H-indol-2-yl, 1H-indol 5-yl, pyridinyl, quinolinyl and isoquinolinyl.

37. The compound according to claim 36 or a pharmaceutically acceptable salt thereof, wherein Z is selected from pyridine-4-yl, pyridine-3-yl, quinolin-3-yl, isoquinolin-6-yl and isoquinolin-7-yl.

38. The compound according to claim 1, wherein the compound is selected from the compounds in the following table:

| Example |  |
|---|---|
| 104 | (structure) |
| 299 | (structure) |
| 300 | (structure) |
| 303 | (structure) |
| 304 | (structure) | or a pharmaceutically acceptable salt thereof.

39. The pharmaceutical composition according to claim 23, comprising a compound having the formula I-3:

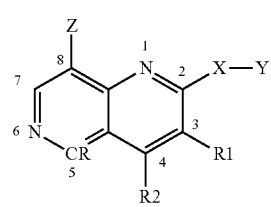

(I-3)

wherein
R represents hydrogen, OH or NH$_2$;
R1 and R2 independently of each other, represent hydrogen, halogen, NH$_2$, C1-C4alkyl, C1-C4haloenalkyl, C1-C4alkoxy, or C1-C4halogenalkoxy;
R3 represents, independently at each occurrence, hydrogen or methyl;
R3a represents, independently at each occurrence, hydrogen or methyl;
R4 represents independently, at each occurrence hydrogen, halogen, cyano, OH, NH$_2$, NH(CH$_3$) or N(CH$_3$)$_2$;
X represents C(R3a)$_2$-, —NR3a or—O—;
Y is selected from substituted monocyclic saturated 5-, 6- or 7-membered cycloalkyl, which comprise at least one substituent selected from NH$_2$, NH(CH$_3$), unsubstituted or substituted monocyclic saturated 5-, 6- or 7-membered heterocycloalkyl which comprises 1 or 2 nitrogen heteroatoms and optionally at least one substituent selected from NH$_2$NH(CH$_3$) and N(CH$_3$)$_2$, and an unsubstituted or substituted mono- or bicyclic heteroarly group, which which comprises 1 or 2 nitrogen heteroatoms per cycle present in said heteroaryl group and optionally at least one substituent selected from NH$_2$, NH(CH$_3$) and N(CH$_3$)$_2$;
and wherein Y may be additionally substituted by one group slected from C1-C4alkyl, hydroxy, nitro, C1-C4alkoxy, C1-C4fluoroalkyl, cyano, halogen, and C1-C4alkoxycarbonyl;
Z is selected from:
(E) an unsubstituted aryl group or an aryl group substituted as defined below, said aryl group being selected from
(Ea): phenyl; and
(F): an unsubstituted heteroaryl group or a heteroaryl group substituted as defined below, said heteroaryl group being selected from the group of formula:

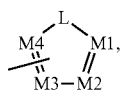
(Fa)

wherein L is selected from NH, O and S and one or two of M1, M2, M3 and M4 may be nitrogen and all others are selected from CH and C substituted as defined below;

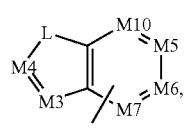
(Fc)

wherein L is selected from NH, O and S one of M3 and M4 may be nitrogen, CH or C substituted as defined below, the other is CH or C substituted as defined below and one or two of M5, M6, M7 and M10 nitrogen and all others are selected from CH and C substituted as defined below, and the linking bond may be located at both cycles of the group; and
when-substituted group Z is substituted by one, two or more substituents selected from halogen, cyano, nitro, R4-C1-C4alkyl, R4-C1-C4haloqenoalkyl, OH N(R3)$_2$, and R4-C1-C4alkoxy;

including tautomers of said compound, mixtures of two tautomeric forms of said compound, or a pharmaceutically acceptable salt of said compound, including tautomers thereof or mixtures of two tautomeric forms thereof, and a pharmaceutically acceptable carrier.

40. The pharmaceutical composition according to claim 23, comprising a compound of formula I-3:

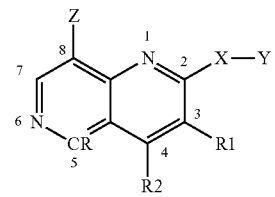
(I-3)

wherein:
represents hydrogen or —NH$_2$;
R1 and R2, independently of one another, represent hydrogen, fluoro, chloro, hydroxy, methoxy, ethoxy, propoxy, —NH$_2$ or nitro;
X—Y is selected from

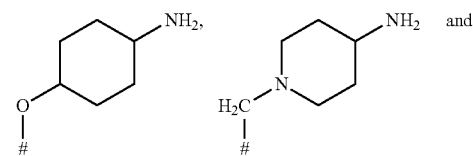

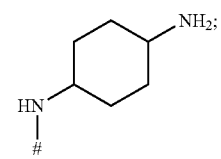

Z is selected from phenyl, which is unsubstituted of substituted by one or two substituents selected from fluoro and chloro; and a group of one of the formulae

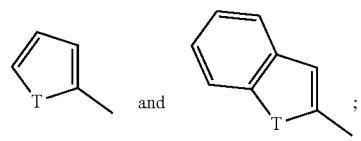

T is selected from an O- or S-atom,
including tautomers of said compound, mixtures of two tautomeric forms of said compound, or a pharmaceutically acceptable salt of said compound, including tautomers thereof or mixtures of two tautomeric forms thereof, and a pharmaceutically acceptable carrier.

41. The pharmaceutical composition according to claim 23, comprising a compound selected from the compounds in the following table:

| Example | |
|---|---|
| 104 | 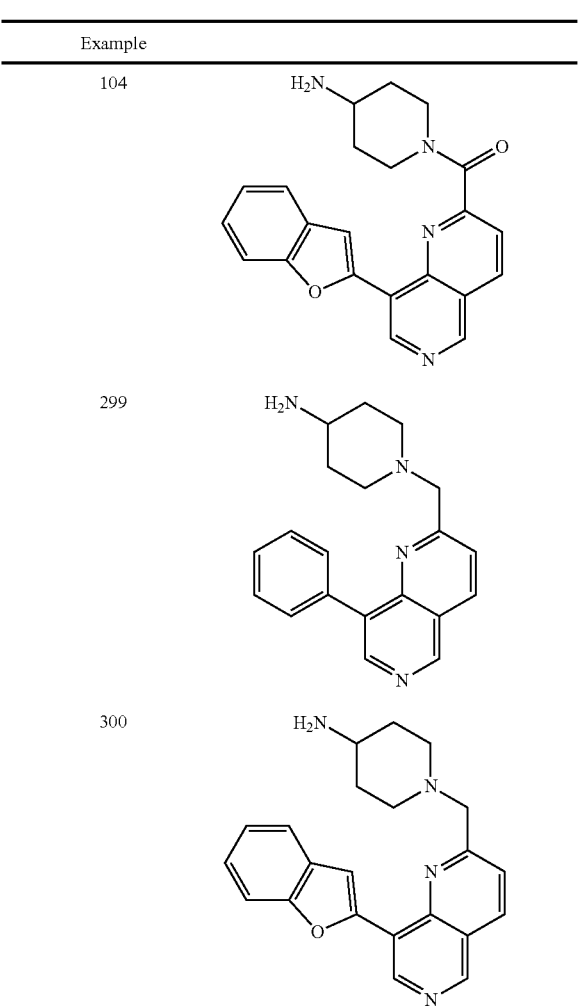 |
| 299 | |
| 300 | |
-continued
| Example | |
|---|---|
| 303 | 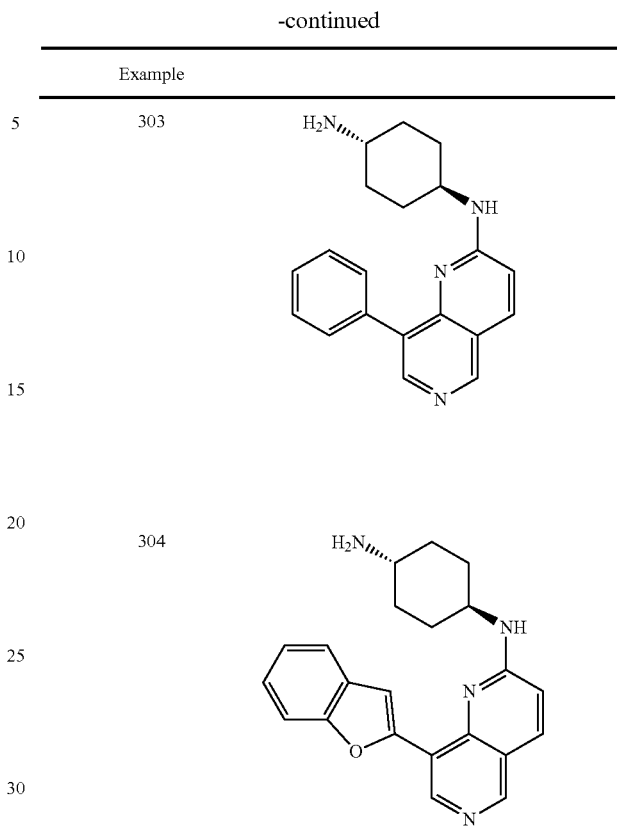 |
| 304 | |
including tautomers of said compound, mixtures of two tautomeric forms of said compound, or a pharmaceutically acceptable salt of said compound, including tautomers thereof or mixtures of two tautomeric forms thereof, and a pharmaceutically acceptable carrier.
\* \* \* \* \*

UNITED STATES PATENT AND TRADEMARK OFFICE
CERTIFICATE OF CORRECTION

PATENT NO. : 10,487,075 B2
APPLICATION NO. : 15/545149
DATED : November 26, 2019
INVENTOR(S) : Jens Pohlmann et al.

It is certified that error appears in the above-identified patent and that said Letters Patent is hereby corrected as shown below:

In the Claims

At Column 391, Line 39, "stibstituent" should be printed as "substituent."
At Column 391, Lines 65 and 67, "monocycle" should be printed as "monocyclic."
At Column 391, Line 65, "bicycle" should be printed as "bicyclic."
At Column 392, Line 42, "heteroaryi" should be printed as "heteroaryl."
At Column 393, Line 7, "R4-C1 C4halogenoalkythio" should be printed as "R4-C1 C4halogenoalkylthio."
At Column 393, Line 11, "C3-C6cycloakyl" should be printed as "C3-C6cycloalkyl."
At Column 393, Line 14, "bv" should be printed as "by."
At Column 393, Line 16, "R4-C1C4alkoxy" should be printed as "R4-C1-C4alkoxy."
At Column 393, Line 39, "sulthr" should be printed as "sulfur."
At Column 395, Line 34, "he" should be printed as "be."
At Column 396, Line 67, "grow" should be printed as "group."
At Column 397, Line 34, "haying" should be printed as "having."
At Column 397, Line 64, "N(CH3)7" should be printed as "N(CH3)2."
At Column 398, Line 39, "he" should be printed as "be."
At Column 398, Line 64, "C1 C4alkyl," should be added before "C1 C4halogenoalkyl."
At Column 400, Line 60, "SB" should be printed as "SH."
At Column 400, Line 62, "R4-C1 C4halogenoalkythio" should be printed as "R4-C1 C4halogenoalkylthio."
At Column 401, Line 9, "pyrrolidin-3" should be printed as "pyrrolidin-3-yl."
At Column 401, Line 11, "pyrimidin-4-yl" should be added before "or pyridazinium-1-yl."
At Column 401, Lines 18 and 19, "R4-C1 C4halogem-alkylthio" should be printed as "R4-C1 C4halogenoalkylthio."
At Column 401, Line 39, "thiophen-2" should be printed as "thiophen-2yl."
At Column 403, Line 4, "C4haloenalkyl" should be printed as "C4halogenalkyl."
At Column 403, Lines 20 and 21, "heteroarly group, which which comprises" should be printed as "heteroaryl group which comprises."

Signed and Sealed this
Thirty-first Day of March, 2020

Andrei Iancu
*Director of the United States Patent and Trademark Office*

CERTIFICATE OF CORRECTION (continued)
U.S. Pat. No. 10,487,075 B2

At Column 403, Line 26, "sleeted" should be printed as "selected."
At Column 403, Lines 60 and 61, "one or two of M5, M6, M7 and M10 nitrogen" should be printed as "one or two of M5, M6, M7, and M10 may be nitrogen."
At Column 403, Line 66, "R4-C1 C4haloqenoalkyl" should be printed as "R4-C1 C4halogenoalkyl."